United States Patent
Siddiqui et al.

(10) Patent No.: US 8,796,460 B2
(45) Date of Patent: Aug. 5, 2014

(54) COMPOUNDS FOR INHIBITING KSP KINESIN ACTIVITY

(75) Inventors: M. Arshad Siddiqui, Newton, MA (US); Chaoyang Dai, Acton, MA (US); Umar Faruk Mansoor, Framingham, MA (US); Liping Yang, Arlington, MA (US); Lalalnthi Dilrukshi Vitharana, Somerville, MA (US); Angie R. Angeles, Boston, MA (US)

(73) Assignee: Mercky Sharp & Dohme Corp., Rahway, NY (US)

( * ) Notice: Subject to any disclaimer, the term of this patent is extended or adjusted under 35 U.S.C. 154(b) by 631 days.

(21) Appl. No.: 12/738,537

(22) PCT Filed: Oct. 16, 2008

(86) PCT No.: PCT/US2008/080164
§ 371 (c)(1), (2), (4) Date: Jul. 23, 2010

(87) PCT Pub. No.: WO2009/052288
PCT Pub. Date: Apr. 23, 2009

(65) Prior Publication Data
US 2011/0123435 A1    May 26, 2011

Related U.S. Application Data

(60) Provisional application No. 60/981,288, filed on Oct. 19, 2007.

(51) Int. Cl.
C07D 211/26 (2006.01)
A61K 31/397 (2006.01)
C07D 211/14 (2006.01)
C07D 471/04 (2006.01)

(52) U.S. Cl.
CPC ................... *C07D 211/14* (2013.01); *C07D 471/04* (2013.01)
USPC ....................... 546/229; 514/210.21

(58) Field of Classification Search
CPC ............................ C07D 211/14; C07D 471/04
USPC ....................... 546/229; 514/210.21
See application file for complete search history.

(56) References Cited

U.S. PATENT DOCUMENTS

| | | |
|---|---|---|
| 2004/0192739 A1 | 9/2004 | Solow-Cordero et al. |
| 2006/0247178 A1 | 11/2006 | Hans et al. |
| 2006/0258699 A1 | 11/2006 | Doll et al. |
| 2007/0037853 A1 | 2/2007 | Barsanti et al. |
| 2007/0112044 A1 | 5/2007 | Murakata et al. |
| 2007/0155804 A1 | 7/2007 | Murakata et al. |
| 2007/0213380 A1 | 9/2007 | Murakata et al. |
| 2007/0249636 A1 | 10/2007 | Aquila et al. |
| 2007/0287703 A1 | 12/2007 | Block et al. |
| 2008/0153854 A1 | 6/2008 | Aquila et al. |
| 2008/0194653 A1 | 8/2008 | Murakata et al. |
| 2011/0171172 A1* | 7/2011 | Siddiqui et al. ............. 424/85.4 |
| 2012/0070370 A1* | 3/2012 | Siddiqui et al. ............. 424/1.11 |

FOREIGN PATENT DOCUMENTS

| | | |
|---|---|---|
| WO | 2003/079973 A2 | 10/2003 |
| WO | 2004/037171 A2 | 5/2004 |
| WO | 2004/058148 A2 | 7/2004 |
| WO | 2004/058700 A2 | 7/2004 |
| WO | 2004/087050 A2 | 10/2004 |
| WO | 2004/092147 A1 | 10/2004 |
| WO | 2004/111023 A1 | 12/2004 |
| WO | 2004/111193 A2 | 12/2004 |
| WO | 2004/112699 A2 | 12/2004 |
| WO | 2005/017190 A2 | 2/2005 |
| WO | 2005/018547 A2 | 3/2005 |
| WO | 2005/018638 A1 | 3/2005 |
| WO | 2005/019205 A1 | 3/2005 |
| WO | 2005/019206 A1 | 3/2005 |
| WO | 2005/035512 A1 | 4/2005 |
| WO | 2005/092011 A2 | 10/2005 |
| WO | 2005/102996 A2 | 11/2005 |
| WO | 2005/108355 A2 | 11/2005 |
| WO | 2003/105855 A1 | 12/2005 |
| WO | 2006/002726 A1 | 1/2006 |
| WO | 2006/007491 A1 | 1/2006 |
| WO | 2006/007496 A2 | 1/2006 |

(Continued)

OTHER PUBLICATIONS

Budarina et al Russian Journal of Organic Chemistry 2005, 41(5), 758-761.*

(Continued)

*Primary Examiner* — John Mabry
(74) *Attorney, Agent, or Firm* — Li Su; Laura Ginkel

(57) ABSTRACT

The present invention relates to compounds of Formula (I), below, (wherein X, R1, R2, R3, p, E, ring A, and ring B are as defined herein). The present invention also relates to compositions (including pharmaceutically acceptable compositions) comprising these compounds, alone and in combination with one or more additional therapeutic agents, and to methods for their use in inhibiting KSP kinesin activity, and for treating cellular proliferative diseases or disorders associated with KSP kinesin activity. Formula I (I)

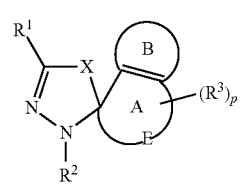

37 Claims, No Drawings

(56) References Cited

FOREIGN PATENT DOCUMENTS

| WO | 2006/007497 A2 | 1/2006 |
|---|---|---|
| WO | 2006/007501 A2 | 1/2006 |
| WO | 2006/023083 A1 | 3/2006 |
| WO | 2006/023440 A2 | 3/2006 |
| WO | 2006/031348 A2 | 3/2006 |
| WO | 2006/031607 A2 | 3/2006 |
| WO | 2006/044825 A2 | 4/2006 |
| WO | 2006044825 A2 | 4/2006 |
| WO | 2006/068933 A2 | 6/2006 |
| WO | 2006/086358 A2 | 8/2006 |
| WO | 2006/094602 A1 | 9/2006 |
| WO | 2006/101102 A1 | 9/2006 |
| WO | 2006/101103 A1 | 9/2006 |
| WO | 2006/101104 A1 | 9/2006 |
| WO | 2006/101105 A1 | 9/2006 |
| WO | 2006/101761 A2 | 9/2006 |
| WO | 2006/101780 A1 | 9/2006 |
| WO | WO2006/098961 A2 | 9/2006 |
| WO | WO2006/098962 A1 | 9/2006 |
| WO | 2006/110390 A1 | 10/2006 |
| WO | 2006/119146 A1 | 11/2006 |
| WO | 2006119146 A1 | 11/2006 |
| WO | 2006/133805 A1 | 12/2006 |
| WO | 2006/133821 A1 | 12/2006 |
| WO | 2006/137490 A1 | 12/2006 |
| WO | 2007/054138 A1 | 5/2007 |
| WO | 2007146138 A2 | 12/2007 |
| WO | WO2008/042928 A2 | 4/2008 |
| WO | 2009061595 A1 | 5/2009 |
| WO | 2009061597 A1 | 5/2009 |
| WO | 2010132520 A1 | 11/2010 |

OTHER PUBLICATIONS

Patani et al Chem. Rev. 1996, 96, 3147-3176.*
Solomons et al Organic Chemistry 9th Edition Feb. 2007, "Isomers" pp. 183-184.*
Somogyi et al Tetrahedron 1985, 41, 5187-5190.*
Budarina, Ev et al. Russian Journal of Organic Chemistry, vol. 41, No. 5 (2005), pp. 758-760, "Heterocyclic thiones and their analogs in reactions of 1,3-dipolar addition: V.*Reactions of 2,3,3-triphenyl-1thioxophthalimidine with nitrile imines".
Budarina, Ev et al., Russian Journal of Organic Chemistry, vol. 41, No. 3, (2005), pp. 455-460, "Heterocyclic thiones and their analogs in 1,3-dipolar cycloaddition reactions: IV.* Reactions of 4-aryl-2-phenyl-1,2-dihydrophthalazine-1-thiones with nitrile imides".
Mandelkow and Mandelkow, Trends Cell Biol. 2002, 12:585-591.
Blangy et al., Cell 1995, 83:1159-1169.
Kaiser et al., J. Biol. Chem. 1999, 274:18925-18931.
Sakowicz et al., Science 1998, 280:292-295.
Hopkins et al., Biochemistry 2000, 39:2805-2814.
Mayer et al., Science 1999, 286:971-974.
Labeish et al., Heterocyclic Thiones and their analogs in 1,3-dipolar cycloaddition reactions I. Reactions of 1,2-dithiophthalides with nitrilimines, XP 002510749, Russian Journal of Organic Chemistry, 33(3), 381-387, 1997.
Korchevin et al., Alpha, Beta—unsaturated sulfur compounds XX, [2+3]-Cycloadditoin of 3-amino-2-aryl-1-indenethiones to nitrilium betains and azidobenzene, Zhurnal Organicheskoi Khimit, 22(6), 1276-82 Coden: ZORKAE; ISSN: 0514-7492, 1986.
Sain et al., "Studies on Chromone derivatives: regioselective 1,3-dipolar and 1,4-cycloaddition reactions of 3-cyano-4H-1-benzopyran-4-thione" & Bulletin De La Societe Chimique De France, 131(3), 313-16 Coden: BSCFAS ISSN: 0037-8968, 1994.
Database Chemcats Chemical Abstracts Services, Columbus, Ohio, US; XP002510752 & Zelinsky Screening Library Apr. 9, 2007 Zelinsky Institute of Organic Chemistry, 47 Leninsky Prospect Moscow, 117913 Russia.

* cited by examiner

COMPOUNDS FOR INHIBITING KSP KINESIN ACTIVITY

PRIORITY

This application claims the benefit of priority of U.S. Provisional Application No. 60/981,288, filed, Oct. 19, 2007, the contents of which are incorporated in their entirety herein by reference.

FIELD OF THE INVENTION

The present invention relates to compounds and compositions that are useful for treating cellular proliferative diseases or disorders associated with Kinesin Spindle Protein ("KSP") kinesin activity and for inhibiting KSP kinesin activity.

BACKGROUND OF THE INVENTION

Cancer is a leading cause of death in the United States and throughout the world. Cancer cells are often characterized by constitutive proliferative signals, defects in cell cycle checkpoints, as well as defects in apoptotic pathways. There is a great need for the development of new chemotherapeutic drugs that can block cell proliferation and enhance apoptosis of tumor cells.

Conventional therapeutic agents used to treat cancer include taxanes and vinca alkaloids, which target microtubules. Microtubules are an integral structural element of the mitotic spindle, which is responsible for the distribution of the duplicated sister chromatids to each of the daughter cells that result from cell division. Disruption of microtubules or interference with microtubule dynamics can inhibit cell division and induce apoptosis.

However, microtubules are also important structural elements in non-proliferative cells. For example, they are required for organelle and vesicle transport within the cell or along axons. Since microtubule-targeted drugs do not discriminate between these different structures, they can have undesirable side effects that limit usefulness and dosage. There is a need for chemotherapeutic agents with improved specificity to avoid side effects and improve efficacy.

Microtubules rely on two classes of motor proteins, the kinesins and dyneins, for their function. Kinesins are motor proteins that generate motion along microtubules. They are characterized by a conserved motor domain, which is approximately 320 amino acids in length. The motor domain binds and hydrolyses ATP as an energy source to drive directional movement of cellular cargo along microtubules and also contains the microtubule binding interface (Mandelkow and Mandelkow, Trends Cell Biol. 2002, 12:585-591).

Kinesins exhibit a high degree of functional diversity, and several kinesins are specifically required during mitosis and cell division. Different mitotic kinesins are involved in all aspects of mitosis, including the formation of a bipolar spindle, spindle dynamics, and chromosome movement. Thus, interference with the function of mitotic kinesins can disrupt normal mitosis and block cell division. Specifically, the mitotic kinesin KSP (also termed EG5), which is required for centrosome separation, was shown to have an essential function during mitosis. Cells in which KSP function is inhibited arrest in mitosis with unseparated centrosomes (Blangy et al., Cell 1995, 83:1159-1169). This leads to the formation of a monoastral array of microtubules, at the end of which the duplicated chromatids are attached in a rosette-like configuration. Further, this mitotic arrest leads to growth inhibition of tumor cells (Kaiser et al., J. Biol. Chem. 1999, 274:18925-18931). Inhibitors of KSP would be desirable for the treatment of proliferative diseases, such as cancer.

Kinesin inhibitors are known, and several molecules have recently been described in the literature. For example, adociasulfate-2 inhibits the microtubule-stimulated ATPase activity of several kinesins, including CEINIP-E (Sakowitz et al., Science 1998, 280:292-295). Rose Bengal lactone, another non-selective inhibitor, interferes with kinesin function by blocking the microtubule binding site (Hopkins et al., Biochemistry 2000, 39:2805-2814). Monastrol, a compound that has been isolated using a phenotypic screen, is a selective inhibitor of the KSP motor domain (Mayer et al., Science 1999, 286:971-974). Treatment of cells with monastrol arrests cells in mitosis with monopolar spindles.

KSP inhibitors have been disclosed in patents or publications, including: WO2006/031348, WO2006/110390, WO2006/068933, WO2006/023083, WO2006/007491, WO2006/086358, WO2003/105855, WO2006/023440, WO2003/079973, WO2004/087050, WO2004/111193, WO2004/112699, WO2006/007497, WO2006/101761, WO2006/007496, WO2005/017190, WO0224/037171, WO2005/019205, WO2005/019206, WO2005/102996, WO2006/101780, WO2006/007501, WO2005/018547, WO2004/058148, WO2004/058700, WO2005/018638, WO2007/054138, WO2006/133805, WO2006/002726, WO2006/133821, WO2005/108355, WO2006/094602, WO2005/092011, WO2006/031607, WO2004/111023, WO2006/137490, WO2006/101102, WO2006/101103, WO2006/101104, WO2006/101105, WO2004/092147, WO2005/035512, WO2006/044825, WO2006/044825, WO2006/119146, US2006/0247178, WO2006/098961, WO2006/098962, US2006/0258699, US2007/0213380, US2007/0112044, US2007/0155804, US2008/0194653, WO2008/042928, US2007/0249636, US2007/0287703, US2008/0153854, and US2007/0037853.

KSP, as well as other mitotic kinesins, are attractive targets for the discovery of novel chemotherapeutics with anti-proliferative activity. There is a need for compounds useful in the inhibition of KSP, and in the treatment of proliferative diseases, such as cancer.

SUMMARY OF THE INVENTION

In one embodiment, the present invention provides a compound, or pharmaceutically acceptable salts, solvates, esters, prodrugs, or isomers of said compound, said compound having the general structure shown in Formula (I):

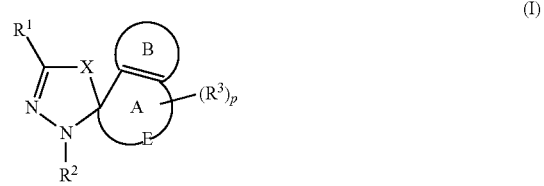

wherein X, $R^1$, $R^2$, $R^3$, p, E, ring A, and ring B are selected independently of each other and wherein:

p is 0, 1, 2, 3, or 4;

X is selected from the group consisting of S, S(O), and $S(O)_2$;

ring A (including E and the unsaturation shown) is a 4-8 membered cycloalkenyl or heterocycloalkenyl ring;

E is selected from the group consisting of —O—, —S—, —S(O)—, —S(O)$_2$—, —C($R^4$)($R^5$)—, —N($R^6$)—, —N(C(Y)$R^7$)—, —N(C(Y)O$R^8$)—, —N(C(Y)N($R^9$)

$(R^{10}))$—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N=N—, —C($R^7$)=N—, —C(O)—C($R^7$)=N—, —C(O)—N=N—, —O—C(Y)—N($R^{11}$)—, —N($R^{11}$)—C(Y)—O—, —N($R^{11}$)—C(Y)—N($R^{12}$)—, —C(Y)—N($R^{11}$)—O—, —C(Y)—N($R^{11}$)—N($R^{12}$)—; —O—N($R^{11}$)—C(Y)—, and —N($R^{12}$)—N($R^{11}$)—C(Y)—, wherein each Y is independently selected from the group consisting of (=O), (=S), (=N($R^{13}$)), (=N(CN)), (=N(O$R^{14}$)), (=N($R^{15}$)($R^{16}$)), and (=C($R^{17}$)($R^{18}$));

ring B is an aromatic or heteroaromatic ring, or a partially unsaturated alicyclic ring, or a partially unsaturated heterocyclic ring, wherein said ring is unsubstituted or optionally independently substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(O)$R^{20}$, —S$R^{19}$, —S(O)$R^{19}$, —SO$_2R^{19}$, —OC(O)$R^{24}$, —C(O)N$R^{25}R^{26}$, —N$R^{23}$C(N—CN)N$R^{25}R^{26}$ and —N$R^{23}$C(O)N$R^{25}R^{26}$;

$R^1$ is selected from the group consisting of aryl, heteroaryl, cycloalkyl, cycloalkenyl, heterocycloalkyl, and heterocycloalkenyl, wherein each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(O)O$R^{20}$, —S$R^{10}$, —S(O)$R^{19}$, —SO$_2R^{19}$, —OC(O)$R^{24}$, —C(O)N$R^{25}R^{26}$, —N$R^{23}$C(N—CN)N$R^{25}R^{26}$ and —N$R^{23}$C(O)N$R^{25}R^{26}$;

$R^2$ is selected from the group consisting of —C(Z)$R^7$, —C(Z)N$R^9R^{10}$, —C(Z)O$R^8$, —SO$_2$N$R^9R^{10}$, alkyl, heteroalkyl, aryl, heteroaryl, -cycloalkyl, cycloalkenyl, heterocycloalkyl, and heterocycloalkenyl, wherein each Z is independently selected from the group consisting of (=O), (=S), (=N($R^{13}$)), (=N(CN)), (=N(O$R^{14}$)), (=N($R^{15}$)($R^{16}$)), and (=C($R^{17}$)($R^{18}$)), and wherein each said alkyl, each said heteroalkyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group consisting of oxo (with the proviso that said aryl and said heteroaryl are not substituted with oxo), halogen, —CN, —NO$_2$, alkyl, heteroalkyl, haloalkyl, alkenyl, haloalkenyl, alkynyl, haloalkynyl, aryl, heteroaryl, aryl-alkyl, heteroaryl-alkyl, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(O)O$R^{20}$, —S$R^{19}$, —S(O)$R^{19}$, —SO$_2R^{19}$, —OC(O)$R^{24}$, —C(O)N$R^{25}R^{26}$, —N$R^{23}$C(N—CN)N$R^{25}R^{26}$ and —N$R^{23}$C(O)N$R^{25}R^{26}$;

each $R^3$ (when present) is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(S)$R^{24}$, —C(O)O$R^{20}$, —S$R^{19}$, —S(O)$R^{19}$, —SO$_2R^{19}$, —OC(O)$R^{24}$, —C(O)N$R^{25}R^{26}$, —N$R^{23}$C(N—CN)N$R^{25}R^{26}$, —N$R^{23}$C(O)N$R^{25}R^{26}$, and —N$R^{23}$—C(NH)—N($R^{26}$)$_2$, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(O)O$R^{20}$, —S$R^{19}$, —S(O)$R^{19}$, —SO$_2R^{19}$, —OC(O)$R^{24}$, —C(O)N$R^{25}R^{26}$, N$^{23}$C(N—CN)N$R^{25}R^{26}$ and —N$R^{23}$C(O)N$R^{25}R^{26}$, or, alternatively, when p is 2, 3, or 4, any two $R^3$ groups bound to the same ring carbon atom are taken together with the carbon atom to which they are attached to form a spirocycloalkyl, a spirocycloalkenyl, or a spiroheterocycloalkyl ring containing from one to three ring heteroatoms independently selected from the group consisting of —NH—, —N$R^6$—, —S—, —S(O)—, —S(O)$_2$—, and —O—, or a spiroheterocycloalkenyl ring containing from one to three ring heteroatoms independently selected from the group consisting of —NH—, —N$R^6$—, —S—, —S(O)—, —S(O)$_2$—, and —O—, or, alternatively, $R^2$ and $R^3$, together with the atom to which they are attached, are taken together with the carbon atom to which they are attached to form a cycloalkyl, a cycloalkenyl, a heterocycloalkyl ring containing from one to three ring heteroatoms independently selected from the group consisting of —NH—, —N$R^6$—, —S—, —S(O)—, —S(O)$_2$—, and —O—, or a heterocycloalkenyl ring containing from one to three ring heteroatoms independently selected from the group consisting of —NH—, —N$R^6$—, —S—, —S(O)—, —S(O)$_2$—, and —O—;

each $R^4$ (when not joined with $R^5$) is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(O)O$R^{20}$, —S$R^{19}$, —S(O)$R^{19}$, —SO$_2R^{19}$, —OC(O)$R^{24}$, —C(O)N$R^{25}R^{26}$, —N$R^{23}$C(N—CN)N$R^{25}R^{26}$ and —N$R^{23}$C(O)N$R^{25}R^{26}$, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

each R$^5$ (when not joined with R$^4$) is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, NR$^{23}$SO$_2$R$^{24}$, —NR$^{23}$C(O)OR$^{20}$, NR$^{23}$C(O)R$^{24}$, SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —N$^{23}$C(N—CN)NR$^{25}$R$^{26}$ and —NR$^{23}$C(O)NR$^{25}$R$^{26}$;

or, alternatively, R$^4$ and R$^5$, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S, wherein said heterocycloalkyl ring and said heterocycloalkenyl ring are each unsubstituted or optionally independently substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

each R$^6$ is independently selected from the group consisting of H, alkyl, —C(O)R$^{24}$, —C(O)OR$^{20}$, —C(S)R$^{24}$, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(S)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

each R$^7$ is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{20}$R$^{29}$ and —NR$^{23}$C(O)NR$^{25}$R$^{26}$;

each R$^8$ is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{12}$, —C(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

each R$^9$ (when not joined with R$^{10}$) is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N═CN)NR$^{25}$R$^{26}$ and —NR$^{23}$C(O)NR$^{25}$R$^{26}$;

each R$^{10}$ (when not joined with R$^9$) is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N═CN)NR$^{25}$R$^{26}$ and —NR$^{23}$C(O)NR$^{25}$R$^{26}$;

or, alternatively, R$^9$ and R$^{10}$, together with the N atom to which they are attached, form a heterocycloalkyl or a heterocycloalkenyl ring containing from one to three heteroatoms selected from the group consisting of N, O, and S, wherein said heterocycloalkyl ring and said heterocycloalkenyl ring are each unsubstituted or optionally independently substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N═CN)NR$^{25}$R$^{26}$ and —NR$^{23}$C(O)NR$^{25}$R$^{26}$;

each R$^{11}$ is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N═CN)NR$^{25}$R$^{26}$ and —NR$^{23}$C(O)NR$^{25}$R$^{26}$;

each R$^{12}$ is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{10}$, —S(O)R$^{19}$, —SO$_2$R$^{19}$, —OC(O)R$^{24}$, —C(O)NR$^{25}$R$^{26}$, —NR$^{23}$C(N═CN)NR$^{25}$R$^{26}$ and —NR$^{23}$C(O)NR$^{25}$R$^{26}$;

each R$^{13}$ is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N═CN)NR$^{25}$R$^{26}$ and —NR$^{23}$C(O)NR$^{25}$R$^{26}$;

each R$^{14}$ is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

each R$^{15}$ (when not joined with R$^{16}$) is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

each R$^{16}$ (when not joined with R$^{15}$) is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

or, alternatively, R$^{15}$ and R$^{16}$, together with the N atom to which they are attached, form a heterocycloalkyl or a heterocycloalkenyl ring containing from one to three heteroatoms selected from the group consisting of N, O, and S, wherein said heterocycloalkyl ring and said heterocycloalkenyl ring are each unsubstituted or optionally independently substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

each R$^{17}$ (when not joined with R$^{18}$) is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, —CN, —OC(O)OR$^{20}$, —OR$^{19}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)OR$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$, wherein each said alkyl, each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

each R$^{18}$ (when not joined with R$^{17}$) is independently selected from the group consisting of H, alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, —CN, —OC(O)OR$^{20}$, —OR$^{19}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$, wherein each said alkyl; each said heteroalkyl, each said alkenyl, each said heteroalkenyl, each said alkynyl, each said heteroalkynyl, each said aryl, each said heteroaryl, each said cycloalkyl, each said cycloalkenyl, each said heterocycloalkyl, and each said heterocycloalkenyl is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

or, alternatively, R$^{17}$ and R$^{18}$, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S, wherein said heterocycloalkyl ring and said heterocycloalkenyl ring are each unsubstituted or optionally independently substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, aryl-alkyl-, heteroaryl, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$;

each R$^{19}$ is independently selected from the group consisting of H, alkyl, haloalkyl, heteroalkyl, haloheteroalkyl, aryl, heteroaryl, cycloalkyl, halocycloalkyl;

each R$^{20}$ is independently selected from the group consisting of H, haloalkyl, heteroalkyl, haloheteroalkyl, aryl, heteroaryl, cycloalkyl, halocycloalkyl;

each R$^{21}$ (when not joined with R$^{22}$) is independently selected from the group consisting of H, alkyl, haloalkyl, heteroalkyl, haloheteroalkyl, aryl, heteroaryl, cycloalkyl, halocycloalkyl;

each R$^{22}$ (when not joined with R$^{21}$) is independently-selected from the group consisting of H, alkyl, haloalkyl, heteroalkyl, haloheteroalkyl, aryl, heteroaryl, cycloalkyl, halocycloalkyl;

or, alternatively, R$^{21}$ and R$^{22}$, together with the N atom to which they are attached, form a heterocycloalkyl or a heterocycloalkenyl ring containing from one to three heteroatoms selected from the group consisting of N, O, and S;

each R$^{23}$ is independently selected from the group consisting of H, alkyl, haloalkyl, heteroalkyl, haloheteroalkyl, aryl, heteroaryl, cycloalkyl, halocycloalkyl;

each R$^{24}$ is independently selected from the group consisting of H, alkyl, haloalkyl, heteroalkyl, haloheteroalkyl, aryl, heteroaryl, cycloalkyl, halocycloalkyl;

each R$^{25}$ (when not joined with R$^{26}$) is independently selected from the group consisting of H, alkyl, haloalkyl, heteroalkyl, haloheteroalkyl, aryl, heteroaryl, cycloalkyl, halocycloalkyl; and each R$^{26}$ (when not joined with R$^{25}$) is independently selected from the group consisting of H, alkyl, haloalkyl, heteroalkyl, haloheteroalkyl, aryl, heteroaryl, cycloalkyl, halocycloalkyl;

or, alternatively, R$^{25}$ and R$^{26}$, together with the N atom to which they are attached, form a heterocycloalkyl or a heterocycloalkenyl ring containing from one to three heteroatoms selected from the group consisting of N, O, and S.

As explained in more detail below, it shall be understood that ring A can have unsaturation in addition to the unsaturation shown in the generic formulas provided herein.

Pharmaceutical formulations or compositions comprising a therapeutically effective amount of at least one of the inventive compounds, and/or pharmaceutically acceptable salts, solvates, esters, prodrugs, or isomers thereof and a pharmaceutically acceptable carrier also are provided. Pharmaceutical formulations or compositions comprising a therapeutically effective amount of at least one of the inventive compounds (and/or pharmaceutically acceptable salts, solvates, esters, prodrugs, or isomers thereof) and a pharmaceutically acceptable carrier together with one or more additional active ingredients are also contemplated.

Methods of treating cellular proliferative diseases, disorders associated with KSP kinesin activity and/or for inhibiting KSP kinesin activity in a subject comprising administering to a subject in need of such treatment an effective amount of at least one of the inventive compounds or formulations or compositions according to the invention are also are provided. The methods according to the invention may be used in a single agent regimen or as part of a multiple agent regimen as is determined appropriate by those skilled in the art.

Other than in the operating examples, or where otherwise indicated, all numbers expressing quantities of ingredients, reaction conditions, and so forth used in the specification and claims are to be understood as being modified in all instances by the term "about"

DETAILED DESCRIPTION

In one embodiment, the compounds of the invention have a structure shown in Formula (I) and include pharmaceutically acceptable salts, solvates, esters, prodrugs, or isomers of said compounds.

As stated in Formula (I) (and in other formulas described herein depicting various embodiments of the compounds of the invention), ring A is a 4-8 membered cycloalkenyl or heterocycloalkenyl ring. It shall be understood that such cycloalkenyl or heterocycloalkenyl rings of ring A can have unsaturation that is in addition to the unsaturation shown in the generic formulas provided herein. For purposes of illustration only, non-limiting examples of such additional unsaturation in ring A include:

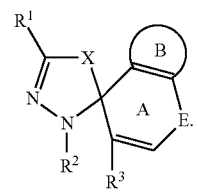

Additional non-limiting examples include:

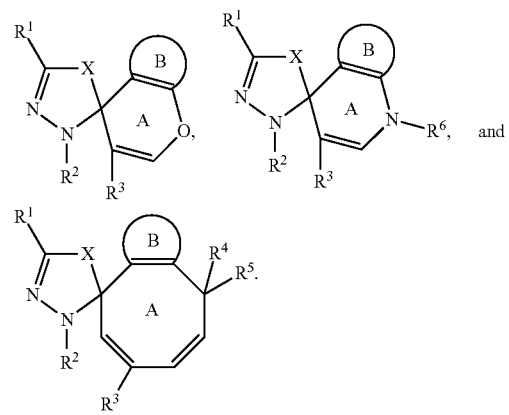

In one embodiment, in Formula (I), X is S.
In one embodiment, in Formula (I), X is S(O).
In one embodiment, in Formula (I), X is S(O)$_2$.
In one embodiment, in Formula (I), ring A is a cycloalkenyl ring.
In one embodiment, in Formula (I), ring A is a heterocycloalkenyl ring.
In one embodiment, in Formula (I), ring A is a 4-membered ring.
In one embodiment, in Formula (I), ring A is a 5-membered ring.
In one embodiment, in Formula (I), ring A is a 6-membered ring.

In one embodiment, in Formula (I), ring A is a 7-membered ring.

In one embodiment, in Formula (I), ring A is an 8-membered ring.

In one embodiment, in Formula (I), ring A (including the unsaturation shown) is mono-unsaturated.

In one embodiment, in Formula (I), ring A (including the unsaturation shown) is poly-unsaturated.

In one embodiment, in Formula (I), E is —C($R^4$)($R^5$)—.

In one embodiment, in Formula (I), E is selected from the group consisting of —O—, —S—, —S(O)—, —S(O)$_2$—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N=N—, —C($R^7$)=N—, —C(O)—C($R^7$)=N—, —C(O)—N=N—, —O—C(Y)—N($R^{11}$)—, —N($R^{11}$)—C(Y)—O—, —N($R^{11}$)—C(Y)—N($R^{12}$)—, —C(Y)—N($R^{11}$)—O—, —C(Y)—N($R^{11}$)—N($R^{12}$)—, and —N($R^{12}$)—N($R^{11}$)—C(Y)—.

In one embodiment, in Formula (I), E is selected from the group consisting of —O—, —S—, —S(O)—, —S(O)$_2$—, and —N($R^6$)—.

In one embodiment, in Formula (I), E is selected from the group consisting of —O—, —S—, —S(O)—, —S(O)$_2$—, and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), E is selected from the group consisting of —O— and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), when E is —N($R^6$)—, then p is 0 and $R^3$ is absent. In such embodiments, non-limiting examples of $R^6$ include Ft, alkyl, —C(O)$R^{24}$, —C(O)O$R^{20}$, and —C(S)$R^{24}$.

In one embodiment, in Formula (I), E is —O—.
In one embodiment, in Formula (I), E is —S—.
In one embodiment, in Formula (I), E is —S(O)—.
In one embodiment, in Formula (I), E is —S(O)$_2$—.
In one embodiment, in Formula (I), E is —CH$_2$—.
In one embodiment, in Formula (I), E is —CH$R^4$—.
In one embodiment, in Formula (I), E is —C$R^4$$R^5$—.
In one embodiment, in Formula (I), E is —N($R^6$)—.
In one embodiment, in Formula (I), E is —N(C(Y)$R^7$)—.
In one embodiment, in Formula (I), E is —N(C(Y)O$R^6$)—.
In one embodiment, in Formula (I), E is —N(C(Y)N($R^9$)($R^{10}$))—.
In one embodiment, in Formula (I), E is —C(O)—N($R^{11}$)—.
In one embodiment, in Formula (I), E is —N($R^{11}$)—C(O)—.
In one embodiment, in Formula (I), E is —S(O)$_2$—N($R^{11}$)—.
In one embodiment, in Formula (I), E is —N($R^{11}$)—S(O)$_2$—.
In one embodiment, in Formula (I), E is —C(O)—O—.
In one embodiment, in Formula (I), E is —O—C(O)—.
In one embodiment, in Formula (I), E is —O—N($R^6$)—.
In one embodiment, in Formula (I), E is —N($R^6$)—O—.
In one embodiment, in Formula (I), E is —N($R^6$)—N($R^{12}$)—.
In one embodiment, in Formula (I), E is —N=N—.
In one embodiment, in Formula (I), E is —C($R^7$)=N—.
In one embodiment, in Formula (I), E is —C(O)—C($R^7$)=N—.
In one embodiment, in Formula (I), E is —C(O)—N=N—.

In one embodiment, in Formula (I), E is —O—C(Y)—N($R^{11}$)—.
In one embodiment, in Formula (I), E is —N($R^{11}$)—C(Y)—O—.
In one embodiment, in Formula (I), E is —N($R^{11}$)—C(Y)—N($R^{12}$)—.
In one embodiment, in Formula (I), E is —C(Y)—N($R^{11}$)—O—.
In one embodiment, in Formula (I), E is C(Y)—N($R^{11}$)—N($R^{12}$)—.
In one embodiment, in Formula (I), E is —O—N($R^{11}$)—C(Y)—.
In one embodiment, in Formula (I), E is —N($R^{12}$)—N($R^{11}$)—C(Y)—.
In one embodiment, in Formula (I), Y is (=O).
In one embodiment, in Formula (I), Y is (=S).
In one embodiment, in Formula (I), Y is (=N($R^{13}$)).
In one embodiment, in Formula (I), Y is (=N(CN)).
In one embodiment, in Formula (I), Y is (=N(O$R^{14}$)).
In one embodiment, in Formula (I), Y is (=N($R^{15}$)($R^{16}$)).
In one embodiment, in Formula (I), Y is (=C($R^{17}$)($R^{18}$)).

In one embodiment, in Formula (I), ring A is a 4-7-membered cycloalkylene ring and E is —C($R^4$)($R^5$)—.

In one embodiment, in Formula (I), ring A is a 5-7-membered heterocycloalkylene ring and E is selected from the group consisting of —O—, —S—, —S(O)—, —S(O)$_2$—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N=N—, —C($R^7$)=N—, —C(O)—C($R^7$)=N—, —C(O)—N=N—, —O—C(Y)—N($R^{11}$)—, —N($R^{11}$)—C(Y)—O—, —N($R^{11}$)—C(Y)—N($R^{12}$)—, —C(Y)—N($R^{11}$)—O—, —C(Y)—N($R^{11}$)—N($R^{12}$)—, —O—N($R^{11}$)—C(Y)—, and —N($R^{12}$)—N($R^{11}$)—C(Y)—.

In one embodiment, in Formula (I), ring A is a 5-6-membered heterocycloalkylene ring and E is selected from the group consisting of —O—, —S—, —S(O)$_2$—, —N($R^6$)—, —C(O)—N($R^{11}$)—, and —N($R^{11}$)—C(O)—.

In one embodiment, in Formula (I), ring A is a 5-6-membered heterocycloalkylene ring and E is selected from the group consisting of —O—, —S—, —S(O)—, —S(O)$_2$—, and —N($R^6$)—. In one such embodiment, in Formula (I), $R^6$ is selected from the group consisting of H, alkyl, —C(O)$R^{24}$, —C(O)O$R^{20}$, and —C(S)$R^{24}$.

In one embodiment, in Formula (I), ring A is a 5-6-membered heterocycloalkylene ring and E is selected from the group consisting of —O— and —N($R^6$)—. In one such embodiment, in Formula (I), $R^6$ is selected from the group consisting of H, alkyl, —C(O)$R^{24}$, —C(O)O$R^{20}$, and —C(S)$R^{24}$. In one such embodiment, in Formula (I), ring A is a 5-membered heterocycloalkylene ring. In another such embodiment, in Formula (I), ring A is a 6-membered heterocycloalkylene ring.

In one embodiment, in Formula (I), ring A is a 4-membered ring and E is —C($R^4$)($R^5$)—.

In one embodiment, in Formula (I), ring A is a 4-membered ring and E is selected from the group consisting of —O—, —S—, —S(O)—, —S(O)$_2$—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N=N—, —C($R^7$)=N—, —C(O)—C($R^7$)=N—, —C(O)—N=N—, —O—C(Y)—N($R^{11}$)—, —N($R^{11}$)—C(Y)—O—, —N($R^{11}$)—C(Y)—N($R^{12}$)—, —C(Y)—N $(R^{11})$—O—, —C(Y)—N($R^{11}$)—N($R^{12}$)—, —O—N($R^{11}$)—C(Y)—, and —N($R^{12}$)—N($R^{11}$)—C(Y)—.

In one embodiment, in Formula (I), ring A is a 4-membered ring and E is selected from the group consisting of —O—, —S—, —S(O)—, —S(O)$_2$—, and —N($R^6$)—.

In one embodiment, in Formula (I), ring A is a 4-membered ring and E is selected from the group consisting of —O—, —S—, —S(O)—, —S(O)$_2$—, and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), ring A is a 4-membered ring and E is selected from the group consisting of —O— and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), ring A is a 4-membered ring and E is selected from the group consisting of —O—, —S—, —S(O)—, —S(O)$_2$—, —C($R^4$)($R^5$)—, —N($R^6$)—, —N(C(Y)$R^7$)—, —N(C(Y)O$R^8$)—, —N(C(Y)N($R^9$)($R^{10}$))—.

In one embodiment, in Formula (I), A is a 4-membered ring and E is selected from the group consisting of —CH$_2$—, —CH($R^4$)—, —C($R^4$)($R^5$)—.

In one embodiment, in Formula (I), ring A is a 5-membered ring and E is —C($R^4$)($R^5$)—.

In one embodiment, in Formula (I), ring A is a 5-membered ring and E is selected from the group consisting of —O—, —S—, —S(O)—, —S(O)$_2$—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N=N—, —C($R^7$)=N—, —C(O)—C($R^7$)=N—, —C(O)—N=N—, —O—C(Y)—N($R^{11}$)—, —N($R^{11}$)—C(Y)—O—, —N($R^{11}$)—C(Y)—N($R^{12}$)—, —C(Y)—N($R^{11}$)—O—, —C(Y)—N($R^{11}$)—N($R^{12}$)—, —O—N($R^{11}$)—C(Y)—, and —N($R^{12}$)—N($R^{11}$)—C(Y)—.

In one embodiment, in Formula (I), ring A is a 5-membered ring and E is selected from the group consisting of —O—, —S—, —S(O)—, —S(O)$_2$—, and —N($R^6$)—.

In one embodiment, in Formula (I), ring A is a 5-membered ring and E is selected from the group consisting of —O—, —S—, —S(O)—, —S(O)$_2$—, and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), ring A is a 5-membered ring and E is selected from the group consisting of —O— and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), ring A is a 5-membered ring and E is selected from the group consisting of —O—, —S—, —S(O)—, —S(O)$_2$—, —C($R^4$)($R^5$)—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N=N—, and —C($R^7$)=N—.

In one embodiment, in Formula (I), A is a 5-membered ring and E is —O—.

In one embodiment, in Formula (I), A is a 5-membered ring and E is —S—.

In one embodiment, in Formula (I), A is a 5-membered ring and E is —S(O)—.

In one embodiment, in Formula (I), A is a 5-membered ring and E is —S(O)$_2$—.

In one embodiment, in Formula (I), A is a 5-membered ring and E is —C($R^4$)($R^5$)—.

In one embodiment, in Formula (I), A is a 5-membered ring and E is —N($R^6$)—.

In one embodiment, in Formula (I), A is a 5-membered ring and E is —N(C(Y)$R^7$)—.

In one embodiment, in Formula (I), A is a 5-membered ring and E is —N(C(Y)O$R^8$)—.

In one embodiment, in Formula (I), A is a 5-membered ring and E is —N(C(Y)N($R^9$)($R^{10}$))—.

In one embodiment, in Formula (I), A is a 5-membered ring and E is —C(O)—N($R^{11}$)—.

In one embodiment, in Formula (I), A is a 5-membered ring and E is —N($R^{11}$)—C(O)—.

In one embodiment, in Formula (I), A is a 5-membered ring and E is —S(O)$_2$—N($R^{11}$)—.

In one embodiment, in Formula (I), A is a 5-membered ring and E is —N($R^{11}$)—S(O)$_2$—.

In one embodiment, in Formula (I), A is a 5-membered ring and E is —C(O)—O—.

In one embodiment, in Formula (I), A is a 5-membered ring and E is —O—C(O)—.

In one embodiment, in Formula (I), A is a 5-membered ring and E is —O—N($R^6$)—.

In one embodiment, in Formula (I), A is a 5-membered ring and Ets —N($R^6$)—O—.

In one embodiment, in Formula (I), A is a 5-membered ring and E is —N($R^6$)—N($R^{12}$)—.

In one embodiment, in Formula (I), A is a 5-membered ring and E is —N=N—.

In one embodiment, in Formula (I), A is a 5-membered ring and E is —C($R^7$)=N—.

In one embodiment, in Formula (I), ring A is a 6-membered ring and E is —C($R^4$)($R^8$)—.

In one embodiment, in Formula (I), ring A is a 6-membered ring and E is selected from the group consisting of —O—, —S—, —S(O)—, —S(O)$_2$—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N=N—, —C($R^7$)=N—, —C(O)—C($R^7$)=N—, —C(O)—N=N—, —O—C(Y)—N($R^{11}$)—, —N($R^{11}$)—C(Y)—O—, —N($R^{11}$)—C(Y)—N($R^{12}$)—, —C(Y)—N($R^{11}$)—O—, —C(Y)—N($R^{11}$)—N($R^{12}$)—, and —N($R^{12}$)—N($R^{11}$)—C(Y)—.

In one embodiment, in Formula (I), ring A is a 6-membered ring and E is selected from the group consisting of —O—, —S—, —S(O)—, —S(O)$_2$—, and —N($R^6$)—.

In one embodiment, in Formula (I), ring A is a 6-membered ring and E is selected from the group consisting of —O—, —S—, —S(O)—, —S(O)$_2$—, and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), ring A is a 6-membered ring and E is selected from the group consisting of —O— and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), ring A is a 6-membered ring and E is selected from the group consisting of —O—, —S—, —S(O)—, —S(O)$_2$—, —C($R^4$)($R^5$)—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)2-, —C(O)—O—, —O—C(O)—, —O—N(R6)-, —N(R6)-O—, —N(R6)-N(R12)-, —N=N—, —C(R7)=N—, —C(O)—C(R7)=N—, —C(O)—N=N—, —O—C(Y)—N($R^{11}$)—, —N($R^{11}$)—C(Y)—O—, —N($R^{11}$)—C(Y)—N($R^{12}$)—, —C(Y)—N ($R^{11}$)—O—, —C(Y)—N($R^{11}$)—N($R^{12}$)—, —O—N($R^{11}$)—C(Y)—, and —N($R^{12}$)—N($R^{11}$)—C(Y)—.

In one embodiment, in Formula (I), ring A is a 6-membered ring and E is —O—.

In one embodiment, in Formula (I), ring A is a 6-membered ring and E is —S—.

In one embodiment, in Formula (I), ring A is a 6-membered ring and E is —S(O)—.

In one embodiment, in Formula (I), ring A is a 6-membered ring and E is —S(O)$_2$—.

In one embodiment, in Formula (I), ring A is a 6-membered ring and E is —C($R^4$)($R^5$)—.

In one embodiment, in Formula (I), ring A is a 6-membered ring and E is —N($R^6$)—.

In one embodiment, in Formula (I), ring A is a 6-membered ring and E is —N(C(Y)$R^7$)—.

In one embodiment, in Formula (I), ring A is a 6-membered ring and E is —N(C(Y)O$R^8$)—.

In one embodiment, in Formula (I), ring A is a 6-membered ring and E is —N(C(Y)N($R^9$)($R^{10}$))—.

In one embodiment, in Formula (I), ring A is a 6-membered ring and E is —C(O)—N($R^{11}$)—.

In one embodiment, in Formula (I), ring A is a 6-membered ring and E is —N($R^{11}$)—C(O)—.

In one embodiment, in Formula (I), ring A is a 6 membered ring and E is —S(O)$_2$—N($R^{11}$)—.

In one embodiment, in Formula (I), ring A is a 6-membered ring and E is —N($R^{11}$)—S(O)$_2$—.

In one embodiment, in Formula (I), ring A is a 6-membered ring and E is —C(O)—O—.

In one embodiment, in Formula (I), ring A is a 6-membered ring and E is —O—C(O)—.

In one embodiment, in Formula (I), ring A is a 6-membered ring and E is —O—N($R^6$)—.

In one embodiment, in Formula (I), ring A is a 6-membered ring and E is —N($R^6$)—O—.

In one embodiment, in Formula (I), ring A is a 6-membered ring and E is —N(R6)-N(R12)-.

In one embodiment, in Formula (I), ring A is a 6-membered ring and E is —N=N—.

In one embodiment, in Formula (I), ring A is a 6-membered ring and E is —C(R7)=N—.

In one embodiment, in Formula (I), ring A is a 6-membered ring and E is —C(O)—C(R7)=N—.

In one embodiment, in Formula (I), ring A is a 6-membered ring and E is —C(O)—N=N—.

In one embodiment, in Formula (I), ring A is a 6-membered ring and E is —O—C(Y)—N($R^{11}$)—.

In one embodiment, in Formula (I), ring A is a 6-membered ring and E is —N($R^{11}$)—C(Y)—O—.

In one embodiment, in Formula (I), ring A is a 6-membered ring and E is —N($R^{11}$)—C(Y)—N($R^{12}$)—.

In one embodiment, in Formula (I), ring A is a 6-membered ring and E is —C(Y)—N($R^{11}$)—O—.

In one embodiment, in Formula (I), ring A is a 6-membered ring and E is —C(Y)—N($R^{11}$)—N($R^{12}$)—.

In one embodiment, in Formula (I), ring A is a 6-membered ring and E is —O—N($R^{11}$)—C(Y)—.

In one embodiment, in Formula (I), ring A is a 6-membered ring and E is —N($R^{12}$)—N($R^{11}$)—C(Y)—.

In one embodiment, in Formula (I), ring A is a 7-membered ring and E is —C($R^4$)($R^5$)—.

In one embodiment, in Formula (I), ring A is a 7-membered ring and E is selected from the group consisting of —O—, —S—, —S(O)—, —S(O)$_2$—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N=N—, —C($R^7$)=N—, —C(O)—C($R^7$)=N—, —C(O)—N=N—, —O—C(Y)—N($R^{11}$)—, —N($R^{11}$)—C(Y)—O—, —N($R^{11}$)—C(Y)—N($R^{12}$)—, —C(Y)—N($R^{11}$)—O—, —C(Y)—N($R^{11}$)—N($R^{12}$)—, —O—N($R^{11}$)—C(Y)—, and —N($R^{12}$)—N($R^{11}$)—C(Y)—.

In one embodiment, in Formula (I), ring A is a 7-membered ring and E is selected from the group consisting of —O—, —S—, —S(O)—, —S(O)$_2$—, and —N($R^6$)—.

In one embodiment, in Formula (I), ring A is a 7-membered ring and E is selected from the group consisting of —O—, —S—, —S(O)—, —S(O)$_2$—, and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), ring A is a 7-membered ring and E is selected from the group consisting of —O— and —N($R^6$)—, wherein $R^6$ is selected from the group consisting of H, alkyl, —C(O)$R^{24}$, —C(O)O$R^{20}$, and —C(S)$R^{24}$.

In one embodiment, in Formula (I), ring A is a 7-membered ring and E is selected from the group consisting of —O—, —S—, —S(O)—, —S(O)$_2$—, —C($R^4$)($R^5$)—, —N($R^6$)—, —N(C(Y)$R^7$)—, —N(C(Y)OR8)-, —N(C(Y)N(R9)(R10))-, —C(O)—N(R11)-, —N(R11)-C(O)—, —S(O)2-N(R11)—, —N(R11)—S(O)2-, —C(O)—O—, —O—C(O)—, —O—N(R6)-, —N(R6)-O—, —N(R6)-N(R12)-, —N=N—, —C(R7)=N—, —C(O)—C(R7)=N—, —C(O)—N=N—, —O—C(Y)—N(R11)-, —N(R11)-C(Y)—O—, —N(R11)-C(Y)—N(R12)-, —C(Y)—N(R11)-O—, —C(Y)—N(R11)-N(R12)-, —O—N(R11)-C(Y)—, and —N(R12)-N(R11)-C(Y)—.

In one embodiment, in Formula (I), A is a 7-membered ring and E is —O—.

In one embodiment, in Formula (I), A is a 7-membered ring and E is —S—.

In one embodiment, in Formula (I), A is a 7-membered ring and E is —S(O)—.

In one embodiment, in Formula (I), A is a 7-membered ring and E is —S(O)$_2$—.

In one embodiment, in Formula (I), A is a 7-membered ring and E is —C($R^4$)($R^5$)—.

In one embodiment, in Formula (I), A is a 7-membered ring and E is —N($R^6$)—.

In one embodiment, in Formula (I), A is a 7-membered ring and E is —N(C(Y)$R^7$)—.

In one embodiment, in Formula (I), A is a 7-membered ring and E is —N(C(Y)O$R^8$)—.

In one embodiment, in Formula (I), A is a 7-membered ring and E is —N(C(Y)N($R^9$)($R^{10}$))—.

In one embodiment, in Formula (I), A is a 7-membered ring and E is —C(O)—N($R^{11}$)—.

In one embodiment, in Formula (I), A is a 7-membered ring and E is —N($R^{11}$)—C(O)—.

In one embodiment, in Formula (I), A is a 7-membered ring and E is —S(O)$_2$—N($R^{11}$)—.

In one embodiment, in Formula (I), A is a 7-membered ring and E is —N($R^{11}$)—S(O)$_2$—.

In one embodiment, in Formula (I), A is a 7-membered ring and E is —C(O)—O—.

In one embodiment, in Formula (I), A is a 7-membered ring and E is —O—C(O)—.

In one embodiment, in Formula (I), A is a 7-membered ring and E is —O—N($R^6$)—.

In one embodiment, in Formula (I), A is a 7-membered ring and E is —N($R^6$)—O—.

In one embodiment, in Formula (I), A is a 7-membered ring and E is —N($R^6$)—N($R^{12}$)—.

In one embodiment, in Formula (I), A is a 7-membered ring and E is —N=N—.

In one embodiment, in Formula (I), A is a 7-membered ring and E is —C(R$^7$)=N—.

In one embodiment, in Formula (I), A is a 7-membered ring and E is —C(O)—C(R$^7$)=N—.

In one embodiment, in Formula (I), A is a 7-membered ring and E is —C(O)—N=N—.

In one embodiment, in Formula (I), A is a 7-membered ring and E is —O—C(Y)—N(R$^{11}$)—.

In one embodiment, in Formula (I), A is a 7-membered ring and E is —N(R$^{11}$)—C(Y)—O—.

In one embodiment, in Formula (I), A is a 7-membered ring and E is —N(R$^{11}$)—C(Y)—N(R$^{12}$)—.

In one embodiment, in Formula (I), A is a 7-membered ring and E is —C(Y)—N(R$^{11}$)—O—.

In one embodiment, in Formula (I), A is a 7-membered ring and E is —C(Y)—N(R$^{11}$)—N(R$^{12}$)—.

In one embodiment, in Formula (I), A is a 7-membered ring and E is —O—N(R$^{11}$)—C(Y)—.

In one embodiment, in Formula (I), A is a 7-membered ring and E is —N(R$^{12}$)—N(R$^{11}$)—C(Y)—.

In one embodiment, in Formula (I), ring A is a 8-membered ring and E is —C(R$^4$)(R$^5$)—.

In one embodiment, in Formula (I), ring A is a 8-membered ring and E is selected from the group consisting of —O—, —S—, —S(O)—, —S(O)$_2$—, —N(R$^6$)—, —N(C(Y)R$^7$)—, —N(C(Y)OR$^8$)—, —N(C(Y)N(R$^9$)(R$^{10}$))—, —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^6$)—O—, —N(R$^6$)—N(R$^{12}$)—, —N=N—, —C(R$^7$)=N—, —C(O)—C(R$^7$)=N—, —C(O)—N=N—, —O—C(Y)—N(R$^{11}$)—, —N(R$^{11}$)—C(Y)—O—, —N(R$^{11}$)—C(Y)—N(R$^{12}$)—, —C(Y)—N(R$^{11}$)—O—, —C(Y)—N(R$^{11}$)—N(R$^{12}$)—C(Y)—, and —N(R$^{12}$)—N(R$^{11}$)—C(Y)—.

In one embodiment, in Formula (I), ring A is a 8-membered ring and E is selected from the group consisting of —O—, —S—, —S(O)—, —S(O)$_2$—, and —N(R$^6$)—.

In one embodiment, in Formula (I), ring A is a 8-membered ring and E is selected from the group consisting of —O—, —S—, —S(O)—, —S(O)$_2$—, and —N(R$^6$)—, wherein R$^6$ is selected from the group consisting of H, alkyl, —C(O)R$^{24}$, —C(O)OR$^{20}$, and —C(S)R$^{24}$.

In one embodiment, in Formula (I), ring A is a 8-membered ring and E is selected from the group consisting of —O— and —N(R$^6$)—, wherein R$^6$ is selected from the group consisting of H, alkyl, —C(O)R$^{24}$, —C(O)OR$^{20}$, and —C(S)R$^{24}$.

In one embodiment, in Formula (I), ring A is a 8-membered ring and E is selected from the group consisting of —O—, —S—, —S(O)—, —S(O)$_2$—, —C(R$^4$)(R$^5$)—, —N(R$^6$)—, —N(C(Y)R$^7$)—, —N(C(Y)OR$^8$)—, —N(C(Y)N(R$^9$)(R$^{10}$))—, —C(O)—N(R$^{11}$)—, —N(R$^{11}$)—C(O)—, —S(O)$_2$—N(R$^{11}$)—, —N(R$^{10}$)—S(O)$_2$—, —C(O)—O—, —O—C(O)—, —O—N(R$^6$)—, —N(R$^6$)—O—, —N(R$^6$)—N(R$^{12}$)—, —N=N—, —C(R$^7$)=N—, —C(O)—C(R$^7$)=N—, —C(O)—N=N—, —O—C(Y)—N(R$^{11}$)—, —N(R$^{11}$)—C(Y)—O—, —N(R$^{11}$)—C(Y)—N(R$^{12}$)—, —C(Y)—N(R$^{11}$)—O—, —C(Y)—N(R$^{11}$)—N(R$^{12}$)—, —O—N(R$^{11}$)—C(Y)—, and —N(R$^{12}$)—N(R$^{11}$)—C(Y)—.

In one embodiment, in Formula (I), A is a 8-membered ring and E is —O—.

In one embodiment, in Formula (I), A is a 8-membered ring and E is —S—.

In one embodiment, in Formula (I), A is a 8-membered ring and E is —S(O)—.

In one embodiment, in Formula (I), A is a 8-membered ring and E is —S(O)$_2$—.

In one embodiment, in Formula (I), A is a 8-membered ring and E is —C(R$^4$)(R$^5$)—.

In one embodiment, in Formula (I), A is a 8-membered ring and E is —N(R$^6$)—.

In one embodiment, in Formula (I), A is a 8-membered ring and E is —N(C(Y)R$^7$)—.

In one embodiment, in Formula (I), A is a 8-membered ring and E is —N(C(Y)OR$^8$)—.

In one embodiment, in Formula (I), A is a 8-membered ring and E is —N(C(Y)N(R$^9$)(R$^{10}$))—.

In one embodiment, in Formula (I), A is a 8-membered ring and E is —C(O)—N(R$^{11}$)—.

In one embodiment, in Formula (I), A is a 8-membered ring and E is —N(R$^{11}$)—C(O)—.

In one embodiment, in Formula (I), A is a 8-membered ring and E is —S(O)$_2$—N(R$^{11}$)—.

In one embodiment, in Formula (I), A is a 8-membered ring and E is —N(R$^{11}$)—S(O)$_2$—.

In one embodiment, in Formula (I), A is a 8-membered ring and E is —C(O)—O—.

In one embodiment, in Formula (I), A is a 8-membered ring and E is —O—C(O)—.

In one embodiment, in Formula (I), A is a 8-membered ring and E is —O—N(R$^6$)—.

In one embodiment, in Formula (I), A is a 8-membered ring and E is —N(R$^8$)—O—.

In one embodiment, in Formula (I), A is a 8-membered ring and E is —N(R$^6$)—N(R$^{12}$)—.

In one embodiment, in Formula (I), A is a 8-membered ring and E is —N=N—.

In one embodiment, in Formula (I), A is a 8-membered ring and E is —C(R$^7$)=N—.

In one embodiment, in Formula (I), A is a 8-membered ring and E is —C(O)—C(R$^7$)=N—.

In one embodiment, in Formula (I), A is a 8-membered ring and E is —C(O)—N=N—.

In one embodiment, in Formula (I), A is a 8-membered ring and E is —O—C(Y)—N(R$^{11}$)—.

In one embodiment, in Formula (I), A is a 8-membered ring and E is —N(R$^{11}$)—C(Y)—O—.

In one embodiment, in Formula (I), A is a 8-membered ring and E is —N(R$^{11}$)—C(Y)—N(R$^{12}$)—.

In one embodiment, in Formula (I), A is a 8-membered ring and E is —C(Y)—N(R$^{11}$)—O—.

In one embodiment, in Formula (I), A is a 8-membered ring and E is —C(Y)—N(R$^{11}$)—N(R$^{12}$)—.

In one embodiment, in Formula (I), A is a 8-membered ring and E is —O—N(R$^{11}$)—C(Y)—.

In one embodiment, in Formula (I), A is a 8-membered ring and E is —N(R$^{12}$)—N(R$^{11}$)—C(Y)—.

In one embodiment, in Formula (I), ring B is an unsubstituted or substituted benzo or an unsubstituted or substituted thiophenyl ring.

In one embodiment, in Formula (I), ring B is an unsubstituted benzo or an unsubstituted thiophenyl ring.

In one embodiment, in Formula (I), ring B is an unsubstituted aromatic ring or an aromatic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (I), ring B is an unsubstituted benzo ring or a benzo ring which is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (I), ring B is an unsubstituted or substituted heteroaromatic ring or a substituted heteroaromatic ring which is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$. In one such embodiment, in Formula (I), ring B is a 5-6-membered heteroaromatic ring having from 1-3 ring heteroatoms, which can be the same or different, each hetero ring atom being independently selected from the group consisting of N, S, O, S(O), and $S(O)_2$.

In one embodiment, in Formula (I), ring B is an unsubstituted or substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl.

In one embodiment, in Formula (I), ring B is an unsubstituted aromatic ring.

In one embodiment, in Formula (I), ring B is an unsubstituted benzo ring, and Formula (I) has the general structure:

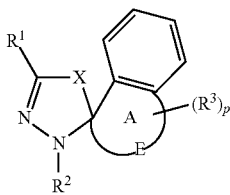

In one embodiment, in Formula (I), B is an aromatic ring which is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (I), B is a benzo ring which is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (I), B is an unsubstituted heteroaromatic ring.

In one embodiment, in Formula (I), B is an unsubstituted 5-6-membered heteroaromatic ring having from 1-3 ring heteroatoms, which can be the same or different, each hetero ring atom being independently selected from the group consisting of N, S, O, S(O), and $S(O)_2$.

In one embodiment, in Formula (I), B is a heteroaromatic ring which is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (I), B is a 5-6-membered heteroaromatic ring having from 1-3 ring heteroatoms, which can be the same or different, each hetero ring atom being independently selected from the group consisting of N, S, O, S(O), and $S(O)_2$, which heteroaromatic ring is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (I), B is an unsubstituted 6-membered heteroaromatic ring having from 1-3 ring heteroatoms, which can be the same or different, each hetero ring atom being independently selected from the group consisting of N, S, and O.

In one embodiment, in Formula (I), B is a 6-membered heteroaromatic ring having from 1-3 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)$ OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), B is an unsubstituted 6-membered heteroaromatic ring having 2 ring heteroatoms, each ring heteroatom being independently selected from of N, S, and O.

In one embodiment, in Formula (I), B is a 6-membered heteroaromatic ring having 2 ring heteroatoms, each ring heteroatom being independently selected from of N, S, and O, which heteroaromatic ring is substituted with one or more substituents, which can be the same or different, each substituent being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), B is an unsubstituted 5-membered heteroaromatic ring having from 1-2 ring heteroatoms, which can be the same or different, each hetero ring atom being independently selected from the group consisting of N, S, and O.

In one embodiment, in Formula (I), B is a 5-membered heteroaromatic ring having from 1-2 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)R²⁴, —SO₂NR²⁵R²⁶, —C(O)R²⁴, —C(O)OR²⁰, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), B is an unsubstituted 5-membered heteroaromatic ring having 1 ring heteroatom selected from of N, S, and O.

In one embodiment, in Formula (I), B is a 5-membered heteroaromatic ring having 1 ring heteroatom selected from of N, S, and O, which heteroaromatic ring is substituted with one or more substituents, which can be the same or different, each substituent being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), B is a 5-membered heteroaromatic ring having S as the ring heteroatom, which heteroaromatic ring is substituted with one or more substituents, which can be the same or different, each substituent being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), B is an unsubstituted 5-membered heteroaromatic ring having S as the ring heteroatom.

In one embodiment, in Formula (I), B is a thiophenyl group.

In one embodiment, in Formula (I), B is selected from the group consisting of

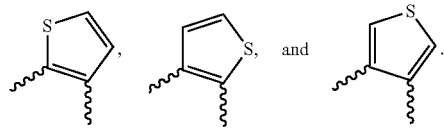

In one embodiment, in Formula (I), B is a pyridine.

In one embodiment, in Formula (I), B is a partially unsaturated alicyclic ring, which ring is unsubstituted.

In one embodiment, in Formula (I), B is a partially unsaturated alicyclic ring which is substituted with one or more substituents, which can be the same or different, each substituent being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), B is a partially unsaturated heterocyclic ring, which ring is unsubstituted.

In one embodiment, in Formula (I), B is a partially unsaturated heterocyclic ring which is substituted with one or more substituents, which can be the same or different, each substituent being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁵, —NR²³C(N—CN)NR²⁵R²⁶ and —NR²³C(O)NR²⁵R²⁶.

In one embodiment, in Formula (I), R¹ is unsubstituted aryl or aryl substituted with one or more substituents, which can be the same or different, each substituent being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), R¹ is phenyl substituted with one to four substituents, which can be the same or different, each substituent being independently selected from the group consisting of halo, —OH, —CN, —NO$_2$, —NR$^{21}$R$^{22}$, and haloalkyl.

In one embodiment, in Formula (I), R$^1$ is unsubstituted aryl.

In one embodiment, in Formula (I), R$^1$ is unsubstituted phenyl.

In one embodiment, in Formula (I), R$^1$ is unsubstituted naphthyl.

In one embodiment, in Formula (I), R$^1$ is substituted aryl.

In one embodiment, in Formula (I), R$^1$ is substituted phenyl.

In one embodiment, in Formula (I), R$^1$ is substituted naphthyl.

In one embodiment, in Formula (I), R$^1$ is aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N=CN)NR$^{25}$R$^{26}$ and —NR$^{23}$C(O)NR$^{25}$R$^{26}$.

In one embodiment, in Formula (I), R$^1$ is phenyl substituted with one or more substituents, which can be the same or different, each substituent being independently selected from the group consisting halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N=CN)NR$^{25}$R$^{26}$ and —NR$^{23}$C(O)NR$^{25}$R$^{26}$.

In one embodiment, in Formula (I), R$^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In one embodiment, in Formula (I), R$^1$ is selected from the group consisting of:

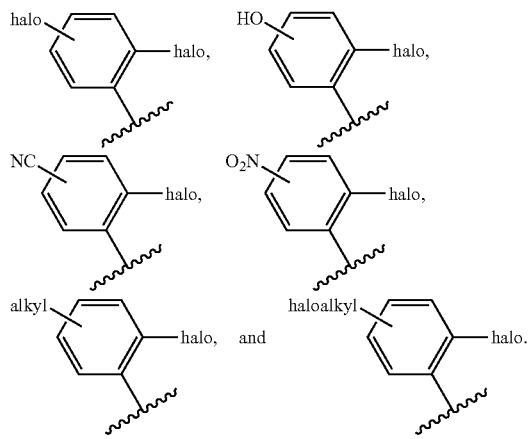

In one embodiment, in Formula (I), R$^1$ is:

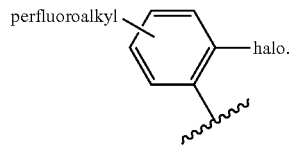

In one embodiment, in Formula (I), R$^1$ is phenyl substituted with one to three fluoro groups.

In one embodiment, in Formula (I), R$^1$ is phenyl substituted with two fluoro groups.

In one embodiment, in Formula (I), R$^1$ is phenyl substituted with one fluoro group.

In one embodiment, in Formula (I), R$^1$ is:

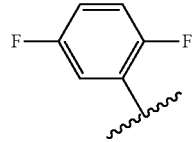

In one embodiment, in Formula (I), R$^2$ is selected from the group consisting of —C(O)R$^7$, —C(O)NR$^9$R$^{10}$, and —C(O)OR$^8$.

In one embodiment, in Formula (I), R$^2$ is —C(Z)R$^7$.
In one embodiment, in Formula (I), R$^2$ is —C(Z)NR$^9$R$^{10}$.
In one embodiment, in Formula (I), R$^2$ is —C(Z)OR$^8$.
In one embodiment, in Formula (I), R$^2$ is —SO$_2$NR$^9$R$^{10}$.
In one embodiment, in Formula (I), R$^2$ is alkyl.
In one embodiment, in Formula (I), R$^2$ is heteroalkyl.
In one embodiment, in Formula (I), R$^2$ is aryl.
In one embodiment, in Formula (I), R$^2$ is heteroaryl.
In one embodiment, in Formula (I), R$^2$ is cycloalkyl.
In one embodiment, in Formula (I), R$^2$ is cycloalkenyl.
In one embodiment, in Formula (I), R$^2$ is heterocycloalkyl.
In one embodiment, in Formula (I), R$^2$ is heterocycloalkenyl.
In one embodiment, in Formula (I), Z is (=O).
In one embodiment, in Formula (I), Z is (=S).
In one embodiment, in Formula (I), Z is (=N(R$^{13}$)).
In one embodiment, in Formula (I), Z is (=N(CN)).
In one embodiment, in Formula (I), Z is (=N(OR$^{14}$)).
In one embodiment, in Formula (I), Z is (=N(R$^{15}$)(R$^{16}$)).
In one embodiment, in Formula (I), Z is (=C(R$^{17}$)(R$^{18}$)).
In one embodiment, in Formula (I), R$^2$ is —C(Z)R$^7$, and Z is (=O).
In one embodiment, in Formula (I), R$^2$ is —C(O)H.
In one embodiment, in Formula (I), R$^2$ is —C(O)alkyl.
In one embodiment, in Formula (I), R$^2$ is —C(O)CH$_3$.

In one embodiment, in Formula (I), R$^2$ is —C(O)R$^7$, wherein said R$^7$ is alkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, OC(O)R$^{24}$, —C(O)NR$^{25}$R$^{26}$, —NR$^{23}$C(N=CN)NR$^{25}$R$^{26}$ and —NR$^{23}$C(O)NR$^{25}$R$^{26}$.

In one embodiment, in Formula (I), R$^2$ is —C(O)R$^7$, wherein said R$^7$ is alkyl substituted with one to three substituents, which can be the same or different, each substituent being independently selected from the group consisting of —OR$^{19}$, —NR$^{21}$R$^{22}$, and cycloalkyl.

In one embodiment, in Formula (I), R$^2$ is —C(O)R$^7$, wherein said R$^7$ is alkyl, wherein said alkyl is substituted with alkyl and —OH.

In one embodiment, in Formula (I), R$^2$ is —C(O)R$^7$, wherein said R$^7$ is alkyl substituted with one to three substituents, which can be the same or different, each substituent being independently selected from the group consisting of —OH, —NH$_2$, and cyclopropyl.

In one embodiment, in Formula (I), R$^2$ is —C(O)R$^7$, wherein said R$^7$ is alkyl substituted with one to two substituents, which can be the same or different, each substituent being independently selected from the group consisting of —NH$_2$, and cyclopropyl.

In one embodiment, in Formula (I), R$^2$ is —C(O)R$^7$, wherein said R$^7$ is alkyl substituted with —OH.

In one embodiment, in Formula (I), R$^2$ is —C(O)R$^7$, wherein said R$^7$ is unsubstituted heterocycloalkyl.

In one embodiment, in Formula (I), R$^2$ is —C(O)R$^7$, wherein said R$^7$ is substituted heterocycloalkyl.

In one embodiment, in Formula (I), R$^2$ is —C(O)R$^7$, wherein said R$^7$ is heterocycloalkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (I), R$^2$ is —C(O)R$^7$, wherein said R$^7$ is selected from the group consisting of substituted piperidine, substituted piperazine, substituted morpholine, substituted pyrrolidine, and substituted azetidine.

In one embodiment, in Formula (I), R$^2$ is a moiety selected from the group consisting of:

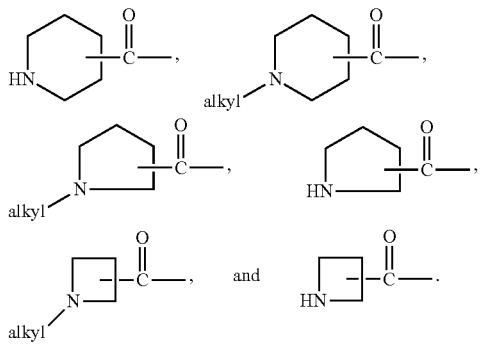

In one embodiment, in Formula (I), R$^2$ is —C(O)NR$^9$R$^{10}$.
In one embodiment, in Formula (I), R$^2$ is —C(O)NH$_2$.
In one embodiment, in Formula (I), R$^2$ is —C(O)NR$^9$R$^{10}$, wherein R$^9$ and R$^{10}$ can be the same or different, each being independently selected from alkyl.
In one embodiment, in Formula (I), R$^2$ is —C(O)NR$^9$R$^{10}$, wherein R$^9$ is unsubstituted heterocycloalkyl and R$^{10}$ is selected from the group consisting of H and alkyl.
In one embodiment, in Formula (I), R$^2$ is —C(O)NR$^9$R$^{10}$, wherein R$^9$ is substituted heterocycloalkyl and R$^{10}$ is selected from the group consisting of H and alkyl.

In one embodiment, in Formula (I), R$^2$ is —C(O)NR$^9$R$^{10}$, wherein R$^9$ is heterocycloalkyl substituted with from one to three substituents, which can be the same or different, each substituent being independently selected from alkyl, and R$^{10}$ is selected from the group consisting of H and alkyl.

In one embodiment, in Formula (I), R$^2$ is selected from the group consisting of: alkyl, haloalkyl, heteroalkyl, heterohaloalkyl, —C(O)R$^7$, —C(O)OR$^9$, and —C(O)NR$^9$R$^{10}$.

Non-limiting examples of R$^2$ include the following moieties:

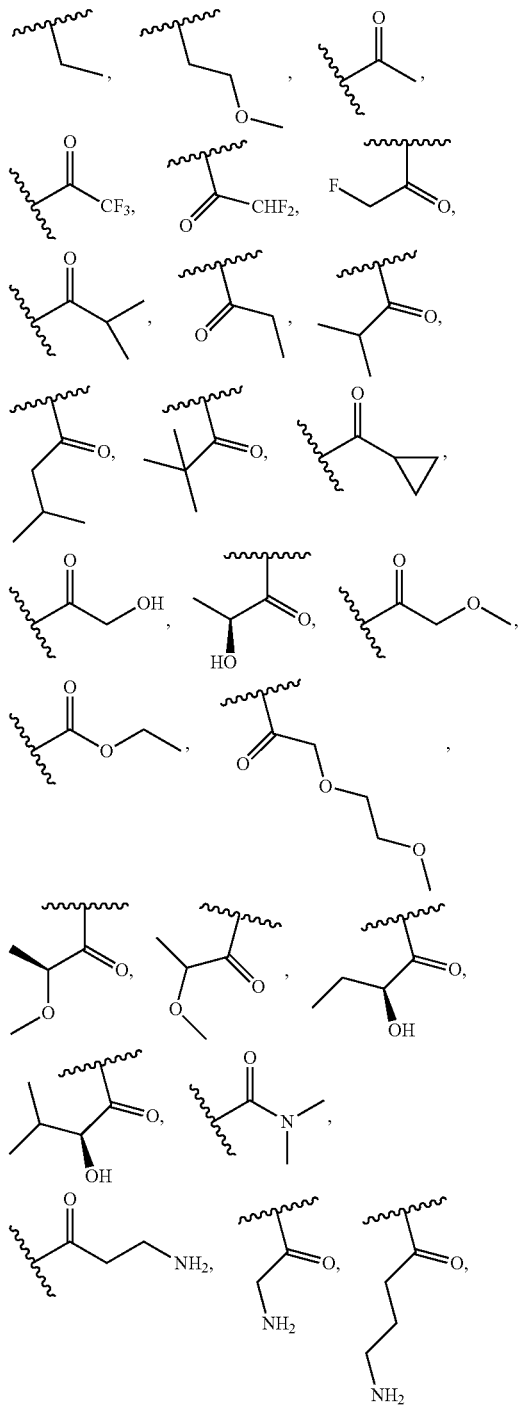

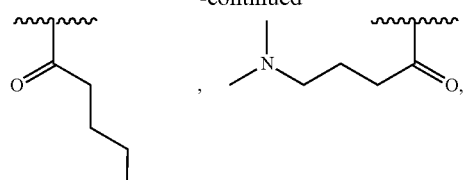
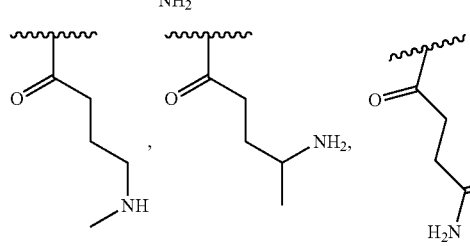
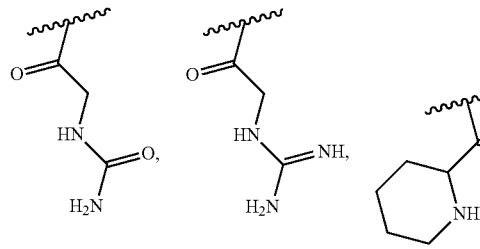
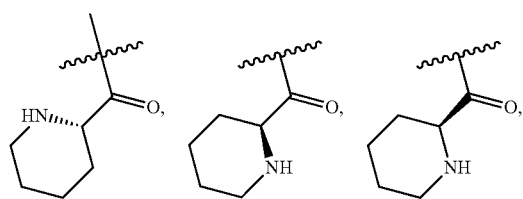
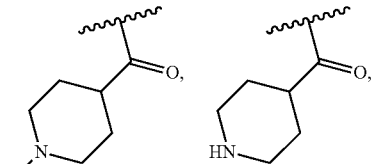
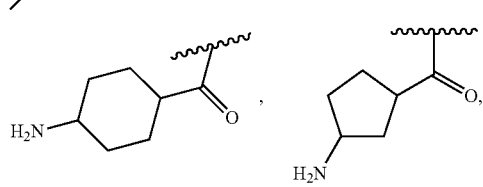
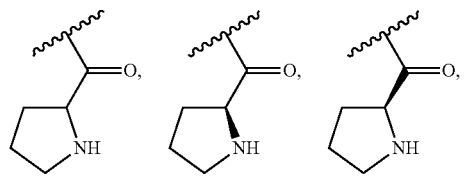
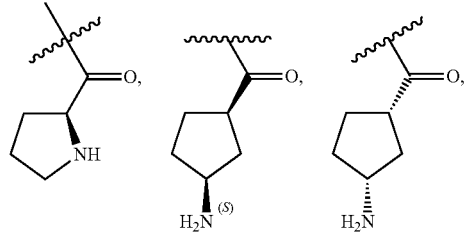
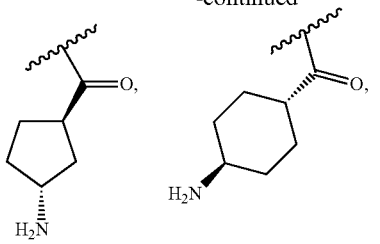
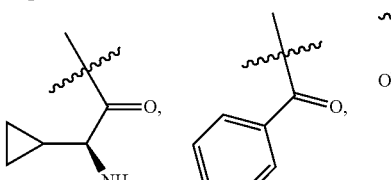
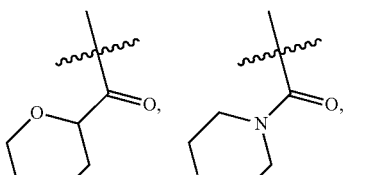
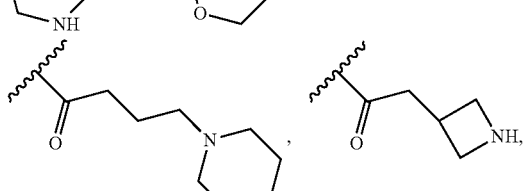
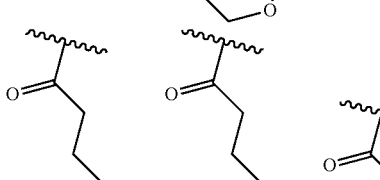
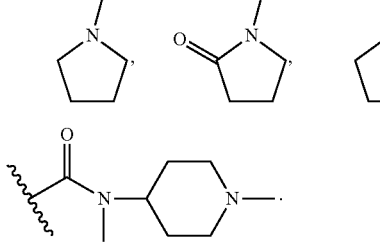
and
In one embodiment, in Formula (I), $R^2$ is
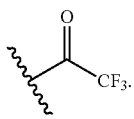
In one embodiment, in Formula (I), $R^2$ is
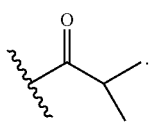 [SMILES: *C(=O)C(C)C]

In one embodiment, in Formula (I), R² is

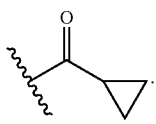

In one embodiment, in Formula (I), R² is

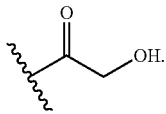 [SMILES: *C(=O)CO]

In one embodiment, in Formula (I), R² is

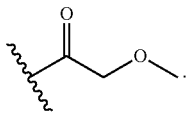 [SMILES: *C(=O)COC]

In one embodiment, in Formula (I), R² is

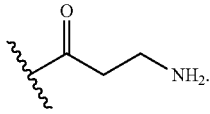 [SMILES: *C(=O)CCN]

In one embodiment, in Formula (I), R² is

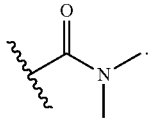

In one embodiment, in Formula (I), R² is

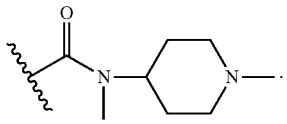

In one embodiment, in Formula (I), p is 0 and R³ is not present.
In one embodiment, in Formula (I), p is 1.
In one embodiment, in Formula (I), p is 2.
In one embodiment, in Formula (I), p is 3.
In one embodiment, in Formula (I), p is 4.
In one embodiment, in Formula (I), p is 2, 3, or 4, and at least two groups R³ are attached to the same ring atom.
In one embodiment, in Formula (I), p is 1, 2, 3, or 4 and each R³ is independently selected from the group consisting of alkyl, heteroalkyl, alkenyl, heteroalkenyl, —CN, —NO₂, —OR¹⁹, —OC(O)OR²⁰, —NR²¹R²², —C(O)R²⁴, —C(S) OR²⁴, —C(O)OR²⁰, and —C(O)NR²⁵R²⁶,
wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO₂, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), p is 1 and R³ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), p is 2, 3, or 4 and each R³ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), p is 2, 3, or 4 and at least two groups R³ are bound to the same ring carbon atom, wherein each R³, which may be the same or different, is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (I), p is 2, 3, or 4 and at least two groups R³ are bound to the same ring carbon atom, wherein two R³ groups, which may be the same or different, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S.

In one embodiment, in Formula (I), each R³ (when present) is independently selected from the group consisting of alkyl, heteroalkyl, alkenyl, heteroalkenyl, —CN, —NO₂, —OR¹⁹, —OC(O)OR²⁰, —NR², R²², —NR²³SO₂R²⁴, —NR²³C(O)OR²⁰, —NR²³C(O)R²⁴, —SO₂NR²⁵R²⁶, —C(O)R²⁴, —C(S)R²⁴, —C(O)OR²⁰, —SR¹⁹, —S(O)R¹⁹, R²⁶, —SO₂R¹⁹, —OC(O)R²⁴, —C(O)NR²⁵R²⁶, —NR²³C(N—CN)NR²⁵R²⁶, —NR²³C(O)NR²⁵ and —NR²³—C(NH)—NR²⁵R²⁶, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N$—$CN)NR^{25}R^{26}$ and —$NR^{23}C(O)NR^{25}R^{26}$.

In one embodiment, in Formula (I), each $R^3$ (when present) is independently selected from the group consisting of alkyl, heteroalkyl, alkenyl, heteroalkenyl, —CN, —$NO_2$, —$OR^{19}$, —$OC(O)OR^{20}$, —$NR^{21}R^{22}$, $C(O)R^{24}$, —$C(S)R^{24}$, —$C(O)OR^{20}$, and —$C(O)NR^{25}R^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N$—$CN)NR^{25}R^{26}$ and —$NR^{23}C(O)NR^{25}R^{26}$.

In one embodiment, in Formula (I), p is 1 and $R^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N$—$CN)NR^{25}R^{26}$ and —$NR^{23}C(O)NR^{25}R^{26}$.

In one embodiment, in Formula (I), p is 2, 3, or 4, and any two $R^3$ groups bound to the same ring A atom are taken together with the carbon atom to which they are attached to form a spirocycloalkyl, a spirocycloalkenyl, a spiroheterocycloalkyl ring containing from one to three ring heteroatoms independently selected from the group consisting of —NH—, —$NR^6$—, —S—, —S(O)—, —$S(O)_2$—, and —O—, or a spiroheterocycloalkenyl ring containing from one to three ring heteroatoms independently selected from the group consisting of —NH—, —$NR^6$—, —S—, —S(O)—, —$S(O)_2$—, and —O—. Non-limiting examples of compounds of the invention in which two $R^3$ groups are thus taken together include:

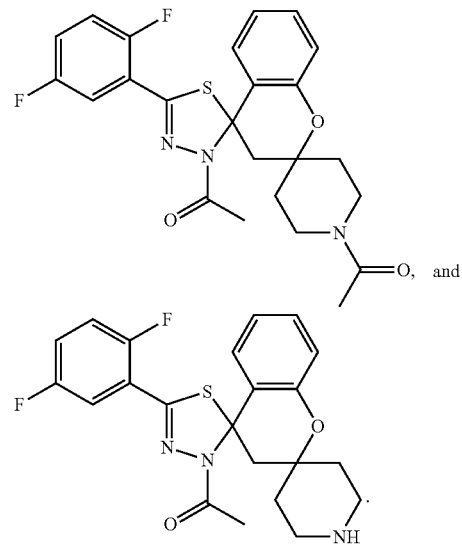

In one embodiment, in Formula (I), $R^2$ and $R^3$ are taken together with the carbon atom to which they are attached to form a cycloalkyl, a cycloalkenyl, a heterocycloalkyl ring containing from one to three ring heteroatoms independently selected from the group consisting of —NH—, —$NR^6$—, —S—, —S(O)—, —$S(O)_2$—, and —O—, or a hetercioycloalkenyl ring containing from one to three ring heteroatoms independently selected from the group consisting of —NH—, —$NR^6$—, —S—, —S(O)—, —$S(O)_2$—, and —O—. Non-limiting examples of a compound of the invention in which $R^2$ and $R^3$ are thus taken together include the following compound:

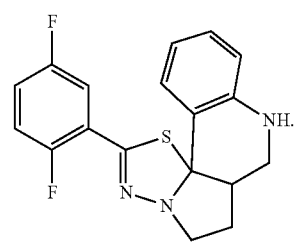 [SMILES: Fc1ccc(F)c(C2=NN3CCC4CNc5ccccc5C43S2)c1]

In one embodiment, in Formula (I), $R^3$ is alkyl.
In one embodiment, in Formula (I), $R^3$ is heteroalkyl.
In one embodiment, in Formula (I), $R^3$ is alkenyl.
In one embodiment, in Formula (I), $R^3$ is heteroalkenyl.
In one embodiment, in Formula (I), $R^3$ is alkynyl.
In one embodiment, in Formula (I), $R^3$ is heteroalkynyl.
In one embodiment, in Formula (I), $R^3$ is aryl.
In one embodiment, in Formula (I), $R^3$ is heteroaryl.
In one embodiment, in Formula (I), $R^3$ is cycloalkyl.
In one embodiment, in Formula (I), $R^3$ is cycloalkenyl.
In one embodiment, in Formula (I), $R^3$ is heterocycloalkyl.
In one embodiment, in Formula (I), $R^3$ is heterocycloalkenyl.
In one embodiment, in Formula (I), $R^3$ is halogen.
In one embodiment, in Formula (I), $R^3$ is —CN.
In one embodiment, in Formula (I), $R^3$ is —$NO_2$.
In one embodiment, in Formula (I), $R^3$ is —$OR^{19}$.
In one embodiment, in Formula (I), $R^3$ is —$OC(O)OR^{20}$.
In one embodiment, in Formula (I), $R^3$ is —$NR^{21}R^{22}$, In one embodiment, in Formula (I), $R^3$ is $-NR^{23}SO_2R^{24}$.

In one embodiment, in Formula (I), $R^3$ is $-NR^{23}C(O)OR^{20}$.

In one embodiment, in Formula (I), $R^3$ is $-NR^{23}C(O)R^{24}R^{26}$.

In one embodiment, in Formula (I), $R^3$ is $-SO_2NR^{25}$.

In one embodiment, in Formula (I), $R^3$ is $-C(O)R^{24}$.

In one embodiment, in Formula (I), $R^3$ is $-C(S)R^{24}$.

In one embodiment, in Formula (I), $R^3$ is $-C(O)OR^{20}$.

In one embodiment, in Formula (I), $R^3$ is $-SR^{13}$.

In one embodiment, in Formula (I), $R^3$ is $-S(O)R^{19}$.

In one embodiment, in Formula (I), $R^3$ is $-SO_2R^{19}$.

In one embodiment, in Formula (I), $R^3$ is $-OC(O)R^{24}$.

In one embodiment, in Formula (I), $R^3$ is $-C(O)NR^{25}R^{26}$.

In one embodiment, in Formula (I), $R^3$ is $-NR^{23}C(N-CN)NR^{25}R^{26}$. $R^{26}$.

In one embodiment, in Formula (I), $R^3$ is $-NR^{23}C(O)NR^{25}R^{26}$.

Non-limiting examples of $R^3$ include the following: methyl, ethyl, propyl (straight or branched), butyl (straight or branched), pentyl (straight or branched), phenyl,

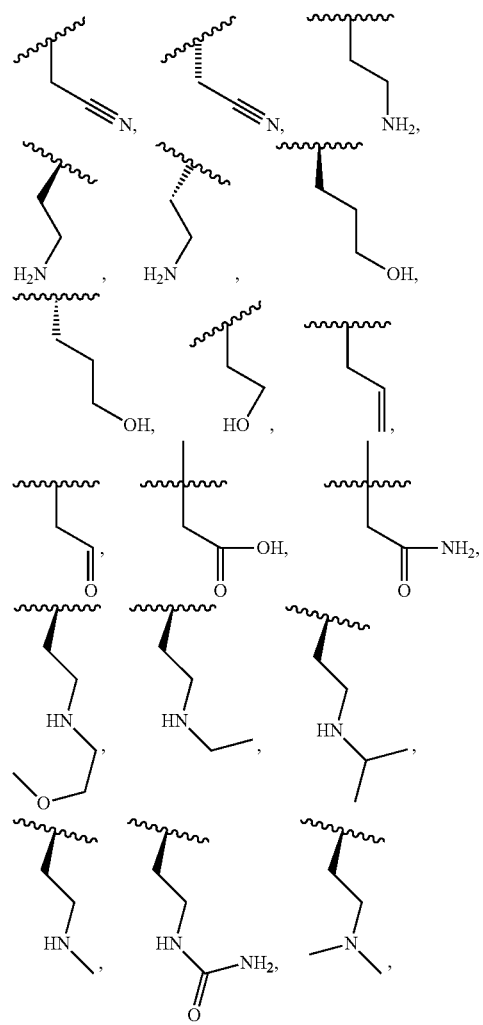

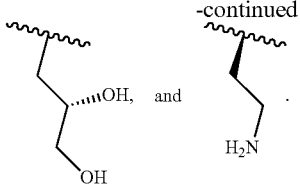

In one embodiment, in Formula (I), when E is $-NR^6-$, $R^3$ is absent.

In one embodiment, Formula (I) has the general structure shown in Formula (I.a):

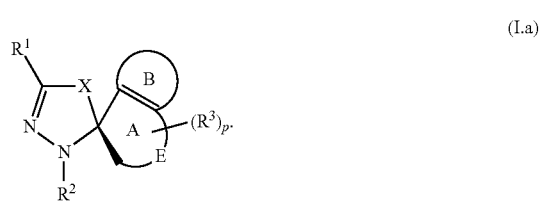

In one embodiment, Formula (I) has the general structure shown in Formula (I.b):

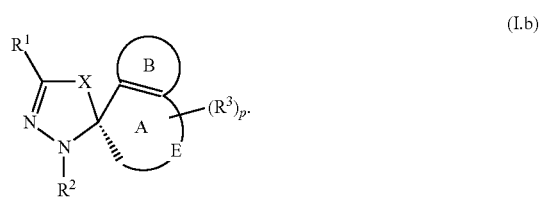

In one embodiment, Formula (I) has the general structure shown in Formula (I.c):

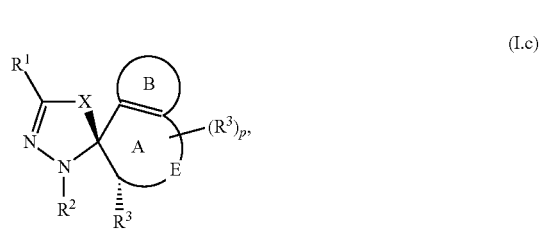

wherein p is 0, 1, 2, or 3.

In one embodiment, Formula (I) has the general structure shown in Formula (I.d):

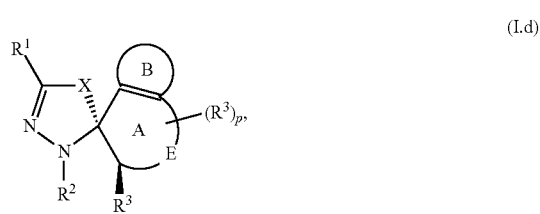

wherein p is 0, 1, 2, or 3.

In one embodiment, Formula (I) has the general structure shown in Formula (I.e):

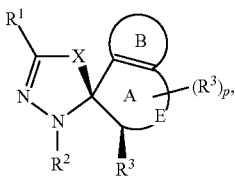

(I.e)

wherein p is 0, 1, 2, or 3.

In one embodiment, Formula (I) has the general structure shown in Formula (I.f):

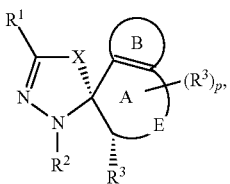

(I.f)

wherein p is 0, 1, 2, or 3.

In one embodiment, Formula (I) has the general structure shown in Formula (I.g):

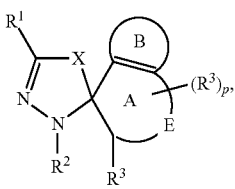

(I.g)

wherein p is 0, 1, 2, or 3.

In some embodiments, in each of formulas (I), (I.a), (I.b), (I.c), (I.d), (I.e), (I.f), and (I.g), $R^1$ is

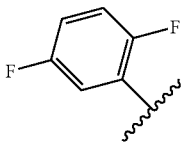 [SMILES: *c1cc(F)ccc1F]

and the compounds of the invention have the general structure shown in Formula (I.h):

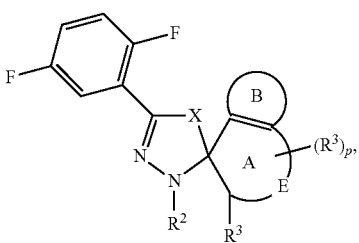

(I.h)

wherein p is 0, 1, 2, or 3.

In some embodiments, in each of Formulas (I), (I.a), (I.b), (I.c), (I.d), (I.e), (I.f), (I.g), and (I.h), p is 0.

For the various embodiments of the present invention described herein, it shall be understood that any variable of a structural formula not explicitly defined therein is as defined in the formula to which the embodiment refers. It shall also be understood that each $R^3$, when present, is attached to a ring atom or ring heteroatom of ring A by replacement of an available hydrogen atom.

In other embodiments, in each of Formulas (I), (I.a), (I.b), (I.c), (I.d), (I.e), (I.f), (I.g), and (I.h):
ring A is a 4-7 membered cycloalkenyl ring;
E is —C($R^4$)($R^5$)—; and
ring B is a benzo ring or a 5-6 membered heteroaromatic ring,
wherein said ring is unsubstituted or optionally independently substituted with from 1 to 3 substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —OC(O)$OR^{20}$, —$NR^{21}R^{22}$, —$NR^{23}SO_2R^{24}$, —$NR^{23}$C(O)$OR^{20}$, —$NR^{23}$C(O)$R^{24}$, —$SO_2NR^{25}R^{26}$, —C(O)$R^{24}$, —C(O)$OR^{20}$, —$SR^{19}$, —S(O)$R^{19}$, —$SO_2R^{19}$, —OC(O)$R^{24}$, —C(O)$NR^{25}R^{26}$, —$NR^{23}$C(N—CN)$NR^{25}R^{26}$ and —$NR^{23}$C(O)$NR^{25}R^{26}$.

In other embodiments, in each of Formulas (I), (I.a), (I.b), (I.c), (I.d), (I.e), (I.f), and (I.g):
ring A is a 4-7 membered cycloalkenyl ring;
E is —C($R^4$)($R^5$)—; and
ring B is a benzo ring or a 5-6 membered heteroaromatic ring,
wherein said ring is unsubstituted or optionally independently substituted with from 1 to 3 substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —OC(O)$OR^{20}$, —$NR^{21}R^{22}$, —$NR^{23}SO_2R^{24}$, —$NR^{23}$C(O)$OR^{20}$, —$NR^{23}$C(O)$R^{24}$, —$SO_2NR^{25}R^{26}$, —C(O)$R^{24}$, —C(O)$OR^{20}$, —$SR^{19}$, —S(O)$R^{19}$, —$SO_2R^{19}$, —OC(O)$R^{24}$, —C(O)$NR^{25}R^{26}$, —$NR^{23}$C(N—CN)$NR^{25}R^{26}$ and —$NR^{23}$C(O)$NR^{25}R^{26}$;
$R^1$ is phenyl substituted with one to four substituents, which can be the same or different, each substituent being independently selected from the group consisting of halo, —OH, —CN, —$NO_2$, —$NR^{21}R^{22}$, and haloalkyl;
$R^2$ is selected from the group consisting of: alkyl, haloalkyl, heteroalkyl, heterohaloalkyl, —C(O)$R^7$, —C(O)$OR^8$, and —C(O)$NR^9R^{10}$; and
each $R^3$ (when present) is independently selected from the group consisting of alkyl, heteroalkyl, alkenyl, heteroalkenyl, —CN, —$NO_2$, —OC(O)$OR^{20}$, —$NR^{21}R^{22}$, —$NR^{23}SO_2R^{24}$, —$NR^{23}$C(O)$OR^{20}$, —$NR^{23}$C(O)$R^{24}$, —$SO_2NR^{25}R^{26}$, —C(O)$R^{24}$, —C(S)$R^{24}$, —C(O)$OR^{20}$, —S(O)$R^{19}$, —$SO_2R^{19}$, —OC(O)$R^{24}$, —C(O)$NR^{25}R^{26}$, —$NR^{23}$C(N—CN)$NR^{25}R^{26}$, —$NR^{23}$C(O)$NR^{25}R^{26}$, and —$NR^{23}$—C(NH)—$NR^{25}R^{26}$,
wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In other embodiments, in each of Formulas (I), (I.a), (I.b), (I.c), (I.d), (I.e), (I.f), and (I.g):
ring A is a 4-7 membered cycloalkenyl ring;
E is —C(R$^4$)(R$^5$)—;
ring B is a benzo ring or a 5-6 membered heteroaromatic ring, wherein said ring is unsubstituted or optionally independently substituted with from 1 to 3 substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{24}$, —NR$^{23}$C(O)R$^{24}$, —SO$_2$NR$^{25}$R$^{26}$, —O(O)R$^{24}$, —C(O)OR$^{20}$, —SR$^{19}$, —S(O)R$^{19}$, —SO$_2$R$^{19}$, —OC(O)R$^{24}$, —O(O)NR$^{25}$R$^{26}$, —NR$^{23}$C(N—CN)NR$^{25}$R$^{26}$ and —NR$^{23}$C(O)NR$^{25}$R$^{26}$;

R$^1$ is phenyl substituted with one to four substituents, which can be the same or different, each substituent being independently selected from the group consisting of halo, —OH, —CN, —NO$_2$, —NR$^{21}$R$^{22}$, and haloalkyl;

R$^2$ is selected from the group consisting of: alkyl, haloalkyl, heteroalkyl, heterohaloalkyl, —C(O)R$^7$, —C(O)OR$^8$, and —C(O)NR$^9$R$^{10}$; and each R$^3$ (when present) is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —C(O)R$^{24}$, —C(S)R$^{24}$, —C(O)OR$^{20}$, and —C(O)NR$^{25}$R$^{26}$,
wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O) OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In other embodiments, in each of Formulas (I), (I.a), (I.b), (I.c), (I.d), (I.e), (I.f), and (I.g):
ring A is a 4-7 membered cycloalkenyl ring;
E is —C(R$^4$)(R$^5$)—; and
ring B is a benzo ring or a 5-6 mernbered heteroaromatic ring, wherein said ring is unsubstituted or optionally independently substituted with from 1 to 3 substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

R$^1$ is phenyl substituted with one to four substituents, which can be the same or different, each substituent being independently selected from the group consisting of halo, —OH, —CN, —NO$_2$, —NR$^{21}$R$^{22}$, and haloalkyl;

R$^2$ is selected from the group consisting of: alkyl, haloalkyl, heteroalkyl, heterohaloalkyl, —C(O)R$^7$, —C(O)OR$^8$, and —C(O)NR$^9$R$^{10}$; and p is 1 and R$^3$ is selected from the group consisting of alkyl, heteroalkyl, alkenyl, and heteroalkenyl,
wherein each said alkyl, each said heteroalkyl, each said alkenyl, and each said heteroalkenyl, is unsubstituted or optionally independently substituted with from 1 to 3 substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O) OR$^{20}$, —NR$^{21}$R$^{22}$, —NR$^{23}$SO$_2$R$^{24}$, —NIR$^{23}$C(O) OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC (O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In other embodiments, in each of Formulas (I), (I.a), (I.b), (I.c), (I.d), (I.e), (I.f), (I.g), and (I.h):
ring A is a 5-6 membered heterocycloalkenyl ring;
E is selected from the group consisting of —O—, —S—, —S(O)—, —S(O)$_2$—, —N(R$^6$)—, —N(C(Y)R$^7$)—, —N(C(Y)OR$^8$)—, —N(C(Y)N(R$^3$)(R$^{16}$))—, —C(O)—N (R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^6$)—O—, —N(R$^6$)—N(R$^{12}$)—, —N═N—, —C(R$^7$)═N—, —C(O)—C(R$^7$)═N—, —C(O)—N═N—, —O—C(Y)—N(R$^{11}$)—, —N(R$^{11}$)—C(Y)—O—, —N(R$^{11}$)—C(Y)—N(R$^{12}$)—, —C(Y)—N (R$^{11}$)—N(R$^{12}$)—, —O—N(R$^{11}$)—C(Y)—, and —N(R$^{12}$)—N(R$^{11}$)—C(Y)—; and
ring B is a benzo ring or a 5-6 membered heteroaromatic ring, wherein said ring is unsubstituted or optionally independently substituted with from 1 to 3 substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O) NR$^{25}$R$^{26}$.

In other embodiments, in each of Formulas (I), (I.a), (I.b), (I.c), (I.d), (I.e), (I.f), and (I.g):
ring A is a 5-6 membered heterocycloalkenyl ring;
E is selected from the group consisting —O—, —S—, —S(O)—, —S(O)$_2$—, and —N(R$^6$)—, wherein R$^6$ is selected from the group consisting of H, alkyl, —C(O)R$^{24}$, —C(O)OR$^{20}$, and —C(S)R$^{24}$;

ring B is a benzo ring or a 5-6 membered heteroaromatic ring,
  wherein said ring is unsubstituted or optionally independently substituted with from 1 to 3 substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

R$^1$ is phenyl substituted with one to four substituents, which can be the same or different, each substituent being independently selected from the group consisting of halo, —OH, —CN, —NO$_2$, —NR$^{21}$R$^{22}$, and haloalkyl;

R$^2$ is selected from the group consisting of: alkyl, haloalkyl, heteroalkyl, heterohaloalkyl, —C(O)R$^7$, —C(O)OR$^8$, and —C(O)NR$^9$R$^{10}$; and each R$^3$ (when present) is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$, —NR$^{23}$C(O)NR$^{25}$R$^{26}$, and —NR$^{23}$—C(NH)—NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In other embodiments, in each of Formulas (I), (I.a), (I.b), (I.c), (I.d), (I.e), (I.f), and (I.g):

ring A is a 5-6 membered heterocycloalkenyl ring;

E is selected from the group consisting —O—, —S—, —S(O)—, —S(O)$_2$—, and —N(R$^6$)—, wherein R$^6$ is selected from the group consisting of H, alkyl, —C(O)R$^{24}$, —C(O)OR$^{20}$, and —C(S)R$^{24}$;

ring B is a benzo ring or a 5-6 membered heteroaromatic ring,
  wherein said ring is unsubstituted or optionally independently substituted with from 1 to 3 substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O) NR$^{25}$R$^{26}$;

R$^1$ is phenyl substituted with one to four substituents, which can be the same or different, each substituent being independently selected from the group consisting of halo, —OH, —CN, —NO$_2$, —NR$^{21}$R$^{22}$, and haloalkyl;

R$^2$ is selected from the group consisting of: alkyl, haloalkyl, heteroalkyl, heterohaloalkyl, —C(O)R$^7$, —C(O)OR$^8$, and —C(O)NR$^9$R$^{10}$; and each R$^3$ (when present) is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —C(O)R$^{24}$, —C(S)R$^{24}$, —C(O)OR$^{20}$, and —C(O)NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{36}$.

In other embodiments, in each of Formulas (I), (I.a), (I.b), (I.c), (I.d), (I.e), (I.f), and (I.g):

ring A is a 5-6 membered heterocycloalkenyl ring;

E is selected from the group consisting —O—, —S—, —S(O)—, —S(O)$_2$—, and —N(R$^6$)—, wherein R$^6$ is selected from the group consisting of H, alkyl, —C(O)R$^{24}$, —C(O)OR$^{20}$, and —C(S)R$^{24}$;

ring B is a benzo ring or a 5-6 membered heteroaromatic ring,
  wherein said ring is unsubstituted or optionally independently substituted with from 1 to 3 substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O) NR$^{25}$R$^{26}$;

R$^1$ is phenyl substituted with one to four substituents, which can be the same or different, each substituent being independently selected from the group consisting of halo, —OH, —CN, —NO$_2$, —NR$^{21}$R$^{22}$, and haloalkyl;

R$^2$ is selected from the group consisting of: alkyl, haloalkyl, heteroalkyl, heterohaloalkyl, —C(O)R$^7$, —C(O)OR$^8$, and —C(O)NR$^9$R$^{10}$; and p is 1 and R$^3$ is selected from the group consisting of alkyl, heteroalkyl, alkenyl, and heteroalkenyl,
  wherein each said alkyl, each said heteroalkyl, each said alkenyl, and each said heteroalkenyl, is unsubstituted or optionally independently substituted with from 1 to 3 substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)

OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, the compounds of the invention have a structure shown in Formula (II) and include pharmaceutically acceptable salts, solvates, esters, prodrugs, or isomers of said compounds:

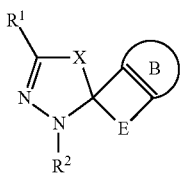

(II)

wherein X, R¹, R², E, and ring B are selected independently of each other and wherein E is selected from the group consisting of —O—, —S—, —S(O)—, —S(O)₂—, —C(R⁴)(R⁵)—, —N(R⁵)—, —N(C(Y)R⁷)—, —N(C(Y)OR⁸)—, —N(C(Y)N(R⁹)(R¹⁰))—;

and ring B, X, R¹, R², R⁴, R⁵, R⁶, R⁷, R⁸, R⁹, R¹⁰, Y, and the optional substituents on ring B are as defined in any of the embodiments described above in Formula (I).

In one embodiment, in Formula (II):
E is selected from the group consisting of —O—, —S—, —S(O)—, —S(O)₂—, —C(R⁴)(R⁵)—, and —N(R⁶)—;
ring B is an unsubstituted or substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and friazinyl;
R¹ is phenyl substituted with one to four substituents, which can be the same or different, each substituent being independently selected from the group consisting of halo, —OH, —CN, —NO₂, —NR²¹R²², and haloalkyl; and
R² is selected from the group consisting of —C(O)R⁷, —C(O)NR⁹R¹⁰, and —C(O)OR⁹.

In one embodiment, in Formula (II):
R¹ is:

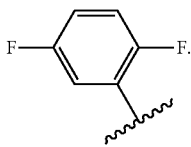

In one embodiment, the compounds of the invention have a structure shown in Formula (II.a) and include pharmaceutically acceptable salts, solvates, esters, prodrugs, or isomers of said compounds:

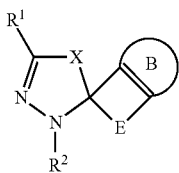

(II.a)

wherein X, R¹, R², E, and ring B are selected independently of each other and wherein:

E is selected from the group consisting of —O—, —S—, —S(O)—, —S(O)₂—, —C(R⁴)(R⁵)—, —N(R⁶)—, —N(C(Y)R⁷)—, —N(C(Y)OR⁸)—, —N(C(Y)N(R⁹)(R¹⁰))—.

ring B is a substituted or unsubstituted aromatic ring;
and X, R¹, R², R⁴, R⁵, R⁶, R⁷, R⁸, R⁹, R¹⁰, Y, r and the optional substituents on ring B are as defined in any of the embodiments described above in Formula (I).

In one embodiment, Formula (II.a.) has the general structure shown in Formula (II.a.1):

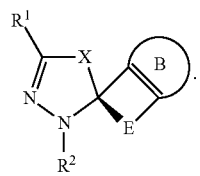

(II.a.1)

In one embodiment, Formula (II.a.) has the general structure shown in Formula (II.a.2):

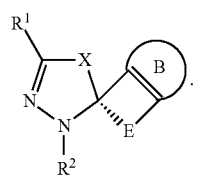

(II.a.2)

In some embodiments, in each of Formulas (II.a.), (II.a.1), and (II.a.2), X is S.

In some embodiments, in each of Formulas (II.a.), (II.a.1), and (II.a.2), X is S(O).

In some embodiments, in each of Formulas (II.a.), (II.a.1), and (II.a.2), X is S(O)₂.

In some embodiments, in each of Formulas (II.a.), (II.a.1), and (II.a.2), E is —C(R⁴)(R⁵)—.

In some embodiments, in each of Formulas (II.a.), (II.a.1), and (II.a2), E is selected from the group consisting of —O—, —S—, —S(O)—, —S(O)₂—, and —N(R⁶)—.

In some embodiments, in each of Formulas (II.a.), (II.a.1), and (II.a.2), E is selected from the group consisting of —O—, —S—, —S(O)—, —S(O)₂—, and —N(R⁶)—, wherein R⁶ is selected from the group consisting of H, alkyl, —C(O)R²⁴, and —C(S)R²⁴.

In some embodiments, in each of Formulas (II.a.), (II.a.1), and (II.a.2), E is selected from the group consisting of —O— and —N(R⁶)—, wherein R⁶ is selected from the group consisting of H, alkyl, —C(O)R²⁴, and —C(S)R²⁴.

In some embodiments, in each of Formulas (II.a.), (II.a.1), and (II.a.2), E is —O—.

In some embodiments, in each of Formulas (II.a.), (II.a.1), and (II.a.2), E is —S—.

In some embodiments, in each of Formulas (II.a.), (II.a.1), and (II.a.2), E is —S(O)—.

In some embodiments, in each of Formulas (II.a.), (II.a.1), and (II.a.2), E is —S(O)₂—.

In some embodiments, in each of Formulas (II.a.), (II.a.1), and (II.a.2), E is —C(R⁴)(R⁵)—.

In some embodiments, in each of Formulas (II.a.), (II.a.1), and (II.a.2), E is —N($R^6$)—.

In some embodiments, in each of Formulas (II.a.), (II.a.1), and (II.a.2), E is —N(C(Y)$R^7$)—.

In some embodiments, in each of Formulas (II.a.), (II.a.1), and (II.a.2), E is —N(C(Y)O$R^6$)—.

In some embodiments, in each of Formulas (II.a.), (II.a.1), and (II.a.2), E is —N(C(Y)N($R^9$)($R^{10}$))—, In some embodiments, in each of Formulas (II.a.), (II.a.1), and (II.a.2), Y is (=O).

In some embodiments, in each of Formulas (II.a.), (II.a.1), and (II.a.2), Y is (=S).

In some embodiments, in each of Formulas (II.a.), (II.a.1), and (II.a.2), Y is (=N($R^{13}$)).

In some embodiments, in each of Formulas (II.a.), (II.a.1), and (II.a.2), Y is (=N(CN)).

In some embodiments, in each of Formulas (II.a.), (II.a.1), and (II.a.2), Y is (=N(O$R^{14}$)).

In some embodiments, in each of Formulas (II.a.), (II.a.1), and (II.a.2), Y is (=N($R^{15}$)($R^{16}$)).

In some embodiments, in each of Formulas (II.a.), (II.a.1), and (II.a.2), Y is (=C($R^{17}$)($R^{18}$)).

In some embodiments, in each of Formulas (II.a.), (II.a.1), and (II.a.2), B is an unsubstituted aromatic ring.

In some embodiments, in each of Formulas (II.a.), (II.a.1), and (II.a.2), B is an unsubstituted benzo ring, and Formula (II.a.) has the general structure:

[Chemical structure: fused bicyclic system with $R^1$, X, E, $R^2$, N substituents]

In some embodiments, in each of Formulas (II.a.), (II.a.1), and (II.a.2), B is an unsubstituted benzo ring, and Formula (II.a.) has the general structure:

[Chemical structure: fused bicyclic system with $R^1$, X, N, $R^2$ substituents]

In some embodiments, in each of Formulas (II.a.), (II.a.1), and (II.a.2), B is an aromatic ring which is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}SO_2R^{24}$, —N$R^{23}$C(O)O$R^{20}$, —N$R^{23}$C(O)$R^{24}$, —$SO_2$N$R^{25}R^{26}$, —C(O)$R^{24}$, —C(O)O$R^{20}$, —S$R^{19}$, —S(O)$R^{19}$, —$SO_2R^{19}$, —OC(O)$R^{24}$, —C(O)N$R^{25}R^{26}$, —N$R^{23}$C(N—CN)N$R^{25}R^{26}$ and —N$R^{23}$C(O)N$R^{25}R^{26}$.

In some embodiments, in each of Formulas (II.a.), (II.a.1), and (II.a.2), B is a benzo ring which is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}SO_2R^{24}$, —N$R^{23}$C(O)O$R^{20}$, —N$R^{23}$C(O)$R^{24}$, —$SO_2$N$R^{25}R^{26}$, —C(O)$R^{24}$, —C(O)O$R^{20}$, —S$R^{19}$, —S(O)$R^{19}$, —$SO_2R^{19}$, —OC(O)$R^{24}$, —C(O)N$R^{25}R^{26}$, —N$R^{23}$C(N—CN)N$R^{25}R^{26}$ and —N$R^{23}$C(O)N$R^{25}R^{26}$.

In some embodiments, in each of Formulas (II.a.), (II.a.1), and (II.a.2), $R^1$ is unsubstituted aryl.

In some embodiments, in each of Formulas (II.a.), (II.a.1), and (II.a.2), $R^1$ is unsubstituted phenyl.

In some embodiments, in each of Formulas (II.a.), (II.a.1), and (II.a.2), $R^1$ is unsubstituted naphthyl.

In some embodiments, in each of Formulas (II.a.), (II.a.1), and (II.a.2), $R^1$ is substituted aryl.

In some embodiments, in each of Formulas (II.a.), (II.a.1), and (II.a.2), $R^1$ is substituted phenyl.

In some embodiments, in each of Formulas (II.a.), (II.a.1), and (II.a.2), $R^1$ is substituted naphthyl.

In some embodiments, in each of Formulas (II.a.), (II.a.1), and (II.a.2), $R^1$ is aryl substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}SO_2R^{24}$, —N$R^{23}$C(O)O$R^{20}$, —N$R^{23}$C(O)$R^{24}$, —$SO_2$N$R^{25}R^{26}$, —C(O)$R^{24}$, —C(O)O$R^{20}$, —S$R^{19}$, —S(O)$R^{19}$, —$SO_2R^{19}$, —OC(O)$R^{24}$, —C(O)N$R^{25}R^{26}$, —N$R^{23}$C(N—CN)N$R^{25}R^{20}$ and —N$R^{23}$C(O)N$R^{25}R^{26}$, In some embodiments, in each of Formulas (II.a.), (II.a.1), and (II.a.2), $R^1$ is phenyl substituted with one or more substituents, which can be the same or different, each substituent being independently selected from the group consisting halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}SO_2R^{24}$, —N$R^{23}$C(O)O$R^{20}$, —N$R^{23}$C(O)$R^{24}$, —$SO_2$N$R^{25}R^{26}$, —C(O)$R^{24}$, —C(O)O$R^{20}$, —S$R^{19}$, —S(O)$R^{19}$, —$SO_2R^{19}$, —OC(O)$R^{24}$, —C(O)N$R^{25}R^{26}$, —N$R^{23}$C(N—CN)N$R^{25}R^{26}$ and —N$R^{23}$C(O)N$R^{25}R^{26}$.

In some embodiments, in each of Formulas (II.a.), (II.a.1), and (II.a.2), $R^1$ is phenyl substituted with one to four substituents, which can be the same or different, each substituent being independently selected from the group consisting of halo, —OH, —CN, —$NO_2$, —N$R^{21}R^{22}$, and haloalkyl.

In some embodiments, in each of Formulas (II.a.), (II.a.1), and (II.a.2), $R^1$ is selected from the group consisting of:

[Four chemical structures: phenyl rings substituted with halo/halo, HO/halo, NC/halo, and $O_2N$/halo respectively, each with wavy bond attachment point]

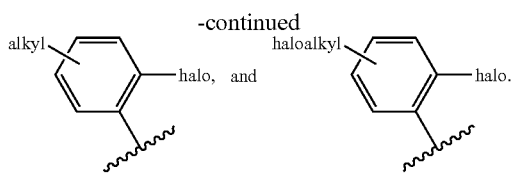

In some embodiments, in each of Formulas (II.a.), (II.a.1), and (II.a.2), $R^1$ is:

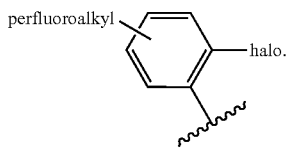

In some embodiments, in each of Formulas (II.a.), (II.a.1), and (II.a.2), $R^1$ is phenyl substituted with one to three fluoro groups.

In some embodiments, in each of Formulas (II.a.), (II.a.1), and (II.a.2), $R^1$ is phenyl substituted with two fluoro groups.

In some embodiments, in each of Formulas (II.a.), (II.a.1), and (II.a.2), $R^1$ is phenyl substituted with one fluoro group.

In some embodiments, in each of Formulas (II.a.), (II.a.1), and (II.a.2), $R^1$ is:

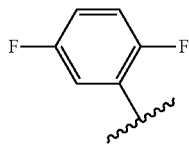

In some embodiments, in each of Formulas (II.a.), (II.a.1), and (II.a.2), $R^2$ is —C(Z)$R^7$.

In some embodiments, in each of Formulas (II.a.), (II.a.1), and (II.a.2), $R^2$ is —C(Z)N$R^9R^{10}$.

In some embodiments, in each of Formulas (II.a.), (II.a.1), and (II.a.2), $R^2$ is —C(Z)O$R^8$.

In some embodiments, in each of Formulas (II.a.), (II.a.1), and (II.a.2), $R^2$ is —SO$_2$N$R^9R^{10}$.

In some embodiments, in each of Formulas (II.a.), (II.a.1), and (II.a.2), $R^2$ is alkyl.

In some embodiments, in each of Formulas (II.a.), (II.a.1), and (II.a.2), $R^2$ is heteroalkyl.

In some embodiments, in each of Formulas (II.a.), (II.a.1), and (II.a.2), $R^2$ is aryl.

In some embodiments, in each of Formulas (II.a.), (II.a.1), and (II.a.2), $R^2$ is heteroaryl.

In some embodiments, in each of Formulas (II.a.), (II.a.1), and (II.a.2), $R^2$ is cycloalkyl.

In some embodiments, in each of Formulas (II.a.), (II.a.1), and (II.a.2), $R^2$ is cycloalkenyl.

In some embodiments, in each of Formulas (II.a.), (II.a.1), and (II.a.2), $R^2$ is heterocycloalkyl.

In some embodiments, in each of Formulas (II.a.), (II.a.1), and (II.a.2), $R^2$ is heterocycloalkenyl.

In some embodiments, in each of Formulas (II.a.), (II.a.1), and (II.a.2), Z is (═O). In some embodiments, in each of Formulas (II.a.), (II.a.1), and (II.a.2), Z is (═S).

In some embodiments, in each of Formulas (II.a.), (II.a.1), and (II.a.2), Z is (═N($R^{13}$)).

In some embodiments, in each of Formulas (II.a.), (II.a.1), and (II.a.2), Z is (═N(CN)).

In some embodiments, in each of Formulas (II.a.), (II.a.1), and (II.a.2), Z is (═N(O$R^{14}$)).

In some embodiments, in each of Formulas (II.a.), (II.a.1), and (II.a.2), Z is (═N($R^{15}$)($R^{16}$)).

In some embodiments, in each of Formulas (II.a.), (II.a.1), and (II.a.2), Z is (═C($R^{17}$)($R^{18}$)).

In some embodiments, in each of Formulas (II.a.), (II.a.1), and (II.a.2), $R^2$ is —C(Z)$R^7$, and Z is (═O).

In some embodiments, in each of Formulas (II.a.), (II.a.1), and (II.a.2), $R^2$ is —C(O)H.

In some embodiments, in each of Formulas (II.a.), (II.a.1), and (II.a.2), $R^2$ is —C(O)alkyl.

In some embodiments, in each of Formulas (II.a.), (II.a.1), and (II.a.2), $R^2$ is —C(O)CH$_3$.

In some embodiments, in each of Formulas (IIa.), (II.a.1), and (II.a.2), $R^2$ is —C(O)$R^7$, wherein said $R^7$ is alkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(O)O$R^{20}$, —S$R^{19}$, —S(O)$R^{19}$, —SO$_2R^{19}$, —OC(O)$R^{24}$, —C(O)N$R^{25}R^{26}$, —N$R^{23}$C(N═CN)N$R^{25}R^{26}$ and —N$R^{23}$C(O)N$R^{25}R^{26}$.

In some embodiments, in each of Formulas (II.a.), (II.a.1), and (II.a.2), $R^2$ is —C(O)$R^7$, wherein said $R^7$ is alkyl substituted with one to three substituents, which can be the same or different, each substituent being independently selected from the group consisting of —O$R^{19}$, —N$R^{21}R^{22}$, and cycloalkyl.

In some embodiments, in each of Formulas (II.a.), (II.a.1), and (II.a.2), $R^2$ is —C(O)$R^7$, wherein said $R^7$ is alkyl, wherein said alkyl is substituted with alkyl and —OH.

In some embodiments, in each of Formulas (II.a.), (II.a.1), and (II.a.2), $R^2$ is —C(O)$R^7$, wherein said $R^7$ is alkyl substituted with one to three substituents, which can be the same or different, each substituent being independently selected from the group consisting of —OH, —NH$_2$, and cyclopropyl.

In some embodiments, in each of Formulas (II.a.), (II.a.1), and (II.a.2), $R^2$ is —C(O)$R^7$, wherein said $R^7$ is alkyl substituted with one to two substituents, which can be the same or different, each substituent being independently selected from the group consisting of —NH$_2$, and cyclopropyl.

In some embodiments, in each of Formulas (II.a.), (II.a.1), and (II.a.2), $R^2$ is —C(O)$R^7$, wherein said $R^7$ is alkyl substituted with —OH.

In some embodiments, in each of Formulas (II.a.), (II.a.1), and (II.a.2), $R^2$ is —C(O)$R^7$, wherein said $R^7$ is unsubstituted heterocycloalkyl.

In some embodiments, in each of Formulas (II.a.), (II.a.1), and (II.a.2), $R^2$ is —C(O)$R^7$, wherein said $R^7$ is substituted heterocycloalkyl.

In some embodiments, in each of Formulas (II.a.), (II.a.1), and (II.a.2), $R^2$ is —C(O)$R^7$, wherein said $R^7$ is heterocycloalkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(O)OR²⁰, —S(O)R¹⁹, —SO₂R¹⁹, —OC(O)R²⁴, —C(O)NR²⁵R²⁶, —NR²³C(N═CN)NR²⁵R²⁶ and —NR²³C(O)NR²⁵R²⁶.

In some embodiments, in each of Formulas (II.a.), (II.a.1), and (II.a.2), R² is —C(O)R⁷, wherein said R⁷ is selected from the group consisting of substituted piperidine, substituted piperazine, substituted morpholine, substituted pyrrolidine, and substituted azetidine.

In some embodiments, in each of Formulas (II.a.), (II.a.1), and (II.a.2), R² is selected from:

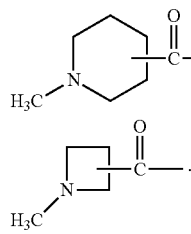

In some embodiments, in each of Formulas (II.a.), (II.a.1), and (II.a.2), R² is —C(O)NR⁹R¹⁰.

In some embodiments, in each of Formulas (II.a.), (II.a.1), and (II.a.2), R² is —C(O)NH₂.

In some embodiments, in each of Formulas (II.a.), (II.a.1), and (II.a.2), R² is —C(O)NR⁹R¹⁰, wherein R⁹ and R¹⁰ can be the same or different, each being independently selected from alkyl.

In some embodiments, in each of Formulas (II.a.), (II.a.1), and (II.a.2), R² is —C(O)NR⁹R¹⁰, wherein R⁹ is unsubstituted heterocycloalkyl and R¹⁰ is selected from the group consisting of H and alkyl.

In some embodiments, in each of Formulas (II.a.), (II.a.1), and (II.a.2), R² is —C(O)NR⁹R¹⁰, wherein R⁹ is substituted heterocycloalkyl and R¹⁰ is selected from the group consisting of H and alkyl.

In some embodiments, in each of Formulas (II.a.), (II.a.1), and (II.a.2), R² is —C(O)NR⁹R¹⁰, wherein R⁹ is heterocycloalkyl substituted with from one to three substituents, which can be the same or different, each substituent being independently selected from alkyl, and R¹⁰ is selected from the group consisting of H and alkyl.

In some embodiments, in each of Formulas (II.a.), (II.a.1), and (II.a.2), R² is selected from the group consisting of: alkyl, haloalkyl, heteroalkyl, heterohaloalkyl, —C(O)R⁷, —C(O)OR⁸, and —C(O)NR⁹R¹⁰.

Non-limiting examples of R² include the following moieties:

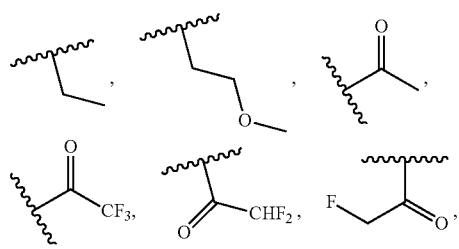

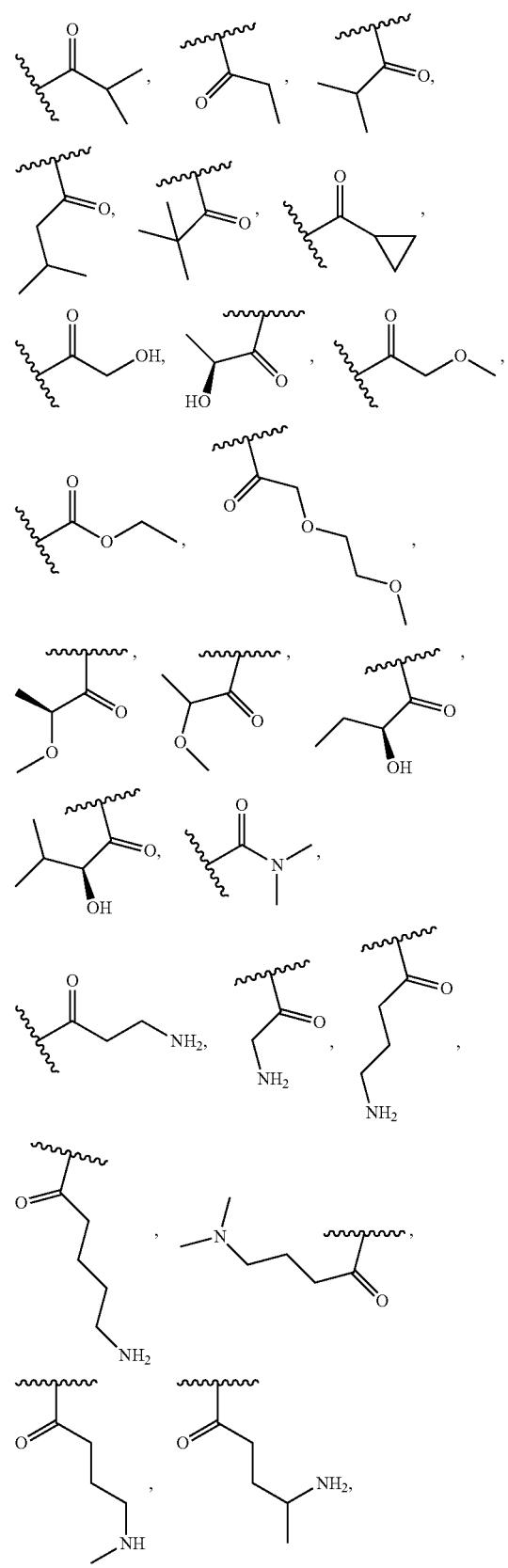

-continued
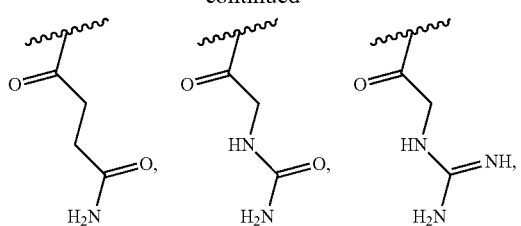
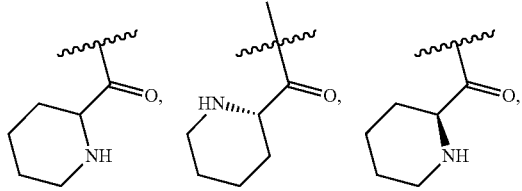
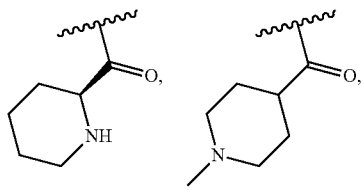
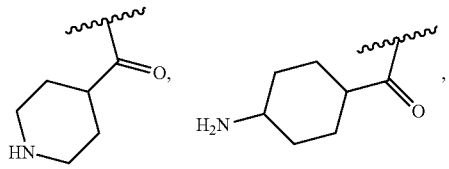
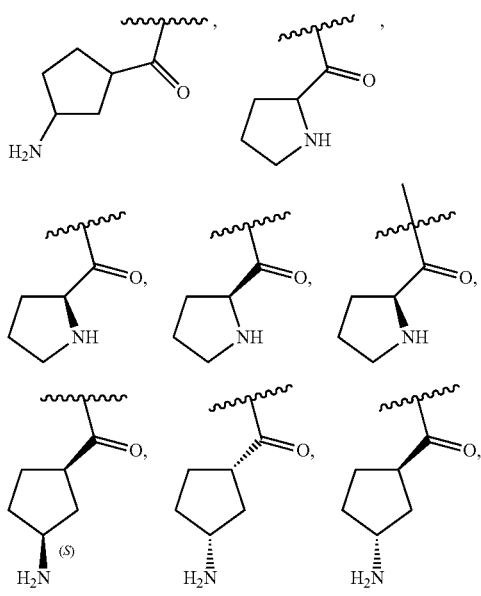
-continued
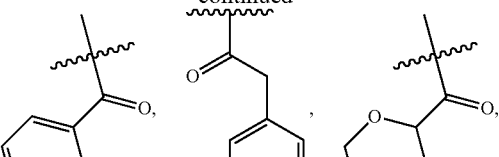
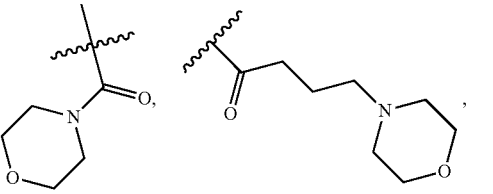
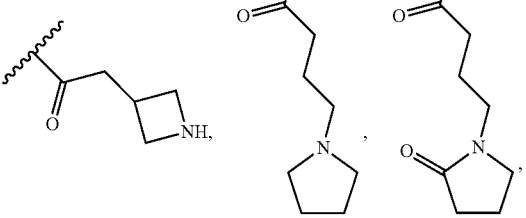
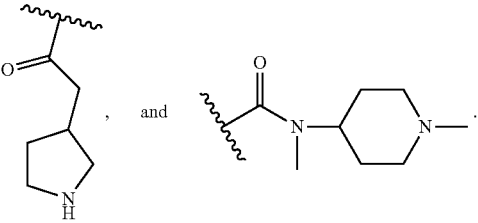
In some embodiments, in each of Formulas (II.a.), (II.a.1), and (II.a.2), $R^2$ is
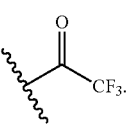 [SMILES: *C(=O)C(F)(F)F]
In some embodiments, in each of Formulas (II.a.), (II.a.1), and (II.a.2), $R^2$ is
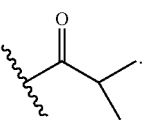
In some embodiments, in each of Formulas (II.a.), (II.a.1), and (II.a.2), $R^2$ is
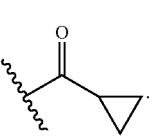

In some embodiments, in each of Formulas (II.a.), (II.a.1), and (II.a.2), R² is

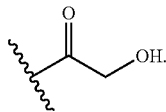 [SMILES: *C(=O)CO]

In some embodiments, in each of Formulas (II.a.), (II.a.1), and (II.a.2), R² is

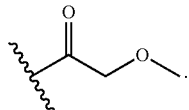 [SMILES: *C(=O)COC]

In some embodiments, in each of Formulas (II.a.), (II.a.1), and (II.a.2), R² is

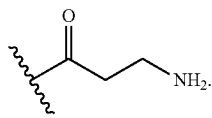 [SMILES: *C(=O)CCN]

In some embodiments, in each of Formulas (II.a.), (II.a.1), and (II.a.2), R² is

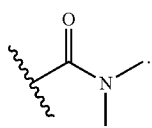 [SMILES: *C(=O)N(C)C]

In some embodiments, in each of Formulas (II.a.), (II.a.1), and (II.a.2), R² is

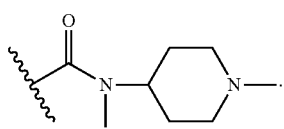

In one embodiment, the compounds of the invention have a structure shown in Formula (II.b) and include pharmaceutically acceptable salts, solvates, esters, prodrugs, or isomers of said compounds:

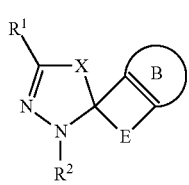

(II.b.)

wherein X, R¹, R², E, and ring B are selected independently of each other and wherein:

E is selected from the group consisting of —O—, —S—, —S(O)—, —S(O)$_2$—, —C(R⁴)(R⁵)—, —N(R⁸)—, —N(C(Y)R⁷)—, —N(C(Y)OR⁸)—, —N(C(Y)N(R⁹)(R¹⁰))—.

ring B is a substituted or unsubstituted heteroaromatic ring; and X, R¹, R², R⁴, R⁵, R⁶, R⁷, R⁸, R⁹, R¹⁰, Y, and the optional substituents on ring B are as defined in any of the embodiments described above in Formula (I).

In one embodiment, Formula (II.b.) has the general structure shown in Formula (II.b.1):

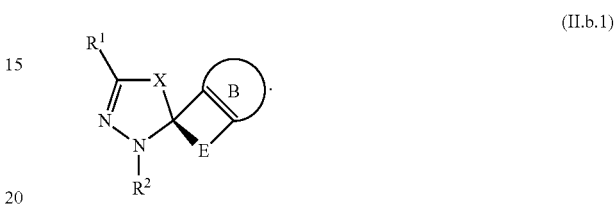

(II.b.1)

In one embodiment, Formula (II.b.) has the general structure shown in Formula (II.b.2):

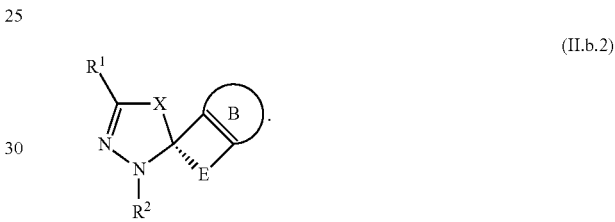

(II.b.2)

In some embodiments, in each of Formulas (II.b), (II.b.1), and (II.b.2), X is S.

In some embodiments, in each of Formulas (II.b), (II.b.1), and (II.b.2), X is S(O).

In some embodiments, in each of Formulas (II.b), (II.b.1), and (II.b.2), X is S(O)$_2$.

In some embodiments, in each of Formulas (II.b), (II.b.1), and (II.b.2), E is —C(R⁴)(R⁵)—.

In some embodiments, in each of Formulas (II.b), (II.b.1), and (II.b.2), E is selected from the group consisting of —O—, —S—, —S(O)—, —S(O)$_2$—, and —N(R⁶)—.

In some embodiments, in each of Formulas (II.b), (II.b.1), and (II.b.2), E is selected from the group consisting of —O—, —S—, —S(O)—, —S(O)$_2$—, and —N(R⁶)—, wherein R⁶ is selected from the group consisting of H, alkyl, —C(O)R²⁴, and —C(S)R²⁴.

In some embodiments, in each of Formulas (II.b), (II.b.1), and (II.b.2), E is selected from the group consisting of —O— and —N(R⁶)—, wherein R⁶ is selected from the group consisting of H, alkyl, —C(O)R²⁴, and —C(S)R²⁴.

In some embodiments, in each of Formulas (II.b), (II.b.1), and (II.b.2), E is —O—.

In some embodiments, in each of Formulas (II.b), (II.b.1), and (II.b.2), E is —S—.

In some embodiments, in each of Formulas (II.b), (II.b.1), and (II.b.2), E is —S(O)—.

In some embodiments, in each of Formulas (II.b), (II.b.1), and (II.b.2), E is —S(O)$_2$—.

In some embodiments, in each of Formulas (II.b), (II.b.1), and (II.b.2), E is —C(R⁴)(R⁵)—.

In some embodiments, in each of Formulas (II.b), (II.b.1), and (II.b.2), E is —N(R⁶)—.

In some embodiments, in each of Formulas (II.b), (II.b.1), and (II.b.2), E is —N(C(Y)R$^7$)—.

In some embodiments, in each of Formulas (II.b), (II.b.1), and (II.b.2), E is —N(C(Y)OR$^8$)—.

In some embodiments, in each of Formulas (II.b), (II.b.1), and (II.b.2), E is —N(C(Y)N(R$^9$)(R$^{10}$)—.

In some embodiments, in each of Formulas (II.b), (II.b.1), and (II.b.2), Y is (=O).

In some embodiments, in each of Formulas (II.b), (II.b.1), and (II.b.2), Y is (=S).

In some embodiments, in each of Formulas (II.b), (II.b.1), and (II.b.2), Y is (=N(R$^{13}$)).

In some embodiments, in each of Formulas (II.b), (II.b.1), and (II.b.2), Y is (=N(CN)).

In some embodiments, in each of Formulas (II.b), (II.b.1), and (II.b.2), Y is (=N(OR$^{14}$)).

In some embodiments, in each of Formulas (II.b), (II.b.1), and (II.b.2), Y is (=N(R$^{15}$)(R$^{16}$)).

In some embodiments, in each of Formulas (II.b), (II.b.1), and (II.b.2), Y is (=C(R$^{17}$)(R$^{18}$)).

In some embodiments, in each of Formulas (II.b), (II.b.1), and (II.b.2), B is an unsubstituted heteroaromatic ring.

In some embodiments, in each of Formulas (II.b), (II.b.1), and (II.b.2), B is an unsubstituted 5-6-membered heteroaromatic ring having from 1-3 ring heteroatoms, which can be the same or different, each hetero ring atom being independently selected from the group consisting of N, S, O, S(O), and S(O)$_2$.

In some embodiments, in each of Formulas (II.b), (II.b.1), and (II.b.2), B is a heteroaromatic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (II.b), (II.b.1), and (II.b.2), B is a 5-6-membered heteroaromatic ring having from 1-3 ring heteroatoms, which can be the same or different, each hetero ring atom being independently selected from the group consisting of N, S, O, S(O), and S(O)$_2$, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (II.b), (II.b.1), and (II.b.2), B is an unsubstituted 6-membered heteroaromatic ring having from 1-3 ring heteroatoms, which can be the same or different, each hetero ring atom being independently selected from the group consisting of N, S, and O.

In some embodiments, in each of Formulas (II.b), (II.b.1), and (II.b.2), B is a 6-membered heteroaromatic ring having from 1-3 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (II.b), (II.b.1), and (II.b.2), B is an unsubstituted 6-membered heteroaromatic ring having 2 ring heteroatoms, each ring heteroatom being independently selected from of N, S, and O.

In some embodiments, in each of Formulas (II.b), (II.b.1), and (II.b.2), B is a 6-membered heteroaromatic ring having 2 ring heteroatoms, each ring heteroatom being independently selected from of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —NR$^{21}$R$^{22}$, —C(O)R$^{24}$, —C(O)OR$^{20}$, —SR$^{19}$, —S(O)R$^{19}$, —SO$_2$R$^{19}$, —OC(O)R$^{24}$, and —C(O)NR$^{25}$R$^{26}$.

In some embodiments, in each of Formulas (II.b), (II.b.1), and (II.b.2), B is an unsubstituted 5-membered heteroaromatic ring having from 1-2 ring heteroatoms, which can be the same or different, each hetero ring atom being independently selected from the group consisting of N, S, and O.

In some embodiments, in each of Formulas (II.b), (II.b.1), and (II.b.2), B is a 5-membered heteroaromatic ring having from 1-2 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (II.b), (II.b.1), and (II.b.2), B is an unsubstituted 5-membered heteroaromatic ring having 1 ring heteroatom selected from of N, S, and O.

In some embodiments, in each of Formulas (II.b), (II.b.1), and (II.b.2), B is a 5-membered heteroaromatic ring having 1 ring heteroatom selected from of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —NR$^{21}$R$^{22}$, —C(O)R$^{24}$, —C(O)OR$^{20}$, —SR$^{19}$, —S(O)R$^{19}$, —SO$_2$R$^{19}$, —OC(O)R$^{24}$, and —C(O)NR$^{25}$R$^{26}$.

In some embodiments, in each of Formulas (II.b), (II.b.1), and (II.b.2), B is a 5-membered heteroaromatic ring having S as the ring heteroatom, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —NR$^{21}$R$^{22}$, —C(O)R$^{24}$, —C(O)OR$^{20}$, —SR$^{19}$, —S(O)R$^{19}$, —SO$_2$R$^{19}$, —OC(O)R$^{24}$, and —C(O)NR$^{25}$R$^{26}$.

In some embodiments, in each of Formulas (II.b), (II.b.1), and (II.b.2), B is an unsubstituted 5-membered heteroaromatic ring having S as the ring heteroatom.

In one embodiment, Formula (II.b.) has the general structure:

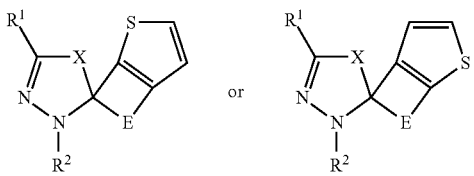

In one embodiment, Formula (II.b.) has the general structure:

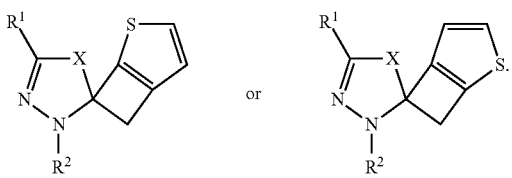

In some embodiments, in each of Formulas (II.b), (II.b.1), and (II.b.2), R$^1$ is unsubstituted aryl.

In some embodiments, in each of Formulas (II.b), (II.b.1), and (II.b.2), R$^1$ is unsubstituted phenyl.

In some embodiments, in each of Formulas (II.b), (II.b.1), and (II.b.2), R$^1$ is unsubstituted naphthyl.

In some embodiments, in each of Formulas (II.b), (II.b.1), and (II.b.2), R$^1$ is substituted aryl.

In some embodiments, in each of Formulas (II.b), (II.b.1), and (II.b.2), R$^1$ is substituted phenyl.

In some embodiments, in each of Formulas (II.b), (II.b.1), and (II.b.2), R$^1$ is substituted naphthyl.

In some embodiments, in each of Formulas (II.b), (II.b.1), and (II.b.2), R$^1$ is aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, arylalkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (II.b), (II.b.1), and (II.b.2), R$^1$ is phenyl substituted with one or more substituents, which can be the same or different, each substituent being independently selected from the group consisting halogen, —CN, —NO$_2$, alkyl, heteroalkyl, haloalkyl, alkenyl, haloalkenyl, alkynyl, haloalkynyl, aryl, heteroaryl, arylalkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (II.b), (II.b.1), and (II.b.2), R$^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In some embodiments, in each of Formulas (II.b), (II.b.1), and (II.b.2), R$^1$ is selected from the group consisting of:

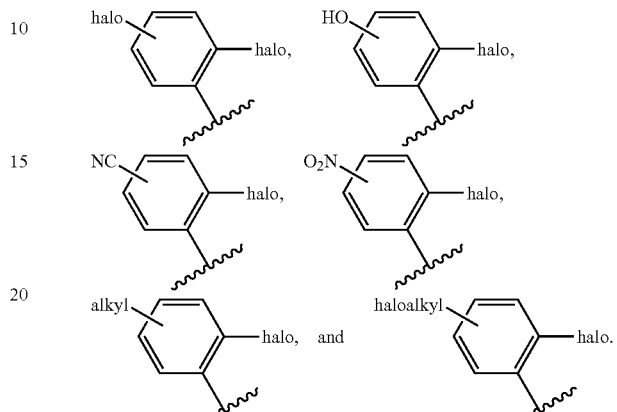

In some embodiments, in each of Formulas (II.b), (II.b.1), and (II.b.2), R$^1$ is:

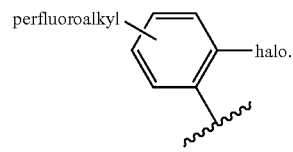

In some embodiments, in each of Formulas (II.b), (II.b.1), and (II.b.2), R$^1$ is phenyl substituted with one to three fluoro groups.

In some embodiments, in each of Formulas (II.b), (II.b.1), and (II.b.2), R$^1$ is phenyl substituted with two fluoro groups.

In some embodiments, in each of Formulas (II.b), (II.b.1), and (II.b.2), R$^1$ is phenyl substituted with one fluoro group.

In some embodiments, in each of Formulas (II.b), (II.b.1), and (II.b.2), R$^1$ is:

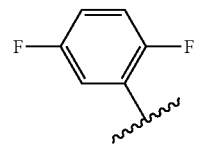

In some embodiments, in each of Formulas (II.b), (II.b.1), and (II.b.2), R$^2$ is —C(Z)R$^7$.

In some embodiments, in each of Formulas (II.b), (II.b.1), and (II.b.2), R$^2$ is —C(Z)NR$^9$R$^{10}$.

In some embodiments, in each of Formulas (II.b), (II.b.1), and (II.b.2), R$^2$ is —C(Z)OR$^8$.

In some embodiments, in each of Formulas (II.b), (II.b.1), and (II.b.2), R$^2$ is —SO$_2$NR$^9$R$^{10}$.

In some embodiments, in each of Formulas (II.b), (II.b.1), and (II.b.2), R$^2$ is alkyl.

In some embodiments, in each of Formulas (II.b), (II.b.1), and (II.b.2), R$^2$ is heteroalkyl.

In some embodiments, in each of Formulas (II.b), (II.b.1), and (II.b.2), $R^2$ is aryl.

In some embodiments, in each of Formulas (II.b), (II.b.1), and (II.b.2), $R^2$ is heteroaryl.

In some embodiments, in each of Formulas (II.b), (II.b.1), and (II.b.2), $R^2$ is cycloalkyl.

In some embodiments, in each of Formulas (II.b), (II.b.1), and (II.b.2), $R^2$ is cycloalkenyl.

In some embodiments, in each of Formulas (II.b), (II.b.1), and (II.b.2), $R^2$ is heterocycloalkyl.

In some embodiments, in each of Formulas (II.b), (II.b.1), and (II.b.2), $R^2$ is heterocycloalkenyl.

In some embodiments, in each of Formulas (II.b), (II.b.1), and (II.b.2), Z is (=O).

In some embodiments, in each of Formulas (II.b), (II.b.1), and (II.b.2), Z is (=S).

In some embodiments, in each of Formulas (II.b), (II.b.1), and (II.b.2), Z is (=N($R^{13}$)).

In some embodiments, in each of Formulas (II.b), (II.b.1), and (II.b.2), Z is (=N(CN)).

In some embodiments, in each of Formulas (II.b), (II.b.1), and (II.b.2), Z is (=N($OR^{14}$)).

In some embodiments, in each of Formulas (II.b), (II.b.1), and (II.b.2), Z is (=N($R^{15}$)($R^{16}$)).

In some embodiments, in each of Formulas (II.b), (II.b.1), and (II.b.2), Z is (=C($R^{17}$)($R^{16}$)).

In some embodiments, in each of Formulas (II.b), (II.b.1), and (II.b.2), $R^2$ is —C(Z)$R^7$, and Z is (=O).

In some embodiments, in each of Formulas (II.b), (II.b.1), and (II.b.2), $R^2$ is —C(O)H.

In some embodiments, in each of Formulas (II.b), (II.b.1), and (II.b.2), $R^2$ is —C(O)alkyl.

In some embodiments, in each of Formulas (II.b), (II.b.1), and (II.b.2), $R^2$ is —C(O)$CH_3$.

In some embodiments, in each of Formulas (II.b), (II.b.1), and (II.b.2), $R^2$ is —C(O)$R^7$, wherein said $R^7$ is alkyl substituted with one or more substituents, which can be the same or different, each substituent being independently selected from the group consisting of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, azido, —$OR^{19}$, —OC(O)$OR^{20}$, —$NR^{21}R^{22}$, —$NR^{23}SO_2R^{24}$, —$NR^{23}$C(O)$OR^{20}$, —$NR^{23}$C(O)$R^{24}$, —$SO_2NR^{25}R^{26}$, —C(O)$R^{24}$, —C(O)$OR^{20}$, —S(O)$R^{19}$, —$SO_2R^{19}$, —OC(O)$R^{24}$, —C(O)$NR^{25}R^{26}$, —$NR^{23}$C(N—CN)$NR^{25}R^{26}$ and —$NR^{23}$C(O)$NR^{25}R^{26}$.

In some embodiments, in each of Formulas (II.b), (II.b.1), and (II.b.2), $R^2$ is —C(O)$R^7$, wherein said $R^7$ is alkyl substituted with one to three substituents, which can be the same or different, each substituent being independently selected from the group consisting of —$OR^{19}$, —$NR^{21}R^{22}$, and cycloalkyl.

In some embodiments, in each of Formulas (II.b), (II.b.1), and (II.b.2), $R^2$ is —C(O)$R^7$, wherein said $R^7$ is alkyl, wherein said alkyl is substituted with alkyl and —OH.

In some embodiments, in each of Formulas (II.b), (II.b.1), and (II.b.2), $R^2$ is —C(O)$R^7$, wherein said $R^7$ is alkyl substituted with one to three substituents, which can be the same or different, each substituent being independently selected from the group consisting of —OH, —$NH_2$, and cyclopropyl.

In some embodiments, in each of Formulas (II.b), (II.b.1), and (II.b.2), $R^2$ is —C(O)$R^7$, wherein said $R^7$ is alkyl substituted with one to two substituents, which can be the same or different, each substituent being independently selected from the group consisting of —$NH_2$, and cyclopropyl.

In some embodiments, in each of Formulas (II.b), (II.b.1), and (II.b.2), $R^2$ is —C(O)$R^7$, wherein said $R^7$ is alkyl substituted with —OH.

In some embodiments, in each of Formulas (II.b), (II.b.1), and (II.b.2), $R^2$ is —C(O)$R^7$, wherein said $R^7$ is unsubstituted heterocycloalkyl.

In some embodiments, in each of Formulas (II.b), (II.b.1), and (II.b.2), $R^2$ is —C(O)$R^7$, wherein said $R^7$ is substituted heterocycloalkyl.

In some embodiments, in each of Formulas (II.b), (II.b.1), and (II.b.2), $R^2$ is —C(O)$R^7$, wherein said $R^7$ is heterocycloalkyl substituted with one or more substituents, which can be the same or different, each substituent being independently selected from the group consisting of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —$OR^{19}$, —OC(O)$OR^{20}$, —$NR^{21}R^{22}$, —$NR^{23}SO_2R^{24}$, —$NR^{23}$C(O)$OR^{20}$, —$NR^{23}$C(O)$R^{24}$, —$SO_2NR^{25}R^{26}$, —C(O)$R^{24}$, —C(O)$OR^{20}$, —$SR^{19}$, —S(O)$R^{19}$, —$SO_2R^{19}$, —OC(O)$R^{24}$, —C(O)$NR^{25}R^{26}$, —$NR^{23}$C(N—CN)$NR^{25}R^{26}$ and —$NR^{23}$C(O)$NR^{25}R^{26}$.

In some embodiments, in each of Formulas (II.b), (II.b.1), and (II.b.2), $R^2$ is —C(O)$R^7$, wherein said $R^7$ is selected from the group consisting of substituted piperidine, substituted piperazine, substituted morpholine, substituted pyrrolidine, and substituted azetidine.

In some embodiments, in each of Formulas (II.b), (II.b.1), and (II.b2), $R^2$ is selected from:

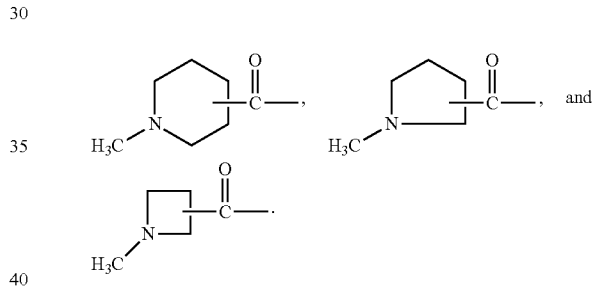

In some embodiments, in each of Formulas (II.b), (II.b.1), and (II.b.2), $R^2$ is —C(O)$NR^9R^{10}$.

In some embodiments, in each of Formulas (II.b), (II.b.1); and (II.b.2), $R^2$ is —C(O)$NH_2$.

In some embodiments, in each of Formulas (II.b), (II.b.1), and (II.b.2), $R^2$ is —C(O)$NR^9R^{10}$, wherein $R^9$ and $R^{10}$ can be the same or different, each being independently selected from alkyl.

In some embodiments, in each of Formulas (II.b), (II.b.1), and (II.b.2), $R^2$ is —C(O)$NR^9R^{10}$, wherein $R^9$ is unsubstituted heterocycloalkyl and $R^{10}$ is selected from the group consisting of H and alkyl.

In some embodiments, in each of Formulas (II.b), (II.b.1), and (II.b.2), $R^2$ is —C(O)$NR^9R^{10}$, wherein $R^9$ is substituted heterocycloalkyl and $R^{10}$ is selected from the group consisting of H and alkyl.

In some embodiments, in each of Formulas (II.b), (II.b.1), and (II.b.2), $R^2$ is —C(O)$NR^9R^{10}$, wherein $R^9$ is heterocycloalkyl substituted with from one to three substituents, which can be the same or different, each substituent being independently selected from alkyl, and $R^{10}$ is selected from the group consisting of H and alkyl.

In some embodiments, in each of Formulas (II.b), (II.b.1), and (II.b.2), $R^2$ is selected from the group consisting of: alkyl, haloalkyl, heteroalkyl, heterohaloalkyl, —C(O)$R^7$, —C(O)$OR^8$, and —C(O)$NR^9R^{10}$.

Non-limiting examples of $R^2$ include the following moieties:
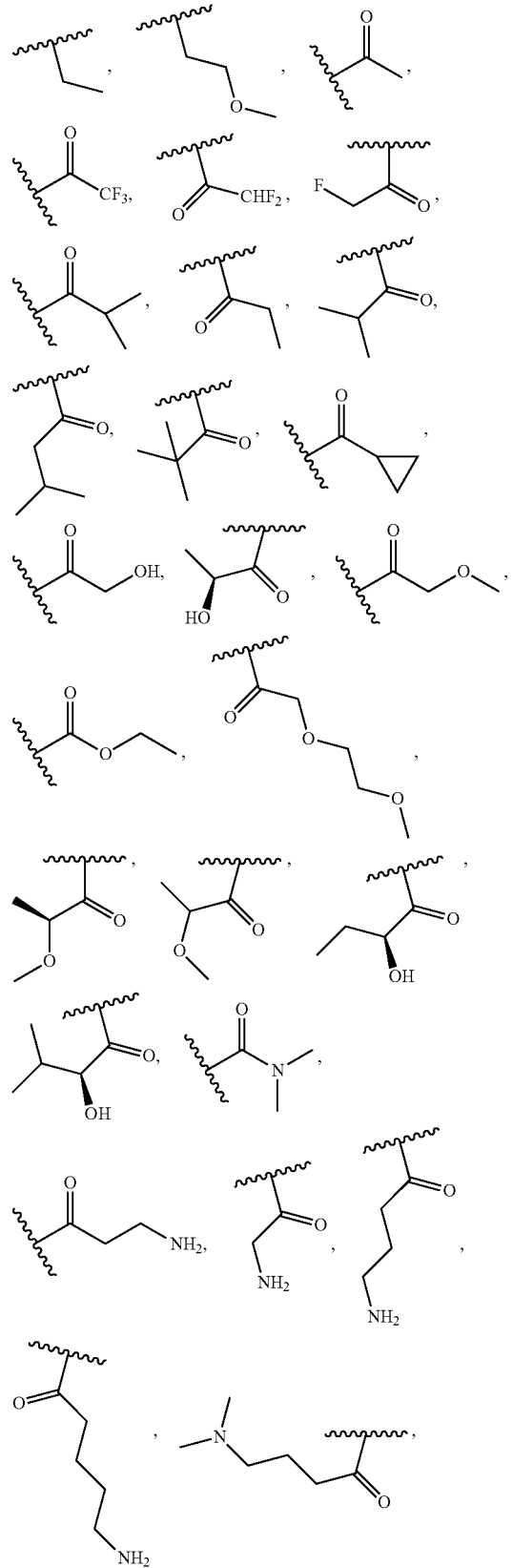
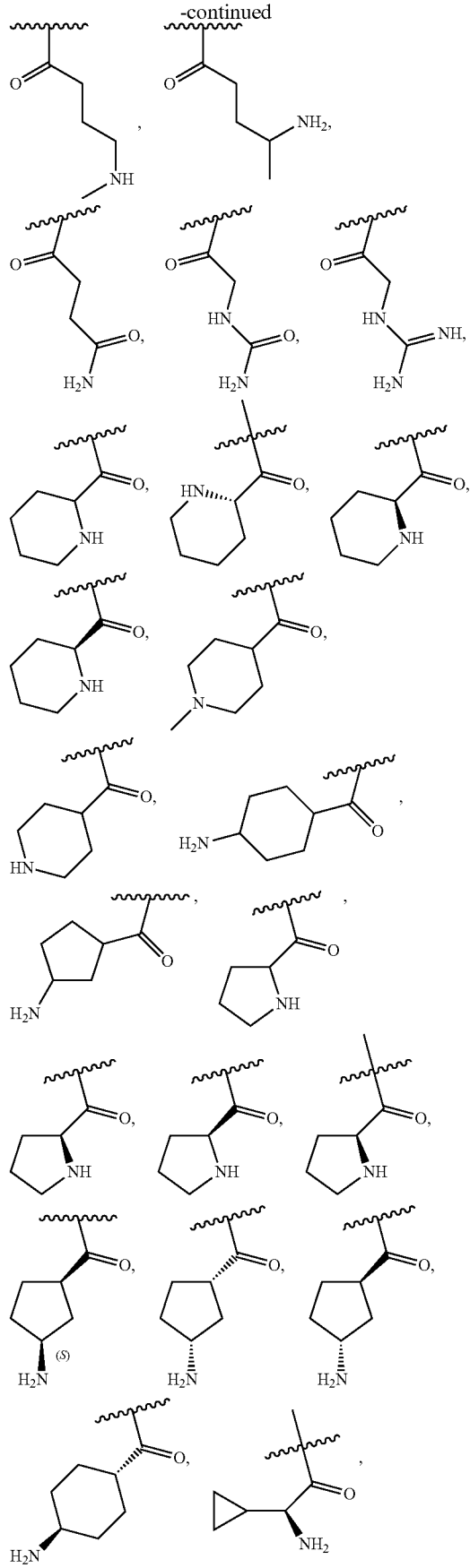

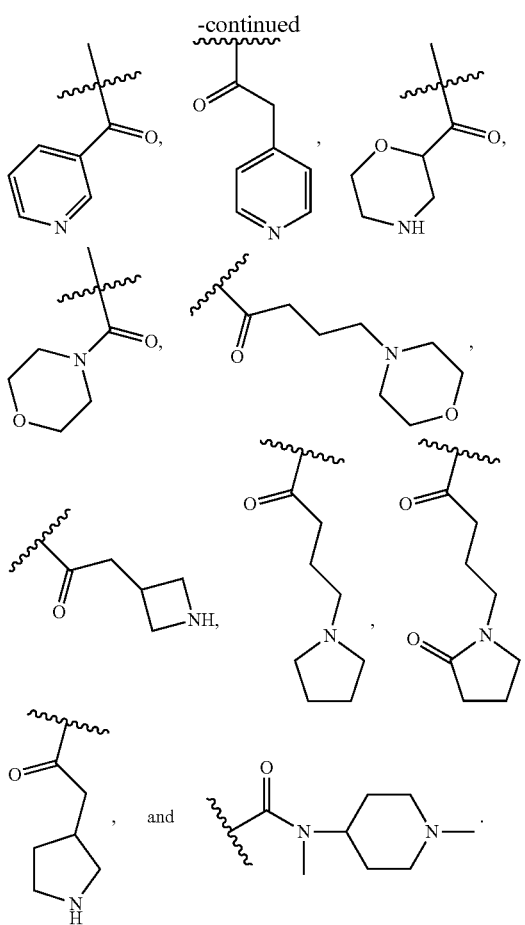

In some embodiments, in each of Formulas (II.b), (II.b.1), and (II.b.2), R² is

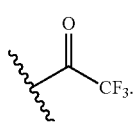

In some embodiments, in each of Formulas (II.b), (II.b.1), and (II.b.2), R² is

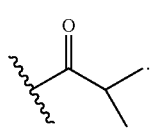 [SMILES: *C(=O)C(C)C]

In some embodiments, in each of Formulas (II.b), (II.b.1), and (II.b.2), R² is

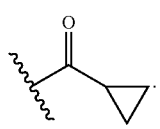

In some embodiments, in each of Formulas (II.b), (II.b.1), and (II.b.2), R² is

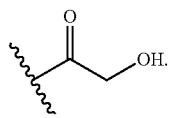 [SMILES: *C(=O)CO]

In some embodiments, in each of Formulas (II.b), (II.b.1), and (II.b.2), R² is

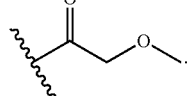

In some embodiments, in each of Formulas (II.b), (II.b.1), and (II.b.2), R² is

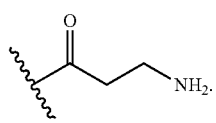 [SMILES: *C(=O)CCN]

In some embodiments, in each of Formulas (II.b), (II.b.1), and (II.b.2), R² is

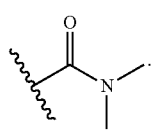 [SMILES: *C(=O)N(C)C]

In some embodiments, in each of Formulas (II.b), (II.b.1), and (II.b.2), R² is

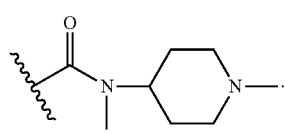

In one embodiment, the compounds of the invention have a structure shown in Formula (III.1) and include pharmaceutically acceptable salts, solvates, esters, prodrugs, or isomers of said compounds:

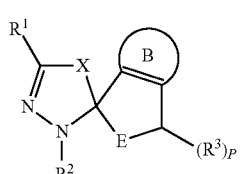

(III.1)

wherein X, R¹, R², R³, p, E, and ring B are selected independently of each other and wherein:

E is selected from the group consisting of —O—, —S—, —S(O)—, —S(O)$_2$—, —C(R$^4$)(R$^5$)—, —N(R$^6$)—, —N(C(Y)R$^7$)—, —N(C(Y)OR$^8$)—, and —N(C(Y)N(R$^9$)(R$^{10}$))—; and p is 0, 1, or 2; and ring B, X, R$^1$, R$^2$, R$^4$, R$^5$, R$^6$, R$^7$, R$^8$, R$^9$, R$^{10}$, Y, and the optional substituents on ring B are as defined in any of the embodiments described above in Formula (I).

In one embodiment, in Formula (III.1):

E is selected from the group consisting of —C(R$^4$)(R$^5$)—, —O—, —S—, —S(O)—, —S(O)$_2$—, and —N(R$^6$)—;

ring B is an unsubstituted or substituted aromatic ring or an unsubstituted or substituted 5-6-membered heteroaromatic ring having from 1-3 ring heteroatoms, which ring heteroatoms can be the same or different, each ring heteroatom being independently selected from the group consisting of N, S, O, S(O), and S(O)$_2$, said substituents on said aromatic ring or said heteroaromatic ring (when present) being independently selected from the group consisting of halogen, —CN, —NO$_2$, alkyl, heteroalkyl, haloalkyl, alkenyl, haloalkenyl, alkynyl, haloalkynyl, aryl, heteroaryl, arylalkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

R$^1$ is unsubstituted aryl or aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

R$^2$ is selected from the group consisting of —C(O)R$^7$, —C(O)NR$^9$R$^{10}$, and —C(O)OR$^8$;

p is 0 or 1; and each R$^3$ (when present) is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —C(O)R$^{24}$, —C(S)R$^{24}$, —C(O)OR$^{20}$, and —C(O)NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.1):

ring B is an unsubstituted or substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl;

R$^1$ is phenyl substituted with one to four substituents, which can be the same or different, each substituent being independently selected from the group consisting of halo, —OH, —CN, —NO$_2$, —NR$^{21}$R$^{22}$, and haloalkyl;

R$^2$ is selected from the group consisting of —C(O)R$^7$, —C(O)NR$^9$R$^{10}$, and —C(O)OR$^8$;

p is 0 or 1; and each R$^3$ (when present) is independently selected from the group consisting of alkyl, heteroalkyl, alkenyl, heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one such embodiment, in Formula (III.1):

R$^1$ is:

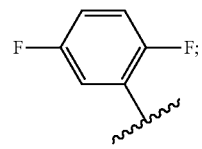

and

R$^6$ is selected from the group consisting of H, alkyl, —C(O)R$^{24}$, —C(O)OR$^{20}$, and —C(S)R$^{24}$.

In one embodiment, the compounds of the invention have a structure shown in Formula (III.2) and include pharmaceutically acceptable salts, solvates, esters, prodrugs, or isomers of said compounds:

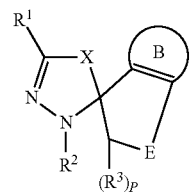

(III.2)

wherein X, R$^1$, R$^2$, R$^3$, p, E, and ring B are selected independently of each other and wherein:

E is selected from the group consisting of —O—, —S—, —S(O)—, —S(O)$_2$—, —C(R$^4$)(R$^5$)—, —N(R$^6$)—, —N(C(Y)R$^7$)—, —N(C(Y)OR$^8$)—, and —N(C(Y)N(R$^9$)(R$^{10}$))—; and p is 0, 1, or 2, and ring B, X, R$^1$, R$^2$, R$^4$, R$^5$, R$^6$, R$^7$, R$^8$, R$^9$, R$^{10}$, Y, and the optional substituents on ring B are as defined in any of the embodiments described above in Formula (I).

In one embodiment, in Formula (III.2):

E is selected from the group consisting of —C(R⁴)(R⁵)—, —O—, —S—, —S(O)—, —S(O)₂—, and —N(R⁶)—;

ring B is an unsubstituted or substituted aromatic ring or an unsubstituted or substituted 5-6-membered heteroaromatic ring having from 1-3 ring heteroatoms, which ring heteroatoms can be the same or different, each ring heteroatom being independently selected from the group consisting of N, S, O, S(O), and S(O)₂, said substituents on said aromatic ring or said heteroaromatic ring (when present) being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶;

R¹ is unsubstituted aryl or aryl substituted with one or more substituents, which can be the same or different, each substituent being independently selected from the group consisting of halogen, —CN, —NO₂, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶;

R² is selected from the group consisting of —C(O)R⁷, —C(O)NR⁹R¹⁰, and —C(O)OR⁸;

p is 0 or 1; and each R³ (when present) is independently selected from the group consisting of alkyl, heteroalkyl, alkenyl, heteroalkenyl, —CN, —NO₂, —OR¹⁹, —OC(O)OR²⁰, —NR²¹R²², —C(O)R²⁴, —C(S)R²⁴, C(O)OR²⁰, and —C(O)NR²⁵R²⁶, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO₂, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (III.2):

ring B is an unsubstituted or substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl;

R¹ is phenyl substituted with one to four substituents, which can be the same or different, each substituent being independently selected from the group consisting of halo, —OH, —CN, —NO₂, —NR²¹R²², and haloalkyl;

R² is selected from the group consisting of —C(O)R⁷, —C(O)NR⁹R¹⁰, and —C(O)OR⁸;

p is 0 or 1; and each R³ (when present) is independently selected from the group consisting of alkyl, heteroalkyl, alkenyl, heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO₂, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one such embodiment, in Formula (III.2):

R¹ is:

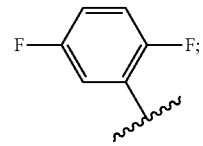 [SMILES: *c1cc(F)ccc1F]

and

R⁶ is selected from the group consisting of H, alkyl, —C(O)R²⁴, —C(O)OR²⁰, and —C(S)R²⁴.

In one embodiment, the compounds of the invention have a structure shown in Formula (III.a) and include pharmaceutically acceptable salts, solvates, esters, prodrugs, or isomers of said compounds:

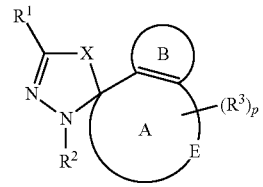

(III.a.)

wherein X, R¹, R², R³, p, E, ring A, and ring B are selected independently of each other and wherein:

ring A (including. E and the unsaturation shown) is a 5-membered cycloalkenyl or heterocycloalkenyl ring;

E is selected from the group consisting of —O—, —S—, —S(O)—, —S(O)₂—, —C(R⁴)(R⁵)—, —N(R⁶)—, —N(C(Y)R⁷)—, —N(C(Y)OR⁸)—, —N(C(Y)N(R⁹)(R¹⁰))—, —C(O)—N(R¹¹)—, —N(R¹¹)—C(O)—, —S(O)₂—N(R¹¹)—, —N(R¹¹)—S(O)₂—, —C(O)—O—, —O—C(O)—, —O—N(R⁶)—, —N(R⁶)—O—, —N(R⁶)—N(R¹²)—, —N=N—, and —C(R⁷)=N—;

ring B is a substituted or unsubstituted aromatic ring;

p, X, R¹, R², R³, R⁴, R⁵, R⁶, R⁷, R⁸, R⁹, R¹⁰R¹¹, R¹², Y, and the optional substituents on ring B are as defined in any of the embodiments described above in Formula (I).

In one embodiment, Formula (III.a) has the general structure:

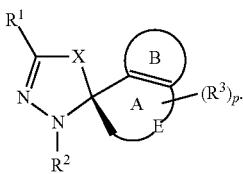

In one embodiment, Formula (III.a) has the general structure:

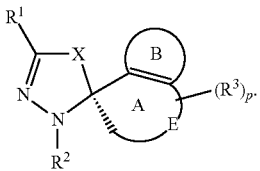

In one embodiment, in Formula (III.a.), p is 0, 1, or 2;
In one embodiment, in Formula (III.a.), X is —S—.
In one embodiment, in Formula (III.a.), X is —S(O)—.
In one embodiment, in Formula (III.a.), X is —S(O)$_2$—.
In one embodiment, in Formula (III.a.), ring A is a cycloalkenyl ring and E is —C(R$^4$)(R$^5$)—.

In one embodiment, in Formula (III.a.), ring A is a heterocycloalkenyl ring and E is selected from the group consisting of —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^6$)—O—, —N(R$^6$)—N(R$^{12}$)—, —N=N—, and —C(R$^7$)=N—. By way of non-limiting illustration, an example of a compound of Formula (III.a.) wherein E is —C(O)—N(R$^{11}$)—includes:

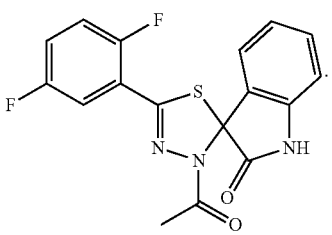 [SMILES: CC(=O)N1N=C(c2cc(F)ccc2F)SC12C(=O)Nc1ccccc12]

In one embodiment, in Formula (III.a.), ring A is a heterocycloalkenyl ring and E is selected from the group consisting of —O—, —S—, —S(O)—, —S(O)$_2$—, and —N(R$^6$)—.
In one embodiment, in Formula (III.a.), E is selected from the group consisting of —O—, —S—, —S(O)—, —S(O)$_2$—, and —N(R$^6$)—, wherein R$^6$ is selected from the group consisting of H, alkyl, —C(O)R$^{24}$, and —C(S)R$^{24}$.
In one embodiment, in Formula (III.a.), E is selected from the group consisting of —O— and —N(R$^6$)—, wherein R$^6$ is selected from the group consisting of H, alkyl, —C(O)R$^{24}$, and —C(S)R$^{24}$.
In one embodiment, in Formula (III.a.), E is —O—.
In one embodiment, in Formula (III.a.), E is —S—.
In one embodiment, in Formula (III.a.), E is —S(O)—.
In one embodiment, in Formula (III.a.), E is —S(O)$_2$—.
In one embodiment, in Formula (III.a.), E is —C(R$^4$)(R$^5$)—.
In one embodiment, in Formula (III.a.), E is —N(R$^6$)—.
In one embodiment, in Formula (III.a.), E is —N(C(Y)R$^7$)—.
In one embodiment, in Formula (III.a.), E is —N(C(Y)OR$^8$)—.
In one embodiment, in Formula (III.a.), E is —N(C(Y)N(R$^9$)(R$^{10}$))—.
In one embodiment, in Formula (III.a.), E is —C(O)—N(R$^{11}$)—.
In one embodiment, in Formula (III.a.), E is —N(R$^{11}$)—C(O)—.
In one embodiment, in Formula (III.a.), E is —S(O)$_2$—N(R$^{11}$)—.
In one embodiment, in Formula (III.a.), E is —N(R$^{11}$)—S(O)$_2$—.
In one embodiment, in Formula (III.a.), E is —C(O)—O—.
In one embodiment, in Formula (III.a.), E is —O—C(O)—.
In one embodiment, in Formula (III.a.), E is —O—N(R$^6$)—.
In one embodiment, in Formula (III.a.), E is —N(R$^6$)—O—.
In one embodiment, in Formula (III.a.), E is —N(R$^6$)—N(R$^{12}$)—.
In one embodiment, in Formula (III.a.), E is —N=N—.
In one embodiment, in Formula (III.a.), E is —C(R$^7$)=N—.
In one embodiment, in Formula (III.a.), Y is (=O).
In one embodiment, in Formula (III.a.), Y is (=S).
In one embodiment, in Formula (III.a.), Y is (=N(R$^{13}$)).
In one embodiment, in Formula (III.a.), Y is (=N(CN)).
In one embodiment, in Formula (III.a.), Y is (=N(OR$^{14}$)).
In one embodiment, in Formula (III.a.), Y is (=N(R$^{15}$)(R$^{16}$)).
In one embodiment, in Formula (III.a.), Y is (=C(R$^{17}$)(R$^{18}$)).
In one embodiment, in Formula (III.a.), B is an unsubstituted aromatic ring.
In one embodiment, in Formula (III.a.), B is an unsubstituted benzo ring, and Formula (III.a.) has the general structure:

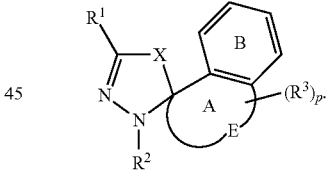

In one embodiment, in Formula (III.a.), B is an aromatic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.a.), B is a benzo ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.a.), R$^1$ is unsubstituted aryl.

In one embodiment, in Formula (III.a.), R$^1$ is unsubstituted phenyl.

In one embodiment, in Formula (III.a.), R$^1$ is unsubstituted naphthyl.

In one embodiment, in Formula (III.a.), R$^1$ is substituted aryl.

In one embodiment, in Formula (III.a.), R$^1$ is substituted phenyl.

In one embodiment, in Formula (III.a.), R$^1$ is substituted naphthyl.

In one embodiment, in Formula (III.a.), R$^1$ is aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.a.), R$^1$ is phenyl substituted with one or more substituents, which can be the same or different, each substituent being independently selected from the group consisting halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.a.), R$^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In one embodiment, in Formula (III.a.), R$^1$ is selected from the group consisting of:

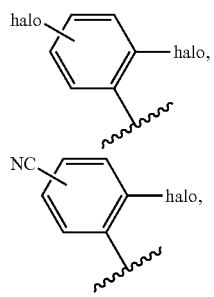
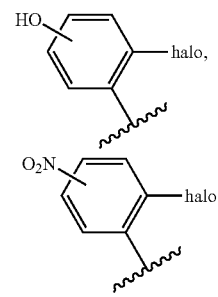

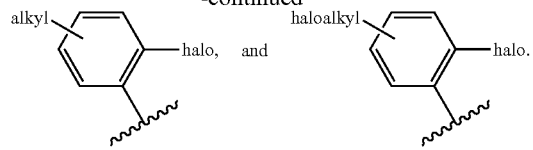

In one embodiment, in Formula (III.a.), R$^1$ is:

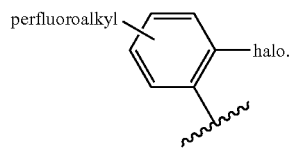

In one embodiment, in Formula (III.a.), R$^1$ is phenyl substituted with one to three fluoro groups.

In one embodiment, in Formula (III.a.), R$^1$ is phenyl substituted with two fluoro groups.

In one embodiment, in Formula (III.a.), R$^1$ is phenyl substituted with one fluoro group.

In one embodiment, in Formula (III.a.), R$^1$ is:

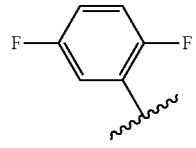 [SMILES: *c1cc(F)ccc1F]

In one embodiment, in Formula (III.a.), R$^2$ is —C(Z)R$^7$.
In one embodiment, in Formula (III.a.), R$^2$ is —C(Z)NR$^9$R$^{10}$.
In one embodiment, in Formula (III.a.), R$^2$ is —C(Z)OR$^8$.
In one embodiment, in Formula (III.a.), R$^2$ is —SO$_2$NR$^9$R$^{10}$.
In one embodiment, in Formula (III.a.), R$^2$ is alkyl.
In one embodiment, in Formula (III.a.), R$^2$ is heteroalkyl.
In one embodiment, in Formula (III.a.), R$^2$ is aryl.
In one embodiment, in Formula (III.a.), R$^2$ is heteroaryl.
In one embodiment, in Formula (III.a.), R$^2$ is cycloalkyl.
In one embodiment, in Formula (III.a.), R$^2$ is cycloalkenyl.
In one embodiment, in Formula (III.a.), R$^2$ is heterocycloalkyl.
In one embodiment, in Formula (III.a.), R$^2$ is heterocycloalkenyl.
In one embodiment, in Formula (III.a.), Z is (=O).
In one embodiment, in Formula (III.a.), Z is (=S).
In one embodiment, in Formula (III.a.), Z is (=N(R$^{13}$)).
In one embodiment, in Formula (III.a.), Z is (=N(CN)).
In one embodiment, in Formula (III.a.), Z is (=N(OR$^{14}$)).
In one embodiment, in Formula (III.a.), Z is (=N(R$^{15}$)(R$^{16}$)).
In one embodiment, in Formula (III.a.), Z is (=C(R$^{17}$)(R$^{18}$)).
In one embodiment, in Formula (III.a.), R$^2$ is —C(Z)R$^7$, and Z is (=O).
In one embodiment, in Formula (III.a.), R$^2$ is —C(O)H.
In one embodiment, in Formula (III.a.), R$^2$ is —C(O)alkyl.
In one embodiment, in Formula (III.a.), R$^2$ is —C(O)CH$_3$.
In one embodiment, in Formula (III.a.), R$^2$ is —C(O)R$^7$, wherein said R$^7$ is alkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.a.), R$^2$ is —C(O)$_{1-3}$R$^7$, wherein said R$^7$ is alkyl substituted with one to three substituents, which can be the same or different, each substituent being independently selected from the group consisting of —OR$^{19}$, —NR$^{21}$R$^{22}$, and cycloalkyl.

In one embodiment, in Formula (III.a.), R$^2$ is —C(O)R$^7$, wherein said R$^7$ is alkyl, wherein said alkyl is substituted with alkyl and —OH.

In one embodiment, in Formula (III.a.), R$^2$ is —C(O)R$^7$, wherein said R$^7$ is alkyl substituted with one to three substituents, which can be the same or different, each substituent being independently selected from the group consisting of —OH, —NH$_2$, and cyclopropyl.

In one embodiment, in Formula (III.a.), R$^2$ is —C(O)R$^7$, wherein said R$^7$ is alkyl substituted with one to two substituents, which can be the same or different, each substituent being independently selected from the group consisting of —NH$_2$, and cyclopropyl.

In one embodiment, in Formula (III.a.), R$^2$ is —C(O)R$^7$, wherein said R$^7$ is alkyl substituted with —OH.

In one embodiment, in Formula (III.a.), R$^2$ is —C(O)R$^7$, wherein said R$^7$ is unsubstituted heterocycloalkyl.

In one embodiment, in Formula (III.a.), R$^2$ is —C(O)R$^7$, wherein said R$^7$ is substituted heterocycloalkyl.

In one embodiment, in Formula (III.a.), R$^2$ is —C(O)R$^7$, wherein said R$^7$ is heterocycloalkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.a.), R$^2$ is —C(O)R$^7$, wherein said R$^7$ is selected from the group consisting of substituted piperidine, substituted piperazine, substituted morpholine, substituted pyrrolidine, and substituted azetidine.

In one embodiment, in Formula (III.a.), R$^2$ is selected from:

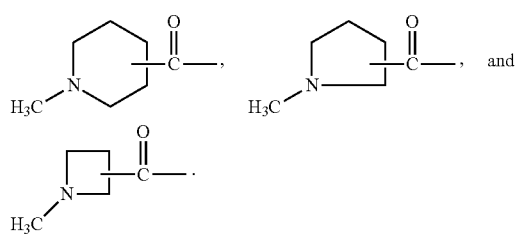

In one embodiment, in Formula (III.a.), R$^2$ is —C(O)NR$^9$R$^{10}$.

In one embodiment, in Formula (III.a.), R$^2$ is —C(O)NH$_2$.

In one embodiment, in Formula (III.a.), R$^2$ is —C(O)NR$^9$R$^{10}$, wherein R$^9$ and R$^{10}$ can be the same or different, each being independently selected from alkyl.

In one embodiment, in Formula (III.a.), R$^2$ is —C(O)NR$^9$R$^{10}$, wherein R$^9$ is unsubstituted heterocycloalkyl and R$^{10}$ is selected from the group consisting of H and alkyl.

In one embodiment, in Formula (III.a.), R$^2$ is —C(O)NR$^9$R$^{10}$, wherein R$^9$ is substituted heterocycloalkyl and R$^{10}$ is selected from the group consisting of H and alkyl.

In one embodiment, in Formula (III.a.), R$^2$ is —C(O)NR$^9$R$^{10}$, wherein R$^9$ is heterocycloalkyl substituted with from one to three substituents, which can be the same or different, each substituent being independently selected from alkyl, and R$^{10}$ is selected from the group consisting of H and alkyl.

In one embodiment, in Formula (III.a.), R$^2$ is selected from the group consisting of: alkyl, haloalkyl, heteroalkyl, heterohaloalkyl, —C(O)R$^7$, —C(O)OR$^8$, and —C(O)NR$^9$R$^{10}$.

In one embodiment, in Formula (III.a.), R$^2$ is selected from the group consisting of

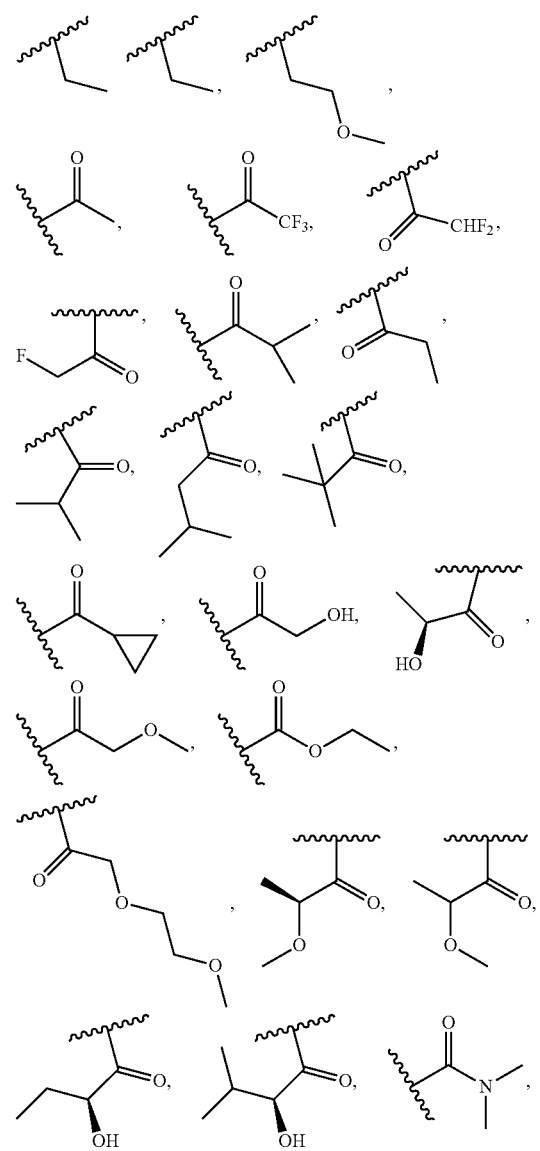

75
-continued
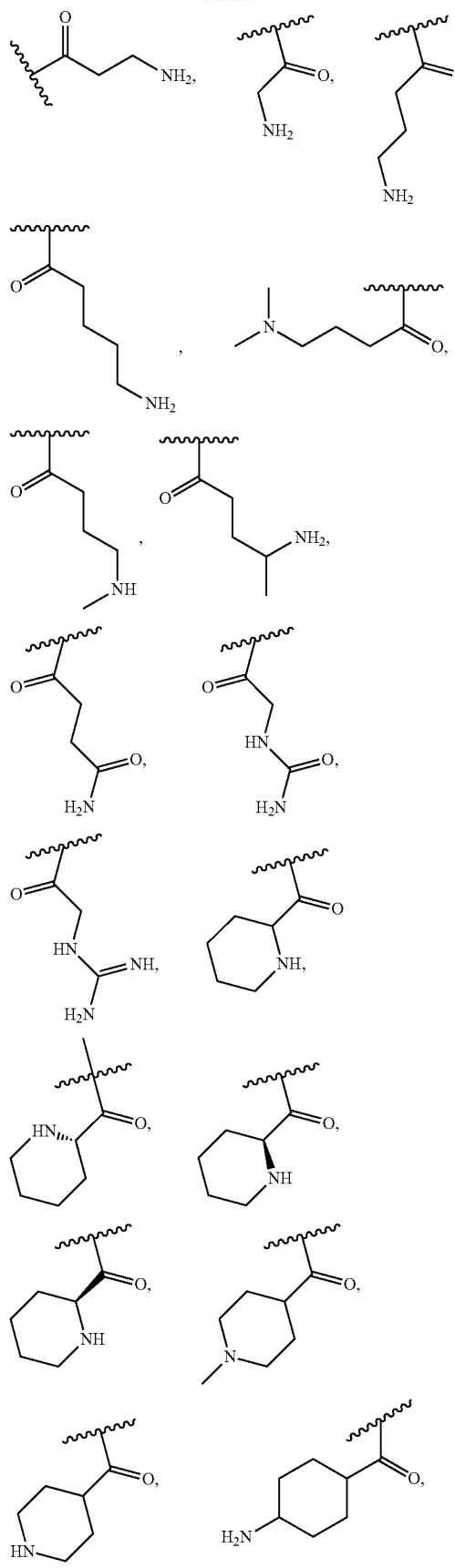
76
-continued
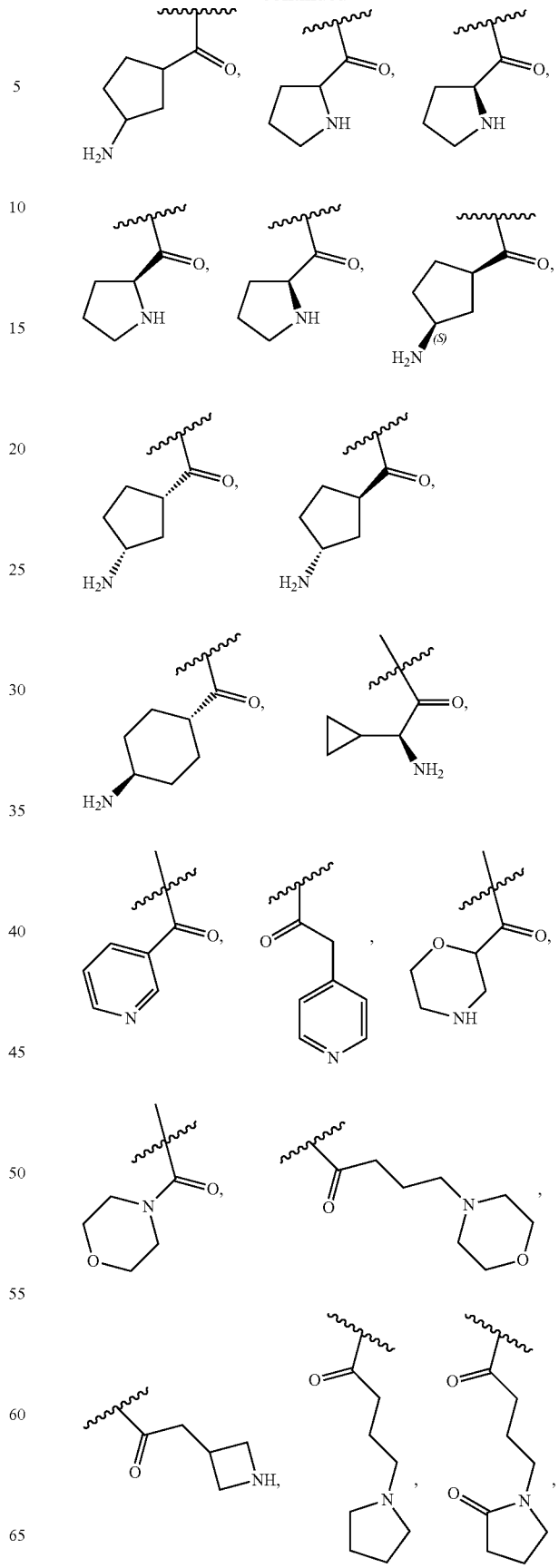

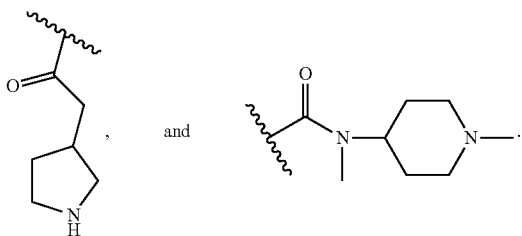

In one embodiment, in Formula (III.a.), R² is

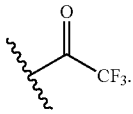

In one embodiment, in Formula (III.a.), R² is

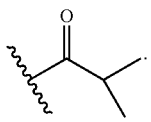

In one embodiment, in Formula (III.a.), R² is

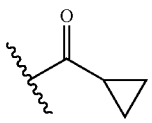

In one embodiment, in Formula (III.a.), R² is

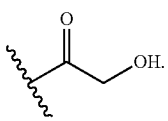 [SMILES: *C(=O)CO]

In one embodiment, in Formula (III.a.), R² is

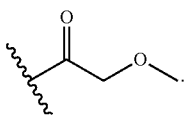

In one embodiment, in Formula (III.a.), R² is

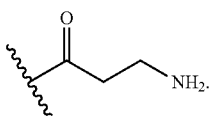 [SMILES: *C(=O)CCN]

In one embodiment, in Formula (III.a.), R² is

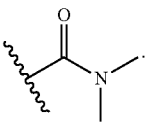 [SMILES: *C(=O)N(C)C]

In one embodiment, in Formula (III.a.), R² is

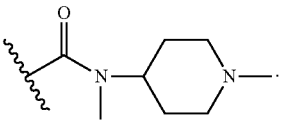

In one embodiment, in Formula (III.a.), p is 0 and R³ is not present.
In one embodiment, in Formula (III.a.), p is 1.
In one embodiment, in Formula (III.a.), p is 2.
In one embodiment, in Formula (III.a.), p is 3.
In one embodiment, in Formula (III.a.), p is 4.
In one embodiment, in Formula (III.a.), p is ≥2 and at least two groups R³ are attached to the same ring atom.
In one embodiment, in Formula (III.a.), p is 1 and R³ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (III.a.), p is 2, 3, or 4 and each R³ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (III.a.), p is 2, 3, or 4 and at least two groups R³ are bound to the same ring carbon atom, wherein each R³, which may be the same or different, is independently selected from the group consisting of alkyl; heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (III.a.), p is 2, 3, or 4 and at least two groups R³ are bound to the same ring carbon atom, wherein two R³ groups, which may be the same or different, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S.

In one embodiment, in Formula (III.a.), p is 1 or 2 and each R³ is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$, —NR$^{23}$C(O)NR$^{25}$R$^{26}$, and —NR$^{23}$—C(NH)—NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.a.), p is 1 and R$^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.a.), p is 2 and any two R$^3$ groups bound to the same ring A atom are taken together to form a —C(O)— group.

In one embodiment, in Formula (III.a.), p is 2 and any two R$^3$ groups bound to the same ring A atom are taken together to form a spiroheterocycloalkyl group having from 1 to 3 ring heteroatoms independently selected from the group consisting of —NH—, O, S, S(O), and S(O)$_2$, or spiroheterocycloalkenyl group having from 1 to 3 ring heteroatoms independently selected from the group consisting of —NH—, —NR$^6$—, O, S, S(O), and S(O)$_2$.

In one embodiment, in Formula (III.a.), R$^3$ is alkyl.
In one embodiment, in Formula (III.a.), R$^3$ is heteroalkyl.
In one embodiment, in Formula (III.a.), R$^3$ is alkenyl.
In one embodiment, in Formula (III.a.), R$^3$ is heteroalkenyl.
In one embodiment, in Formula (III.a.), R$^3$ is alkynyl.
In one embodiment, in Formula (III.a.), R$^3$ is heteroalkynyl.
In one embodiment, in Formula (III.a.), R$^3$ is aryl.
In one embodiment, in Formula (III.a.), R$^3$ is heteroaryl.
In one embodiment, in Formula (III.a.), R$^3$ is cycloalkyl.
In one embodiment, in Formula (III.a.), R$^3$ is cycloalkenyl.
In one embodiment, in Formula (III.a.), R$^3$ is heterocycloalkyl.
In one embodiment, in Formula (III.a.), R$^3$ is heterocycloalkenyl.
In one embodiment, in Formula (III.a.), R$^3$ is halogen.
In one embodiment, in Formula (III.a.), R$^3$ is —CN.
In one embodiment, in Formula (III.a.), R$^3$ is —NO$_2$.
In one embodiment, in Formula (III.a.), R$^3$ is —OR$^{19}$.
In one embodiment, in Formula (III.a.), R$^3$ is —OC(O)OR$^{20}$.
In one embodiment, in Formula (III.a.), R$^3$ is —NR$^{21}$R$^{22}$.
In one embodiment, in Formula (III.a.), R$^3$ is —NR$^{23}$SO$_2$R$^{24}$.
In one embodiment, in Formula (III.a.), R$^3$ is —NR$^{23}$C(O)OR$^{20}$.
In one embodiment, in Formula (III.a.), R$^3$ is —NR$^{23}$C(O)R$^{24}$.
In one embodiment, in Formula (III.a.), R$^3$ is —SO$_2$NR$^{25}$R$^{26}$.
In one embodiment, in Formula (III.a.), R$^3$ is —C(O)R$^{24}$.
In one embodiment, in Formula (III.a.), R$^3$ is —C(O)OR$^{25}$.
In one embodiment, in Formula (III.a.), R$^3$ is —SR$^{19}$.
In one embodiment, in Formula (III.a.), R$^3$ is —S(O)R$^{19}$.
In one embodiment, in Formula (III.a.), R$^3$ is —SO$_2$R$^{19}$.
In one embodiment, in Formula (III.a.), R$^3$ is —OC(O)R$^{24}$.
In one embodiment, in Formula (III.a.), R$^3$ is —C(O)NR$^{25}$R$^{26}$.
In one embodiment, in Formula (III.a.), R$^3$ is —NR$^{23}$C(N—CN)NR$^{25}$R$^{26}$.
In one embodiment, in Formula (III.a.), R$^3$ is —NR$^{23}$C(O)NR$^{25}$R$^{26}$.

In one embodiment, in Formula (III.a.), R$^3$ is selected from the group consisting of: methyl, ethyl, propyl (straight or branched), butyl (straight or branched), pentyl (straight or branched), phenyl, -continued

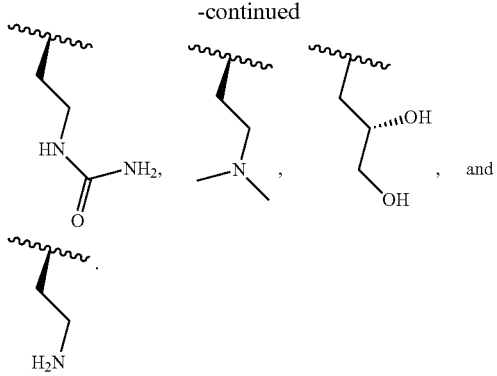

In one embodiment, in Formula (III.a.), when E is —NR⁶—, R³ is absent.

In one embodiment, Formula (III.a.) has the general structure (III.a.1):

(III.a.1)

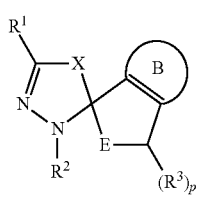

wherein X, R¹, R², R³, p, E, and ring B are selected independently of each other and wherein:

E is selected from the group consisting of —O—, —S—, —S(O)—, —S(O)₂—, —C(R⁴)(R⁵)—, —N(R⁶)—, —N(C(Y)R⁷)—, —N(C(Y)OR⁸)—, and —N(C(Y)N(R²)(R¹⁶))—; and p, X, R¹, R², R³, R⁴, R⁵, R⁶, R⁷, R⁸, R⁹, R¹⁰, Y, and the optional substituents on ring B are as defined in any of the embodiments described above in Formula (III.a.).

In one embodiment, Formula (III.a.1) has the general structure shown in Formula (III.a.1.1):

(III.a.1.1)

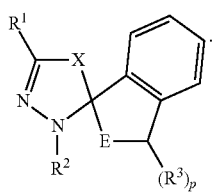

In one embodiment, Formula (III.a.) has the general structure III.a.2:

(III.a.2)

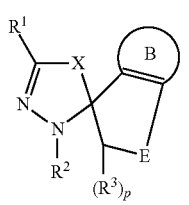

wherein X, R¹, R², R³, p, E, and ring B are selected independently of each other and wherein:

E is selected from the group consisting of —O—, —S—, —S(O)—, —S(O)₂—, —C(R⁴)(R⁵)—, —N(R⁶)—, —N(C(Y)R⁷)—, —N(C(Y)OR⁸)—, and —N(C(Y)N(R³)(R¹⁰))—; and p, X, R¹, R², R³, R⁴, R⁵, R⁶, R⁷, R⁸, R⁹, R¹⁰, Y, and the optional substituents on ring B are as defined in any of the embodiments described above in Formula (III.a.).

In one embodiment, Formula (III.a.2) has the general structure shown in Formula (III.a.2.1):

(III.a.2.1)

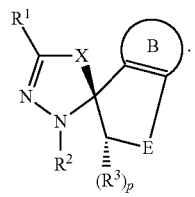

In one embodiment, Formula (III.a.2) has the general structure shown in Formula (III.a.2.2):

(III.a.2.2)

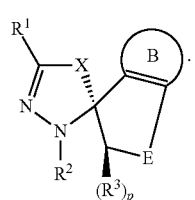

In one embodiment, Formula (III.a.2) has the general structure shown in Formula (III.a.2.3):

(III.a.2.3)

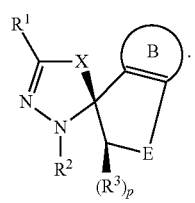

In one embodiment, Formula (III.a.2) has the general structure shown in Formula (III.a.2.4):

(III.a.2.4)

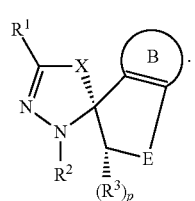

In some embodiments, in each of Formulas (III.a.1), (III.a.1.1), (III.a.2), (III.a.2.1), (III.a.2.2), (III.a.2.3), and (III.a.2.4), p is 0.

In some embodiments, in each of Formulas (III.a.1), (III.a.1.1), (III.a.2), (III.a.2.1), (III.a.2.2), (III.a.2.3), and (III.a.2.4), p is 1.

In some embodiments, in each of Formulas (III.a.1), (III.a.1.1), (III.a.2), (III.a.2.1), (III.a.2.2), (III.a.2.3), and (III.a.2.4), p is 2.

In some embodiments, in each of Formulas (III.a.1), (III.a.1.1), (III.a.2), (III.a.2.1), (III.a2.2), (III.a.2.3), and (III.a.2.4), E is —C(R$^4$)(R$^5$)—.

In some embodiments, in each of Formulas (III.a.1), (III.a.1.1), (III.a.2), (III.a.2.1), (III.a.2.2), (III.a.2.3), and (III.a.2.4), E is selected from the group consisting of —O—, —S—, —S(O)—, —S(O)$_2$—, and —N(R$^6$)—.

In some embodiments, in each of Formulas (III.a.1), (III.a.1.1), (111a.2), (III.a.2.1), (III.a.2.2), (III.a.2.3), and (III.a.2.4), E is selected from the group consisting of —O—, —S—, —S(O)—, —S(O)$_2$—, and —N(R$^6$)—, wherein R$^6$ is selected from the group consisting of H, alkyl, —C(O)R$^{24}$, and —C(S)R$^{24}$.

In some embodiments, in each of Formulas (III.a.1), (III.a.1.1), (III.a.2), (III.a.2.1), (III.a.2.2), (III.a.2.3), and (III.a.2.4), E is selected from the group consisting of —O— and —N(R$^6$)—, wherein R$^6$ is selected from the group consisting of H, alkyl, —C(O)R$^{24}$, and —C(S)R$^{24}$.

In some embodiments, in each of Formulas (III.a.1), (111a.1.1), (III.a.2), (III.a.2.1), (III.a.2.2), (III.a.2.3), and (III.a.2.4), E is —O—.

In some embodiments, in each of Formulas (III.a.1), (III.a.1.1), (III.a.2), (III.a.2.1), (III.a.2.2), (III.a.2.3), and (III.a.2.4), E is —S—.

In some embodiments, in each of Formulas (III.a.1), (III.a.1.1), (III.a.2), (III.a.2.1), (III.a.2.2), (III.a.2.3), and (III.a.2.4), E is —S(O)—.

In some embodiments, in each of Formulas (III.a.1), (III.a.1.1), (III.a.2), (III.a.2.1), (III.a.2.2), (III.a.2.3), and (III.a.2.4), E is —S(O)$_2$—.

In some embodiments, in each of Formulas (III.a.1), (III.a.1.1), (III.a.2), (III.a.2.1), (III.a.2.2), (III.a.2.3), and (III.a.2.4), E is —C(R$^4$)(R$^5$)—.

In some embodiments, in each of Formulas (III.a.1), (III.a.1.1), (III.a.2), (III.a.2.1), (III.a.2.2), (III.a.2.3), and (III.a.2.4), E is —N(R$^6$)—.

In some embodiments, in each of Formulas (III.a.1), (III.a.1.1), (III.a.2), (III.a.2.1), (III.a.2.2), (III.a.2.3), and (III.a.2.4), E is —N(C(Y)R$^7$)—.

In some embodiments, in each of Formulas (III.a.1), (III.a.1.1), (III.a.2), (III.a.2.1), (III.a.2.2), (III.a.2.3), and (III.a.2.4), E is —N(C(Y)OR$^8$)—.

In some embodiments, in each of Formulas (III.a.1), (III.a.1.1), (III.a.2), (III.a.2.1), (III.a.2.2), (III.a.2.3), and (III.a.2.4), E is —N(C(Y)N(R$^8$)(R$^{16}$))—.

In some embodiments, in each of Formulas (III.a.1), (III.a.1.1), (III.a.2), (III.a.2.1), (III.a.2.2), (III.a.2.3), and (III.a.2.4), Y is (=O).

In some embodiments, in each of Formulas (III.a.1), (III.a.1.1), (III.a.2), (III.a.2.1), (III.a.2.2), (III.a.2.3), and (III.a.2.4), Y is (=S).

In some embodiments, in each of Formulas (III.a.1), (III.a.1.1), (III.a.2), (III.a.2.1), (III.a.2.2), (III.a.2.3), and (III.a.2.4), Y is (=N(R$^{13}$)).

In some.eMbodiments, in each of Formulas (III.a.1), (III.a.2), (III.a.2.2), (III.a.2.3), and (III.a.2.4), Y is (=N(CN)).

In some embodiments, in each of Formulas (III.a.1), (III.a.1.1), (III.a.2), (III.a.2.1), (III.a.2.2), (III.a.2.3), and (III.a.2.4), Y is (=N(OR$^{14}$)).

In some embodiments, in each of Formulas (III.a.1), (III.a.1.1), (III.a.2), (III.a.2.1), (III.a.2.2), (III.a.2.3), and (III.a.2.4), Y is (=N(R$^{15}$)(R$^{16}$)).

In some embodiments, in each of Formulas (III.a.1), (III.a.1.1), (III.a.2), (III.a.2.1), (III.a.2.2), (III.a.2.3), and (III.a.2.4), Y is (=C(R$^{17}$)(R$^{18}$)).

In some embodiments, in each of Formulas (III.a.1), (III.a.1.1), (III.a.2), (III.a.2.1), (III.a.2.2), (III.a.2.3), and (III.a.2.4), R$^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In some embodiments, in each of Formulas (III.a.1), (III.a.1.1), (111.a.2.2), (III.a.2.3), and (111.a.2.4), R$^1$ is selected from the group consisting of:

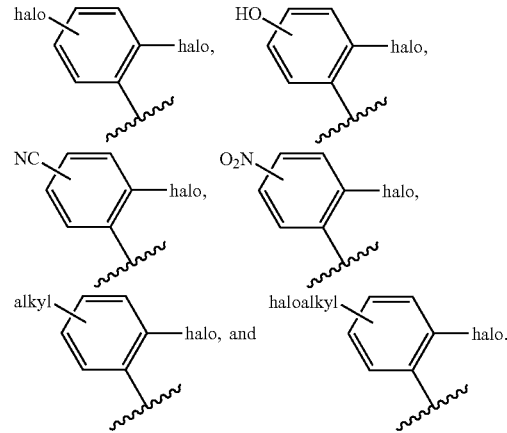

In one embodiment, in Formula (I), R$^1$ is:

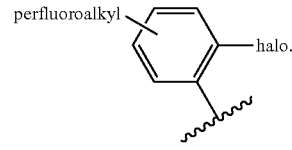

In some embodiments, in each of Formulas (III.a.1), (III.a.1.1), (III.a.2), (III.a.2.1), (III.a.2.2), (III.a.2.3), and (III.a.2.4), R$^1$ is phenyl substituted with one to three fluoro groups.

In some embodiments, in each of Formulas (III.a.1), (III.a.1.1), (III.a.2), (III.a.2.2), (III.a.2.3), and (III.a.2.4), R$^1$ is phenyl substituted with two fluoro groups.

In some embodiments, in each of Formulas (III.a.1), (III.a.1.1), (III.a.2), (III.a.2.1), (III.a.2.2), (III.a.2.3), and (III.a.2.4), R$^1$ is phenyl substituted with one fluoro group.

In some embodiments, in each of Formulas (III.a.1), (III.a.1.1), (III.a.2), (III.a.2.1), (III.a.2.2), (III.a.2.3), and (III.a.2.4), R$^1$ is:

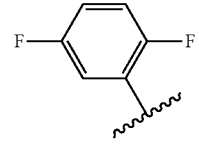 [SMILES: *c1cc(F)ccc1F]

In some embodiments, in each of Formulas (III.a.1), (III.a.1.1), (III.a.2), (III.a.2.1), (III.a.2.2), (III.a.2.3), and (III.a.2.4), R$^2$ is selected from the group consisting of: alkyl, haloalkyl, heteroalkyl, heterohaloalkyl, —C(O)R$^7$, —C(O)OR$^8$, and —C(O)NR$^9$R$^{10}$.

In some embodiments, in each of Formulas (III.a.1), (III.a.1.1), (III.a.2), (III.a.2.1), (III.a.2.2), (III.a.2.3), and (III.a.2.4), $R^2$ is selected from the group consisting of:
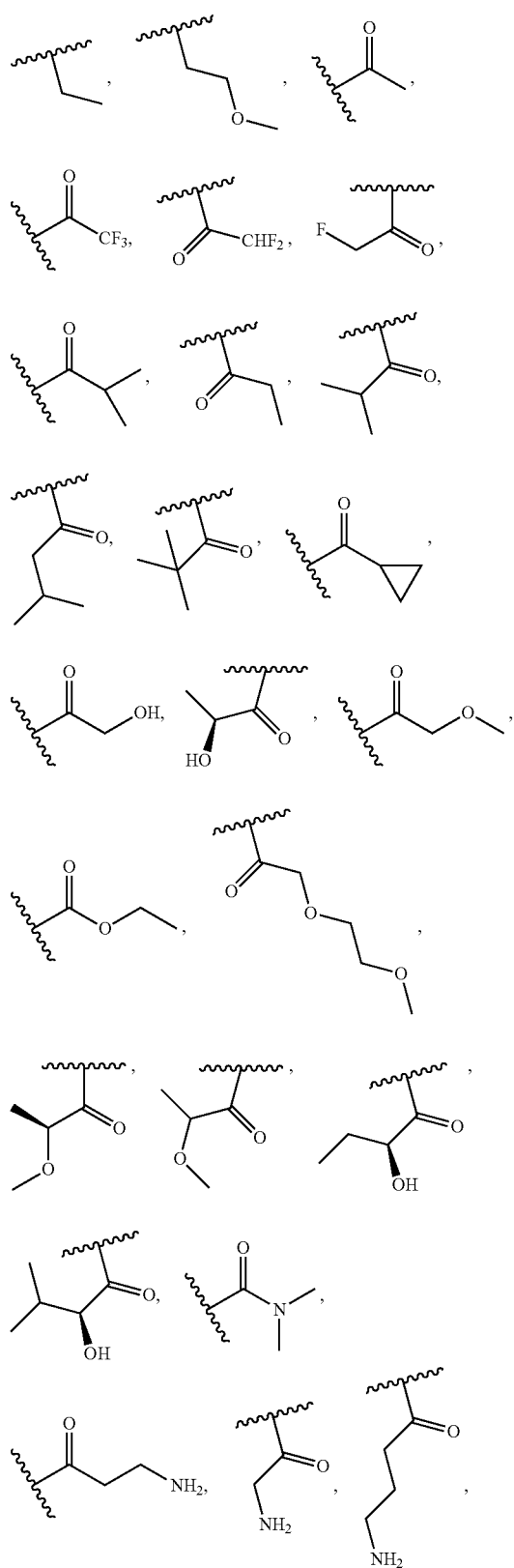
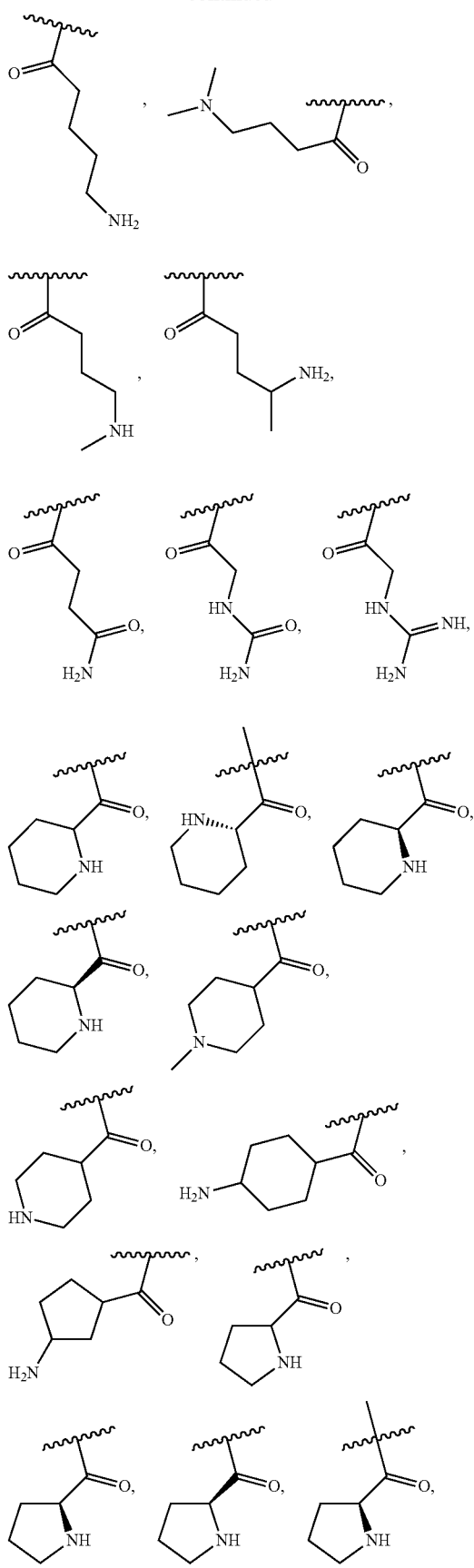

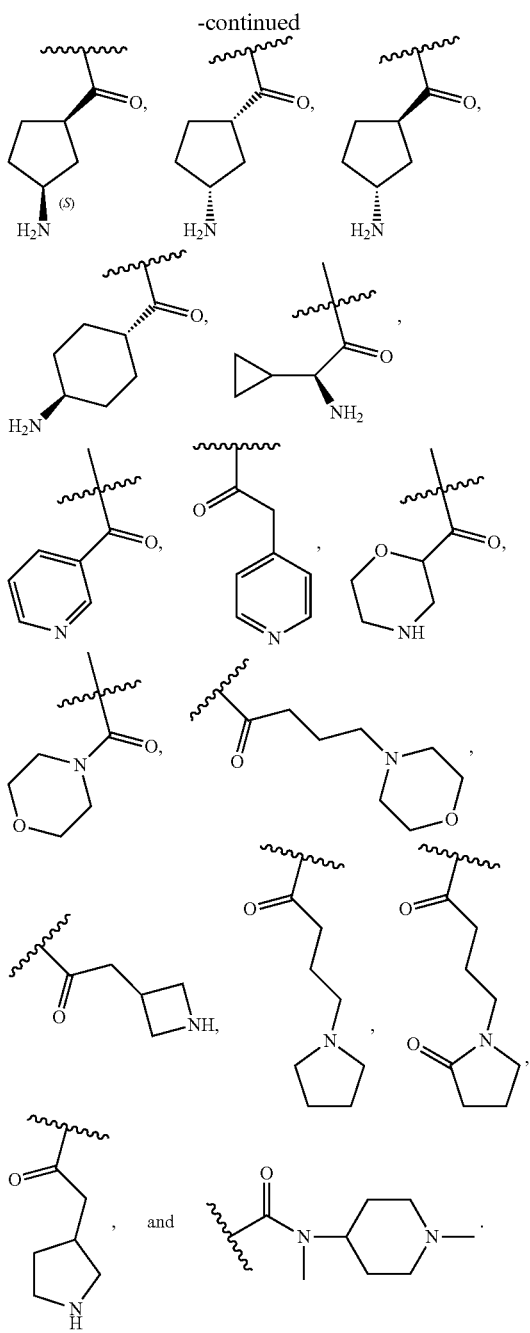

In some embodiments, in each of Formulas (III.a.1), (III.a.1.1), (III.a.2), (III.a.2.1), (III.a.2.2), (III.a.2.3), and (III.a.2.4), p is 1 or 2 and each $R^3$ is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$, —NR$^{23}$C(O)NR$^{25}$R$^{26}$, and —NR$^{23}$—C(NH)—NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (III.a.1), (III.a.1.1), (III.a.2), (III.a.2.1), (III.a.2.2), (III.a.2.3), and (III.a.2.4), p is 1 and $R^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (III.a.1), (III.a.1.1), (III.a.2), (III.a.2.1), (III.a.2.2), (III.a.2.3), and (III.a.2.4), p is 2 and any two $R^3$ groups bound to the same ring A atom are taken together to form a —C(O)— group.

In some embodiments, in each of Formulas (III.a.1), (III.a.1.1), (III.a.2), (III.a.2.1), (III.a.2.2), (III.a.2.3), and (III.a.2.4), p is 2 and any two $R^3$ groups bound to the same ring A atom are taken together to form a spiroheterocycloalkyl group having from 1 to 3 ring heteroatoms independently selected from the group consisting of —NH—, —NR$^6$—, O, S, S(O), and S(O)$_2$, or spiroheterocycloalkenyl group having from 1 to 3 ring heteroatoms independently selected from the group consisting of —NH—, —NR$^6$—, O, S, S(O), and S(O)$_2$.

In one embodiment, the compounds of the invention have a structure shown in Formula (III.b) and include pharmaceutically acceptable salts, solvates, esters, prodrugs, or isomers of said compounds:

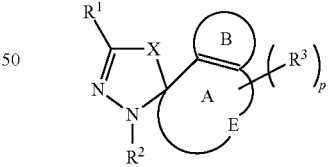

(III.b.)

wherein X, $R^1$, $R^2$, $R^3$, p, E, ring A, and ring B are selected independently of each other and wherein:

ring A (including E and the unsaturation shown) is a 5-membered cycloalkenyl or heterocycloalkenyl ring;

E is selected from the group consisting of —O—, —S—, —S(O)—, —S(O)$_2$—, —C(R$^4$)(R$^5$)—, —N(R$^6$)—, —N(C(Y)R$^7$)—, —N(C(Y)OR$^6$)—, —N(C(Y)N(R$^9$)(R$^{10}$))—, —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^6$)—O—, —N(R$^6$)—N(R$^{12}$)—, —N=N—, and —C(R$^7$)=N—;

ring B is a substituted or unsubstituted heteroaromatic ring;

and p, X, $R^1$, $R^2$, $R^3$, $R^4$, $R^5$, $R^6$, $R^7$, $R^8$, $R^9$, $R^{10}$, $R^{11}$, $R^{12}$, Y, and the optional substituents on ring B are as defined in any of the embodiments described above in Formula (I).

In one embodiment, Formula (III.b) has the general structure:

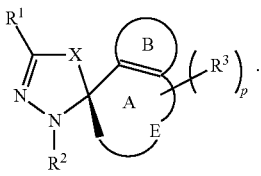

In one embodiment, Formula (III.1a) has the general structure:

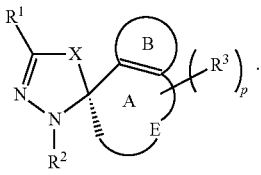

In one embodiment, in Formula (III.b), p is 0, 1, or 2.
In one embodiment, in Formula (III.b), X is S.
In one embodiment, in Formula (III.b), X is S(O).
In one embodiment, in Formula (III.b), X is $S(O)_2$.
In one embodiment, in Formula (III.b), ring A is a cycloalkenyl ring and E is —$C(R^4)(R^5)$—.
In one embodiment, in Formula (III.b), ring A is a heterocycloalkenyl ring and E is selected from the group consisting of —C(O)—$N(R^{11})$—, —$N(R^{11})$—C(O)—, —$S(O)_2$—$N(R^{11})$—, —$N(R^{11})$—$S(O)_2$—, —C(O)—O—, —O—C(O)—, —O—$N(R^6)$—, —$N(R^6)$—O—, —$N(R^6)$—$N(R^{12})$—, —N=N—, and —$C(R^7)$=N—. By way of non-limiting illustration, an example of a compound of Formula (III.a.) wherein E is —C(O)—$N(R^{11})$—< includes:

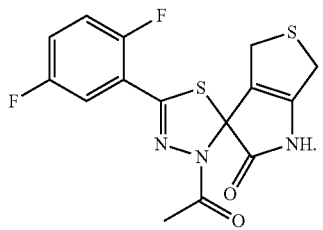 [SMILES: CC(=O)N1N=C(c2cc(F)ccc2F)SC12C(=O)NC1=C2CSC1]

In one embodiment, in Formula (III.b), ring A is a heterocycloalkenyl ring and E is selected from the group consisting of —O—, —S—, —S(O)—, —$S(O)_2$—, and —$N(R^6)$—.
In one embodiment, in Formula (III.b), E is selected from the group consisting of —O—, —S—, —S(O)—, —$S(O)_2$—, and —$N(R^6)$—, wherein $R^6$ is selected from the group consisting of H, alkyl, —$C(O)R^{24}$, and —$C(S)R^{24}$.
In one embodiment, in Formula (III.b), E is selected from the group consisting of —O— and —$N(R^6)$—, wherein $R^6$ is selected from the group consisting of H, alkyl, —$C(O)R^{24}$, and —$C(S)R^{24}$.
In one embodiment, in Formula (III.b), E is —O—.
In one embodiment, in Formula (III.b), E is —S—.
In one embodiment, in Formula (III.b), E is —S(O)—.

In one embodiment, in Formula (III.b), E is —$S(O)_2$—.
In one embodiment, in Formula (III.b), E is —$C(R^4)(R^5)$—.
In one embodiment, in Formula (III.b), E is —$N(R^6)$—.
In one embodiment, in Formula (III.b), E is —N(C(Y)$R^7$)—.
In one embodiment, in Formula (III.b), E is —N(C(Y)$OR^6$)—.
In one embodiment, in Formula (III.b), E is —N(C(Y)N($R^9$)($R^{10}$)),
In one embodiment, in Formula (III.b), E is —C(O)—N($R^{11}$)—.
In one embodiment, in Formula (III.b), E is —N($R^{11}$)—C(O)—.
In one embodiment, in Formula (III.b), E is —$S(O)_2$—N($R^{11}$)—.
In one embodiment, in Formula (III.b), E is —N($R^{11}$)—$S(O)_2$—.
In one embodiment, in Formula (III.b), E is —C(O)—O—.
In one embodiment, in Formula (III.b), E is —O—C(O)—.
In one embodiment, in Formula (III.b), E is —O—N($R^6$)—.
In one embodiment, in Formula (III.b), E is —N($R^6$)—O—.
In one embodiment, in Formula (III.b), E is —N($R^6$)—N($R^{12}$)—.
In one embodiment, in Formula (III.b), E is —N=N—.
In one embodiment, in Formula (III.b), E is —$C(R^7)$=N—.
In one embodiment, in Formula (III.b), Y is (=O).
In one embodiment, in Formula (III.b), Y is (=S).
In one embodiment, in Formula (III.b), Y is (=N($R^{11}$)).
In one embodiment, in Formula (III.b), Y is (=N(CN)).
In one embodiment, in Formula (III.b), Y is (=N($OR^{14}$)).
In one embodiment, in Formula (III.b), Y is (=N($R^{15}$)($R^{16}$)).
In one embodiment, in Formula (III.b), Y is (=$C(R^{11})(R^{18})$).
In one embodiment, in Formula (III.b), B is an unsubstituted heteroaromatic ring.
In one embodiment, in Formula (III.b), B is an unsubstituted 5-6-membered heteroaromatic ring having from 1-3 ring heteroatoms, which can be the same or different, each hetero ring atom being independently selected from the group consisting of N, S, O, S(O), and $S(O)_2$.
In one embodiment, in Formula (III.b), B is a heteroaromatic ring which is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NIR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{16}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (III.b), B is a 5-6-membered heteroaromatic ring having from 1-3 ring heteroatoms, which can be the same or different, each hetero ring atom being independently selected from the group consisting of N, S, O, S(O), and $S(O)_2$, which heteroaromatic ring is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{16}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (III.b.), B is an unsubstituted 6-membered heteroaromatic ring having from 1-3 ring heteroatoms, which can be the same or different, each hetero ring atom being independently selected from the group consisting of N, S, and O.

In one embodiment, in Formula (III.b.), B is a 6-membered heteroaromatic ring having from 1-3 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$S(O)R^{19}$, —$SO_2R^{19}$, —$OC(O)R^{24}$, —$C(O)NR^{25}R^{26}$, —$NR^{23}C(N—CN)NR^{25}R^{25}$ and —$NR^{23}C(O)NR^{25}R^{26}$.

In one embodiment, in Formula (III.b.), B is an unsubstituted 6-membered heteroaromatic ring having 2 ring heteroatoms, each ring heteroatom being independently selected from of N, S, and O.

In one embodiment, in Formula (IIIt.), B is a 6-membered heteroaromatic ring having 2 ring heteroatoms, each ring heteroatom being independently selected from of N, S, and O, which heteroaromatic ring is substituted with one or more substituents, which can be the same or different, each substituent being independently selected from the group consisting of halogen, —CN, —$NO_2$, alkyl, heteroalkyl, haloalkyl, —$NR^{21}R^{22}$, —$C(O)R^{24}$, —$C(O)OR^{20}$, —$SR^{19}$, —$S(O)R^{19}$, —$SO_2R^{19}$, —$OC(O)R^{24}$, and —$C(O)NR^{25}R^{26}$.

In one embodiment, in Formula (III.b.), B is an unsubstituted 5-membered heteroaromatic ring having from 1-2 ring heteroatoms, which can be the same or different, each hetero ring atom being independently selected from the group consisting of N, S, and O.

In one embodiment, in Formula (III.b.), B is a 5-membered heteroaromatic ring having from 1-2 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$S(O)R^{19}$, —$SO_2R^{19}$, —$OC(O)R^{24}$, —$C(O)NR^{25}R^{26}$, —$NR^{23}C(N—CN)NFt^{25}R^{26}$ and —$NR^{23}C(O)NR^{25}R^{26}$.

In one embodiment, in Formula (III.b.), B is an unsubstituted 5-membered heteroaromatic ring having 1 ring heteroatom selected from of N, S, and O.

In one embodiment, in Formula (III.b.), B is a 5-membered heteroaromatic ring having 1 ring heteroatom selected from of N, S, and O, which heteroaromatic ring is substituted with one or more substituents, which can be the same or different, each substituent being independently selected from the group consisting of halogen, —CN, —$NO_2$, alkyl, heteroalkyl, haloalkyl, —$OR^{19}$, —$NR^{21}R^{22}$, —$C(O)R^{24}$, —$C(O)OR^{20}$, —$SR^{19}$, —$S(O)R^{19}$, —$SO_2R^{19}$, —$OC(O)R^{24}$, and —$C(O)NR^{25}R^{26}$.

In one embodiment, in Formula (III.13.), B is a 5-membered heteroaromatic ring having S as the ring heteroatom, which heteroaromatic ring is substituted with one or more substituents, which can be the same or different, each substituent being independently selected from the group consisting halogen, —CN, —$NO_2$, alkyl, heteroalkyl, haloalkyl, —$OR^{19}$, —$NR^{21}R^{22}$, —$C(O)OR^{20}$, —$SR^{19}$, —$S(O)R^{19}$, —$SO_2R^{19}$, —$OC(O)R^{24}$, and —$C(O)NR^{25}R^{26}$.

In one embodiment, in Formula (III.b.), B is an unsubstituted 5-membered heteroaromatic ring having S as the ring heteroatom.

In one embodiment, in Formula (III.b.), B is selected from the group consisting of

In one embodiment, in Formula (III.b.), $R^1$ is unsubstituted aryl.

In one embodiment, in Formula (III.b.), $R^1$ is unsubstituted phenyl.

In one embodiment, in Formula (III.b.), $R^1$ is unsubstituted naphthyl.

In one embodiment, in Formula (III.b.), $R^1$ is substituted aryl.

In one embodiment, in Formula (III.b.), $R^1$ is substituted phenyl.

In one embodiment, in Formula (III.b.), $R^1$ is substituted naphthyl.

In one embodiment, in Formula (III.b.), $R^1$ is aryl substituted with one or more substituents, which can be the same or different, each substituent being independently selected from the group consisting of halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula (III.b.), $R^1$ is phenyl substituted with one or more substituents, which can be the same or different, each substituent being independently selected from the group consisting halogen, —CN, —$NO_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)$ $OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In one embodiment, in Formula $R^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In one embodiment, in Formula (III.b.), $R^1$ is selected from the group consisting of:

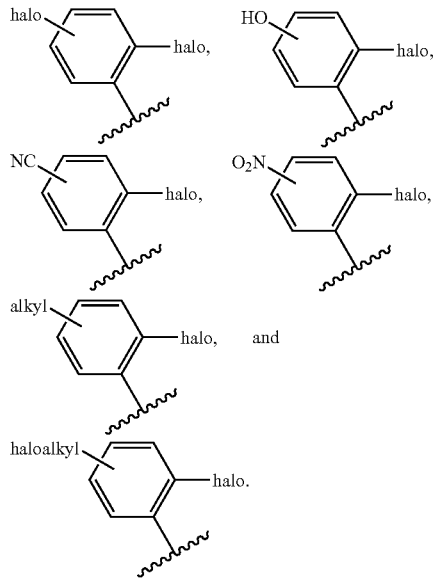

In one embodiment, in Formula $R^1$ is:

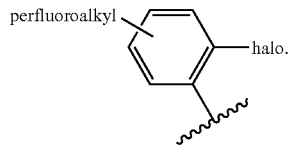

In one embodiment, in Formula (III.b.), is phenyl substituted with one to three fluoro groups.

In one embodiment, in Formula (III.b.), $R^1$ is phenyl substituted with two fluoro groups.

In one embodiment, in Formula (III.b.), $R^1$ is phenyl substituted with one fluoro group.

In one embodiment, in Formula (III.b.), $R^1$ is:

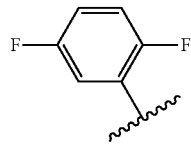 [SMILES: *c1cc(F)ccc1F]

In one embodiment, in Formula (III.b.), $R^2$ is —C(Z)R$^7$.
In one embodiment, in Formula (III.b.), $R^2$ is —C(Z)NR$^9$R$^{10}$.
In one embodiment, in Formula (III.b.), $R^2$ is —C(Z)OR$^B$.
In one embodiment, in Formula (III.b.), $R^2$ is —SO$_2$NR$^9$R$^{10}$.
In one embodiment, in Formula (III.b.), $R^2$ is alkyl.
In one embodiment, in Formula (III.b.), $R^2$ is heteroalkyl.
In one embodiment, in Formula (III.b.), $R^2$ is aryl.
In one embodiment, in Formula (IIIb.), $R^2$ is heteroaryl.
In one embodiment, in Formula (III.b.), $R^2$ is cycloalkyl.
In one embodiment, in Formula (III.b.), $R^2$ is cycloalkenyl.
In one embodiment, in Formula (III.b.), $R^2$ is heterocycloalkyl.
In one embodiment, in Formula (III.b.), $R^2$ is heterocycloalkenyl.
In one embodiment, in Formula (III.b.), Z is (=O).
In one embodiment, in Formula (III.b.), Z is (=S).
In one embodiment, in Formula (III.b.), Z is (=N(R$^{13}$)).
In one embodiment, in Formula (III.b.), Z is (=N(CN)).
In one embodiment, in Formula (III.b.), Z is (=N(OR$^{14}$)).
In one embodiment, in Formula (III.b.), Z is (=N(R$^{15}$)(R$^{16}$)).
In one embodiment, in Formula (III.b.), Z is (=C(R$^{17}$)(R$^{18}$)).
In one embodiment, in Formula (III.b.), $R^2$ is —C(Z)R$^7$, and Z is (=O).
In one embodiment, in Formula (III.b.), $R^2$ is —C(O)H.
In one embodiment, in Formula (III.b.), $R^2$ is —C(O)alkyl.
In one embodiment, in Formula (III.b.), $R^2$ is —C(O)CH$_3$.
In one embodiment, in Formula (III.b.), $R^2$ is —C(O)R$^7$, wherein said R$^7$ is alkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.b.), $R^2$ is —C(O)R$^7$, wherein said R$^7$ is alkyl substituted with one to three substituents, which can be the same or different, each substituent being independently selected from the group consisting of —OR$^{19}$, —NR$^{21}$R$^{22}$, and cycloalkyl.

In one embodiment, in Formula (III.b.), $R^2$ is —C(O)R$^7$, wherein said R$^7$ is alkyl, wherein said alkyl is substituted with alkyl and —OH.

In one embodiment, in Formula (III.13.), $R^2$ is —C(O)R$^7$, wherein said R$^7$ is alkyl substituted with one to three substituents, which can be the same or different, each substituent being independently selected from the group consisting of —OH, —NH$_2$, and cyclopropyl.

In one embodiment, in Formula (III.b.), $R^2$ is —C(O)R$^7$, wherein said R$^7$ is alkyl substituted with one to two substituents, which can be the same or different, each substituent being independently selected from the group consisting of —NH$_2$, and cyclopropyl.

In one embodiment, in Formula (III.b.), $R^2$ is —C(O)R$^7$, wherein said R$^7$ is alkyl substituted with —OH.

In one embodiment, in Formula (III.b.), $R^2$ is —C(O)R$^7$, wherein said R$^7$ is unsubstituted heterocycloalkyl.

In one embodiment, in Formula (III.b.), $R^2$ is —C(O)R$^7$, wherein said R$^7$ is substituted heterocycloalkyl.

In one embodiment, in Formula (III.b.), $R^2$ is —C(O)R$^7$, wherein said R$^7$ is heterocycloalkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.b.), R$^2$ is —C(O)R$^7$, wherein said R$^7$ is selected from the group consisting of substituted piperidine, substituted piperazine, substituted morpholine, substituted pyrrolidine, and substituted azetidine.

In one embodiment, in Formula (III.b.), R$^2$ is selected from:

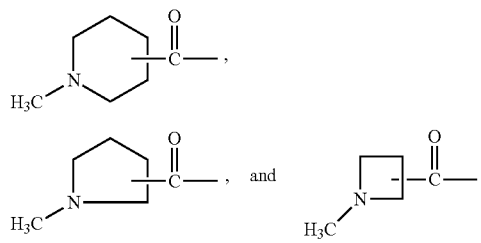

In one embodiment, in Formula (III.b.), R$^2$ is —C(O)NR$^9$R$^{10}$.

In one embodiment, in Formula (III.b.), R$^2$ is —C(O)NH$_2$.

In one embodiment, in Formula (III.b.), R$^2$ is —C(O)NR$^9$R$^{10}$, wherein R$^9$ and R$^{10}$ can be the same or different, each being independently selected from alkyl.

In one embodiment, in Formula (III.b.), R$^2$ is —C(O)NR$^9$R$^{10}$, wherein R$^9$ is unsubstituted heterocycloalkyl and R$^{10}$ is selected from the group consisting of H and alkyl.

In one embodiment, in Formula (III.b.), R$^2$ is —C(O)NR$^9$R$^{10}$, wherein R$^9$ is substituted heterocycloalkyl and R$^{10}$ is selected from the group consisting of H and alkyl.

In one embodiment, in Formula (III.b.), R$^2$ is —C(O)NR$^9$R$^{10}$, wherein R$^9$ is heterocycloalkyl substituted with from one to three substituents, which can be the same or different, each substituent being independently selected from alkyl, and R$^{10}$ is selected from the group consisting of H and alkyl.

In one embodiment, in Formula (III.b.), R$^2$ is selected from the group consisting of: alkyl, haloalkyl, heteroalkyl, heterohaloalkyl, —C(O)R$^7$, —C(O)OR$^8$, and —C(O)NR$^9$R$^{10}$.

In one embodiment, in Formula (III.b.), R$^2$ is selected from the group consisting of

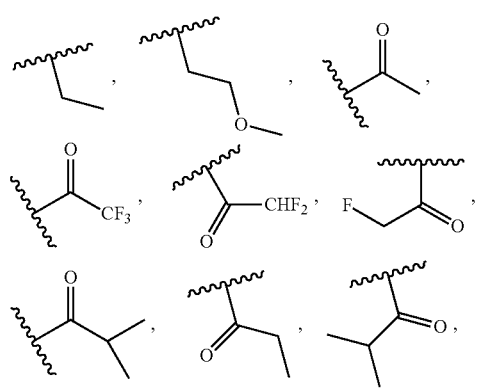

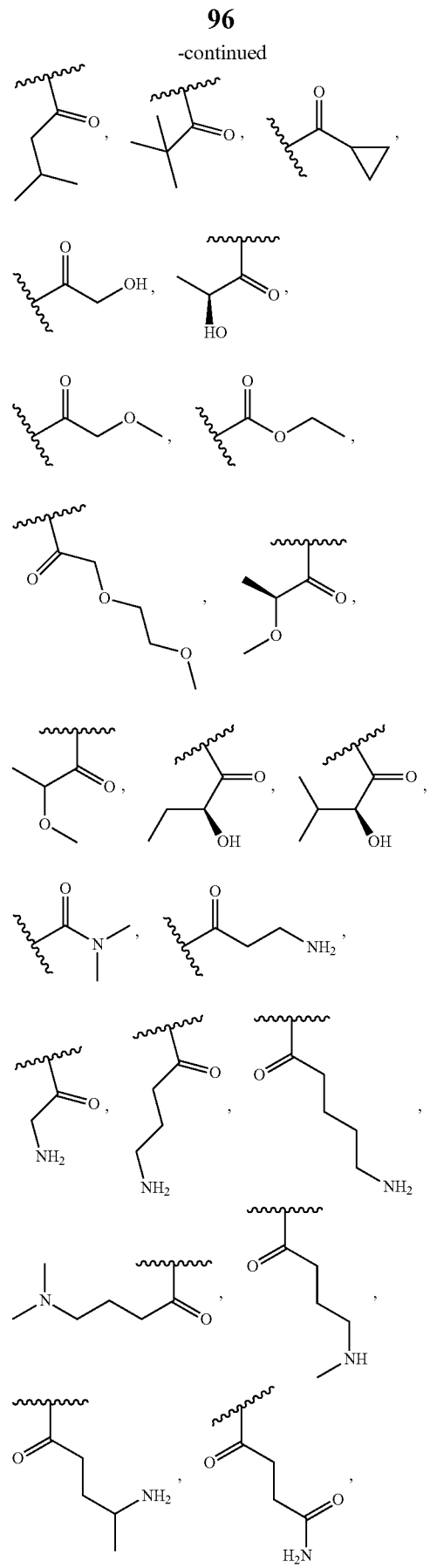

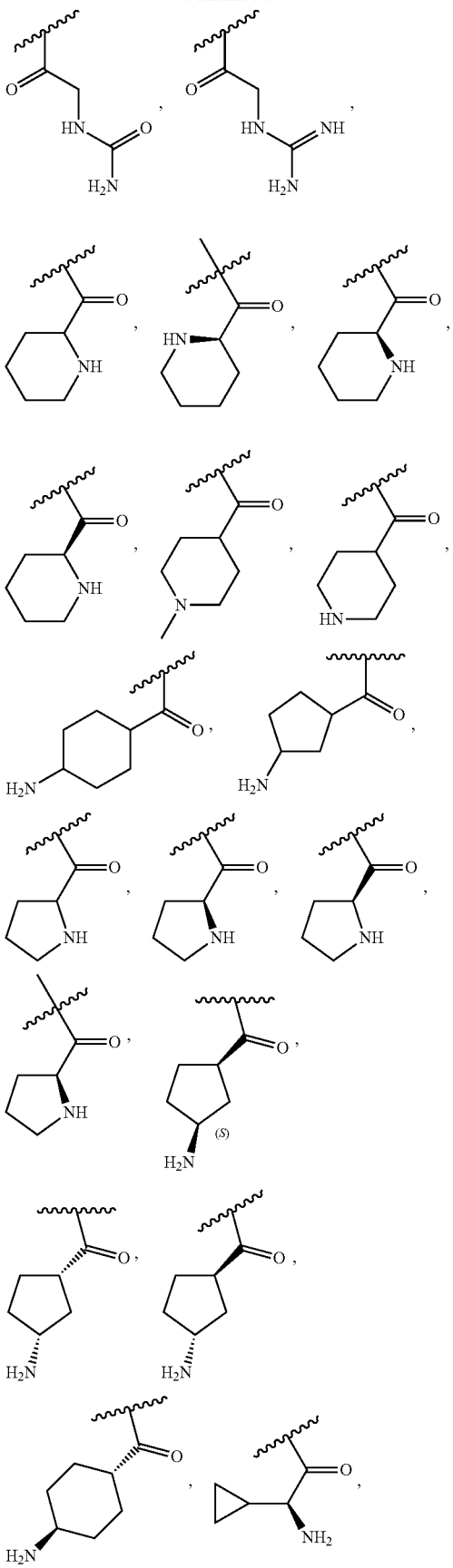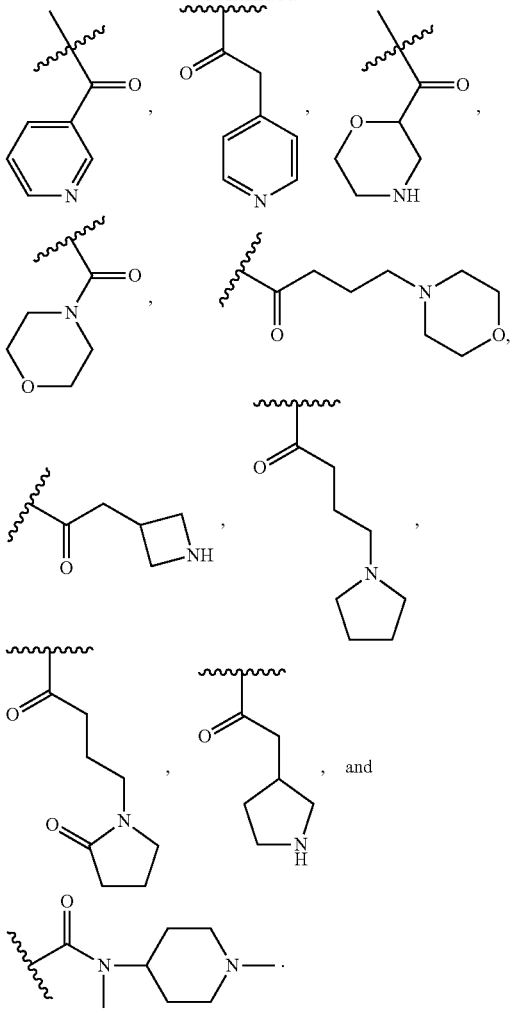
In one embodiment, in Formula (III.b.), $R^2$ is
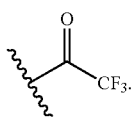
In one embodiment, in Formula (III.b.), $R^2$ is
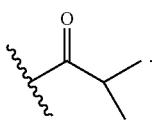 [SMILES: *C(=O)C(C)C]
In one embodiment, in Formula (III.b.), $R^2$ is
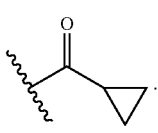 [SMILES: *C(=O)C1CC1]

In one embodiment, in Formula (III.b.), $R^2$ is

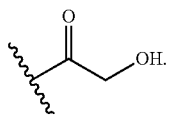 [SMILES: *C(=O)CO]

In one embodiment, in Formula $R^2$ is

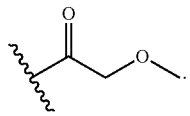

In one embodiment, in Formula (III.b.), $R^2$ is

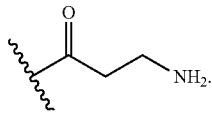 [SMILES: *C(=O)CCN]

In one embodiment, in Formula $R^2$ is

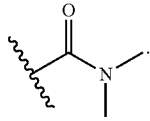 [SMILES: *C(=O)N(C)C]

In one embodiment, in Formula (III.b.), $R^2$ is

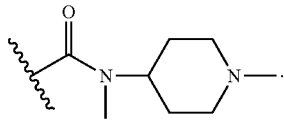

In one embodiment, in Formula (III.b.), p is 0 and $R^3$ is not present.
In one embodiment, in Formula (III.b.), p is 1.
In one embodiment, in Formula (III.b.), p is 2.
In one embodiment, in Formula (III.b.), p is 3.
In one embodiment, in Formula (III.b.), p is 4.
In one embodiment, in Formula (III.b.), p is >2 and at least two groups $R^3$ are attached to the same ring atom.

In one embodiment, in Formula (III.b.), p is 1 and $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.b) p is 2, 3, or 4 and each $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.b.), p is 2, 3, or 4 and at least two groups $R^3$ are bound to the same ring carbon atom, wherein each $R^3$, which may be the same or different, is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, NO$_2$, OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.b.), p is 2, 3, or 4 and at least two groups $R^3$ are bound to the same ring carbon atom, wherein two $R^3$ groups, which may be the same or different, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S.

In one embodiment, in Formula (III.b.), p is 1 or 2 and each $R^3$ is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$, —NR$^{23}$C(O)NR$^{25}$R$^{26}$, and —NR$^{23}$—C(NH)—NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.b.), p is 1 and $R^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (III.b.), p is 2 and any two $R^3$ groups bound to the same ring A atom are taken together to form a —C(O)— group.

In one embodiment, in Formula (III.b.), p is 2 and any two $R^3$ groups bound to the same ring A atom are taken together to form a spiroheterocycloalkyl group having from 1 to 3 ring heteroatoms independently selected from the group consisting of —NH—, —NR$^6$—, O, S, S(O), and S(O)$_2$, or spiroheterocycloalkenyl group having from 1 to 3 ring heteroatoms independently selected from the group consisting of —NH—, —NR$^6$—, O, S, S(O), and S(O)$_2$.

In one embodiment, in Formula (III.b.), R$^3$ is alkyl.
In one embodiment, in Formula (III.b.), R$^3$ is heteroalkyl.
In one embodiment, in Formula (III.b.), R$^3$ is alkenyl.
In one embodiment, in Formula (III.b.), R$^3$ is heteroalkenyl.
In one embodiment, in Formula (III.b.), R$^3$ is alkynyl.
In one embodiment, in Formula (III.b.), R$^3$ is heteroalkynyl.
In one embodiment, in Formula (III.b.), R$^3$ is aryl.
In one embodiment, in Formula (III.b.), R$^3$ is heteroaryl.
In one embodiment, in Formula (III.b.), R$^3$ is cycloalkyl.
In one embodiment, in Formula (III.b.), R$^3$ is cycloalkenyl.
In one embodiment, in Formula (III.b.), R$^3$ is heterocycloalkyl.
In one embodiment, in Formula (III.b.), R$^3$ is heterocycloalkenyl.
In one embodiment, in Formula (III.b.), R$^3$ is halogen.
In one embodiment, in Formula (III.b.), R$^3$ is —CN.
In one embodiment, in Formula (III.b.), R$^3$ is —NO$_2$.
In one embodiment, in Formula (III.b.), R$^3$ is —OR$^{19}$.
In one embodiment, in Formula (III.b.), R$^3$ is —OC(O)OR$^{20}$.
In one embodiment, in Formula (III.b.), R$^3$ is —NR$^{21}$R$^{22}$.
In one embodiment, in Formula (III.b.), R$^3$ is —NR$^{23}$SO$_2$R$^{24}$.
In one embodiment, in Formula (III.b.), R$^3$ is —NR$^{23}$C(O)OR$^{20}$.
In one embodiment, in Formula (III.b.), R$^3$ is —NR$^{23}$C(O)R$^{24}$.
In one embodiment, in Formula (III.b.), R$^3$ is —SO$_2$NR$^{25}$R$^{26}$.
In one embodiment, in Formula (III.b.), R$^3$ is —C(O)R$^{24}$.
In one embodiment, in Formula (III.b.), R$^3$ is —C(O)OR$^{29}$.
In one embodiment, in Formula (III.b.), R$^3$ is —SR$^{19}$.
In one embodiment, in Formula (III.b.), R$^3$ is —S(O)R$^{19}$.
In one embodiment, in Formula (III.b.), R$^3$ is —SO$_2$R$^{19}$.
In one embodiment, in Formula (III.b.), R$^3$ is —OC(O)R$^{24}$.
In one embodiment, in Formula (III.b.), R$^3$ is —C(O)NR$^{25}$R$^{26}$.
In one embodiment, in Formula (III.b.), R$^3$ is —NR$^{23}$C(N—CN)NR$^{25}$R$^{26}$.
In one embodiment, in Formula (III.b.), R$^3$ is —NR$^{23}$C(O)NR$^{25}$R$^{26}$.
In one embodiment, in Formula (III.b.), R$^3$ is selected from the group consisting of: methyl, ethyl, propyl (straight or branched), butyl (straight or branched), pentyl (straight or branched), phenyl, In one embodiment, in Formula (III.b.), when E is —NR$^6$—, R$^3$ is absent.

In one embodiment, Formula (III.b.) has the general structure (III.b.1):

(III.b.1)

wherein X, R$^1$, R$^2$, R$^3$, p, E, and ring B are selected independently of each other and wherein:

E Is selected from the group consisting of —O—, —S—, —S(O)—, —S(O)$_2$—, —C(R$^4$)(R$^5$)—, —N(R$^6$); —N(C(Y)R$^7$)—, —N(C(Y)OR$^8$)—, and))—N(C(Y)N(R$^9$)(R$^{10}$))—;

and p, X, R$^1$, R$^2$, R$^3$, R$^4$, R$^5$, R$^6$, R$^7$, R$^8$, R$^9$, R$^{10}$, Y, and the optional substituents on ring B are as defined in any of the embodiments described above in Formula (III.b.).

In one embodiment, Formula (III.b) has the general structure shown in Formula (III.b.2):

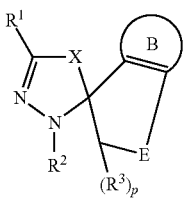
(III.b.2)

In one embodiment, Formula (III.b) has the general structure shown in Formula (III.b.2.1):

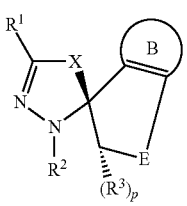
(III.b.2.1)

In one embodiment, Formula (III.b) has the general structure shown in Figure (III.b.2.2):

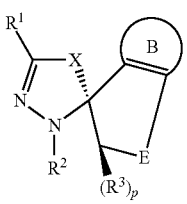
(III.b.2.2)

In one embodiment, Formula (III.b) has the general structure shown in Formula (III.b.2.3):

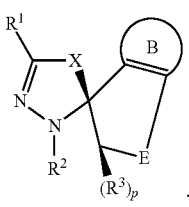
(III.b.2.3)

In one embodiment, Formula (III.b) has the general structure shown in Formula (III.b.2.4):

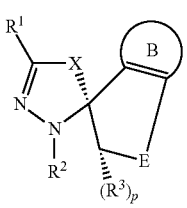
(III.b.2.4)

In some embodiments, in each of Formulas (III.b.1), (III.b.2), (III.b.2.1), (III.b.2.2), (III.b.2.3), and (III.b.2.4), p is 0.

In some embodiments, in each of Formulas (III.b.1), (III.b.2), (III.b.2.1), (III.b.2.2), (III.b.2.3), and (III.b.2.4), p is 1.

In some embodiments, in each of Formulas (III.b.1), (III.b.2), (III.b.2.1), (III.b.2.2), (III.b.2.3), and (III.b.2.4), p is 2.

In some embodiments, in each of Formulas (III.b.1), (III.b.2), (III.b.2.1), (III.b.2.2), (III.b.2.3), and (III.b.2.4), E is $—C(R^4)(R^5)—$.

In some embodiments, in each of Formulas (III.b.1), (III.b.2), (III.b.2.1), (III.b.2.2), (III.b.2.3), and (III.b.2.4), E is selected from the group consisting of —O—, —S—, —S(O)—, $—S(O)_2—$, and $—N(R^6)—$.

In some embodiments, in each of Formulas (III.b.1), (III.b.2), (81.b.2.1), (III.b.2.2), (III.b.2.3), and (III.b.2.4), E is selected from the group consisting of —O—, —S—, —S(O)—, $—S(O)_2—$, and $—N(R^6)—$, wherein $R^6$ is selected from the group consisting of H, alkyl, $—C(O)R^{24}$, and $—C(S)R^{24}$.

In some embodiments, in each of Formulas (III.b.1), (III.b.2), (III.b.2.1), (III.b.2.2), (III.b.2.3), and (III.b.2.4), E is selected from the group consisting of —O— and $—N(R^6)—$, wherein $R^6$ is selected from the group consisting of H, alkyl, $—C(O)R^{24}$, and $—C(S)R^{24}$.

In some embodiments, in each of Formulas (III.b.1), (III.b.2), (III.b.2.1), (III.b.2.2), (III.b.2.3), and (III.b.2.4), E is —O—.

In some embodiments, in each of Formulas (III.b.1), (III.b.2), (III.b.2.1), (III.b.2.2), (III.b.2.3), and (III.b.2.4), E is —S—.

In some embodiments, in each of Formulas (III.b.1), (III.b.2), (III.b.2.1), (III.b.2.2), (III.b.2.3), and (III.b.2.4), E is —S(O)—.

In some embodiments, in each of Formulas (III.b.1), (III.b.2), (111b.2.1), (III.b.2.2), (III.b.2.3), and (III.b.2.4), E is $—S(O)_2—$.

In some embodiments, in each of Formulas (III.b.1), (III.b.2), (III.b.2.1), (III.b.2.2), (III.b.2.3), and (III.b.2.4), E is $—C(R^4)(R^5)—$.

In some embodiments, in each of Formulas (III.b.1), (III.b.2), (III.b.2.1), (III.b.2.2), (III.b.2.3), and (III.b.2.4), E is $—N(R^6)—$.

In some embodiments, in each of Formulas (III.b.1), (III.b.2), (III.b.2.1), (III.b.2.2), (III.b.2.3), and (III.b.2.4), E is $—N(C(Y)R^7)—$.

In some embodiments, in each of Formulas (III.b.1), (III.b.2), (III.b.2.1), (III.b.2.2), (III.b.2.3), and (III.b.2.4), E is $—N(C(Y)OR^8)—$.

In some embodiments, in each of Formulas (III.b.1), (III.b.2), (111.b.2.1), (III.b.2.2), (III.b.2.3), and (III.b2.4), Eis))$—N(C(Y)N(R^9)(R^{10}))—$.

In some embodiments, in each of Formulas (III.b.1), (III.b.2), (III.b.2.1), (III.b.2.2), (III.b.2.3), and (III.b.2.4), Y is (=O).

In some embodiments, in each of Formulas (III.b.1), (III.b.2), (III.b.2.1), (III.b.2.2), (III.b.2.3), and (III.b.2.4), Y is (=S).

In some embodiments, in each of Formulas (III.b.1), (III.b.2), (III.b.2.1), (III.b.2.2), (III.b.2.3), and (III.b.2.4), Y is $(=N(R^{18}))$.

In some embodiments, in each of Formulas (III.b.1), (III.b.2), (III.b.2.1), (III.b.2.2), (III.b2.3), and (III.b.2.4), Y is (=N(CN)).

In some embodiments, in each of Formulas (III.b.1), (III.b.2), (111b.2.1), (III.b.2.2), (III.b.2.3), and (III.b.2.4), Y is (=N(OR$^{14}$)).

In some embodiments, in each of Formulas (III.b.1), (III.b.2), (III.b.2.1), (III.b.2.2), (III.b.2.3), and (III.b.2.4), Y is (=N(R$^{15}$)(R$^{16}$)).

In some embodiments, in each of Formulas (III.b.1), (III.b.2), (III.b.2.1), (III.b.2.2), (III.b.2.3), and (III.b.2.4), Y is (=C(R$^{17}$)(R$^{18}$)).

In some embodiments, in each of Formulas (III.b.1), (III.b.2), (III.b.2.1), (III.b.2.2), (III.b.2.3), and (III.b.2.4), R$^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In some embodiments, in each of Formulas (III.b.1), (III.b.2), (III.b.2.1), (III.b.2.2), (III.b.2.3), and (III.b.2.4), R$^1$ is selected from the group consisting of:

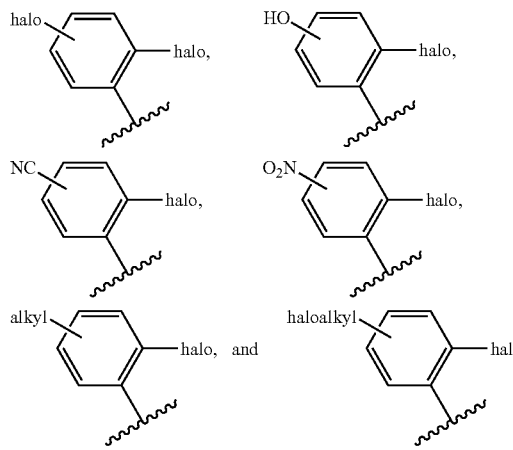

In one embodiment, in Formula (I), R$^1$ is:

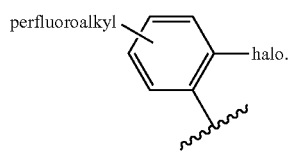

In some embodiments, in each of Formulas (III.b.1), (III.b.2), (III.b.2.1), (III.b.2.2), (110.2.3), and (III.b.2.4), R$^1$ is phenyl substituted with one to three fluoro groups.

In some embodiments, in each of Formulas (III.b.1), (III.b.2), (III.b.2.1), (III.b.2.2), (III.b.2.3), and (III.b.2.4), R$^1$ is phenyl substituted with two fluoro groups.

In some embodiments, in each of Formulas (III.b.1), (III.b.2), (III.b.2.1), (III.b.2.2), (III.b.2.3), and (III.b.2.4), R$^1$ is phenyl substituted with one fluoro group.

In some embodiments, in each of Formulas (III.b.1), (III.b.2), (III.b.2.1), (III.b.2.2), (III.b.2.3), and (III.b.2.4), R$^1$ is:

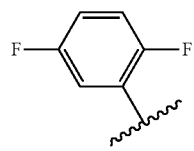

In some embodiments, in each of Formulas (III.b.1), (III.b.2), (III.b.2.1), (III.b.2.2), (III.b.2.3), and (III.b.2.4), R$^2$ is selected from the group consisting of: alkyl, haloalkyl, heteroalkyl, heterohaloalkyl, —C(O)R$^7$, —C(O)OR$^8$, and —C(O)NR$^9$R$^{10}$.

In some embodiments, in each of Formulas (III.b.1), (III.b.2), (III.b.2.2), (III.b.2.3), and (III.b.2.4), R$^2$ is selected from the group consisting of:

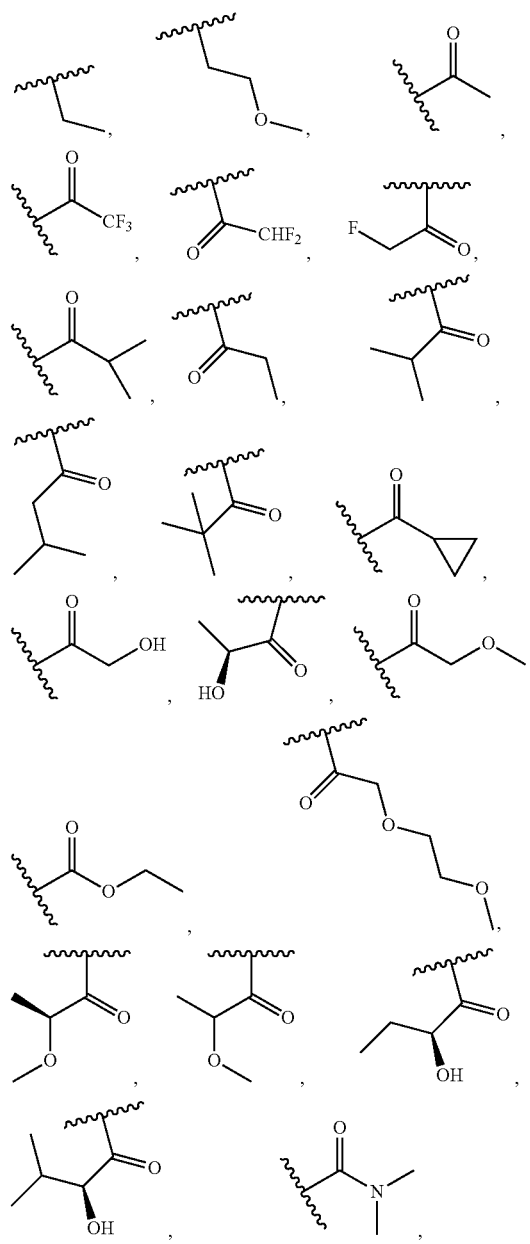

107
-continued
108
-continued
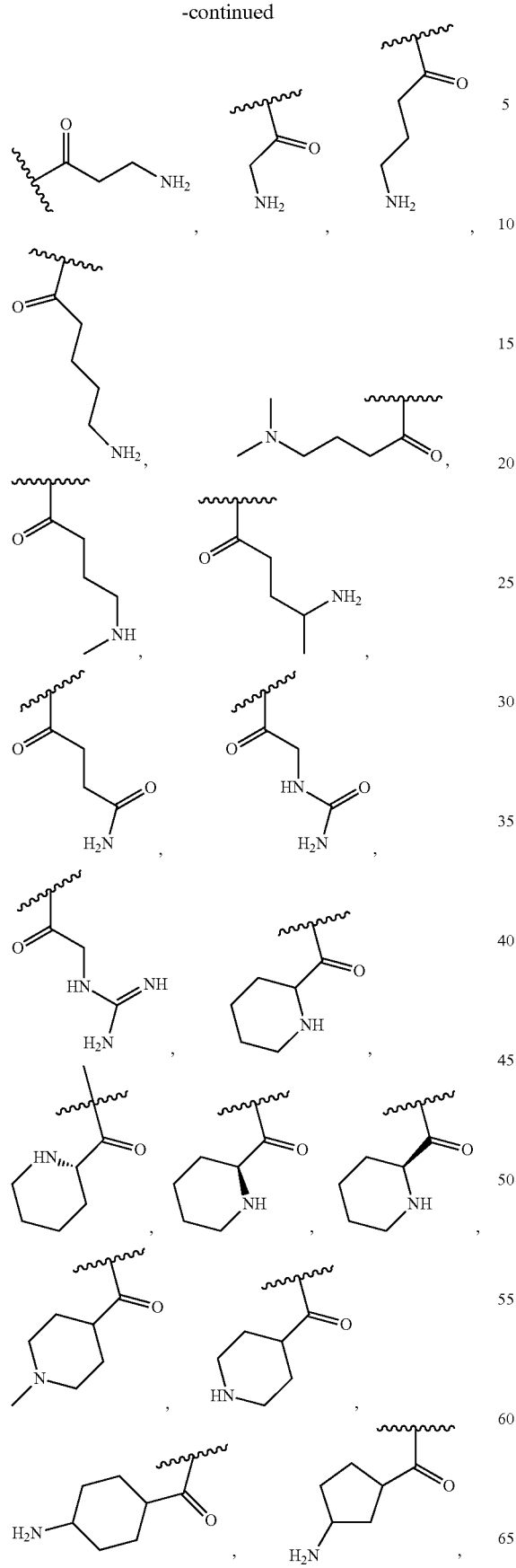
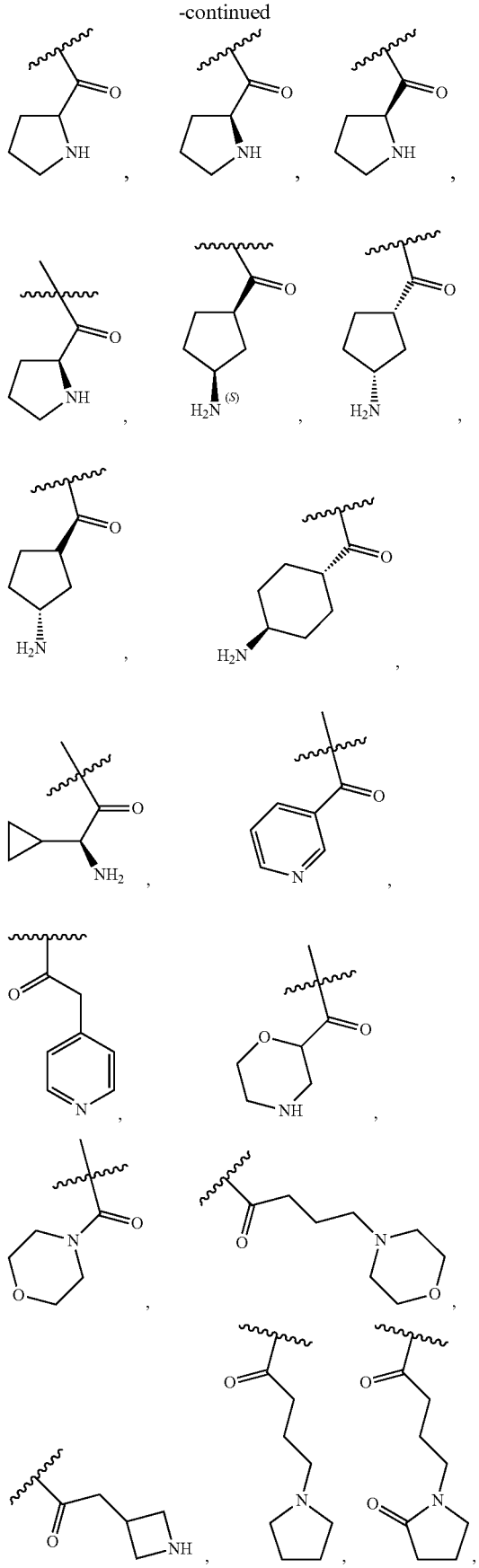

109

-continued

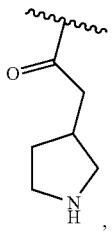, and 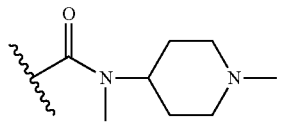.

In some embodiments, in each of Formulas (III.b.1), (III.b.2), (III.b.2.1), (III.b.2.2), (III.b.2.3), and (III.b.2.4), p is 1 or 2 and each $R^3$ is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$, —NR$^{23}$C(O)NR$^{25}$R$^{26}$, and —NR$^{23}$—C(NH)—NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (III.b.1), (III.b.2), (III.b.2.1), (III.b.2.2), (III.b.2.3), and (III.b.2.4), p is 1 and $R^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)$_{1\text{-}1}$$^{13}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (III.b.1), (III.b.2.2), (III.b.2.3), and (III.b.2.4), p is 2 and any two $R^3$ groups bound to the same ring A atom are taken together to form a —C(O)— group.

In some embodiments, in each of Formulas (III.b.1), (111.b.2.1), (III.b.2.2), (III.b.2.3), and (III.b.2.4), p is 2 and any two $R^3$ groups bound to the same ring A atom are taken together to form a spiroheterocycloalkyl group having from 1 to 3 ring heteroatoms independently selected from the group consisting of —NH—, —NR$^6$—, O, S, S(O), and S(O)$_2$, or spiroheterocycloalkenyl group having from 1 to 3 ring heteroatoms independently selected from the group consisting of —NH—, —NR$^6$—, O, S, S(O), and S(O)$_2$.

110

In one embodiment, the compounds of the invention have a structure shown in Formula (IV) and include pharmaceutically acceptable salts, solvates, esters, prodrugs, or isomers of said compounds:

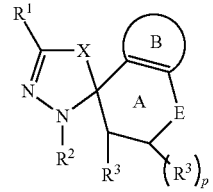

(IV)

wherein X, $R^1$, $R^2$, $R^3$, p, E, ring A, and ring B and the optional groups attached to ring B are each selected independently of each other and wherein:

E is selected from the group consisting of —C(R$^4$)(1R$^6$)—, —O—, —S—, —S(O)—, —S(O)$_2$—, and —N(R$^6$)—;

ring B is an unsubstituted or substituted aromatic ring or an unsubstituted or substituted 5-6-membered heteroaromatic ring having from 1-3 ring heteroatoms, which ring heteroatoms can be the same or different, each ring heteroatom being independently selected from the group consisting of N, S, O, S(O), and S(O)$_2$, said substituents on said aromatic ring or said heteroaromatic ring (when present) being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

$R^1$ is unsubstituted aryl or aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$;

$R^2$ is selected from the group consisting of —C(O)R$^7$, —C(O)NR$^9$R$^{10}$, and —C(O)NR$^8$;

p is 0, 1, or 2; and each $R^3$ (when present) is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —C(O)R$^{24}$, —C(S)R$^{24}$, —C(O)OR$^{20}$, and —C(O)NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR²³C(O)R²⁴, —SO₂NR²⁵R²⁶, —C(O)R²⁴, —C(O)OR²⁰, —S(O)R¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶; and all remaining variables are as defined in each of the embodiments described above in Formula (I).

In one such embodiment, in Formula (IV):

E is selected from the group consisting of —O— and —N(R⁶)—;

ring B is an unsubstituted or substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl;

R¹ is phenyl substituted with one to four substituents, which can be the same or different, each substituent being independently selected from the group consisting of halo, —OH, —CN, —NO₂, —NR²¹R²², and haloalkyl;

R² is selected from the group consisting of —C(O)R⁷, —C(O)NR⁹R¹⁰, and —C(O)OR⁸;

p is 0 or 1; and each R³ (when present) is independently selected from the group consisting of alkyl, heteroalkyl, alkenyl, heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO₂, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one such embodiment, in Formula (IV):

R¹ is:

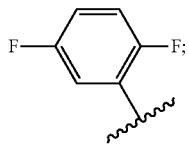 [SMILES: *c1cc(F)ccc1F]

and

R⁶ is selected from the group consisting of H, alkyl, —C(O)R²⁴, —C(O)OR²⁰, and —C(S)R²⁴.

In one embodiment, the compounds of the invention have a structure shown in Formula (IV.a) and include pharmaceutically acceptable salts, solvates, esters, prodrugs, or isomers of said compounds:

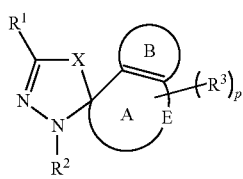

(IV.a)

wherein X, R¹, R², R³, p, E, ring A, and ring B are selected independently of each other and wherein:

ring A (including E and the unsaturation shown) is a 6-membered cycloalkenyl or heterocycloalkenyl ring;

E is selected from the group consisting of —O—, —S—, —S(O)—, —S(O)₂—, —C(R⁴)(R⁵)—, —N(R⁶)—, —N(C(Y)R⁷)—, —N(C(Y)OR⁶)—, —N(C(Y)N(R³)(R¹⁰))—, —C(O)—N(R¹¹)—, —N(R¹¹)—C(O)—, —S(O)₂—N(R¹¹)—, —N(R¹¹)—S(O)₂—, —C(O)—O—, —O—C(O)—, —O—N(R⁶)—, —N(R⁶)—O—, —N(R⁶)—N(R¹²)—, —N=N—, —C(R⁷)=N—, —C(O)—C(R⁷)=N—, —C(O)—N=N—, —O—C(Y)—N(R¹¹)—, —N(R¹¹)—C(Y)—O—, —N(R¹¹)—C(Y)—N(R¹²)—, —C(Y)—N(R¹¹)—O—, —C(Y)—N(R¹¹)—N(R¹²)—, —O—N(R¹¹)—C(Y)—, and —N(R¹²)—N(R¹¹)—C(Y)—, ring B is a substituted or unsubstituted aromatic ring;

and p, X, R¹, R², R³, R⁴, R⁵, R⁶, R⁷, R⁸, R⁹, R¹⁰, R¹¹, R¹², Y, and the optional substituents on ring B are as defined in each of the embodiments described above in Formula (I).

In one embodiment, Formula (IV.a) has the general structure shown in Formula (IV.a.1):

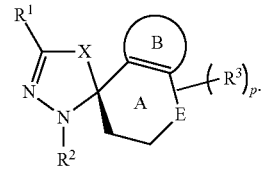

(IV.a.1)

In one embodiment, Formula (IV.a) has the general structure shown in Formula (IV.a.2):

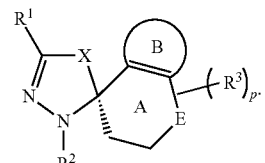

(IV.a.2)

In one embodiment, Formula (IV.a) has the general structure shown in Formula (IV.a.3):

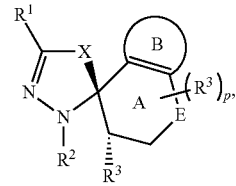

(IV.a.3)

wherein P is 0, 1, 2, or 3.

In one embodiment, Formula (IV.a) has the general structure shown in Formula (IV.a.4):

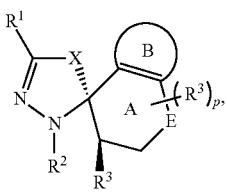

(IV.a.4)

wherein P is 0, 1, 2, or 3.

In one embodiment, Formula (IV.a) has the general structure shown in Formula

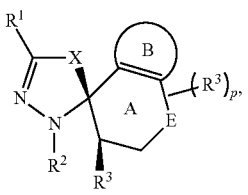

(IV.a.5)

wherein P is 0, 1, 2, or 3.

In one embodiment, Formula (IV.a) has the general structure shown in Formula (IV.a.6):

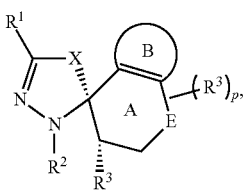

(IV.a.6)

wherein P is 0, 1, 2, or 3.

In some embodiments, in each of Formulas (IV.a), (IV.a.1), (IV.a.2), (IV.a.3), (IV.a.4), (IV.a.5), and (IV.a.6), X is S.

In some embodiments, in each of Formulas (IV.a), (IV.a.1), (IV.a.2), (IV.a.3), (IV.a.4), (IV.a.5), and (IV.a.6), X is S(O).

In some embodiments, in each of Formulas (IV.a), (IV.a.1), (IV.a.2), (IV.a.3), (IV.a.4), (IV.a.5), and (IV.a.6), X is $S(O)_2$.

In some embodiments, in each of Formulas (IV.a), (IV.a.1), (IV.a.2), (IV.a.3), (IV.a.4), (IV.a.5), and (IV.a.6), ring A is a cycloalkenyl ring and E is —$C(R^4)(R^5)$—.

In some embodiments, in each of Formulas (IV.a), (IV.a.1), (IV.a.2), (IV.a.3), (IV.a.4), (IV.a.5), and (IV.a.6), ring A is a heterocycloalkenyl ring and E is selected from the group consisting of —O—, —S—, —S(O)—, —$S(O)_2$—, and —$N(R^6)$—.

In some embodiments, in each of Formulas (IV.a), (IV.a.1), (IV.a.2), (IV.a.3), (IV.a.4), (IV.a.5), and (IV.a.6), ring A is a heterocycloalkenyl ring and E is selected from the group consisting of —O—, —S—, —S(O)—, —$S(O)_2$—, and —$N(R^6)$—, wherein $R^6$ is selected from the group consisting of H, alkyl, —$C(O)R^{24}$, and —$C(S)R^{24}$.

In some embodiments, in each of Formulas (IV.a), (IV.a.1), (IV.a.2), (IV.a.3), (IV.a.4), (IV.a.5), and (IV.a.6), ring A is a heterocycloalkenyl ring and E is selected from the group consisting of —O— and —$N(R^6)$—, wherein $R^6$ is selected from the group consisting of H, alkyl, —$C(O)R^{24}$, and —$C(S)R^{24}$.

In some embodiments, in each of Formulas (IV.a), (IV.a.1), (IV.a.2), (IV.a.3), (IV.a.4), (IV.a.5), and (IV.a.6), E is —O—.

In some embodiments, in each of Formulas (IV.a), (IV.a.1), (IV.a.2), (IV.a.3), (IV.a.4), (IV.a.5), and (IV.a.6), E is —S—.

In some embodiments, in each of Formulas (IV.a), (IV.a.1), (IV.a.2), (IV.a.3), (IV.a.4), (IV.a.5), and (IV.a.6), E is —S(O)—.

In some embodiments, in each of Formulas (IV.a), (IV.a.1), (IV.a.2), (IV.a.3), (IV.a.4), (IV.a.5), and (IV.a.6), E is —$S(O)_2$—.

In some embodiments, in each of Formulas (IV.a), (IV.a.1), (IV.a.2), (IV.a.3), (IV.a.4), (IV.a.5), and (IV.a.6), E is —$C(R^4)(R^5)$—.

In some embodiments, in each of Formulas (IV.a), (IV.a.1), (IV.a.2), (IV.a.3), (IV.a.4), (IV.a.5), and (IV.a.6), E is —$N(R^6)$—.

In some embodiments, in each of Formulas (IV.a), (IV.a.1), (IV.a.2), (IV.a.3), (IV.a.4), (IV.a.5), and (IV.a.6), E is —$N(C(Y)R^7)$—.

In some embodiments, in each of Formulas (IV.a), (IV.a.1), (IV.a.2), (IV.a.3), (IV.a.4), (IV.a.5), and (IV.a.6), E is —$N(C(Y)OR^8)$—.

In some embodiments, in each of Formulas (IV.a), (IV.a.1), (IV.a.2), (IV.a.3), (IV.a.4), (IV.a.5), and (IV.a.6), E is —$N(C(Y)N(R^9)(R^{10}))$—.

In some embodiments, in each of Formulas (IV.a), (IV.a.1), (IV.a.2), (IV.a.3), (IV.a.4), (IV.a.5), and (IV.a.6), E is —C(O)—$N(R^{11})$—.

In some embodiments, in each of Formulas (IV.a), (IV.a.1), (IV.a.2), (IV.a.3), (IV.a.4), (IV.a.5), and (IV.a.6), E is —$N(R^{11})$—C(O)—.

In some embodiments, in each of Formulas (IV.a), (IV.a.1), (IV.a.2), (IV.a.3), (IV.a.4), (IV.a.5), and (IV.a.6), E is —$S(O)_2$—$N(R^{11})$—.

In some embodiments, in each of Formulas (IV.a), (IV.a.1), (IV.a.2), (IV.a.3), (IV.a.4), (IV.a.5), and (IV.a.6), E is —$N(R^{11})$—$S(O)_2$—.

In some embodiments, in each of Formulas (IV.a), (IV.a.1), (IV.a.2), (IV.a.3), (IV.a.4), (IV.a.5), and (IV.a.6), E is —C(O)—O—.

In some embodiments, in each of Formulas (IV.a), (IV.a.1), (IV.a.2), (IV.a.3), (IV.a.4), (IV.a.5), and (IV.a.6), E is —O—C(O)—.

In some embodiments, in each of Formulas (IV.a), (IV.a.1), (IV.a.2), (IV.a.3), (IV.a.4), (IV.a.5), and (IV.a.6), E is —O—$N(R^6)$—.

In some embodiments, in each of Formulas (IV.a), (IV.a.1), (IV.a.2), (IV.a.3), (IV.a.4), (IV.a.5), and (IV.a.6), E is —$N(R^6)$—O—.

In some embodiments, in each of Formulas (IV.a), (IV.a.1), (IV.a.2), (IV.a.3), (IV.a.4), (IV.a.5), and (IV.a.6), E is —$N(R^6)$—$N(R^{12})$—.

In some embodiments, in each of Formulas (IV.a), (IV.a.1), (IV.a.2), (IV.a.3), (IV.a.4), (IV.a.5), and (IV.a.6), E is —N=N—.

In some embodiments, in each of Formulas (IV.a), (IV.a.1), (IV.a.2), (IV.a.3), (IV.a.4), (IV.a.5), and (IV.a.6), E is —$C(R^7)$=N—.

In some embodiments, in each of Formulas (IV.a), (IV.a.1), (IV.a.2), (IV.a.3), (IV.a.4), (IV.a.5), and (IV.a.6), E is —C(O)—$C(R^7)$=N—.

In some embodiments, in each of Formulas (IV.a), (IV.a.1), (IV.a.2), (IV.a.3), (IV.a.4), (IV.a.5), and (IV.a.6), E is —C(O)—N=N—.

In some embodiments, in each of Formulas (IV.a), (IV.a.1), (IV.a.2), (IV.a.3), (IV.a.4), (IV.a.5), and (IV.a.6), E is —O—C(Y)—$N(R^{11})$—.

In some embodiments, in each of Formulas (IV.a), (IV.a.1), (IV.a.2), (IV.a.3), (IV.a.4), (IV.a.5), and (IV.a.6), E is —N(R$^{11}$)—C(Y)—O—.

In some embodiments, in each of Formulas (IV.a), (IV.a.1), (IV.a.2), (IV.a.3), (IV.a.4), (IV.a.5), and (IV.a.6), E is —N(R$^{11}$)—C(Y)—N(R$^{12}$)—.

In some embodiments, in each of Formulas (IV.a), (IV.a.1), (IV.a.2), (IV.a.3), (IV.a.4), (IV.a.5), and (IV.a.6), E is —C(Y)—N(R$^{11}$)—O—.

In some embodiments, in each of Formulas (IV.a), (IV.a.1), (IV.a.2), (IV.a.3), (IV.a.4), (IV.a.5), and (IV.a.6), E is —C(Y)—N(R$^{11}$)—N(R$^{12}$)—.

In some embodiments, in each of Formulas (IV.a), (IV.a.1), (IV.a.2), (IV.a.3), (IV.a.4), (IV.a.5), and (IV.a.6), E is —O—N(R$^{11}$)—C(Y)—.

In some embodiments, in each of Formulas (IV.a), (IV.a.1), (IV.a.2), (IV.a.3), (IV.a.4), (IV.a.5), and (IV.a.6), E is —N(R$^{12}$)—N(R$^{11}$)—C(Y)—.

In some embodiments, in each of Formulas (IV.a), (IV.a.1), (IV.a.2), (IV.a.3), (IV.a.4), (IV.a.5), and (IV.a.6), Y is (═O).

In some embodiments, in each of Formulas (IV.a), (IV.a.1), (IV.a.2), (IV.a.3), (IV.a.4), (IV.a.5), and (IV.a.6), Y is (═S).

In some embodiments, in each of Formulas (IV.a), (IV.a.1), (IV.a.2), (IV.a.3), (IV.a.4), (IV.a.5), and (IV.a.6), Y is (═N(R$^{13}$)).

In some embodiments, in each of Formulas (IV.a), (IV.a.1), (IV.a.2), (IV.a.3), (IV.a.4), (IV.a.5), and (IV.a.6), Y is (═N(CN)).

In some embodiments, in each of Formulas (IV.a), (IV.a.1), (IV.a.2), (IV.a.3), (IV.a.4), (IV.a.5), and (IV.a.6), Y is (═N(OR$^{14}$)).

In some embodiments, in each of Formulas (IV.a), (IV.a.1), (IV.a.2), (IV.a.3), (IV.a.4), (IV.a.5), and (IV.a.6), Y is (═N(R$^{15}$)(R$^{16}$)).

In some embodiments, in each of Formulas (IV.a), (IV.a.1), (IV.a.2), (IV.a.3), (IV.a.4), (IV.a.5), and (IV.a.6), Y is (═C(R$^{17}$)(R$^{18}$)).

In some embodiments, in each of Formulas (IV.a), (IV.a.1), (IV.a.2), (IV.a.3), (IV.a.4), (IV.a.5), and (IV.a.6), B is an unsubstituted aromatic ring.

In some embodiments, in each of Formulas (IV.a), (IV.a.1), (IV.a.2), (IV.a.3), (IV.a.4), (IV.a.5), and (IV.a.6), B is an unsubstituted benzo ring, and Formula (IV.a.) has the general structure:

In some embodiments, in each of Formulas (IV.a), (IV.a.1), (IV.a.2), (IV.a.3), (IV.a.4), (IV.a.5), and (IV.a.6), B is an aromatic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$R$^{26}$, —SO$_2$NR$^{25}$—, —C(O)R$^{24}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.a), (IV.a.1), (IV.a.2), (IV.a.3), (IV.a.4), (IV.a.5), and (IV.a.6), B is a benzo ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$. In one such embodiment, ring B is benzo substituted with from 1 to 3 groups independently selected from halo.

In some embodiments, in each of Formulas (IV.a), (IV.a.1), (IV.a.2), (IV.a.3), (IV.a.4), (IV.a.5), and (IV.a.6), R$^1$ is unsubstituted aryl.

In some embodiments, in each of Formulas (IV.a), (IV.a.1), (IV.a.2), (IV.a.3), (IV.a.4), (IV.a.5), and (IV.a.6), R$^1$ is unsubstituted phenyl.

In some embodiments, in each of Formulas (IV.a), (IV.a.1), (IV.a.2), (IV.a.3), (IV.a.4), (IV.a.5), and (IV.a.6), R$^1$ is unsubstituted naphthyl.

In some embodiments, in each of Formulas (IV.a), (IV.a.1), (IV.a.2), (IV.a.3), (IV.a.4), (IV.a.5), and (IV.a.6), R$^1$ is substituted aryl.

In some embodiments, in each of Formulas (IV.a), (IV.a.1), (IV.a.2), (IV.a.3), (IV.a.4), (IV.a.5), and (IV.a.6), R$^1$ is substituted phenyl.

In some embodiments, in each of Formulas (IV.a), (IV.a.1), (IV.a.2), (IV.a.3), (IV.a.4), (IV.a.5), and (IV.a.6), R$^1$ is substituted naphthyl.

In some embodiments, in each of Formulas (IV.a), (IV.a.1), (IV.a.2), (IV.a.3), (IV.a.4), (IV.a.5), and (IV.a.6), R$^1$ is aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{16}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.a), (IV.a.1), (IV.a.2), (IV.a.3), (IV.a.4), (IV.a.5), and (IV.a.6), R$^1$ is phenyl substituted with one or more substituents, which can be the same or different, each substituent being independently selected from the group consisting halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.a), (IV.a.1), (IV.a.2), (IV.a.3), (IV.a.4), (IV.a.5), and (IV.a.6), R$^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In some embodiments, in each of Formulas (IV.a), (IV.a.1), (IV.a.2), (IV.a.3), (IV.a.4), (IV.a.5), and (IV.a.6), R$^1$ is selected from the group consisting of:

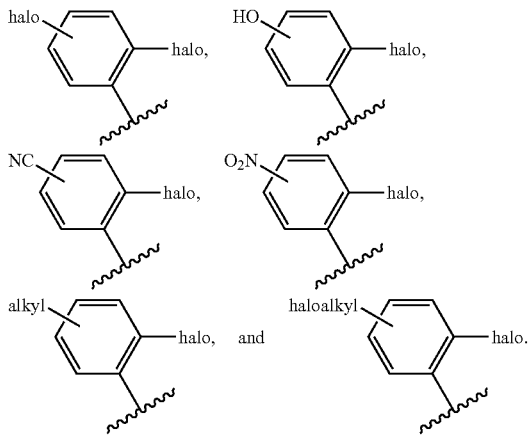

In some embodiments, in each of Formulas (IV.a), (IV.a.1), (IV.a.2), (IV.a.3), (IV.a.4), (IV.a.5), and (IV.a.6), R$^1$ is:

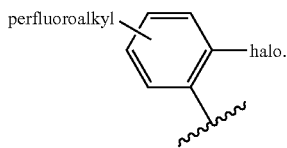

In some embodiments, in each of Formulas (IV.a), (IV.a.1), (IV.a.2), (IV.a.3), (IV.a.4), (IV.a.5), and (IV.a.6), R$^1$ is phenyl substituted with one to three fluoro groups.

In some embodiments, in each of Formulas (IV.a), (IV.a.2), (IV.a.3), (IV.a.4), (IV.a.5), and (IV.a.6), R$^1$ is phenyl substituted with two fluoro groups.

In some embodiments, in each of Formulas (IV.a), (IV.a.1), (IV.a.2), (IV.a.3), (IV.a.4), (IV.a.5), and (IV.a.6), R$^1$ is phenyl substituted with one fluoro group.

In some embodiments, in each of Formulas (IV.a), (IV.a.1), (IV.a.2), (IV.a.3), (IV.a.4), (IV.a.5), and (IV.a.6), R$^1$ is:

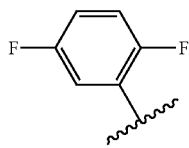 [SMILES: *c1cc(F)ccc1F]

In some embodiments, in each of Formulas (IV.a), (IV.a.1), (IV.a.2), (IV.a.3), (IV.a.4), (IV.a.5), and (IV.a.6), R$^2$ is —C(Z)R$^7$.

In some embodiments, in each of Formulas (IV.a), (IV.a.1), (IV.a.2), (IV.a.3), (IV.a.4), (IV.a.5), and (IV.a.6), R$^2$ is —C(Z)NR$^9$R$^{10}$.

In some embodiments, in each of Formulas (IV.a), (IV.a.1), (IV.a.2), (IV.a.3), (IV.a.4), (IV.a.5), and (IV.a.6), R$^2$ is —C(Z)OR$^8$.

In some embodiments, in each of Formulas (IV.a), (IV.a.1), (IV.a.2), (IV.a.3), (IV.a.4), (IV.a.5), and (IV.a.6), R$^2$ is —SO$_2$NR$^9$R$^{10}$.

In some embodiments, in each of Formulas (IV.a), (IV.a.1), (IV.a.2), (IV.a.3), (IV.a.4), (IV.a.5), and (IV.a.6), R$^2$ is alkyl.

In some embodiments, in each of Formulas (IV.a), (IV.a.1), (IV.a.2), (IV.a.3), (IV.a.4), (IV.a.5), and (IV.a.6), R$^2$ is heteroalkyl.

In some embodiments, in each of Formulas (IV.a), (IV.a.1), (IV.a.2), (IV.a.3), (IV.a.4), (IV.a.5), and (IV.a.6), R$^2$ is aryl.

In some embodiments, in each of Formulas (IV.a), (IV.a.1), (IV.a.2), (IV.a.3), (IV.a.4), (IV.a.5), and (IV.a.6), R$^2$ is heteroaryl.

In some embodiments, in each of Formulas (IV.a), (IV.a.1), (IV.a.2), (IV.a.3), (IV.a.4), (IV.a.5), and (IV.a.6), R$^2$ is cycloalkyl.

In some embodiments, in each of Formulas (IV.a), (IV.a.1), (IV.a.3), (IV.a.4), (IV.a.5), and (IV.a.6), R$^2$ is cycloalkenyl.

In some embodiments, in each of Formulas (IV.a), (IV.a.1), (IV.a.2), (IV.a.3), (IV.a.4), (IV.a.5), and (IV.a.6), R$^2$ is heterocycloalkyl.

In some embodiments, in each of Formulas (IV.a), (IV.a.1), (IV.a.2), (IV.a.3), (IV.a.4), (IV.a.5), and (IV.a.6), R$^2$ is heterocycloalkenyl.

In some embodiments, in each of Formulas (IV.a), (IV.a.1), (IV.a.2), (IV.a.3), (IV.a.4), (IV.a.5), and (IV.a.6), Z is (═O).

In some embodiments, in each of Formulas (IV.a), (IV.a.1), (IV.a.2), (IV.a.3), (IV.a.4), (IV.a.5), and (IV.a.6), Z is (═S).

In some embodiments, in each of Formulas (IV.a), (IV.a.1), (IV.a.2), (IV.a.3), (IV.a.4), (IV.a.5), and (IV.a.6), Z is (═N(R$^{13}$)).

In some embodiments, in each of Formulas (IV.a), (IV.a.1), (IV.a.2), (IV.a.3), (IV.a.4), (IV.a.5), and (IV.a.6), Z is (═N(CN)).

In some embodiments, in each of Formulas (IV.a), (IV.a.1), (IV.a.2), (IV.a.3), (IV.a.4), (IV.a.5), and (IV.a.6), Z is (═N(OR$^{14}$)).

In some embodiments, in each of Formulas (IV.a), (IV.a.1), (IV.a.2), (IV.a.3), (IV.a.4), (IV.a.5), and (IV.a.6), Z is (═N(R$^{15}$)(R$^{76}$)).

In some embodiments, in each of Formulas (IV.a), (IV.a.1), (IV.a.2), (IV.a.3), (IV.a.4), (IV.a.5), and (IV.a.6), Z is (═C(R$^{17}$)(R$^{18}$)).

In some embodiments, in each of Formulas (IV.a), (IV.a.1), (IV.a.2), (IV.a.3), (IV.a.4), (IV.a.5), and (IV.a.6), R$^2$ is —C(Z)R$^7$, and Z is (═O).

In some embodiments, in each of Formulas (IV.a), (IV.a.1), (IV.a.2), (IV.a.3), (IV.a.4), (IV.a.5), and (IV.a.6), R$^2$ is —C(O)H.

In some embodiments, in each of Formulas (IV.a), (IV.a.1), (IV.a.2), (IV.a.3), (IV.a.4), (IV.a.5), and (IV.a.6), R$^2$ is —C(O)alkyl.

In some embodiments, in each of Formulas (IV.a), (IV.a.2), (IV.a.3), (IV.a.4), (IV.a.5), and (IV.a.6), R$^2$ is —C(O)CH$_3$.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is alkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{16}$, —S(O)$_{1-3}$$^{19}$, —SO$_2$R$^{16}$, —OC(O)R$^{24}$, —C(O)NR$^{25}$R$^{26}$, —NR$^{23}$C(N—CN)NR$^{25}$R$^{25}$ and —NR$^{23}$C(O)NR$^{25}$R$^{26}$.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is alkyl substituted with one to three substituents, which can be the same or different, each substituent being independently selected from the group consisting of —OR$^{19}$, —NR$^{21}$R$^{21}$, and cycloalkyl.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is alkyl, wherein said alkyl is substituted with alkyl and —OH.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is alkyl substituted with one to three substituents, which can be the same or different, each substituent being independently selected from the group consisting of —OH, —NH$_2$, and cyclopropyl.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is alkyl substituted with one to two substituents, which can be the same or different, each substituent being independently selected from the group consisting of —NH$_2$, and cyclopropyl.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is alkyl substituted with —OH.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is unsubstituted heterocycloalkyl.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is substituted heterocycloalkyl.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is heterocycloalkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.a), (IV.a.1), (IV.a.2), (IV.a.3), (IV.a.4), (IV.a.5), and (IV.a.6), R$^2$ is —C(O)R$^7$, wherein said R$^7$ is selected from the group consisting of substituted piperidine, substituted piperazine, substituted morpholine, substituted pyrrolidine, and substituted azetidine.

In some embodiments, in each of Formulas (IV.a), (IV.a.1), (IV.a.2), (IV.a.3), (IV.a.4), (IV.a.5), and (IV.a.6), R$^2$ is selected from:

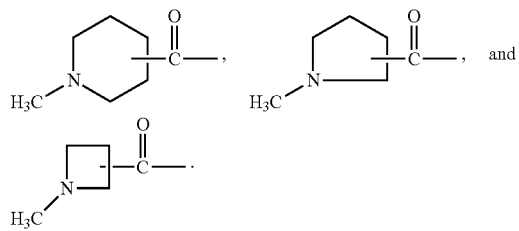

In some embodiments, in each of Formulas (IV.a), (IV.a.1), (IV.a.3), (IV.a.4), (IV.a.5), and (IV.a.6), R$^2$ is —C(O)NR$^9$R$^{10}$.

In some embodiments, in each of Formulas (IV.a), (IV.a.1), (IV.a.2), (IV.a.3), (IV.a.4), (IV.a.5), and (IV.a.6), R$^2$ is —C(O)NH$_2$.

In some embodiments, in each of Formulas (IV.a), (IV.a.1), (IV.a.2), (IV.a.3), (IV.a.4), (IV.a.5), and (IV.a.6), R$^2$ is —C(O)NR$^9$R$^{10}$, wherein R$^9$ and R$^{10}$ can be the same or different, each being independently selected from alkyl.

In some embodiments, in each of Formulas (IV.a), (IV.a.1), (IV.a.2), (IV.a.3), (IV.a.4), (IV.a.5), and (IV.a.6), R$^2$ is —C(O)NR$^9$R$^{10}$, wherein R$^9$ is unsubstituted heterocycloalkyl and R$^{10}$ is selected from the group consisting of H and alkyl.

In some embodiments, in each of Formulas (IV.a), (IV.a.1), (IV.a.2), (IV.a.3), (IV.a.4), (IV.a.5), and (IV.a.6), R$^2$ is —C(O)NR$^9$R$^{10}$, wherein R$^9$ is substituted heterocycloalkyl and R$^{10}$ is selected from the group consisting of H and alkyl.

In some embodiments, in each of Formulas (IV.a), (IV.a.1), (IV.a.2), (IV.a.3), (IV.a.4), (IV.a.5), and (IV.a.6), R$^2$ is —C(O)NR$^9$R$^{10}$, wherein R$^9$ is heterocycloalkyl substituted with from one to three substituents, which can be the same or different, each substituent being independently selected from alkyl, and R$^{10}$ is selected from the group consisting of H and alkyl.

In some embodiments, in each of Formulas (IV.a), (IV.a.1), (IV.a.2), (IV.a.3), (IV.a.4), (IV.a.5), and (IV.a.6), R$^2$ is selected from the group consisting of: alkyl, haloalkyl, heteroalkyl, heterohaloalkyl, —C(O)R$^7$, —C(O)OR$^8$, and —C(O)NR$^9$R$^{10}$.

In some embodiments, in each of Formulas (IV.a), (IV.a.1), (IV.a.2), (IV.a.3), (IV.a.4), (IV.a.5), and (IV.a.6), R$^2$ is selected from the group consisting of

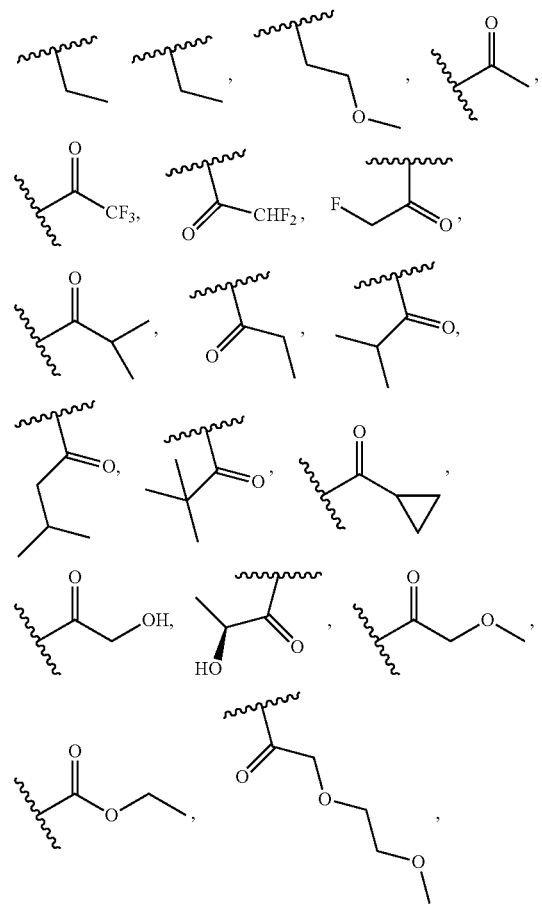

121
-continued
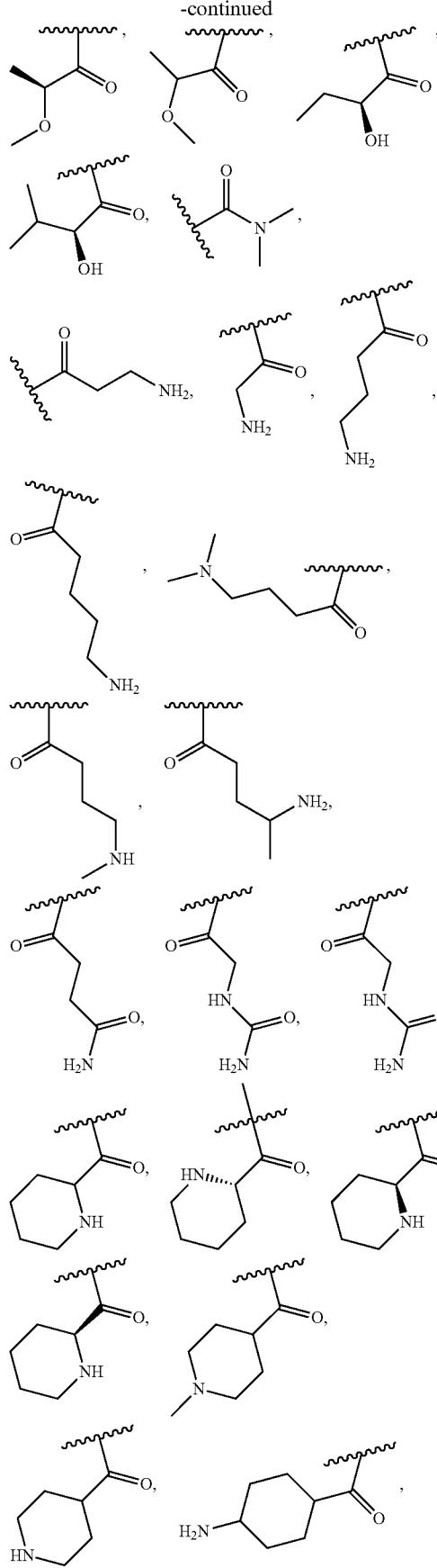
122
-continued
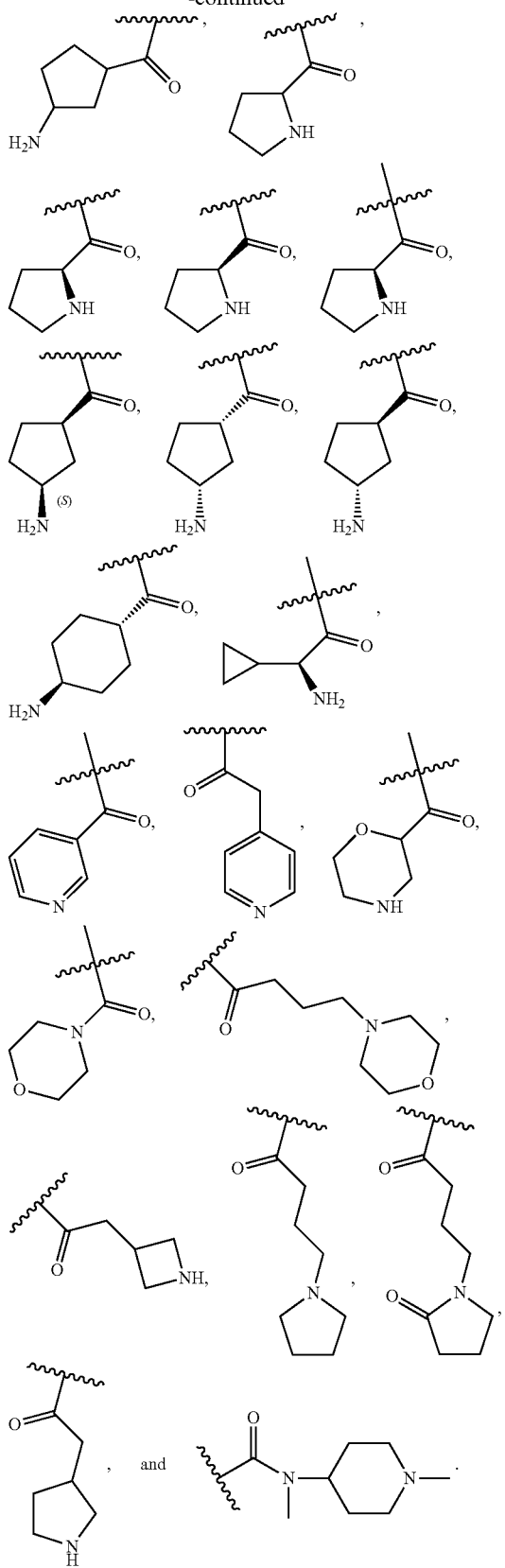
In some embodiments, in each of Formulas (IV.a), (IV.a.1), (IV.a.2), (IV.a.3), (IV.a.4), (IV.a.5), and (IV.a.6), $R^2$ is

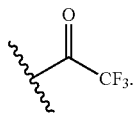

In some embodiments, in each of Formulas (IV.a), (IV.a.1), (IV.a.2), (IV.a.3), (IV.a.4), (IV.a.5), and (IV.a.6), $R^2$ is

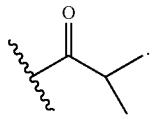

In some embodiments, in each of Formulas (IV.a), (IV.a.1), (IV.a.2), (IV.a.3), (IV.a.4), (IV.a.5), and (IV.a.6), $R^2$ is

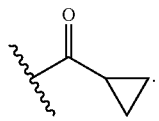

In some embodiments, in each of Formulas (IV.a), (IV.a.1), (IV.a.2), (IV.a.3), (IV.a.4), (IV.a.5), and (IV.a.6), $R^2$ is

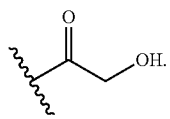 [SMILES: *C(=O)CO]

In some embodiments, in each of Formulas (IV.a), (IV.a.1), (IV.a.2), (IV.a.3), (IV.a.4), (IV.a.5), and (IV.a.6), $R^2$ is

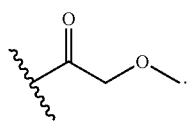 [SMILES: *C(=O)COC]

In some embodiments, in each of Formulas (IV.a), (IV.a.1), (IV.a.2), (IV.a.3), (IV.a.4), (IV.a.5), and (IV.a.6), $R^2$ is

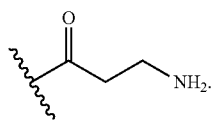 [SMILES: *C(=O)CCN]

In some embodiments, in each of Formulas (IV.a), (IV.a.1), (IV.a.2), (IV.a.3), (IV.a.4), (IV.a.5), and (IV.a.6), $R^2$ is

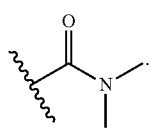

In some embodiments, in each of Formulas (IV.a), (IV.a.1), (IV.a.2), (IV.a.3), (IV.a.4), (IV.a.5), and (IV.a.6), $R^2$ is

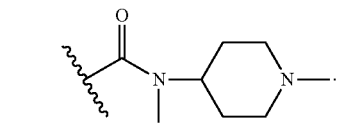

In some embodiments, in each of Formulas (IV.a), (IV.a.1), (IV.a.2), (IV.a.3), (IV.a.4), (IV.a.5), and (IV.a.6), p is 0 and $R^3$ is not present.

In some embodiments, in each of Formulas (IV.a), (IV.a.1), (IV.a.2), (IV.a.3), (IV.a.4), (IV.a.5), and (IV.a.6), p is 1.

In some embodiments, in each of Formulas (IV.a), (IV.a.1), (IV.a.2), (IV.a.3), (IV.a.4), (IV.a.5), and (IV.a.6), p is 2.

In some embodiments, in each of Formulas (IV.a), (IV.a.1), (IV.a.2), (IV.a.3), (IV.a.4), (IV.a.5), and (IV.a.6), p is 3.

In some embodiments, in each of Formulas (IV.a), (IV.a.1), (IV.a.2), (IV.a.3), (IV.a.4), (IV.a.5), and (IV.a.6), p is 4.

In some embodiments, in each of Formulas (IV.a), (IV.a.1), (IV.a.2), (IV.a.3), (IV.a.4), (IV.a.5), and (IV.a.6), p is >2 and at least two groups $R^3$ are attached to the same ring atom.

In some embodiments, in each of Formulas (IV.a), (IV.a.1), (IV.a.2), (IV.a.3), (IV.a.4), (IV.a.5), and (IV.a.6), p is 1 and $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.a), (IV.a.1), (IV.a.2), (IV.a.3), (IV.a.4), (IV.a.5), and (IV.a.6), p is 2, 3, or 4 and each $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.a), (IV.a.1), (IV.a.2), (IV.a.3), (IV.a.4), (IV.a.5), and (IV.a.6), p is 2, 3, or 4 and at least two groups $R^3$ are bound to the same ring carbon atom, wherein each $R^3$, which may be the same or different, is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.a), (IV.a.1), (IV.a.2), (IV.a.4), (IV.a.5), and (IV.a.6), p is 2, 3, or 4 and at least two groups $R^3$ are bound to the same ring carbon atom, wherein two $R^3$ groups, which may be the same or different, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S.

In one embodiment, in Formula (IV.a), p is 1, 2, 3, or 4 and each $R^3$ is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)—R$^{24}$, —SO$_2$NR$^{25}$R$^{26}$, —C(O)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$, —NR$^{23}$C(O)NR$^{25}$R$^{26}$, and —NR$^{23}$—C(NH)—NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (IV.a), p is 1 and $R^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{24}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{16}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (IV.a), p is 2, 3, or 4 and any two $R^3$ groups bound to the same ring A atom are taken together to form a —C(O)— group.

In one embodiment, in Formula (IV.a), p is 2, 3, or 4 and any two $R^3$ groups bound to the same ring A atom are taken together to form a spiroheterocycloalkyl group having from 1 to 3 ring heteroatoms independently selected from the group consisting of —NH—, —NR$^6$—, O, S, S(O), and S(O)$_2$, or spiroheterocycloalkenyl group having from 1 to 3 ring heteroatoms independently selected from the group consisting of —NH—, —NR$^6$—, O, S, S(O), and S(O)$_2$.

In some embodiments, in each of Formulas (IV.a), (IV.a.1), (IV.a.2), (IV.a.3), (IV.a.4), (IV.a.5), and (IV.a.6), $R^3$ is alkyl.

In some embodiments, in each of Formulas (IV.a), (IV.a.1), (IV.a.3), (IV.a.4), (IV.a.5), and (IV.a.6), $R^3$ is heteroalkyl.

In some embodiments, in each of Formulas (IV.a), (IV.a.1), (IV.a.2), (IV.a.3), (IV.a.4), (IV.a.5), and (IV.a.6), $R^3$ is alkenyl.

In some embodiments, in each of Formulas (IV.a), (IV.a.1), (IV.a.2), (V.a.3), (IV.a.4), (IV.a.5), and (IV.a.6), $R^3$ is heteroalkenyl.

In some embodiments, in each of Formulas (IV.a), (IV.a.1), (IV.a.2), (IV.a.3), (IV.a.4), (IV.a.5), and (IV.a.6), $R^3$ is alkynyl.

In some embodiments, in each of Formulas (IV.a), (IV.a.1), (IV.a.2), (IV.a.3), (IV.a.4), (IV.a.5), and (IV.a.6), $R^3$ is heteroalkynyl.

In some embodiments, in each of Formulas (IV.a), (IV.a.1), (IV.a.2), (IV.a.3), (IV.a.4), (IV.a.5), and (IV.a.6), $R^3$ is aryl.

In some embodiments, in each of Formulas (IV.a), (IV.a.1), (IV.a.2), (IV.a.3), (IV.a.4), (IV.a.5), and (IV.a.6), $R^3$ is heteroaryl.

In some embodiments, in each of Formulas (IV.a), (IV.a.1), (IV.a.2), (IV.a.3), (IV.a.4), (IV.a.5), and (IV.a.6), $R^3$ is cycloalkyl.

In some embodiments, in each of Formulas (IV.a), (IV.a.1), (IV.a.2), (IV.a.3), (IV.a.4), (IV.a.5), and (IV.a.6), $R^3$ is cycloalkenyl.

In some embodiments, in each of Formulas (IV.a), (IV.a.1), (IV.a.2), (IV.a.3), (IV.a.4), (IV.a.5), and (IV.a.6), $R^3$ is heterocycloalkyl.

In some embodiments, in each of Formulas (IV.a), (IV.a.1), (IV.a.2), (IV.a.3), (IV.a.4), (IV.a.5), and (IV.a.6), $R^3$ is heterocycloalkenyl.

In some embodiments, in each of Formulas (IV.a), (IV.a.1), (IV.a.2), (IV.a.3), (IV.a.4), (IV.a.5), and (IV.a.6), $R^3$ is halogen.

In some embodiments, in each of Formulas (IV.a), (IV.a.1), (IV.a.2), (IV.a.3), (IV.a.4), (IV.a.5), and (IV.a.6), $R^3$ is —CN.

In some embodiments, in each of Formulas (IV.a), (IV.a.1), (IV.a.2), (IV.a.3), (IV.a.4), (IV.a.5), and (IV.a.6), $R^3$ is —NO$_2$ In some embodiments, in each of Formulas (IV.a), (IV.a.1), (IV.a.2), (IV.a.3), (IV.a.4), (IV.a.5), and (IV.a.6), $R^3$ is —OR$^{19}$.

In some embodiments, in each of Formulas (IV.a), (IV.a.1), (IV.a.2), (IV.a.3), (IV.a.4), (IV.a.5), and (IV.a.6), $R^3$ is —OC(O)OR$^{20}$.

In some embodiments, in each of Formulas (IV.a), (IV.a.1), (IV.a.2), (IV.a.3), (IV.a.4), (IV.a.5), and (IV.a.6), $R^3$ is —NR$^{21}$R$^{22}$.

In some embodiments, in each of Formulas (IV.a), (IV.a.1), (IV.a.2), (IV.a.3), (IV.a.4), (IV.a.5), and (IV.a.6), $R^3$ is —NR$^{23}$SO$_2$R$^{24}$.

In some embodiments, in each of Formulas (IV.a), (IV.a.1), (IV.a.2), (IV.a.3), (IV.a.4), (IV.a.5), and (IV.a.6), $R^3$ is —NR$^{23}$C(O)OR$^{20}$.

In some embodiments, in each of Formulas (IV.a), (IV.a.1), (IV.a.2), (IV.a.4), (IV.a.5), and (IV.a.6), $R^3$ is —NR$^{23}$C(O)R$^{24}$.

In some embodiments, in each of Formulas (IV.a), (IV.a.1), (IV.a.2), (IV.a.3), (IV.a.4), (IV.a.5), and (IV.a.6), $R^3$ is —SO$_2$NR$^{25}$R$^{26}$.

In some embodiments, in each of Formulas (IV.a), (IV.a.1), (IV.a.2), (IV.a.3), (IV.a.4), (IV.a.5), and (IV.a.6), $R^3$ is —C(O)R$^{24}$.

In some embodiments, in each of Formulas (IV.a), (IV.a.1), (IV.a.2), (IV.a.3), (IV.a.4), (IV.a.5), and (IV.a.6), $R^3$ is —C(O)OR$^{29}$.

In some embodiments, in each of Formulas (IV.a), (IV.a.1), (IV.a.2), (IV.a.3), (IV.a.4), (IV.a.5), and (IV.a.6), $R^3$ is —SR$^{19}$.

In some embodiments, in each of Formulas (IV.a), (IV.a.1), (IV.a.2), (IV.a.3), (IV.a.4), (IV.a.5), and (IV.a.6), $R^3$ is —S(O)R$^{19}$.

In some embodiments, in each of Formulas (IV.a), (IV.a.1), (IV.a.2), (IV.a.3), (IV.a.4), (IV.a.5), and (IV.a.6), $R^3$ is —SO$_2$R$^{19}$.

In some embodiments, in each of Formulas (IV.a), (IV.a.1), (IV.a.2), (IV.a.3), (IV.a.4), (IV.a.5), and (IV.a.6), $R^3$ is —OC(O)R$^{24}$.

In some embodiments, in each of Formulas (IV.a), (IV.a.1), (IV.a.2), (IV.a.3), (IV.a.4), (IV.a.5), and (IV.a.6), $R^3$ is —C(O)NR$^{25}$R$^{26}$.

In some embodiments, in each of Formulas (IV.a), (IV.a.1), (IV.a.2), (IV.a.3), (IV.a.4), (IV.a.5), and (IV.a.6), $R^3$ is —NR$^{23}$C(N—CN)NR$^{25}$R$^{26}$.

In some embodiments, in each of Formulas (IV.a), (IV.a.1), (IV.a.2), (IV.a.3), (IV.a.4), (IV.a.5), and (IV.a.6), $R^3$ is $-NR^{23}C(O)NR^{25}R^{26}$.

In some embodiments, in each of Formulas (IV.a), (IV.a.1), (IV.a.2), (IV.a.3), (IV.a.4), (IV.a.5), and (IV.a.6), $R^3$ is selected from the group consisting of: methyl, ethyl, propyl (straight or branched), butyl (straight or branched), pentyl (straight or branched), phenyl,

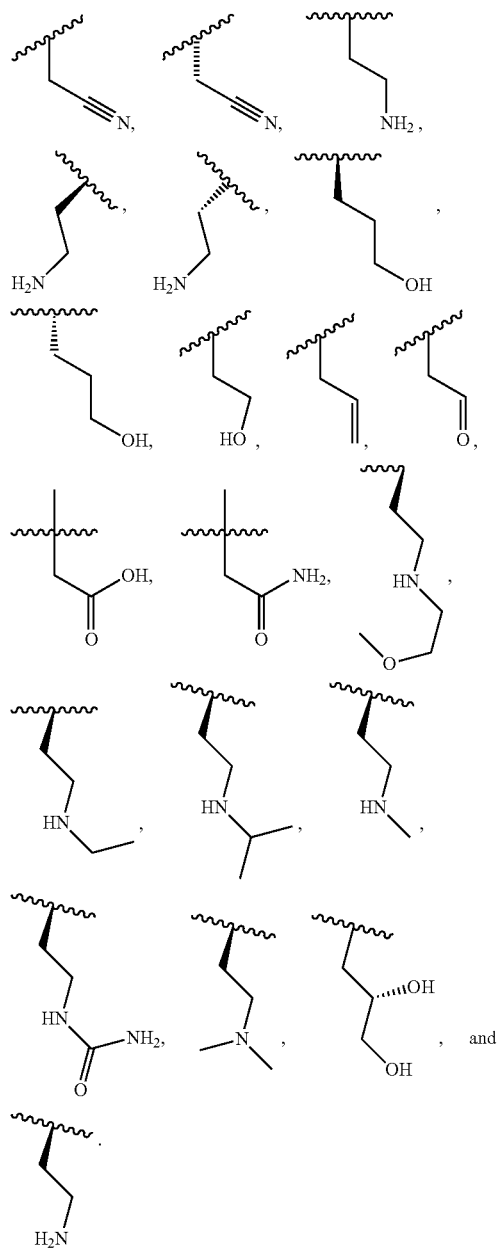

In some embodiments, in each of Formulas (IV.a), (IV.a.1), (IV.a.2), (IV.a.3), (IV.a.4), (IV.a.5), and (IV.a.6), when E is $-NR^6-$, $R^3$ is absent.

In one embodiment, the compounds of the invention have a structure shown in Formula (IV.b) and include pharmaceutically acceptable salts, solvates, esters, prodrugs, or isomers of said compounds:

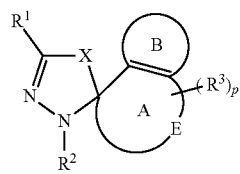

(IV.b.)

wherein X, $R^1$, $R^2$, $R^3$, p, E, ring A, and ring B are selected independently of each other and wherein:

ring A (including E and the unsaturation shown) is a 6-membered cycloalkenyl or heterocycloalkenyl ring;

E is selected from the group consisting of $-O-$, $-S-$, $-S(O)-$, $-S(O)_2-$, $-C(R^4)(R^5)-$, $-N(R^6)-$, $-N(C(Y)R^7)-$, $-N(C(Y)OR^8)-$, $-N(C(Y)N(R^9)(R^{10}))-$, $-C(O)-N(R^{11})-$, $-N(R^{11})-C(O)-$, $-S(O)_2-N(R^{11})-$, $-N(R^{11})-S(O)_2-$, $-C(O)-O-$, $-C(O)-$, $-O-N(R^6)-$, $-N(R^6)-O-$, $-N(R^6)-N(R^{12})-$, $-N=N-$, $-C(R^7)=N-$, $-C(O)-C(R^7)=N-$, $-C(O)-N=N-$, $-O-C(Y)-N(R^{11})-$, $-N(R^{11})-C(Y)-O-$, $-N(R^{11})-C(Y)-N(R^{12})-$, $-C(Y)-N(R^{11})-O-$, $-C(Y)-N(R^{11})-N(R^{12})-$, $-O-N(R^{11})-C(Y)-$, and $-N(R^{12})-N(R^{11})-C(Y)-$;

ring B is a substituted or unsubstituted heteroaromatic ring; and p, X, $R^1$, $R^2$, $R^3$, $R^4$, $R^5$, $R^6$, $R^7$, $R^8$, $R^9$, $R^{10}$, $R^{11}$, $R^{12}$, Y, and the optional substituents on ring B are as defined in any of the embodiments described above in Formula (I).

In one embodiment, Formula (IV.b) has the general structure shown in Formula (IV.b.1):

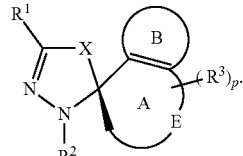

(IV.b.1)

In one embodiment, Formula (IV.b) has the general structure shown in Formula (IV.b.2):

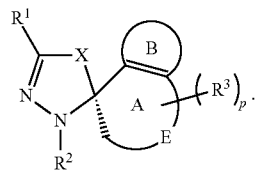

(IV.b.2)

In one embodiment, Formula (IV.b) has the general structure shown in Formula (IV.b.3):

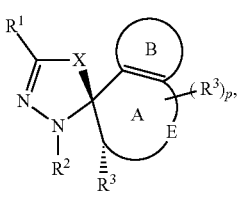

(IV.b.3)

wherein P is 0, 1, 2, or 3.

In one embodiment, Formula (IV.b) has the general structure shown in Formula (IV.b.4):

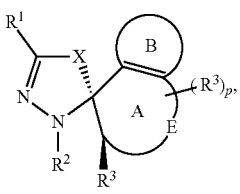

(IV.b.4)

wherein P is 0, 1, 2, or 3.

In one embodiment, Formula (IV.b) has the general structure shown in Formula (IV.b.5):

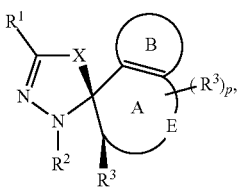

(IV.b.5)

wherein P is 0, 1, 2, or 3.

In one embodiment, Formula (IV.b) has the general structure shown in Formula (IV.b.6):

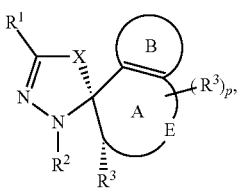

(IV.b.6)

wherein P is 0, 1, 2, or 3.

In some embodiments, in each of Formulas (IV.b), (IV.b.1), (IV.b.2), (IV.b.4), (IV.b.5), and (IV.b.6), X is S.

In some embodiments, in each of Formulas (IV.b), (IV.b.1), (IV.b.2), (IV.b.5), and (IV.b.6), X is S(O).

In some embodiments, in each of Formulas (IV.b), (IV.b.1), (IV.b.2), (IV.b.4), (IV.b.5), and (IV.b.6), X is $S(O)_2$.

In some embodiments, in each of Formulas (IV.b), (IV.b.1), (IV.b.2), (IV.b.3), (IV.b.4), (IV.b.5), and (IV.b.6), ring A is a cycloalkenyl ring and E is —$C(R^4)(R^5)$—.

In some embodiments, in each of Formulas (IV.b), (IV.b.1), (IV.b.2), (IV.b.3), (IV.b.4), (IV.b.5), and (IV.b.6), E is selected from the group consisting of —O—, —S—, —S(O)—, —$S(O)_2$—, and —$N(R^6)$—.

In some embodiments, in each of Formulas (IV.b), (IV.b.1), (IV.b.2), (IV.b.3), (IV.b.4), (IV.b.5), and (IV.b.6), E is selected from the group consisting of —O—, —S—, —S(O)—, —$S(O)_2$—, and —$N(R^6)$—, wherein $R^6$ is selected from the group consisting of H, alkyl, —$C(O)R^{24}$, and —$C(S)R^{24}$.

In some embodiments, in each of Formulas (IV.b), (IV.b.1), (IV.b.2), (IV.b.3), (IV.b.4), (IV.b.5), and (IV.b.6), E is selected from the group consisting of —O— and —$N(R^6)$—, wherein $R^6$ is selected from the group consisting of H, alkyl, —$C(O)R^{24}$, and —$C(S)R^{24}$.

In some embodiments, in each of Formulas (IV.b), (IV.b.1), (IV.b.2), (IV.b.3), (IV.b.4), (IV.b.5), and (IV.b.6), E is —O—.

In some embodiments, in each of Formulas (IV.b), (IV.b.1), (IV.b.2), (IV.b.3), (IV.b.5), and (IV.b.6), E is —S—.

In some embodiments, in each of Formulas (IV.b), (IV.b.1), (IV.b.2), (IV.b.3), (IV.b.4), (IV.b.5), and (IV.b.6), E is —S(O)—.

In some embodiments, in each of Formulas (IV.b), (IV.b.1), (IV.b.2), (IV.b.3), (IV.b.4), (IV.b.5), and (IV.b.6), E is —$S(O)_2$—.

In some embodiments, in each of Formulas (IV.b), (IV.b.1), (IV.b.2), (IV.b.3), (IV.b.4), (IV.b.5), and (IV.b.6), E is —$C(R^4)(R^5)$—.

In some embodiments, in each of Formulas (IV.b), (IV.b.1), (IV.b.2), (IV.b.3), (IV.b.4), (IV.b.5), and (IV.b.6), E is —$N(R^6)$—.

In some embodiments, in each of Formulas (IV.b), (IV.b.1), (IV.b.2), (IV.b.3), (IV.b.4), (IV.b.5), and (IV.b.6), E is —$N(C(Y)R^7)$—.

In some embodiments, in each of Formulas (IV.b), (IV.b.1), (IV.b.2), (IV.b.3), (IV.b.4), (IV.b.5), and (IV.b.6), E is —$N(C(Y)OR^8)$—.

In some embodiments, in each of Formulas (IV.b), (IV.b.1), (IV.b.2), (IV.b.3), (IV.b.4), (IV.b.5), and (IV.b.6), E is —$N(C(Y)N(R^9)(R^{10}))$—.

In some embodiments, in each of Formulas (IV.b), (IV.b.1), (IV.b.2), (IV.b.3), (IV.b.4), (IV.b.5), and (IV.b.6), E is —C(O)—$N(R^{11})$—.

In some embodiments, in each of Formulas (IV.b), (IV.b.1), (IV.b.2), (IV.b.3), (IV.b.4), (IV.b.5), and (IV.b.6), E is —$N(R^{11})$—C(O)—.

In some embodiments, in each of Formulas (IV.b), (IV.b.1), (IV.b.2), (IV.b.3), (IV.b.4), (IV.b.5), and (IV.b.6), E is —$S(O)_2$—$N(R^{11})$—.

In some embodiments, in each of Formulas (IV.b), (IV.b.1), (IV.b.2), (IV.b.3), (IV.b.4), (IV.b.5), and (IV.b.6), E is —$N(R^{11})$—$S(O)_2$—.

In some embodiments, in each of Formulas (IV.b), (IV.b.1), (IV.b.2), (IV.b.3), (IV.b.4), (IV.b.5), and (IV.b.6), E is —C(O)—O—.

In some embodiments, in each of Formulas (IV.b), (IV.b.1), (IV.b.2), (IV.b.3), (IV.b.4), (IV.b.5), and (IV.b.6), E is —O—C(O)—.

In some embodiments, in each of Formulas (IV.b), (IV.b.1), (IV.b.2), (IV.b.3), (IV.b.4), (IV.b.5), and (IV.b.6), E is —O—$N(R^6)$—.

In some embodiments, in each of Formulas (IV.b), (IV.b.1), (IV.b.2), (IV.b.3), (IV.b.4), (IV.b.5), and (IV.b.6), E is —$N(R^8)$—O—.

In some embodiments, in each of Formulas (IV.b), (IV.b.1), (IV.b.2), (IV.b.3), (IV.b.4), (IV.b.5), and (IV.b.6), E is —$N(R^8)$—$N(R^{12})$—.

In some embodiments, in each of Formulas (IV.b), (IV.b.1), (IV.b.2), (IV.b.3), (IV.b.4), (IV.b.5), and (IV.b.6), E is —N=N—.

In some embodiments, in each of Formulas (IV.b), (IV.b.1), (IV.b.2), (IV.b.3), (IV.b.4), (IV.b.5), and (IV.b.6), E is —C(R$^7$)=N—.

In some embodiments, in each of Formulas (IV.b), (IV.b.1), (IV.b.2), (IV.b.3), (IV.b.4), (IV.b.5), and (IV.b.6), E is —C(O)—C(R$^7$)=N—.

In some embodiments, in each of Formulas (IV.b), (IV.b.1), (IV.b.2), (IV.b.3), (IV.b.4), (IV.b.5), and (IV.b.6), E is —C(O)—N=N—.

In some embodiments, in each of Formulas (IV.b), (IV.b.1), (IV.b.2), (IV.b.3), (IV.b.4), (IV.b.5), and (IV.b.6), E is —O—C(Y)—N(R$^{11}$)—.

In some embodiments, in each of Formulas (IV.b), (IV.b.1), (IV.b.2), (IV.b.3), (IV.b.4), (IV.b.5), and (IV.b.6), E is —N(R$^{11}$)—C(Y)—O—.

In some embodiments, in each of Formulas (IV.b), (IV.b.1), (IV.b.2), (IV.b.3), (IV.b.4), (IV.b.5), and (IV.b.6), E is —N(R$^{11}$)—C(Y)—N(R$^{12}$)—.

In some embodiments, in each of Formulas (IV.b), (IV.b.1), (IV.b.2), (IV.b.3), (IV.b.4), (IV.b.5), and (IV.b.6), E is —C(Y)—N(R$^{11}$)—O—.

In some embodiments, in each of Formulas (IV.b), (IV.b.1), (IV.b.2), (IV.b.3), (IV.b.4), (IV.b.5), and (IV.b.6), E is —C(Y)—N(R$^{11}$)—N(R$^{12}$)—.

In some embodiments, in each of Formulas (IV.b), (IV.b.1), (IV.b.2), (IV.b.3), (IV.b.4), (IV.b.5), and (IV.b.6), E is —O—N(R$^{11}$)—C(Y)—.

In some embodiments, in each of Formulas (IV.b), (IV.b.1), (IV.b.2), (IV.b.3), (IV.b.4), (IV.b.5), and (IV.b.6), E is —N(R$^{12}$)—N(R$^{11}$)—C(Y)—.

In some embodiments, in each of Formulas (IV.b), (IV.b.1), (IV.b.2), (IV.b.3), (IV.b.4), (IV.b.5), and (IV.b.6), Y is (=O).

In some embodiments, in each of Formulas (IV.b), (IV.b.1), (IV.b.3), (IV.b.4), (IV.b.5), and (IV.b.6), Y is (=S).

In some embodiments, in each of Formulas (IV.b), (IV.b.1), (IV.b.2), (IV.b.3), (IV.b.4), (IV.b.5), and (IV.b.6), Y is (=N(R$^{13}$)).

In some embodiments, in each of Formulas (IV.b), (IV.b.1), (IV.b.2), (IV.b.3), (IV.b.4), (IV.b.5), and (IV.b.6), Y is (=N(CN)).

In some embodiments, in each of Formulas (IV.b), (IV.b.1), (IV.b.2), (IV.b.3), (IV.b.4), (IV.b.5), and (IV.b.6), Y is (=N(OR$^{14}$)).

In some embodiments, in each of Formulas (IV.b), (IV.b.1), (IV.b.2), (IV.b.3), (IV.b.4), (IV.b.5), and (IV.b.6), Y is (=N(R$^{15}$)(R$^{16}$)).

In some embodiments, in each of Formulas (IV.b), (IV.b.1), (IV.b.2), (IV.b.3), (IV.b.4), (IV.b.5), and (IV.b.6), Y is (=C(R$^{17}$)(R$^{18}$)).

In some embodiments, in each of Formulas (IV.b), (IV.b.1), (IV.b.2), (IV.b.3), (IV.b.4), (IV.b.5), and (IV.b.6), B is an unsubstituted heteroaromatic ring.

In some embodiments, in each of Formulas (IV.b), (IV.b.1), (IV.b.2), (IV.b.3), (IV.b.4), (IV.b.5), and (IV.b.6), B is an unsubstituted 5-6-membered heteroaromatic ring having from 1-3 ring heteroatoms, which can be the same or different, each hetero ring atom being independently selected from the group consisting of N, S, O, S(O)$_2$, and S(O)$_2$.

In some embodiments, in each of Formulas (IV.b), (IV.b.1), (IV.b.2), (IV.b.3), (IV.b.4), (IV.b.5), and (IV.b.6), B is a heteroaromatic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{23}$R$^{26}$, —C(O)R$^{24}$, —C(O)OR$^{20}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), B is a 5-6-membered heteroaromatic ring having from 1-3 ring heteroatoms, which can be the same or different, each hetero ring atom being independently selected from the group consisting of N, S, O, S(O), and S(O)$_2$, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), B is an unsubstituted 6-membered heteroaromatic ring having from 1-3 ring heteroatoms, which can be the same or different, each hetero ring atom being independently selected from the group consisting of N, S, and O.

In some embodiments, in each of Formulas (IV.b), (IV.b.1), (IV.b.2), (IV.b.3), (IV.b.4), (IV.b.5), and (IV.b.6), B is a 6-membered heteroaromatic ring having from 1-3 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$NR$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), B is an unsubstituted 6-membered heteroaromatic ring having 2 ring heteroatoms, each ring heteroatom being independently selected from of N, S, and O.

In some embodiments, in each of Formulas (IV.b), (IV.b.1), (IV.b.2), (IV.b.3), (IV.b.4), (IV.b.5), and (IV.b.6), B is a 6-membered heteroaromatic ring having 2 ring heteroatoms, each ring heteroatom being independently selected from of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —NR$^{21}$R$^{22}$, —C(O)R$^{24}$, —C(O)OR$^{20}$, —SR$^{19}$, —S(O)R$^{19}$, —SO$_2$R$^{19}$, —OC(O)R$^{24}$, and —C(O)NR$^{25}$R$^{26}$.

In some embodiments, in each of Formulas (IV.b), (IV.b.1), (IV.b.4), (IV.b.5), and (IV.b.6), B is an unsubstituted 5-membered heteroaromatic ring having from 1-2 ring heteroatoms, which can be the same or different, each hetero ring atom being independently selected from the group consisting of N, S, and O.

In some embodiments, in each of Formulas (IV.b), (IV.b.1), (IV.b.2), (IV.b.4), (IV.b.5), and (IV.b.6), B is a 5-membered heteroaromatic ring having from 1-2 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), B is an unsubstituted 5-membered heteroaromatic ring having 1 ring heteroatom selected from of N, S, and O.

In some embodiments, in each of Formulas (IV.b), (IV.b.1), (IV.b.2), (IV.b.3), (IV.b.4), (IV.b.5), and (IV.b.6), B is a 5-membered heteroaromatic ring having 1 ring heteroatom selected from of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —N$^{21}$R$^{22}$, —C(O)R$^{24}$, —C(O)OR$^{20}$, —SR$^{19}$, —S(O)R$^{19}$, —SO$_2$R$^{19}$, —OC(O)R$^{24}$, and —C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), B is a 5-membered heteroaromatic ring having S as the ring heteroatom, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —NR$^{21}$R$^{22}$, —C(O)R$^{24}$, —C(O)OR$^{20}$, —SR$^{19}$, —S(O)R$^{19}$, —SO$_2$R$^{19}$, —OC(O)R$^{24}$, and —C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), B is an unsubstituted 5-membered heteroaromatic ring having S as the ring heteroatom.

In some embodiments, in each of Formulas (IV.b), (IV.b.1), (IV.b.2), (IV.b.3), (IV.b.4), (IV.b.5), and (IV.b.6), B is selected from the group consisting of

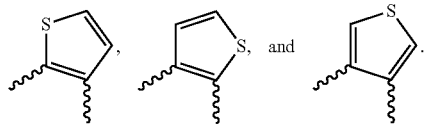

In some embodiments, in each of Formulas (IV.b), (IV.b.1), (IV.b.2), (IV.b.3), (IV.b.4), (IV.b.5), and (IV.b.6), R$^1$ is unsubstituted aryl.

In some embodiments, in each of Formulas (IV.b), (IV.b.1), (IV.b.2), (IV.b.3), (IV.b.4), (IV.b.5), and (IV.b.6), R$^1$ is unsubstituted phenyl.

In some embodiments, in each of Formulas (IV.b), (IV.b.1), (IV.b.2), (IV.b.3), (IV.b.4), (IV.b.5), and (IV.b.6), R$^1$ is unsubstituted naphthyl.

In some embodiments, in each of Formulas (IV.b), (IV.b.1), (IV.b.2), (IV.b.3), (IV.b.4), (IV.b.5), and (IV.b.6), R$^1$ is substituted aryl.

In some embodiments, in each of Formulas (IV.b), (IV.b.1), (IV.b.2), (IV.b.3), (IV.b.4), (IV.b.5), and (IV.b.6), R$^1$ is substituted phenyl.

In some embodiments, in each of Formulas (IV.b), (IV.b.1), (IV.b.2), (IV.b.3), (IV.b.4), (IV.b.5), and (IV.b.6), R$^1$ is substituted naphthyl.

In some embodiments, in each of Formulas (IV.b), (IV.b.1), (IV.b.2), (IV.b.3), (IV.b.4), (IV.b.5), and (IV.b.6), R$^1$ is aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{13}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), R$^1$ is phenyl substituted with one or more substituents, which can be the same or different, each substituent being independently selected from the group consisting halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.5), and (IV.b.6), R$^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In some embodiments, in each of Formulas (IV.b), (IV.b.1), (IV.b.2), (IV.b.3), (IV.b.4), (IV.b.5), and (IV.b.6), R$^1$ is selected from the group consisting of:

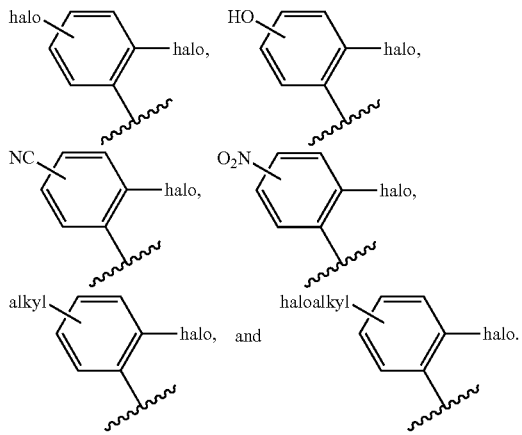

In some embodiments, in each of Formulas (IV.b), (IV.b.1), (IV.b.2), (IV.b.3), (IV.b.4), (IV.b.5), and (IV.b.6), R$^1$ is:

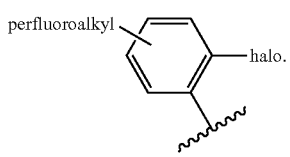

In some embodiments, in each of Formulas (IV.b), (IV.b.1), (IV.b.2), (IV.b.3), (IV.b.4), (IV.b.5), and (IV.b.6), $R^1$ is phenyl substituted with one to three fluoro groups.

In some embodiments, in each of Formulas (IV.b), (IV.b.1), (IV.b.2), (IV.b.3), (IV.b.4), (IV.b.5), and (IV.b.6), $R^1$ is phenyl substituted with two fluoro groups.

In some embodiments, in each of Formulas (IV.b), (IV.b.1), (IV.b.2), (IV.b.3), (IV.b.4), (IV.b.5), and (IV.b.6), $R^1$ is phenyl substituted with one fluoro group.

In some embodiments, in each of Formulas (IV.b), (IV.b.1), (IV.b.2), (IV.b.3), (IV.b.4), (IV.b.5), and (IV.b.6), $R^1$ is:

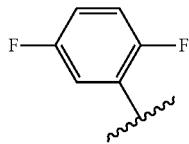

In some embodiments, in each of Formulas (IV.b), (IV.b.1), (IV.b.2), (IV.b.3), (IV.b.4), (IV.b.5), and (IV.b.6), $R^2$ is —C(Z)$R^7$.

In some embodiments, in each of Formulas (IV.b), (IV.b.1), (IV.b.2), (IV.b.3), (IV.b.4), (IV.b.5), and (IV.b.6), $R^2$ is —C(Z)$NR^9R^{10}$.

In some embodiments, in each of Formulas (IV.b), (IV.b.1), (IV.b.2), (IV.b.3), (IV.b.4), (IV.b.5), and (IV.b.6), $R^2$ is —C(Z)$OR^8$.

In some embodiments, in each of Formulas (IV.b), (IV.b.1), (IV.b.2), (IV.b.3), (IV.b.4), (IV.b.5), and (IV.b.6), $R^2$ is —$SO_2NR^9R^{10}$.

In some embodiments, in each of Formulas (IV.b), (IV.b.1), (IV.b.2), (IV.b.3), (IV.b.4), (IV.b.5), and (IV.b.6), $R^2$ is alkyl.

In some embodiments, in each of Formulas (IV.b), (IV.b.1), (IV.b.2), (IV.b.3), (IV.b.4), (IV.b.5), and (IV.b.6), $R^2$ is heteroalkyl.

In some embodiments, in each of Formulas (IV.b), (IV.b.1), (IV.b.2), (IV.b.3), (IV.b.4), (IV.b.5), and (IV.b.6), $R^2$ is aryl.

In some embodiments, in each of Formulas (IV.b), (IV.b.1), (IV.b.2), (IV.b.3), (IV.b.4), (IV.b.5), and (IV.b.6), $R^2$ is heteroaryl. In some embodiments, in each of Formulas (IV.b), (IV.b.1), (IV.b.2), (IV.b.3), (IV.b.4), (IV.b.5), and (IV.b.6), $R^2$ is cycloalkyl.

In some embodiments, in each of Formulas (IV.b), (IV.b.1), (IV.b.2), (IV.b.3), (IV.b.4), (IV.b.5), and (IV.b.6), $R^2$ is cycloalkenyl.

In some embodiments, in each of Formulas (IV.b), (IV.b.1), (IV.b.2), (IV.b.3), (IV.b.4), (IV.b.5), and (IV.b.6), $R^2$ is heterocycloalkyl.

In some embodiments, in each of Formulas (IV.b), (IV.b.1), (IV.b.2), (IV.b.3), (IV.b.4), (IV.b.5), and (IV.b.6), $R^2$ is heterocycloalkenyl.

In some embodiments, in each of Formulas (IV.b), (IV.b.1), (IV.b.2), (IV.b.3), (IV.b.4), (IV.b.5), and (IV.b.6), Z is (=O).

In some embodiments, in each of Formulas (IV.b), (IV.b.1), (IV.b.2), (IV.b.3), (IV.b.4), (IV.b.5), and (IV.b.6), Z is (=S).

In some embodiments, in each of Formulas (IV.b), (IV.b.1), (IV.b.2), (IV.b.3), (IV.b.4), (IV.b.5), and (IV.b.6), Z is (=N($R^{13}$)).

In some embodiments, in each of Formulas (IV.b), (IV.b.1), (IV.b.2), (IV.b.3), (IV.b.4), (IV.b.5), and (IV.b.6), Z is (=N(CN)).

In some embodiments, in each of Formulas (IV.b), (IV.b.1), (IV.b.2), (IV.b.3), (IV.b.4), (IV.b.5), and (IV.b.6), Z is (=N(O$R^{14}$)).

In some embodiments, in each of Formulas (IV.b), (IV.b.1), (IV.b.2), (IV.b.3), (IV.b.4), (IV.b.5), and (IV.b.6), Z is (=N($R^{15}$)($R^{16}$)).

In some embodiments, in each of Formulas (IV.b), (IV.b.1), (IV.b.2), (IV.b.3), (IV.b.4), (IV.b.5), and (IV.b.6), Z is (=C($R^{17}$)($R^{18}$)).

In some embodiments, in each of Formulas (IV.b), (IV.b.1), (IV.b.2), (IV.b.3), (IV.b.4), (IV.b.5), and (IV.b.6), $R^2$ is —C(Z)$R^7$, and Z is (=O).

In some embodiments, in each of Formulas (IV.b), (IV.b.1), (IV.b.2), (IV.b.3), (IV.b.4), (IV.b.5), and (IV.b.6), $R^2$ is —C(O)H.

In some embodiments, in each of Formulas (IV.b), (IV.b.1), (IV.b.2), (IV.b.3), (IV.b.4), (IV.b.5), and (IV.b.6), $R^2$ is —C(O)alkyl.

In some embodiments, in each of Formulas (IV.b), (IV.b.1), (IV.b.2), (IV.b.3), (IV.b.4), (IV.b.5), and (IV.b.6), $R^2$ is —C(O)$CH_3$.

In some embodiments, in each of Formulas (IV.b), (IV.b.1), (IV.b.2), (IV.b.3), (IV.b.4), (IV.b.5), and (IV.b.6), $R^2$ is —C(O)$R^7$, wherein said $R^7$ is alkyl substituted with one or more substituents, which can be the same or different, each substituent being independently selected from the group consisting of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —$OR^{19}$, —OC(O)$R^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —C(O)$R^{24}$, —C(O)$OR^{20}$, —$SR^{19}$, —S(O)$R^{19}$, —$SO_2R^{19}$, —C(O)$R^{24}$, —C(O)$NR^{25}R^{26}$, —$NR^{23}C(N-CN)NR^{25}R^{26}$ and —$NR^{23}C(O)NR^{25}R^{26}$.

In some embodiments, in each of Formulas (IV.b), (IV.b.1), (IV.b.2), (IV.b.3), (IV.b.4), (IV.b.5), and (IV.b.6), $R^2$ is —C(O)$R^7$, wherein said $R^7$ is alkyl substituted with one to three substituents, which can be the same or different, each substituent being independently selected from the group consisting of —$OR^{19}$, —$NR^{21}R^{22}$, and cycloalkyl.

In some embodiments, in each of Formulas (IV.b), (IV.b.1), (IV.b.2), (IV.b.3), (IV.b.4), (IV.b.5), and (IV.b.6), $R^2$ is —C(O)$R^7$, wherein said $R^7$ is alkyl, wherein said alkyl is substituted with alkyl and —OH.

In some embodiments, in each of Formulas (IV.b), (IV.b.1), (IV.b.2), (IV.b.3), (IV.b.4), (IV.b.5), and (IV.b.6), $R^2$ is —C(O)$R^7$, wherein said $R^7$ is alkyl substituted with one to three substituents, which can be the same or different, each substituent being independently selected from the group consisting of —OH, —$NH_2$, and cyclopropyl.

In some embodiments, in each of Formulas (IV.b), (IV.b.1), (IV.b.2), (IV.b.3), (IV.b.4), (IV.b.5), and (IV.b.6), $R^2$ is —C(O)$R^7$, wherein said $R^7$ is alkyl substituted with one to two substituents, which can be the same or different, each substituent being independently selected from the group consisting of —$NH_2$, and cyclopropyl.

In some embodiments, in each of Formulas (IV.b), (IV.b.1), (IV.b.2), (IV.b.3), (IV.b.4), (IV.b.5), and (IV.b.6), $R^2$ is —C(O)$R^7$, wherein said $R^7$ is alkyl substituted with —OH.

In some embodiments, in each of Formulas (IV.b), (IV.b.1), (IV.b.2), (IV.b.3), (IV.b.4), (IV.b.5), and (IV.b.6), $R^2$ is —C(O) $R^7$, wherein said $R^7$ is unsubstituted heterocycloalkyl.

In some embodiments, in each of Formulas (IV.b), (IV.b.1), (IV.b.2), (IV.b.3), (IV.b.4), (IV.b.5), and (IV.b.6), $R^2$ is —C(O) $R^7$, wherein said $R^7$ is substituted heterocycloalkyl.

In some embodiments, in each of Formulas (IV.b), (IV.b.1), (IV.b.2), (IV.b.3), (IV.b.4), (IV.b.5), and (IV.b.6), $R^2$ is —C(O) $R^7$, wherein said $R^7$ is heterocycloalkyl substituted with one or more substituents, which can be the same or different, each substituent being independently selected from the group consisting of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N—CN)NR^{25}R^{26}$ and —$NR^{23}C(O)NR^{25}R^{26}$.

In some embodiments, in each of Formulas (IV.b), (IV.b.1), (IV.b.2), (IV.b.3), (IV.b.4), (IV.b.5), and (IV.b.6), $R^2$ is —C(O) $R^7$, wherein said $R^7$ is selected from the group consisting of substituted piperidine, substituted piperazine, substituted morpholine, substituted pyrrolidine, and substituted azetidine.

In some embodiments, in each of Formulas (IV.b), (IV.b.1), (IV.b.2), (IV.b.3), (IV.b.4), (IV.b.5), and (IV.b.6), $R^2$ is selected from:

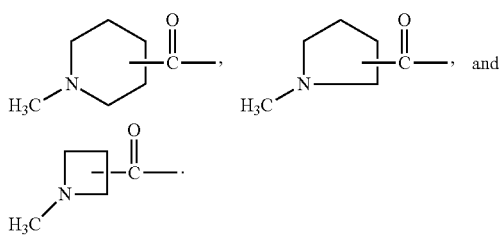

In some embodiments, in each of Formulas (IV.b), (IV.b.1), (IV.b.4), (IV.b.5), and (IV.b.6), $R^2$ is —C(O)$NR^9R^{10}$.

In some embodiments, in each of Formulas (IV.b), (IV.b.1), (IV.b.2), (IV.b.3), (IV.b.4), (IV.b.5), and (IV.b.6), $R^2$ is —C(O) $NH_2$.

In some embodiments, in each of Formulas (IV.b), (IV.b.1), (IV.b.2), (IV.b.3), (IV.b.4), (IV.b.5), and (IV.b.6), $R^2$ is —C(O) $NR^9R^{10}$, wherein $R^9$ and $R^{10}$ can be the same or different, each being independently selected from alkyl.

In some embodiments, in each of Formulas (IV.b), (IV.b.1), (IV.b.2), (IV.b.3), (IV.b.4), (IV.b.5), and (IV.b.6), $R^2$ is —C(O) $NR^9R^{10}$, wherein $R^9$ is unsubstituted heterocycloalkyl and $R^{10}$ is selected from the group consisting of H and alkyl.

In some embodiments, in each of Formulas (IV.b), (IV.b.1), (IV.b.2), (IV.b.3), (IV.b.4), (IV.b.5), and (IV.b.6), $R^2$ is —C(O) $NR^9R^{10}$, wherein $R^9$ is substituted heterocycloalkyl and $R^{10}$ is selected from the group consisting of H and alkyl.

In some embodiments, in each of Formulas (IV.b), (IV.b.1), (IV.b.2), (IV.b.3), (IV.b.4), (IV.b.5), and (IV.b.6), $R^2$ is —C(O) $NR^9R^{10}$, wherein $R^9$ is heterocycloalkyl substituted with from one to three substituents, which can be the same or different, each substituent being independently selected from alkyl, and $R^{10}$ is selected from the group consisting of H and alkyl.

In some embodiments, in each of Formulas (IV.b), (IV.b.1), (IV.b.2), (IV.b.3), (IV.b.4), (IV.b.5), and (IV.b.6), $R^2$ is selected from the group consisting of: alkyl, haloalkyl, heteroalkyl, heterohaloalkyl, —C(O)$R^7$, —C(O)$OR^8$, and —C(O)$NR^9R^{10}$.

In some embodiments, in each of Formulas (IV.b), (IV.b.1), (IV.b.2), (IV.b.3), (IV.b.4), (IV.b.5), and (IV.b.6), $R^2$ is selected from the group consisting of

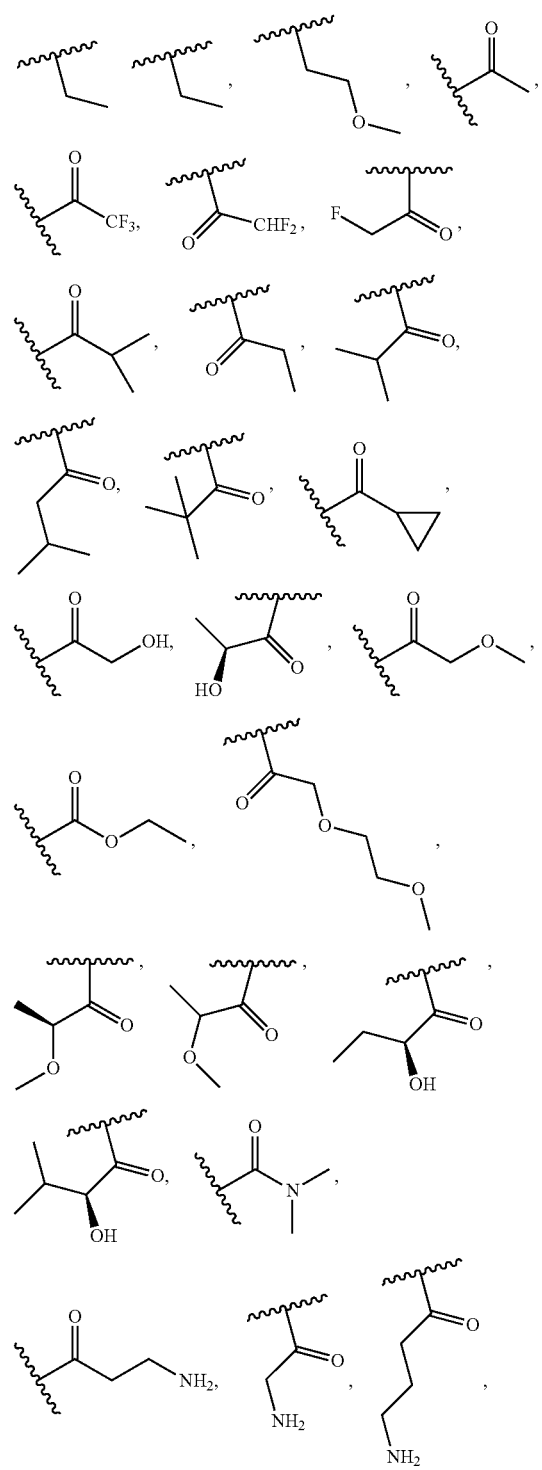

-continued
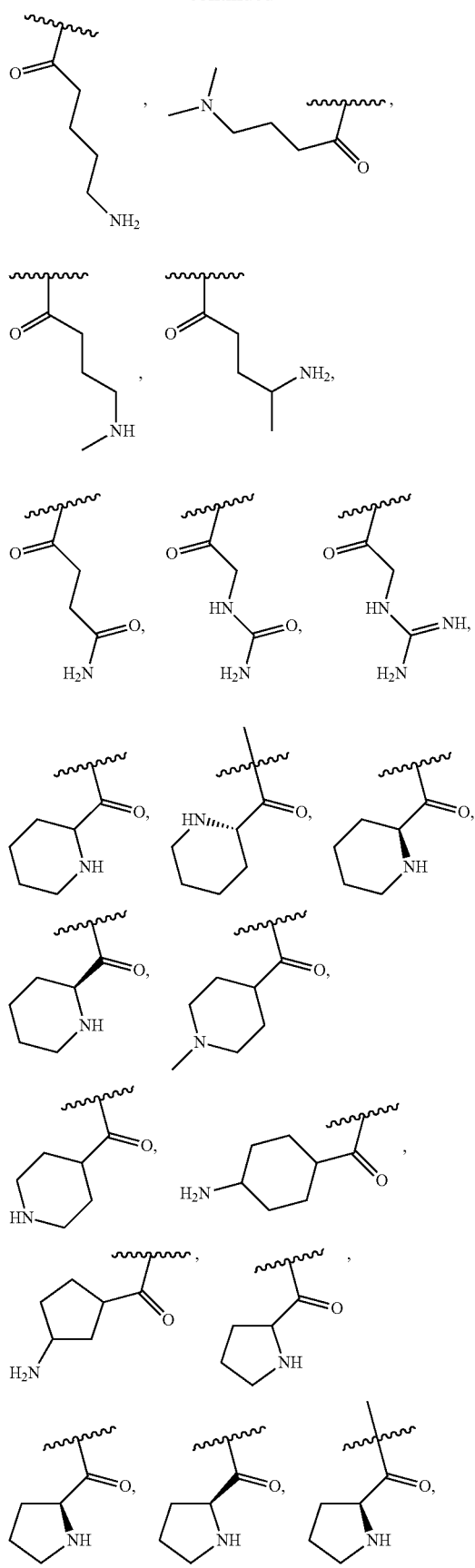
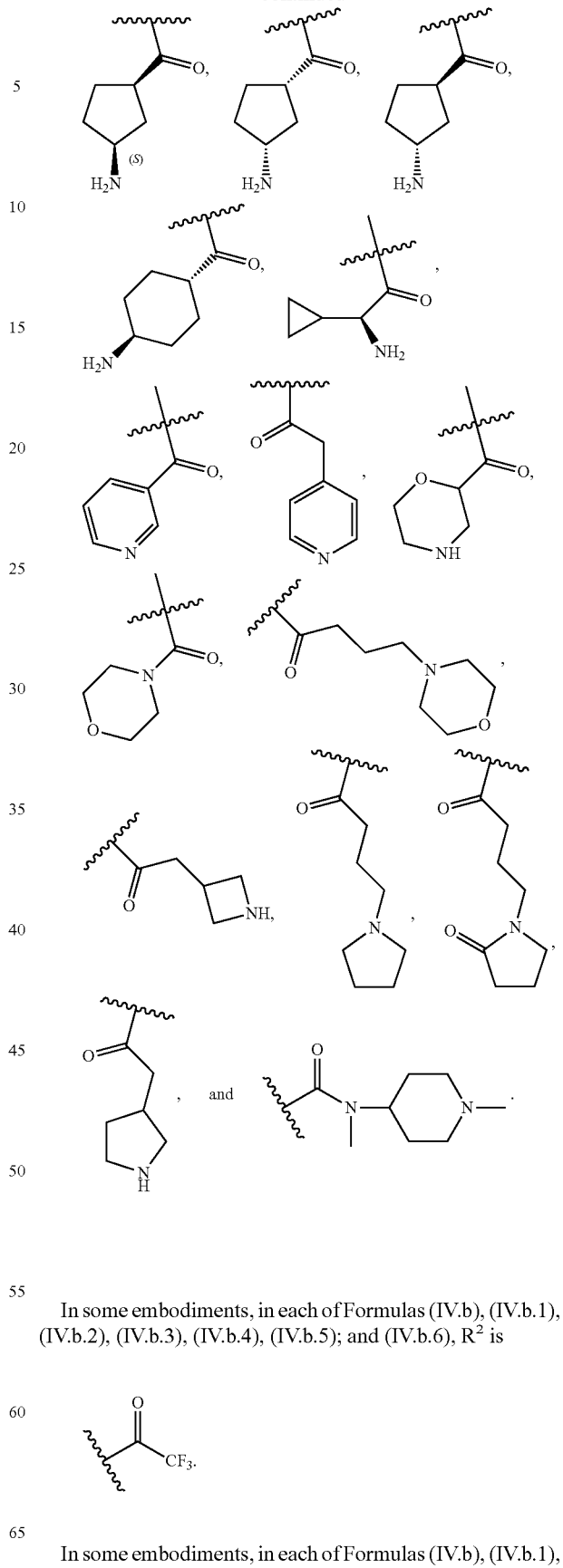
In some embodiments, in each of Formulas (IV.b), (IV.b.1), (IV.b.2), (IV.b.3), (IV.b.4), (IV.b.5); and (IV.b.6), $R^2$ is
In some embodiments, in each of Formulas (IV.b), (IV.b.1), (IV.b.2), (IV.b.3), (IV.b.4), (IV.b.5), and (IV.b.6), $R^2$ is

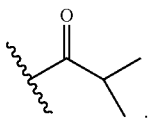 [SMILES: *C(=O)C(C)C ; "."]

In some embodiments, in each of Formulas (IV.b), (IV.b.1), (IV.b.2), (IV.b.3), (IV.b.4), (IV.b.5), and (IV.b.6), $R^2$ is

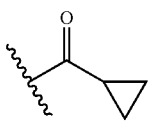

In some embodiments, in each of Formulas (IV.b), (IV.b.1), (IV.b.2), (IV.b.3), (IV.b.4), (IV.b.5), and (IV.b.6), $R^2$ is

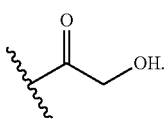 [SMILES: *C(=O)CO]

In some embodiments, in each of Formulas (IV.b), (IV.b.1), (IV.b.2), (IV.b.3), (IV.b.4), (IV.b.5), and (IV.b.6), $R^2$ is

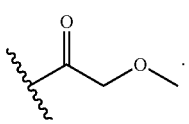 [SMILES: *C(=O)COC ; "."]

In some embodiments, in each of Formulas (IV.b), (IV.b.1), (IV.b.2), (IV.b.3), (IV.b.4), (IV.b.5), and (IV.b.6), $R^2$ is

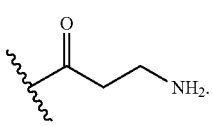 [SMILES: *C(=O)CCN]

In some embodiments, in each of Formulas (IV.b), (IV.b.1), (IV.b.2), (IV.b.3), (IV.b.4), (IV.b.5), and (IV.b.6), $R^2$ is

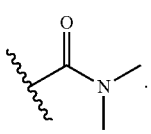

In some embodiments, in each of Formulas (IV.b), (IV.b.1), (IV.b.2), (IV.b.3), (IV.b.4), (IV.b.5), and (IV.b.6), $R^2$ is

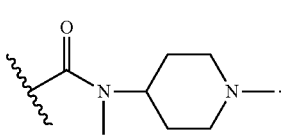

In some embodiments, in each of Formulas (IV.b), (IV.b.1), (IV.b.2), (IV.b.3), (IV.b.4), (IV.b.5), and (IV.b.6), p is 0 and $R^3$ is not present.

In some embodiments, in each of Formulas (IV.b), (IV.b.1), (IV.b.2), (IV.b.3), (IV.b.4), (IV.b.5), and (IV.b.6), p is 1.

In some embodiments, in each of Formulas (IV.b), (IV.b.1), (IV.b.2), (IV.b.3), (IV.b.4), (IV.b.5), and (IV.b.6), p is 2.

In some embodiments, in each of Formulas (IV.b), (IV.b.1), (IV.b.2), (IV.b.3), (IV.b.4), (IV.b.5), and (IV.b.6), p is 3.

In some embodiments, in each of Formulas (IV.b), (IV.b.1), (IV.b.2), (IV.b.3), (IV.b.4), (IV.b.5), and (IV.b.6), p is 4.

In some embodiments, in each of Formulas (IV.b), (IV.b.1), (IV.b.2), (IV.b.3), (IV.b.4), (IV.b.5), and (IV.b.6), p is >2 and at least two groups $R^3$ are attached to the same ring atom.

In some embodiments, in each of Formulas (IV.b), (IV.b.1), (IV.b.2), (IV.b.3), (IV.b.4), (IV.b.5), and (IV.b.6), p is 1 and $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{23}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{13}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), p is 2, 3, or 4 and each $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), p is 2, 3, or 4 and at least two groups $R^3$ are bound to the same ring carbon atom, wherein each $R^3$, which may be the same or different, is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (IV.b), (IV.b.1), (IV.b.2), (IV.b.3), (IV.b.4), (IV.b.5), and (IV.b.6), p is 2, 3, or 4 and at least two groups $R^3$ are bound to the same ring carbon atom, wherein two $R^3$ groups, which may be the same or different, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S.

In one embodiment, in Formula (IV.b), p is 1, 2, 3, or 4, and each $R^3$ is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(S)$_{1\text{-}1}$$^{24}$, —C(O)OR$^{20}$, —SR$^{19}$, —S(O)R$^{19}$, —$SO_2R^{19}$, —$OC(O)R^{24}$, —$C(O)NR^{25}R^{26}$, —$NR^{23}C(N$—$CN)NR^{25}R^{26}$, —$NR^{23}C(O)NR^{25}R^{26}$, and —$NR^{23}$—$C(NH)$—$NR^{25}R^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N$—$CN)NR^{25}R^{26}$ and —$NR^{23}C(O)NR^{25}R^{26}$.

In one embodiment, in Formula (IV.b), p is 1 and $R^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —$NO_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —$OR^{19}$, —$OC(O)OR^{20}$, —$NR^{21}R^{22}$, —$NR^{23}SO_2R^{24}$, —$NR^{23}C(O)OR^{20}$, —$NR^{23}C(O)R^{24}$, —$SO_2NR^{25}R^{26}$, —$C(O)R^{24}$, —$C(O)OR^{20}$, —$SR^{19}$, —$S(O)R^{19}$, —$SO_2R^{19}$, —$OC(O)R^{24}$, —$C(O)NR^{25}R^{26}$, —$NR^{23}C(N$—$CN)NR^{25}R^{26}$ and —$NR^{23}C(O)NR^{25}R^{26}$.

In one embodiment, in Formula (IV.b), p is 2, 3, or 4, and any two $R^3$ groups bound to the same ring A atom are taken together to form a —C(O)— group.

In one embodiment, in Formula (IV.b), p is ≤2 and any two $R^3$ groups bound to the same ring A atom are taken together to form a spiroheterocycloalkyl group having from 1 to 3 ring heteroatoms independently selected from the group consisting of —NH—, —$NR^6$—, O, S, S(O), and $S(O)_2$, or spiroheterocycloalkenyl group having from 1 to 3 ring heteroatoms independently selected from the group consisting of —NH—, —$NR^6$—, O, S, S(O), and $S(O)_2$.

In some embodiments, in each of Formulas (IV.b), (IV.b.1), (IV.b.2), (IV.b.3), (IV.b.4), and (IV.b.6), $R^3$ is alkyl.

In some embodiments, in each of Formulas (IV.b), (IV.b.1), (IV.b.2), (IV.b.3), (IV.b.5), and (IV.b.6), $R^3$ is heteroalkyl.

In some embodiments, in each of Formulas (IV.b), (IV.b.1), (IV.b.2), (IV.b.3), (IV.b.4), (IV.b.5), and (IV.b.6), $R^3$ is alkenyl.

In some embodiments, in each of Formulas (IV.b), (IV.b.1), (IV.b.2), (IV.b.3), (IV.b.4), (IV.b.5), and (IV.b.6), $R^3$ is heteroalkenyl.

In some embodiments, in each of Formulas (IV.b), (IV.b.1), (IV.b.2), (IV.b.3), (IV.b.4), (IV.b.5), and (IV.b.6), $R^3$ is alkynyl.

In some embodiments, in each of Formulas (IV.b), (IV.b.1), (IV.b.2), (IV.b.3), (IV.b.4), (IV.b.5), and (IV.b.6), $R^3$ is heteroalkynyl.

In some embodiments, in each of Formulas (IV.b), (IV.b.1), (IV.b.2), (IV.b.3), (IV.b.4), (IV.b.5), and (IV.b.6), $R^3$ is aryl.

In some embodiments, in each of Formulas (IV.b), (IV.b.1), (IV.b.2), (IV.b.3), (IV.b.4), (IV.b.5), and (IV.b.6), $R^3$ is heteroaryl.

In some embodiments, in each of Formulas (IV.b), (IV.b.1), (IV.b.2), (IV.b.3), (IV.b.4), (IV.b.5), and (IV.b.6), $R^3$ is cycloalkyl.

In some embodiments, in each of Formulas (IV.b), (IV.b.1), (IV.b.2), (IV.b.3), (IV.b.4), (IV.b.5), and (IV.b.6), $R^3$ is cycloalkenyl.

In some embodiments, in each of Formulas (IV.b), (IV.b.1), (IV.b.2), (IV.b.3), (IV.b.4), (IV.b.5), and (IV.b.6), $R^3$ is heterocycloalkyl.

In some embodiments, in each of Formulas (IV.b), (IV.b.1), (IV.b.2), (IV.b.3), (IV.b.4), (IV.b.5), and (IV.b.6), $R^3$ is heterocycloalkenyl.

In some embodiments, in each of Formulas (IV.b), (IV.b.1), (IV.b.2), (IV.b.3), (IV.b.4), (IV.b.5), and (IV.b.6), $R^3$ is halogen.

In some embodiments, in each of Formulas (IV.b), (IV.b.1), (IV.b.2), (IV.b.3), (IV.b.4), (IV.b.5), and (IV.b.6), $R^3$ is —CN.

In some embodiments, in each of Formulas (IV.b), (IV.b.1), (IV.b.2), (IV.b.3), (IV.b.5), and (IV.b.6), $R^3$ is —$NO_2$.

In some embodiments, in each of Formulas (IV.b), (IV.b.1), (IV.b.2), (IV.b.3), (IV.b.4), (IV.b.5), and (IV:b.6), $R^3$ is —$OR^{16}$.

In some embodiments, in each of Formulas (IV.b), (IV.b.1), (IV.b.2), (IV.b.3), (IV.b.4), (IV.b.5), and (IV.b.6), $R^3$ is —$OC(O)OR^{26}$.

In some embodiments, in each of Formulas (IV.b), (IV.b.1), (IV.b.2), (IV.b.3), (IV.b.4), (IV.b.5), and (IV.b.6), $R^3$ is —$NR^{21}R^{22}$.

In some embodiments, in each of Formulas (IV.b), (IV.b.1), (IV.b.2), (IV.b.3), (IV.b.4), (IV.b.5), and (IV.b.6), $R^3$ is —$NR^{23}SO_2R^{24}$.

In some embodiments, in each of Formulas (IV.b), (IV.b.1), (IV.b.2), (IV.b.3), (IV.b.4), (IV.b.5), and (IV.b.6), $R^3$ is —$NR^{23}C(O)OR^{20}$.

In some embodiments, in each of Formulas (IV.b), (IV.b.1), (IV.b.2), (IV.b.3), (IV.b.4), (IV.b.5), and (IV.b.6), $R^3$ is —$NR^{23}C(O)R^{24}$.

In some embodiments, in each of Formulas (IV.b), (IV.b.1), (IV.b.2), (IV.b.3), (IV.b.4), (IV.b.5), and (IV.b.6), $R^3$ is —$SO_2NR^{25}R^{26}$.

In some embodiments, in each of Formulas (IV.b), (IV.b.2), (IV.b.3), (IV.b.4), (IV.b.5), and (IV.b.6), $R^3$ is —$C(O)R^{24}$.

In some embodiments, in each of Formulas (IV.b), (IV.b.1), (IV.b.2), (IV.b.3), (IV.b.4), (IV.b.5), and (IV.b.6), $R^3$ is —$C(O)OR^{26}$.

In some embodiments, in each of Formulas (IV.b), (IV.b.1), (IV.b.2), (IV.b.3), (IV.b.4), (IV.b.5), and (IV.b.6), $R^3$ is —$SR^{19}$.

In some embodiments, in each of Formulas (IV.b), (IV.b.1), (IV.b.2), (IV.b.3), (IV.b.4), (IV.b.5), and (IV.b.6), $R^3$ is —$S(O)R^{19}$.

In some embodiments, in each of Formulas (IV.b), (IV.b.1), (IV.b.2), (IV.b.3), (IV.b.4), (IV.b.5), and (IV.b.6), $R^3$ is —$SO_2R^{19}$.

In some embodiments, in each of Formulas (IV.b), (IV.b.1), (IV.b.2), (IV.b.3), (IV.b.4), (IV.b.5), and (IV.b.6), $R^3$ is —$OC(O)R^{24}$.

In some embodiments, in each of Formulas (IV.b), (IV.b.1), (IV.b.2), (IV.b.3), (IV.b.4), (IV.b.5), and (IV.b.6), $R^3$ is —$C(O)NR^{23}R^{26}$.

In some embodiments, in each of Formulas (IV.b), (IV.b.1), (IV.b.2), (IV.b.3), (IV.b.4), (IV.b.5), and (IV.b.6), $R^3$ is —$NR^{23}C(N$—$CN)NR^{25}R^{26}$.

In some embodiments, in each of Formulas (IV.b), (IV.b.1), (IV.b.2), (IV.b.3), (IV.b.4), (IV.b.5), and (IV.b.6), $R^3$ is —$NR^{23}C(O)NR^{25}R^{26}$.

In some embodiments, in each of Formulas (IV.b), (IV.b.1), (IV.b.2), (IV.b.3), (IV.b.4), (IV.b.5), and (IV.b.6), $R^3$ is selected from the group consisting of: methyl, ethyl, propyl (straight or branched), butyl (straight or branched), pentyl (straight or branched), phenyl,

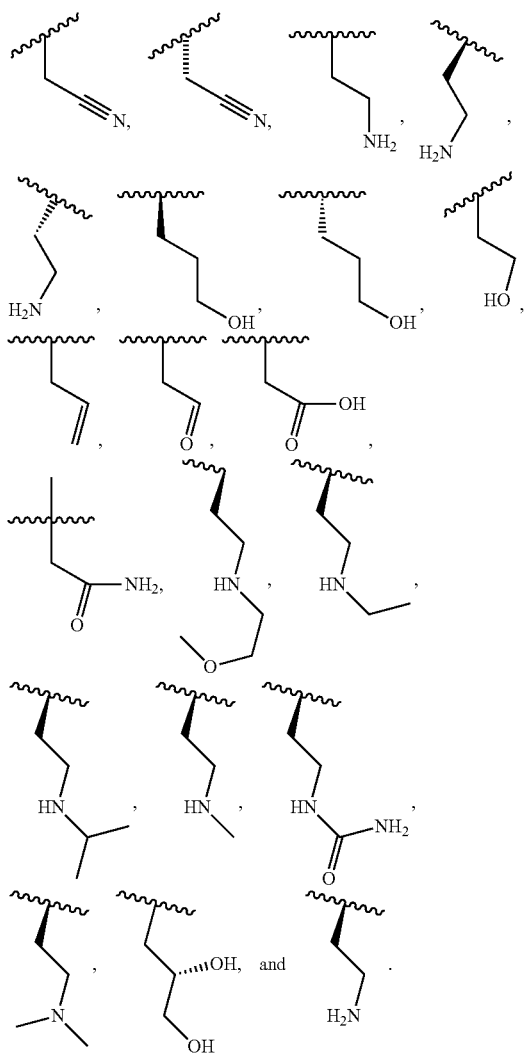

In some embodiments, in each of Formulas (IV.b), (IV.b.1), (IV.b.2), (IV.b.3), (IV.b.4), (IV.b.5), and (IV.b.6), when E is —$NR^6$—, $R^3$ is absent.

In one embodiment, the compounds of the invention have a structure shown in Formula (V.a) and include pharmaceutically acceptable salts, solvates, esters, prodrugs, or isomers of said compounds:

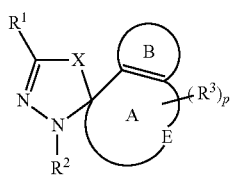

(V.a.)

wherein X, $R^1$, $R^2$, $R^3$, p, E, ring A, and ring B are selected independently of each other and wherein:

ring A (including E and the unsaturation shown) is a 7- to 8-membered cycloalkenyl or heterocycloalkenyl ring;

E is selected from the group consisting of —O—, —S—, —S(O)$_2$—, —C($R^4$)($R^5$)—, —N($R^6$)—, —N(C(Y)$R^7$)—, —N(C(Y)O$R^8$)—, —N(C(Y)N($R^9$)($R^{10}$))—, —C(O)—N($R^{11}$)—, —N($R^{11}$)—C(O)—, —S(O)$_2$—N($R^{11}$)—, —N($R^{11}$)—S(O)$_2$—, —C(O)—O—, —O—C(O)—, —O—N($R^6$)—, —N($R^6$)—O—, —N($R^6$)—N($R^{12}$)—, —N═N—, —C($R^7$)═N—, —C(O)—C($R^7$)═N—, —C(O)—N═N—, —O—C(Y)—N($R^{11}$)—, —N($R^{11}$)—C(Y)—O—, —N($R^{11}$)—C(Y)—N($R^{12}$)—, —C(Y)—N($R^{11}$)—O—, —C(Y)—N($R^{11}$)—N($R^{12}$)—, —O—N($R^{11}$)—C(Y)—, and —N($R^{12}$)—N($R^{11}$)—C(Y)—;

ring B is a substituted or unsubstituted aromatic ring;

and p, X, $R^1$, $R^2$, $R^3$, $R^4$, $R^5$, $R^6$, $R^7$, $R^8$, $R^9$, $R^{10}$, $R^{11}$, $R^{12}$, Y, and the optional substituents on ring B are as defined in each of the embodiments described above in Formula (I).

In one embodiment, Formula (V.a) has the general structure shown in Formula (V.a.1):

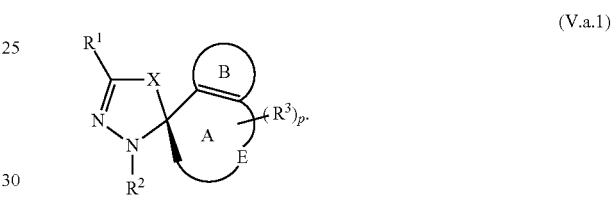

(V.a.1)

In one embodiment, Formula (V.a) has the general structure shown in Formula (V.a.2):

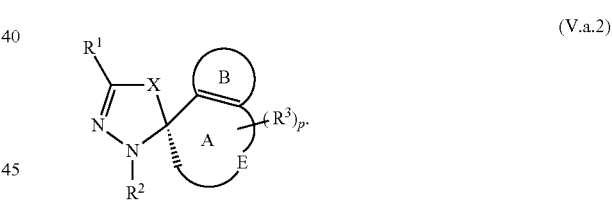

(V.a.2)

In one embodiment, Formula (V.a) has the general structure shown in Formula (V.a.3):

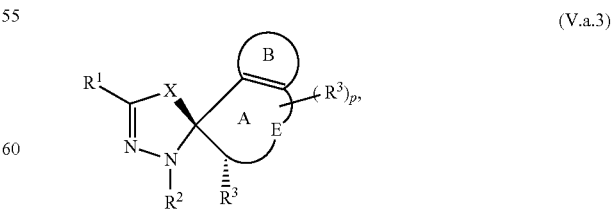

(V.a.3)

wherein P is 0, 1, 2, or 3.

In one embodiment, Formula (V.a) has the general structure shown in Formula (V.a.4):

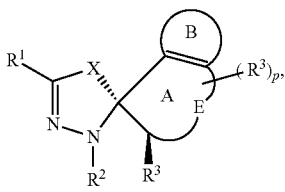

(V.a.4)

wherein P is 0, 1, 2, or 3.

In one embodiment, Formula (V.a) has the general structure shown in Formula (V.a.5):

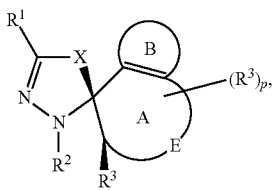

(V.a.5)

wherein P is 0, 1, 2, or 3.

In one embodiment, Formula (V.a) has the general structure shown in Formula (V.a.6):

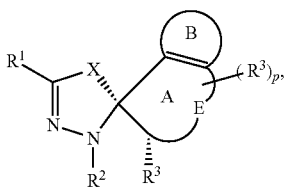

(V.a.6)

wherein P is 0, 1, 2, or 3.

In some embodiments, in each of Formulas (V.a), (V.a.1), (V.a.2), (V.a.3), (V.a.4), (V.a.5), and (V.a.6), X is S.

In some embodiments, in each of Formulas (V.a), (V.a.1), (V.a.2), (V.a.3), (V.a.4), (V.a.5), and (V.a.6), X is S(O).

In some embodiments, in each of Formulas (V.a), (V.a.1), (V.a.2), (V.a.3), (V.a.4), (V.a.5), and (V.a.6), X is $S(O)_2$.

In some embodiments, in each of Formulas (V.a), (V.a.1), (V.a.2), (V.a.3), (V.a.4), (V.a.5), and (V.a.6), ring A is a cycloalkenyl ring and E is $—C(R^4)(R^5)—$.

In some embodiments, in each of Formulas (V.a), (V.a.1), (V.a.2), (V.a.3), (V.a.4), (V.a.5), and (V.a.6), ring A is a heterocycloalkenyl ring and E is selected from the group consisting of —O—, —S—, —S(O)—, $—S(O)_2—$, and $—N(R^6)—$.

In some embodiments, in each of Formulas (V.a), (V.a.1), (V.a.2), (V.a.3), (V.a.4), (V.a.5), and (V.a.6), E is selected from the group consisting of —O—, —S—, —S(O)—, $—S(O)_2—$, and $—N(R^6)—$, wherein $R^6$ is selected from the group consisting of H, alkyl, $—C(O)R^{24}$, and $—C(S)R^{24}$.

In some embodiments, in each of Formulas (V.a), (V.a.1), (V.a.2), (V.a.3), (V.a.4), (V.a.5), and (V.a.6), E is selected from the group consisting of —O— and $—N(R^6)—$, wherein $R^6$ is selected from the group consisting of H, alkyl, $—C(O)R^{24}$, and $—C(S)R^{24}$.

In some embodiments, in each of Formulas (V.a), (V.a.1), (V.a.2), (V.a.3), (V.a.4), (V.a.5), and (V.a.6), E is —O—.

In some embodiments, in each of Formulas (V.a), (V.a.1), (V.a.2), (V.a.3), (V.a.4), (V.a.5), and (V.a.6), E is —S—.

In some embodiments, in each of Formulas (V.a), (V.a.1), (V.a.2), (V.a.3), (V.a.4), (V.a.5), and (V.a.6), E is —S(O)—.

In some embodiments, in each of Formulas (V.a), (V.a.1), (V.a.2), (V.a.3), (V.a.4), (V.a.5), and (V.a.6), E is $—S(O)_2—$.

In some embodiments, in each of Formulas (V.a), (V.a.1), (V.a.2), (V.a.3), (V.a.4), (V.a.5), and (V.a.6), E is $—C(R^4)(R^5)—$.

In some embodiments, in each of Formulas (V.a), (V.a.1), (V.a.2), (V.a.3), (V.a.4), (V.a.5), and (V.a.6), E is $—N(R^6)—$.

In some embodiments, in each of Formulas (V.a), (V.a.1), (V.a.2), (V.a.3), (V.a.4), (V.a.5), and (V.a.6), E is $—N(C(Y)R^7)—$.

In some embodiments, in each of Formulas (V.a), (V.a.1), (V.a.2), (V.a.3), (V.a.4), (V.a.5), and (V.a.6), E is $—N(C(Y)OR^8)—$.

In some embodiments, in each of Formulas (V.a), (V.a.1), (V.a.2), (V.a.3), (V.a.4), (V.a.5), and (V.a.6), E is $—N(C(Y)N(R^9)(R^{10}))—$.

In some embodiments, in each of Formulas (V.a), (V.a.1), (V.a.2), (V.a.3), (V.a.4), (V.a.5), and (V.a.6), E is $—C(O)—N(R^{11})—$.

In some embodiments, in each of Formulas (V.a), (V.a.1), (V.a.2), (V.a.3), (V.a.4), (V.a.5), and (V.a.6), E is $—N(R^{11})—C(O)—$.

In some embodiments, in each of Formulas (V.a), (V.a.1), (V.a.2), (V.a.3), (V.a.4), (V.a.5), and (V.a.6), E is $—S(O)_2—N(R^{11})—$.

In some embodiments, in each of Formulas (V.a), (V.a.1), (V.a.2), (V.a.3), (V.a.4), (V.a.5), and (V.a.6), E is $—N(R^{11})—S(O)_2—$.

In some embodiments, in each of Formulas (V.a), (V.a.1), (V.a.2), (V.a.3), (V.a.4), (V.a.5), and (V.a.6), E is —C(O)—O—.

In some embodiments, in each of Formulas (V.a), (V.a.1), (V.a.2), (V.a.3), (V.a.4), (V.a.5), and (V.a.6), E is —O—C(O)—.

In some embodiments, in each of Formulas (V.a), (V.a.1), (V.a.2), (V.a.3), (V.a.4), (V.a.5), and (V.a.6), E is $—O—N(R^6)—$.

In some embodiments, in each of Formulas (V.a), (V.a.1), (V.a.2), (V.a.3), (V.a.4), (V.a.5), and (V.a.6), E is $—N(R^6)—O—$.

In some embodiments, in each of Formulas (V.a), (V.a.1), (V.a.2), (V.a.3), (V.a.4), (V.a.5), and (V.a.6), E is $—N(R^6)—N(R^{12})—$.

In some embodiments, in each of Formulas (V.a), (V.a.1), (V.a.2), (V.a.3), (V.a.4), (V.a.5), and (V.a.6), E is —N=N—.

In some embodiments, in each of Formulas (V.a), (V.a.1), (V.a.2), (V.a.3), (V.a.4), (V.a.5), and (V.a.6), E is $—C(R^7)=N—$.

In some embodiments, in each of Formulas (V.a), (V.a.1), (V.a.2), (V.a.3), (V.a.4), (V.a.5), and (V.a.6), E is $—C(O)—C(R^7)=N—$.

In some embodiments, in each of Formulas (V.a), (V.a.1), (V.a.2), (V.a.3), (V.a.4), (V.a.5), and (V.a.6), E is —C(O)—N=N—.

In some embodiments, in each of Formulas (V.a), (V.a.1), (V.a.2), (V.a.3), (V.a.4), (V.a.5), and (V.a.6), E is $—O—C(Y)—N(R^{11})—$.

In some embodiments, in each of Formulas (V.a), (V.a.1), (V.a.2), (V.a.3), (V.a.4), (V.a.5), and (V.a.6), E is $—N(R^{11})—C(Y)—O—$.

In some embodiments, in each of Formulas (V.a), (V.a.1), (V.a.2), (V.a.3), (V.a.4), (V.a.5), and (V.a.6), E is $—N(R^{11})—C(Y)—N(R^{12})—$.

In some embodiments, in each of Formulas (V.a), (V.a.1), (V.a.2), (V.a.3), (V.a.4), (V.a.5), and (V.a.6), E is —C(Y)—N(R$^{11}$)—O—.

In some embodiments, in each of Formulas (V.a), (V.a.1), (V.a.2), (V.a.3), (V.a.4), (V.a.5), and (V.a.6), E is —C(Y)—N(R$^{11}$)—N(R$^{12}$)—.

In some embodiments, in each of Formulas (V.a), (V.a.1), (V.a.2), (V.a.3), (V.a.4), (V.a.5), and (V.a.6), E is —O—N(R$^{11}$)—C(Y)—.

In some embodiments, in each of Formulas (V.a), (V.a.1), (V.a.2), (V.a.3), (V.a.4), (V.a.5), and (V.a.6), E is —N(R$^{12}$)—N(R$^{11}$)—C(Y)—.

In some embodiments, in each of Formulas (V.a), (V.a.1), (V.a.2), (V.a.3), (V.a.4), (V.a.5), and (V.a.6), Y is (=O).

In some embodiments, in each of Formulas (V.a), (V.a.1), (V.a.2), (V.a.3), (V.a.4), (V.a.5), and (V.a.6), Y is (=S).

In some embodiments, in each of Formulas (V.a), (V.a.1), (V.a.2), (V.a.3), (V.a.4), (V.a.5), and (V.a.6), Y is (=N(R$^{13}$)).

In some embodiments, in each of Formulas (V.a), (V.a.1), (V.a.2), (V.a.3), (V.a.4), (V.a.5), and (V.a.6), Y is (=N(CN)).

In some embodiments, in each of Formulas (V.a), (V.a.1), (V.a.2), (V.a.3), (V.a.4), (V.a.5), and (V.a.6), Y is (=N(OR$^{14}$)).

In some embodiments, in each of Formulas (V.a), (V.a.1), (V.a.2), (V.a.3), (V.a.4), (V.a.5), and (V.a.6), Y is (=N(R$^{15}$)(R$^{16}$)).

In some embodiments, in each of Formulas (V.a), (V.a.1), (V.a.2), (V.a.3), (V.a.4), (V.a.5), and (V.a.6), Y is (=C(R$^{17}$)(R$^{18}$)).

In some embodiments, in each of Formulas (V.a), (V.a.1), (V.a.2), (V.a.3), (V.a.4), (V.a.5), and (V.a.6), B is an unsubstituted aromatic ring.

In some embodiments, in each of Formulas (V.a), (V.a.1), (V.a.2), (V.a.3), (V.a.4), (V.a.5), and (V.a.6), B is an unsubstituted benzo ring, and Formula (IV.a.) has the general structure:

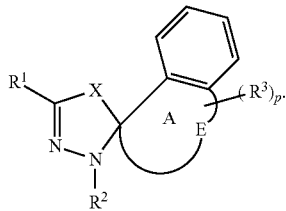

In some embodiments, in each of Formulas (V.a), (V.a.1), (V.a.2), (V.a.3), (V.a.4), (V.a.5), and (V.a.6), B is an aromatic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —S(O)R$^{19}$, —SO$_{2R}$$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (V.a), (V.a.1), (V.a.2), (V.a.3), (V.a.4), (V.a.5), and (V.a.6), B is a benzo ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (V.a), (V.a.1), (V.a.2), (V.a.3), (V.a.4), (V.a.5), and (V.a.6), R$^1$ is unsubstituted aryl.

In some embodiments, in each of Formulas (V.a), (V.a.1), (V.a.2), (V.a.3), (V.a.4), (V.a.5), and (V.a.6), R$^1$ is unsubstituted phenyl.

In some embodiments, in each of Formulas (V.a), (V.a.1), (V.a.2), (V.a.3), (V.a.4), (V.a.5), and (V.a.6), R$^1$ is unsubstituted naphthyl.

In some embodiments, in each of Formulas (V.a), (V.a.1), (V.a.2), (V.a.3), (V.a.4), (V.a.5), and (V.a.6), R$^1$ is substituted aryl.

In some embodiments, in each of Formulas (V.a), (V.a.1), (V.a.2), (V.a.3), (V.a.4), (V.a.5), and (V.a.6), R$^1$ is substituted phenyl.

In some embodiments, in each of Formulas (V.a), (V.a.1), (V.a.2), (V.a.3), (V.a.4), (V.a.5), and (V.a.6), R$^1$ is substituted naphthyl.

In some embodiments, in each of Formulas (V.a), (V.a.1), (V.a.2), (V.a.3), (V.a.4), (V.a.5), and (V.a.6), R$^1$ is aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (V.a), (V.a.1), (V.a.2), (V.a.3), (V.a.4), (V.a.5), and (V.a.6), R$^1$ is phenyl substituted with one or more substituents, which can be the same or different, each substituent being independently selected from the group consisting halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (V.a), (V.a.1), (V.a.2), (V.a.3), (V.a.4), (V.a.5), and (V.a.6), R$^1$ is phenyl substituted with one to four substituents, which can be the same or different, each substituent being independently selected from the group consisting of halo, —OH, —CN, —NO$_2$, —NR$^{21}$R$^{22}$, and haloalkyl.

In some embodiments, in each of Formulas (V.a), (V.a.1), (V.a.2), (V.a.3), (V.a.4), (V.a.5), and (V.a.6), R$^1$ is selected from the group consisting of:

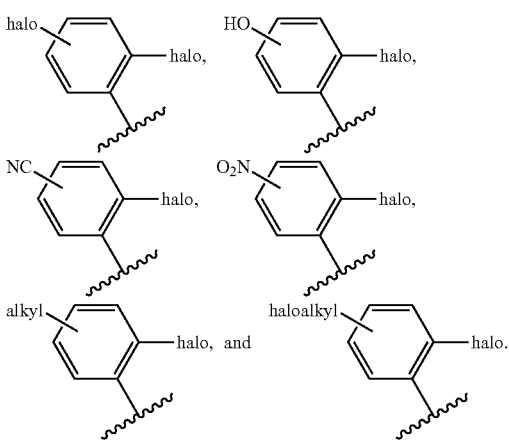

In some embodiments, in each of Formulas (V.a), (V.a.1), (V.a.2), (V.a.3), (V.a.4), (V.a.5), and (V.a.6), $R^1$ is:

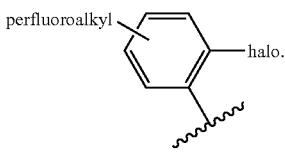

In some embodiments, in each of Formulas (V.a), (V.a.1), (V.a.2), (V.a.3), (V.a.4), (V.a.5), and (V.a.6), $R^1$ is phenyl substituted with one to three fluoro groups.

In some embodiments, in each of Formulas (V.a), (V.a.1), (V.a.2), (V.a.3), (V.a.4), (V.a.5), and (V.a.6), $R^1$ is phenyl substituted with two fluoro groups.

In some embodiments, in each of Formulas (V.a), (V.a.1), (V.a.2), (V.a.3), (V.a.4), (V.a.5), and (V.a.6), $R^1$ is phenyl substituted with one fluoro group.

In some embodiments, in each of Formulas (V.a), (V.a.1), (V.a.2), (V.a.3), (V.a.4), (V.a.5), and (V.a.6), $R^1$ is:

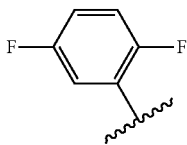 [SMILES: *c1cc(F)ccc1F]

In some embodiments, in each of Formulas (V.a), (V.a.1), (V.a.2), (V.a.3), (V.a.4), (V.a.5), and (V.a.6), $R^2$ is —C(Z)$R^7$.

In some embodiments, in each of Formulas (V.a), (V.a.1), (V.a.2), (V.a.3), (V.a.4), (V.a.5), and (V.a.6), $R^2$ is —C(Z)N$R^9R^{10}$.

In some embodiments, in each of Formulas (V.a), (V.a.1), (V.a.2), (V.a.3), (V.a.4), (V.a.5), and (V.a.6), $R^2$ is —C(Z)O$R^8$.

In some embodiments, in each of Formulas (V.a), (V.a.1), (V.a.2), (V.a.3), (V.a.4), (V.a.5), and (V.a.6), $R^2$ is —SO$_2$N$R^9R^{10}$.

In some embodiments, in each of Formulas (V.a), (V.a.1), (V.a.2), (V.a.3), (V.a.4), (V.a.5), and (V.a.6), $R^2$ is alkyl.

In some embodiments, in each of Formulas (V.a), (V.a.1), (V.a.2), (V.a.3), (V.a.4), (V.a.5), and (V.a.6), $R^2$ is heteroalkyl.

In some embodiments, in each of Formulas (V.a), (V.a.1), (V.a.2), (V.a.3), (V.a.4), (V.a.5), and (V.a.6), $R^2$ is aryl.

In some embodiments, in each of Formulas (V.a), (V.a.1), (V.a.2), (V.a.3), (V.a.4), (V.a.5), and (V.a.6), $R^2$ is heteroaryl.

In some embodiments, in each of Formulas (V.a), (V.a.1), (V.a.2), (V.a.3), (V.a.4), (V.a.5), and (V.a.6), $R^2$ is cycloalkyl.

In some embodiments, in each of Formulas (V.a), (V.a.1), (V.a.2), (V.a.3), (V.a.4), (V.a.5), and (V.a.6), $R^2$ is cycloalkenyl.

In some embodiments, in each of Formulas (V.a), (V.a.1), (V.a.2), (V.a.3), (V.a.4), (V.a.5), and (V.a.6), $R^2$ is heterocycloalkyl.

In some embodiments, in each of Formulas (V.a), (V.a.1), (V.a.2), (V.a.3), (V.a.4), (V.a.5), and (V.a.6), $R^2$ is heterocycloalkenyl.

In some embodiments, in each of Formulas (V.a), (V.a.1), (V.a.2), (V.a.3), (V.a.4), (V.a.5), and (V.a.6), Z is (=O).

In some embodiments, in each of Formulas (V.a), (V.a.1), (V.a.2), (V.a.3), (V.a.4), (V.a.5), and (V.a.6), Z is (=S).

In some embodiments, in each of Formulas (V.a), (V.a.1), (V.a.2), (V.a.3), (V.a.4), (V.a.5), and (V.a.6), Z is (=N($R^{13}$)).

In some embodiments, in each of Formulas (V.a), (V.a.1), (V.a.2), (V.a.3), (V.a.4), (V.a.5), and (V.a.6), Z is (=N(CN)).

In some embodiments, in each of Formulas (V.a), (V.a.1), (V.a.2), (V.a.3), (V.a.4), (V.a.5), and (V.a.6), Z is (=N(O$R^{14}$)).

In some embodiments, in each of Formulas (V.a), (V.a.1), (V.a.2), (V.a.3), (V.a.4), (V.a.5), and (V.a.6), Z is (=N($R^{15}$)($R^{16}$)).

In some embodiments, in each of Formulas (V.a), (V.a.1), (V.a.2), (V.a.3), (V.a.4), (V.a.5), and (V.a.6), Z is (=C($R^{17}$)($R^{18}$)).

In some embodiments, in each of Formulas (V.a), (V.a.1), (V.a.2), (V.a.3), (V.a.4), (V.a.5), and (V.a.6), $R^2$ is —C(Z)$R^7$, and Z is (=O).

In some embodiments, in each of Formulas (V.a), (V.a.1), (V.a.2), (V.a.3), (V.a.4), (V.a.5), and (V.a.6), $R^2$ is —C(O)H.

In some embodiments, in each of Formulas (V.a), (V.a.1), (V.a.2), (V.a.3), (V.a.4), (V.a.5), and (V.a.6), $R^2$ is —C(O)alkyl.

In some embodiments, in each of Formulas (V.a), (V.a.1), (V.a.2), (V.a.4), (V.a.5), and (V.a.6), $R^2$ is —C(O)CH$_3$.

In some embodiments, in each of Formulas (V.a), (V.a.1), (V.a.2), (V.a.3), (V.a.4), (V.a.5), and (V.a.6), $R^2$ is —C(O)$R^7$, wherein said $R^7$ is alkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —O$R^{19}$, —OC(O)O$R^{20}$, —N$R^{21}R^{22}$, —N$R^{23}$SO$_2R^{24}$, —N$R^{23}$C(O)O$R^{20}$, —N$R^{23}$C(O)$R^{24}$, —SO$_2$N$R^{25}R^{26}$, —C(O)$R^{24}$, —C(O)O$R^{20}$, —S$R^{19}$, —S(O)$R^{19}$, —SO$_2R^{19}$, —OC(O)$R^{24}$, —C(O)N$R^{25}R^{26}$, —N$R^{23}$C(N=CN)N$R^{25}R^{26}$ and —N$R^{23}$C(O)N$R^{25}R^{26}$.

In some embodiments, in each of Formulas (V.a), (V.a.1), (V.a.2), (V.a.3), (V.a.4), (V.a.5), and (V.a.6), $R^2$ is —C(O)$R^7$, wherein said $R^7$ is alkyl substituted with one to three substituents, which can be the same or different, each substituent being independently selected from the group consisting of —O$R^{19}$, —N$R^{21}R^{22}$, and cycloalkyl.

In some embodiments, in each of Formulas (V.a), (V.a.1), (V.a.2), (V.a.3), (V.a.4), (V.a.5), and (V.a.6), $R^2$ is —C(O)$R^7$, wherein said $R^7$ is alkyl, wherein said alkyl is substituted with alkyl and —OH.

In some embcidiments, in each of Formulas (V.a), (V.a.1), (V.a.2), (V.a.4), (V.a.5), and (V.a.6), $R^2$ is —C(O)$R^7$, wherein said $R^7$ is alkyl substituted with one to three substituents, which can be the same or different, each substituent being independently selected from the group consisting of —OH, —NH$_2$, and cyclopropyl.

In some embodiments, in each of Formulas (V.a), (V.a.1), (V.a.2), (V.a.3), (V.a.4), (V.a.5), and (V.a.6), R$^2$ is —C(O)R$^7$, wherein said R$^7$ is alkyl substituted with one to two substituents, which can be the same or different, each substituent being independently selected from the group consisting of —NH$_2$, and cyclopropyl.

In some embodiments, in each of Formulas (V.a), (V.a.1), (V.a.2), (V.a.3), (V.a.4), (V.a.5), and (V.a.6), R$^2$ is —C(O)R$^7$, wherein said R$^7$ is alkyl substituted with —OH.

In some embodiments, in each of Formulas (V.a), (V.a.1), (V.a.2), (V.a.3), (V.a.4), (V.a.5), and (V.a.6), R$^2$ is —C(O)R$^7$, wherein said R$^7$ is unsubstituted heterocycloalkyl.

In some embodiments, in each of Formulas (V.a), (V.a.1), (V.a.2), (V.a.3), (V.a.4), (V.a.5), and (V.a.6), R$^2$ is —C(O)R$^7$, wherein said R$^7$ is substituted heterocycloalkyl.

In some embodiments, in each of Formulas (V.a), (V.a.1), (V.a.2), (V.a.3), (V.a.4), (V.a.5), and (V.a.6), R$^2$ is —C(O)R$^7$, wherein said R$^7$ is heterocycloalkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (V.a), (V.a.1), (V.a.2), (V.a.3), (V.a.4), (V.a.5), and (V.a.6), R$^2$ is —C(O)R$^7$, wherein said R$^7$ is selected from the group consisting of substituted piperidine, substituted piperazine, substituted morpholine, substituted pyrrolidine, and substituted azetidine.

In some embodiments, in each of Formulas (V.a), (V.a.1), (V.a.2), (V.a.3), (V.a.4), (V.a.5), and (V.a.6), R$^2$ is selected from:

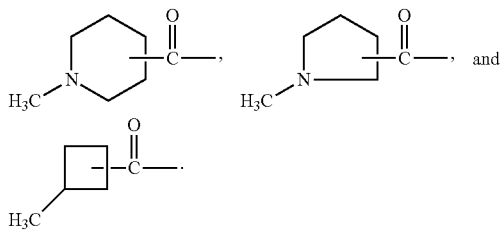

In some embodiments, in each of Formulas (V.a), (V.a.1), (V.a.2), (V.a.3), (V.a.4), (V.a.5), and (V.a.6), R$^2$ is —C(O)NR$^9$R$^{10}$.

In some embodiments, in each of Formulas (V.a), (V.a.1), (V.a.2), (V.a.3), (V.a.4), (V.a.5), and (V.a.6), R$^2$ is —C(O)NH$_2$.

In some embodiments, in each of Formulas (V.a), (V.a.1), (V.a.2), (V.a.3), (V.a.4), (V.a.5), and (V.a.6), R$^2$ is —C(O)NR$^9$R$^{10}$, wherein R$^9$ and R$^{10}$ can be the same or different, each being independently selected from alkyl.

In some embodiments, in each of Formulas (V.a), (V.a.1), (V.a.2), (V.a.3), (V.a.4), (V.a.5), and (V.a.6), R$^2$ is —C(O)NR$^9$R$^{10}$, wherein R$^9$ is unsubstituted heterocycloalkyl and R$^{10}$ is selected from the group consisting of H and alkyl.

In some embodiments, in each of Formulas (V.a), (V.a.1), (V.a.2), (V.a.3),
(V.a.4), (V.a.5), and (V.a.6), R$^2$ is —C(O)NR$^9$R$^{10}$, wherein R$^9$ is substituted heterocycloalkyl and R$^{10}$ is selected from the group consisting of H and alkyl.

In some embodiments, in each of Formulas (V.a), (V.a.1), (V.a.2), (V.a.3), (V.a.4), (V.a.5), and (V.a.6), R$^2$ is —C(O)NR$^9$R$^{10}$, wherein R$^9$ is heterocycloalkyl substituted with from one to three substituents, which can be the same or different, each substituent being independently selected from alkyl, and R$^{10}$ is selected from the group consisting of H and alkyl.

In some embodiments, in each of Formulas (V.a), (V.a.1), (V.a.2), (V.a.3), (V.a.4), (V.a.5), and (V.a.6), R$^2$ is selected from the group consisting of: alkyl, haloalkyl, heteroalkyl, heterohaloalkyl, —C(O)R$^7$, —C(O)OR$^8$, and —C(O)NR$^9$R$^{10}$.

In some embodiments, in each of Formulas (V.a), (V.a.1), (V.a.2), (V.a.3), (V.a.4), (V.a.5), and (V.a.6), R$^2$ is selected from the group consisting of

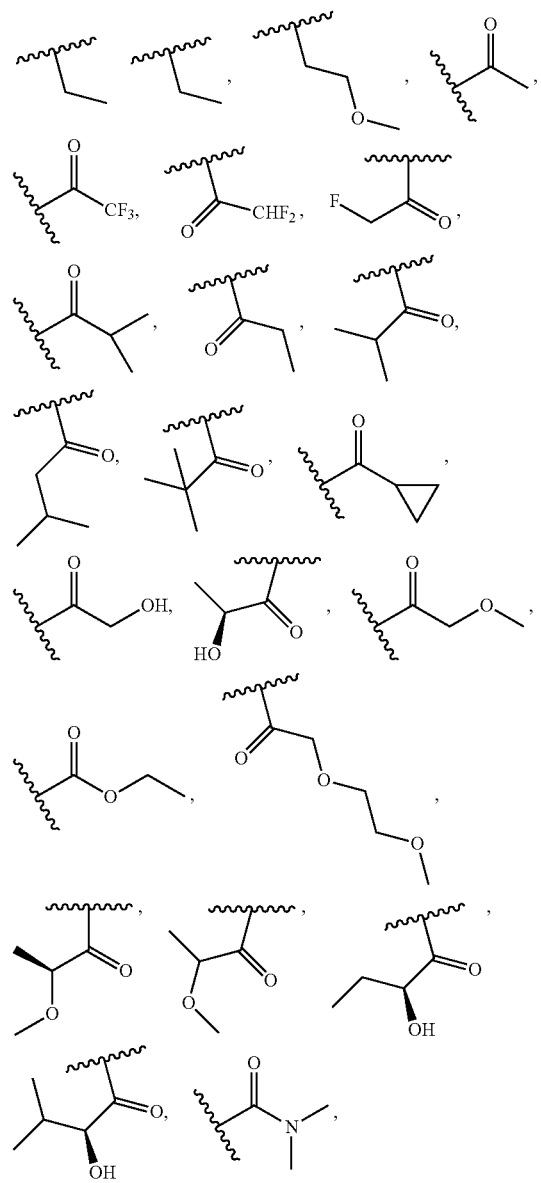

In some embodiments, in each of Formulas (V.a), (V.a.1), (V.a.2), (V.a.3), (V.a.4), (V.a.5), and (V.a.6), R² is

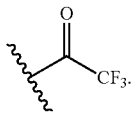

In some embodiments, in each of Formulas (V.a), (V.a.1), (V.a.2), (V.a.3), (V.a.4), (V.a.5), and (V.a.6), $R^2$ is

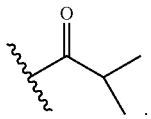 [SMILES: *C(=O)C(C)C ; "."]

In some embodiments, in each of Formulas (V.a), (V.a.1), (V.a.2), (V.a.3), (V.a.4), (V.a.5), and (V.a.6), $R^2$ is

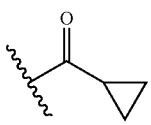

In some embodiments, in each of Formulas (V.a), (V.a.1), (V.a.2), (V.a.3), (V.a.4), (V.a.5), and (V.a.6), $R^2$ is

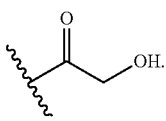

In some embodiments, in each of Formulas (V.a), (V.a.1), (V.a.2), (V.a.3), (V.a.4), (V.a.5), and (V.a.6), $R^2$ is

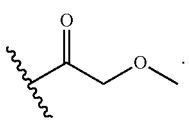 [SMILES: *C(=O)COC ; "."]

In some embodiments, in each of Formulas (V.a), (V.a.1), (V.a.2), (V.a.3), (V.a.4), (V.a.5), and (V.a.6), $R^2$ is

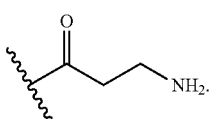 [SMILES: *C(=O)CCN]

In some embodiments, in each of Formulas (V.a), (V.a.1), (V.a.2), (V.a.3), (V.a.4), (V.a.5), and (V.a.6), $R^2$ is

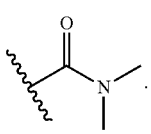

In some embodiments, in each of Formulas (V.a), (V.a.1), (V.a.2), (V.a.3), (V.a.4), (V.a.5), and (V.a.6), $R^2$ is

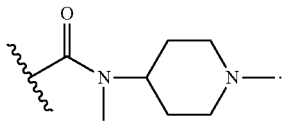

In some embodiments, in each of Formulas (V.a), (V.a.1), (V.a.2), (V.a.3), (V.a.4), (V.a.5), and (V.a.6), p is 0 and $R^3$ is not present.

In some embodiments, in each of Formulas (V.a), (V.a.1), (V.a.2), (V.a.3), (V.a.4), (V.a.5), and (V.a.6), p is 1.

In some embodiments, in each of Formulas (V.a), (V.a.1), (V.a.2), (V.a.3), (V.a.4), (V.a.5), and (V.a.6), p is 2.

In some embodiments, in each of Formulas (V.a), (V.a.1), (V.a.2), (V.a.3), (V.a.4), (V.a.5), and (V.a.6), p is 3.

In some embodiments, in each of Formulas (V.a), (V.a.1), (V.a.2), (V.a.3), (V.a.4), (V.a.5), and (V.a.6), p is 4.

In some embodiments, in each of Formulas (V.a), (V.a.1), (V.a.2), (V.a.3), (V.a.4), (V.a.5), and (V.a.6), p is >2 and at least two groups $R^3$ are attached to the same ring atom.

In some embodiments, in each of Formulas (V.a), (V.a.1), (V.a.2), (V.a.3), (V.a.4), (V.a.5), and (V.a.6), p is 1 and $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (V.a), (V.a.1), (V.a.2), (V.a.3), (V.a.4), (V.a.5), and (V.a.6), p is 2, 3, or 4 and each $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In some embodiments, in each of Formulas (V.a), (V.a.1), (V.a.2), (V.a.3), (V.a.4), (V.a.5), and (V.a.6), p is 2, 3, or 4 and at least two groups $R^3$ are bound to the same ring carbon atom, wherein each $R^3$, which may be the same or different, is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{23}$R$^{26}$, —C(O)R$^{24}$, —C(O)OR$^{20}$, —SR$^{19}$, —S(O)R$^{13}$, —SO$_2$R$^{19}$, —OC(O)R$^{24}$, —C(O)NR$^{23}$R$^{26}$, —NR$^{23}$C(N—CN)NR$^{23}$R$^{26}$ and —NR$^{23}$C(O)NR$^{23}$R$^{26}$.

In some embodiments, in each of Formulas (V.a), (V.a.1), (V.a.2), (V.a.3), (V.a.4), (V.a.5), and (V.a.6), p is 2, 3, or 4 and at least two groups $R^3$ are bound to the same ring carbon atom, wherein two $R^3$ groups, which may be the same or different, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S.

In one embodiment, in Formula (V.a), p is 1, 2, 3, or 4, and each $R^3$ is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)R$^{20}$, —NR$^{23}$C(O)R$^{24}$, —SO$_2$NR$^{25}$R$^{26}$, —C(O)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$, —NR$^{23}$C(O)NR$^{25}$R$^{26}$, and —NR$^{23}$—C(NH)—NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{23}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{13}$, —SO$_2$R$^{19}$, —OC(O)R$^{24}$, —C(O)NR$^{25}$R$^{26}$, —NR$^{23}$C(N—CN)NR$^{23}$R$^{26}$ and —NR$^{23}$C(O)NR$^{23}$R$^{26}$.

In one embodiment, in Formula (V.a), p is 1 and $R^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{16}$, —SO$_2$R$^{16}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (V.a), p is 2, 3, or 4, and any two $R^3$ groups bound to the same ring A atom are taken together to form a —C(O)— group.

In one embodiment, in Formula (V.a), p is 2, 3, or 4, and any two $R^3$ groups bound to the same ring A atom are taken together to form a spiroheterocycloalkyl group having from 1 to 3 ring heteroatoms independently selected from the group consisting of —NH—, —NR$^6$—, O, S, S(O), and S(O)$_2$, or spiroheterocycloalkenyl group having from 1 to 3 ring heteroatoms independently selected from the group consisting of —NH—, —NR$^6$—, O, S, S(O), and S(O)$_2$.

In some embodiments, in each of Formulas (V.a), (V.a.1), (V.a.2), (V.a.3), (V.a.4), (V.a.5), and (V.a.6), $R^3$ is alkyl.

In some embodiments, in each of Formulas (V.a), (V.a.1), (V.a.2), (V.a.3), (V.a.4), (V.a.5), and (V.a.6), $R^3$ is heteroalkyl.

In some embodiments, in each of Formulas (V.a), (V.a.1), (V.a.2), (V.a.3), (V.a.4), (V.a.5), and (V.a.6), $R^3$ is alkenyl.

In some embodiments, in each of Formulas (V.a), (V.a.1), (V.a.2), (V.a.3), (V.a.4), (V.a.5), and (V.a.6), $R^3$ is heteroalkenyl.

In some embodiments, in each of Formulas (V.a), (V.a.1), (V.a.2), (V.a.3), (V.a.4), (V.a.5), and (V.a.6), $R^3$ is alkynyl.

In some embodiments, in each of Formulas (V.a), (V.a.1), (V.a.2), (V.a.3), (V.a.4), (V.a.5), and (V.a.6), $R^3$ is heteroalkynyl.

In some embodiments, in each of Formulas (V.a), (V.a.1), (V.a.2), (V.a.3), (V.a.4), (V.a.5), and (V.a.6), $R^3$ is aryl.

In some embodiments, in each of Formulas (V.a), (V.a.1), (V.a.2), (V.a.3), (V.a.4), (V.a.5), and (V.a.6), $R^3$ is heteroaryl.

In some embodiments, in each of Formulas (V.a), (V.a.1), (V.a.2), (V.a.3), (V.a.4), (V.a.5), and (V.a.6), $R^3$ is cycloalkyl.

In some embodiments, in each of Formulas (V.a), (V.a.1), (V.a.2), (V.a.3), (V.a.4), (V.a.5), and (V.a.6), $R^3$ is cycloalkenyl.

In some embodiments, in each of Formulas (V.a), (V.a.1), (V.a.2), (V.a.3), (V.a.4), (V.a.5), and (V.a.6), $R^3$ is heterocycloalkyl.

In some embodiments, in each of Formulas (V.a), (V.a.1), (V.a.2), (V.a.3), (V.a.4), (V.a.5), and (V.a.6), $R^3$ is heterocycloalkenyl.

In some embodiments, in each of Formulas (V.a), (V.a.1), (V.a.2), (V.a.3), (V.a.4), (V.a.5), and (V.a.6), $R^3$ is halogen.

In some embodiments, in each of Formulas (V.a), (V.a.1), (V.a.2), (V.a.3), (V.a.4), (V.a.5), and (V.a.6), $R^3$ is —CN.

In some embodiments, in each of Formulas (V.a), (V.a.1), (V.a.2), (V.a.3), (V.a.4), (V.a.5), and (V.a.6), $R^3$ is —NO$_2$.

In some embodiments, in each of Formulas (V.a), (V.a.1), (V.a.2), (V.a.3), (V.a.4), (V.a.5), and (V.a.6), $R^3$ is —OR$^{19}$.

In some embodiments, in each of Formulas (V.a), (V.a.1), (V.a.2), (V.a.3), (V.a.4), (V.a.5), and (V.a.6), $R^3$ is —OC(O)OR$^{20}$.

In some embodiments, in each of Formulas (V.a), (V.a.1), (V.a.2), (V.a.3), (V.a.4), (V.a.5), and (V.a.6), $R^3$ is —NR$^{21}$R$^{22}$.

In some embodiments, in each of Formulas (V.a), (V.a.1), (V.a.2), (V.a.3), (V.a.4), (V.a.5), and (V.a.6), $R^3$ is —NR$^{23}$SO$_2$R$^{24}$.

In some embodiments, in each of Formulas (V.a), (V.a.1), (V.a.2), (V.a.3), (V.a.4), (V.a.5), and (V.a.6), $R^3$ is —NR$^{23}$C(O)OR$^{20}$.

In some embodiments, in each of Formulas (V.a), (V.a.1), (V.a.2), (V.a.3), (V.a.4), (V.a.5), and (V.a.6), $R^3$ is —NR$^{23}$C(O)R$^{24}$.

In some embodiments, in each of Formulas (V.a), (V.a.1), (V.a.2), (V.a.3), (V.a.4), (V.a.5), and (V.a.6), $R^3$ is —SO$_2$NR$^{25}$R$^{26}$.

In some embodiments, in each of Formulas (V.a), (V.a.1), (V.a.2), (V.a.3), (V.a.4), (V.a.5), and (V.a.6), $R^3$ is —C(O)R$^{24}$.

In some embodiments, in each of Formulas (V.a), (V.a.1), (V.a.2), (V.a.3), (V.a.4), (V.a.5), and (V.a.6), $R^3$ is —C(O)OR$^{29}$.

In some embodiments, in each of Formulas (V.a), (V.a.1), (V.a.2), (V.a.3), (V.a.4), (V.a.5), and (V.a.6), $R^3$ is —SR$^{19}$.

In some embodiments, in each of Formulas (V.a), (V.a.1), (V.a.2), (V.a.3), (V.a.4), (V.a.5), and (V.a.6), $R^3$ is —S(O)R$^{19}$.

In some embodiments, in each of Formulas (V.a), (V.a.1), (V.a.2), (V.a.3), (V.a.4), (V.a.5), and (V.a.6), $R^3$ is —SO$_2$R$^{19}$.

In some embodiments, in each of Formulas (V.a), (V.a.1), (V.a.2), (V.a.3), (V.a.4), (V.a.5), and (V.a.6), $R^3$ is —OC(O)R$^{24}$.

In some embodiments, in each of Formulas (V.a), (V.a.1), (V.a.2), (V.a.3), (V.a.4), (V.a.5), and (V.a.6), $R^3$ is —C(O)NR$^{25}$R$^{26}$.

In some embodiments, in each of Formulas (V.a), (V.a.1), (V.a.2), (V.a.3), (V.a.4), (V.a.5), and (V.a.6), $R^3$ is —NR$^{23}$C(N—CN)NR$^{25}$R$^{26}$.

In some embodiments, in each of Formulas (V.a), (V.a.1), (V.a.2), (V.a.3), (V.a.4), (V.a.5), and (V.a.6), $R^3$ is —NR$^{23}$C(O)NR$^{25}$R$^{26}$.

In some embodiments, in each of Formulas (V.a), (V.a.1), (V.a.2), (V.a.3), (V.a.4), (V.a.5), and (V.a.6), $R^3$ is selected from the group consisting of: methyl, ethyl, propyl (straight or branched), butyl (straight or branched), pentyl (straight or branched), phenyl,

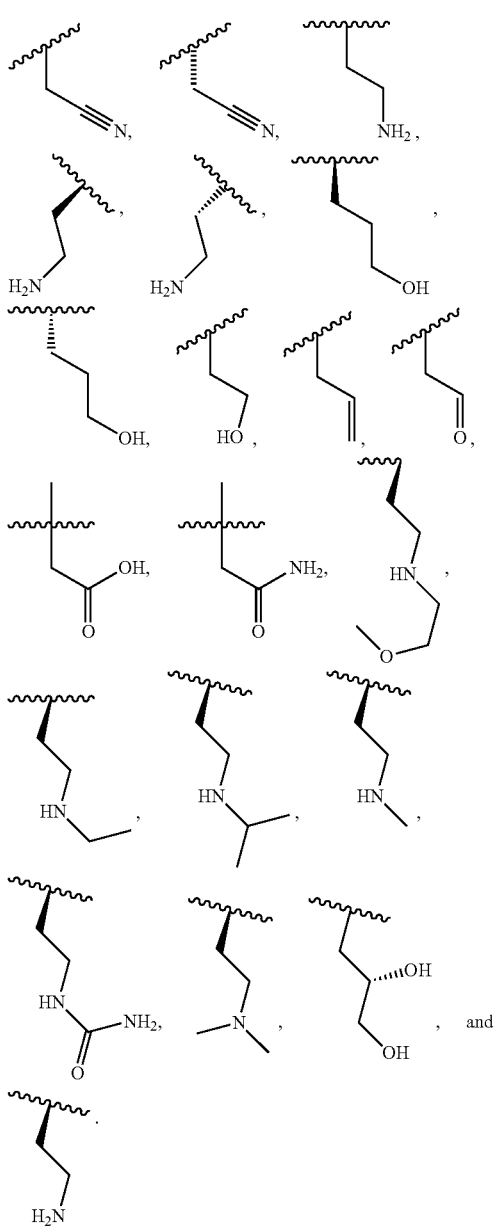

In some embodiments, in each of Formulas (V.a), (V.a.1), (V.a.2), (V.a.3), (V.a.4), (V.a.5), and (V.a.6), when E is —NR$^6$—, R$^3$ is absent.

In one embodiment, the compounds of the invention have a structure shown in Formula (V.b) and include pharmaceutically acceptable salts, solvates, esters, prodrugs, or isomers of said compounds:

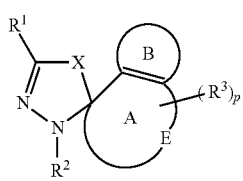

(V.b.)

wherein X, R$^1$, R$^2$, R$^3$, p, E, ring A, and ring B are selected independently of each other and wherein:

ring A (including E and the unsaturation shown) is a 7-8-membered cycloalkenyl or heterocycloalkenyl ring;

E is selected from the group consisting of —O—, —S—, —S(O)—, —S(O)$_2$—, —C(R$^4$)(R$^5$)—, —N(R$^6$)—, —N(C(Y)R$^7$)—, —N(C(Y)OR$^8$)—, —N(C(Y)N(R$^9$)(R$^{10}$))—, —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^6$)—O—, —N(R$^6$)—N(R$^{12}$)—, —N=N—, —C(R$^7$)=N—, —C(O)—C(R$^7$)=N—, —C(O)—N=N—, —O—C(Y)—N(R$^{11}$)—, —N(R$^{11}$)—C(Y)—O—, —N(R$^{11}$)—C(Y)—N(R$^{12}$)—, —C(Y)—N(R$^{11}$)—O—, —C(Y)—N(R$^{11}$)—N(R$^{12}$)—, —O—N(R$^{11}$)—C(Y)—, and —N(R$^{12}$)—N(R$^{11}$)—C(Y)—;

ring B is a substituted or unsubstituted heteroaromatic ring; and p, X, R$^1$, R$^2$, R$^3$, R$^4$, R$^5$, R$^6$, R$^7$, R$^8$, R$^9$, R$^{10}$, R$^{11}$, R$^{12}$, Y, r and the optional substituents on ring B are as defined above in Formula (I).

In one embodiment, in Formula (V.b.), X is S.
In one embodiment, in Formula (V.b.), X is S(O).
In one embodiment, in Formula (V.b.), X is S(O)$_2$.
In one embodiment, in Formula (V.b.), ring A is a cycloalkenyl ring.
In one embodiment, in Formula (V.b.), ring A is a heterocycloalkenyl ring.
In one embodiment, in Formula (V.b.), E is —C(R$^4$)(R$^5$)—.
In one embodiment, in Formula (V.b.), E is selected from the group consisting of —O—, —S—, —S(O)—, —S(O)$_2$—, —N(R$^6$)—, —N(C(Y)R$^7$)—, —N(C(Y)OR$^8$)—, —N(C(Y)N(R$^9$R$^{10}$))—, —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^6$)—O—, —N(R$^6$)—N(R$^{12}$)—, —N=N—, —C(R$^7$)=N—, —C(O)—C(R$^7$)=N—, —C(O)—N=N—, —O—C(Y)—N(R$^{11}$)—, —N(R$^{11}$)—C(Y)—O—, —N(R$^{11}$)—C(Y)—N(R$^{12}$)—, —C(Y)—N(R$^{11}$)—O—, —C(Y)—N(R$^{11}$)—N(R$^{12}$)—, —O—N(R$^{11}$)—C(Y)—, and —N(R$^{12}$)—N(R$^{11}$)—C(Y)—.

In one embodiment, in Formula (V.b.), E is selected from the group consisting of —O—, —S—, —S(O)—, —S(O)$_2$—, and —N(R$^6$)—.

In one embodiment, in Formula (V.b.), E is selected from the group consisting of —O—, —S—, —S(O)—, —S(O)$_2$—, and —N(R$^6$)—, wherein R$^6$ is selected from the group consisting of H, alkyl, —C(O)R$^{24}$, and —C(S)R$^{24}$.

In one embodiment, in Formula (V.b.), E is selected from the group consisting of —O— and —N(R$^6$)—, wherein R$^6$ is selected from the group consisting of H, alkyl, —C(O)R$^{24}$, and —C(S)R$^{24}$.

In one embodiment, in Formula (V.b.), E is —O—.
In one embodiment, in Formula (V.b.), E is —S—.
In one embodiment, in Formula (V.b.), E is —S(O)—.
In one embodiment, in Formula (V.b.), E is —S(O)$_2$—.
In one embodiment, in Formula (V.b.), E is —C(R$^4$)(R$^5$)—.
In one embodiment, in Formula (V.b.), E is —N(R$^6$)—.
In one embodiment, in Formula (V.b.), E is —N(C(Y)R$^7$)—.
In one embodiment, in Formula (V.b.), E is —N(C(Y)OR$^8$)—.
In one embodiment, in Formula (V.b.), E is —N(C(Y)N(R$^9$)(R$^{10}$))—.
In one embodiment, in Formula (V.b.), E is —C(O)—N(R$^{11}$)—.
In one embodiment, in Formula (V.b.), E is —N(R$^{11}$)—C(O)—.

In one embodiment, in Formula (V.b.), E is —S(O)$_2$—N(R$^{11}$)—.

In one embodiment, in Formula (V.b.), E is —N(R$^{11}$)—S(O)$_2$—.

In one embodiment, in Formula (V.b.), E is —C(O)—O—.

In one embodiment, in Formula (V.b.), E is —O—C(O)—.

In one embodiment, in Formula (V.b.), E is —O—N(R$^6$)—. In one embodiment, in Formula (V.b.), E is —N(R$^6$)—O—.

In one embodiment, in Formula (V.b.), E is —N(R$^6$)—N(R$^{12}$)—.

In one embodiment, in Formula (V.b.), E is —N=N—.

In one embodiment, in Formula (V.b.), E is —C(R$^7$)=N—.

In one embodiment, in Formula (V.b.), E is —C(O)—C(R$^7$)=N—.

In one embodiment, in Formula (V.b.), E is —C(O)—N=N—.

In one embodiment, in Formula (V.b.), E is —O—C(Y)—N(R$^{11}$)—.

In one embodiment, in Formula (V.b.), E is —N(R$^{11}$)—C(Y)—O—.

In one embodiment, in Formula (V.b.), E is —N(R$^{11}$)—C(Y)—N(R$^{12}$)—.

In one embodiment, in Formula (V.b.), E is —C(Y)—N(R$^{11}$)—O—.

In one embodiment, in Formula (V.b.), E is —C(Y)—N(R$^{11}$)—N(R$^{12}$)—.

In one embodiment, in Formula (V.b.), E is —O—N(R$^{11}$)—C(Y)—.

In one embodiment, in Formula (V.b.), E is —N(R$^{12}$)—N(R$^{11}$)—C(Y)—.

In one embodiment, in Formula (V.b.), Y is (=O).

In one embodiment, in Formula (V.b.), Y is (=S).

In one embodiment, in Formula (V.b.), Y is (=N(R$^{13}$)).

In one embodiment, in Formula (V.b.), Y is (=N(CN)).

In one embodiment, in Formula (V.b.), Y is (=N(OR$^{14}$)).

In one embodiment, in Formula (V.b.), Y is (=N(R$^{16}$)(R$^{16}$)).

In one embodiment, in Formula (V.b.), Y is (=C(R$^{17}$)(R$^{18}$)).

In one embodiment, in Formula (V.b.), B is an unsubstituted heteroaromatic ring.

In one embodiment, in Formula (V.b.), B is an unsubstituted 5-6-membered heteroaromatic ring having from 1-3 ring heteroatoms, which can be the same or different, each hetero ring atom being independently selected from the group consisting of N, S, O, S(O), and S(O)$_2$.

In one embodiment, in Formula (V.b.), B is a heteroaromatic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{13}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (V.b.), B is a 5-6-membered heteroaromatic ring having from 1-3 ring heteroatoms, which can be the same or different, each hetero ring atom being independently selected from the group consisting of N, S, O, S(O), and S(O)$_2$, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (V.b.), B is an unsubstituted 6-membered heteroaromatic ring having from 1-3 ring heteroatoms, which can be the same or different, each hetero ring atom being independently selected from the group consisting of N, S, and O.

In one embodiment, in Formula (V.b.), B is a 6-membered heteroaromatic ring having from 1-3 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)R$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (V.b.), B is an unsubstituted 6-membered heteroaromatic ring having 2 ring heteroatoms, each ring heteroatom being independently selected from of N, S, and O.

In one embodiment, in Formula (V.b.), B is a 6-membered heteroaromatic ring having 2 ring heteroatoms, each ring heteroatom being independently selected from of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —NR$^{21}$R$^{22}$, C(O)R$^{24}$, —C(O)OR$^{20}$, —S(O)R$^{19}$, —SO$_2$R$^{19}$, —OC(O)R$^{24}$, and —C(O)NR$^{25}$R$^{26}$.

In one embodiment, in Formula (V.b.), B is an unsubstituted 5-membered heteroaromatic ring having from 1-2 ring heteroatoms, which can be the same or different, each hetero ring atom being independently selected from the group consisting of N, S, and O.

In one embodiment, in Formula (V.b.), B is a 5-membered heteroaromatic ring having from 1-2 ring heteroatoms, which can be the same or different, each hetero ring atom being independently selected from the group consisting of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (V.b.), B is an unsubstituted 5-membered heteroaromatic ring having 1 ring heteroatom selected from of N, S, and O.

In one embodiment, in Formula (V.b.), B is a 5-membered heteroaromatic ring having 1 ring heteroatom selected from of N, S, and O, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —NR$^{21}$R$^{22}$, —C(O)R$^{24}$, —C(O)OR$^{20}$, —S(O)R$^{19}$, —SO$_2$R$^{19}$, —OC(O)R$^{24}$, and —C(O)NR$^{25}$R$^{26}$.

In one embodiment, in Formula (V.b.), B is a 5-membered heteroaromatic ring having S as the ring heteroatom, which heteroaromatic ring is substituted with one or more substituents, which can be the same or different, each substituent being independently selected from the group consisting of halogen, —CN, —NO$_2$, alkyl, heteroalkyl, haloalkyl, —OR$^{19}$, —NR$^{21}$R$^{22}$, —C(O)R$^{24}$, —C(O)OR$^{20}$, —SR$^{19}$, —S(O)R$^{19}$, —SO$_2$R$^{19}$, —OC(O)R$^{24}$, and —C(O)NR$^{25}$R$^{26}$.

In one embodiment, in Formula (V.b.), B is an unsubstituted 5-membered heteroaromatic ring having S as the ring heteroatom.

In one embodiment, in Formula (V.b.), B is selected from the group consisting of

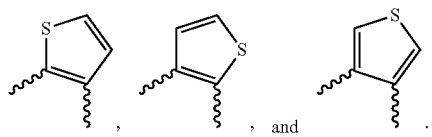
, and .

In one embodiment, in Formula (V.b.), R$^1$ is unsubstituted aryl.

In one embodiment, in Formula (V.b.), R$^1$ is unsubstituted phenyl.

In one embodiment, in Formula (V.b.), R$^1$ is unsubstituted naphthyl.

In one embodiment, in Formula (V.b.), R$^1$ is substituted aryl.

In one embodiment, in Formula (V.b.), R$^1$ is substituted phenyl.

In one embodiment, in Formula (V.b.), R$^1$ is substituted naphthyl.

In one embodiment, in Formula (V.b.), R$^1$ is aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{12}$, —S(O)R$^{12}$, —SO$_2$R$^{12}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (V.b.), R$^1$ is phenyl substituted with one or more substituents, which can be the same or different, each substituent being independently selected from the grOup consisting halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (V.b.), R$^1$ is phenyl substituted with one to four substituents, which can be the same or different, each substituent being independently selected from the group consisting of halo, —OH, —CN, and haloalkyl.

In one embodiment, in Formula (V.b.), R$^1$ is selected from the group consisting of:

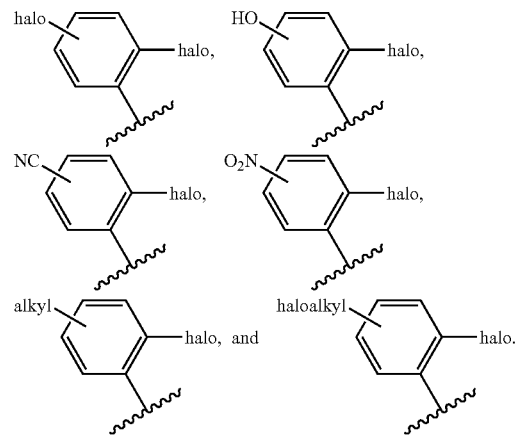

In one embodiment, in Formula (V.b.), R$^1$ is:

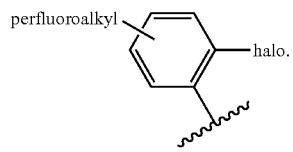

In one embodiment, in Formula (V.b.), R$^1$ is phenyl substituted with one to three fluoro groups.

In one embodiment, in Formula (V.b.), R$^1$ is phenyl substituted with two fluoro groups.

In one embodiment, in Formula (V.b.), R$^1$ is phenyl substituted with one fluoro group.

In one embodiment, in Formula (V.b.), R$^1$ is:

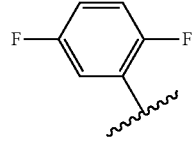

In one embodiment, in Formula (V.b.), R$^2$ is —C(Z)R$^7$.

In one embodiment, in Formula (V.b.), R$^2$ is —C(Z)NR$^9$R$^{10}$.

In one embodiment, in Formula (V.b.), R$^2$ is —C(Z)OR$^8$.

In one embodiment, in Formula (V.b.), R$^2$ is —SO$_2$NR$^9$R$^{10}$.

In one embodiment, in Formula (V.b.), R$^2$ is alkyl.

In one embodiment, in Formula (V.b.), R$^2$ is heteroalkyl.

In one embodiment, in Formula (V.b.), R$^2$ is aryl.

In one embodiment, in Formula (V.b.), R$^2$ is heteroaryl.

In one embodiment, in Formula (V.b.), R$^2$ is cycloalkyl.

In one embodiment, in Formula (V.b.), R$^2$ is cycloalkenyl.

In one embodiment, in Formula (V.b.), R$^2$ is heterocycloalkyl.

In one embodiment, in Formula (V.b.), R$^2$ is heterocycloalkenyl.

In one embodiment, in Formula (V.b.), Z is (=O).
In one embodiment, in Formula (V.b.), Z is (=S).
In one embodiment, in Formula (V.b.), Z is (=N(R$^{13}$)).
In one embodiment, in Formula (V.b.), Z is (=N(CN)).
In one embodiment, in Formula (V.b.), Z is (=N(OR$^{14}$)).
In one embodiment, in Formula (V.b.), Z is (=N(R$^{15}$)(R$^{16}$)).
In one embodiment, in Formula (V.b.), Z is (=C(R$^{17}$)(R$^{18}$)).
In one embodiment, in Formula (V.b.), R$^2$ is —C(Z)R$^7$, and Z is (=O).
In one embodiment, in Formula (V.b.), R$^2$ is —C(O)H.
In one embodiment, in Formula (V.b.), R$^2$ is —C(O)alkyl.
In one embodiment, in Formula (V.b.), R$^2$ is —C(O)CH$_3$.
In one embodiment, in Formula (V.b.), R$^2$ is —C(O)R$^7$, wherein said R$^7$ is alkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.
In one embodiment, in Formula (V.b.), R$^2$ is —C(O)R$^7$, wherein said R$^7$ is alkyl substituted with one to three substituents, which can be the same or different, each substituent being independently selected from the group consisting of —OR$^{19}$, —NR$^{21}$R$^{22}$, and cycloalkyl.
In one embodiment, in Formula (V.b.), R$^2$ is —C(O)R$^7$, wherein said R$^7$ is alkyl, wherein said alkyl is substituted with alkyl and —OH.
In one embodiment, in Formula (V.b.), R$^2$ is —C(O)R$^7$, wherein said R$^7$ is alkyl substituted with one to three substituents, which can be the same or different, each substituent being independently selected from the group consisting of —OH, —NH$_2$, and cyclopropyl.
In one embodiment, in Formula (V.b.), R$^2$ is —C(O)R$^7$, wherein said R$^7$ is alkyl substituted with one to two substituents, which can be the same or different, each substituent being independently selected from the group consisting of —NH$_2$, and cyclopropyl.
In one embodiment, in Formula (V.b.), R$^2$ is —C(O)R$^7$, wherein said R$^7$ is alkyl substituted with —OH.
In one embodiment, in Formula (V.b.), R$^2$ is —C(O)R$^7$, wherein said R$^7$ is unsubstituted heterocycloalkyl.
In one embodiment, in Formula (V.b.), R$^2$ is —C(O)R$^7$, wherein said R$^7$ is substituted heterocycloalkyl.
In one embodiment, in Formula (V.b.), R$^2$ is —C(O)R$^7$, wherein said R$^7$ is heterocycloalkyl substituted with one or more substituents, which can be the same or different, each substituent being independently selected from the group consisting of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.
In one embodiment, in Formula (V.b.), R$^2$ is —C(O)NR$^7$, wherein said R$^7$ is selected from the group consisting of substituted piperidine, substituted piperazine, substituted morpholine, substituted pyrrolidine, and substituted azetidine.

In one embodiment, in Formula (V.b.), R$^2$ is selected from:

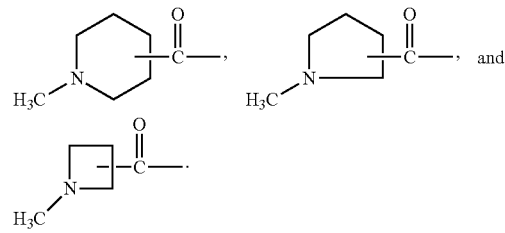

In one embodiment, in Formula (V.b.), R$^2$ is —C(O)NR$^9$R$^{10}$.
In one embodiment, in Formula (V.b.), R$^2$ is —C(O)NR$^9$R$^{10}$.
In one embodiment, in Formula (V.b.), R$^2$ is —C(O)NR$^9$R$^{10}$, wherein R$^9$ and R$^{10}$ can be the same or different, each being independently selected from alkyl.
In one embodiment, in Formula (V.b.), R$^2$ is —C(O)NR$^9$R$^{10}$, wherein R$^9$ is unsubstituted heterocycloalkyl and R$^{10}$ is selected from the group consisting of H and alkyl.
In one embodiment, in Formula (V.b.), R$^2$ is —C(O)NR$^9$R$^{10}$, wherein R$^9$ is substituted heterocycloalkyl and R$^{10}$ is selected from the group consisting of H and alkyl.
In one embodiment, in Formula (V.b.), R$^2$ is —C(O)NR$^9$R$^{10}$, wherein R$^9$ is heterocycloalkyl substituted with from one to three substituents, which can be the same or different, each substituent being independently selected from alkyl, and R$^{10}$ is selected from the group consisting of H and alkyl.

In one embodiment, in Formula (V.b.), R$^2$ is

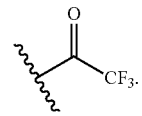

In one embodiment, in Formula (V.b.), R$^2$ is

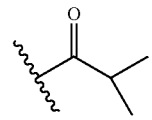

In one embodiment, in Formula (V.b.), R$^2$ is

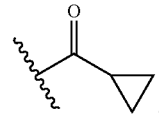

In one embodiment, in Formula (V.b.), R$^2$ is

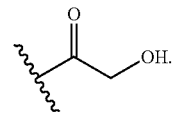

In one embodiment, in Formula (V.b.), R² is

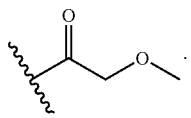 [SMILES: *C(=O)COC ; "."]

In one embodiment, in Formula (V.b.), R² is

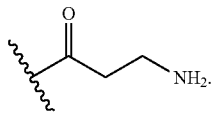 [SMILES: *C(=O)CCN]

In one embodiment, in Formula (V.b.), R² is

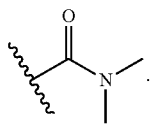

In one embodiment, in Formula (V.b.), R² is

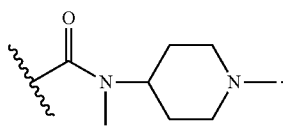

In one embodiment, in Formula (V.b.), p is 0 and R³ is not present.
In one embodiment, in Formula (V.b.), p is 1.
In one embodiment, in Formula (V.b.), p is 2.
In one embodiment, in Formula (V.b.), p is 3.
In one embodiment, in Formula (V.b.), p is 4.
In one embodiment, in Formula (V.b.), p is ≥2 and at least two groups R³ are attached to the same ring atom.
In one embodiment, in Formula (V.b.), p is 1 and R³ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.
In one embodiment, in Formula (V.b.), p is 2, 3, or 4 and each R³ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.
In one embodiment, in Formula (V.b.), p is 2, 3, or 4 and at least two groups R³ are bound to the same ring carbon atom, wherein each R³, which may be the same or different, is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO₂, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴,)H C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (V.b.), p is 2, 3, or 4 and at least two groups R³ are bound to the same ring carbon atom, wherein two R³ groups, which may be the same or different, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S.

In one embodiment, in Formula (V.b), p is >0 and each R³ is independently selected from the group consisting of alkyl, heteroalkyl, alkenyl, heteroalkenyl, —CN, —NO₂, —OR¹⁹, OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(S)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶, —NR²³C(O)NR²⁵R²⁶, and —NR²³—C(NH)—NR²⁵R²⁶,
wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO₂, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (V.b), p is 1 and R³ is selected from the group consisting of alkyl, heteroalkyl, alkenyl, and heteroalkenyl,
wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO₂, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁶, —OC(O)R²⁴, —C(O)NR²⁵R²⁶, —NR²³C(N—CN)NR²⁵R²⁶ and —NR²³C(O)NR²⁵R²⁶.

In one embodiment, in Formula (V.b), p is ≥2 and any two R³ groups bound to the same ring A atom are taken together to form a —C(O)— group.

In one embodiment, in Formula (V.b), p is ≥2 and any two R³ groups bound to the same ring A atom are taken together to form a spiroheterocycloalkyl group having from 1 to 3 ring heteroatoms independently selected from the group consisting of —NH—, —NR⁶—, O, S, S(O), and S(O)₂, or spiroheterocycloalkenyl group having from 1 to 3 ring heteroatoms independently selected from the group consisting of —NH—, —NR$^6$—, O, S, S(O), and S(O)$_2$.

In one embodiment, in Formula (V.b.), R$^3$ is alkyl.
In one embodiment, in Formula (V.b.), R$^3$ is heteroalkyl.
In one embodiment, in Formula (V.b.), R$^3$ is alkenyl.
In one embodiment, in Formula (V.b.), R$^3$ is heteroalkenyl.
In one embodiment, in Formula (V.b.), R$^3$ is alkynyl.
In one embodiment, in Formula (V.b.), R$^3$ is heteroalkynyl.
In one embodiment, in Formula (V.b.), R$^3$ is aryl.
In one embodiment, in Formula (V.b.), R$^3$ is heteroaryl.
In one embodiment, in Formula (V.b.), R$^3$ is cycloalkyl.
In one embodiment, in Formula (V.b.), R$^3$ is cycloalkenyl.
In one embodiment, in Formula (V.b.), R$^3$ is heterocycloalkyl.
In one embodiment, in Formula (V.b.), R$^3$ is heterocycloalkenyl.
In one embodiment, in Formula (V.b.), R$^3$ is halogen.
In one embodiment, in Formula (V.b.), R$^3$ is —CN.
In one embodiment, in Formula (V.b.), R$^3$ is —NO$_2$.
In one embodiment, in Formula (V.b.), R$^3$ is —OR$^{19}$.
In one embodiment, in Formula (V.b.), R$^3$ is —OC(O)OR$^{20}$.
In one embodiment, in Formula (V.b.), R$^3$ is —NR$^{21}$R$^{22}$.
In one embodiment, in Formula (V.b.), R$^3$ is —NR$^{23}$SO$_2$R$^{24}$.
In one embodiment, in Formula (V.b.), R$^3$ is —NR$^{23}$C(O)OR$^{20}$.
In one embodiment, in Formula (V.b.), R$^3$ is —NR$^{23}$C(O)R$^{24}$.
In one embodiment, in Formula (V.b.), R$^3$ is —SO$_2$NR$^{25}$R$^{26}$.
In one embodiment, in Formula (V.b.), R$^3$ is —C(O)R$^{24}$.
In one embodiment, in Formula (V.b.), R$^3$ is —C(O)OR$^{20}$.
In one embodiment, in Formula (V.b.), R$^3$ is —SR$^{19}$.
In one embodiment, in Formula (V.b.), R$^3$ is —S(O)R$^{19}$.
In one embodiment, in Formula (V.b.), R$^3$ is —SO$_2$R$^{19}$.
In one embodiment, in Formula (V.b.), R$^3$ is —OC(O)R$^{24}$.
In one embodiment, in Formula (V.b.), R$^3$ is —C(O)NR$^{25}$R$^{26}$.
In one embodiment, in Formula (V.b.), R$^3$ is —NR$^{23}$C(N—CN)NR$^{25}$R$^{26}$.
In one embodiment, in Formula (V.b.), R$^3$ is —NR$^{23}$C(O)NR$^{25}$R$^{26}$.

In one embodiment, Formula (V.b) has the general structure:

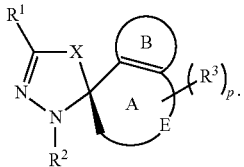

In one embodiment, Formula (V.b) has the general structure:

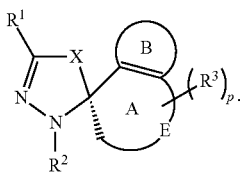

In one embodiment, Formula (V.b) has the general structure:

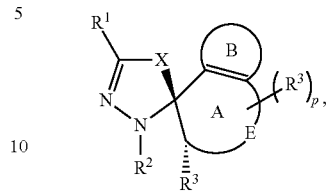

wherein P is 0, 1, 2, or 3.

In one embodiment, Formula (V.b) has the general structure:

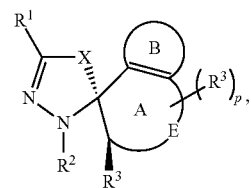

wherein P is 0, 1, 2, or 3.

In one embodiment, Formula (V.b) has the general structure:

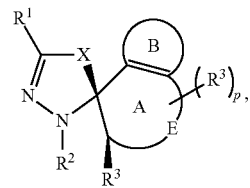

wherein P is 0, 1, 2, or 3.

In one embodiment, Formula (V.b) has the general structure:

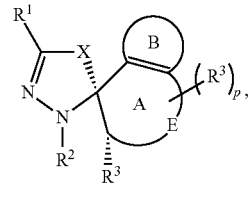

wherein P is 0, 1, 2, or 3.

In one embodiment, the compounds of the invention have a structure shown in Formula (VI) and include pharmaceutically acceptable salts, solvates, esters, prodrugs, or isomers of said compounds:

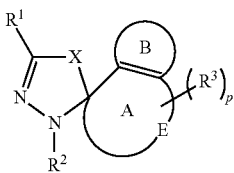

(VI)

wherein X, R¹, R², R³, p, E, ring A, and ring B are selected independently of each other and wherein:

ring A (including E and the unsaturation shown) is a 4-8-membered cycloalkenyl or heterocycloalkenyl ring;

E is selected from the group consisting of —O—, —S—, —S(O)—, —S(O)₂—, —C(R⁴)(R⁵)—, —N(R⁶)—, —N(C(Y)R⁷)—, —N(C(Y)OR⁸)—, —N(C(Y)N(R⁹)(R¹⁰))—, —C(O)—N(R¹¹)—, —N(R¹¹)—C(O)—, —S(O)₂—N(R¹¹)—, —N(R¹¹)—S(O)₂—, —O—N(R⁶)—, —N(R⁶)—O—, —N(R⁶)—N(R¹²)—, —N=N—, —C(R⁷)=N—, —C(O)—C(R⁷)=N—, —C(O)—N=N—, —O—C(Y)—N(R¹¹)—, —N(R¹¹)—C(Y)—O—, —N(R¹¹)—C(Y)—N(R¹²)—, —C(Y)—N(R¹¹)—O—, —C(Y)—N(R¹¹)—N(R¹²)—, —O—N(R¹¹)—C(Y)—, and —N(R¹²)—N(R¹¹)—C(Y)—;

ring B is an unsubstituted or optionally independently substituted partially unsaturated alicyclic ring, or a partially unsaturated heterocyclic ring, and p, X, R¹, R², R³, R⁴, R⁵, R⁶, R⁷, R⁸, R⁹, R¹⁰, R¹¹, R¹², Y, and the optional substituents on ring B are as defined above in Formula (I).

In one embodiment, in Formula (VI), X is S.
In one embodiment, in Formula (VI), X is S(O).
In one embodiment, in Formula (VI), X is S(O)₂.
In one embodiment, in Formula (VI), ring A is a cycloalkenyl ring.
In one embodiment, in Formula (VI), ring A is a heterocycloalkenyl ring.
In one embodiment, in Formula (VI), ring A is a 4-membered ring.
In one embodiment, in Formula (VI), ring A is a 5-membered ring.
In one embodiment, in Formula (VI), ring A is a 6-membered ring.
In one embodiment, in Formula (VI), ring A is a 7-membered ring.
In one embodiment, in Formula (VI), ring A is an 8-membered ring.
In one embodiment, in Formula (VI), E is —C(R⁴)(R⁵)—.
In one embodiment, in Formula (VI), E is selected from the group consisting of —O—, —S—, —S(O)—, —S(O)₂—, —N(R⁶)—, —N(C(Y)R⁷)—, —N(C(Y)OR⁸)—, —N(C(Y)N(R⁹)(R¹⁰))—, —C(O)—N(R¹¹)—, —N(R¹¹)—C(O)—, —S(O)₂—N(R¹¹)—, —N(R¹¹)—S(O)₂—, —C(O)—O—, —O—C(O)—, —O—N(R⁶)—, —N(R⁶)—O—, —N(R⁶)—N(R¹²)—, —N=N—, —C(R⁷)=N—, —(O)—C(R⁷)=N—, —C(O)—N=N—, —O—C(Y)—N(R¹¹)—, —N(R¹¹)—C(Y)—O—, —N(R¹¹)—C(Y)—N(R¹²)—, —C(Y)—N(R¹¹)—O—, —C(Y)—N(R¹¹)—N(R¹²)—, —O—N(R¹¹)—C(Y)—, and —N(R¹²)—N(R¹¹)—C(Y)—.

In one embodiment, in Formula (VI), E is selected from the group consisting of —O—, —S—, —S(O)—, —S(O)₂—, and —N(R⁶)—.

In one embodiment, in Formula (VI), E is selected from the group consisting of —O—, —S—, —S(O)—, —S(O)₂—, and —N(R⁶)—, wherein R⁶ is selected from the group consisting of H, alkyl, —C(O)R²⁴, and —C(S)R²⁴.

In one embodiment, in Formula (VI), E is selected from the group consisting of —O— and —N(R⁶)—, wherein R⁶ is selected from the group consisting of H, alkyl, —C(O)R²⁴, and —C(S)R²⁴.

In one embodiment, in Formula (VI), E is —O—.
In one embodiment, in Formula (VI), E is —S—.
In one embodiment, in Formula (VI), E is —S(O)—.
In one embodiment, in Formula (VI), E is —S(O)₂—.
In one embodiment, in Formula (VI), E is —C(R⁴)(R⁵)—.
In one embodiment, in Formula (VI), E is —N(R⁶)—.
In one embodiment, in Formula (VI), E is —N(C(Y)R⁷)—.
In one embodiment, in Formula (VI), E is —N(C(Y)OR⁸)—.
In one embodiment, in Formula (VI), E is —N(C(Y)N(R⁹)(R¹⁶))—.
In one embodiment, in Formula (VI), E is —C(O)—N(R¹¹)—.
In one embodiment, in Formula (VI), E is —N(R¹¹)—C(O)—.
In one embodiment, in Formula (VI), E is —S(O)₂—N(R¹¹)—.
In one embodiment, in Formula (VI), E is —N(R¹¹)—S(O)₂—.
In one embodiment, in Formula (VI), E is —C(O)—O—.
In one embodiment, in Formula (VI), E is —O—C(O)—.
In one embodiment, in Formula (VI), E is —O—N(R⁶)—.
In one embodiment, in Formula (VI), E is —N(R⁶)—O—.
In one embodiment, in Formula (VI), E is —N(R⁶)—N(R¹²)—.
In one embodiment, in Formula (VI), E is —N=N—.
In one embodiment, in Formula (VI), E is —C(R⁷)=N—.
In one embodiment, in Formula (VI), E is —C(O)—C(R⁷)=N—.
In one embodiment, in Formula (VI), E is —C(O)—N=N—.
In one embodiment, in Formula (VI), E is —O—C(Y)—N(R¹¹)—.
In one embodiment, in Formula (VI), E is —N(R¹¹)—C(Y)—O—.
In one embodiment, in Formula (VI), E is —N(R¹¹)—C(Y)—N(R¹²)—.
In one embodiment, in Formula (VI), E is —C(Y)—N(R¹¹)—O—.
In one embodiment, in Formula (VI), E is —C(Y)—N(R¹¹)—N(R¹²)—.
In one embodiment, in Formula (VI), E is —O—N(R¹¹)—C(Y)—.
In one embodiment, in Formula (VI), E is —N(R¹²)—N(R¹¹)—C(Y)—.
In one embodiment, in Formula (VI), Y is (=O).
In one embodiment, in Formula (VI), Y is (=S).
In one embodiment, in Formula (VI), Y is (=N(R¹³)).
In one embodiment, in Formula (VI), Y is (=N(CN)).
In one embodiment, in Formula (VI), Y is (=N(OR¹⁴)).
In one embodiment, in Formula (VI), Y is (=N(R¹⁵)(R¹⁶)).
In one embodiment, in Formula (VI), Y is (=C(R¹⁷)(R¹⁸)).
In one embodiment, in Formula (VI), ring A is a 4-membered ring and E is selected from the group consisting of —O—, —S—, —S(O)—, —S(O)₂—, —C(R⁴)(R⁵)—, —N(R⁶)—, —N(C(Y)R⁷)—, —N(C(Y)OR⁸)—, —N(C(Y)N(R⁶)(R¹⁶))—.

In one embodiment, in Formula (VI), A is a 4-membered ring and E is selected from the group consisting of —CH₂—, —CH(R⁴)—, —C(R⁴)(R⁵)—.

In one embodiment, in Formula (VI), A is a 5-membered ring and E is selected from the group consisting of —O—, —S—, —S(O)—, —S(O)$_2$—, —C(R$^4$)(R$^5$)—, —N(R$^6$)—, —N(C(Y)R$^7$)—, —N(C(Y)OR$^8$)—, —N(C(Y)N(R$^9$)(R$^{10}$))—, —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^8$)—O—, —N(R$^8$)—N(R$^{12}$)—, —N=N—, and —C(R$^7$)=N—.

In one embodiment, in Formula (VI), A is a 5-membered ring and E is —O—.

In one embodiment, in Formula (VI), A is a 5-membered ring and E is —S—.

In one embodiment, in Formula (VI), A is a 5-membered ring and E is —S(O)—.

In one embodiment, in Formula (VI), A is a 5-membered ring and E is —S(O)$_2$—.

In one embodiment, in Formula (VI), A is a 5-membered ring and E is —C(R$^4$)(R$^5$)—.

In one embodiment, in Formula (VI), A is a 5-membered ring and E is —N(R$^6$)—.

In one embodiment, in Formula (VI), A is a 5-membered ring and E is —N(C(Y)R$^7$)—.

In one embodiment, in Formula (VI), A is a 5-membered ring and E is —N(C(Y)OR$^8$)—.

In one embodiment, in Formula (VI), A is a 5-membered ring and E is —N(C(Y)N(R$^9$)(R$^{10}$))—.

In one embodiment, in Formula (VI), A is a 5-membered ring and E is —C(O)—N(R$^{11}$)—.

In one embodiment, in Formula (VI), A is a 5-membered ring and E is —N(R$^{11}$)—C(O)—.

In one embodiment, in Formula (VI), A is a 5-membered ring and E is —S(O)$_2$—N(R$^{11}$)—.

In one embodiment, in Formula (VI), A is a 5-membered ring and E is —N(R$^{11}$)—S(O)$_2$—.

In one embodiment, in Formula (VI), A is a 5-membered ring and E is —C(O)—O—.

In one embodiment, in Formula (VI), A is a 5-membered ring and E is —O—C(O)—.

In one embodiment, in Formula (VI), A is a 5-membered ring and E is —O—N(R$^6$)—.

In one embodiment, in Formula (VI), A is a 5-membered ring and E is —N(R$^6$)—O—.

In one embodiment, in Formula (VI), A is a 5-membered ring and E is —N(R$^6$)—N(R$^{12}$)—.

In one embodiment, in Formula (VI), A is a 5-membered ring and E is —N=N—.

In one embodiment, in Formula (VI), A is a 5-membered ring and E is —C(R$^7$)=N—.

In one embodiment, in Formula (VI), A is a 6-membered ring and E is selected from the group consisting of —O—, —S—, —S(O)—, —S(O)$_2$—, —C(R$^4$)(R$^8$)—, —N(R$^6$)—, —N(C(Y)R$^7$)—, —N(C(Y)OR$^8$)—, —N(C(Y)N(R$^9$)(R$^{10}$))—, —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^8$)—, —N(R$^8$)—O—, —N(R$^6$)—N(R$^{12}$)—, —N=N—, —C(O)—C(R$^7$)=N—, —C(O)—N=N—, —O—C(Y)—N(R$^{11}$)—, —N(R$^{11}$)—C(Y)—O—, —N(R$^{11}$)—C(Y)—N(R$^{12}$)—, —C(Y)—O—, —C(Y)—N(R$^{12}$)—, —O—N(R$^{11}$)—C(Y)—, and —N(R$^{12}$)—N(R$^{11}$)—C(Y)—.

In one embodiment, in Formula (VI), A is a 6-membered ring and E is —O—.

In one embodiment, in Formula (VI), A is a 6-membered ring and E is —S—.

In one embodiment, in Formula (VI), A is a 6-membered ring and E is —S(O)—.

In one embodiment, in Formula (VI), A is a 6-membered ring and E is —S(O)$_2$—.

In one embodiment, in Formula (VI), A is a 6-membered ring and E is —C(R$^4$)(R$^5$)—.

In one embodiment, in Formula (VI), A is a 6-membered ring and E is —N(R$^6$)—.

In one embodiment, in Formula (VI), A is a 6-membered ring and E is —N(C(Y)R$^7$)—.

In one embodiment, in Formula (VI), A is a 6-membered ring and E is —N(C(Y)OR$^8$)—.

In one embodiment, in Formula (VI), A is a 6-membered ring and E is —N(C(Y)N(R$^9$)(R$^{10}$))—.

In one embodiment, in Formula (VI), A is a 6-membered ring and E is —C(O)—N(R$^{11}$)—.

In one embodiment, in Formula (VI), A is a 6-membered ring and E is —N(R$^{11}$)—C(O)—.

In one embodiment, in Formula (VI), A is a 6-membered ring and E is —S(O)$_2$—N(R$^{11}$)—.

In one embodiment, in Formula (VI), A is a 6-membered ring and E is —N(R$^{11}$)—S(O)$_2$—.

In one embodiment, in Formula (VI), A is a 6-membered ring and E is —C(O)—O—.

In one embodiment, in Formula (VI), A is a 6-membered ring and E is —O—C(O)—.

In one embodiment, in Formula (VI), A is a 6-membered ring and E is —O—N(R$^6$)—.

In one embodiment, in Formula (VI), A is a 6-membered ring and E is —N(R$^6$)—O—.

In one embodiment, in Formula (VI), A is a 6-membered ring and E is —N(R$^6$)—N(R$^{12}$)—.

In one embodiment, in Formula (VI), A is a 6-membered ring and E is —N=N—.

In one embodiment, in Formula (VI), A is a 6-membered ring and E is —C(R$^7$)=N—.

In one embodiment, in Formula (VI), A is a 6-membered ring and E is —C(O)—C(R$^7$)=N—.

In one embodiment, in Formula (VI), A is a 6-membered ring and E is —C(O)—N=N—.

In one embodiment, in Formula (VI), A is a 6-membered ring and E is —O—C(Y)—N(R$^{11}$)—.

In one embodiment, in Formula (VI), A is a 6-membered ring and E is —N(R$^{11}$)—C(Y)—O—.

In one embodiment, in Formula (VI), A is a 6-membered ring and E is —N(R$^{11}$)—C(Y)—N(R$^{12}$)—.

In one embodiment, in Formula (VI), A is a 6-membered ring and E is —N(R$^{11}$)—C(Y)—N(R$^{12}$)—.

In one embodiment, in Formula (VI), A is a 6-membered ring and E is —C(Y)—N(R$^{11}$)—N(R$^{12}$)—.

In one embodiment, in Formula (VI), A is a 6-membered ring and E is —O—N(R$^{11}$)—C(Y)—.

In one embodiment, in Formula (VI), A is a 6-membered ring and E is —N(R$^{12}$)—N(R$^{11}$)—C(Y)—.

In one embodiment, in Formula (VI), A is a 7-membered ring and E is selected from the group consisting of —O—, —S—, —S(O)—, —S(O)$_2$—, —C(R$^4$)(R$^5$)—, —N(R$^6$)—, —N(C(Y)R$^7$)—, —N(C(Y)OR$^8$)—, —N(C(Y)N(R$^8$)(R$^{16}$))—, —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^6$)—O—, —N(R$^6$)—N(R$^{12}$)—, —N=N—, —C(R$^7$)=N—, —C(O)—C(R$^7$)=N—, —C(O)—N=N—, —O—C(Y)—N(R$^{11}$)—, —N(R$^{11}$)—C(Y)—O—, —N(R$^{11}$)—C(Y)—N(R$^{12}$)—, —C(Y)—N(R$^{11}$)—O—, —C(Y)—N(R$^{11}$)—N(R$^{12}$)—, —O—N(R$^{11}$)—C(Y)—, and —N(R$^{12}$)—N(R$^{11}$)—C(Y)—.

In one embodiment, in Formula (VI), A is a 7-membered ring and E is —O—.

In one embodiment, in Formula (VI), A is a 7-membered ring and E is —S—.

In one embodiment, in Formula (VI), A is a 7-membered ring and E is —S(O)—.

In one embodiment, in Formula (VI), A is a 7-membered ring and E is —S(O)$_2$—.

In one embodiment, in Formula (VI), A is a 7-membered ring and E is —C(R$^4$)(R$^5$)—.

In one embodiment, in Formula (VI), A is a 7-membered ring and E is —N(R$^6$)—.

In one embodiment, in Formula (VI), A is a 7-membered ring and E is —N(C(Y)R$^7$)—.

In one embodiment, in Formula (VI), A is a 7-membered ring and E is —N(C(Y)OR$^8$)—.

In one embodiment, in Formula (VI), A is a 7-membered ring and E is —N(C(Y)N(R$^6$)(R$^{16}$))—.

In one embodiment, in Formula (VI), A is a 7-membered ring and E is —C(O)—N(R$^{11}$)—.

In one embodiment, in Formula (VI), A is a 7-membered ring and E is —N(R$^{11}$)—C(O)—.

In one embodiment, in Formula (VI), A is a 7-membered ring and E is —S(O)$_2$—N(R$^{11}$)—.

In one embodiment, in Formula (VI), A is a 7-membered ring and E is —N(R$^{11}$)—S(O)$_2$—.

In one embodiment, in Formula (VI), A is a 7-membered ring and E is —C(O)—O—.

In one embodiment, in Formula (VI), A is a 7-membered ring and E is —O—C(O)—.

In one embodiment, in Formula (VI), A is a 7-membered ring and E is —O—N(R$^6$)—.

In one embodiment, in Formula (VI), A is a 7-membered ring and E is —N(R$^6$)—O—.

In one embodiment, in Formula (VI), A is a 7-membered ring and E is —N(R$^6$)—N(R$^{12}$)—.

In one embodiment, in Formula (VI), A is a 7-membered ring and E is —N=N—.

In one embodiment, in Formula (VI), A is a 7-membered ring and E is —C(R$^7$)=N—.

In one embodiment, in Formula (VI), A is a 7-membered ring and E is —C(O)—C(R$^7$)=N—.

In one embodiment, in Formula (VI), A is a 7-membered ring and E is —C(O)—N=N—.

In one embodiment, in Formula (VI), A is a 7-membered ring and E is —O—C(Y)—N(R$^{11}$)—.

In one embodiment, in Formula (VI), A is a 7-membered ring and E is —N(R$^{11}$)—C(Y)—O—.

In one embodiment, in Formula (VI), A is a 7-membered ring and E is —N(R$^{11}$)—C(Y)—N(R$^{12}$)—.

In one embodiment, in Formula (VI), A is a 7-membered ring and E is —C(Y)—N(R$^{11}$)—O—.

In one embodiment, in Formula (VI), A is a 7-membered ring and E is —C(Y)—N(R$^{11}$)—N(R$^{12}$)—.

In one embodiment, in Formula (VI), A is a 7-membered ring and E is —O—N(R$^{11}$)—C(Y)—.

In one embodiment, in Formula (VI), A is a 7-membered ring and E is —N(R$^{12}$)—N(R$^{11}$)—C(Y)—.

In one embodiment, in Formula (VI), A is a 8-membered ring and E is selected from the group consisting of —O—, —S—, —S(O)—, —S(O)$_2$—, —C(R$^4$)(R$^5$)—, —N(R$^6$)—, —N(C(Y)R$^7$)—, —N(C(Y)OR$^8$)—, —N(C(Y)N(R$^9$)(R$^{10}$))—, —C(O)—N(R$^{11}$)—, —N(R$^{11}$)—C(O)—, —S(O)$_2$—N(R$^{11}$)—, —N(R$^{11}$)—S(O)$_2$—, —C(O)—O—, —O—C(O)—, —O—N(R$^6$)—, —N(R$^6$)—O—, —N(R$^6$)—N(R$^{12}$)—, —N=N—, —C(R$^7$)=N—, —C(O)—C(R$^7$)=N—, —C(O)—N=N—, —O—C(Y)—N(R$^{11}$)—, —N(R$^{11}$)—C(Y)—O—, —N(R$^{11}$)—C(Y)—N(R$^{12}$)—, —C(Y)—N(R$^{11}$)—O—, —C(Y)—N(R$^{11}$)—N(R$^{12}$)—, —O—N(R$^{11}$)—C(Y)—, and —N(R$^{12}$)—N(R$^{11}$)—C(Y)—.

In one embodiment, in Formula (VI), A is a 8-membered ring and E is —O—.

In one embodiment, in Formula (VI), A is a 8-membered ring and E is —S—.

In one embodiment, in Formula (VI), A is a 8-membered ring and E is —S(O)—.

In one embodiment, in Formula (VI), A is a 8-membered ring and E is —S(O)$_2$—.

In one embodiment, in Formula (VI), A is a 8-membered ring and E is —C(R$^4$)(R$^5$)—.

In one embodiment, in Formula (VI), A is a 8-membered ring and E is —N(R$^6$)—.

In one embodiment, in Formula (VI), A is a 8-membered ring and E is —N(C(Y)R$^7$)—.

In one embodiment, in Formula (VI), A is a 8-membered ring and E is —N(C(Y)OR$^6$)—.

In one embodiment, in Formula (VI), A is a 8-membered ring and E is —N(C(Y)N(R$^9$)(R$^{10}$))—.

In one embodiment, in Formula (VI), A is a 8-membered ring and E is —C(O)—N(R$^{11}$)—.

In one embodiment, in Formula (VI), A is a 8-membered ring and E is —N(R$^{11}$)—C(O)—.

In one embodiment, in Formula (VI), A is a 8-membered ring and E is —S(O)$_2$—N(R$^{11}$)—.

In one embodiment, in Formula (VI), A is a 8-membered ring and E is —N(R$^{11}$)—S(O)$_2$—.

In one embodiment, in Formula (VI), A is a 8-membered ring and E is —C(O)—O—.

In one embodiment, in Formula (VI), A is a 8-membered ring and E is —O—C(O)—.

In one embodiment, in Formula (VI), A is a 8-membered ring and E is —O—N(R$^6$)—.

In one embodiment, in Formula (VI), A is a 8-membered ring and E is —N(R$^6$)—O—.

In one embodiment, in Formula (VI), A is a 8-membered ring and E is —N(R$^6$)—N(R$^{12}$)—.

In one embodiment, in Formula (VI), A is a 8-membered ring and E is —N=N—.

In one embodiment, in Formula (VI), A is a 8-membered ring and E is —C(R$^7$)=N—.

In one embodiment, in Formula (VI), A is a 8-membered ring and E is —C(O)—C(R$^7$)=N—.

In one embodiment, in Formula (VI), A is a 8-membered ring and E is —C(O)—N=N—.

In one embodiment, in Formula on (VI), A is a 8-membered ring and E is —O—C(Y)—N(R$^{11}$)—.

In one embodiment, in Formula (VI), A is a 8-membered ring and E is —N(R$^{11}$)—C(Y)—O—.

In one embodiment, in Formula (VI), A is a 8-membered ring and E is —N(R$^{11}$)—C(Y)—N(R$^{12}$)—

In one embodiment, in Formula (VI), A is a 8-membered ring and E is —C(Y)—N(R$^{11}$)—O—.

In one embodiment, in Formula (VI), A is a 8-membered ring and E is —C(Y)—N(R$^{11}$)—N(R$^{12}$)—.

In one embodiment, in Formula (VI), A is a 8-membered ring and E is —O—N(R$^{11}$)—C(Y)—.

In one embodiment, in Formula (VI), A is a 8-membered ring and E is —N(R$^{12}$)—N(R$^{11}$)—C(Y)—.

In one embodiment, in Formula (VI), B is a partially unsaturated alicyclic ring, which ring is unsubstituted.

In one embodiment, in Formula (VI), B is a partially unsaturated alicyclic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N=CN)NR$^{25}$R$^{26}$ and —NR$^{23}$C(O)NR$^{25}$R$^{26}$.

In one embodiment, in Formula (VI), B is a partially unsaturated heterocyclic ring, which ring is unsubstituted.

In one embodiment, in Formula (VI), B is a partially unsaturated heterocyclic ring which is substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl-, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{a5}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N=CN)NR$^{25}$R$^{26}$ and —NR$^{23}$C(O)NR$^{25}$R$^{26}$.

In one embodiment, in Formula (VI), R$^1$ is unsubstituted aryl.

In one embodiment, in Formula (VI), R$^1$ is unsubstituted phenyl.

In one embodiment, in Formula (VI), R$^1$ is unsubstituted naphthyl.

In one embodiment, in Formula (VI), R$^1$ is substituted aryl.

In one embodiment, in Formula (VI), R$^1$ is substituted phenyl.

In one embodiment, in Formula (VI), R$^1$ is substituted naphthyl.

In one embodiment, in Formula (VI), R$^1$ is aryl substituted with one or more substituents, which can be the same or different, each substituent being independently selected from the group consisting of halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N=CN)NR$^{25}$R$^{26}$ and —NR$^{23}$C(O)NR$^{25}$R$^{26}$.

In one embodiment, in Formula (VI), R$^1$ is phenyl substituted with one or more substituents, which can be the same or different, each substituent being independently selected from the group consisting halogen, —CN, —NO$_2$, alkyl, heteroalkyl, haloalkyl, alkenyl, haloalkenyl, alkynyl, haloalkynyl, aryl, heteroaryl, aryl-alkyl-, heteroaryl-alkyl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N=CN)NR$^{25}$R$^{26}$ and —NR$^{23}$C(O)NR$^{25}$R$^{26}$.

In one embodiment, in Formula (VI), R$^1$ is phenyl substituted with one to four substituents, which can be the same or different, each substituent being independently selected from the group consisting of halo, —OH, —CN, —NO$_2$, and —NR$^{21}$R$^{22}$, and haloalkyl.

In one embodiment, in Formula (VI), R$^1$ is selected from the group consisting of:

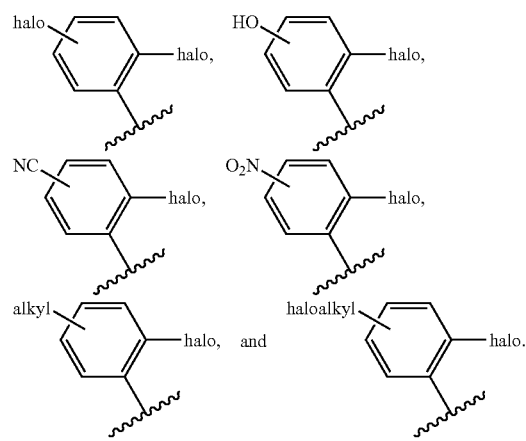

In one embodiment, in Formula (VI), R$^1$ is:

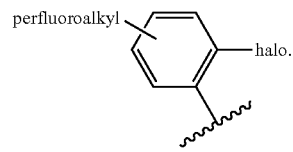

In one embodiment, in Formula (VI), R$^1$ is phenyl substituted with one to three fluoro groups.

In one embodiment, in Formula (VI), R$^1$ is phenyl substituted with two fluoro groups.

In one embodiment, in Formula (VI), R$^1$ is phenyl substituted with one fluoro group.

In one embodiment, in Formula (VI), IV is:

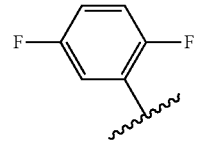

In one embodiment, in Formula (VI), R$^2$ is —C(Z)R$^7$.
In one embodiment, in Formula (VI), R$^2$ is —C(Z)NR$^9$R$^{10}$.
In one embodiment, in Formula (VI), R$^2$ is —C(Z)OR$^8$.
In one embodiment, in Formula (VI), R$^2$ is —SO$_2$NR$^9$R$^{10}$.
In one embodiment, in Formula (VI), R$^2$ is alkyl.
In one embodiment, in Formula (VI), R$^2$ is heteroalkyl.
In one embodiment, in Formula (VI), R$^2$ is aryl.
In one embodiment, in Formula (VI), R$^2$ is heteroaryl.
In one embodiment, in Formula (VI), R$^2$ is cycloalkyl.
In one embodiment, in Formula (VI), R$^2$ is cycloalkenyl.
In one embodiment, in Formula (VI), R$^2$ is heterocycloalkyl.
In one embodiment, in Formula (VI), R$^2$ is heterocycloalkenyl.
In one embodiment, in Formula (VI), Z is (=O).
In one embodiment, in Formula (VI), Z is (=S).
In one embodiment, in Formula (VI), Z is (=N(R$^{13}$)).
In one embodiment, in Formula (VI), Z is (=N(CN)).
In one embodiment, in Formula (VI), Z is (=N(OR$^{14}$)).
In one embodiment, in Formula (VI), Z is (=N(R$^{15}$)(R$^{16}$)).
In one embodiment, in Formula (VI), Z is (=C(R$^{17}$)(R$^{18}$)).
In one embodiment, in Formula (VI), R$^2$ is —C(Z)R$^7$, and Z is (=O).

In one embodiment, in Formula (VI), R² is —C(O)H.

In one embodiment, in Formula (VI), R² is —C(O)alkyl.

In one embodiment, in Formula (VI), R² is —C(O)CH₃.

In one embodiment, in Formula (VI), R² is —C(O)R⁷, wherein said R⁷ is alkyl substituted with one or more substituents, which can be the same or different, each substituent being independently selected from the group consisting of oxo, halogen, —CN, —NO₂, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)O R²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (VI), R² is —C(O)R⁷, wherein said R⁷ is alkyl substituted with one to three substituents, which can be the same or different, each substituent being independently selected from the group consisting of —OR¹⁹, —NR²¹R²², and cycloalkyl.

In one embodiment, in Formula (VI), R² is —C(O)R⁷, wherein said R⁷ is alkyl, wherein said alkyl is substituted with alkyl and —OH.

In one embodiment, in Formula (VI), R² is —C(O)R⁷, wherein said R⁷ is alkyl substituted with one to three substituents, which can be the same or different, each substituent being independently selected from the group consisting of —OH, —NH₂, and cyclopropyl.

In one embodiment, in Formula (VI), R² is —C(O)R⁷, wherein said R⁷ is alkyl substituted with one to two substituents, which can be the same or different, each substituent being independently selected from the group consisting of —NH₂, and cyclopropyl.

In one embodiment, in Formula (VI), R² is —C(O)R⁷, wherein said R⁷ is alkyl substituted with —OH.

In one embodiment, in Formula (VI), R² is —C(O)R⁷, wherein said R⁷ is unsubstituted heterocycloalkyl.

In one embodiment, in Formula (VI), R² is —C(O)R⁷, wherein said R⁷ is substituted heterocycloalkyl.

In one embodiment, in Formula (VI), R² is —C(O)R⁷, wherein said R⁷ is heterocycloalkyl substituted with one or more substituents, which can be the same or different, each substituent being independently selected from the group consisting of oxo, halogen, —CN, —NO₂, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR¹⁹, —OC(O)OR²⁰, —NR²¹R²², —NR²³SO₂R²⁴, —NR²³C(O)OR²⁰, —NR²³C(O)R²⁴, —SO₂NR²⁵R²⁶, —C(O)R²⁴, —C(O)OR²⁰, —SR¹⁹, —S(O)R¹⁹, —SO₂R¹⁹, —OC(O)R²⁴, —C(O)NR²⁵R²⁶, —NR²³C(N—CN)NR²⁵R²⁶ and —NR²³C(O)NR²⁵R²⁶.

In one embodiment, in Formula (VI), R² is —C(O)R⁷, wherein said R⁷ is selected from the group consisting of substituted piperidine, substituted piperazine, substituted morpholine, substituted pyrrolidine, and substituted azetidine.

In one embodiment, in Formula (VI); R² is selected from:

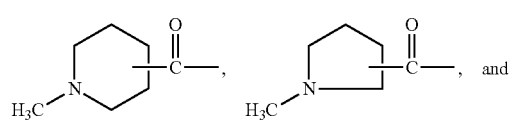, and

-continued

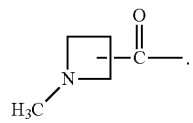.

In one embodiment, in Formula (VI), R² is —C(O)NR⁹R¹⁰.

In one embodiment, in Formula (VI), R² is —C(O)NH₂.

In one embodiment, in Formula (VI), R² is —C(O)NR⁹R¹⁰, wherein R⁹ and R¹⁰ can be the same or different, each being independently selected from alkyl.

In one embodiment, in Formula (VI), R² is —C(O)NR⁹R¹⁰, wherein R⁹ is unsubstituted heterocycloalkyl and R¹⁰ is selected from the group consisting of H and alkyl.

In one embodiment, in Formula (VI), R² is —C(O)NR⁹R¹⁰, wherein R⁹ is substituted heterocycloalkyl and R¹⁰ is selected from the group consisting of H and alkyl.

In one embodiment, in Formula (VI), R² is selected from the group consisting of:
alkyl, haloalkyl, heteroalkyl, heterohaloalkyl, —C(O)R⁷, —C(O)OR⁹, and —C(O)NR⁹R¹⁰.

In one embodiment, in Formula (VI), R² is selected from the group consisting of:

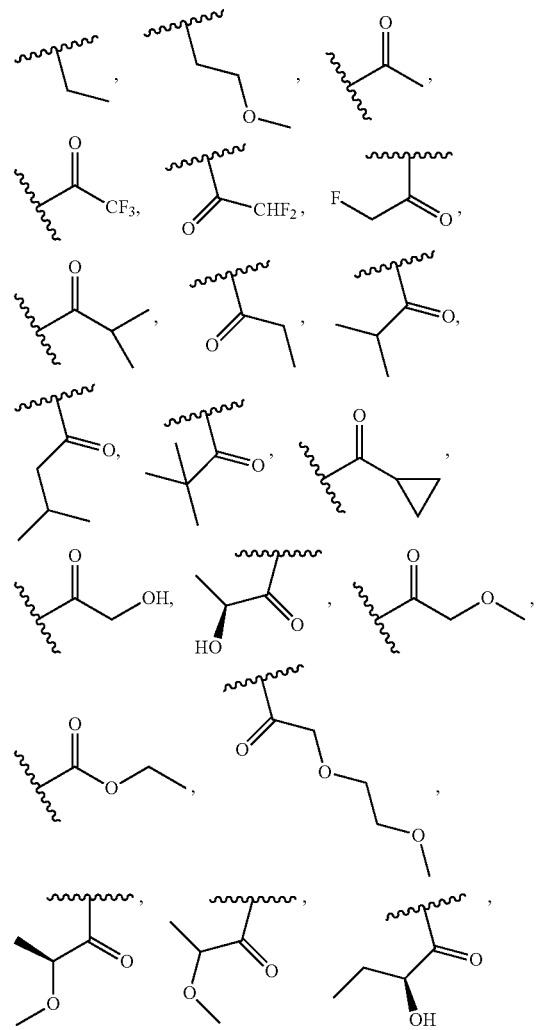

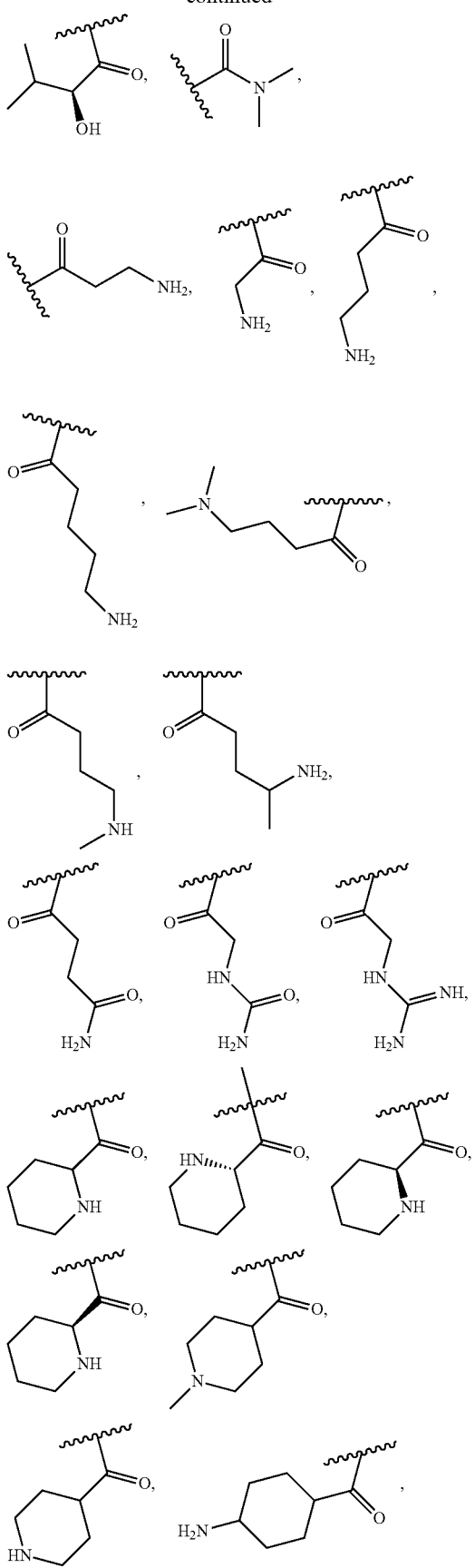
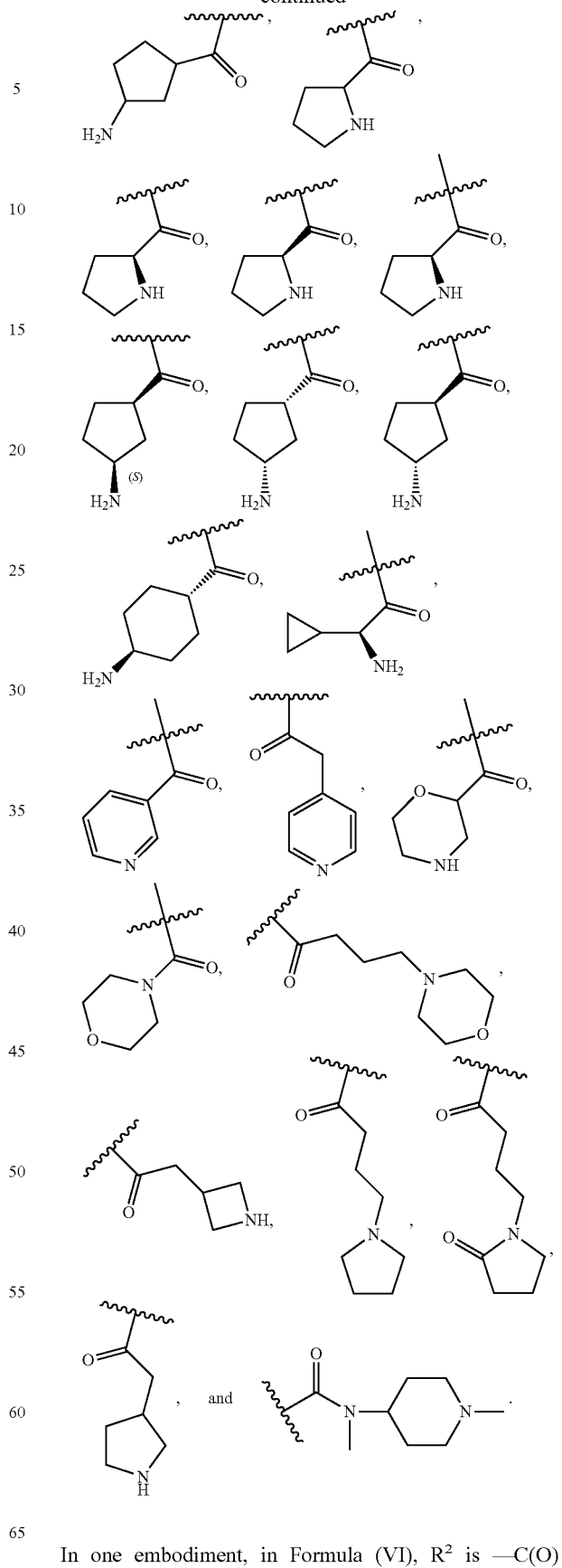
In one embodiment, in Formula (VI), $R^2$ is —C(O)$NR^9R^{10}$, wherein $R^9$ is heterocycloalkyl substituted with from one to three substituents, which can be the same or different, each substituent being independently selected from alkyl, and $R^{10}$ is selected from the group consisting of H and alkyl.

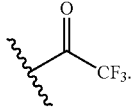

In one embodiment, in Formula (VI), $R^2$ is

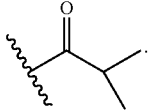

In one embodiment, in Formula (VI), $R^2$ is

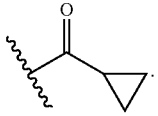

In one embodiment, in Formula (VI), $R^2$ is

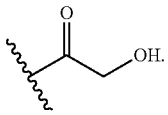 [SMILES: *C(=O)CO]

In one embodiment, in Formula (VI), $R^2$ is

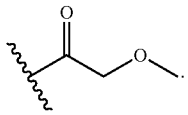

In one embodiment, in Formula (VI), $R^2$ is

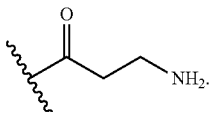 [SMILES: *C(=O)CCN]

In one embodiment, in Formula (VI), $R^2$ is

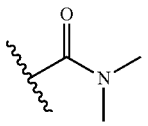

In one embodiment, in Formula (VI), $R^2$ is

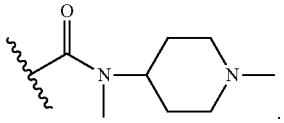 [SMILES: *C(=O)N(C)C1CCN(C)CC1]

In one embodiment, in Formula (VI), $R^2$ is

In one embodiment, in Formula (VI), p is 0 and $R^3$ is not present.
In one embodiment, in Formula (VI), p is 1.
In one embodiment, in Formula (VI), p is 2.
In one embodiment, in Formula (VI), p is 3.
In one embodiment, in Formula (VI), p is 4.
In one embodiment, in Formula (VI), p is ≥2 and at least two groups $R^3$ are attached to the same ring atom.
In one embodiment, in Formula (VI), p is 1 and $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{25}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (VI), p is 2, 3, or 4 and each $R^3$ is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (VI), p is 2, 3, or 4 and at least two groups $R^3$ are bound to the same ring carbon atom, wherein each $R^3$, which may be the same or different, is independently selected from the group consisting of alkyl, heteroalkyl, alkenyl, heteroalkenyl, alkynyl, heteroalkynyl, aryl, heteroaryl, cycloalkyl, cycloalkenyl, heterocycloalkyl, heterocycloalkenyl, halogen, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (VI), p is 2, 3, or 4 and at least two groups $R^3$ are bound to the same ring carbon atom, wherein two $R^3$ groups, which may be the same or different, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S.

In one embodiment, in Formula (VI), p is >0 and each $R^3$ is independently selected from the group consisting of alkyl, heteroalkyl, alkenyl, heteroalkenyl, —CN, —NO$_2$, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(S)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$, —NR$^{23}$C(O)NR$^{25}$R$^{26}$, and —NR$^{23}$—C(NH)—NR$^{25}$R$^{26}$, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (VI), p is 1 and R$^3$ is selected from the group consisting of alkyl, heteroalkyl, alkenyl, and heteroalkenyl, wherein each said alkyl, each said heteroalkyl, each said alkenyl, and each said heteroalkenyl, is unsubstituted or optionally independently substituted with one or more substituents, which can be the same or different, each substituent being independently selected from the group of oxo, halogen, —CN, —NO$_2$, alkyl, heteroalkyl, haloalkyl, alkenyl, haloalkenyl, alkynyl, haloalkynyl, aryl, heteroaryl, cycloalkyl, cycloalkenyl, heterocycloalkyl, heterocycloalkenyl, azido, —OR$^{19}$, —OC(O)OR$^{20}$, —NR$^{21}$R$^{22}$, —NR$^{23}$SO$_2$R$^{24}$, —NR$^{23}$C(O)OR$^{20}$, —NR$^{23}$C(O)R$^{24}$, —SO$_2$NR$^{25}$R$^{26}$, —C(O)R$^{24}$, —C(O)OR$^{20}$, —SR$^{19}$, —S(O)R$^{19}$, —SO$_2$R$^{19}$, —OC(O)R$^{24}$, —C(O)NR$^{25}$R$^{26}$, —NR$^{23}$C(N—CN)NR$^{25}$R$^{26}$ and —NR$^{23}$C(O)NR$^{25}$R$^{26}$.

In one embodiment, in Formula (VI), p is 2, 3, or 4, and any two R$^3$ groups bound to the same ring A atom are taken together to form a —C(O)— group.

In one embodiment, in Formula (IV), p is 2, 3, or 4, and any two R$^3$ groups bound to the same ring A atom are taken together with the carbon atom to which they are attached to form a spirocycloalkyl, a spirocycloalkenyl, a spiroheterocycloalkyl ring containing from one to three ring heteroatoms independently selected from the group consisting of —NH—, —NR$^6$—, —S—, —S(O)—, —S(O)$_2$—, and —O—, or a spiroheterocycloalkenyl ring containing from one to three ring heteroatoms independently selected from the group consisting of —NH—, —NR$^6$—, —S—, —S(O)—, —S(O)$_2$—, and —O—.

In one embodiment, in Formula (IV), p is >0 and R$^2$ and R$^3$ are taken together with the carbon atom to which they are attached to form a cycloalkyl, a cycloalkenyl, a heterocycloalkyl ring containing from one to three ring heteroatoms independently selected from the group consisting of —NH—, —NR$^6$—, —S—, —S(O)—, —S(O)$_2$—, and —O—, or a heterocycloalkenyl ring containing from one to three ring heteroatoms independently selected from the group consisting of —NH—, —NR$^6$—, —S—, —S(O)—, —S(O)$_2$—, and In one embodiment, in Formula (VI), R$^3$ is alkyl.
In one embodiment, in Formula (VI), R$^3$ is heteroalkyl.
In one embodiment, in Formula (VI), R$^3$ is alkenyl.
In one embodiment, in Formula (VI), R$^3$ is heteroalkenyl.
In one embodiment, in Formula (VI), R$^3$ is alkynyl.
In one embodiment, in Formula (VI), R$^3$ is heteroalkynyl.
In one embodiment, in Formula (VI), R$^3$ is aryl.
In one embodiment, in Formula (VI), R$^3$ is heteroaryl.
In one embodiment, in Formula (VI), R$^3$ is cycloalkyl.
In one embodiment, in Formula (VI), R$^3$ is cycloalkenyl.
In one embodiment, in Formula (VI), R$^3$ is heterocycloalkyl.

In one embodiment, in Formula (VI), R$^3$ is heterocycloalkenyl.
In one embodiment, in Formula (VI), R$^3$ is halogen.
In one embodiment, in Formula (VI), R$^3$ is —CN.
In one embodiment, in Formula (VI), R$^3$ is —NO$_2$.
In one embodiment, in Formula (VI), R$^3$ is —OR$^{16}$.
In one embodiment, in Formula (VI), R$^3$ is —OC(O)OR$^{20}$.
In one embodiment, in Formula (VI), R$^3$ is —NR$^{21}$R$^{22}$.
In one embodiment, in Formula (VI), R$^3$ is —NR$^{23}$SO$_2$R$^{24}$.
In one embodiment, in Formula (VI), R$^3$ is —NR$^{23}$C(O)OR$^{20}$.
In one embodiment, in Formula (VI), R$^3$ is —NR$^{23}$C(O)R$^{24}$.
In one embodiment, in Formula (VI), R$^3$ is —SO$_2$NR$^{25}$R$^{26}$.
In one embodiment, in Formula (VI), R$^3$ is —C(O)R$^{24}$.
In one embodiment, in Formula (VI), R$^3$ is —C(S)R$^{24}$.
In one embodiment, in Formula (VI), R$^3$ is —C(O)OR$^{20}$.
In one embodiment, in Formula (VI), R$^3$ is —SR$^{19}$.
In one embodiment, in Formula (VI), R$^3$ is —S(O)R$^{19}$.
In one embodiment, in Formula (VI), R$^3$ is —SO$_2$R$^{19}$.
In one embodiment, in Formula (VI), R$^3$ is —OC(O)R$^{24}$.
In one embodiment, in Formula (VI), R$^3$ is —C(O)NR$^{25}$R$^{26}$.
In one embodiment, in Formula (VI), R$^3$ is —NR$^{23}$C(N—CN)NR$^{25}$R$^{26}$.
In one embodiment, in Formula (VI), R$^3$ is —NR$^{23}$C(O)NR$^{25}$R$^{26}$.

In one embodiment, in Formula (VI), R$^3$ is selected from the group consisting of methyl, ethyl, propyl (straight or branched), butyl (straight or branched), pentyl (straight or branched), phenyl,

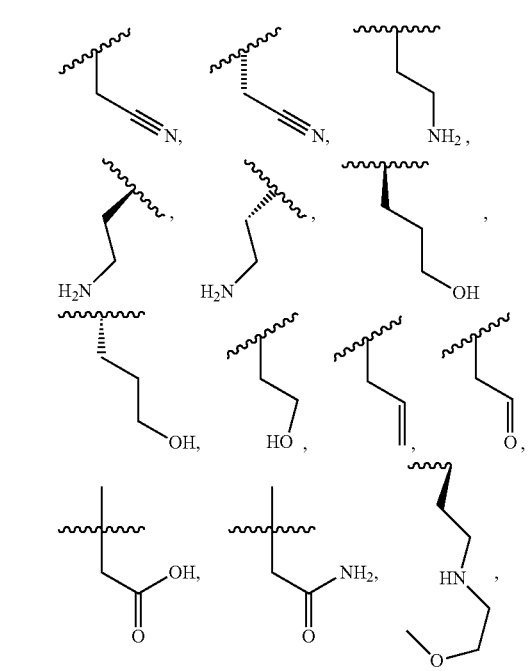

-continued

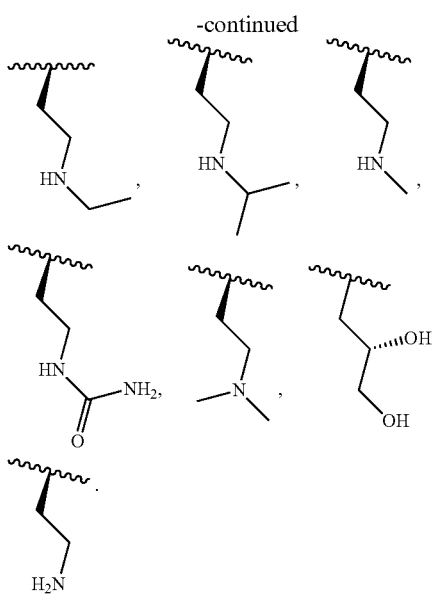

In one embodiment, in Formula (IV), when E is —NR⁶—, R³ is absent.

In one embodiment, Formula (VI) has the general structure:

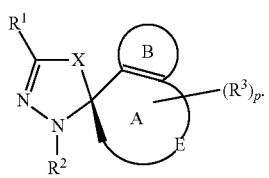

In one embodiment, Formula (VI) has the general structure:

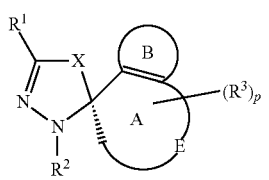

In one embodiment, Formula (VI) has the general structure:

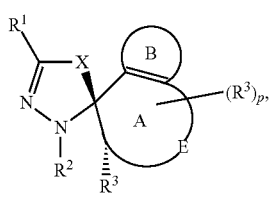

wherein P is 0, 1, 2, or 3.

In one embodiment, Formula (VI) has the general structure:

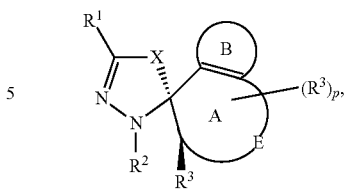

wherein P is 0, 1, 2, or 3.

In one embodiment, Formula (VI) has the general structure:

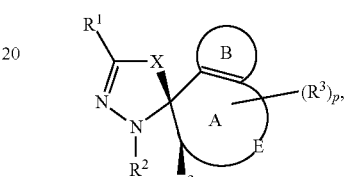

wherein P is 0, 1, 2, or 3.

In one embodiment, Formula (VI) has the general structure:

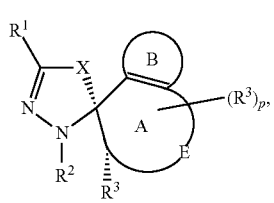

wherein P is 0, 1, 2, or 3.

In one embodiment, the compounds of the invention have a structure shown in the Table below, and include pharmaceutically acceptable salts, solvates, esters, prodrugs, or isomers of said compounds.

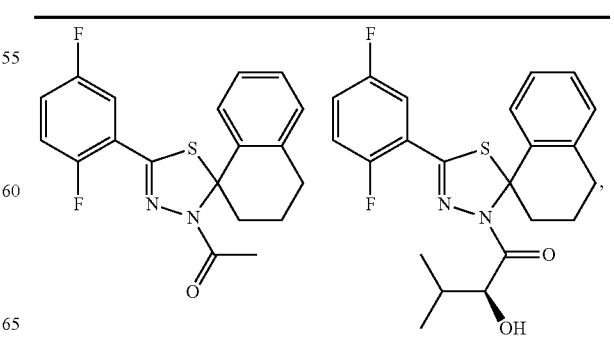

191
-continued
192
-continued
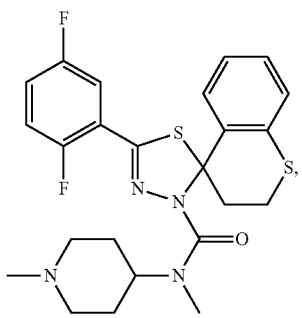 [SMILES: CN1CCC(N(C)C(=O)N2N=C(c3cc(F)ccc3F)SC23CCSc2ccccc23)CC1]
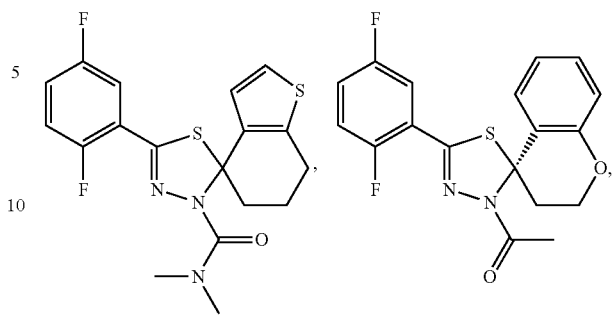
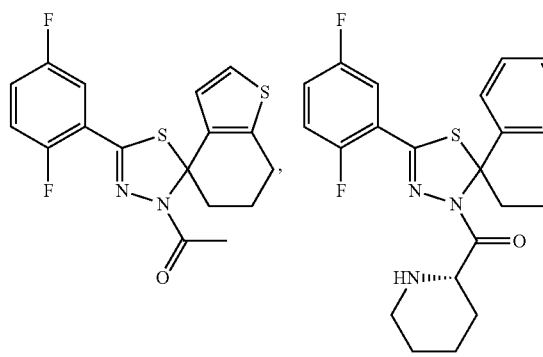
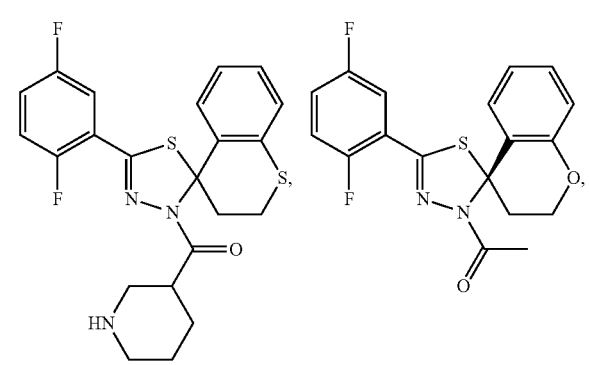
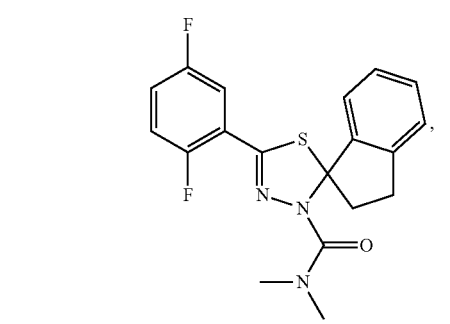 [SMILES: CN(C)C(=O)N1N=C(c2cc(F)ccc2F)SC12CCc1ccccc12]
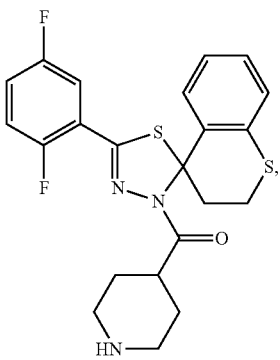
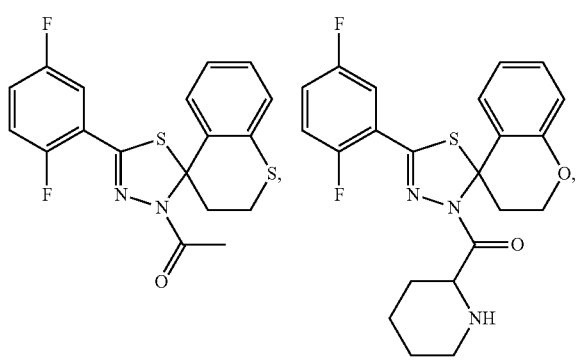
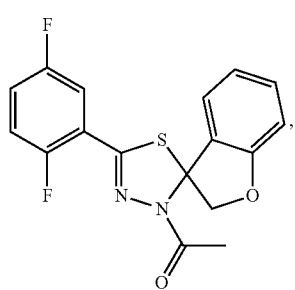 [SMILES: CC(=O)N1N=C(c2cc(F)ccc2F)SC12COc1ccccc12]

193
-continued
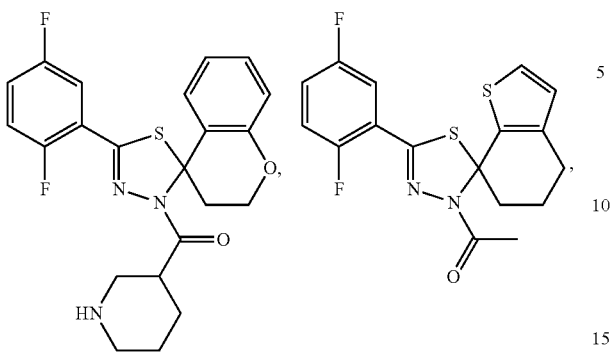
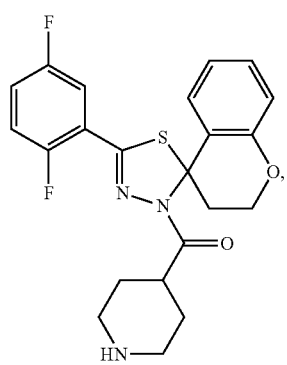 [SMILES: O=C(C1CCNCC1)N1N=C(c2cc(F)ccc2F)SC12CCOc1ccccc12]
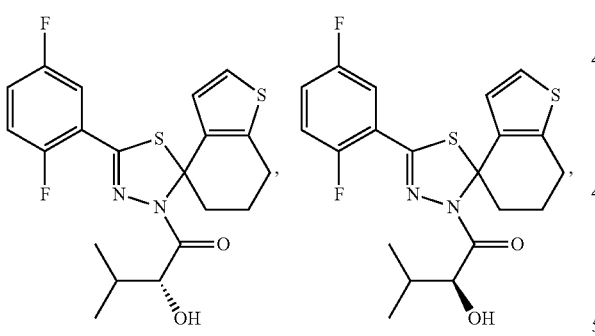
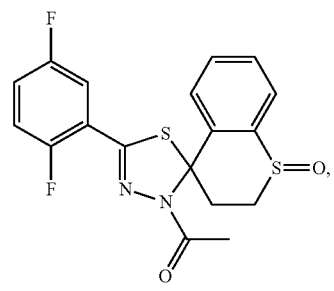 [SMILES: CC(=O)N1N=C(c2cc(F)ccc2F)SC12CCS(=O)c1ccccc12]
194
-continued
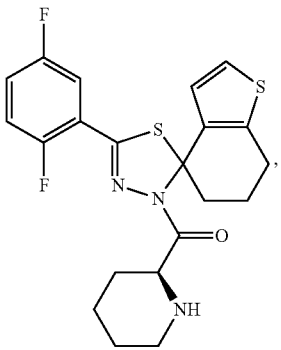 [SMILES: O=C([C@@H]1CCCCN1)N1N=C(c2cc(F)ccc2F)SC12CCCc1sccc12 ; ","]
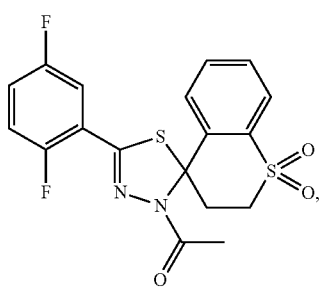 [SMILES: CC(=O)N1N=C(c2cc(F)ccc2F)SC12CCS(=O)(=O)c1ccccc12]
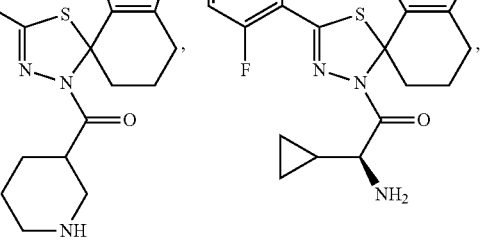
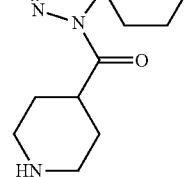
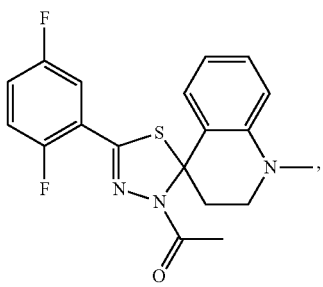 [SMILES: CC(=O)N1N=C(c2cc(F)ccc2F)SC12CCN(C)c1ccccc12 ; ","]

195
-continued
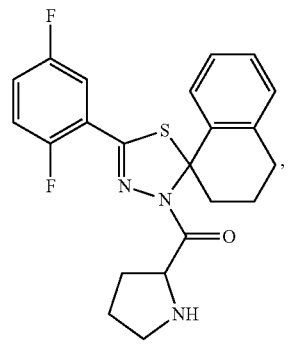 [SMILES: O=C(C1CCCN1)N1N=C(c2cc(F)ccc2F)SC12CCCc1ccccc12 ; ","]
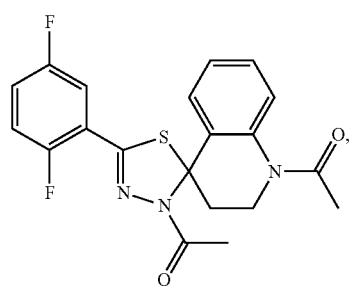 [SMILES: CC(=O)N1CCC2(SC(c3cc(F)ccc3F)=NN2C(C)=O)c2ccccc21]
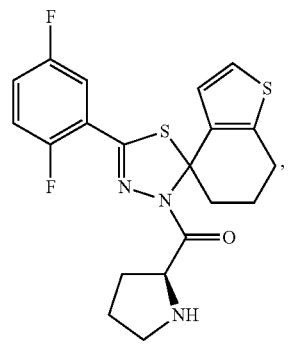 [SMILES: O=C([C@@H]1CCCN1)N1N=C(c2cc(F)ccc2F)SC12CCCc1sccc12 ; ","]
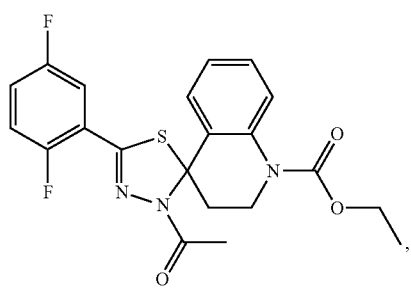 [SMILES: CCOC(=O)N1CCC2(SC(c3cc(F)ccc3F)=NN2C(C)=O)c2ccccc21]
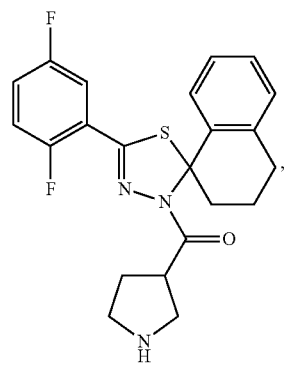 [SMILES: O=C(C1CCNC1)N1N=C(c2cc(F)ccc2F)SC12CCCc1ccccc12 ; ","]
196
-continued
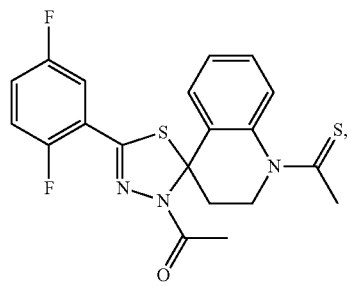
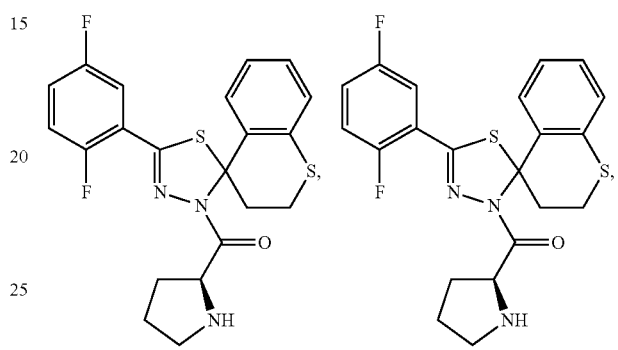
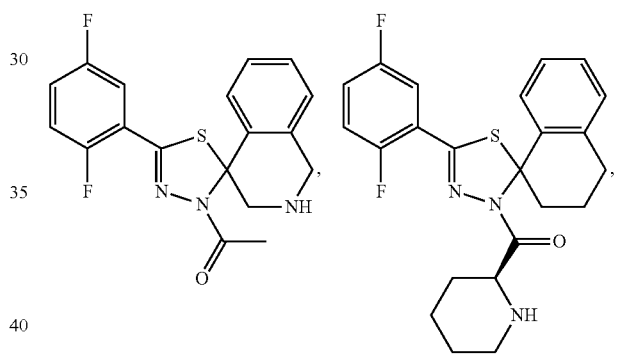
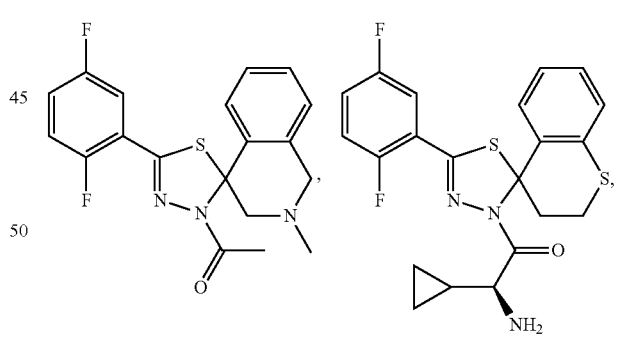
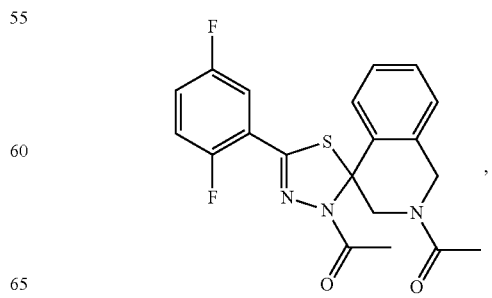

197
-continued
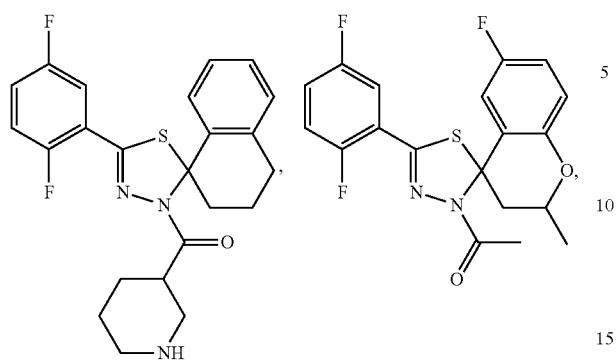
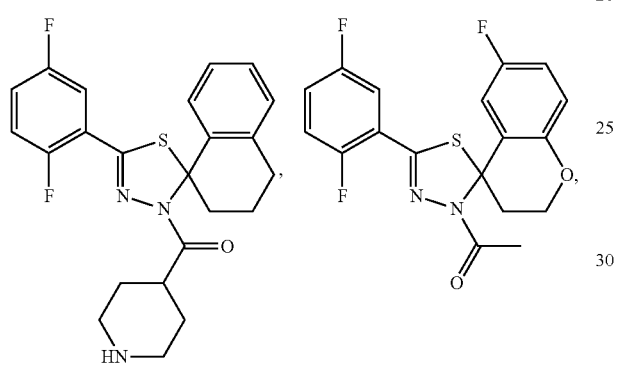
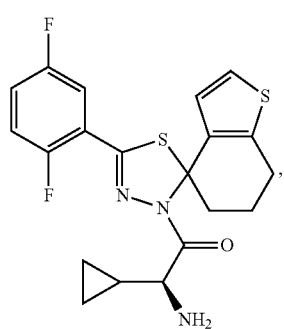 [SMILES: N[C@H](C(=O)N1N=C(c2cc(F)ccc2F)SC12CCCc1sccc12)C1CC1 ; ","]
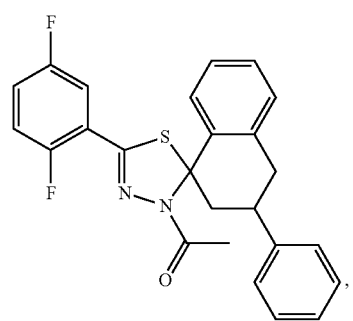 [SMILES: CC(=O)N1N=C(c2cc(F)ccc2F)SC12CC(c1ccccc1)Cc1ccccc12]
198
-continued
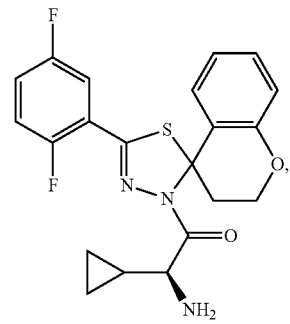 [SMILES: N[C@H](C(=O)N1N=C(c2cc(F)ccc2F)SC12CCOc1ccccc12)C1CC1]
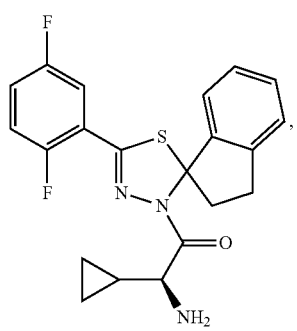 [SMILES: N[C@H](C(=O)N1N=C(c2cc(F)ccc2F)SC12CCc1ccccc12)C1CC1]
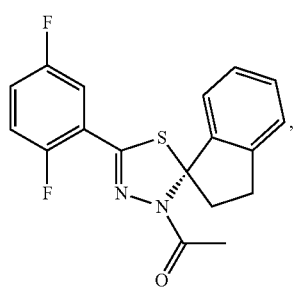 [SMILES: CC(=O)N1N=C(c2cc(F)ccc2F)S[C@@]12CCc1ccccc12]
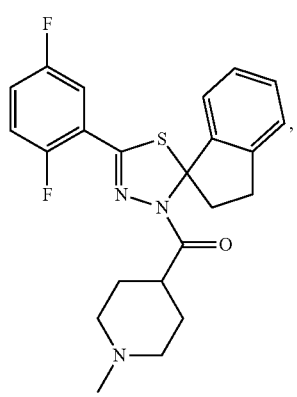 [SMILES: CN1CCC(C(=O)N2N=C(c3cc(F)ccc3F)SC23CCc2ccccc23)CC1]
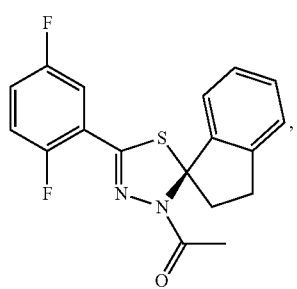 [SMILES: CC(=O)N1N=C(c2cc(F)ccc2F)S[C@]12CCc1ccccc12]

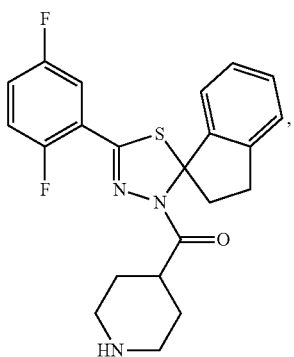 [SMILES: O=C(C1CCNCC1)N1N=C(c2cc(F)ccc2F)SC12CCc1ccccc12]
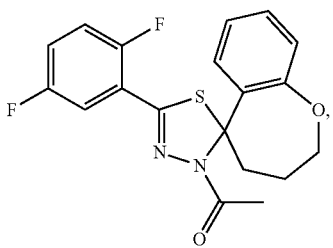 [SMILES: CC(=O)N1N=C(c2cc(F)ccc2F)SC12CCCOc1ccccc12]
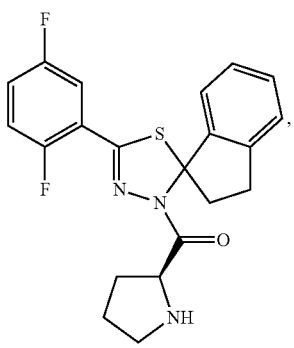 [SMILES: O=C([C@@H]1CCCN1)N1N=C(c2cc(F)ccc2F)SC12CCc1ccccc12]
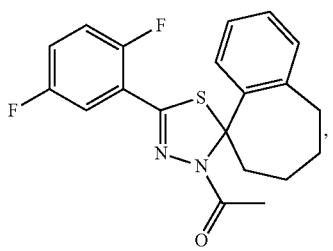 [SMILES: CC(=O)N1N=C(c2cc(F)ccc2F)SC12CCCCc1ccccc12]
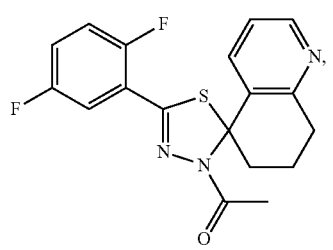 [SMILES: CC(=O)N1N=C(c2cc(F)ccc2F)SC12CCCc1ncccc12]
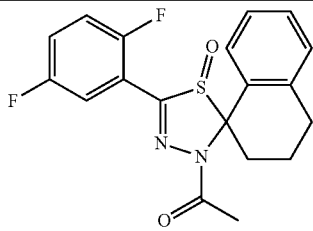
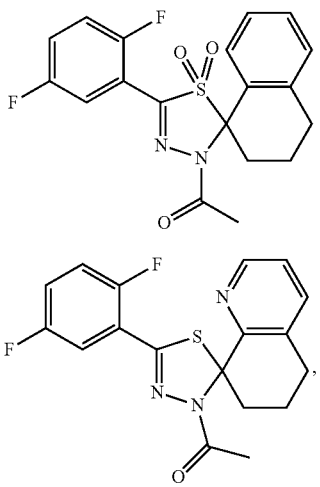
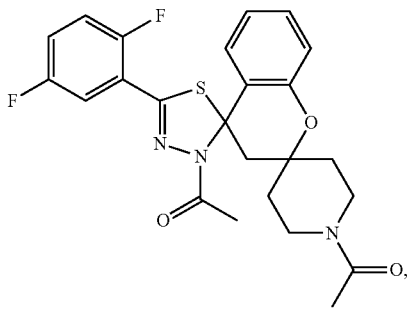 [SMILES: CC(=O)N1CCC2(CC1)CC1(SC(c3cc(F)ccc3F)=NN1C(C)=O)c1ccccc1O2]
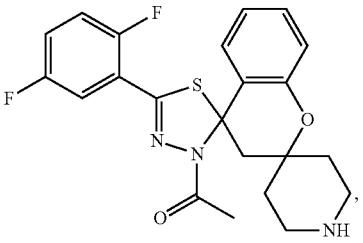 [SMILES: CC(=O)N1N=C(c2cc(F)ccc2F)SC12CC1(CCNCC1)Oc1ccccc12]
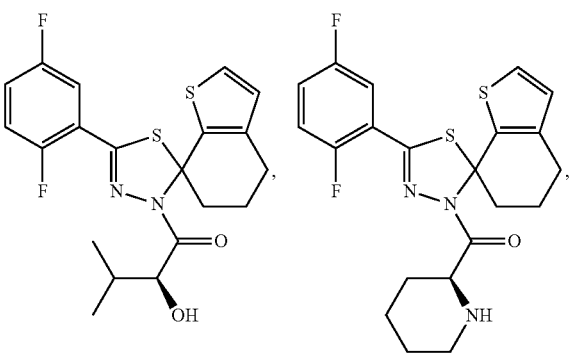

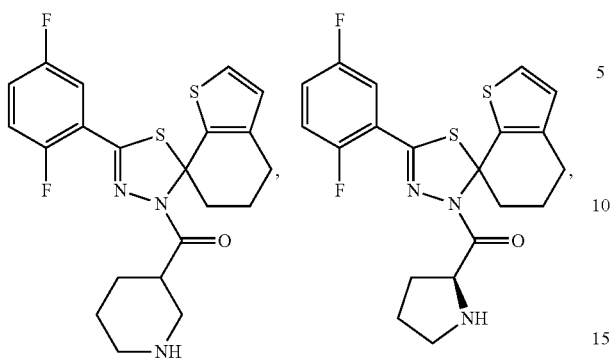
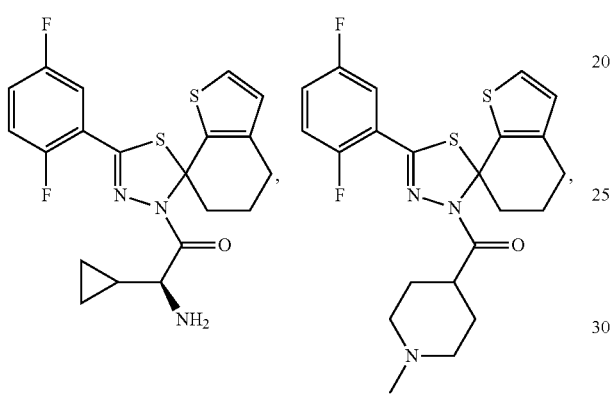
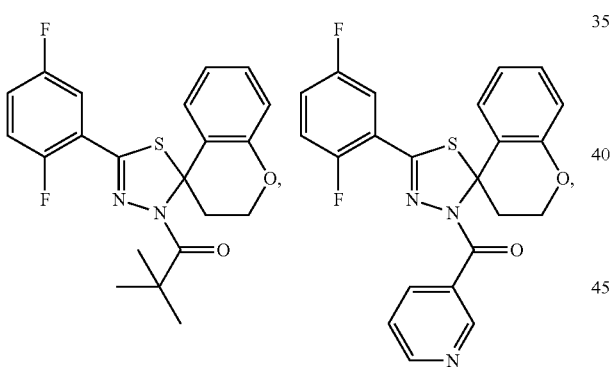
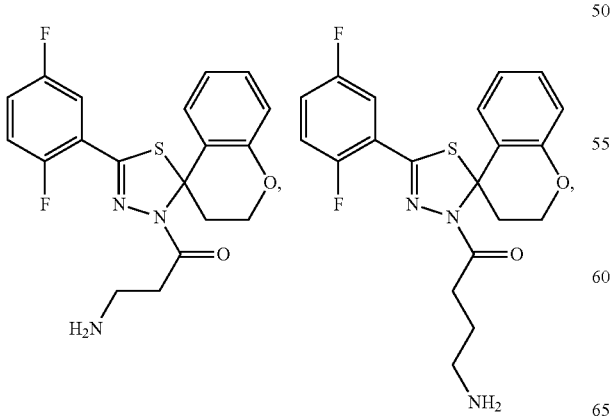
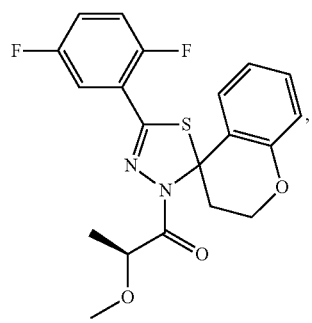 [SMILES: CO[C@@H](C)C(=O)N1N=C(c2cc(F)ccc2F)SC12CCOc1ccccc12]
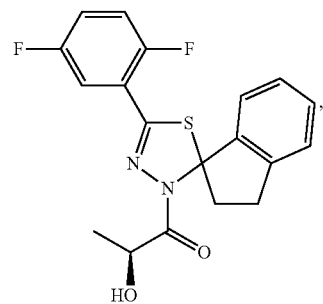 [SMILES: C[C@H](O)C(=O)N1N=C(c2cc(F)ccc2F)SC12CCc1ccccc12]
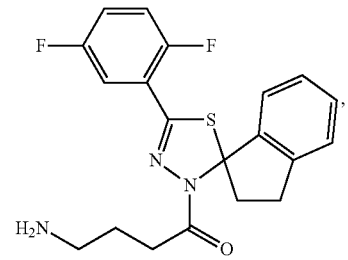 [SMILES: NCCCC(=O)N1N=C(c2cc(F)ccc2F)SC12CCc1ccccc12]
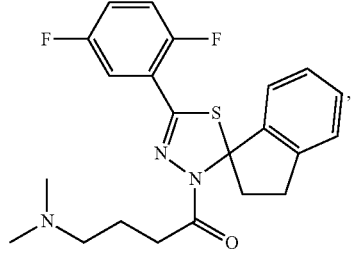 [SMILES: CN(C)CCCC(=O)N1N=C(c2cc(F)ccc2F)SC12CCc1ccccc12]
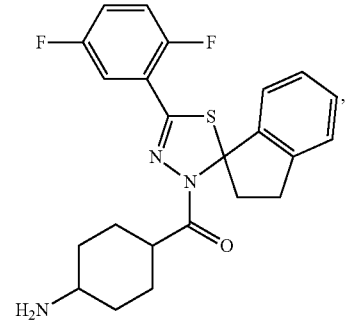 [SMILES: NC1CCC(C(=O)N2N=C(c3cc(F)ccc3F)SC23CCc2ccccc23)CC1]

| 203 -continued | 204 -continued |
|---|---|
| 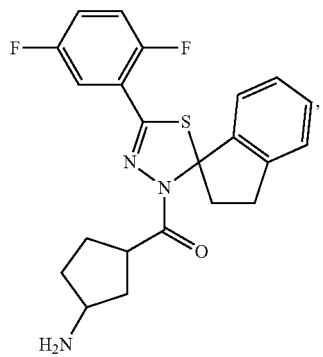 [SMILES: NC1CCC(C(=O)N2N=C(c3cc(F)ccc3F)SC23CCc2ccccc23)C1] | 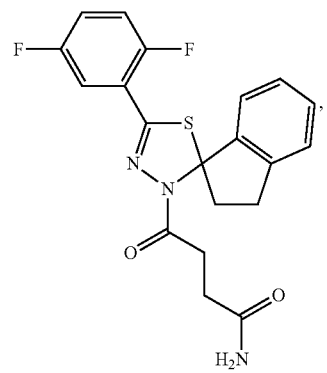 [SMILES: NC(=O)CCC(=O)N1N=C(c2cc(F)ccc2F)SC12CCc1ccccc12] |
| 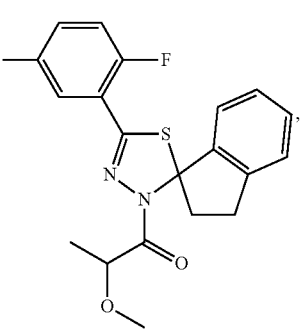 | 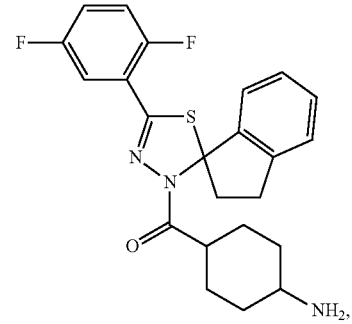 [SMILES: NC1CCC(C(=O)N2N=C(c3cc(F)ccc3F)SC23CCc2ccccc23)CC1] |
| 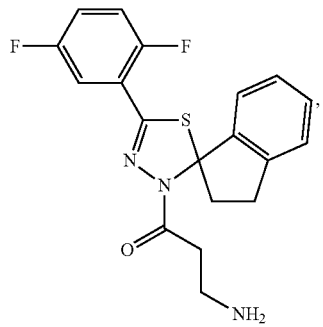 | 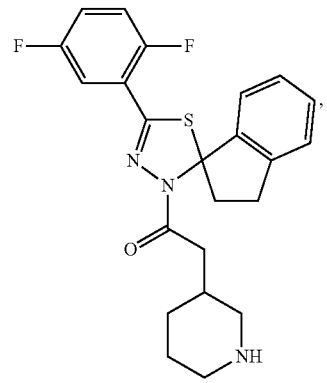 [SMILES: O=C(CC1CCCNC1)N1N=C(c2cc(F)ccc2F)SC12CCc1ccccc12] |
| 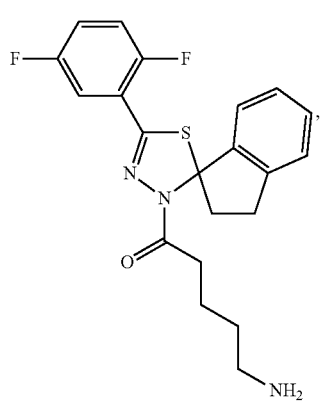 | 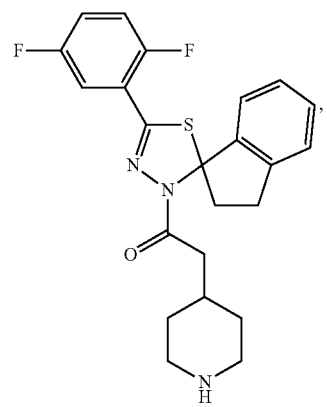 [SMILES: O=C(CC1CCNCC1)N1N=C(c2cc(F)ccc2F)SC12CCc1ccccc12] |

| 205 -continued | 206 -continued |
|---|---|
| 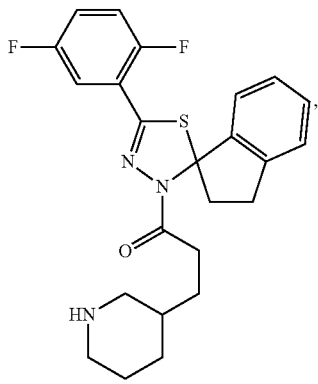 [SMILES: O=C(CCC1CCCNC1)N1N=C(c2cc(F)ccc2F)SC12CCc1ccccc12] | 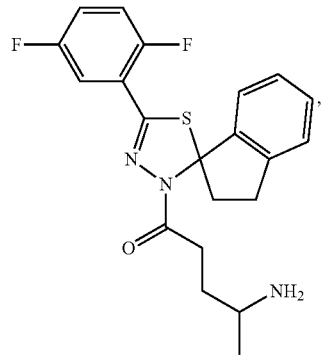 |
| 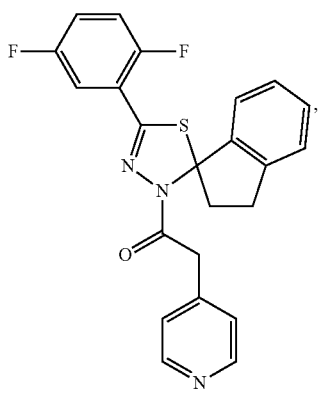 [SMILES: O=C(Cc1ccncc1)N1N=C(c2cc(F)ccc2F)SC12CCc1ccccc12] | 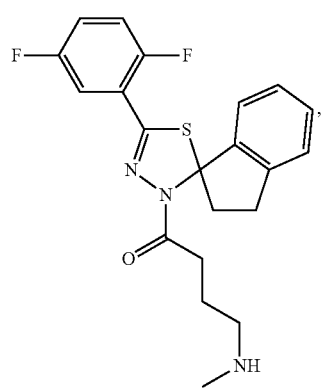 |
| 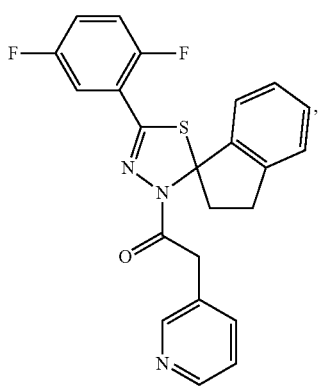 [SMILES: O=C(Cc1cccnc1)N1N=C(c2cc(F)ccc2F)SC12CCc1ccccc12] | 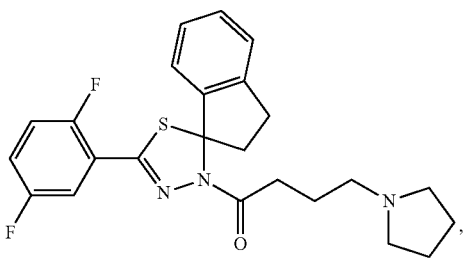 |
| 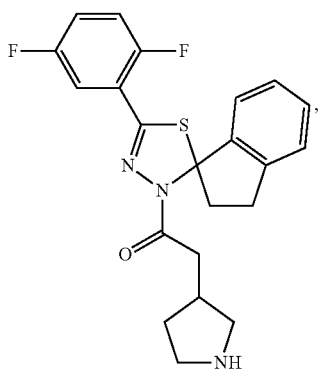 [SMILES: O=C(CC1CCNC1)N1N=C(c2cc(F)ccc2F)SC12CCc1ccccc12] | 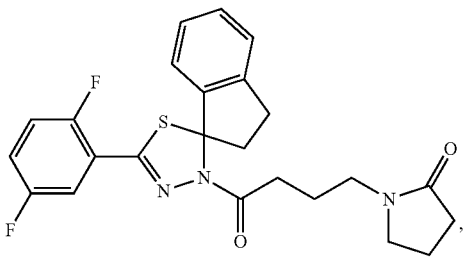 [SMILES: O=C1CCCN1CCCC(=O)N1N=C(c2cc(F)ccc2F)SC12CCc1ccccc12] |
| | 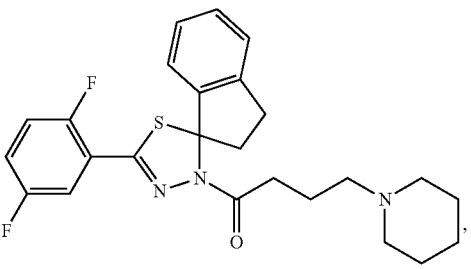 [SMILES: O=C(CCCN1CCCCC1)N1N=C(c2cc(F)ccc2F)SC12CCc1ccccc12] |

207
-continued
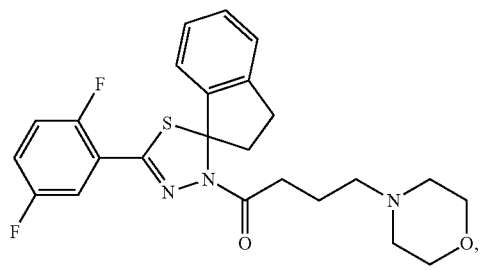 [SMILES: O=C(CCCN1CCOCC1)N1N=C(c2cc(F)ccc2F)SC12CCc1ccccc12]
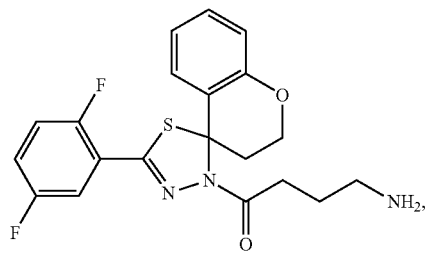 [SMILES: NCCCC(=O)N1N=C(c2cc(F)ccc2F)SC12CCOc1ccccc12]
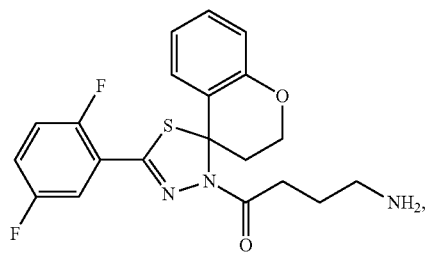 [SMILES: NCCCC(=O)N1N=C(c2cc(F)ccc2F)SC12CCOc1ccccc12]
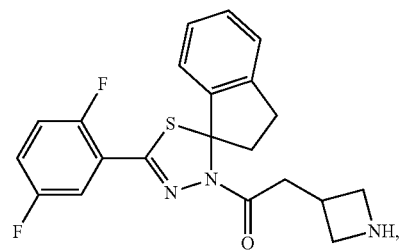 [SMILES: O=C(CC1CNC1)N1N=C(c2cc(F)ccc2F)SC12CCc1ccccc12]
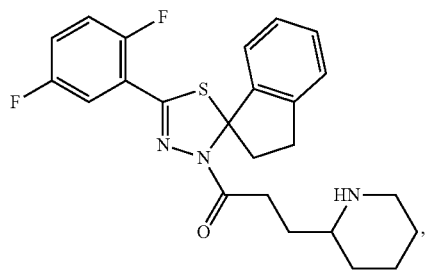 [SMILES: O=C(CCC1CCCCN1)N1N=C(c2cc(F)ccc2F)SC12CCc1ccccc12]
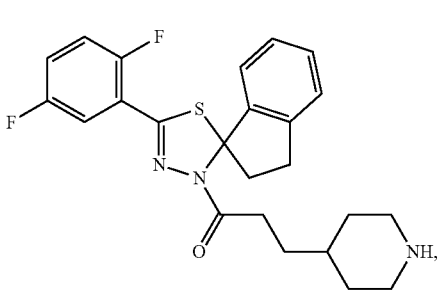 [SMILES: O=C(CCC1CCNCC1)N1N=C(c2cc(F)ccc2F)SC12CCc1ccccc12]
208
-continued
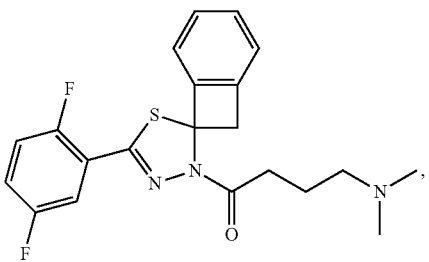 [SMILES: CN(C)CCCC(=O)N1N=C(c2cc(F)ccc2F)SC12Cc1ccccc12]
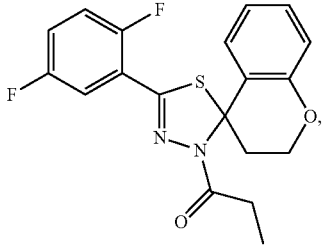 [SMILES: CCC(=O)N1N=C(c2cc(F)ccc2F)SC12CCOc1ccccc12]
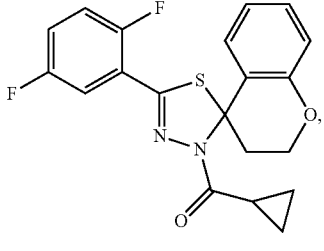
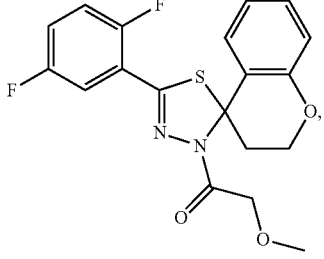
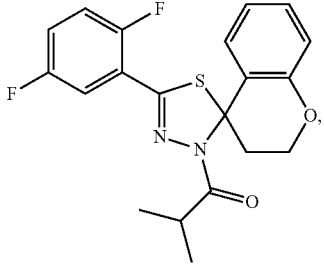 [SMILES: CC(C)C(=O)N1N=C(c2cc(F)ccc2F)SC12CCOc1ccccc12]
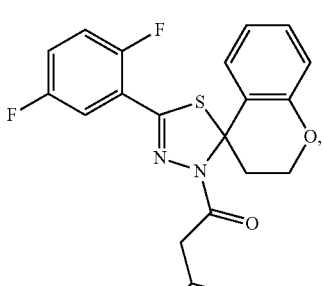

209
-continued
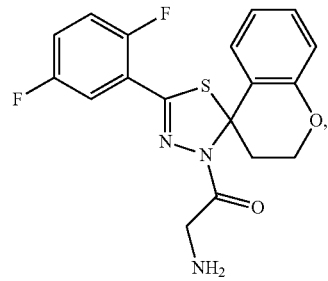 [SMILES: NCC(=O)N1N=C(c2cc(F)ccc2F)SC12CCOc1ccccc12]
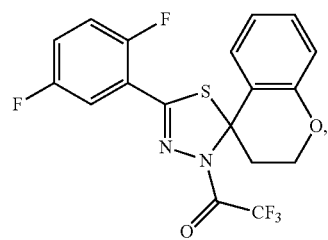
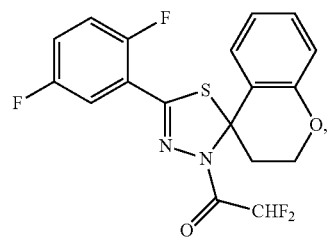 [SMILES: O=C(C(F)F)N1N=C(c2cc(F)ccc2F)SC12CCOc1ccccc12]
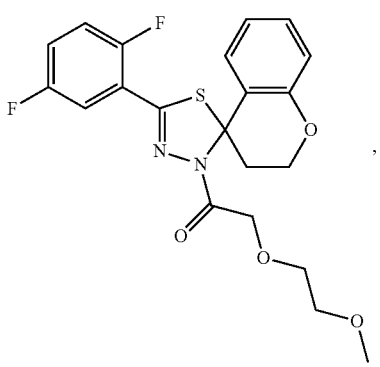 [SMILES: COCCOCC(=O)N1N=C(c2cc(F)ccc2F)SC12CCOc1ccccc12]
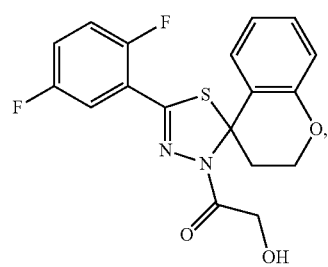 [SMILES: O=C(CO)N1N=C(c2cc(F)ccc2F)SC12CCOc1ccccc12]
210
-continued
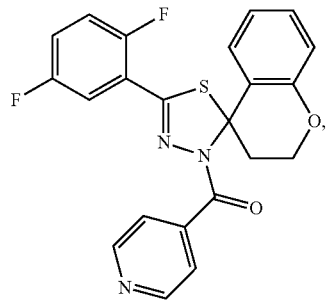 [SMILES: O=C(c1ccncc1)N1N=C(c2cc(F)ccc2F)SC12CCOc1ccccc12]
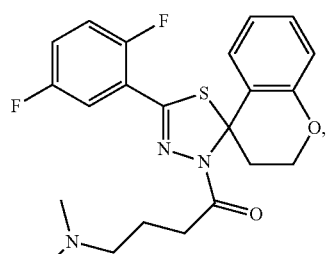
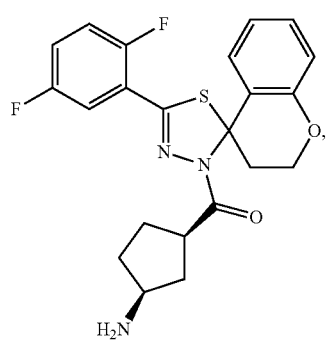 [SMILES: N[C@H]1CC[C@@H](C(=O)N2N=C(c3cc(F)ccc3F)SC23CCOc2ccccc23)C1]
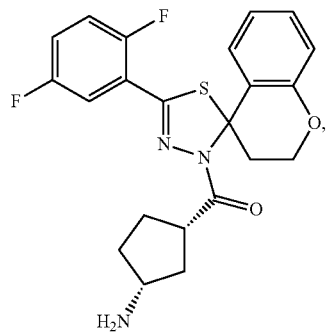 [SMILES: N[C@@H]1CC[C@H](C(=O)N2N=C(c3cc(F)ccc3F)SC23CCOc2ccccc23)C1]
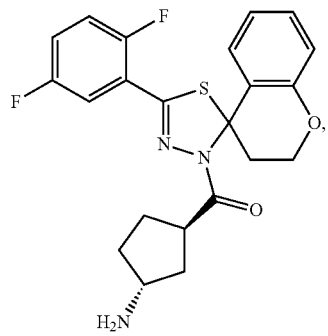 [SMILES: N[C@@H]1CC[C@@H](C(=O)N2N=C(c3cc(F)ccc3F)SC23CCOc2ccccc23)C1]

| 211 -continued | 212 -continued |
|---|---|
| 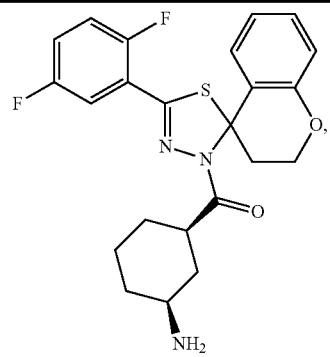 | 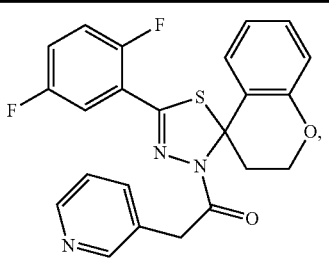 |
| 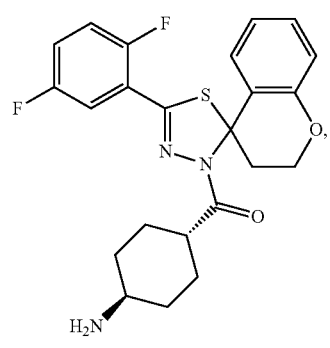 [SMILES: N[C@H]1CC[C@H](C(=O)N2N=C(c3cc(F)ccc3F)SC23CCOc2ccccc23)CC1] | 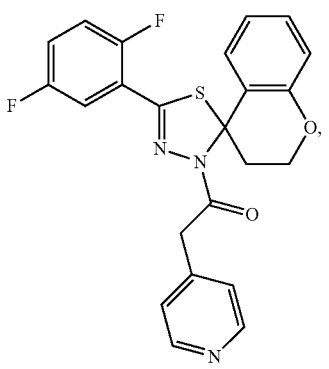 |
| 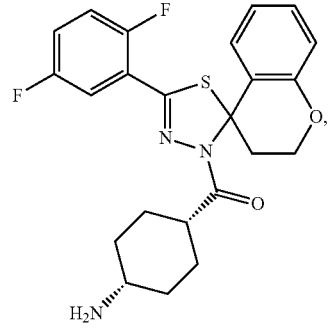 [SMILES: N[C@H]1CC[C@@H](C(=O)N2N=C(c3cc(F)ccc3F)SC23CCOc2ccccc23)CC1] | 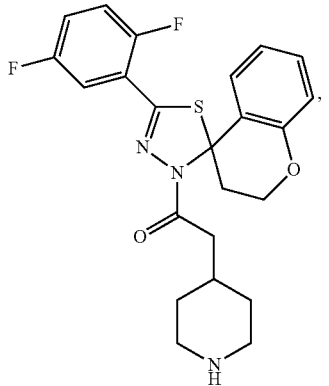 |
| 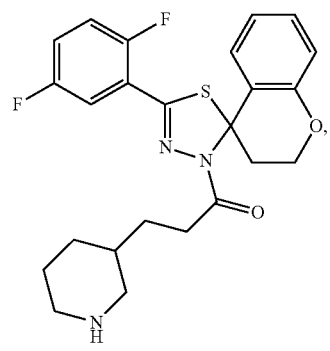 [SMILES: O=C(CCC1CCCNC1)N1N=C(c2cc(F)ccc2F)SC12CCOc1ccccc12] | 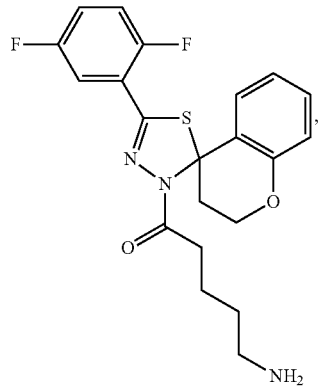 |
| 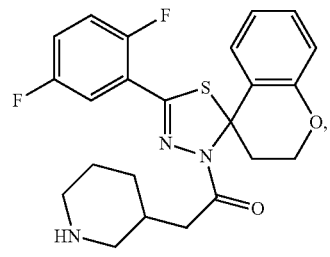 [SMILES: O=C(CC1CCCNC1)N1N=C(c2cc(F)ccc2F)SC12CCOc1ccccc12] | |

213
-continued
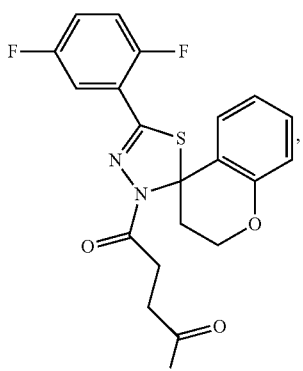
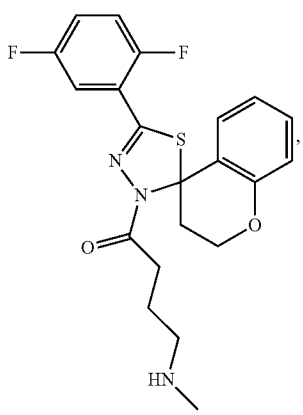 [SMILES: CNCCCC(=O)N1N=C(c2cc(F)ccc2F)SC12CCOc1ccccc12]
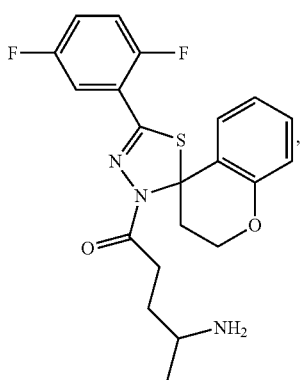 [SMILES: CC(N)CCC(=O)N1N=C(c2cc(F)ccc2F)SC12CCOc1ccccc12]
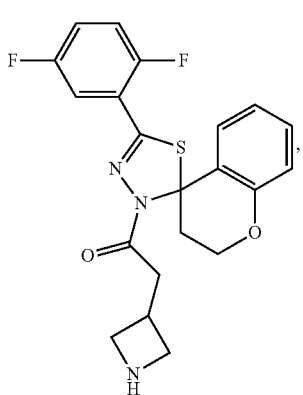 [SMILES: O=C(CC1CNC1)N1N=C(c2cc(F)ccc2F)SC12CCOc1ccccc12]
214
-continued
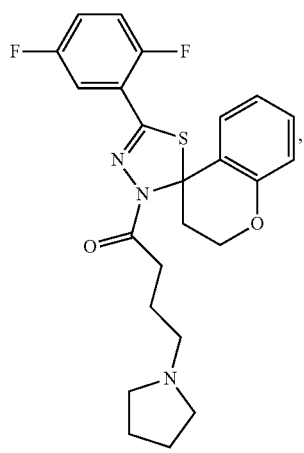 [SMILES: O=C(CCCN1CCCC1)N1N=C(c2cc(F)ccc2F)SC12CCOc1ccccc12]
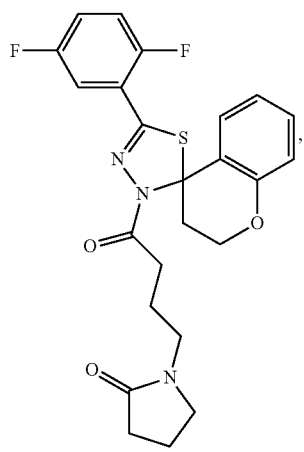 [SMILES: O=C1CCCN1CCCC(=O)N1N=C(c2cc(F)ccc2F)SC12CCOc1ccccc12]
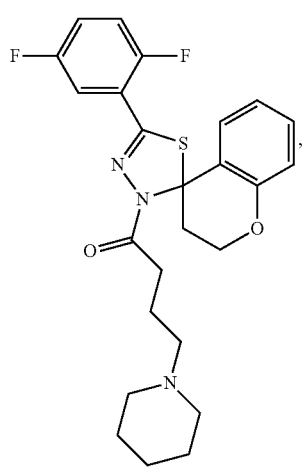 [SMILES: O=C(CCCN1CCCCC1)N1N=C(c2cc(F)ccc2F)SC12CCOc1ccccc12]

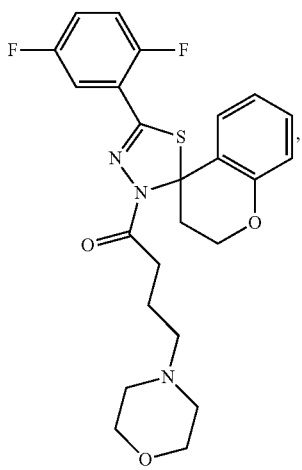 [SMILES: O=C(CCCN1CCOCC1)N1N=C(c2cc(F)ccc2F)SC12CCOc1ccccc12],
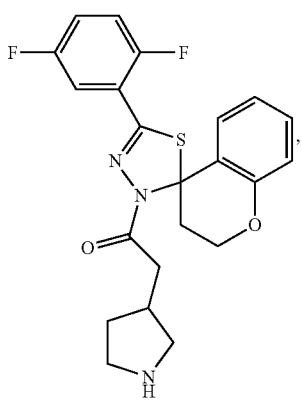 [SMILES: O=C(CC1CCNC1)N1N=C(c2cc(F)ccc2F)SC12CCOc1ccccc12],
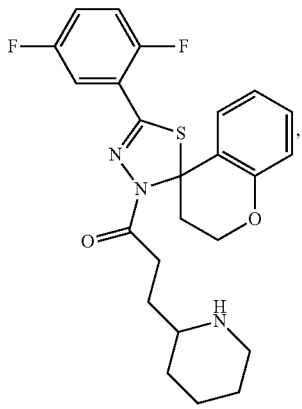 [SMILES: O=C(CCC1CCCCN1)N1N=C(c2cc(F)ccc2F)SC12CCOc1ccccc12],
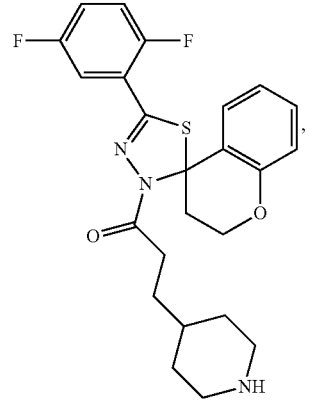 [SMILES: O=C(CCC1CCNCC1)N1N=C(c2cc(F)ccc2F)SC12CCOc1ccccc12],
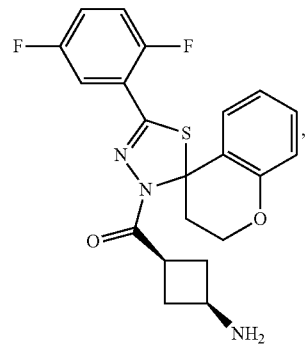 [SMILES: N[C@H]1C[C@@H](C(=O)N2N=C(c3cc(F)ccc3F)SC23CCOc2ccccc23)C1],
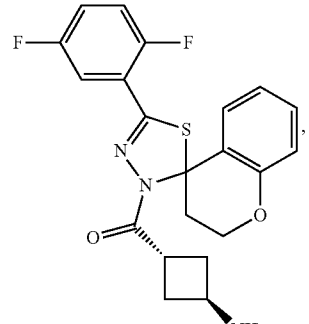,
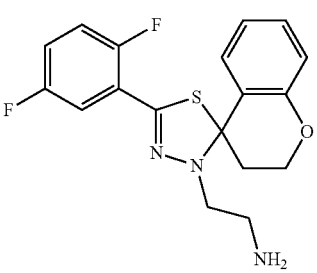 [SMILES: NCCN1N=C(c2cc(F)ccc2F)SC12CCOc1ccccc12],
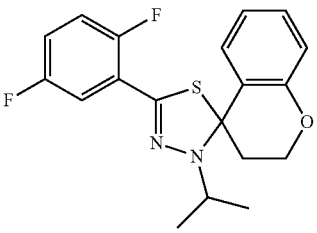 [SMILES: CC(C)N1N=C(c2cc(F)ccc2F)SC12CCOc1ccccc12]

217
-continued
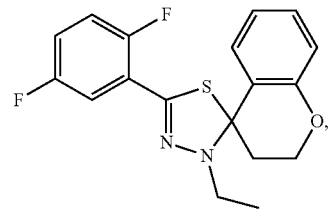 [SMILES: CCN1N=C(c2cc(F)ccc2F)SC12CCOc1ccccc12]
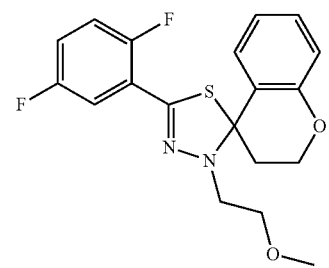 [SMILES: COCCN1N=C(c2cc(F)ccc2F)SC12CCOc1ccccc12]
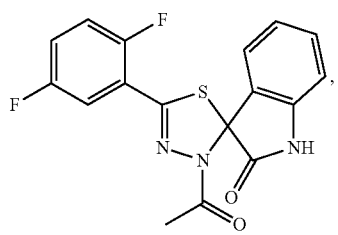
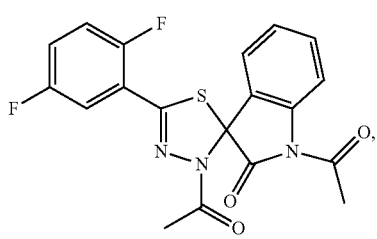 [SMILES: CC(=O)N1C(=O)C2(SC(c3cc(F)ccc3F)=NN2C(C)=O)c2ccccc21]
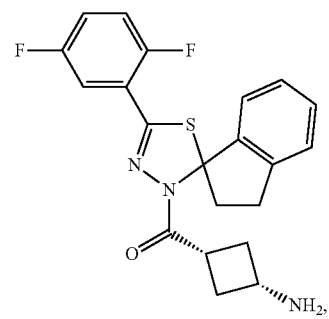 [SMILES: N[C@H]1C[C@@H](C(=O)N2N=C(c3cc(F)ccc3F)SC23CCc2ccccc23)C1]
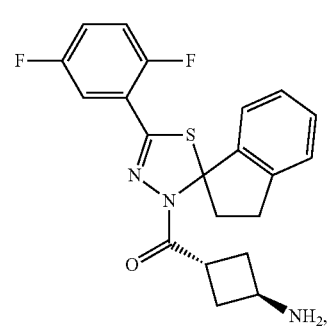 [SMILES: N[C@H]1C[C@H](C(=O)N2N=C(c3cc(F)ccc3F)SC23CCc2ccccc23)C1]
218
-continued
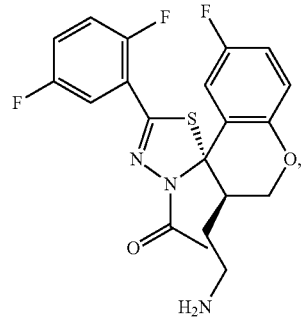
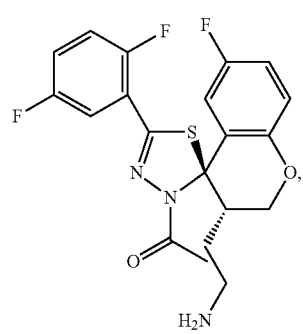 [SMILES: CC(=O)N1N=C(c2cc(F)ccc2F)S[C@]12c1cc(F)ccc1OC[C@@H]2CCN]
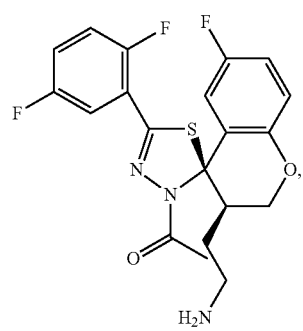 [SMILES: CC(=O)N1N=C(c2cc(F)ccc2F)S[C@]12c1cc(F)ccc1OC[C@H]2CCN]
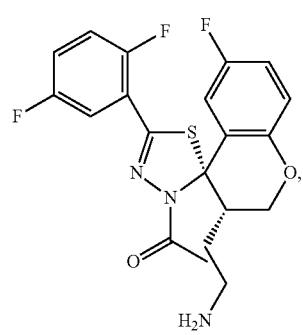 [SMILES: CC(=O)N1N=C(c2cc(F)ccc2F)S[C@@]12c1cc(F)ccc1OC[C@@H]2CCN]
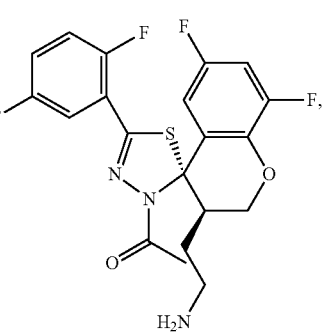

| 219 -continued | 220 -continued |
|---|---|
| 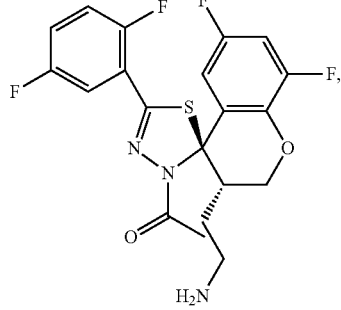 | 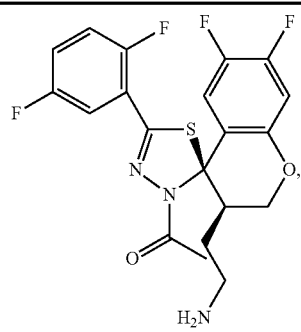 |
| 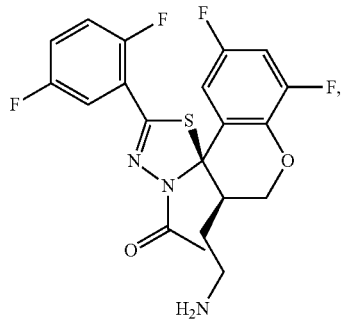 [SMILES: CC(=O)N1N=C(c2cc(F)ccc2F)S[C@]12c1cc(F)cc(F)c1OC[C@H]2CCN] | 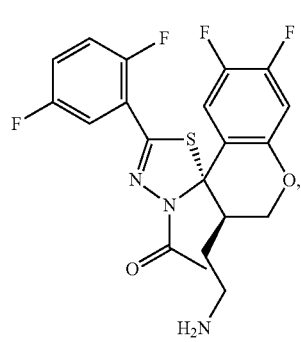 |
| 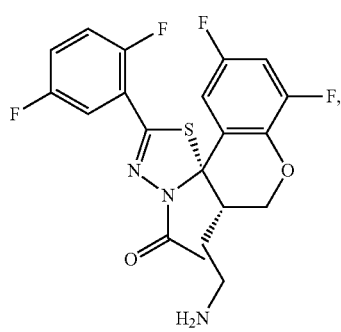 [SMILES: CC(=O)N1N=C(c2cc(F)ccc2F)S[C@@]12c1cc(F)cc(F)c1OC[C@@H]2CCN] | 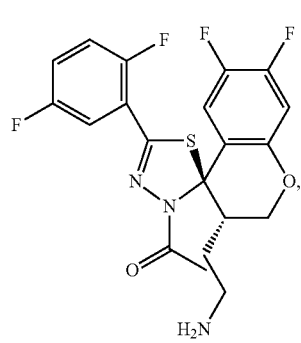 [SMILES: CC(=O)N1N=C(c2cc(F)ccc2F)S[C@]12c1cc(F)c(F)cc1OC[C@@H]2CCN] |
| 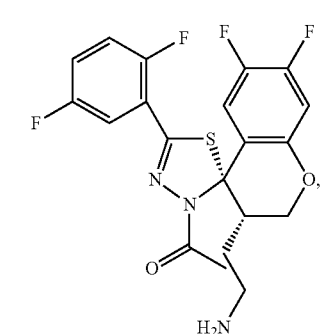 | 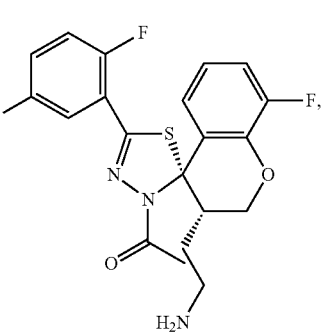 |
| | 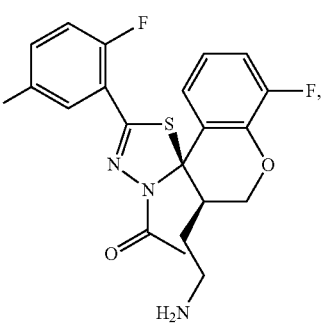 |

| 221 -continued | 222 -continued |
|---|---|
| 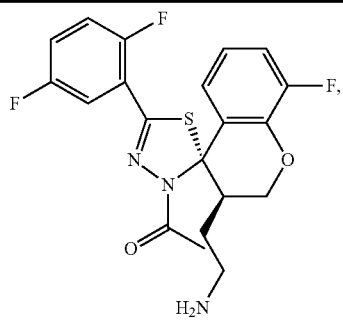 | 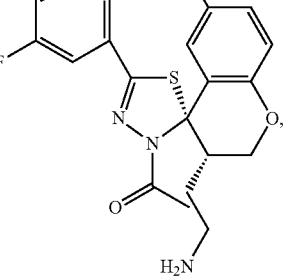 |
| 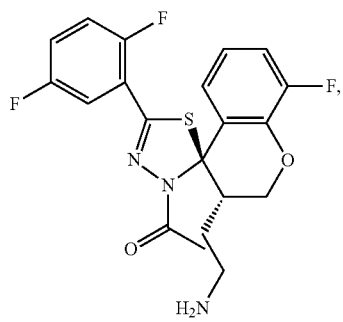 [SMILES: CC(=O)N1N=C(c2cc(F)ccc2F)S[C@]12c1cccc(F)c1OC[C@@H]2CCN] | 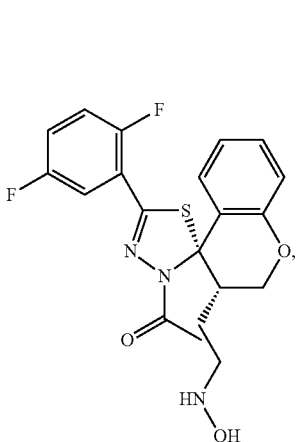 |
| 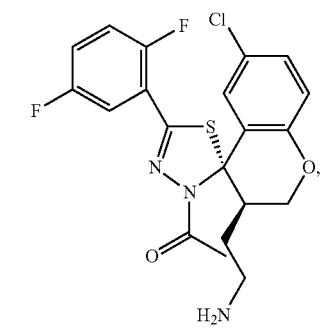 [SMILES: CC(=O)N1N=C(c2cc(F)ccc2F)S[C@@]12c1cc(Cl)ccc1OC[C@H]2CCN] | 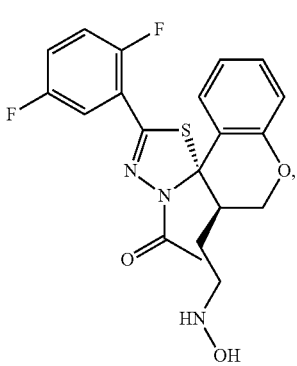 |
| 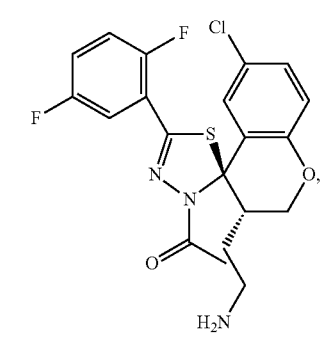 [SMILES: CC(=O)N1N=C(c2cc(F)ccc2F)S[C@]12c1cc(Cl)ccc1OC[C@@H]2CCN] | 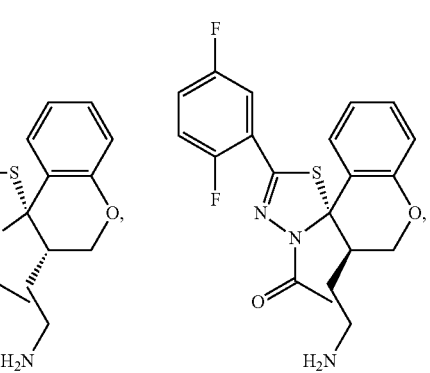 |
| 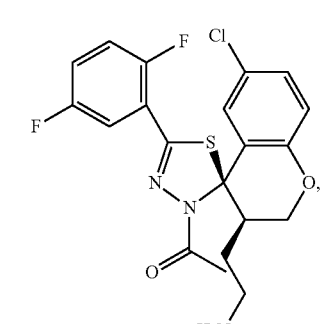 | |

223
-continued
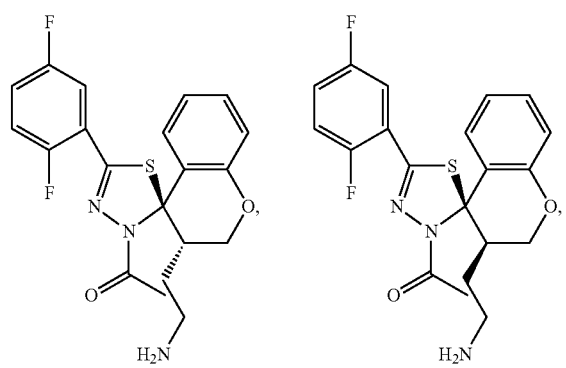 [SMILES: CC(=O)N1N=C(c2cc(F)ccc2F)S[C@]12c1ccccc1OC[C@@H]2CCN ; CC(=O)N1N=C(c2cc(F)ccc2F)S[C@]12c1ccccc1OC[C@H]2CCN]
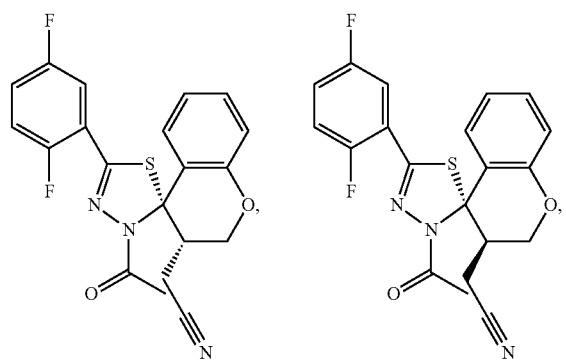 [SMILES: CC(=O)N1N=C(c2cc(F)ccc2F)S[C@@]12c1ccccc1OC[C@@H]2CC#N ; CC(=O)N1N=C(c2cc(F)ccc2F)S[C@@]12c1ccccc1OC[C@H]2CC#N]
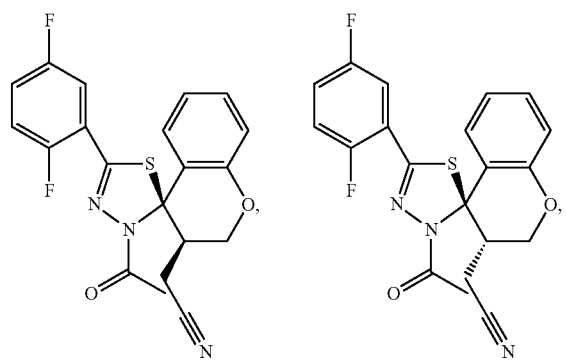 [SMILES: CC(=O)N1N=C(c2cc(F)ccc2F)S[C@]12c1ccccc1OC[C@H]2CC#N ; CC(=O)N1N=C(c2cc(F)ccc2F)S[C@]12c1ccccc1OC[C@@H]2CC#N]
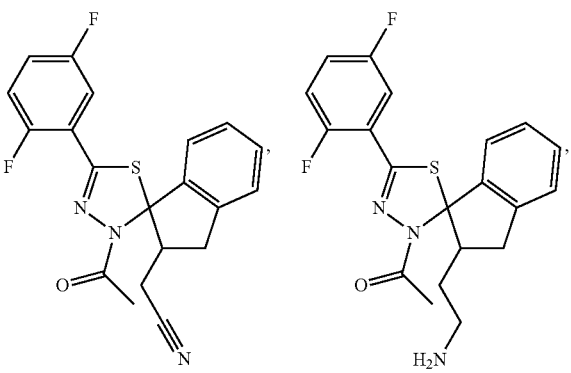
224
-continued
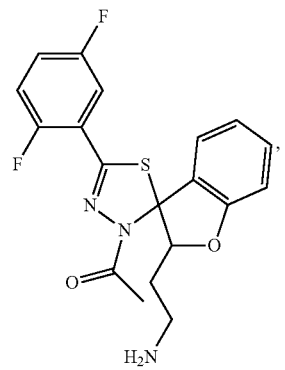 [SMILES: CC(=O)N1N=C(c2cc(F)ccc2F)SC12c1ccccc1OC2CCN]
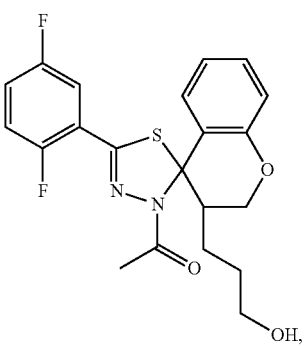 [SMILES: CC(=O)N1N=C(c2cc(F)ccc2F)SC12c1ccccc1OCC2CCCO]
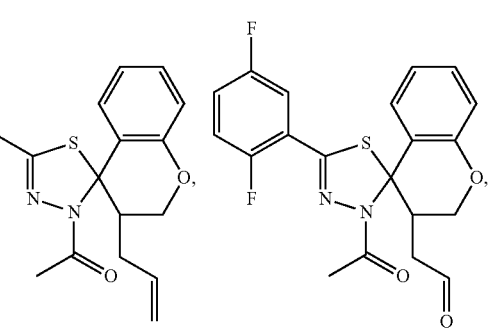
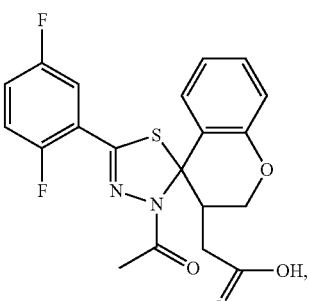

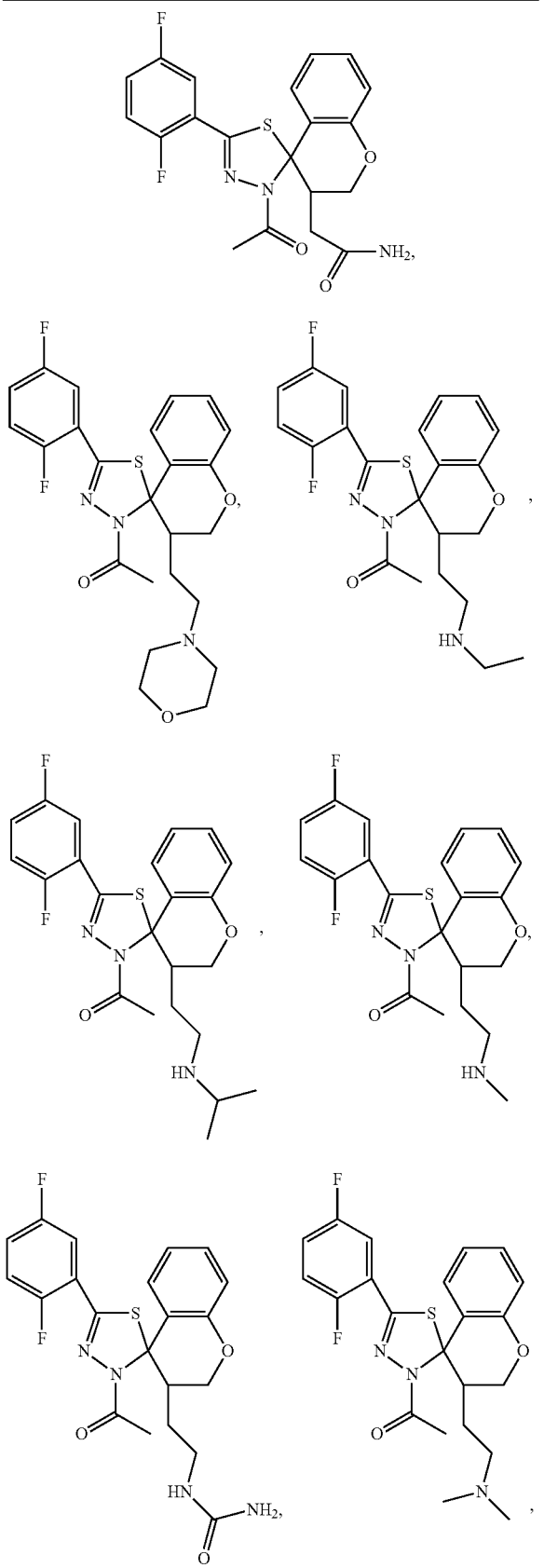
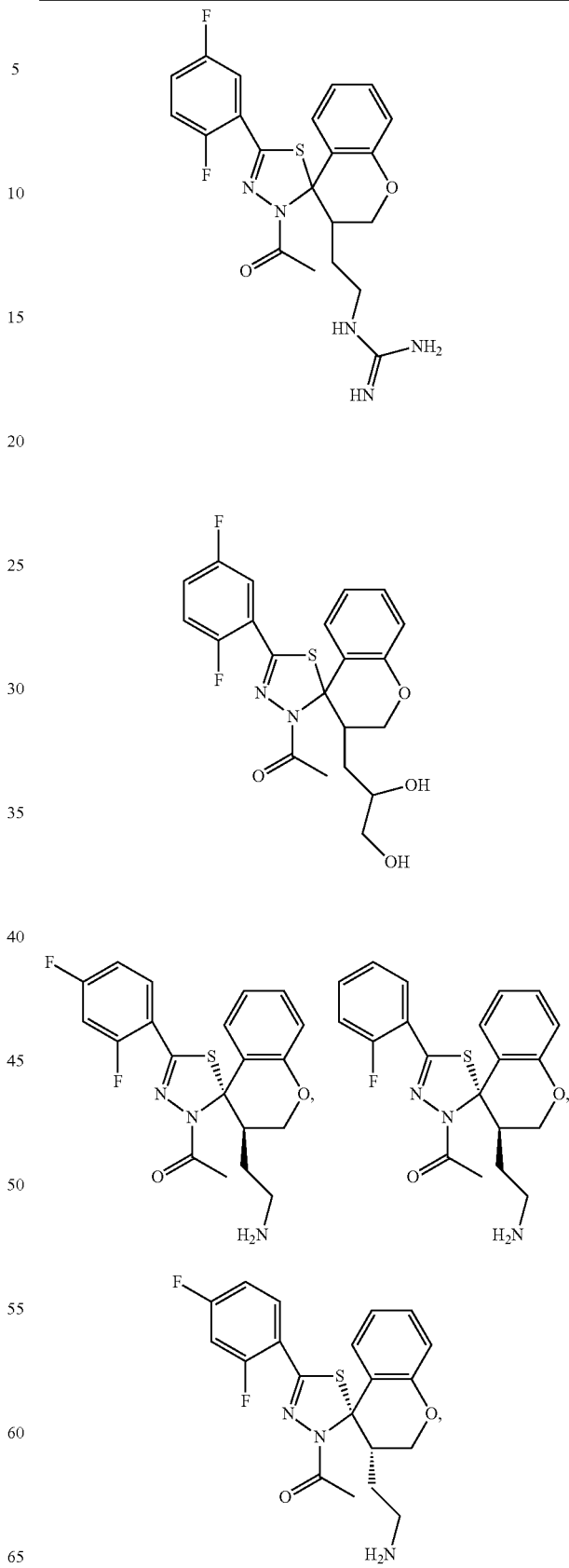

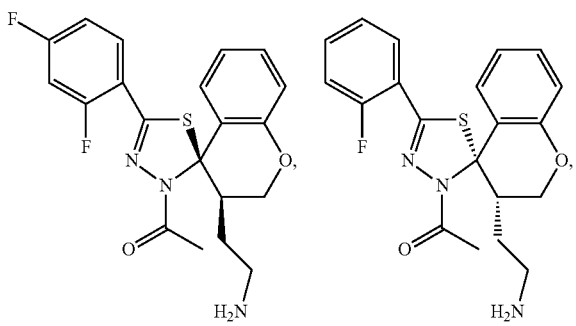
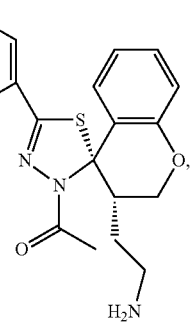
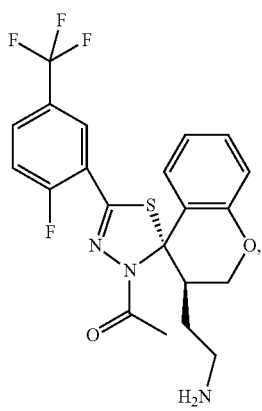
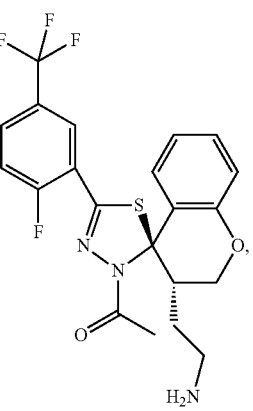
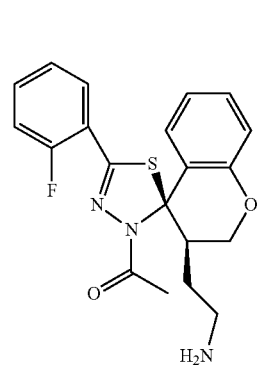
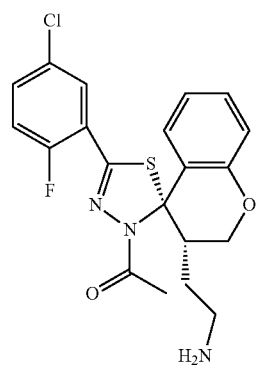
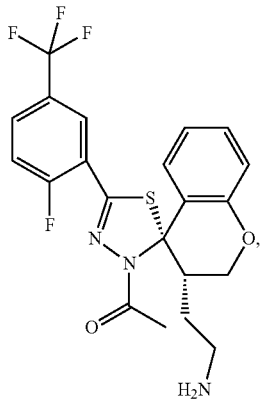
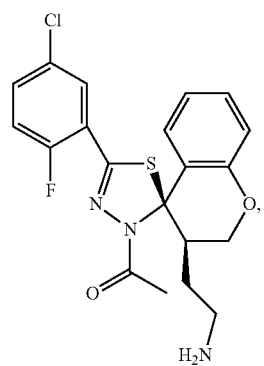
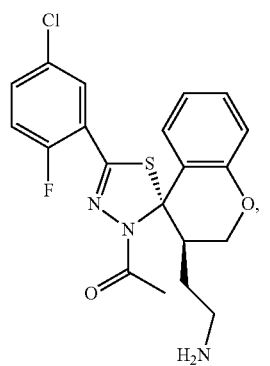
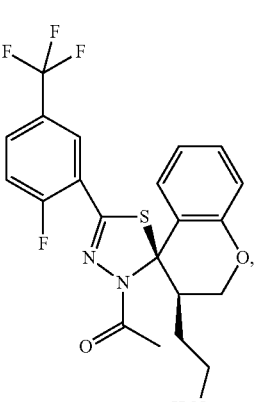
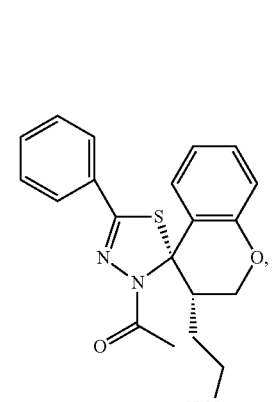
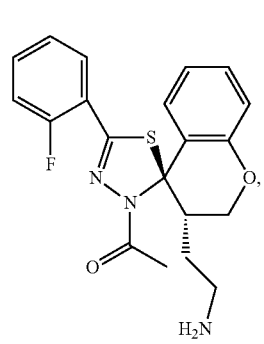
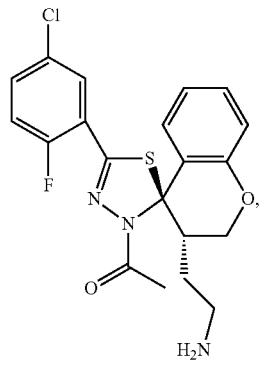
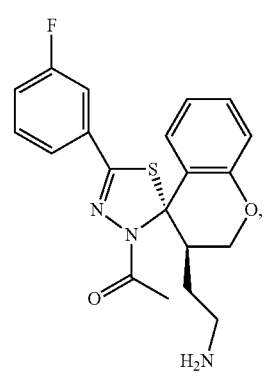

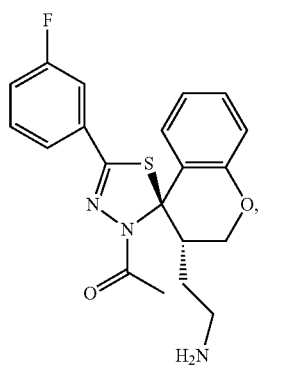 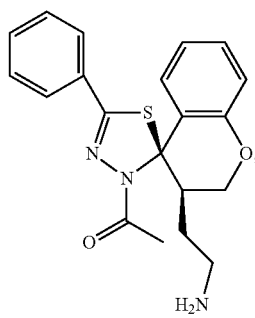 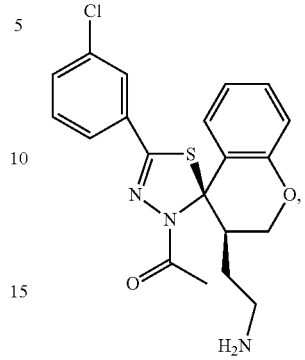 [SMILES: CC(=O)N1N=C(c2cc(F)cc(F)c2)S[C@]12c1ccccc1OC[C@H]2CCN] 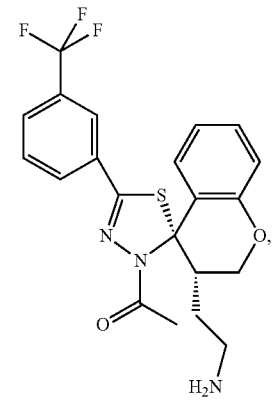
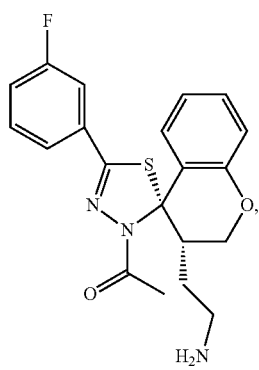 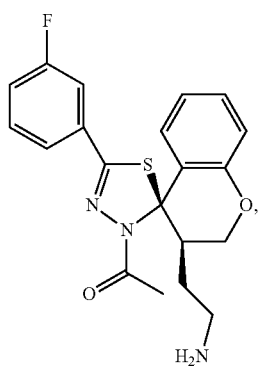 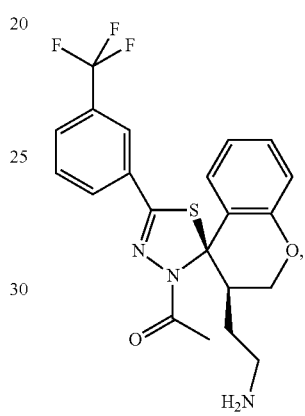 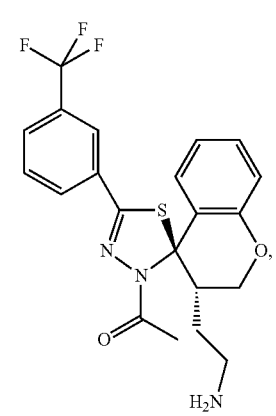
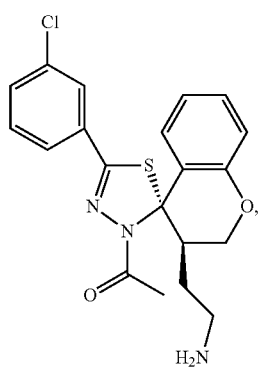 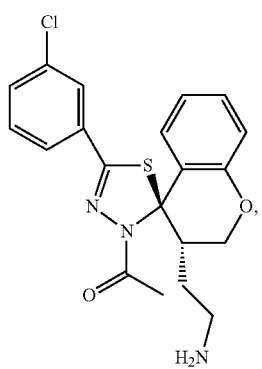 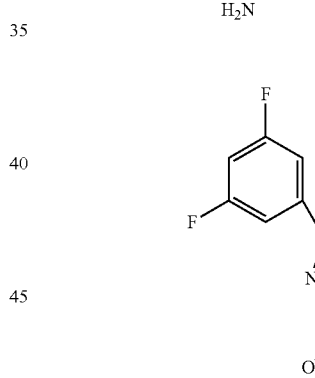
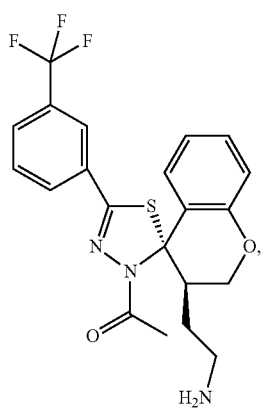 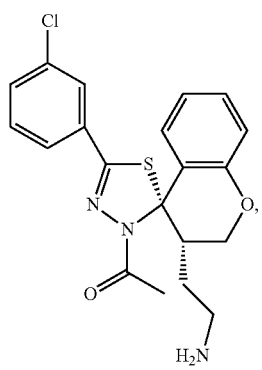 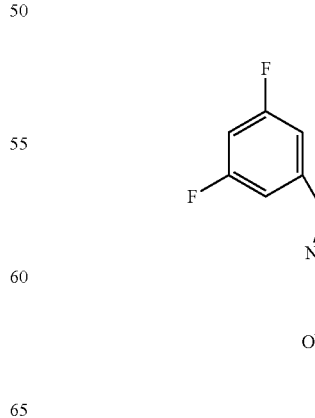

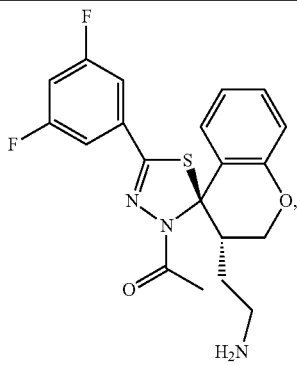
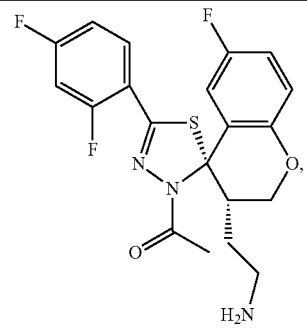
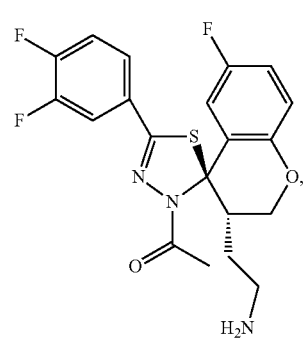 [SMILES: CC(=O)N1N=C(c2ccc(F)c(F)c2)S[C@]12c1cc(F)ccc1OC[C@@H]2CCN]
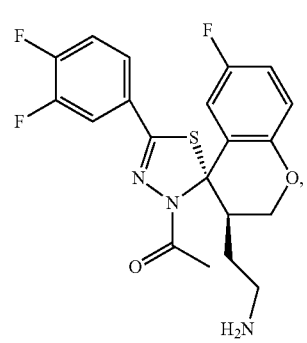 [SMILES: CC(=O)N1N=C(c2ccc(F)c(F)c2)S[C@@]12c1cc(F)ccc1OC[C@H]2CCN]

233
-continued
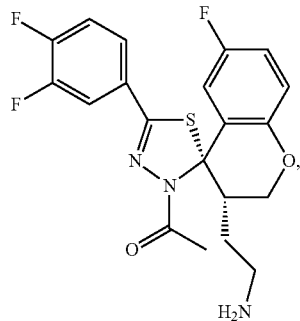 [SMILES: CC(=O)N1N=C(c2ccc(F)c(F)c2)S[C@@]12c1cc(F)ccc1OC[C@@H]2CCN]
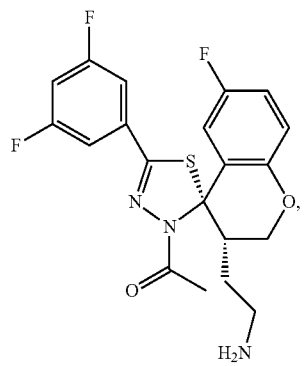 [SMILES: CC(=O)N1N=C(c2cc(F)cc(F)c2)S[C@@]12c1cc(F)ccc1OC[C@@H]2CCN]
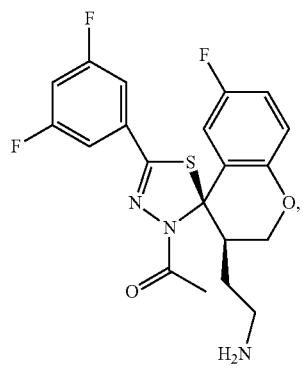 [SMILES: CC(=O)N1N=C(c2cc(F)cc(F)c2)S[C@]12c1cc(F)ccc1OC[C@H]2CCN]
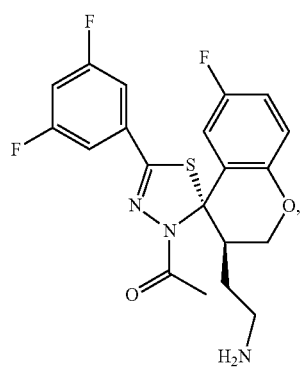 [SMILES: CC(=O)N1N=C(c2cc(F)cc(F)c2)S[C@@]12c1cc(F)ccc1OC[C@H]2CCN]
234
-continued
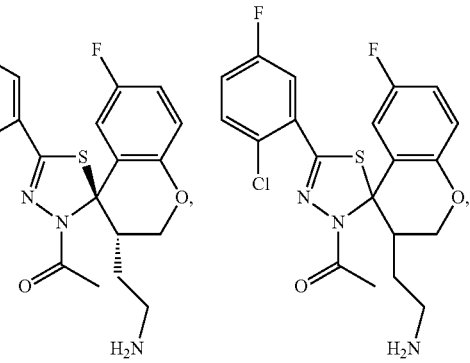
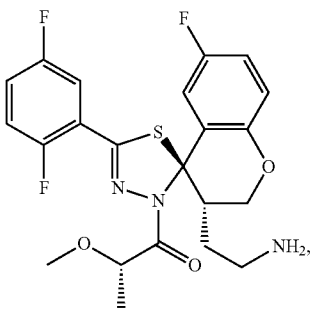 [SMILES: CO[C@@H](C)C(=O)N1N=C(c2cc(F)ccc2F)S[C@]12c1cc(F)ccc1OC[C@@H]2CCN]
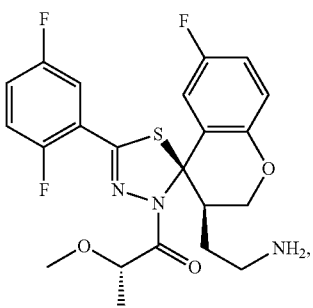
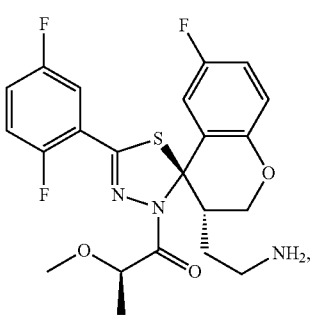 [SMILES: CO[C@H](C)C(=O)N1N=C(c2cc(F)ccc2F)S[C@]12c1cc(F)ccc1OC[C@@H]2CCN]
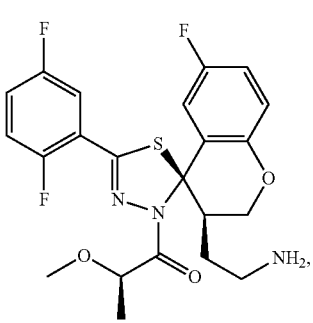 [SMILES: CO[C@H](C)C(=O)N1N=C(c2cc(F)ccc2F)S[C@]12c1cc(F)ccc1OC[C@H]2CCN]

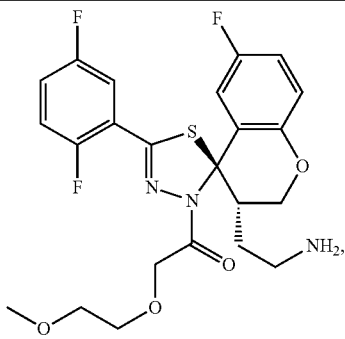
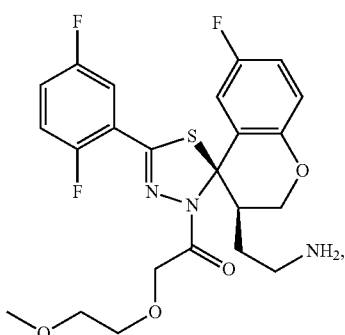
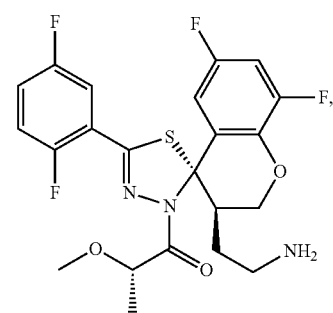 [SMILES: CO[C@@H](C)C(=O)N1N=C(c2cc(F)ccc2F)S[C@@]12c1cc(F)cc(F)c1OC[C@H]2CCN]
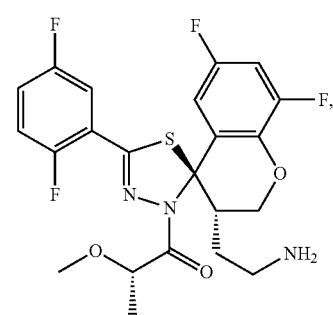 [SMILES: CO[C@@H](C)C(=O)N1N=C(c2cc(F)ccc2F)S[C@]12c1cc(F)cc(F)c1OC[C@@H]2CCN]
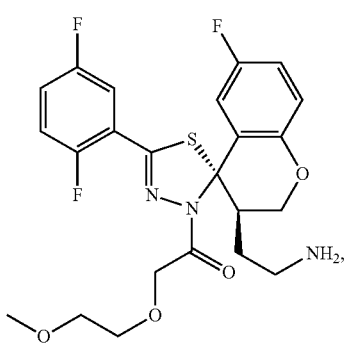 [SMILES: COCCOCC(=O)N1N=C(c2cc(F)ccc2F)S[C@@]12c1cc(F)ccc1OC[C@H]2CCN]
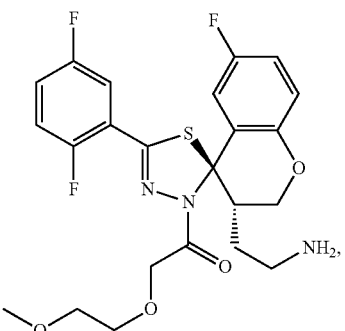
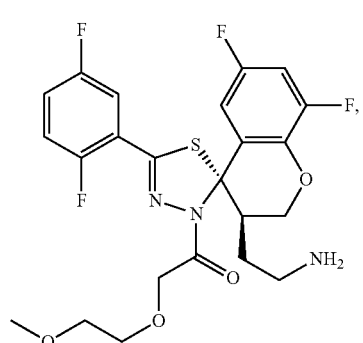
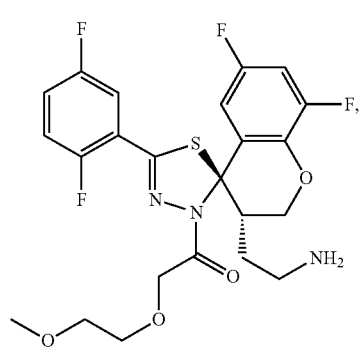 [SMILES: COCCOCC(=O)N1N=C(c2cc(F)ccc2F)S[C@]12c1cc(F)cc(F)c1OC[C@@H]2CCN]
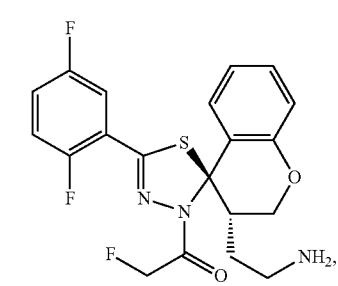 [SMILES: NCC[C@H]1COc2ccccc2[C@]12SC(c1cc(F)ccc1F)=NN2C(=O)CF]
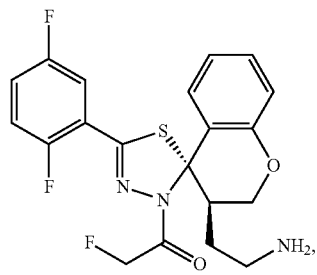 [SMILES: NCC[C@@H]1COc2ccccc2[C@@]12SC(c1cc(F)ccc1F)=NN2C(=O)CF]

237
-continued
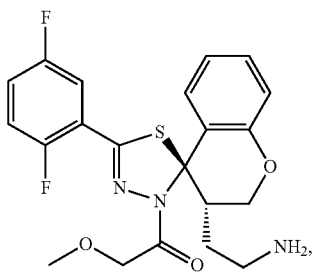 [SMILES: COCC(=O)N1N=C(c2cc(F)ccc2F)S[C@]12c1ccccc1OC[C@@H]2CCN]
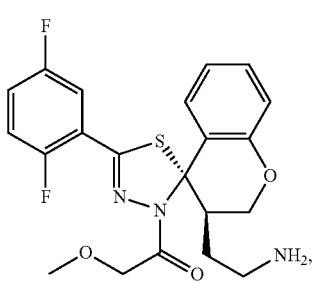 [SMILES: COCC(=O)N1N=C(c2cc(F)ccc2F)S[C@@]12c1ccccc1OC[C@H]2CCN]
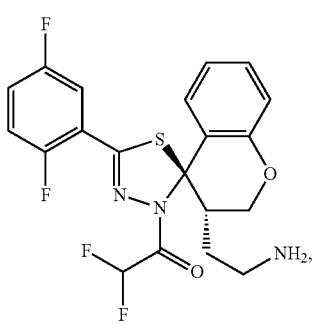 [SMILES: NCC[C@H]1COc2ccccc2[C@]12SC(c1cc(F)ccc1F)=NN2C(=O)C(F)F]
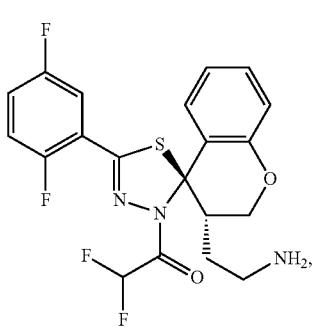 [SMILES: NCC[C@H]1COc2ccccc2[C@]12SC(c1cc(F)ccc1F)=NN2C(=O)C(F)F]
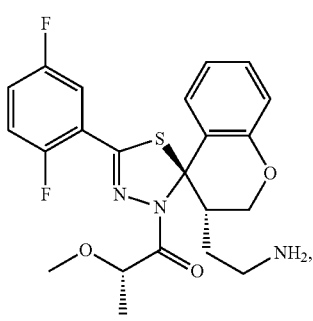 [SMILES: CO[C@@H](C)C(=O)N1N=C(c2cc(F)ccc2F)S[C@]12c1ccccc1OC[C@@H]2CCN]
238
-continued
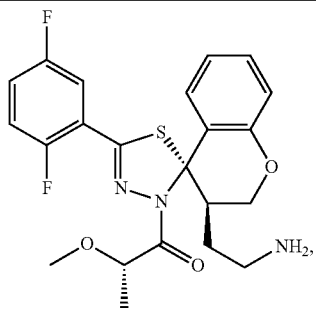
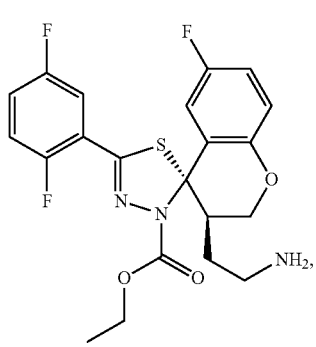 [SMILES: CCOC(=O)N1N=C(c2cc(F)ccc2F)S[C@@]12c1cc(F)ccc1OC[C@H]2CCN]
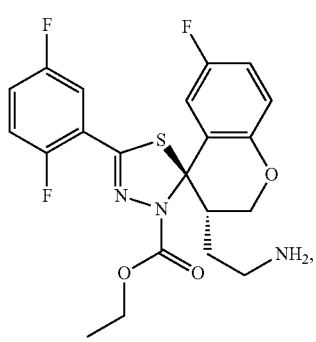 [SMILES: CCOC(=O)N1N=C(c2cc(F)ccc2F)S[C@]12c1cc(F)ccc1OC[C@@H]2CCN]
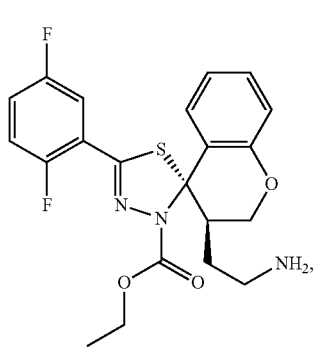 [SMILES: CCOC(=O)N1N=C(c2cc(F)ccc2F)S[C@@]12c1ccccc1OC[C@H]2CCN]
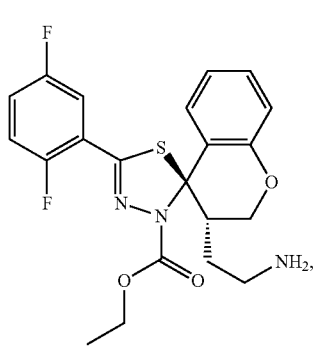 [SMILES: CCOC(=O)N1N=C(c2cc(F)ccc2F)S[C@]12c1ccccc1OC[C@@H]2CCN]

239
-continued
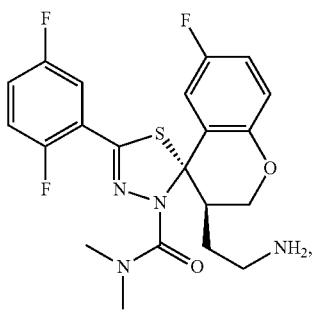 [SMILES: CN(C)C(=O)N1N=C(c2cc(F)ccc2F)S[C@@]12c1cc(F)ccc1OC[C@H]2CCN]
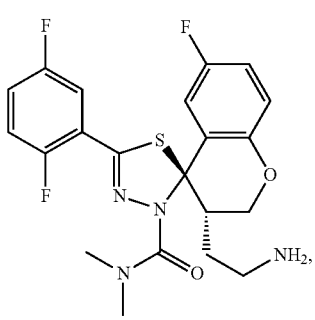 [SMILES: CN(C)C(=O)N1N=C(c2cc(F)ccc2F)S[C@]12c1cc(F)ccc1OC[C@@H]2CCN]
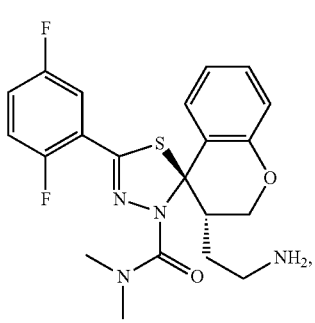 [SMILES: CN(C)C(=O)N1N=C(c2cc(F)ccc2F)S[C@]12c1ccccc1OC[C@@H]2CCN]
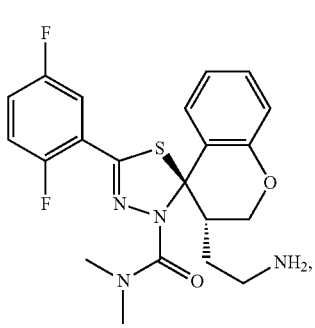 [SMILES: CN(C)C(=O)N1N=C(c2cc(F)ccc2F)S[C@]12c1ccccc1OC[C@@H]2CCN]
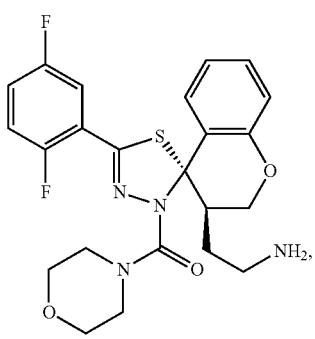 [SMILES: NCC[C@@H]1COc2ccccc2[C@@]12SC(c1cc(F)ccc1F)=NN2C(=O)N1CCOCC1]
240
-continued
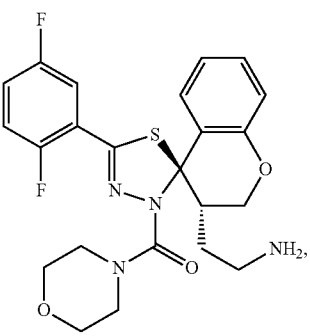 [SMILES: NCC[C@H]1COc2ccccc2[C@]12SC(c1cc(F)ccc1F)=NN2C(=O)N1CCOCC1]
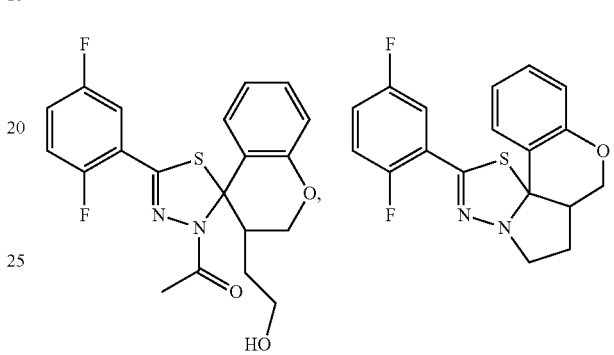
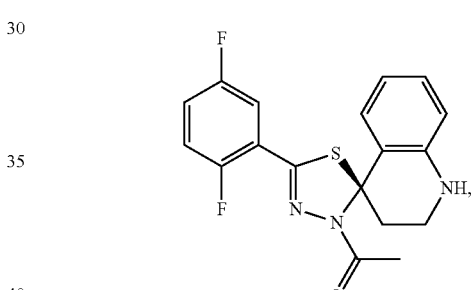
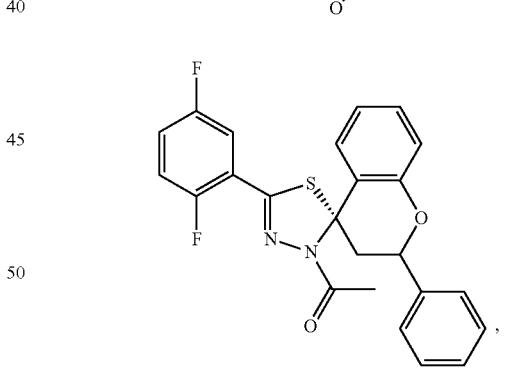
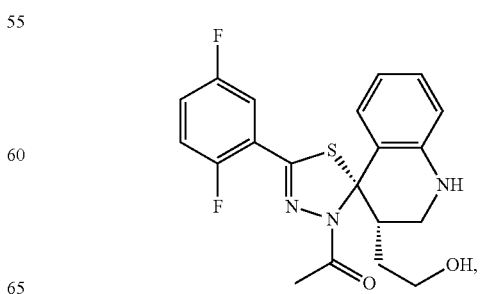

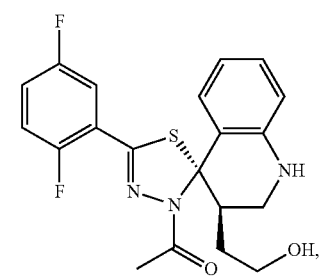 [SMILES: CC(=O)N1N=C(c2cc(F)ccc2F)S[C@@]12c1ccccc1NC[C@H]2CCO]
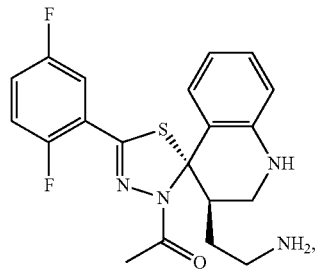
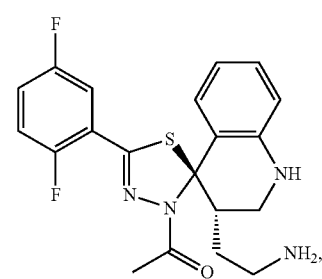 [SMILES: CC(=O)N1N=C(c2cc(F)ccc2F)S[C@]12c1ccccc1NC[C@@H]2CCN]
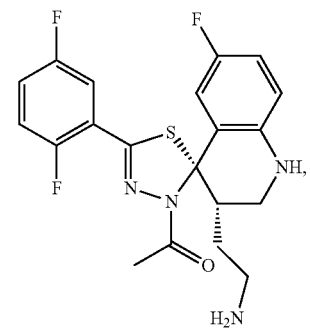
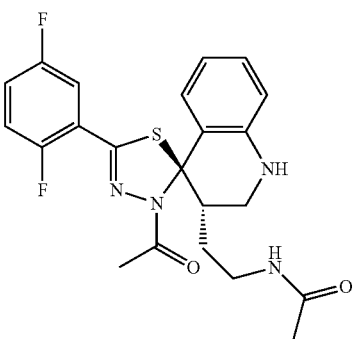 [SMILES: CC(=O)NCC[C@H]1CNc2ccccc2[C@]12SC(c1cc(F)ccc1F)=NN2C(C)=O]
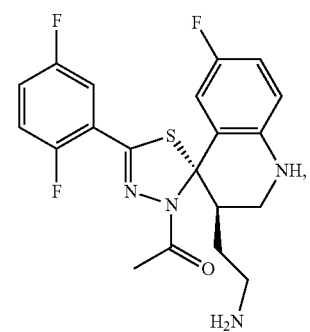
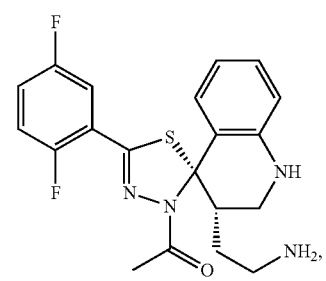 [SMILES: CC(=O)N1N=C(c2cc(F)ccc2F)S[C@@]12c1ccccc1NC[C@@H]2CCN]
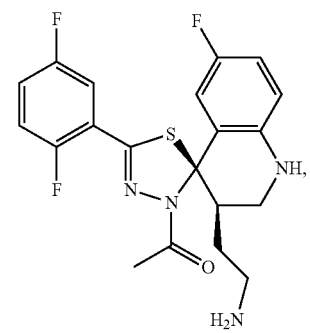
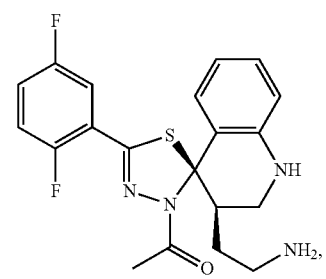 [SMILES: CC(=O)N1N=C(c2cc(F)ccc2F)S[C@]12c1ccccc1NC[C@H]2CCN]
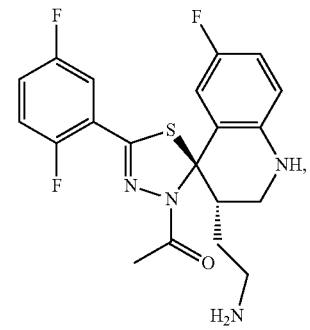 [SMILES: CC(=O)N1N=C(c2cc(F)ccc2F)S[C@]12c1cc(F)ccc1NC[C@@H]2CCN]

-continued

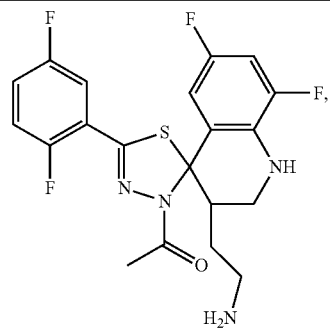

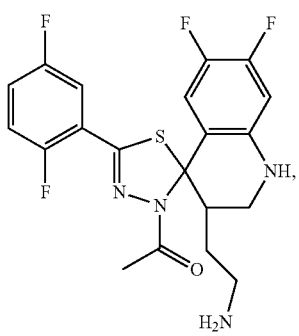 [SMILES: CC(=O)N1N=C(c2cc(F)ccc2F)SC12c1cc(F)c(F)cc1NCC2CCN]

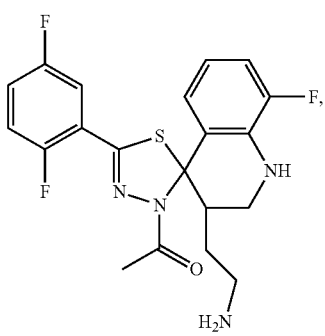 [SMILES: CC(=O)N1N=C(c2cc(F)ccc2F)SC12c1cccc(F)c1NCC2CCN]

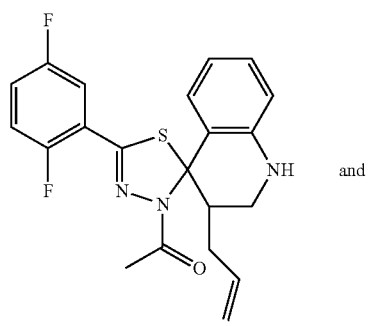 [SMILES: C=CCC1CNc2ccccc2C12SC(c1cc(F)ccc1F)=NN2C(C)=O ; "and"] and

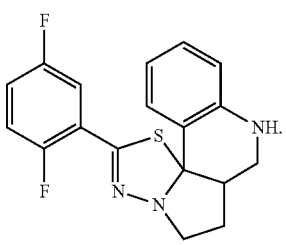 [SMILES: Fc1ccc(F)c(C2=NN3CCC4CNc5ccccc5C43S2)c1]

In other embodiments, the present invention provides processes for producing the compounds described in each of the various embodiments above, pharmaceutical formulations or compositions comprising one or more of such compounds, and methods of treating or preventing one or more conditions or diseases associated with KSP kinesin activity such as those discussed in detail below.

As used above, and throughout the specification, the following terms, unless otherwise indicated, shall be understood to have the following meanings:

"Subject" includes both mammals and non-mammalian animals.

"Mammal" includes humans and other mammalian animals.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents as described herein. Non-limiting examples of suitable alkyl groups include methyl, ethyl, n-propyl, isopropyl and t-butyl. "Alkyl" includes "Alkylene" which refers to a difunctional group obtained by removal of a hydrogen atom from an alkyl group that is defined above. Non-limiting examples of alkylene include methylene ($-CH_2-$), ethylene ($-CH_2CH_2-$) and propylene ($-C_3H_6-$); which may be linear or branched.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, (and S(O), S(O)$_2$, etc.) and N. Non-limiting examples include ethers, thioethers, amines, 2-aminoethyl, 2-dimethylaminoethyl, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain.

"Lower alkenyl" means about 2 to about 6 carbon atoms in the chain which may be straight or branched. "Alkenyl" may be unsubstituted or optionally substituted by one or more substituents as described herein. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents as described herein.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl, is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to a ring system (such as an aromatic, heteroaromatic, saturated or partially unsaturated alicyclic or heterocyclic ring systems) which, for example, replaces an available hydrogen on a carbon atom or a heteroatom of the ring system. "Ring system substituents" may be referred to as such, or may be referred to as a variable or specific functional group or groups that are attached to a ring system. For example, when $R^2$ in Formula (I) is $—C(O)R^{17}$ and $R^{17}$ is a substituted heterocycloalkyl, the substituent attached to the heterocycloalkyl is a ring system substituent. If two or more ring system substituents are present on a given ring, such multiple substituents may be attached to the same or different available ring carbon or heteroatom. Ring system substituents may be the same or different, and are as described herein. Other non-limiting examples of ring system substituents include alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $—C(=N—CN)—NH_2$, $—C(=NH)—NH_2$, $—C(=NH)—NH(alkyl)$, $Y_1Y_2N—$, $Y_1Y_2N—$ alkyl-, $Y_1Y_2NC(O)—$, $Y_1Y_2NSO_2—$ and $—SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, $—C(CH_3)_2—$ and the like which form moieties such as, for example:

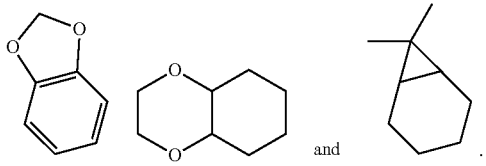

"Heteroarylalkyl" (or "heteroaryl-alkyl-") means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" (or "heterocycloalkyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, azetidinyl, lactam, lactone, and the like.

"Heterocyclyl" also includes rings wherein =O replaces two available hydrogens on the same carbon atom (i.e., heterocyclyl includes rings having a carbonyl group in the ring). An example of such moiety is pyrrolidone:

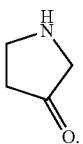

"Heterocyclylalkyl" (or "heterocycloalkylalkyl" or "heterocycloalkyl-alkyl-") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" (or "heterocycloalkenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

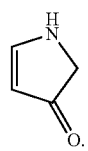

"Heterocycleriylalkyl" (or "heterocycloalkenylalkyl" or "heterococloalkenyl-alkyl-") means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

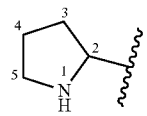

there is no —OH attached directly to carbons marked 2 and 5.
It should also be noted that tautomeric forms such as, for example, the moieties:

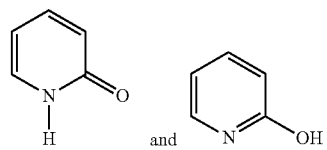 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1- naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkylsilyl" means an alkyl-Si- group in which alkyl is as previously defined and the point of attachment to the parent moiety is on Si. Preferred alkylsilyls contain lower alkyl. An example of an alkylsilyl group is trimethylsilyl (—Si(CH$_3$)$_3$).

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure", it is meant a compound that is sufficiently robust to survive isolation to a useful degree of purity from a reaction mixture, and formulation into an efficacious therapeutic agent.

The term "optionally substituted" means optional substitution with the specified or implied groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R$^2$, etc.) occurs more than one time in any constituent or in any one of The invention, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N- or di-N,N—$(C_1-C_6)$alkylaminoalkyl, —$C(Y^4)Y^5$ wherein $Y^4$ is H or methyl and $Y^5$ is mono-N- or di-N,N-$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H2O.

One or more compounds of the invention may optionally be converted to a solvate. Preparation of solvates is generally known. Thus, for example, M. Caira et al, *J. Pharmaceutical Sci.*, 93(3) 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of any one of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the The invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, federates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl of al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the compounds of the invention include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of The invention, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

PREPARATIVE EXAMPLES

Generally, the compounds of the invention can be prepared by a variety of methods well known to those skilled in the art, for example, by the methods as outlined in the general scheme below and in the examples that follow. The examples should not be construed to limit the scope of the disclosure. Alternative mechanistic pathways and analogous structures will be apparent to those skilled in the art.

$EC_{50}$ values for the exemplified compounds appearing in the Table below are indicated according to the following ranges:

A—≤500 nM
B—>500 nM
C—>500 nM to ≤1000 nM
D—>1000 nM

The following abbreviations are used in the procedures and schemes:

ACN Acetonitrile
AcOH Acetic acid
Aq Aqueous
BOC tert-Butoxycarbonyl
BOC-ON [2-(tert-butoxycarbonyloxyimino)-2-phenylacetonitrile]
BOC$_2$O BOC Anhydride
C degrees Celsius
Cpd Compound
CBZCl Benzyl chloroformate
DCM Dichloromethane
DEAD Diethyl azodicarboxylate
DIAD Diisopropylazodicarboxylate
DIEA Diisopropylethylamine
DMA N,N-Dimethylacetamide
DMAP 4-N,N-Dimethylaminopyridine
DME Dimethoxyethane
DMF Dimethylformamide
DMSO Dimethyl sulfoxide
EDCl 1-(3-Dimethylaminopropyl)-3-ethylcarbodiimide hydrochloride
EI Electron ionization
Eq Equivalents
EtOAc Ethyl acetate
EtOH Ethanol
g grams
h. hours
$^1$H proton
HATU N,N,N',N'-Tetramethyl-O-(7-Azabenzotriazol-1-yl) Uronium hexafluorophosphate
Hex hexanes
HOBT 1-Hydroxybenzotriazole
HPLC High pressure liquid chromatography
KSP Kinesin spindle protein
LAH Lithium aluminum hydride
LDA Lithium diisopropylamide
LHMDS Lithium hexamethyldisilylamide
M Molar
mmol milimolar
mCPBA meta-Chloroperoxybenzoic acid
Me Methyl
MeCN Acetonitrile
MeOH Methanol
min Minutes
mg Milligrams
MHZ Megahertz
mL Milliliter
MPLC Medium Pressure Liquid Chromatography
NMR Nuclear Magnetic Resonance
MS Mass Spectroscopy
NBS N-Bromosuccinimide
NIS N-Iodosuccinimide
NMM N-Methylmorpholine
NMP 1-methyl-2-pyrrolidone
ON Overnight
PCC Pyridinium Chlorochromate
PTLC Preparative thin layer chromatography
Pyr Pyridine
RT Room temperature
sgc Silica gel 60 chromatography
tBOC tert-Butoxycarbonyl
TEA Triethylamine
TFA Trifluoroacetic acid
THF Tetrahydrofuran TLC Thin layer chromatography
$t_R$ Retention time

EXAMPLES

General Scheme 1:

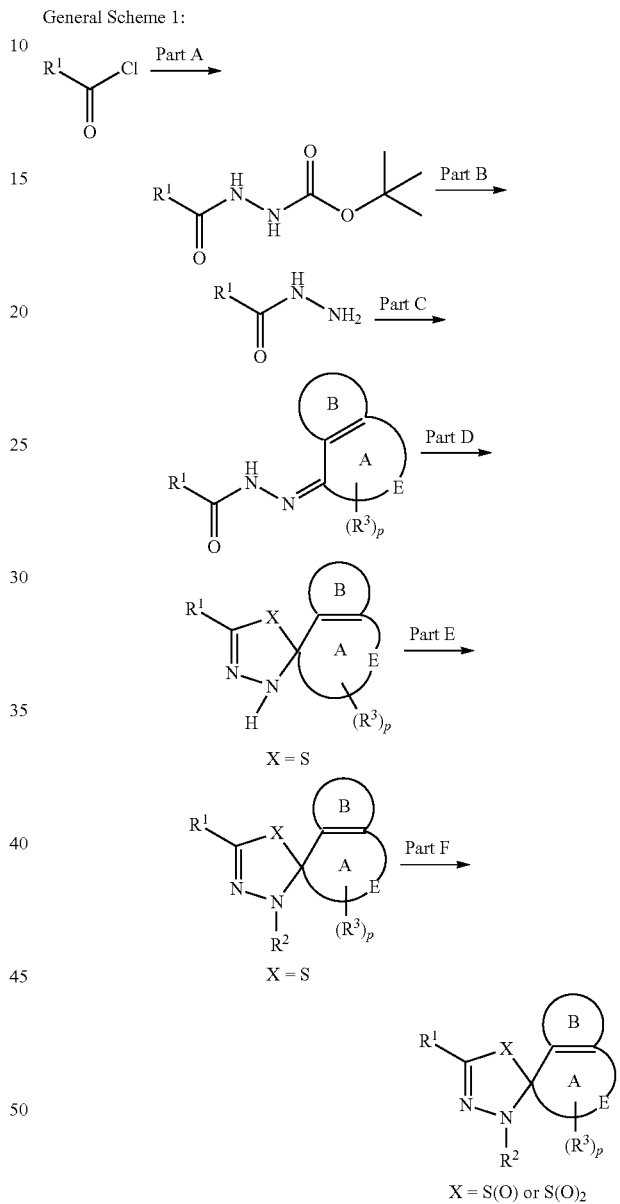

General Scheme 2:

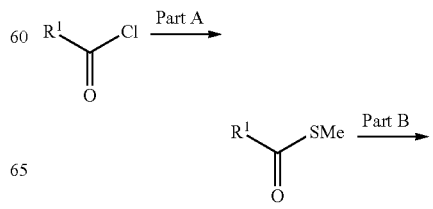

257
-continued

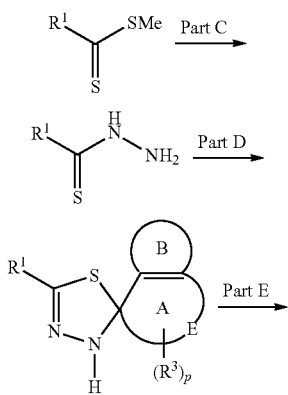

General Scheme 3:

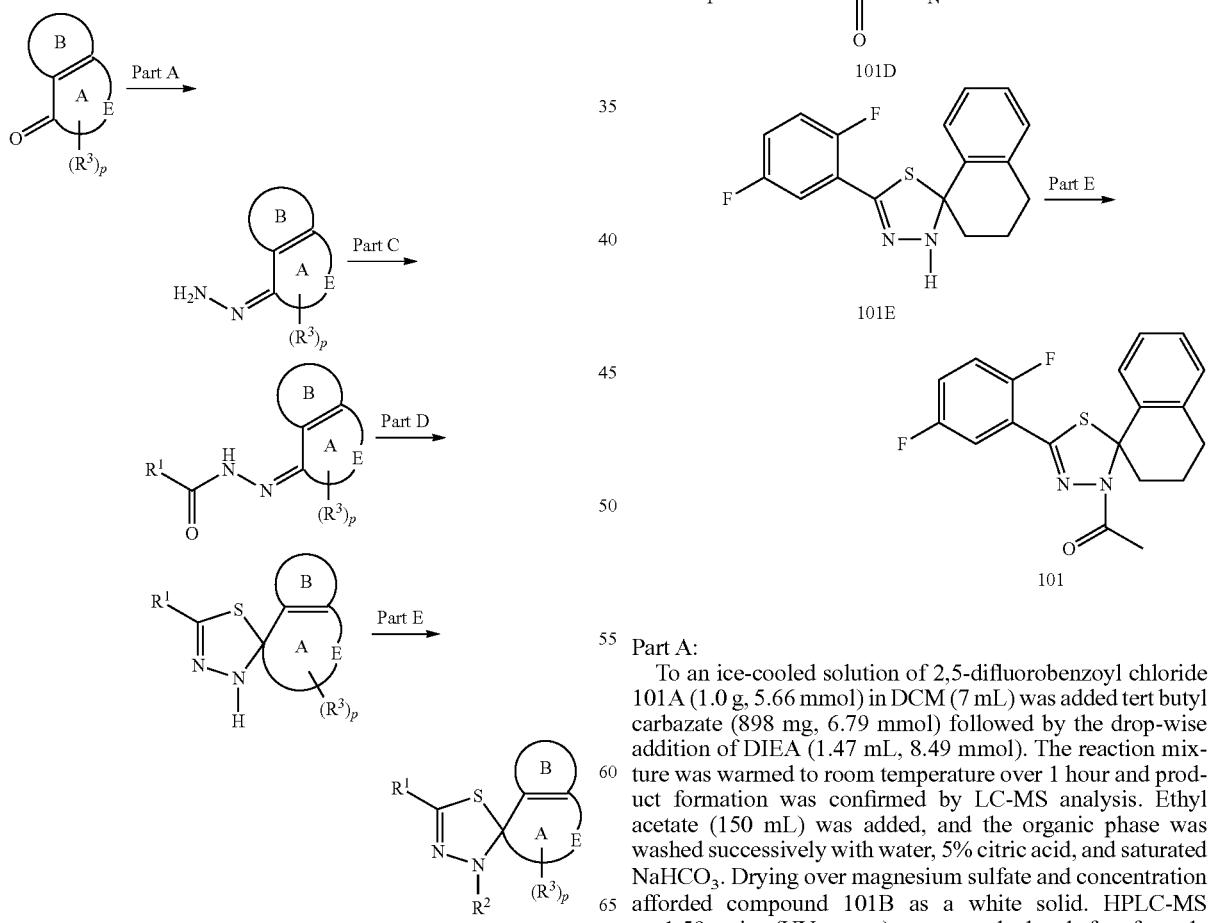

Example 101

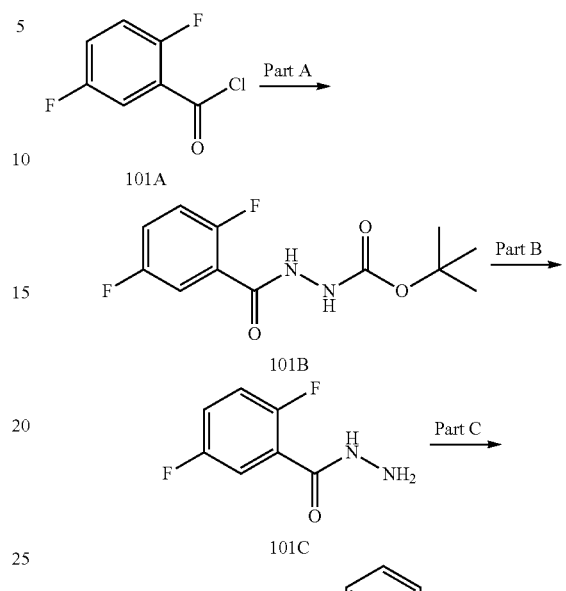

Part A:
To an ice-cooled solution of 2,5-difluorobenzoyl chloride 101A (1.0 g, 5.66 mmol) in DCM (7 mL) was added tert butyl carbazate (898 mg, 6.79 mmol) followed by the drop-wise addition of DIEA (1.47 mL, 8.49 mmol). The reaction mixture was warmed to room temperature over 1 hour and product formation was confirmed by LC-MS analysis. Ethyl acetate (150 mL) was added, and the organic phase was washed successively with water, 5% citric acid, and saturated NaHCO$_3$. Drying over magnesium sulfate and concentration afforded compound 101B as a white solid. HPLC-MS $t_R$=1.59 min (UV$_{254\ nm}$); mass calculated for formula $C_{12}H_{14}F_2N_2O_3$ 272.1, observed LCMS m/z 295.1 (M+Na).

Part B:

To an ice-cooled solution of compound 101B (3.4 g, 12.49 mmol) in DCM (30 mL) was added trifluoroacetic acid (30 mL). The reaction mixture was warmed to room temperature over 2 hours. LC-MS analysis indicated the reaction was complete. The volatiles were removed in vacuo, the residue was re-dissolved in DCM and washed with saturated NaHCO$_3$. Drying over magnesium sulfate and concentration afforded compound 101C as a white solid. HPLC-MS $t_R$=0.64 min (UV$_{254}$ nm); mass calculated for formula C$_7$H$_6$F$_2$N$_2$O 172.1, observed LCMS m/z 173.1 (M+H).

Part C:

To a solution of 2,5-difluorobenzoic acid hydrazide 101C (800 mg, 4.65 mmol) in EtOH (10 mL) was added 1-tetralone (6.05 mmol) and acetic acid (200 µL). The reaction was heated in a microwave at 145° C. for 20 minutes. The reaction mixture was concentrated and then re-dissolved in cold EtOH (4 mL) to yield compound 101D as a white solid after filtration. HPLC-MS $t_R$=1.62 min (UV$_{254\,nm}$); mass calculated for formula C17H14F2N2O 300.1, observed LCMS m/z 301.1 (M+H).

Part D:

To a solution of compound 101D (50 mg, 0.16 mmol) in THF (3 mL) was added P$_2$S$_5$ (100 mg, 0.22 mmol) and the reaction mixture was heated in a microwave at 100° C. for 40 minutes. The reaction mixture was concentrated, diluted with EtOAc and passed through a plug of silica to afford compound 101E as yellow solid which was used in the next step without further purification. HPLC-MS $t_R$=2.09 min (UV$_{254\,nm}$); mass calculated for formula C17H$_{14}$F$_2$N$_2$S 316.08, observed LCMS m/z 317.1 (M+H).

Part E:

A mixture of compound 101E (0.16 mmol), acyl chloride (25 mg, 0.32 mmol) and DIEA (34 µL, 0.19 mmol) in DCM (2 mL) was stirred at room temperature for 16 hours. The reaction mixture was concentrated and purified by HPLC to afford compound 101 as an white solid (30 mg, 52%) HPLC-MS $t_R$=4.84 min (UV$_{254\,nm}$); mass calculated for formula C19H16F2N2OS 358.10, observed LCMS m/z 359.3 (M+H).

The compounds shown in Table 101 were synthesized using this procedure:

TABLE 101

| Cpd ID | Structure | Exact mass | MS m/z (M$^+$ + H) | tR (min) | ED50 (nM) Range |
|---|---|---|---|---|---|
| 101 | 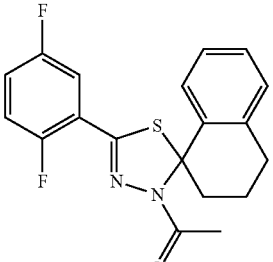 | 358.1 | 359.2 | 4.84 | D |
| 102 | 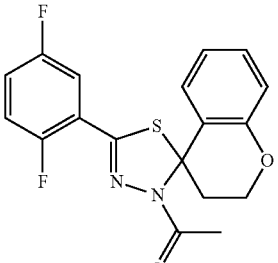 | 360.1 | 361.1 | 6.39 | A |
| 103 | 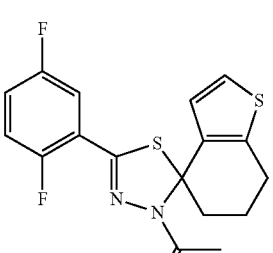 | 364.1 | 365.1 | 4.71 | D |

TABLE 101-continued

| Cpd ID | Structure | Exact mass | MS m/z (M+ + H) | tR (min) | ED50 (nM) Range |
|---|---|---|---|---|---|
| 104 | 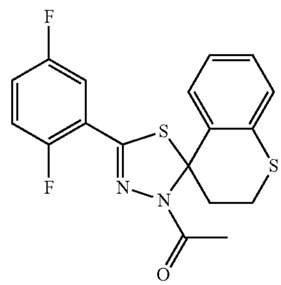 [SMILES: CC(=O)N1N=C(c2cc(F)ccc2F)SC12CCSc1ccccc12] | 376.1 | 377.1 | 4.67 | D |
| 105 | 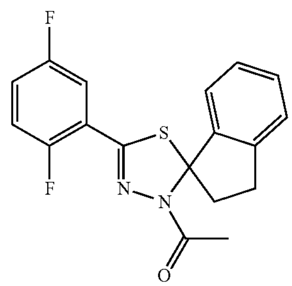 [SMILES: CC(=O)N1N=C(c2cc(F)ccc2F)SC12CCc1ccccc12] | 344.1 | 345.2 | 4.73 | A |
| 106 | 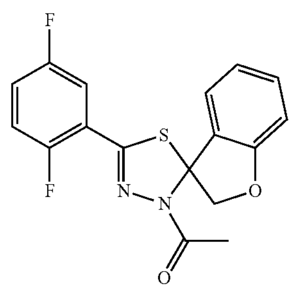 [SMILES: CC(=O)N1N=C(c2cc(F)ccc2F)SC12COc1ccccc12] | 346.1 | 347.0 | 5.00 | A |
| 107 | 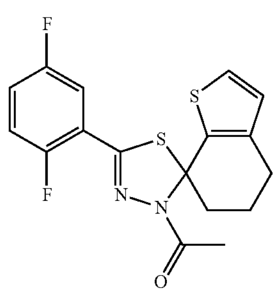 [SMILES: CC(=O)N1N=C(c2cc(F)ccc2F)SC12CCCc1ccsc12] | 364.1 | 365.1 | 4.73 | B |
| 108 | 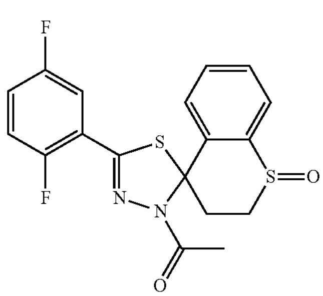 [SMILES: CC(=O)N1N=C(c2cc(F)ccc2F)SC12CCS(=O)c1ccccc12] | 392.1 | 393.1 | 3.61 | D |

TABLE 101-continued

| Cpd ID | Structure | Exact mass | MS m/z (M+ + H) | tR (min) | ED50 (nM) Range |
|---|---|---|---|---|---|
| 109 | 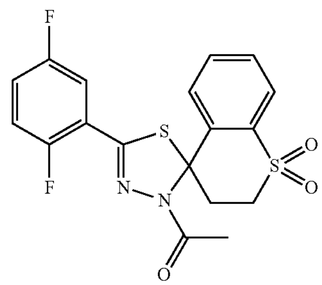 [SMILES: CC(=O)N1N=C(c2cc(F)ccc2F)SC12CCS(=O)(=O)c1ccccc12] | 408.0 | 409.0 | 3.77 | D |
| 110 | 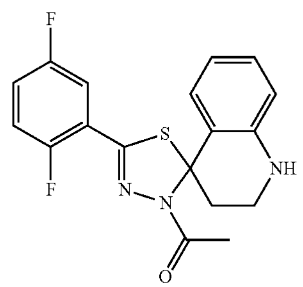 [SMILES: CC(=O)N1N=C(c2cc(F)ccc2F)SC12CCNc1ccccc12] | 359.1 | 360.1 | 4.07 | A |
| 111 | 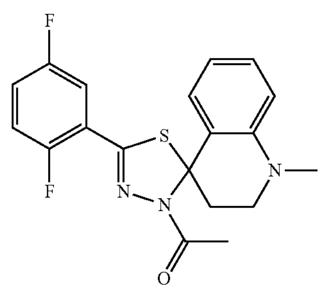 [SMILES: CC(=O)N1N=C(c2cc(F)ccc2F)SC12CCN(C)c1ccccc12] | 373.1 | 374.1 | 4.52 | D |
| 112 | 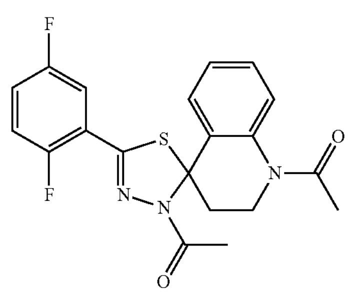 | 401.1 | 402.1 | 4.05 | D |
| 113 | 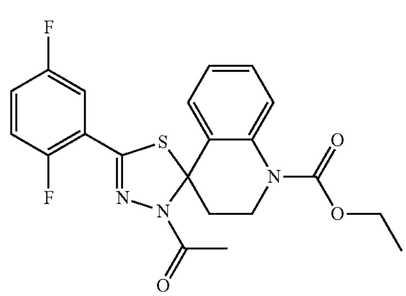 [SMILES: CCOC(=O)N1CCC2(SC(c3cc(F)ccc3F)=NN2C(C)=O)c2ccccc21] | 431.1 | 432.1 | 4.62 | D |

TABLE 101-continued

| Cpd ID | Structure | Exact mass | MS m/z (M+ + H) | tR (min) | ED50 (nM) Range |
|---|---|---|---|---|---|
| 114 | 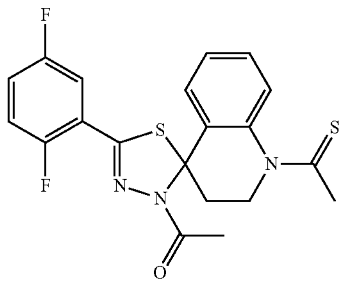 [SMILES: CC(=O)N1N=C(c2cc(F)ccc2F)SC12CCN(C(C)=S)c1ccccc12] | 417.1 | 418.1 | 4.42 | D |
| 115 | 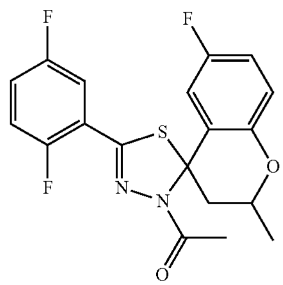 [SMILES: CC(=O)N1N=C(c2cc(F)ccc2F)SC12CC(C)Oc1ccc(F)cc12] | 392.1 | 393.1 | 6.75 | D |
| 116 | 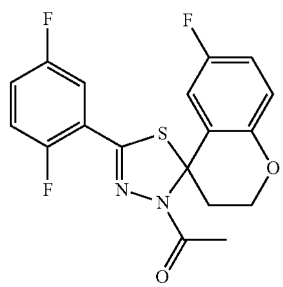 [SMILES: CC(=O)N1N=C(c2cc(F)ccc2F)SC12CCOc1ccc(F)cc12] | 378.1 | 379.1 | 4.44 | A |
| 117 | 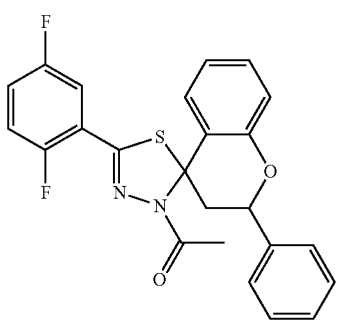 [SMILES: CC(=O)N1N=C(c2cc(F)ccc2F)SC12CC(c1ccccc1)Oc1ccccc12] | 436.1 | 437.0 | 5.09 | D |
| 118 | 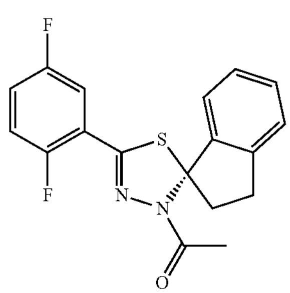 [SMILES: CC(=O)N1N=C(c2cc(F)ccc2F)S[C@@]12CCc1ccccc12] | 344.1 | 345.1 | 5.34 | A |

TABLE 101-continued

| Cpd ID | Structure | Exact mass | MS m/z (M+ + H) | tR (min) | ED50 (nM) Range |
|---|---|---|---|---|---|
| 119 | 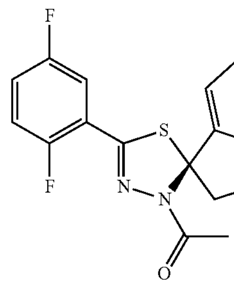 | 344.1 | 345.1 | 5.33 | C |
| 120 | 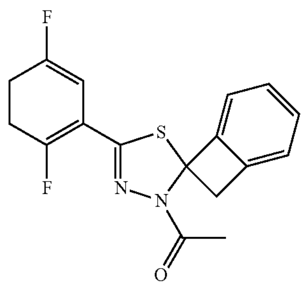 [SMILES: CC(=O)N1N=C(C2=C(F)CCC(F)=C2)SC12Cc1ccccc12] | 330.1 | 331.3 | 4.51 | A |
| 121 | 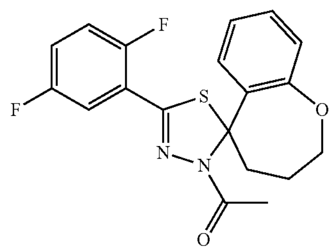 | 374.09 | 375.09 | 4.48 | D |
| 122 | 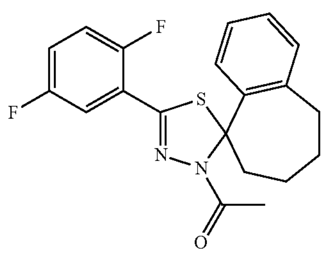 [SMILES: CC(=O)N1N=C(c2cc(F)ccc2F)SC12CCCCc1ccccc12] | 372.11 | 373.11 | 4.93 | D |
| 123 | 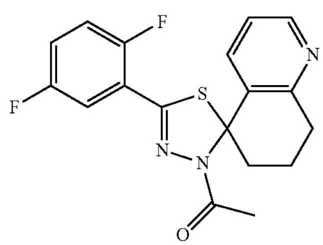 [SMILES: CC(=O)N1N=C(c2cc(F)ccc2F)SC12CCCc1ncccc12] | 359.09 | 360.09 | 2.96 | D |
| 124 | 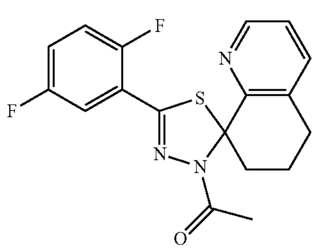 [SMILES: CC(=O)N1N=C(c2cc(F)ccc2F)SC12CCCc1cccnc12] | 359.09 | 360.09 | 3.54 | D |

TABLE 101-continued

| Cpd ID | Structure | Exact mass | MS m/z (M+ + H) | tR (min) | ED50 (nM) Range |
|---|---|---|---|---|---|
| 125 | 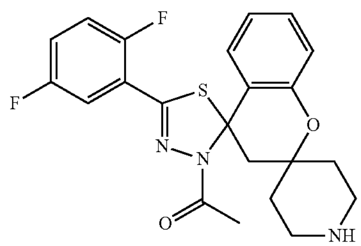 [SMILES: CC(=O)N1N=C(c2cc(F)ccc2F)SC12CC1(CCNCC1)Oc1ccccc12] | 429.13 | 430.13 | 3.32 | D |
| 126 | 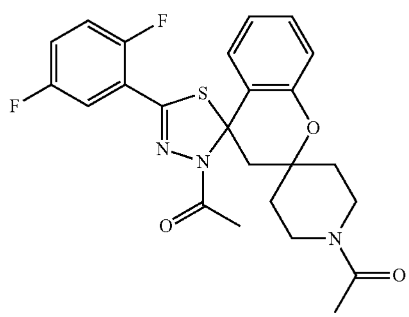 [SMILES: CC(=O)N1CCC2(CC1)CC1(SC(c3cc(F)ccc3F)=NN1C(C)=O)c1ccccc1O2] | 471.14 | 472.14 | 4.18 | D |
| 127 | 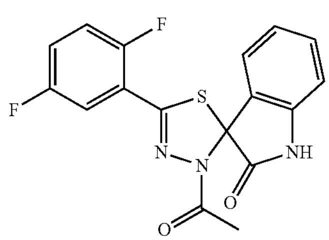 [SMILES: CC(=O)N1N=C(c2cc(F)ccc2F)SC12C(=O)Nc1ccccc12] | 359.05 | 360.0 | 3.54 | D |
| 128 | 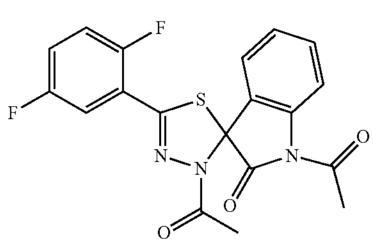 [SMILES: CC(=O)N1C(=O)C2(SC(c3cc(F)ccc3F)=NN2C(C)=O)c2ccccc21] | 401.06 | 402.0 | 4.05 | D |

Example 201

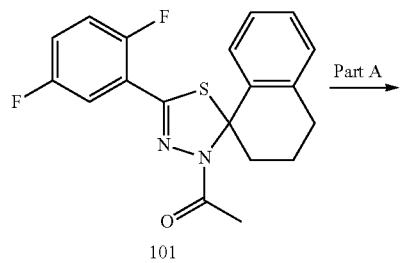
101

Part A

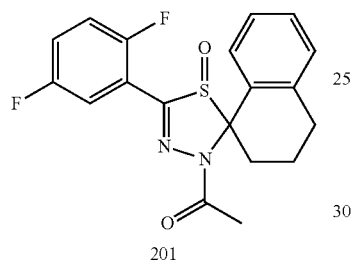
201

Part A:

Compound 101 (10 mg, 0.028 mmol) in DCM (5 mL) was added 3-chloroper benzoic acid (6.9 mg, 0.031 mmol) at 0° C. The reaction mixture was allowed to stir at room temperature for 2 h. The solution was concentrated, preparative LC-MS afforded compound 201 as two isomers. Isomer 201a: HPLC-MS $t_R$=3.56 min (UV$_{254\ nm}$); mass calculated for formula C19H16F2N2O2S 374.1, observed LCMS m/z 375.1 (M+1); Isomer 201b: HPLC-MS $t_R$=3.86 min (UV$_{25}$4 nm); mass calculated for formula C19H16F2N2O2S 374.1, observed LCMS m/z 375.1 (M+1).

Example 301

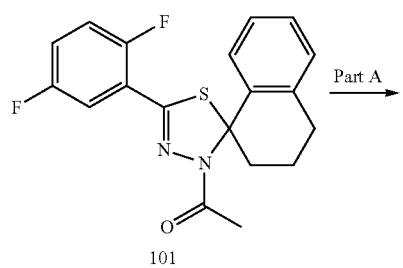
101

Part A

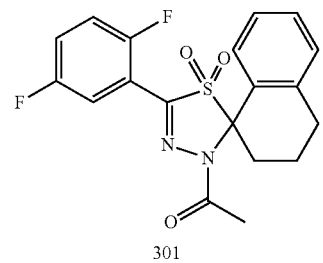
301

Part A:

Compound 101 (10 mg, 0.028 mmol) in DCM (5 mL) was added 3-chloroper benzoic acid (15.7 mg, 0.007 mmol) at 0° C. The reaction mixture was allowed to stir at room temperature for 24 h. The solution was concentrated, preparative LC-MS afforded compound 301 as a white powder. HPLC-MS $t_R$=4.10 min (UV$_{254\ nm}$); mass calculated for formula C19H6F2N2O3S 390.1, observed LCMS m/z 391.1 (M+1).

Example 401

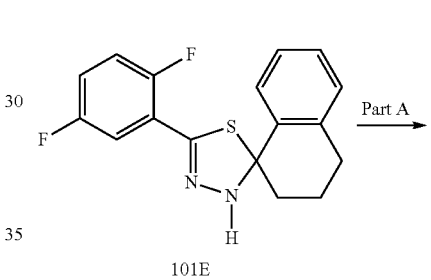
101E

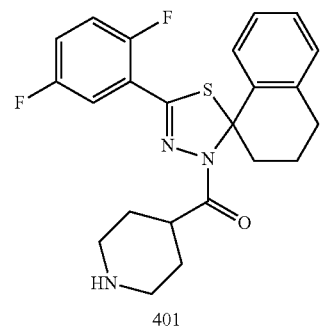
401

Part A:

To a mixture of compound 101E (60 mg, 0.19 mmol) and O-(7-Azabenzotriazol-1-yl)-N,N,N',N'-tetramethyluronium hexafluorophosphate (HATU) (72 mg, 0.19 mmol) in DMF (2 mL) was added Boc-L-isonipecotic acid (43.6 mg, 0.19 mmol) and DIEA (34 μL, 0.19 mmol). The reaction mixture was stirred at room temperature for 12 hours. The volatiles were removed in vacuo, the residue was stirred in trifluoroacetic acid (2 mL) at room temperature for 2 minutes. Concentration and purification by prep.HPLC afforded compound 401 as a white solid (15 mg, 18%). HPLC-MS $t_R$=3.90 min (UV$_{254\ nm}$); mass calculated for formula C23H23F2N3OS 427.2, observed LCMS m/z 428.3 (M+H).

The following compounds in Table 401 were synthesized using this procedure:

TABLE 401

| Cpd ID | Structure | Exact mass | MS m/z (M+ + H) | tR (min) | ED50 (nM) Range |
|---|---|---|---|---|---|
| 401 | 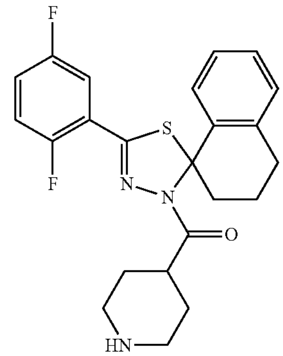 [SMILES: O=C(C1CCNCC1)N1N=C(c2cc(F)ccc2F)SC12CCCc1ccccc12] | 427.2 | 428.2 | 3.90 | D |
| 402 | 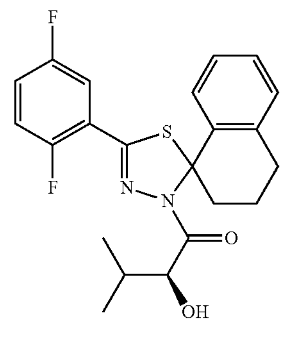 | 416.1 | 417.2 | 5.10 | D |
| 403 | 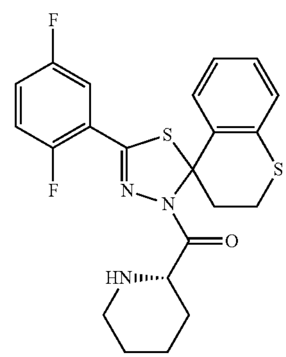 [SMILES: O=C([C@@H]1CCCCN1)N1N=C(c2cc(F)ccc2F)SC12CCSc1ccccc12] | 445.1 | 446.1 | 3.74 | D |
| 404 | 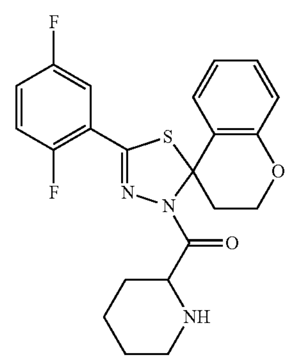 [SMILES: O=C(C1CCCCN1)N1N=C(c2cc(F)ccc2F)SC12CCOc1ccccc12] | 429.1 | 430.2 | 3.96 | D |

TABLE 401-continued

| Cpd ID | Structure | Exact mass | MS m/z (M+ + H) | tR (min) | ED50 (nM) Range |
|---|---|---|---|---|---|
| 405 | 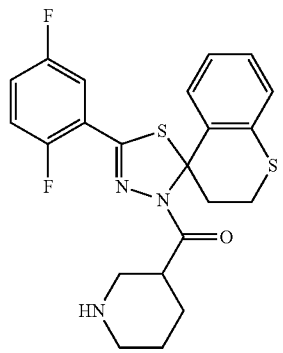 [SMILES: O=C(C1CCCNC1)N1N=C(c2cc(F)ccc2F)SC12CCSc1ccccc12] | 445.1 | 446.1 | 3.79 | D |
| 406 | 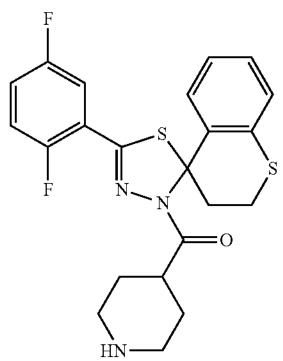 [SMILES: O=C(C1CCNCC1)N1N=C(c2cc(F)ccc2F)SC12CCSc1ccccc12] | 445.1 | 446.1 | 3.79 | D |
| 407 | 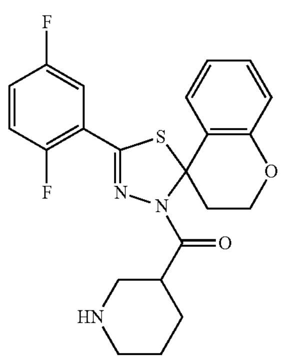 [SMILES: O=C(C1CCCNC1)N1N=C(c2cc(F)ccc2F)SC12CCOc1ccccc12] | 429.1 | 430.0 | 3.75 | D |
| 408 | 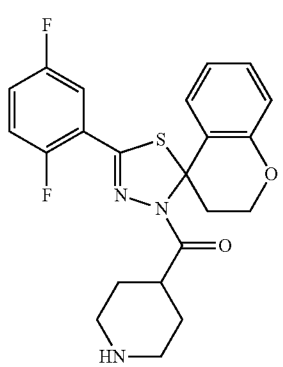 [SMILES: O=C(C1CCNCC1)N1N=C(c2cc(F)ccc2F)SC12CCOc1ccccc12] | 429.1 | 430.0 | 3.59 | D |

TABLE 401-continued

| Cpd ID | Structure | Exact mass | MS m/z (M+ + H) | tR (min) | ED50 (nM) Range |
|---|---|---|---|---|---|
| 409 | 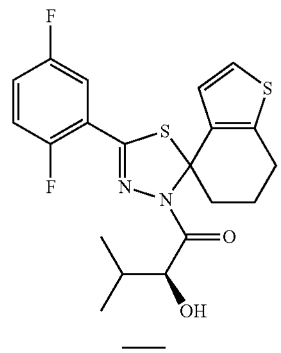 | 422.1 | 423.1 | 4.93 | D |
| 410 | 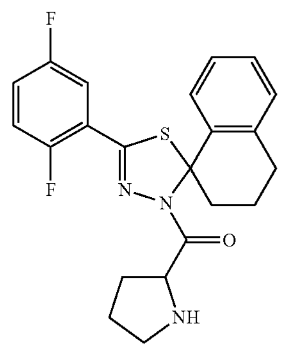 [SMILES: O=C(C1CCCN1)N1N=C(c2cc(F)ccc2F)SC12CCCc1ccccc12] | 413.1 | 414.1 | 3.83 | D |
| 411 | 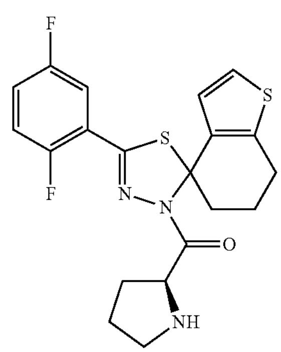 [SMILES: O=C([C@@H]1CCCN1)N1N=C(c2cc(F)ccc2F)SC12CCCc1sccc12] | 419.1 | 420.1 | 3.70 | D |
| 412 | 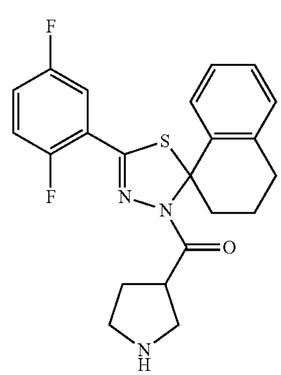 [SMILES: O=C(C1CCNC1)N1N=C(c2cc(F)ccc2F)SC12CCCc1ccccc12] | 413.1 | 414.1 | 3.78 | D |

TABLE 401-continued
| Cpd ID | Structure | Exact mass | MS m/z (M+ + H) | tR (min) | ED50 (nM) Range |
|---|---|---|---|---|---|
| 413 | 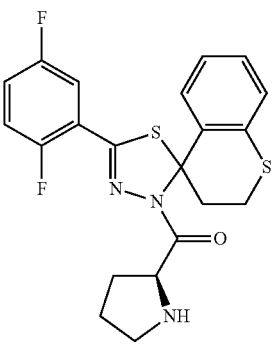 [SMILES: O=C([C@@H]1CCCN1)N1N=C(c2cc(F)ccc2F)SC12CCSc1ccccc12] | 431.1 | 432.1 | 3.71 | D |
| 414 | 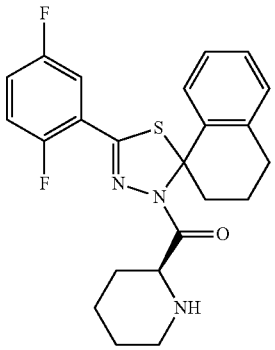 [SMILES: O=C([C@@H]1CCCCN1)N1N=C(c2cc(F)ccc2F)SC12CCCc1ccccc12] | 427.2 | 428.1 | 3.86 | D |
| 415 | 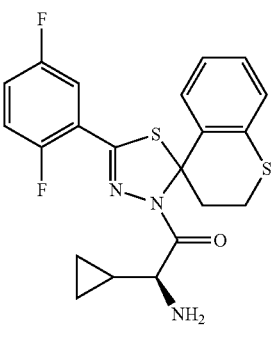 [SMILES: N[C@H](C(=O)N1N=C(c2cc(F)ccc2F)SC12CCSc1ccccc12)C1CC1] | 431.1 | 432.1 | 3.71 | D |
| 416 | 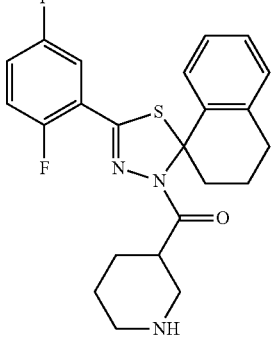 | 427.2 | 428.1 | 3.92 | D |

TABLE 401-continued

| Cpd ID | Structure | Exact mass | MS m/z ($M^+ + H$) | tR (min) | ED50 (nM) Range |
|---|---|---|---|---|---|
| 417 | 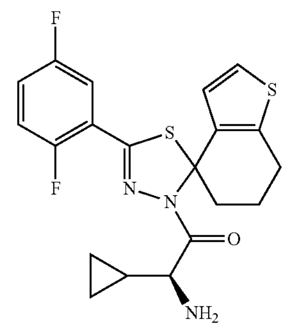 [SMILES: N[C@H](C(=O)N1N=C(c2cc(F)ccc2F)SC12CCCc1sccc12)C1CC1] | 419.1 | 420.1 | 3.75 | D |
| 418 | 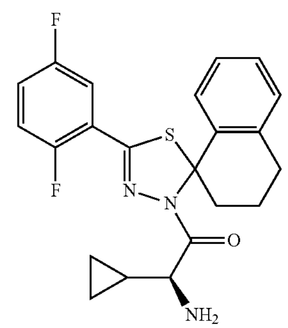 [SMILES: N[C@H](C(=O)N1N=C(c2cc(F)ccc2F)SC12CCCc1ccccc12)C1CC1] | 413.1 | 414.1 | 3.86 | D |
| 419 | 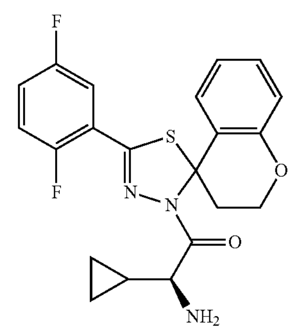 [SMILES: N[C@H](C(=O)N1N=C(c2cc(F)ccc2F)SC12CCOc1ccccc12)C1CC1] | 415.1 | 416.1 | 3.56 | D |
| 420 | 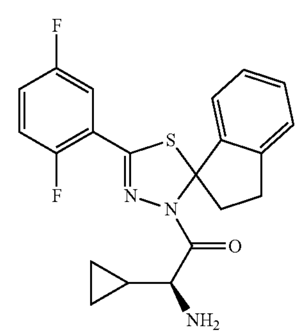 [SMILES: N[C@H](C(=O)N1N=C(c2cc(F)ccc2F)SC12CCc1ccccc12)C1CC1] | 399.1 | 400.1 | 3.60 | D |

TABLE 401-continued

| Cpd ID | Structure | Exact mass | MS m/z (M+ + H) | tR (min) | ED50 (nM) Range |
|---|---|---|---|---|---|
| 421 | 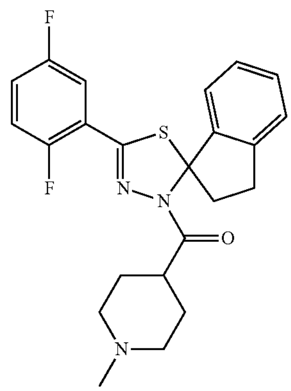 [SMILES: CN1CCC(C(=O)N2N=C(c3cc(F)ccc3F)SC23CCc2ccccc23)CC1] | 427.2 | 428.2 | 3.84 | D |
| 422 | 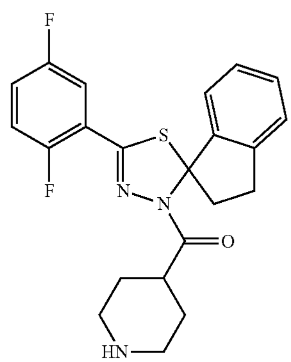 [SMILES: O=C(C1CCNCC1)N1N=C(c2cc(F)ccc2F)SC12CCc1ccccc12] | 413.1 | 414.2 | 3.69 | D |
| 423 | 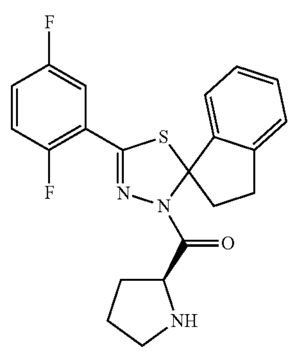 [SMILES: O=C([C@@H]1CCCN1)N1N=C(c2cc(F)ccc2F)SC12CCc1ccccc12] | 399.1 | 400.1 | 3.57 | D |
| 424 | 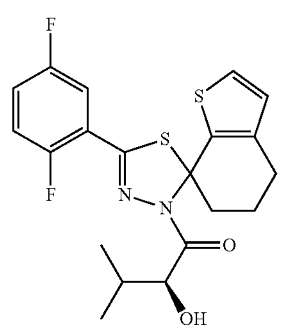 [SMILES: CC(C)[C@H](O)C(=O)N1N=C(c2cc(F)ccc2F)SC12CCCc1ccsc12] | 422.1 | 423.1 | 4.95 | D |

TABLE 401-continued

| Cpd ID | Structure | Exact mass | MS m/z (M⁺ + H) | tR (min) | ED50 (nM) Range |
|---|---|---|---|---|---|
| 425 | 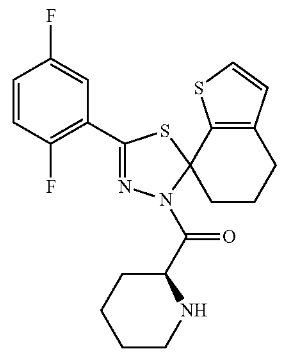 [SMILES: O=C([C@@H]1CCCCN1)N1N=C(c2cc(F)ccc2F)SC12CCCc1ccsc12] | 433.1 | 434.1 | 3.76 | D |
| 426 | 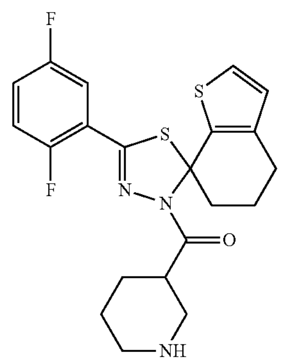 [SMILES: O=C(C1CCCNC1)N1N=C(c2cc(F)ccc2F)SC12CCCc1ccsc12] | 433.1 | 434.1 | 3.82 | D |
| 427 | 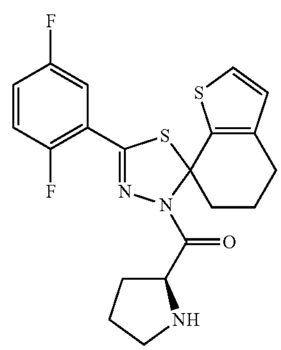 [SMILES: O=C([C@@H]1CCCN1)N1N=C(c2cc(F)ccc2F)SC12CCCc1ccsc12] | 419.1 | 420.1 | 3.74 | D |
| 428 | 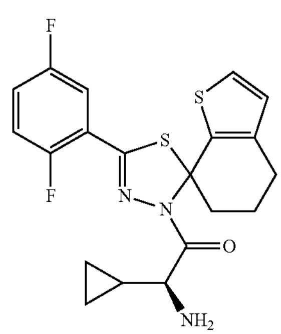 [SMILES: N[C@H](C(=O)N1N=C(c2cc(F)ccc2F)SC12CCCc1ccsc12)C1CC1] | 419.1 | 420.1 | 3.73 | D |

TABLE 401-continued

| Cpd ID | Structure | Exact mass | MS m/z (M+ + H) | tR (min) | ED50 (nM) Range |
|---|---|---|---|---|---|
| 429 | 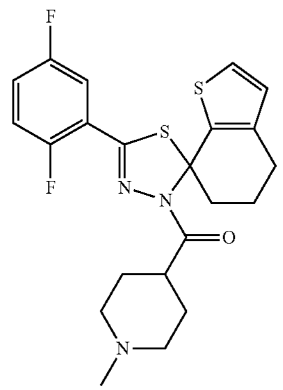 [SMILES: CN1CCC(C(=O)N2N=C(c3cc(F)ccc3F)SC23CCCc2ccsc23)CC1] | 447.1 | 448.1 | 3.85 | D |
| 430 | 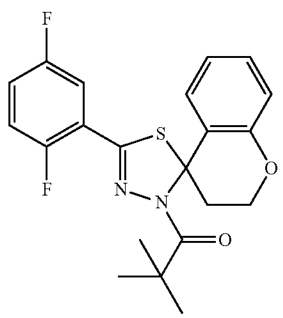 [SMILES: CC(C)(C)C(=O)N1N=C(c2cc(F)ccc2F)SC12CCOc1ccccc12] | 402.1 | 403.1 | 5.18 | D |
| 431 | 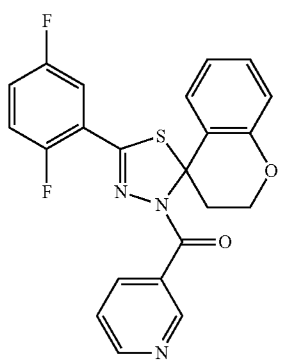 [SMILES: O=C(c1cccnc1)N1N=C(c2cc(F)ccc2F)SC12CCOc1ccccc12] | 423.1 | 424.1 | 4.19 | D |
| 432 | 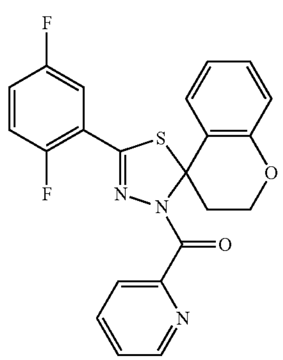 [SMILES: O=C(c1ccccn1)N1N=C(c2cc(F)ccc2F)SC12CCOc1ccccc12] | 423.1 | 424.1 | 4.21 | D |

TABLE 401-continued

| Cpd ID | Structure | Exact mass | MS m/z (M⁺ + H) | tR (min) | ED50 (nM) Range |
|---|---|---|---|---|---|
| 433 | 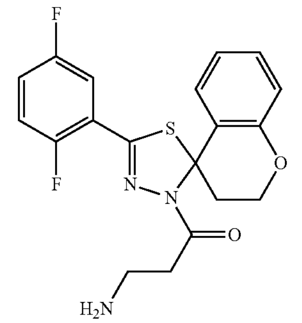 [SMILES: NCCC(=O)N1N=C(c2cc(F)ccc2F)SC12CCOc1ccccc12] | 389.1 | 390.1 | 3.62 | C |
| 434 | 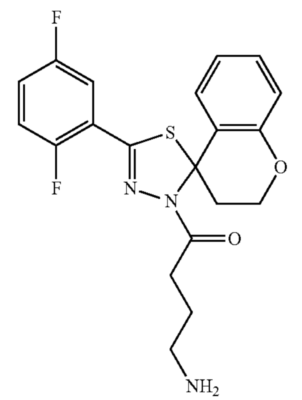 [SMILES: NCCCC(=O)N1N=C(c2cc(F)ccc2F)SC12CCOc1ccccc12] | 403.1 | 404.1 | 3.64 | A |
| 435 | 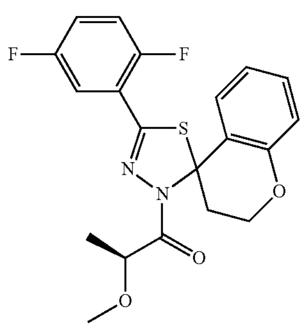 [SMILES: CO[C@@H](C)C(=O)N1N=C(c2cc(F)ccc2F)SC12CCOc1ccccc12] | 404.1 | 405.2 | 4.38 | C |
| 436 | 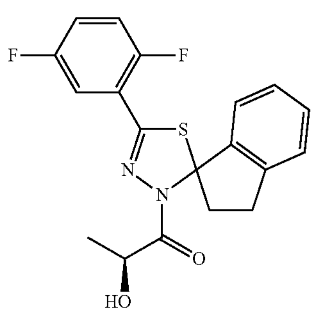 [SMILES: C[C@H](O)C(=O)N1N=C(c2cc(F)ccc2F)SC12CCc1ccccc12] | 374.1 | 375.2 | 4.26 | A |

TABLE 401-continued

| Cpd ID | Structure | Exact mass | MS m/z (M+ + H) | tR (min) | ED50 (nM) Range |
|---|---|---|---|---|---|
| 437 | 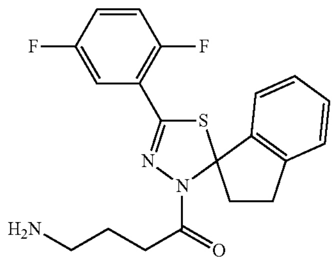 [SMILES: NCCCC(=O)N1N=C(c2cc(F)ccc2F)SC12CCc1ccccc12] | 387.1 | 388.1 | 4.59 | A |
| 438 | 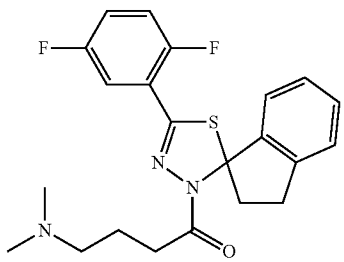 [SMILES: CN(C)CCCC(=O)N1N=C(c2cc(F)ccc2F)SC12CCc1ccccc12] | 415.2 | 416.2 | 4.69 | A |
| 439 | 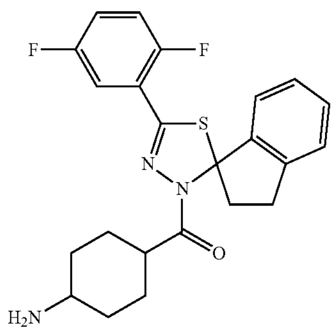 [SMILES: NC1CCC(C(=O)N2N=C(c3cc(F)ccc3F)SC23CCc2ccccc23)CC1] | 427.2 | 428.2 | 4.77 | C |
| 440 | 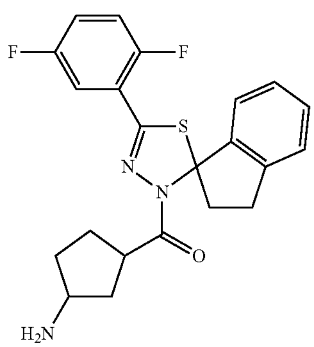 [SMILES: NC1CCC(C(=O)N2N=C(c3cc(F)ccc3F)SC23CCc2ccccc23)C1] | 413.1 | 414.1 | 4.80 | A |
| 441 | 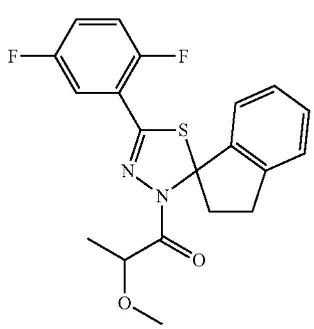 [SMILES: COC(C)C(=O)N1N=C(c2cc(F)ccc2F)SC12CCc1ccccc12] | 388.1 | 389.1 | 6.72 | A |

TABLE 401-continued

| Cpd ID | Structure | Exact mass | MS m/z (M+ + H) | tR (min) | ED50 (nM) Range |
|---|---|---|---|---|---|
| 442 | 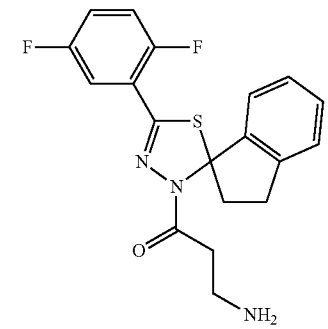 [SMILES: NCCC(=O)N1N=C(c2cc(F)ccc2F)SC12CCc1ccccc12] | 373.1 | 374.1 | 3.91 | A |
| 443 | 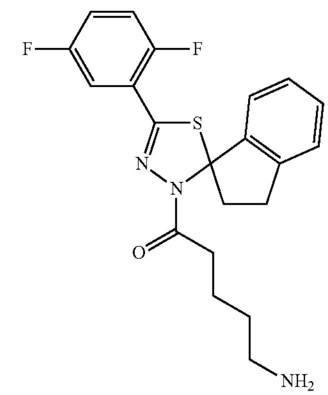 [SMILES: NCCCCC(=O)N1N=C(c2cc(F)ccc2F)SC12CCc1ccccc12] | 401.1 | 402.1 | 4.04 | A |
| 444 | 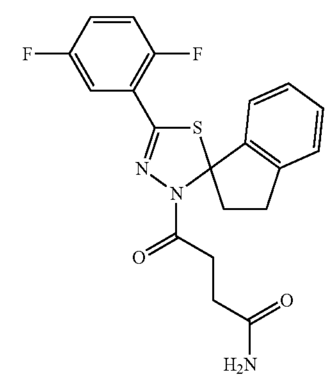 [SMILES: NC(=O)CCC(=O)N1N=C(c2cc(F)ccc2F)SC12CCc1ccccc12] | 401.1 | 402.2 | 3.96 | A |
| 445 | 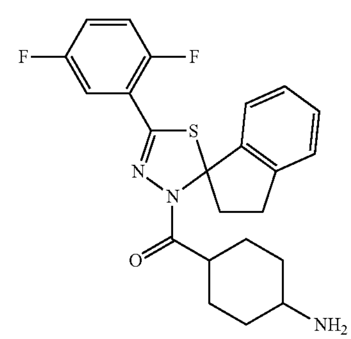 [SMILES: NC1CCC(C(=O)N2N=C(c3cc(F)ccc3F)SC23CCc2ccccc23)CC1] | 427.2 | 428.2 | 4.31 | D |

TABLE 401-continued

| Cpd ID | Structure | Exact mass | MS m/z (M+ + H) | tR (min) | ED50 (nM) Range |
|---|---|---|---|---|---|
| 446 | 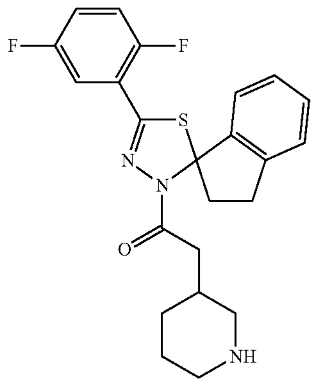 [SMILES: O=C(CC1CCCNC1)N1N=C(c2cc(F)ccc2F)SC12CCc1ccccc12] | 427.2 | 428.2 | 4.20 | C |
| 447 | 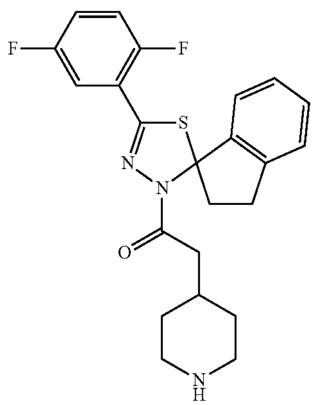 [SMILES: O=C(CC1CCNCC1)N1N=C(c2cc(F)ccc2F)SC12CCc1ccccc12] | 427.2 | 428.2 | 4.31 | A |
| 448 | 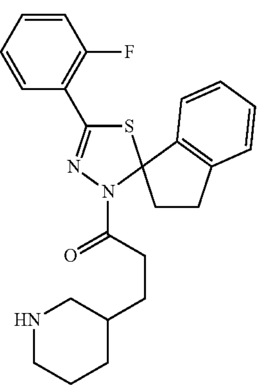 | 441.2 | 442.1 | 5.03 | D |
| 449 | 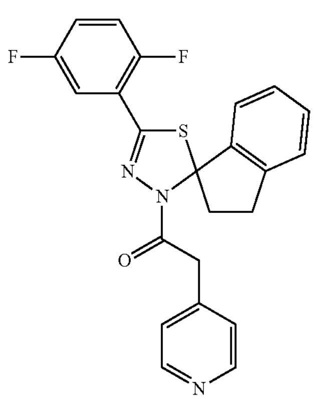 [SMILES: O=C(Cc1ccncc1)N1N=C(c2cc(F)ccc2F)SC12CCc1ccccc12] | 421.1 | 422.1 | 4.74 | A |

TABLE 401-continued

| Cpd ID | Structure | Exact mass | MS m/z (M⁺ + H) | tR (min) | ED50 (nM) Range |
|---|---|---|---|---|---|
| 450 | 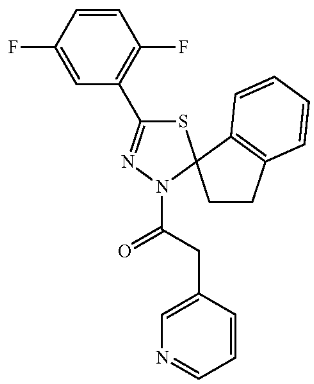 [SMILES: O=C(Cc1cccnc1)N1N=C(c2cc(F)ccc2F)SC12CCc1ccccc12] | 421.1 | 422.2 | 3.72 | C |
| 451 | 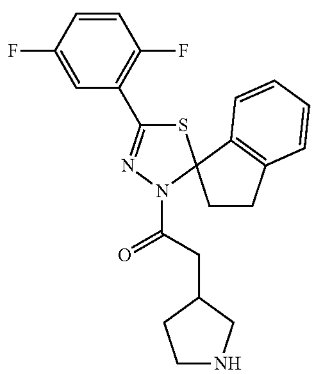 [SMILES: O=C(CC1CCNC1)N1N=C(c2cc(F)ccc2F)SC12CCc1ccccc12] | 413.1 | 414.2 | 3.74 | A |
| 452 | 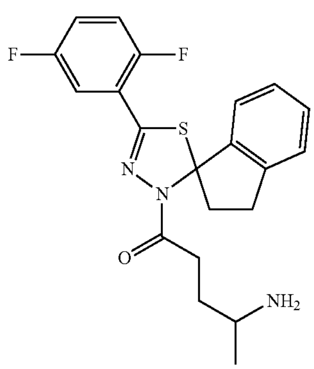 [SMILES: CC(N)CCC(=O)N1N=C(c2cc(F)ccc2F)SC12CCc1ccccc12] | 401.1 | 402.3 | 3.68 | A |
| 453 | 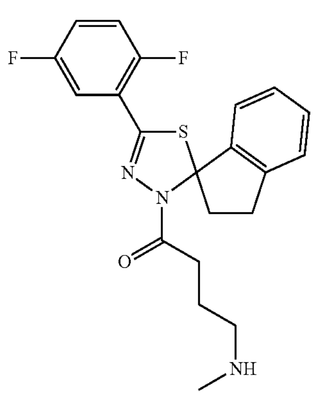 [SMILES: CNCCCC(=O)N1N=C(c2cc(F)ccc2F)SC12CCc1ccccc12] | 401.1 | 402.1 | 4.73 | B |

TABLE 401-continued

| Cpd ID | Structure | Exact mass | MS m/z (M⁺ + H) | tR (min) | ED50 (nM) Range |
|---|---|---|---|---|---|
| 454 | 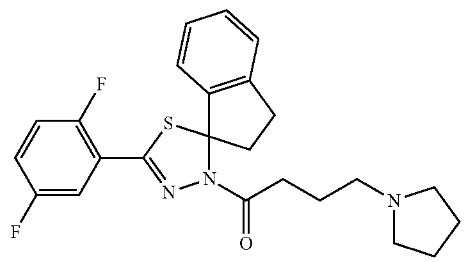 [SMILES: O=C(CCCN1CCCC1)N1N=C(c2cc(F)ccc2F)SC12CCc1ccccc12] | 441.2 | 442.3 | 3.88 | A |
| 455 | 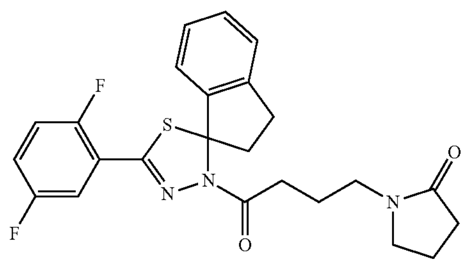 [SMILES: O=C1CCCN1CCCC(=O)N1N=C(c2cc(F)ccc2F)SC12CCc1ccccc12] | 455.2 | 456.3 | 4.49 | C |
| 456 | 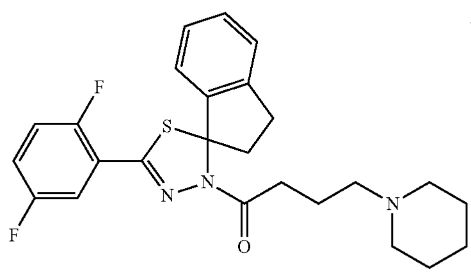 [SMILES: O=C(CCCN1CCOCC1)N1N=C(c2cc(F)ccc2F)SC12CCc1ccccc12] | 455.2 | 456.3 | 3.93 | A |
| 457 | 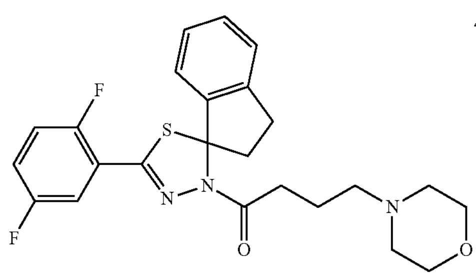 | 457.2 | 458.3 | 3.72 | A |
| 458 | 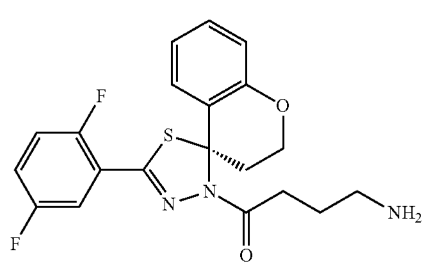 [SMILES: NCCCC(=O)N1N=C(c2cc(F)ccc2F)S[C@]12CCOc1ccccc12] | 403.1 | 404.1 | 4.25 | A |

TABLE 401-continued

| Cpd ID | Structure | Exact mass | MS m/z (M+ + H) | tR (min) | ED50 (nM) Range |
|---|---|---|---|---|---|
| 459 | 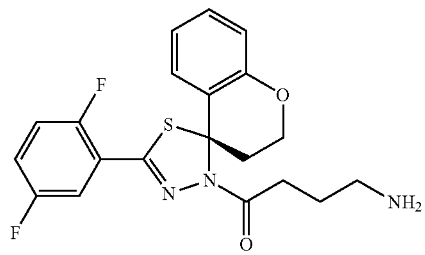 [SMILES: NCCCC(=O)N1N=C(c2cc(F)ccc2F)S[C@@]12CCOc1ccccc12] | 403.1 | 404.1 | 4.31 | B |
| 460 | 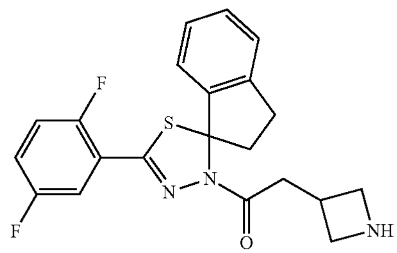 [SMILES: O=C(CC1CNC1)N1N=C(c2cc(F)ccc2F)SC12CCc1ccccc12] | 399.1 | 400.3 | 3.63 | A |
| 461 | 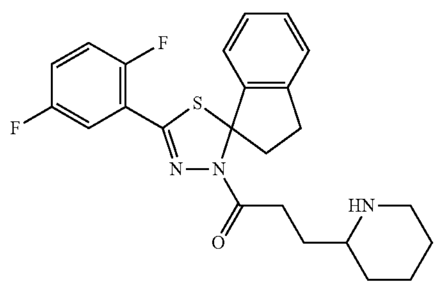 [SMILES: O=C(CCC1CCCCN1)N1N=C(c2cc(F)ccc2F)SC12CCc1ccccc12] | 441.2 | 442.3 | 3.84 | B |
| 462 | 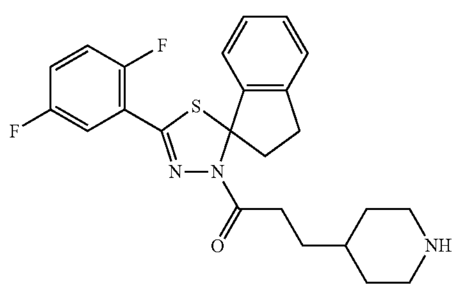 [SMILES: O=C(CCC1CCNCC1)N1N=C(c2cc(F)ccc2F)SC12CCc1ccccc12] | 441.2 | 442.3 | 3.91 | A |
| 463 | 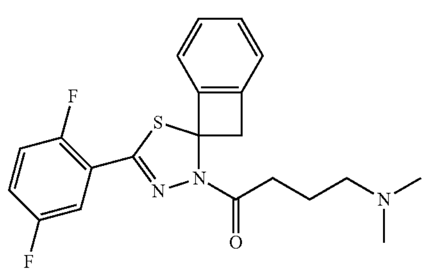 [SMILES: CN(C)CCCC(=O)N1N=C(c2cc(F)ccc2F)SC12Cc1ccccc12] | 401.1 | 402.3 | 3.69 | A |

TABLE 401-continued

| Cpd ID | Structure | Exact mass | MS m/z (M+ + H) | tR (min) | ED50 (nM) Range |
|---|---|---|---|---|---|
| 464 | 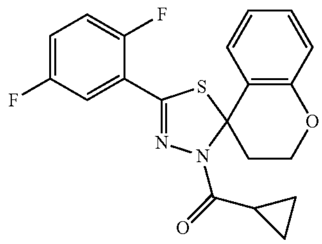 [SMILES: O=C(C1CC1)N1N=C(c2cc(F)ccc2F)SC12CCOc1ccccc12] | 386.09 | 387.09 | 4.77 | C |
| 465 | 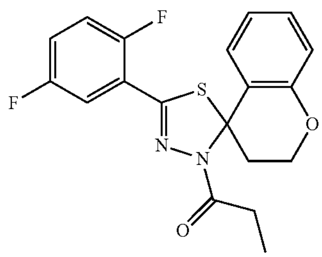 [SMILES: CCC(=O)N1N=C(c2cc(F)ccc2F)SC12CCOc1ccccc12] | 374.09 | 375.09 | 4.69 | A |
| 466 | 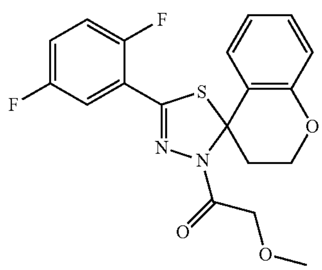 [SMILES: COCC(=O)N1N=C(c2cc(F)ccc2F)SC12CCOc1ccccc12] | 390.09 | 391.09 | 4.25 | D |
| 467 | 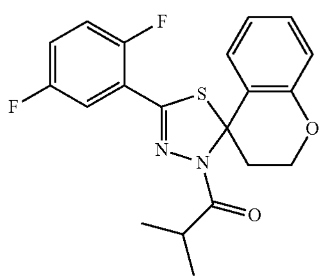 [SMILES: CC(C)C(=O)N1N=C(c2cc(F)ccc2F)SC12CCOc1ccccc12] | 388.11 | 389.11 | 4.94 | D |
| 468 | 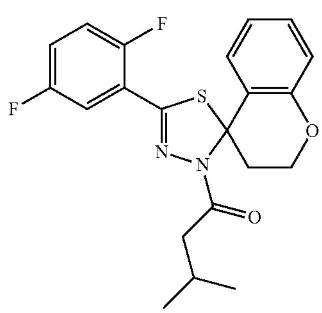 [SMILES: CC(C)CC(=O)N1N=C(c2cc(F)ccc2F)SC12CCOc1ccccc12] | 402.12 | 402.12 | 5.16 | D |

TABLE 401-continued

| Cpd ID | Structure | Exact mass | MS m/z (M⁺ + H) | tR (min) | ED50 (nM) Range |
|---|---|---|---|---|---|
| 469 | 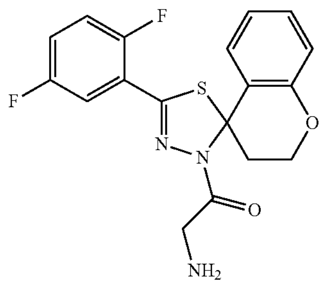 [SMILES: NCC(=O)N1N=C(c2cc(F)ccc2F)SC12CCOc1ccccc12] | 375.09 | 376.09 | 3.17 | D |
| 470 | 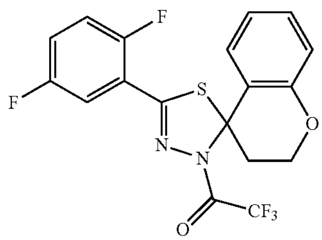 [SMILES: O=C(N1N=C(c2cc(F)ccc2F)SC12CCOc1ccccc12)C(F)(F)F] | 414.05 | 415.05 | 4.90 | D |
| 471 | 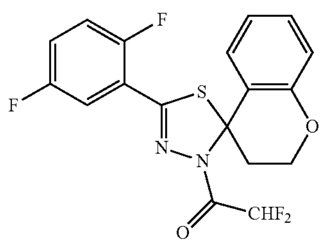 [SMILES: O=C(C(F)F)N1N=C(c2cc(F)ccc2F)SC12CCOc1ccccc12] | 396.06 | 397.06 | 4.43 | A |
| 472 | 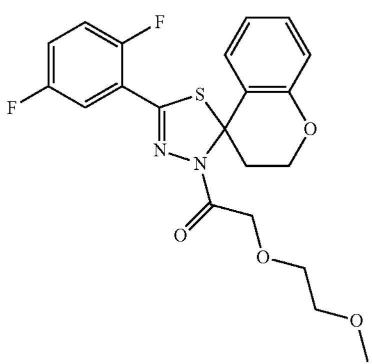 [SMILES: COCCOCC(=O)N1N=C(c2cc(F)ccc2F)SC12CCOc1ccccc12] | 434.11 | 435.11 | 2.05 | D |
| 473 | 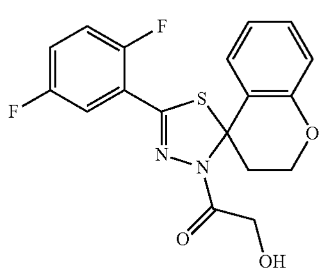 [SMILES: O=C(CO)N1N=C(c2cc(F)ccc2F)SC12CCOc1ccccc12] | 376.07 | 377.07 | 2.17 | C |

TABLE 401-continued

| Cpd ID | Structure | Exact mass | MS m/z (M⁺ + H) | tR (min) | ED50 (nM) Range |
|---|---|---|---|---|---|
| 474 | 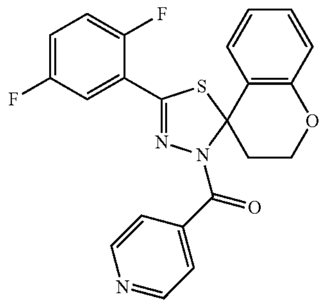 [SMILES: O=C(c1ccncc1)N1N=C(c2cc(F)ccc2F)SC12CCOc1ccccc12] | 423.09 | 424.09 | 3.58 | D |
| 475 | 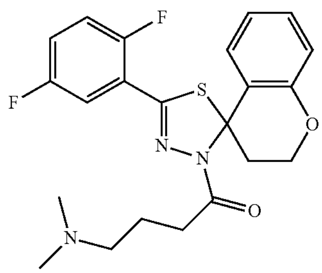 [SMILES: CN(C)CCCC(=O)N1N=C(c2cc(F)ccc2F)SC12CCOc1ccccc12] | 431.15 | 432.15 | 3.58 | A |
| 476 | 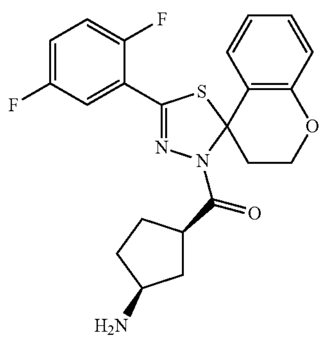 [SMILES: N[C@H]1CC[C@@H](C(=O)N2N=C(c3cc(F)ccc3F)SC23CCOc2ccccc23)C1] | 429.13 | 430.13 | 3.58 | B |
| 477 | 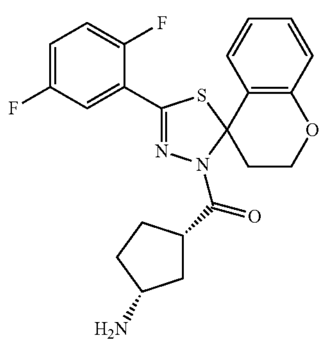 [SMILES: N[C@@H]1CC[C@H](C(=O)N2N=C(c3cc(F)ccc3F)SC23CCOc2ccccc23)C1] | 429.13 | 430.13 | 3.56 | B |

TABLE 401-continued

| Cpd ID | Structure | Exact mass | MS m/z (M+ + H) | tR (min) | ED50 (nM) Range |
|---|---|---|---|---|---|
| 478 | 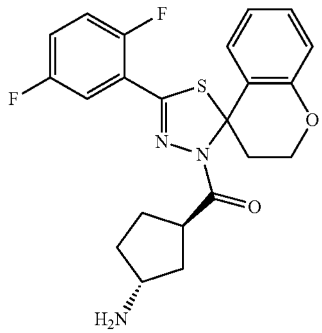 [SMILES: N[C@@H]1CC[C@@H](C(=O)N2N=C(c3cc(F)ccc3F)SC23CCOc2ccccc23)C1] | 429.13 | 430.29 | 3.51 | B |
| 479 | 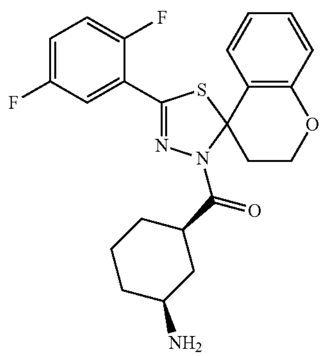 [SMILES: N[C@H]1CCC[C@@H](C(=O)N2N=C(c3cc(F)ccc3F)SC23CCOc2ccccc23)C1] | 443.15 | 444.15 | 3.59 | B |
| 480 | 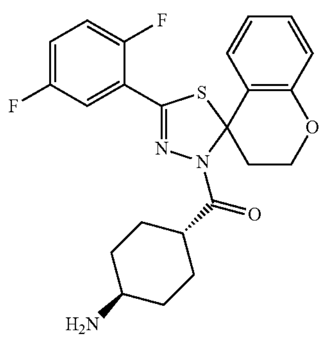 [SMILES: N[C@H]1CC[C@H](C(=O)N2N=C(c3cc(F)ccc3F)SC23CCOc2ccccc23)CC1] | 443.15 | 444.15 | 3.55 | B |
| 481 | 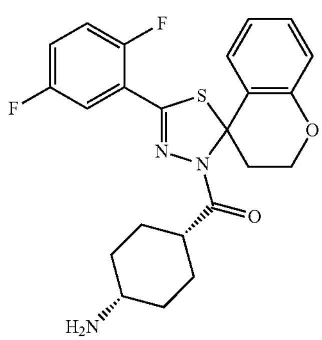 [SMILES: N[C@H]1CC[C@@H](C(=O)N2N=C(c3cc(F)ccc3F)SC23CCOc2ccccc23)CC1] | 443.15 | 444.15 | 3.65 | B |

TABLE 401-continued

| Cpd ID | Structure | Exact mass | MS m/z (M⁺ + H) | tR (min) | ED50 (nM) Range |
|---|---|---|---|---|---|
| 482 | 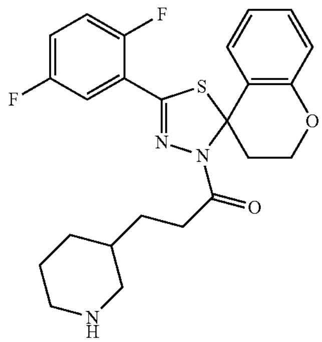 [SMILES: O=C(CCC1CCCNC1)N1N=C(c2cc(F)ccc2F)SC12CCOc1ccccc12] | 457.16 | 458.16 | 3.71 | A |
| 483 | 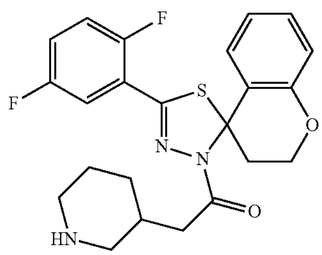 [SMILES: O=C(CC1CCCNC1)N1N=C(c2cc(F)ccc2F)SC12CCOc1ccccc12] | 443.15 | 444.15 | 3.61 | C |
| 484 | 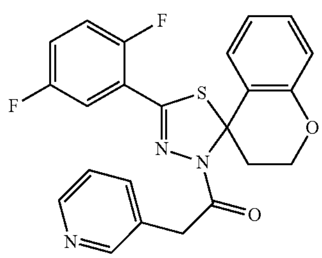 [SMILES: O=C(Cc1cccnc1)N1N=C(c2cc(F)ccc2F)SC12CCOc1ccccc12] | 437.10 | 438.10 | 3.48 | C |
| 485 | 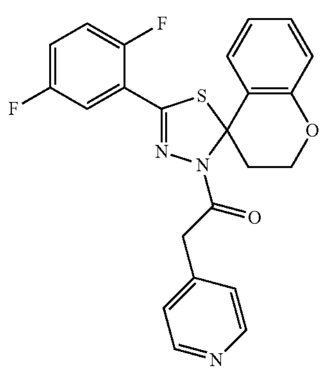 [SMILES: O=C(Cc1ccncc1)N1N=C(c2cc(F)ccc2F)SC12CCOc1ccccc12] | 437.10 | 438.10 | 3.47 | A |

TABLE 401-continued

| Cpd ID | Structure | Exact mass | MS m/z (M+ + H) | tR (min) | ED50 (nM) Range |
|---|---|---|---|---|---|
| 486 | 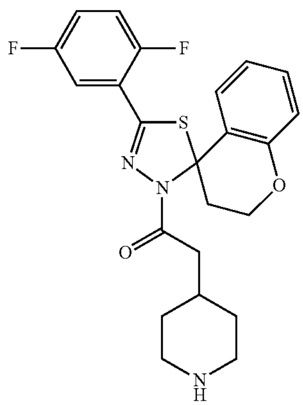 [SMILES: O=C(CC1CCNCC1)N1N=C(c2cc(F)ccc2F)SC12CCOc1ccccc12] | 443.15 | 444.15 | 3.55 | C |
| 487 | 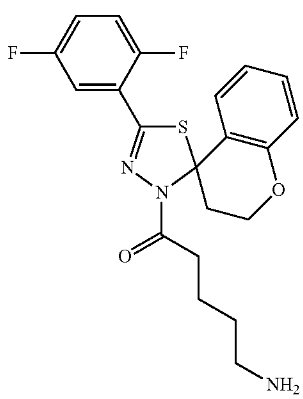 [SMILES: NCCCCC(=O)N1N=C(c2cc(F)ccc2F)SC12CCOc1ccccc12] | 417.13 | 418.13 | 3.47 | A |
| 488 | 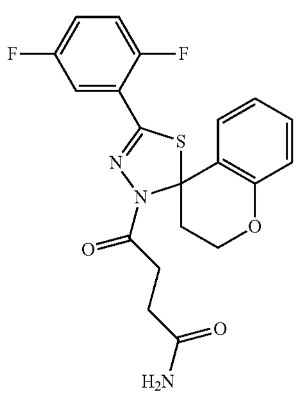 [SMILES: NC(=O)CCC(=O)N1N=C(c2cc(F)ccc2F)SC12CCOc1ccccc12] | 417.10 | 418.10 | 3.71 | B |

TABLE 401-continued

| Cpd ID | Structure | Exact mass | MS m/z (M+ + H) | tR (min) | ED50 (nM) Range |
|---|---|---|---|---|---|
| 489 | 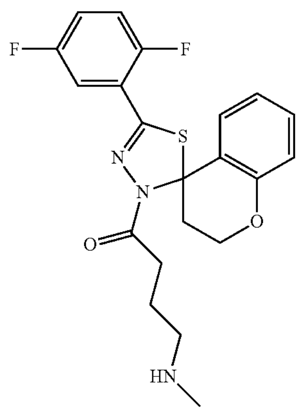 [SMILES: CNCCCC(=O)N1N=C(c2cc(F)ccc2F)SC12CCOc1ccccc12] | 417.13 | 418.13 | 3.43 | A |
| 490 | 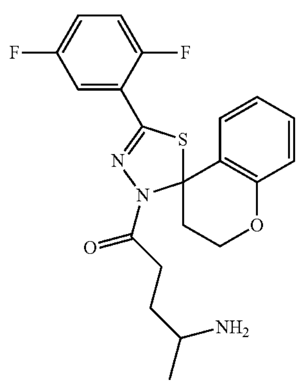 [SMILES: CC(N)CCC(=O)N1N=C(c2cc(F)ccc2F)SC12CCOc1ccccc12] | 417.13 | 418.17 | 3.40 | A |
| 491 | 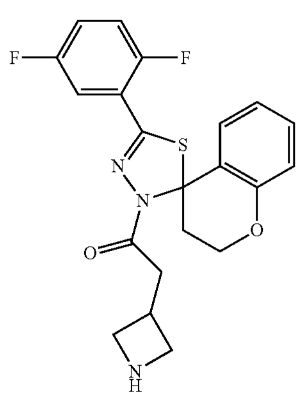 [SMILES: O=C(CC1CNC1)N1N=C(c2cc(F)ccc2F)SC12CCOc1ccccc12] | 415.12 | 416.12 | 3.38 | C |

TABLE 401-continued

| Cpd ID | Structure | Exact mass | MS m/z (M+ + H) | tR (min) | ED50 (nM) Range |
|---|---|---|---|---|---|
| 492 | 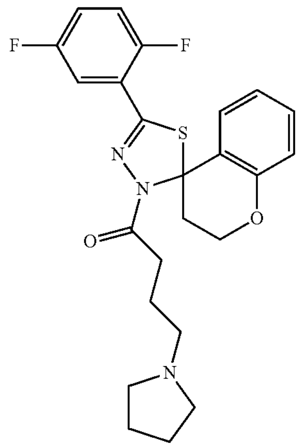 [SMILES: O=C(CCCN1CCCC1)N1N=C(c2cc(F)ccc2F)SC12CCOc1ccccc12] | 457.16 | 458.16 | 3.63 | A |
| 493 | 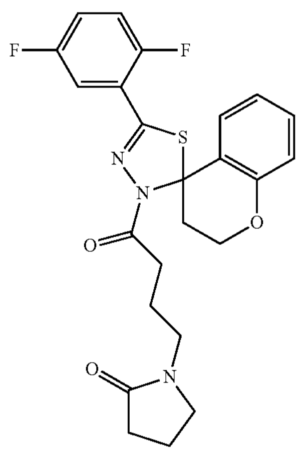 [SMILES: O=C1CCCN1CCCC(=O)N1N=C(c2cc(F)ccc2F)SC12CCOc1ccccc12] | 471.14 | 472.13 | 4.23 | B |
| 494 | 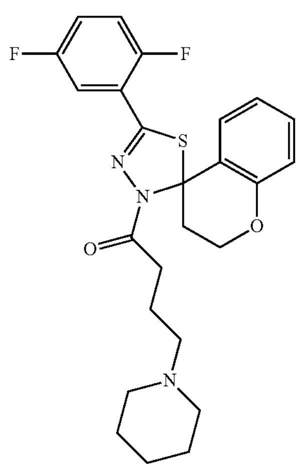 [SMILES: O=C(CCCN1CCCCC1)N1N=C(c2cc(F)ccc2F)SC12CCOc1ccccc12] | 471.18 | 472.18 | 3.70 | A |

TABLE 401-continued

| Cpd ID | Structure | Exact mass | MS m/z (M+ + H) | tR (min) | ED50 (nM) Range |
|---|---|---|---|---|---|
| 495 | 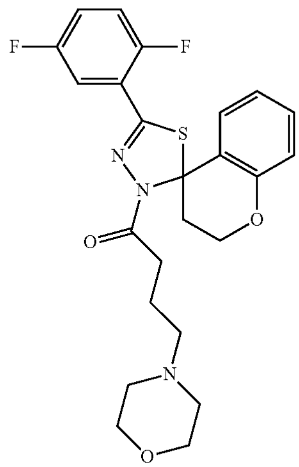 [SMILES: O=C(CCCN1CCOCC1)N1N=C(c2cc(F)ccc2F)SC12CCOc1ccccc12] | 473.16 | 474.16 | 3.48 | B |
| 496 | 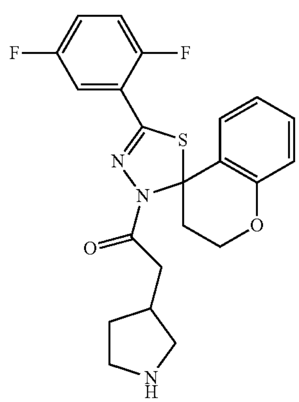 [SMILES: O=C(CC1CCNC1)N1N=C(c2cc(F)ccc2F)SC12CCOc1ccccc12] | 429.13 | 430.13 | 3.51 | A |
| 497 | 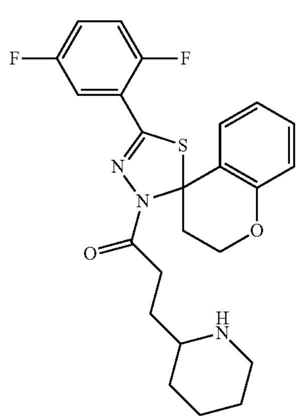 [SMILES: O=C(CCC1CCCCN1)N1N=C(c2cc(F)ccc2F)SC12CCOc1ccccc12] | 457.16 | 458.17 | 3.66 | C |

TABLE 401-continued

| Cpd ID | Structure | Exact mass | MS m/z (M+ + H) | tR (min) | ED50 (nM) Range |
|---|---|---|---|---|---|
| 498 | 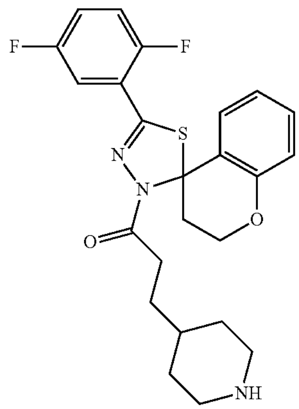 [SMILES: O=C(CCC1CCNCC1)N1N=C(c2cc(F)ccc2F)SC12CCOc1ccccc12] | 457.16 | 458.17 | 3.67 | A |
| 499 | 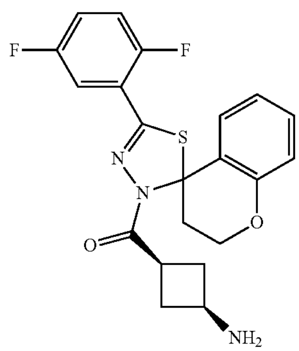 [SMILES: N[C@H]1C[C@@H](C(=O)N2N=C(c3cc(F)ccc3F)SC23CCOc2ccccc23)C1] | 414.11 | 415.11 | 4.04 | C |
| 500 | 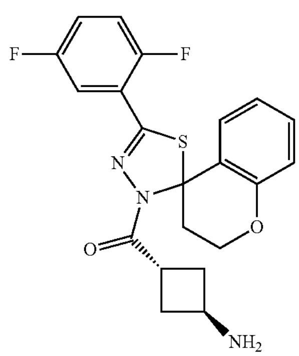 [SMILES: N[C@H]1C[C@H](C(=O)N2N=C(c3cc(F)ccc3F)SC23CCOc2ccccc23)C1] | 414.11 | 415.11 | 4.39 | B |
| 501 | 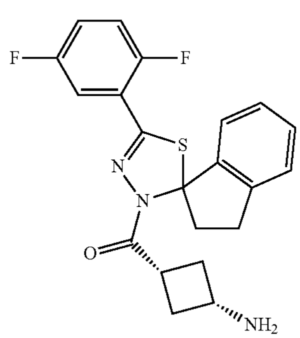 [SMILES: N[C@H]1C[C@@H](C(=O)N2N=C(c3cc(F)ccc3F)SC23CCc2ccccc23)C1] | 399.1 | 400.1 | 4.10 | A |

TABLE 401-continued

| Cpd ID | Structure | Exact mass | MS m/z (M⁺ + H) | tR (min) | ED50 (nM) Range |
|---|---|---|---|---|---|
| 502 | 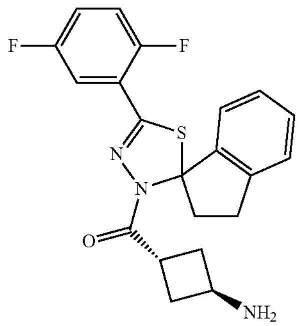 [SMILES: N[C@H]1C[C@H](C(=O)N2N=C(c3cc(F)ccc3F)SC23CCc2ccccc23)C1] | 399.1 | 400.1 | 4.56 | A |

Example 601

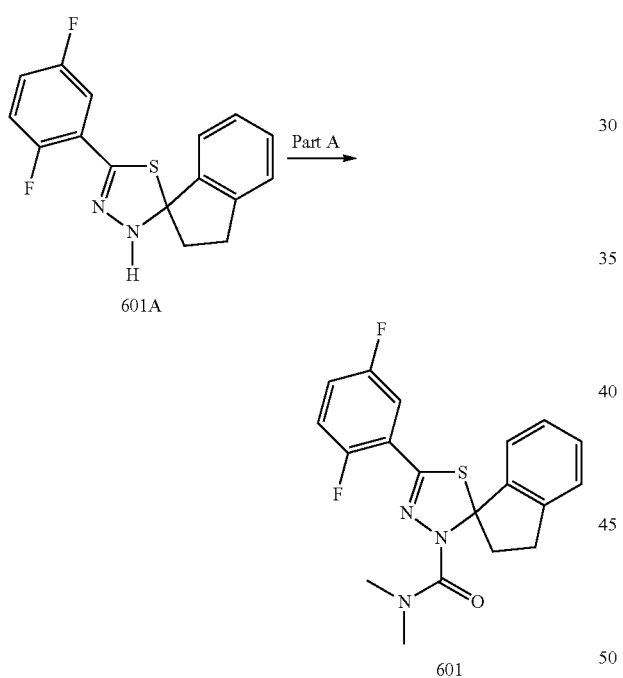

Part A:

Compound 601A was prepared in the same procedure as 101E from 1-indanone and 101C. To a solution of 601A (40 mg, 0.13 mmols) in DMF (2 mL) was added Dimethylcarbonyl chloride (16 mg, 0.15 mmols), diisopropylethylamine (73 µL, 0.42 mmol). The reaction mixture was stirred at room temperature for 16 hours, then was concentrated and purified by HPLC to afford compound 601 as a white solid (15 mg, 31%). HPLC-MS $t_R$=4.79 min ($UV_{254nm}$); mass calculated for formula C19H17F2N3OS 373.11, observed LCMS m/z 374.2 (M+H).

The following compounds in Table 601 were synthesized using this procedure:

TABLE 601
| Cpd ID | Structure | Exact mass | MS m/z (M+ + H) | tR (min) | EC50 (nM) Range |
|---|---|---|---|---|---|
| 601 | 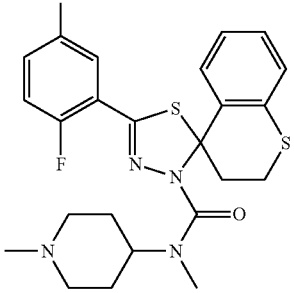 | 394.1 | 4.78 | 4.62 | D |
| 602 | 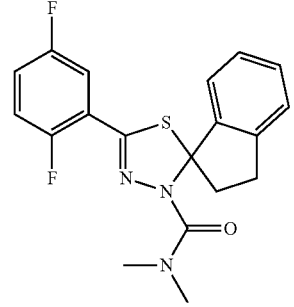 [SMILES: CN(C)C(=O)N1N=C(c2cc(F)ccc2F)SC12CCc1ccccc12] | 373.1 | 374.3 | 4.79 | C |
| 603 | 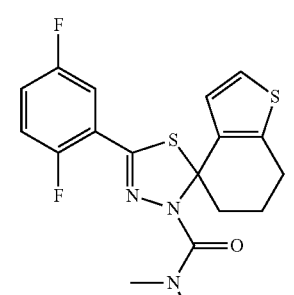 | 393.1 | 394.1 | 4.78 | D |

Example 701

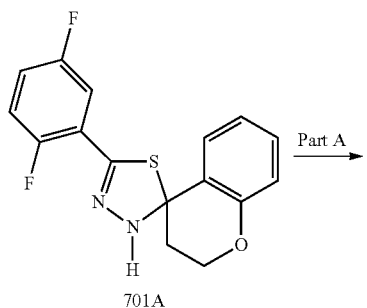

701A

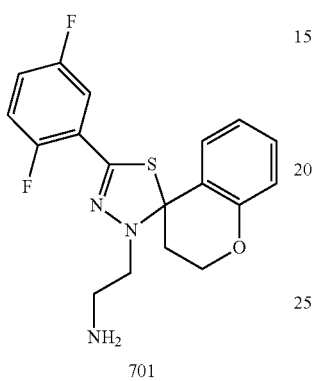

701

Compound 701A was prepared in the same procedure as 101E from chroman-4-one and 101C. A mixture of compound 701A (40 mg, 0.126 mmol), 2-boc-amino ethyl bromide (0.062 g, 0.277 mmol) and $K_2CO_3$ (0.052 g, 0.377 mmol) in DMF (2 mL) was stirred at 50° C. for 12 hours. The reaction mixture was concentrated and added TFA (1 mL). After stirring at rt for 2 min, the reaction was concentrated and purified by prep.HPLC to afford compound 701 (4 mg, 7%) as an off white solid. HPLC-MS $t_R$=3.79 min ($UV_{254\ nm}$) and the mass calculated for formula $C_{18}H_{17}F_2N_3OS$ 361.11, observed LCMS m/z 362.11 (M+H).

The following compounds in Table 701 were synthesized using this procedure:

TABLE 701

| Cpd ID | Structure | Exact mass | MS m/z ($M^+ + H$) | tR (min) | EC50 (nM) Range |
|---|---|---|---|---|---|
| 701 | 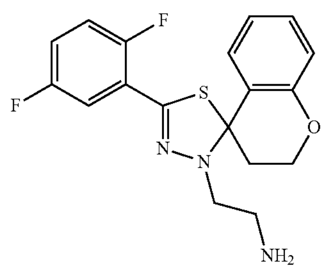 | 394.1 | 4.78 | 4.62 | D |
| 702 | 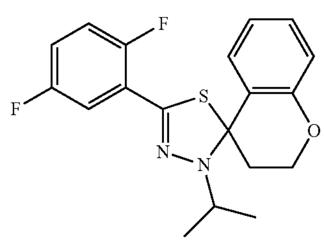 [SMILES: CC(C)N1N=C(c2cc(F)ccc2F)SC12CCOc1ccccc12] | 360.11 | 361.11 | 4.62 | D |
| 703 | 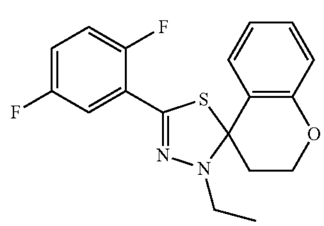 [SMILES: CCN1N=C(c2cc(F)ccc2F)SC12CCOc1ccccc12] | 346.10 | 347.10 | 4.79 | D |

TABLE 701-continued
| Cpd ID | Structure | Exact mass | MS m/z (M+ + H) | tR (min) | EC50 (nM) Range |
|---|---|---|---|---|---|
| 704 | 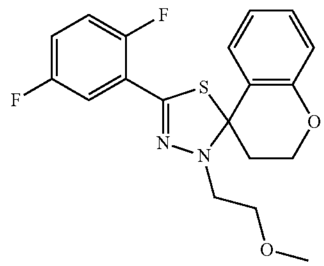 | 376.11 | 377.11 | 4.78 | D |
Example 801
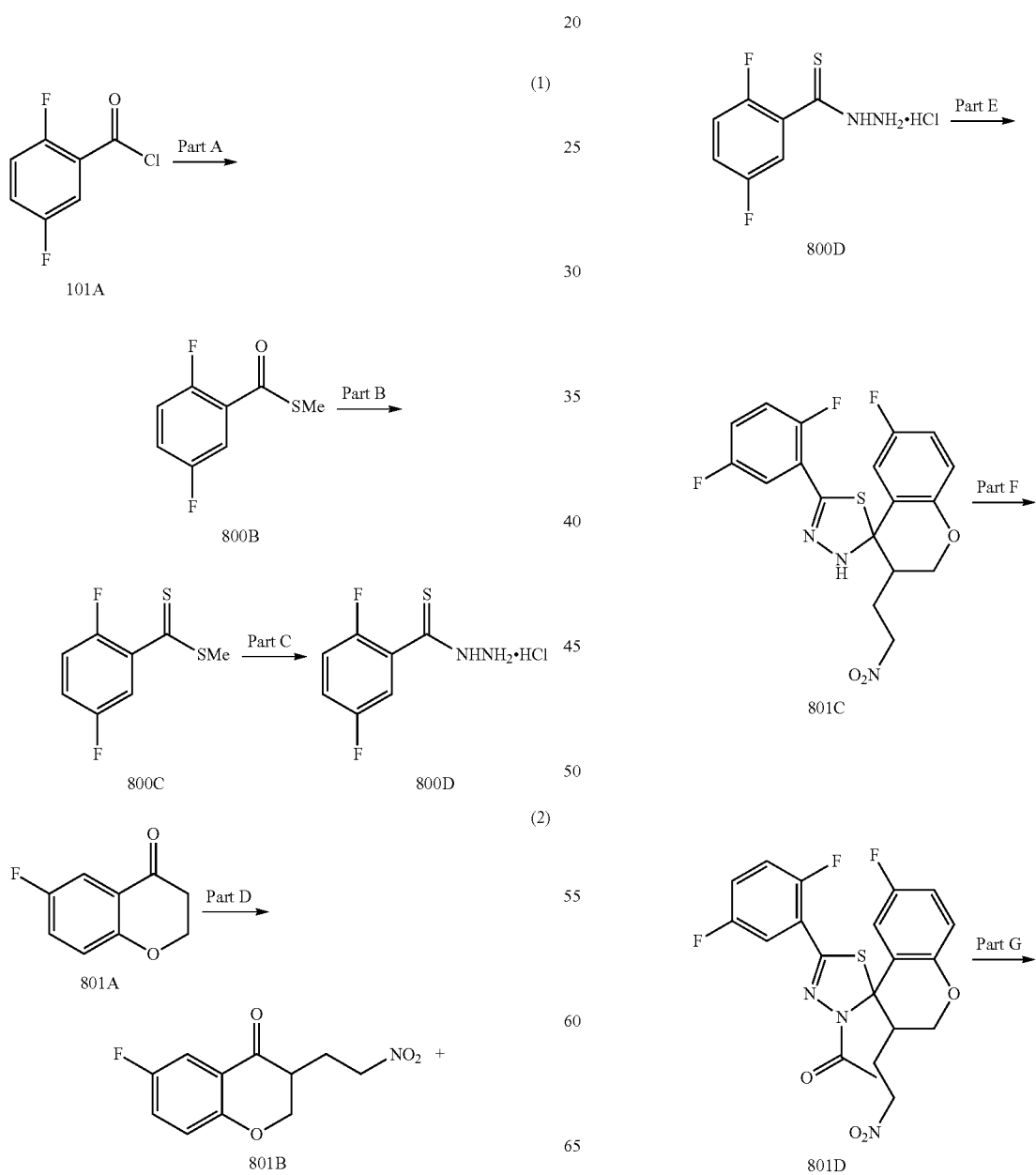

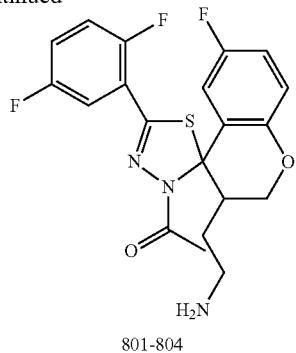

801-804

Part A:

2,5-Difluorobenzoyl chloride (compound 101A, 50g, 0.28 mol) in dichloromethane (50 mL) was added dropwise at 0° C. to a suspension of sodium methanethiolate (21.83 g, 0.31 mol, 1.1 equiv) in 200 mL of dichloromethane. After stirring at room temperature for 4 h, the solution was washed with 1N HCl (50 mL×2), saturated NaHCO$_3$ (50 mL×2) and brine (50 mL). It was then dried over Na$_2$SO$_4$ and concentrated by rotary evaporation, giving rise to Compound 800B as a colorless oil (55.1 g, 103%), which later was solidified into a white solid. $^1$H NMR (400 MHz, CDCl$_3$) δ 7.57-7.52 (m, 1H), 7.22-7.10 (m, 2H), 2.49 (s 3H).

Part B:

Lawesson's reagent (142 g, 0.35 mol) was added into a solution of compound 800B (55.1 g, 0.29 mol) in toluene (400 mL). The mixture was stirred and heated under argon to reflux for 72 h. It was then cooled to 0° C. with a ice/H2O bath. The solid was removed by suction filtration; the solution was concentrated by rotary evaporation. Flash column chromatography with silica gel (EtOAc/hexane 5:95) afforded compound 800C as a red liquid (57.0 g, 96.2%). $^1$H NMR (400 MHz, CDCl$_3$) δ 7.33-7.29 (m, 1H), 7.11-7.06 (m, 2H), 2.78 (s 3H).

Part C:

Compound 800C (57 g, 0.279 mol) in dry THF (50 mL) was added dropwise at 0° C. to a solution of hydrazine (1M, 560 mL, 0.560 mol) in THF. The red color of compound 800C disappeared almost instantly upon mixing with hydrazine. After stirring at room temperature for 1 h, the reaction mixture was concentrated to dryness by rotary evaporation. The resulting solid was then added with anhydrous EtOH (200 mL) and stirred for 10 min. The precipitate was filtered off, and toward the filtrate at 0° C. was added slowly 4 N HCl in dioxane (100 mL, 0.4 mol). Large amount of precipitate was formed, which was removed by filtration. The solution was then concentrated to dryness by rotary evaporation, affording compound 800D as a yellow solid (48.5 g, 77%). $^1$H NMR (400 MHz, DMSO-d$^6$) δ 7.31-7.28 (m, 3H).

Part D:

LHMDS (1M in THF) (33.1 mL, 33.11 mmol) was added dropwise at −78° C. under argon atmosphere to a solution of 6-fluorochroman-2-one 801A (5 g, 30.1 mmol) in 30 mL of THF. The mixture was stirred at −78° C. for 30 minutes. A solution of nitroethylene [G. D. Buckley. C. W. Scaife, J. Chem. Soc., 1947, 1471] (3.3 g, 45.1 mmol) in THF (10 mL) was added dropwise (Note: The color changed from green to blue green to orange). The reaction mixture was stirred at −78° C. for 1- h. The reaction was quenched with 1N HCl at −78° C., followed by the addition of 5 mL of H$_2$O. The −78° C. bath was removed and addition of 1N HCl was continued until the pH of the aqueous layer is around 6. The aqueous solution was extracted with ethyl acetate (3×75 mL). The combined extracts were dried over Na$_2$SO$_4$ and concentrated under reduced pressure. Purification of the crude material via Isco (10% ethyl acetate/hexanes) gave rise to the desired γ-nitro ketone Compound 801B (5.1 g, 71%) as a yellow oil, which solidified upon standing.

Part E:

To a solution of Compound 801B (5.3 g, 22.2 mmol) in 40 mL of anhydrous EtOH was added all at once Compound 800D (7.5 g, 33.2 mmol). The mixture was stirred at room temperature for 48 h. The reaction was quenched with saturated aqueous sodium bicarbonate (25 mL) and the aqueous solution was extracted with ethyl acetate (3×25 mL). The combined extracts were dried over Na$_2$SO$_4$ and concentrated under reduced pressure. Purification of the crude material via Isco (20% ethyl acetate/hexanes) gave rise to Compound 801C (8.5 g, 6:6:1:1 trans/cis) as a yellow oil. Compound 801C was used directly into the next step without further re-purification.

Part F:

To a solution of Compound 801C (8.5 g, 20.8 mmol) in 15 mL of CH$_2$Cl$_2$ was added pyridine (5.0 mL, 62.4 mmol) at 0° C., followed by acetic anhydride (2.9 mL, 31.2 mmol). The reaction mixture was warmed to room temperature and stirring was continued for 12 h. The reaction mixture was poured into H$_2$O (15 mL) and stirred for 5 minutes. The layers were separated and the aqueous solution was extracted with CH$_2$Cl$_2$ (3×15 mL). The combined extracts were dried over Na$_2$SO$_4$ and concentrated under reduced pressure. Purification of the crude material via Isco (20% ethyl acetate/hexanes) gave rise to all 4 isomers of spire thiadiazoline Compound 801D (7.8 g, 78% yield over 2 steps) as a light yellow oil, which were analyzed by chiral HPLC to contain isomers in 1:6:1:6 ratio. Chiral HPLC (100% MeOH, OD column, Chiralcel) furnished four isomers (801D1, 801D2, 801D3, 801D4) with retention times of 19.0, 19.2, 25.1, 28.3 min respectively. $^1$H NMR analysis indicated that compounds 801D1 and 801D3 were two cis isomers whereas compounds 801D2 and 801D4 were two trans isomers. $^1$H NMR (400 MHz, CDCl$_3$) for Compounds 801D1 and 801D3: δ 7.60 (m, 1 H), 7.19 (m, 2 H), 6.95 (dd, J=9.2, 2.8 Hz, 1 H), 6.89 (m, 1 H), 6.78 (dd, J=8.8, 4.8 Hz, 1H), 4.45 (app t, J=6.8 Hz, 2H), 4.30 (dd, J=12.0, 3.6 Hz, 1H), 3.85 (t, J=11.6 Hz, 1 H), 3.70 (m, 1 H), 2.49 (s, 3 H), 2.35 (m, 1 H), 2.08 (m, 1 H). $^1$H NMR (400 MHz, CDCl$_3$) for Compounds 801D2 and 801D4: $^1$H NMR (400 MHz, CDCl$_3$) δ 7.61 (m, 1 H), 7.19 (m, 3 H), 6.92 (m, 1 H), 6.81 (dd, J=8.8, 4.4 Hz, 1 H), 4.6 (t, J=11.6 Hz, 1 H), 4.51 (m, 2 H), 4.15 (dd, J=11.6, 4.8 Hz, 1 H), 2.59 (m, 1 H), 2.47 (m, 1 H), 2.40 (s, 3 H), 2.0 (m, 1 H). Furthermore, X-ray crystallography determined that Compound 801D4 had a (R,S) configuration.

Part G:

To a solution of Compound 801D2 (128 mg, 0.283 mmol) in EtOH (3 mL) was added AcOH (0.45 mL) and Zinc dust (200 mg, 3.08 mmol). The reaction mixture was stirred at room temperature for 12 h. The solution was filtered through a pad of celite and the filtrate was concentrated. The crude material was purified by reverse phase HPLC (Varian Pursuit XRs 10µ C-18 250×21.2 mm) to afford the desired compound 802 (56 mg, 47%) as the major product and the partial reduction compound (hydroxylamine) as the minor product (24 mg, 20%). HPLC-MS $t_R$=3.53 min (UV$_{254\,nm}$); mass calculated for formula $C_{20}H_{18}F_3N_3O_2S$ 421.1, observed LCMS m/z 422.1 (M+H).

The following compounds in Table 801 were synthesized using this procedure:

TABLE 801

| Cpd ID | Structure | Exact mass | MS m/z (M⁺ + H) | tR (min) | 1H NMR | EC50 (nM) Range |
|---|---|---|---|---|---|---|
| 801 | 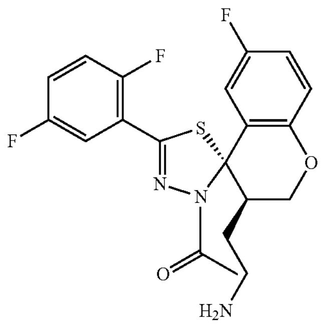 [SMILES: CC(=O)N1N=C(c2cc(F)ccc2F)S[C@@]12c1cc(F)ccc1OC[C@H]2CCN] | 421.1 | 422.1 | 3.53 | (CD₃OD) δ: 7.80-7.67 (m, 1 H), 7.35-7.31 (m, 2 H), 7.26 (dd, J = 9.6, 3.2 Hz, 1 H), 6.98 (ddd, J = 10.8, 8.4, 2.8 Hz 1 H), 6.84 (dd, J = 9.2, 4.8 Hz, 1 H), 4.45 (t, J = 11.2 Hz, 1 H), 4.30 (dd, J = 10.4, 4.0 Hz, 1H), 3.15-3.05 (m, 2 H), 3.70 (m, 1 H), 2.72-2.70 (m, 1 H), 2.41 (s, 3 H), 2.09-2.01 (m, 1 H), 1.90-1.50 (m, 1 H). | A |
| 802 | 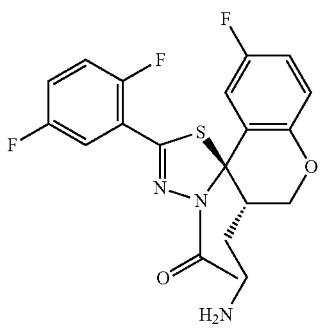 [SMILES: CC(=O)N1N=C(c2cc(F)ccc2F)S[C@]12c1cc(F)ccc1OC[C@@H]2CCN] | 421.1 | 422.1 | 3.57 | (CD₃OD) δ: 7.80-7.67 (m, 1 H), 7.35-7.31 (m, 2 H), 7.26 (dd, J = 9.6, 3.2 Hz, 1 H), 6.98 (ddd, J = 10.8, 8.4, 2.8 Hz 1 H), 6.84 (dd, J = 9.2, 4.8 Hz, 1 H), 4.45 (t, J = 11.2 Hz, 1 H), 4.30 (dd, J = 10.4, 4.0 Hz, 1H), 3.15-3.05 (m, 2 H), 3.70 (m, 1 H), 2.72-2.70 (m, 1 H), 2.41 (s, 3 H), 2.09-2.01 (m, 1 H), 1.90-1.50 (m, 1 H). | D |
| 803 | 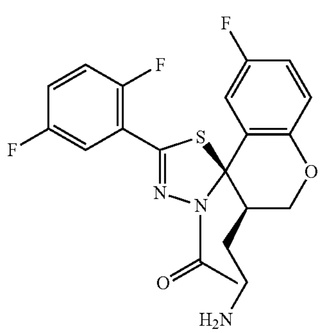 [SMILES: CC(=O)N1N=C(c2cc(F)ccc2F)S[C@]12c1cc(F)ccc1OC[C@H]2CCN] | 421.1 | 422.1 | 3.52 | (CD₃OD) δ: 7.33-7.29 (m, 2 H), 7.08 (dd, J = 9.6, 3.2 Hz, 1 H), 6.95 (ddd, J = 11.2, 8.0, 3.2 Hz 1 H), 6.80 (dd, J = 9.2, 4.4 Hz, 1 H), 4.63 (app dd, J = 12.8, 7.2 Hz, 2 H), 4.43 (dd, J = 11.6, 3.2 Hz, 1 H), 3.84 (t, J = 12 Hz, 1 H), 3.53-3.47 (m, 1 H), 2.47 (s, 3 H), 2.38-2.33 (m, 1 H), 2.03-1.90 (m, 1 H). | A |

TABLE 801-continued

| Cpd ID | Structure | Exact mass | MS m/z (M⁺ + H) | tR (min) | 1H NMR | EC50 (nM) Range |
|---|---|---|---|---|---|---|
| 804 | 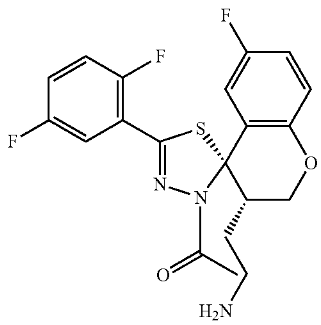 [SMILES: CC(=O)N1N=C(c2cc(F)ccc2F)S[C@@]12c1cc(F)ccc1OC[C@@H]2CCN] | 421.1 | 422.1 | 3.55 | (CD₃OD) δ: 7.33-7.29 (m, 2 H), 7.08 (dd, J = 9.6, 3.2 Hz, 1 H), 6.95 (ddd, J = 11.2, 8.0, 3.2 Hz 1 H), 6.80 (dd, J = 9.2, 4.4 Hz, 1 H), 4.63 (app dd, J = 12.8, 7.2 Hz, 2 H), 4.43 (dd, J = 11.6, 3.2 Hz, 1 H), 3.84 (t, J = 12 Hz, 1 H), 3.53-3.47 (m, 1 H), 2.47 (s. 3 H), 238-2.33 (m, 1 H), 2.03-1.90 (m, 1 H). | A |
| 805 | 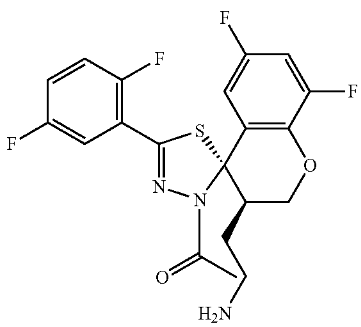 [SMILES: CC(=O)N1N=C(c2cc(F)ccc2F)S[C@@]12c1cc(F)cc(F)c1OC[C@H]2CCN] | 360.1 | 361.1 | 4.11 | (CD₃OD) δ: 7.80-7.69 (m, 1 H), 7.36-7.32 (m, 2 H), 7.18-7.14 (m, 1 H), 7.00-6.95 (m, 1 H), 4.55 (1, J = 10.8 Hz, 1 H), 4.35 (dd, J = 10.8, 4.4 Hz, 1H), 3.15-3.05 (m, 2 H), 2.80-2.70 (m, 1 H), 2.40 (a, 3 H), 2.09-2.06 (m, 1 H), 1.80-1,60 (m, 1 H). | A |
| 806 | 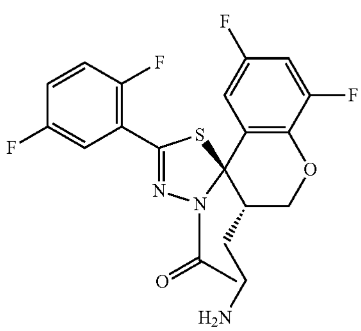 [SMILES: CC(=O)N1N=C(c2cc(F)ccc2F)S[C@]12c1cc(F)cc(F)c1OC[C@@H]2CCN] | 360.1 | 361.1 | 4.18 | (CD₃OD) δ: 7.80-7.69 (m, 1 H), 7.36-7.32 (m, 2 H), 7.18-7.14 (m, 1 H), 7.00-6.95 (m, 1 H), 4.55 (t, J = 10.8 Hz, 1 H), 4.35 (dd, J = 10.8, 4.4 Hz, 1H), 3.15-3.05 (m, 2 H), 2.80-2.70 (m, 1 H), 2.40 (s, 3 H), 2.09-2.06 (m, 1 H), 1.80-1.60 (m, 1 H). | D |
| 807 | 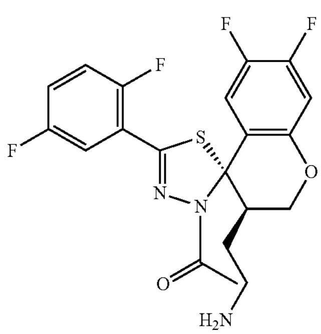 [SMILES: CC(=O)N1N=C(c2cc(F)ccc2F)S[C@@]12c1cc(F)c(F)cc1OC[C@H]2CCN] | 439.1 | 440.1 | 4.20 | (CD₃OD) δ: 7.80-7.69 (m, 1 H), 7.51 (dd, J = 11.6, 8.8 Hz, 1 H), 7.36-7.31 (m, 2 H), 6.76 (dd, J = 11.6, 72 Hz, 1 H), 4.52 (t, J = 10.8 Hz, 1 H), 4.27 (dd, J = 11.6, 4.8 Hz, 1 H), 3.14-3.02 (m, 2 H), 2.72-2.70 (m, 1 H), 2.41 (s, 3 H), 2.09-2.00 (m, 1 H), 1.90-1.50 (m, 1 H). | A |

TABLE 801-continued

| Cpd ID | Structure | Exact mass | MS m/z (M⁺ + H) | tR (min) | 1H NMR | EC50 (nM) Range |
|---|---|---|---|---|---|---|
| 808 | 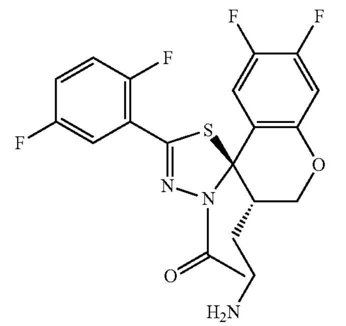 [SMILES: CC(=O)N1N=C(c2cc(F)ccc2F)S[C@]12c1cc(F)c(F)cc1OC[C@@H]2CCN] | 439.1 | 440.1 | 4.22 | (CD₃OD) δ: 7.80-7.69 (m, 1 H), 7.51 (dd, J = 11.6, 8.8 Hz, 1 H), 7.36-7.31 (m, 2 H), 6.76 (dd, J = 11.6, 7.2 Hz, 1 H), 4.52 (t, J = 10.8 Hz, 1 H), 4.27 (dd, J = 11.6, 4.8 Hz, 1 H), 3.14-3.02 (m, 2 H), 2.72-2.70 (m, 1 H), 2.41 (s, 3 H), 2.09-2.00 (m, 1 H), 1.90-1.50 (m, 1 H). | D |
| 809 | 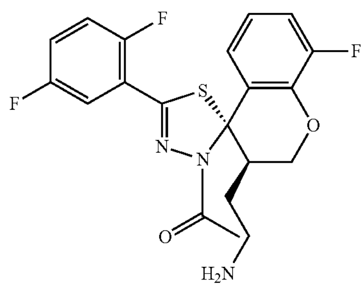 [SMILES: CC(=O)N1N=C(c2cc(F)ccc2F)S[C@@]12c1cccc(F)c1OC[C@H]2CCN] | 421.1 | 422.1 | 4.02 | (CD₃OD) δ: 7.80-7.69 (m, 1 H), 7.37-7.31 (m, 2 H), 7.07-7.02 (m, 1 H), 6.90 (ddd, J = 16, 8.4, 4.8 Hz, 1 H), 4.58 (t, J = 10.4 Hz, 1 H), 4.36 (dd, J = 11.2, 4.8 Hz, 1 H), 3.16-3.06 (m, 2 H), 2.80-2.73 (m, 1 H), 2.38 (s, 3 H), 2.15-2.03 (m, 1 H), 1.79-1.55 (m, 1 H). | A |
| 810 | 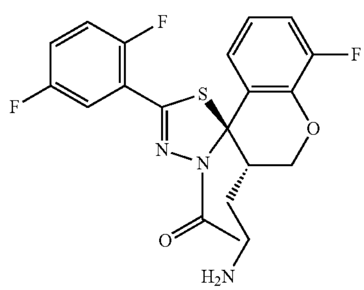 [SMILES: CC(=O)N1N=C(c2cc(F)ccc2F)S[C@]12c1cccc(F)c1OC[C@@H]2CCN] | 421.1 | 422.1 | 4.00 | (CD₃OD) δ: 7.60-7.69 (m, 1 H), 7.37-7.31 (m, 2 H), 7.07-7.02 (m, 1 H), 6.90 (ddd, J = 16, 8.4, 4.8 Hz, 1 H), 4.58 (t, J = 10.4 Hz, 1 H), 4.36 (dd, J = 11.2, 4.8 Hz, 1 H), 3.16-3.06 (m, 2 H), 2.80-2.73 (m, 1 H), 2.38 (s, 3 H), 2.15-2.03 (m, 1 H), 1.79-1.55 (m, 1 H). | D |
| 811 | | 437.1 | 438.1 | 4.41 | (CD₃OD) δ: 7.80-7.69 (m, 1 H), 7.52 (d, J = 2.4 Hz, 1 H), 7.36-729 (m, 2 H), 7.20 (dd, J = 9.2, 3.2 Hz, 1 H), 6.8 (d, J = 9.2 Hz, 1 H), 4.49 (t, J = 10.8 Hz, 1 H), 4.27 (dd, J = 11.2, 4.4 Hz, 1 H), 3.16-3.02 (m, 2 H), 2.73-2.65 (m, 1 H), 2.40 (s, 3 H), 2.10-2.02 (m, 1 H), 1.79-1.55 (m, 1 H). | A | ns

TABLE 801-continued

| Cpd ID | Structure | Exact mass | MS m/z (M+ + H) | tR (min) | 1H NMR | EC50 (nM) Range |
|---|---|---|---|---|---|---|
| 812 | 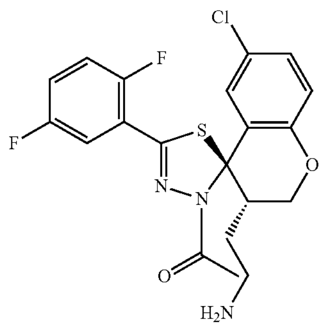 [SMILES: CC(=O)N1N=C(c2cc(F)ccc2F)S[C@]12c1cc(Cl)ccc1OC[C@@H]2CCN] | 437.1 | 438.1 | 4.41 | (CD₃OD) δ: 7.80-7.69 (m, 1 H), 7.52 (d, J = 2.4 Hz, 1 H), 7.36-7.29 (m, 2 H), 7.20 (dd, J = 9.2, 3.2 Hz, 1 H), 6.8 (d, J = 9.2 Hz, 1 H), 4.49 (t, J = 10.8 Hz, 1 H), 4.27 (dd, J = 11.2, 4.4 Hz, 1 H), 3.16-3.02 (m, 2 H), 2.73-2.65 (m, 1 H), 2.40 (s, 3 H), 2.10-2.02 (m, 1 H), 1.79-1.55 (m, 1 H). | D |
| 813 | 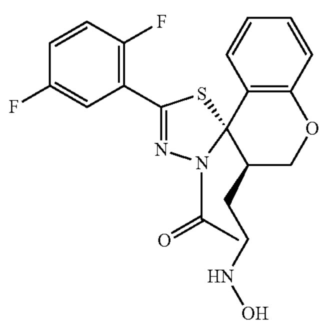 [SMILES: CC(=O)N1N=C(c2cc(F)ccc2F)S[C@@]12c1ccccc1OC[C@H]2CCNO] | 419.1 | 420.1 | 3.66 | (CD₃CN) δ: 7.75-7.70 (m, 1 H), 7.60 (dd, J = 8.0, 1.6 Hz, 1 H), 7.33-7.29 (m, 2 H), 7.25-7.21 (m, 1 H), 6.99-6.95 (m, 1 H), 6.83 (dd, J = 8.4, 2.4 Hz, 1 H), 4.50 (t, J = 11.6 Hz, 1 H), 4.27 (dd, J = 10.8, 4.8 Hz, 1 H), 3.42-3.28 (m, 2 H), 2.74-2.67 (m, 1 H), 2.30 (s, 3 H), 2.20-2.12 (m, 1 H), 1.79-1.55 (m, 1 H). | A |
| 814 | 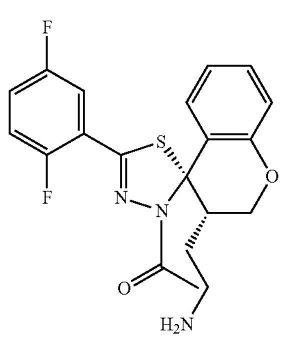 [SMILES: CC(=O)N1N=C(c2cc(F)ccc2F)S[C@@]12c1ccccc1OC[C@@H]2CCN] | 403.1 | 404.3 | 3.23 | (CD₃OD) δ: 7.70-7.65 (m, 1 H), 7.34-7.28 (m, 3 H), 7.21-7.16 (m, 1 H), 6.97-6.93 (m, 1 H), 6.81 (dd, J = 8.2, 1.2 Hz, 1 H), 4.48 (dd, J = 12.1, 3.5 Hz, 1 H), 3.89 (t, 1 H), 3.71-3.64 (m, 1 H), 3.18-3.11 (m, 1 H), 3.04-2.97 (m, 1 H), 2.47 (s, 3 H), 2.02-1.94 (m, 1 H), 1.88-1.79 (m, 1 H) | A |

TABLE 801-continued

| Cpd ID | Structure | Exact mass | MS m/z (M⁺ + H) | tR (min) | 1H NMR | EC50 (nM) Range |
|---|---|---|---|---|---|---|
| 815 | 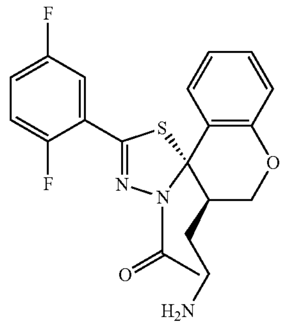 [SMILES: CC(=O)N1N=C(c2cc(F)ccc2F)S[C@@]12c1ccccc1OC[C@H]2CCN] | 403.1 | 404.2 | 3.19 | (CD₃OD) δ: 7.72-7.68 (m, 1 H), 7.55-7.52 (m, 1 H), 7.35-7.31 (m, 2 H), 7.22-7.18 (m, 1 H), 6.97-6.93 (m, 1 H), 6.82 (dd, J = 8.6, 1.1 Hz, 1 H), 4.55 (t, J = 16.3 Hz, 1 H), 4.26 (dd, J = 10.9, 4.3 Hz, 1 H), 3.18-3.02 (m, 2 H), 2.76-2.69 (m, 1 H), 2.38 (s, 3 H), 2.14-2.05 (m, 1 H), 1.73-1.65 (m, 1 H) | A |
| 816 | 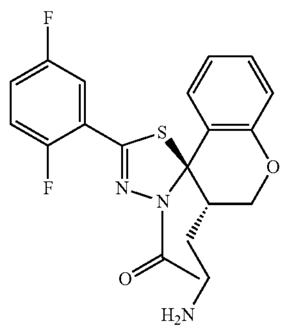 [SMILES: CC(=O)N1N=C(c2cc(F)ccc2F)S[C@]12c1ccccc1OC[C@@H]2CCN] | 403.1 | 404.3 | 3.26 | (CD₃OD) δ: 7.72-7.68 (m, 1 H), 7.55-7.52 (m, 1 H), 7.35.7.31 (m, 2 H), 7.22-7.18 (m, 1 H), 6.97-6.93 (m, 1 H), 6.82 (dd, J = 8.6, 1.1 Hz, 1 H), 4.55 (t, J = 16.3 Hz, 1 H), 4.26 (dd, J = 10.9, 4.3 Hz, 1 H), 3.18-3.02 (m, 2 H), 2.76-2.69 (m, 1 H), 2.38 (s, 3 H), 2.14-2.05 (m, 1 H), 1.73-1.65 (m, 1 H) | D |
| 817 | 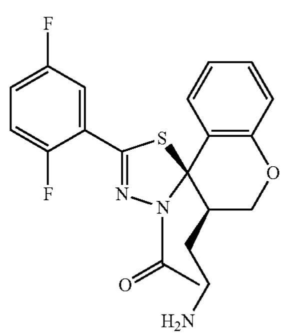 [SMILES: CC(=O)N1N=C(c2cc(F)ccc2F)S[C@]12c1ccccc1OC[C@H]2CCN] | 403.1 | 404.3 | 3.26 | (CD₃OD) δ: 7.70-7.65 (m, 1 H), 7.34-7.28 (m, 3 H), 7.21-7.16 (m, 1 H), 6.97-6.93 (m, 1 H), 6.81 (dd, J = 8.2, 1.2 Hz, 1 H), 4.48 (dd, J = 12.1, 3.5 Hz, 1 H), 3.89 (t, 1H), 3.71-3.64 (m, 1 H), 3.18-3.11 (m, 1 H), 3.04-2.97 (m, 1 H), 2.47 (s, 3 H), 2.02-1.94 (m, 1 H), 1.88-1.79 (m, 1 H) | A |

It is contemplated that the following compounds represent additional non-limiting examples of compounds of the invention which can be made, for example, according to the above procedure:

| Cpd ID | Structure |
|---|---|
| 818 | 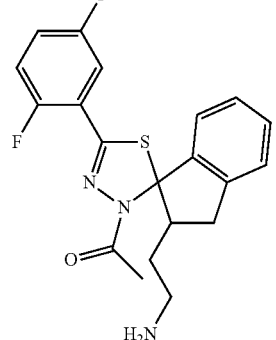 |
| 819 | 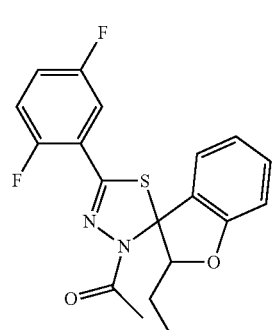 | and.

Example 901

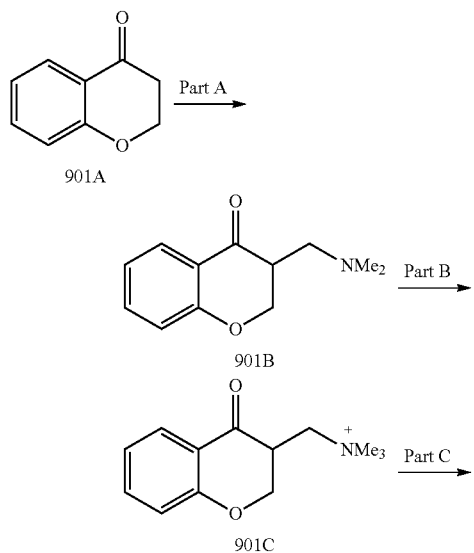

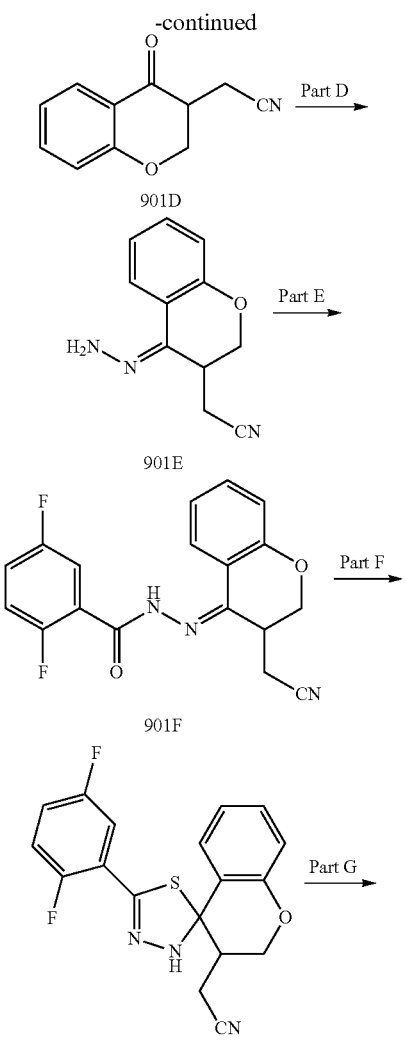

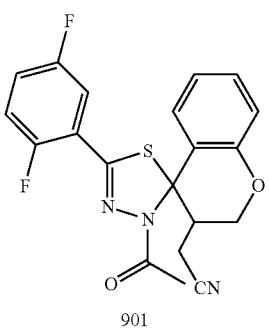

Part A:

To a solution of 4-chromanone 901A (20 g, 135.0 mmol) and Dimethyl amine (11.0 g, 135.0 mmol) in Ethanol (40 mL) in a 150 mL high pressure vessel were added 4 N HCl to keep PH around 2 and paraformaldehyde (12.2 g, 135.0 mmol). The reaction mixture was stirred at 100° C. for 3 h. After removal of solvent, the solution was washed with dimethyl chloride (50 mL), Sat. NaHCO$_3$ (100 mL), extracted with Ethyl acetate (30 mL×3). The combined organic layers were dried over Na$_2$SO$_4$, and then evaporated solvent under vacuum to afford oil 901B (21.0 g, 78%). The product was used for next step without further purification.

Part B:

To a solution of 901B (21 g, 102.4 mmol) in Acetone (50 mL) in a 100 mL round bottom flask was added methyl iodide (12.7 mL, 204.9 mmol). The result mixture was stirred at room temperature over night. A lot of white solid precipitated. Filtrated solution, and then the solids were washed with ethyl ether to afford 901C (24g, 68%).

Part C:

To a cloudy solution of 901C (5 g, 14.41 mmol) in DMSO (40 mL) and $H_2O$ (5 mL) was added potassium cyanide (1.2 g, 18.7 mmol) in a 100 mL round bottom flask. Reaction mixture stirred at rt for 2 h, then 20 ml water was added to quench it. The result solution was extracted with Ethyl acetate (30 mL×3). The combined organic layers were dried over $Na_2SO_4$, and then evaporated solvent under Vacuum. The residue was purified from isco (20% Ethyl acetate in hexanes) to afforded 901D (1.2 g, 64%).

Part D:

To a solution of 901D (2.0 g, 10.7 mmol) and hydrazine monohydrate (1.6 mL, 32.05 mmol) in Ethanol (40 mL) was added acetic acid (100 mL). The reaction mixture was stirred at rt overnight. After removal of solvent, the residue was dissolved in Ethyl acetate (50 mL) and then washed with Sat. $NaHCO_3$ (100 mL) and brine. The organic layer was dried over $Na_2SO_4$, and then evaporated solvent under vacuum to afford oil 901E which was used for next step without further purification.

Part E:

To a solution of 901E (2.1 g, 10.7 mmol) in THF (50 mL) in a 250 mL round bottom flask was added pyridine (1.04 mL, 12.8 mmol). The result mixture was cooled to 0° C. then added 2,5-difluorobenzoyl chloride (1.46 mL, 11.8 mmol) solution in THF (8 mL). Reaction mixture was stirred at low temperature for 40 minutes and raised to rt for 1 h. A lot of white solid precipitated. Evaporated solvent and added Ethanol (10 mL) to solidification. Filtrated solution, and then the solid were washed with ethyl ether to afford 901F (2.5 g, 89%).

Part F-G:

To a solution of 901F (300 mg, 0.88 mmol) in THF (5 mL) was added $P_2S_5$ (500 mg, 1.12 mmol) and HMDO (1.5 mL, 7.05 mmol). The reaction was heated in Microwave at 100° C. for 25 minutes. The reaction was concentrated, diluted with EtOAc and passed through plug of silica to afford compound 901G as yellow oil. To a solution of 901G in THF (5 mL) was added AcCl (1 mL), DIEA (0.6 mL, 4.3 mmol) and the reaction was stirred at rt overnight. The solvent was removed under reduced pressure and the residue was dissolved in EtOAC (200 mL) which was then washed with 1 N HCl, Brine, dried over sodium sulfate and concentrated. The residue was purified by column chromatography to provide 901. HPLC-MS $t_R$=5.93 min ($UV_{254\ nm}$); mass calculated for formula C20H15F2N3O2S 399.09, observed LCMS m/z 400.0 (M+H). Chiral HPLC separation afforded isomers 902-905.

The following compounds were synthesized using this procedure:

| Cpd ID | Structure | Exact mass | MS m/z (M⁺ + H) | tR (min) | 1H NMR | EC50 (nM) Range |
|---|---|---|---|---|---|---|
| 902 | 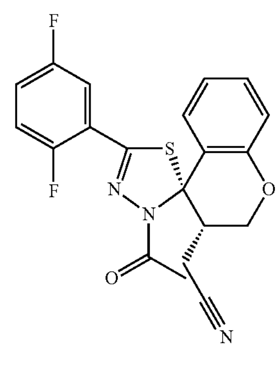 [SMILES: CC(=O)N1N=C(c2cc(F)ccc2F)S[C@@]12c1ccccc1OC[C@@H]2CC#N] | 399.1 | 400.1 | 5.97 | (CD₃OD) δ: 7.72-7.67 (m, 1 H), 7.56 (dd, J = 8.2, 1.6 Hz, 1 H), 7.33-7.29 (m, 2 H), 7.23-7.19 (m, 1H), 6.98-6.94 (m, 1 H), 6.84 (dd, J = 8.2, 1.2 Hz, 1 H), 4.60 (dd, J = 11.3, 9.4 Hz, 1 H), 4.34 (dd, J = 11.0, 3.9 Hz, 1 H), 3.04-2.99 (m, 1 H), 2.91 (dd, J = 17.2, 6.2 Hz, 1 H), 2.75 (dd, J = 17.2, 7.0 Hz, 1 H), 2.39 (s, 3 H) | A |
| 903 | 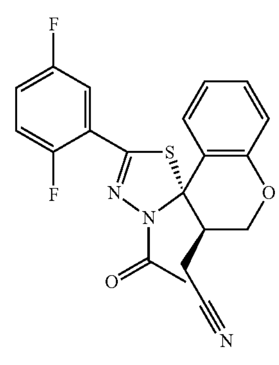 [SMILES: CC(=O)N1N=C(c2cc(F)ccc2F)S[C@@]12c1ccccc1OC[C@H]2CC#N] | 399.1 | 400.1 | 5.97 | (CDCl₃) δ: 7.63-7.59 (m, 1 H), 7.48 (d, J = 7.8 Hz, 1 H), 7.31-7.14 (m, 3 H), 6.97 (t, J = 7.0 Hz, 1 H), 6.88 (d, J = 8.6 Hz, 1 H), 4.67 (dd, J = 10.9, 9.0 Hz, 1 H), 4.00 (dd, J = 11.3, 3.9 Hz, 1 H), 2.94-2.90 (m, 1 H), 2.80 (dd, J = 16.8, 5.1 Hz, 1 H), 2.54 (dd, J = 17.2, 9.4 Hz, 1 H), 2.41 (s, 3 H) | A |

| Cpd ID | Structure | Exact mass | MS m/z (M+ + H) | tR (min) | 1H NMR | EC50 (nM) Range |
|---|---|---|---|---|---|---|
| 904 | 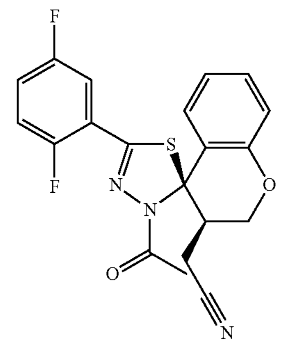 [SMILES: CC(=O)N1N=C(c2cc(F)ccc2F)S[C@]12c1ccccc1OC[C@H]2CC#N] | 399.1 | 400 | 5.98 | (CD3OD) δ: 7.72-7.67 (m, 1 H), 7.56 (dd, J = 8.2, 1.6 Hz, 1 H), 7.33-7.29 (m, 2 H), 7.23-7.19 (m, 1H), 6.98-6.94 (m, 1 H), 6.84 (dd, J = 8.2, 1.2 Hz, 1 H), 4.60 (dd, J = 11.3, 9.4 Hz, 1 H), 4.34 (dd, J = 11.0, 3.9 Hz, 1 H), 3.04-2.99 (m, 1 H), 2.91 (dd, J = 17.2, 6.2 Hz, 1 H), 2.75 (dd, J = 17.2, 7.0 Hz, 1 H), 2.39 (s, 3 H) | C |
| 905 | 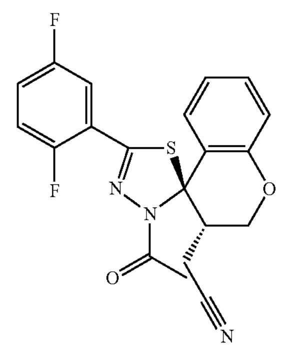 [SMILES: CC(=O)N1N=C(c2cc(F)ccc2F)S[C@]12c1ccccc1OC[C@@H]2CC#N] | 399.1 | 400 | 5.98 | (CDCl3) δ: 7.63-7.59 (m, 1 H), 7.48 (d, J = 7.8 Hz, 1 H), 7.31-7.14 (m, 3 H), 6.97 (1, J = 7.0 Hz, 1 H), 6.88 (d, J = 8.6 Hz, 1 H), 4.67 (dd, J = 10.9, 9.0 Hz, 1 H), 4.00 (dd, J = 11.3, 3.9 Hz, 1 H), 2.94-2.90 (m, 1 H), 2.80 (dd, J = 16.8, 5.1 Hz, 1 H), 2.54 (dd, J = 17.2, 9.4 Hz, 1 H), 2.41 (s, 3 H) | D |
| 906 | 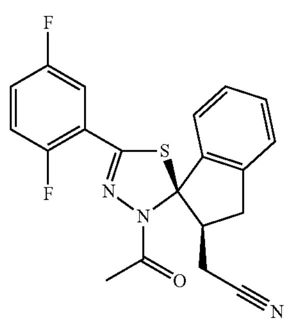 [SMILES: CC(=O)N1N=C(c2cc(F)ccc2F)S[C@]12c1ccccc1C[C@H]2CC#N] | 383.09 | 384.09 | 4.02 | | A |
| 907 | 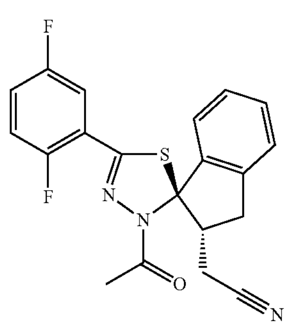 [SMILES: CC(=O)N1N=C(c2cc(F)ccc2F)S[C@]12c1ccccc1C[C@@H]2CC#N] | 383.09 | 384.09 | 4.13 | | A |

Example 1001

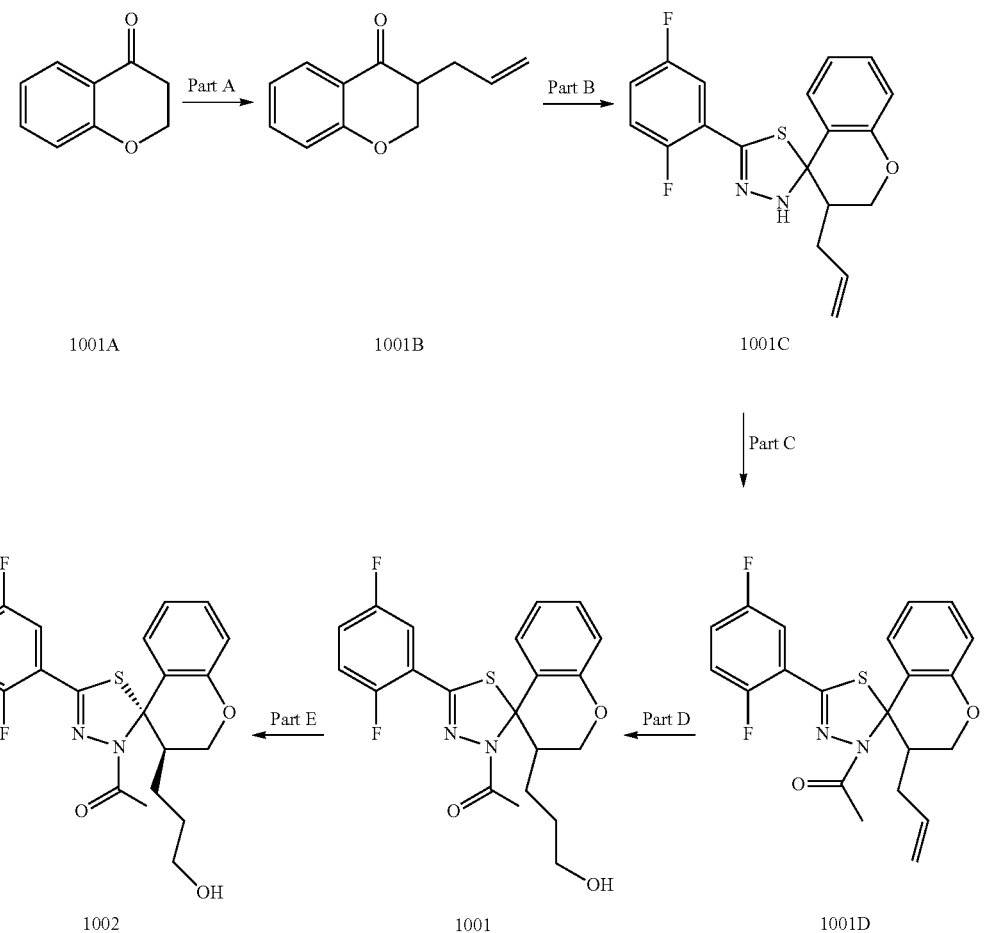

Part A:
To a solution of 1 (10.0 g, 67.5 mmol) allyl alcohol (13.8 mL, 202.5 mmol) and xylene (80 mL) in a reseal able tube were added 2,2-dimethoxypropane (12.4 mL, 101.3 mmol), p-toluenesulfonic acid (2 g, 11.5 mmol) and 3 Å molecular sieves (10g). The tube was sealed and heated in oil bath at 200° C. overnight. After the reaction mixture was cool, the solids were filtered. The solution was concentrated and purified by column chromatography to provide compound 1001B (4.5 g, 35° A)).

Part B:
To a solution of compound 1001B (4.4 g, 23.4 mmol) in EtOH (60 mL) was added thiolhydrazide (7.9 g, 35.1 mmol). The reaction was stirred at rt overnight. The reaction mixture was concentrated and then purified by column chromatography to obtain compound 1001C as yellow oil which was used in the next step. HPLC-MS $t_R$=2.50 min ($UV_{254\ nm}$); mass calculated for formula C19H16F2N2OS 358.10, observed LCMS m/z 359.1 (M+H).

Part C:
A mixture of compound 1001C (7 g, 19.55 mmol), acetic anhydride (3.0 mL, 29.4 mmol) and pyridine (5 mL, 61.9 mmol) in DCM (5 mL) was stirred at room temperature for 16 hours. After removal of solvent, the residue was dissolved in Ethyl acetate (150 mL) and then washed with Sat. NaHCO₃ (100 mL) and brine. The organic layer was dried over Na₂SO₄, and then evaporated solvent under vacuum. The residue was purified by column chromatography to afford compound 1001D as a white solid (6.9 g, 88%). HPLC-MS $t_R$=2.57 min ($UV_{254\ nm}$); mass calculated for formula C21H18F2N2O2S 400.11, observed LCMS m/z 401.1 (M+H).

Part D:
A solution of compound 1001D (700 mg, 1.75 mmol) in THF (2 mL) was added 0.5 M, 9-BBN THF solution (25 mL, 12.5 mmol). After the reaction mixture was stirred at rt 2 h, 1 N NaOH (5 mL) was added followed by adding 35 wt % H₂O₂ in water (5 mL). The result mixture was stirred another 1 h. Quanched by 1 N HCl to pH 1 and diluted with DCM. The organic layer was washed with brine, dried over Na₂SO₄, and then evaporated solvent under vacuum. The residue was purified by column chromatography to afford compound 1001 as a white solid (630.0 mg, 86%). HPLC-MS $t_R$=2.10 min ($UV_{254\ nm}$); mass calculated for formula C21H20F2N2O3S 418.12, observed LCMS m/z 419.1 (M+H).

Part E:
The two Trans isomers were separated using a chiralcel OD column (30% EtOH in Hexs) to obtain desired white solid compound 1002 at first peak and compound 1003 at second peak. HPLC-MS=5.46 min ($UV_{254\ nm}$); mass calculated for formula C21H20F3N2O3S 418.12, observerd LCMS m/z 419.2 (M+H).

| Cpd ID | Structure | Exact mass | MS m/z (M+ + H) | tR (min) | 1H NMR | EC50 (nM) Range |
|---|---|---|---|---|---|---|
| 1002 | 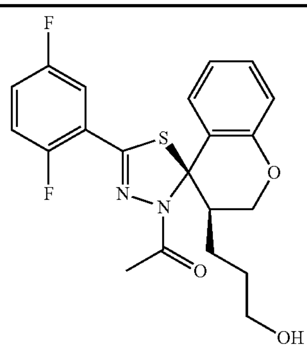 | 418.1 | 419.2 | 5.5 | (CDCl₃) δ: 7.63-7.56 (m, 1 H), 7.52-7.49 (m, 1 H), 7.21-7.13 (m, 3 H), 6.97-6.91 (m, 1 H), 6.85-6.83 (m, 1 H), 4.62-4.55 (m, Hz, 1 H), 4.37 (t, J = 6.3 Hz, 1 H), 4.26-4.19 (m, 1H), 4.11 (br, s, 1 H), 3.71 (t, J = 6.6 Hz, 1 H), 2.58-2.41 (m, 1H), 2.39 (s, 3 H), 2.10-1.58 (m, 3 H), 1.42-1.33 (m, 1 H) | A |
| 1003 | 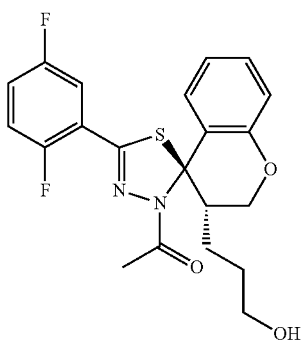 [SMILES: CC(=O)N1N=C(c2cc(F)ccc2F)S[C@]12c1ccccc1OC[C@@H]2CCCO] | 418.1 | 419.2 | 5.5 | (CDCl₃) δ: 7.63-7.58 (m, 1 H), 7.52-7.49 (m, 1 H), 7.21-7.13 (m, 3 H), 6.97-6.91 (m, 1 H), 6.85-6.83 (m, 1 H), 4.62-4.55 (m, Hz, 1 H), 4.37 (t, J = 6.3 Hz, 1 H), 4.26-4.19 (m, 1H), 4.11 (br, s, 1 H), 3.71 (t, J = 6.6 Hz, 1 H), 2.58-2.41 (m, 1 H), 2.39 (s, 3 H), 2.10-1.58 (m, 3 H), 1.42-1.33 (m, 1 H) | D |
Example 1004

353
-continued

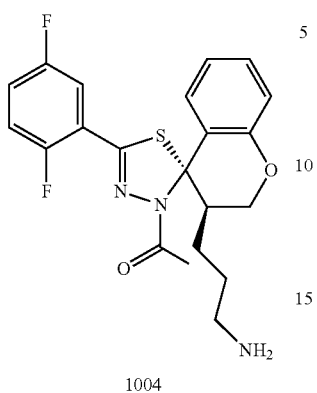

1004

354

Part A:

To a solution of 1002 (160.0 mg, 0.38 mmol) in dry toluene (5 mL) were added polymer-triphenylphosphine (3 mmol/g, 191.0 mg, 0.57), DIAD (0.115 mL, 0.57) and DPPA (157.0 mg, 0.57 mmol). The reaction mixture was stirred at rt overnight. After the solids were filtered, filtrate was concentrated and purified by column chromatography to provide 1004B (60.0 mg, 37%).

Part B:

A mixture of 1004B (60 mg, 0.14 mmol) and polymer-triphenylphosphine (130 mg) in Toluene (5 mL) was stirred at 120° C. 15 min and then water (1 mL) was added. After the result mixture stirred for another 40 min, the solids were filtered. The filtrate was concentrated and purified by HPLC to afford white HCl solid 1004 (22.8 mg, 38%). HPLC-MS $t_R$=4.18 min (UV$_{254\ nm}$); mass calculated for formula C21H21F2N3O2S 417.13, observed LCMS m/z 418.3 (M+H).

| Cpd ID | Structure | Exact mass | MS m/z (M$^+$ + H) | tR (min) | 1H NMR | EC50 (nM) Range |
|---|---|---|---|---|---|---|
| 1004 | 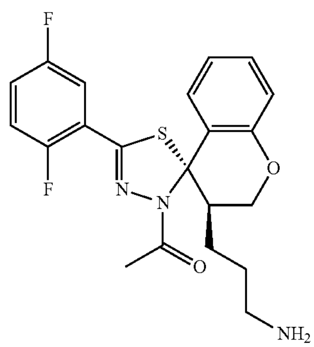 [SMILES: CC(=O)N1N=C(c2cc(F)ccc2F)S[C@@]12c1ccccc1OC[C@H]2CCCN] | 417.1 | 418.3 | 4.21 | (CD$_3$OD) δ: 7.71-7.67 (m, 1 H) 7.51 (dd, J = 7.8, 1.6 Hz, 1 H), 7.34-7.29 (m, 2 H), 7.20-7.16 (m, 1 H), 6.95-6.91 (m, 1 H), 6.80 (dd, J = 8.2, 1.2 Hz, 1 H), 4.52 (t, J = 11.3 Hz, 1 H), 4.28 (dd, J = 10.9, 4.7 Hz, 1H), 3.01-2.91 (m, 2 H), 2.61-2.57 (m, 1 H), 2.37 (s, 3 H), 1.94-1.70 (m, 3 H), 1.46-1.35 (m, 1 H) | A |
| 1005 | 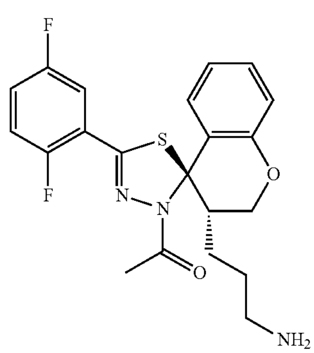 [SMILES: CC(=O)N1N=C(c2cc(F)ccc2F)S[C@]12c1ccccc1OC[C@@H]2CCCN] | 417.1 | 418.3 | 4.11 | (CD$_3$OD) δ: 7.71-7.67 (m, 1 H), 7.51 (dd, J = 7.8, 1.6 Hz, 1 H), 7.34-7.29 (m, 2 H), 7.20-7.16 (m, 1 H), 6.95-6.91 (m, 1 H), 6.80 (dd, J = 8.2, 1.2 Hz, 1 H), 4.52 (t, J = 11.3 Hz, 1 H), 4.28 (dd, J = 10.9, 4.7 Hz, 1H), 3.01-2.91 (m, 2 H), 2.61-2.57 (m, 1 H), 2.37 (s, 3 H), 1.94-1.70 (m, 3 H), 1.46-1.35 (m, 1 H) | B |

Example 1101

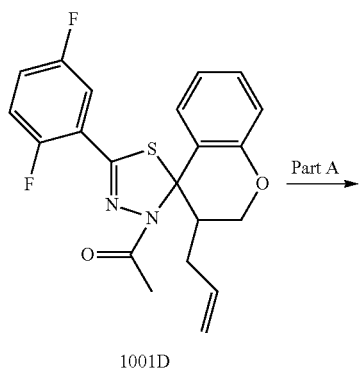

1001D

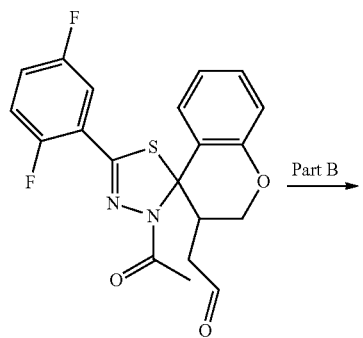

1101

Part A:
A mixture of compound 1001D (200.0 mg, 0.5 mmol), 2,6-lutidine (0.23 mL, 2.0 mmol) and 2.5% O₅O₄ in t-BuOH (0.41 mL, 0.01 mmol) in solution of dioxane (10 mL) and water (2 mL) was stirred at room temperature 10 min, and then added NaIO₄ (515.0 mg, 2 mmol). The result mixture was stirred at rt for 16 hours. Sat. NaHCO₃ and Ethyl acetate (150 mL) was added. Organic layer was washed with brine and dried over MgSO₄, and then evaporated solvent under vacuum. The residue was purified by column chromatography to afford compound 1101 (160.0 mg, 80%). HPLC-MS $t_R$=4.4 min (UV$_{254\ nm}$); mass calculated for formula C20H16F2N2O3S 402.08, observed LCMS m/z 403.1 (M+H).

Part B:
A solution of compound 1101 (140.0 mg, 0.35 mmol) and NaClO₂ (47.0 mg, 0.52 mmol) in solution of t-BuOH (3.5 mL), dioxane (2 mL) and water (1 mL) was stirred at rt for 2 days. The solution was concentrated and purified by HPLC to afford acid 1102 (100.0 mg, 68%). HPLC-MS $t_R$=5.29 min (UV$_{254\ nm}$); mass calculated for formula C20H16F2N2O4S 418.08, observed LCMS m/z 419.2 (M+H).

Part C:
To a solution of 1103 (90.0 mg, 0.22 mmol), TEA (0.06 mL, 0.43 mmol) in DCM (10 mL) were added EDCI (49.5 mg, 0.26 mmol) and NH₄Cl (23.0 mg, 0.43 mmol). The result mixture was stirred at rt for 16 hours. Sat. NaHCO₃ and Ethyl acetate (150 mL) was added. Organic layer was washed with brine and dried over MgSO₄, and the solution was concentrated and purified by HPLC to afford 18 (1.4 mg, 1.6%). HPLC-MS $t_R$=4.87 min (UV$_{254\ nm}$); mass calculated for formula C20H17F2N3O3S 417.10, observed LCMS m/z 418.1 (M+H).

Example 1201

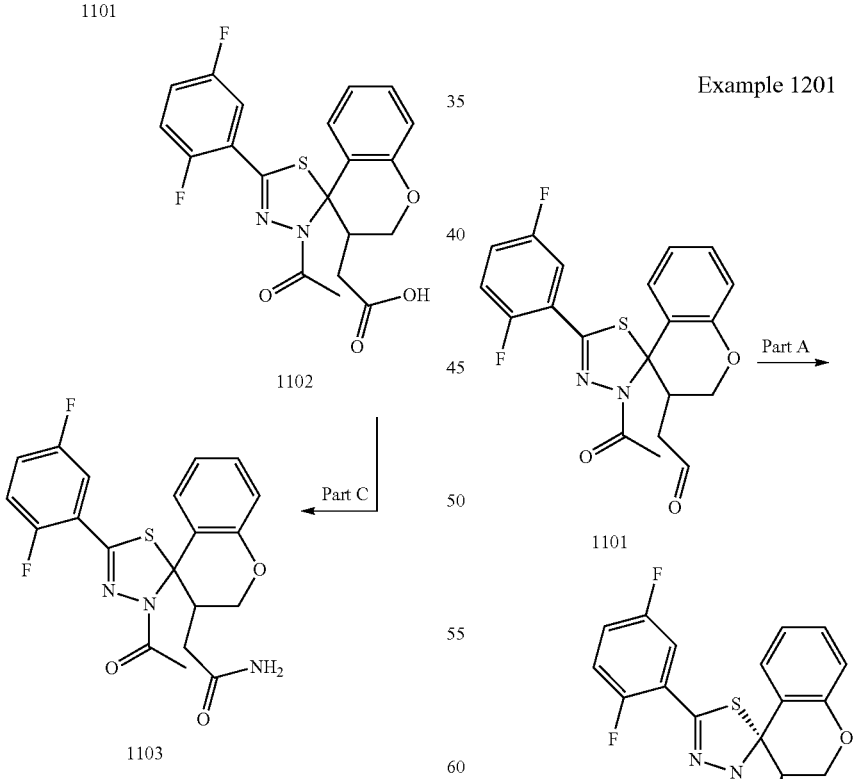

-continued

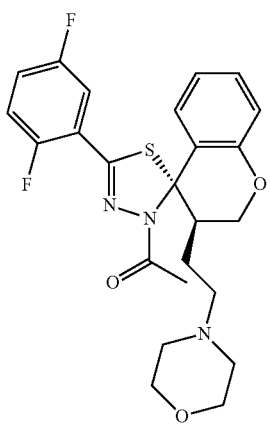

1201

Part A:

The four isomers of 1101 were separated using a chiralpak AD column (40% EtOH in Hexs) to obtain desired white solid 1200 at second peak.

Part B:

To a solution of morpholine (11.2 mg, 0.14 mmol) in 1,2-dichloroethane (2 mL) were added 4 Å molecular sieves (200 mg), aldehyde 1200 (55.0 mg, 0.14 mmol), acetic acid (1 drop), and sodium triacetoxyborohydride (89.0 mg, 0.42 mmol). The result mixture was stirred at rt overnight. Sat. NaHCO$_3$ and Ethyl acetate (150 mL) was added. Organic layer was washed with brine and dried over Na$_2$SO$_4$, and the solution was concentrated and purified by HPLC to afford compound 1201 as white HCl salt (24.6 mg, 34%). HPLC-MS $t_R$=3.41 min (UV$_{254\ nm}$); mass calculated for formula C24H25F2N3O3S 473.16, observed LCMS m/z 474.1 (M+H).

The following compounds in Table 1201 were synthesized using this procedure:

TABLE 1201

| Cpd ID | Structure | Exact mass | MS m/z (M$^+$ + H) | tR (min) | 1H NMR | EC50 (nM) Range |
|---|---|---|---|---|---|---|
| 1201 | 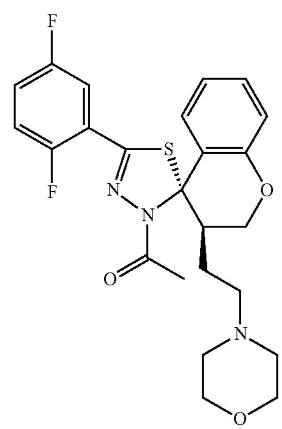 [SMILES: CC(=O)N1N=C(c2cc(F)ccc2F)S[C@@]12c1ccccc1OC[C@H]2CCN1CCOCC1] | 473.2 | 474.2 | 3.44 | (CD$_3$OD) δ: 7.74-7.70 (m, 1 H), 7.52 (dd, J = 8.2, 1.6 Hz, 1 H), 7.35-7.31 (m, 2 H), 7.22-7.18 (m, 1 H), 6.98-6.94 (m, 1 H), 6.82 (dd, J = 8.2, 0.8 Hz, 1 H), 4.58 (t, J = 10.9 Hz, 1 H), 4.27 (dd, J = 10.9, 4.3 Hz, 1H), 4.05-4.01 (m, 2 H), 3.77-3.70 (m, 2 H), 3.54-3.33 (m, 4 H), 3.16-3.12 (m, 2 H), 2.75-2.70 (m, 1 H), 2.40 (s, 3 H), 2.23-2.15 (m, 1 H), 1.88-1.79 (m, 1 H) | A |
| 1202 | 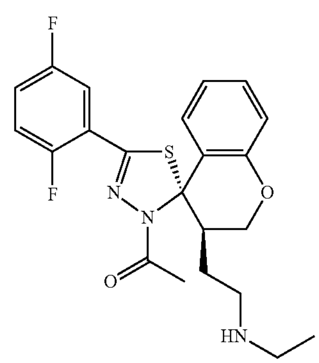 [SMILES: CCNCC[C@@H]1COc2ccccc2[C@@]12SC(c1cc(F)ccc1F)=NN2C(C)=O] | 431.1 | 432.2 | 4.23 | (CD$_3$OD) δ: 7.73-7.67 (m, 1 H), 7.54 (dd, J = 7.8, 1.6 Hz, 1 H), 7.35-7.31 (m, 2 H), 7.22-7.18 (m, 1 H), 6.98-6.93 (m, 1 H), 6.82 (dd, J = 8.2, 1.2 Hz, 1 H), 4.56 (t, J = 11.3 Hz, 1 H), 4.28 (dd, J = 10.9, 4.7 Hz, 1H), 3.21-3.03 (m, 4 H), 2.73-2.71 (m, 1 H), 2.38 (s, 3 H), 2.15-2.07 (m, 1 H), 1.76-1.66 (m, 1 H), 1.27 (t, J = 7.4 Hz, 3 H) | A |

TABLE 1201-continued

| Cpd ID | Structure | Exact mass | MS m/z (M+ + H) | tR (min) | 1H NMR | EC50 (nM) Range |
|---|---|---|---|---|---|---|
| 1203 | 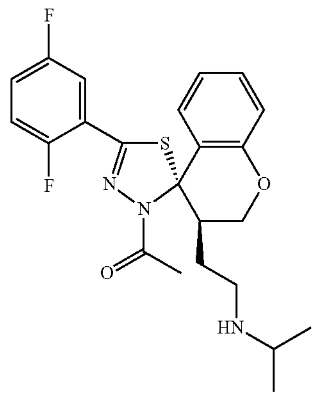 [SMILES: CC(=O)N1N=C(c2cc(F)ccc2F)S[C@@]12c1ccccc1OC[C@H]2CCNC(C)C] | 445.2 | 446.3 | 4.32 | (CD$_3$OD) δ: 7.72-7.68 (m, 1 H), 7.54 (dd, J = 7.8, 1.6 Hz, 1 H), 7.35-7.31 (m, 2 H), 7.23-7.18 (m, 1 H), 6.98-6.94 (m, 1 H), 6.82 (dd, J = 8.2, 1.1 Hz, 1 H), 4.56 (t, J = 10.9 Hz, 1 H), 4.29 (dd, J = 11.3, 4.7 Hz, 1H), 3.38-3.31 (m, 1 H), 3.27-3.11 (m, 2 H), 2.78-2.71 (m, 1 H), 2.38 (s, 3 H), 2.14-2.06 (m, 1 H), 1.76-1.66 (m, 1 H), 1.33-1.29 (m, 6 H) | A |

Example 1301

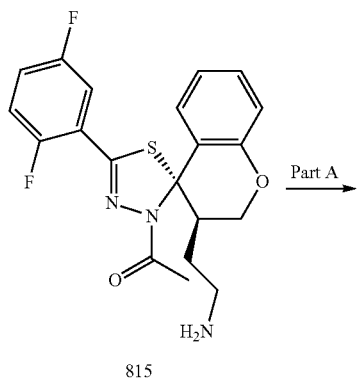
815

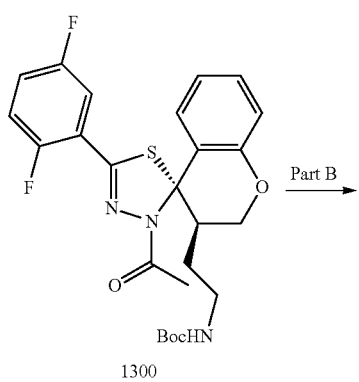
1300

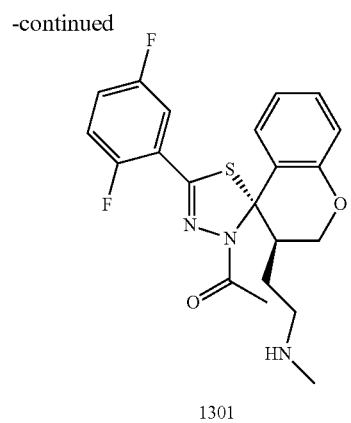
1301

Part A:
To a solution of compound 815 (3.0 g, 7.4 mmol) in THF (40 mL) and H$_2$O (10 mL) were added NaHCO$_3$ (1.3 g, 15.6 mmol) and (Boc)$_2$O (1.8 g, 8.2 mmol). The result mixture was stirred at rt 3 h. Sat. NaHCO$_3$ and Ethyl acetate (150 mL) was added. Organic layer was washed with brine and dried over Na$_2$SO$_4$, and the solution was concentrated and the residue was purified by column chromatography to afford compound 1300 (1.7 g, 45%). HPLC-MS t$_R$=2.4 min (UV$_{254\,nm}$); mass calculated for formula C25H27F2N3O4S 503.17, observed LCMS m/z 504.1 (M+H).

Part B:
To a solution of compound 1300 (100 mg, 0.2 mmol) in DMF (3 mL) was added NaH (60%, 18 mg, 0.45 mmol). After the mixture was stirred at rt 30 min, Methyl iodide (0.1 mL, 1.6 mmol) was added. The result mixture was stirred at rt overnight and then solids were filtered and evaporated solvent. The residue was dissolved in EtOAc (200 mL) and washed with Sat. NaHCO$_3$, brine, dried over Na$_2$SO$_4$. The solution was concentrated and purified by column chromatography to afford desired compound which was then treated with TFA (1 mL) for 10 min. The solution was concentrated and purified by HPLC to afford white HCl salt of compound 1301 (6.6 mg, 7.3%). HPLC-MS t$_R$=3.89 min (UV$_{254\,nm}$); mass calculated for formula C21H21F2N3O2S 417.13, observed LCMS m/z 418.2 (M+H).

Example 1401

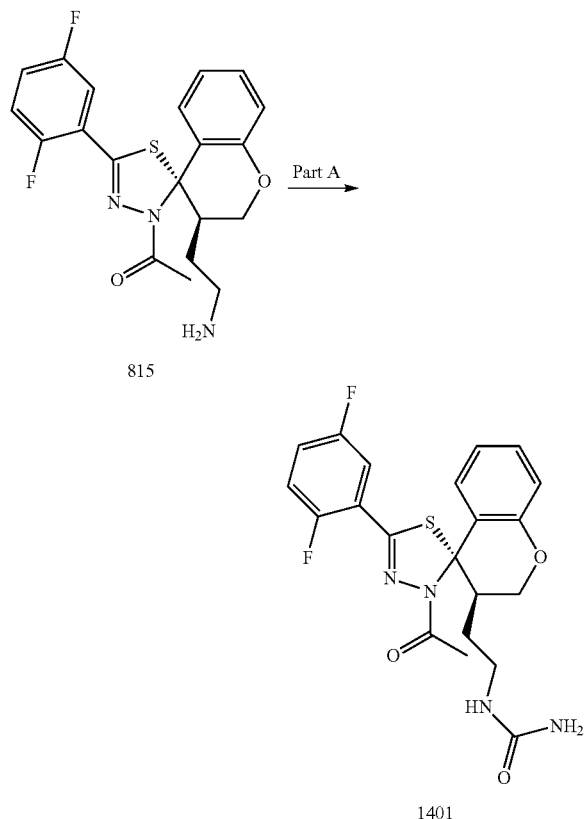

Part A:

A mixture of amine 815 (130.0 mg, 0.32 mmol) and potassium cyanate (230.0 mg, 2.8 mmol) in EtOH (2 mL) and $H_2O$ (5 mL) was heated at 100° C. in the microwave for 20 min. The reaction mixture purified by HPLC to afford compound 1401 (64.8 mg, 45%). HPLC-MS $t_R$=4.71 min ($UV_{254\ nm}$); mass calculated for formula C21H2OF2N4O3S 446.12, observed LCMS m/z 447.2 (M+H).

Example 1501

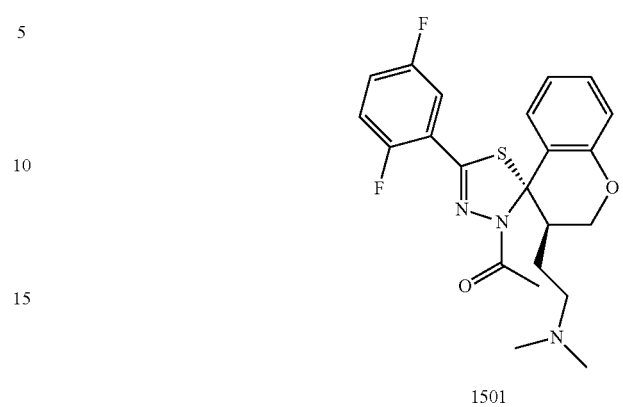

Part A:

To a solution of amine 815 (50.0 mg, 0.12 mmol), 37% formaldehyde in water (1 mL) in solution of dioxane (2 mL) and water (2 mL) were added HOAc (2 mL) and Zinc granules (200 mg, 3.0 mmol). The result mixture was stirred at rt overnight and then heated at 35° C. for 4 h. Solids were filtered and evaporated solvent. The residue was purified by HPLC to afford compound 1501 (5.0 mg, 10%). HPLC-MS $t_R$=4.20 min ($UV_{254\ nm}$); mass calculated for formula C22H23F2N3O2S 431.15, observed LCMS m/z 432.2 (M+H).

Example 1601

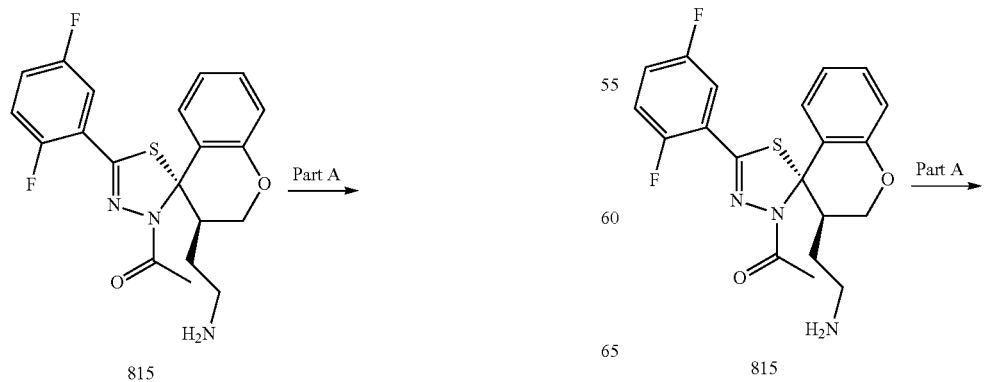

-continued

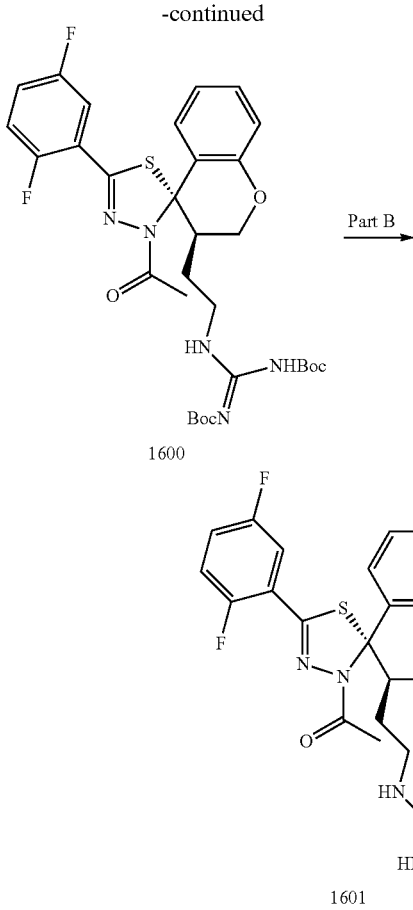

1600

1601

Part A-B:

A solution of HCl salt of compound 815 (150.0 mg, 0.34 mmol) in DMF (10 mL) was added N,N-bis(tert-butoxy carbonyl) thioureu (123.0 mg, 0.44 mmol) and NEt₃ (0.17 mL, 1.2 mmol). The mixture was cooled to 0° C. and added Mercury (II) chloride (129.0 mg, 0.48 mmol) under Ar atmosphere. The suspension warmed to rt and stirred overnight. Solids were filtered through a pad of celite and filtrate was concentrated. The residue was purified by column chromatography to afford desired compound 1600 (150.0 mg, 68%), which was then treated with TFA (1 mL) for 15 min. The solution was concentrated and purified by HPLC to afford white 1501 (22.5 mg, 15%). HPLC-MS $t_R$=4.07 min (UV$_{254\,nm}$); mass calculated for formula C21H21F2N5O2S 445.14, observed LCMS m/z 446.2 (M+H).

Example 1701

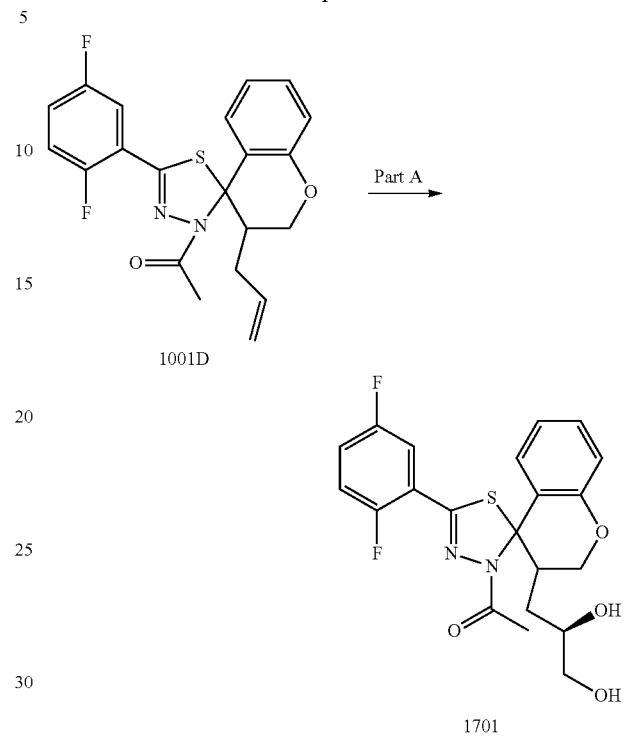

1001D

1701

A 100 mL round bottom flask filled with water (5 mL) was cooled to 0° C., potassium ferricyanide (III) (1.2 g, 3.6 mmol), K₂CO₃ (863.0 mg, 6.3 mmol) and methanesulfonamide (131.0 mg, 1.4 mmol) were subsequently added, followed by 2.5 wt % Osmium tetroxide in t-BuOH (0.78 mL, 0.06 mmol), (DHQ)₂PHAL, compound 1001D (500.0 mg, 1.3 mmol) and t-BuOH. The reaction mixture stirred overnight at low temperature overnight. Solids were filtered through a pad of celite and filtrate was concentrated. The residue was purified by column chromatography to afford compound 1701 as a white solid (440.0 mg, 81%). HPLC-MS $t_R$=4.93 min (UV$_{254\,nm}$); mass calculated for formula C21H20F2N2O4S 434.11, observed LCMS m/z 435.1 (M+H).

Example 1801

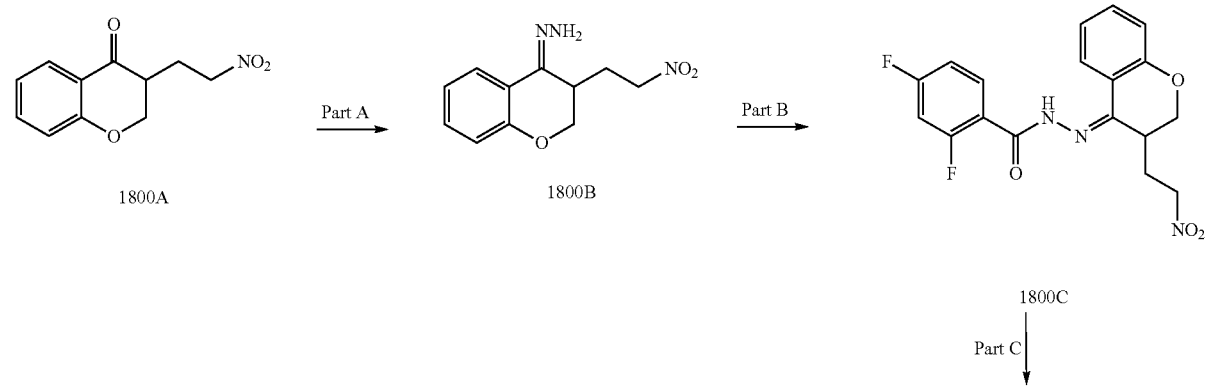

1800A      1800B      1800C

Part C

-continued

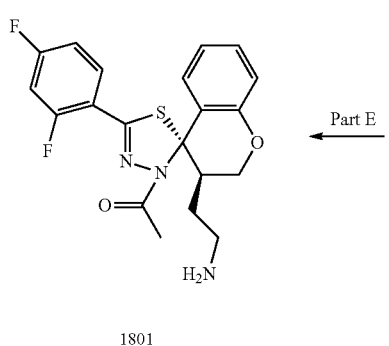

1801

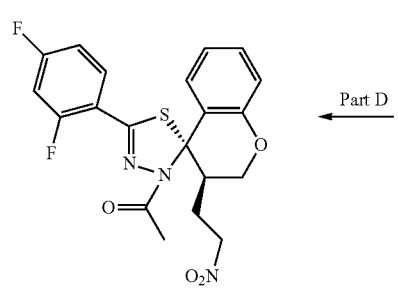

1800

Part A:
A mixture of ketone 1800A (prepared from the same procedure as 801B in example 801, 1.0 g, 4.5 mmol) hydrazine hydrate (1.1 mL, 55 mmol) and HOAc (5 drops) in EtOH (5 mL) was heated at 100° C. in the microwave for 20 min. Evaporated solvent. The residue was dissolved in EtOAc (200 mL) and washed with Sat. NaHCO₃, brine, dried over Na₂SO₄. The solution was concentrated compound 1800B which was used for next step without further purification.

Part B:
To an ice-cooled solution of compound 1800B (528.8 mg, 2.3 mmol) and pyridine (0.22 mL, 2.7 mmol) in THF (5 mL) was added 2,4-difluorobenzoyl chloride (469.4 mg, 2.5 mmol) solution in THF (2 mL). The reaction mixture was warmed to room temperature over 2 hour and product formation was confirmed by LC-MS analysis. Solvent was evaporated and added ethanol (5 mL) to solidify product which was filtered and washed with ethyl ether to obtain compound 180° C. as a pale solid (500.0 mg, 58%).

Part C:
To a solution of compound 180° C. (500 mg, 1.3 mmol) in THF (5 mL) was added P₂S₅ (889.0 mg, 2.0 mmol) and the reaction mixture was stirred at rt overnight. Solids were filtered and compound 1800D filtrate was used directly for next step.

Part D:
A mixture of compound 1800D (1.33 mmol), acetic anhydride (0.27 mL, 2.7 mmol) and pyridine (0.33 mL, 4.0 mmol) in THF (10 mL) was stirred at room temperature for 16 hours. The reaction mixture was concentrated. The residue was dissolved in EtOAc (200 mL) and washed with Sat. NaHCO₃, brine, dried over Na₂SO₄. The solution was concentrated and purified by column chromatography to afford desired compounds. The four isomers were separated using a chiralcel OD column (100% Ethanol) to obtain desired white solid compound 1800 at first peak (180.0 mg, 31%). HPLC-MS $t_R$=2.1 min (UV$_{254\ nm}$); mass calculated for formula C20H17F2N3O4S 433.09, observed LCMS m/z 434.2 (M+H).

Part E:
A mixture of compound 1800 (180.0 mg, 0.42 mmol), Zinc dust (500.0 mg, 7.6 mmol) and HOAc (1 mL) in EtOH (20 mL) was stirred 3 h. Solids were filtered through a pad of celite and filtrate was concentrated. The residue was purified by HPLC to afford desired compound 1801 (71.6 mg, 42%). HPLC-MS $t_R$=3.98 min (UV254 nm); mass calculated for formula C20H19F2N3O2S 403.12, observed LCMS m/z 404.2 (M+H).

TABLE 1201

| Cpd ID | Structure | Exact mass | MS m/z (M⁺ + H) | tR (min) | 1H NMR | EC50 (nM) Range |
|---|---|---|---|---|---|---|
| 1801 | 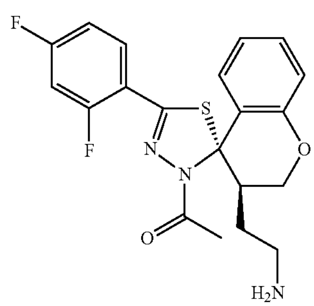 [SMILES: CC(=O)N1N=C(c2ccc(F)cc2F)S[C@@]12c1ccccc1OC[C@H]2CCN] | 403.1 | 404.2 | 3.98 | (CD₃OD) δ: 8.03-7.97 (m, 1 H), 7.53 (dd, J = 7.8, 1.2 Hz, 1 H), 7.22-7.13 (m, 3 H), 6.97-6.93 (m, 1 H), 6.82 (dd, J = 8.2, 0.8 Hz, 1 H), 4.56 (t, J = 10.9 Hz, 1 H), 4.26 (dd, J = 10.9, 4.3 Hz, 1H), 3.18-3.02 (m, 2 H), 2.76-2.69 (m, 1 H), 2.37 (s, 3 H), 2.14-2.06 (m, 1 H), 1.74-1.64 (m, 1 H) | A |

TABLE 1201-continued

| Cpd ID | Structure | Exact mass | MS m/z (M⁺ + H) | tR (min) | 1H NMR | EC50 (nM) Range |
|---|---|---|---|---|---|---|
| 1802 | 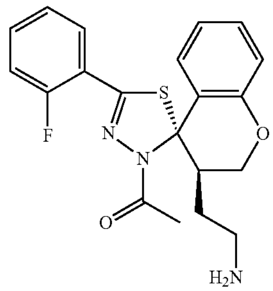 [SMILES: CC(=O)N1N=C(c2ccccc2F)S[C@@]12c1ccccc1OC[C@H]2CCN] | 385.1 | 386.2 | 3.91 | (CD₃OD) δ: 7.95 (t, J = 7.4 Hz, 1 H), 7.57-7.51 (m, 2 H), 7.34-7.16 (m, 3 H), 6.94 (t, J = 7.0 Hz, 1 H), 6.81 (d, J = 8.2, Hz, 1 H), 4.55 (t, J = 10.9 Hz, 1 H), 4.26 (dd, J = 10.9, 4.7 Hz, 1H), 3.18-3.02 (m, 2 H), 2.74-2.69 (m, 1 H), 2.38 (s, 3 H), 2.15-2.07 (m, 1 H), 1.77-1.67 (m, 1 H) | A |
| 1803 | 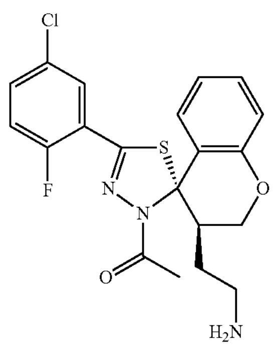 [SMILES: CC(=O)N1N=C(c2cc(Cl)ccc2F)S[C@@]12c1ccccc1OC[C@H]2CCN] | 419.1 | 420.2 | 4.2 | (CD₃OD) δ: 7.94 (dd, J = 6.2, 2.7 Hz, 1 H), 7.59-7.53 (m, 2 H), 7.31 (dd, J = 10.5, 9.0 Hz, 1 H), 7.22-7.18 (m, 1 H), 6.97-6.93 (m, 1 H), 6.82 (dd, J = 8.2, 0.8 Hz, 1 H), 4.55 (t, J = 10.9 Hz, 1 H), 4.26 (dd, J = 10.9, 4.3 Hz, 1H), 3.18-3.02 (m, 2 H), 2.76-2.68 (m, 1 H), 2.38 (s, 3 H), 2.13-2.04 (m, 1 H), 1.73-1.64 (m, 1 H) | A |
| 1804 | 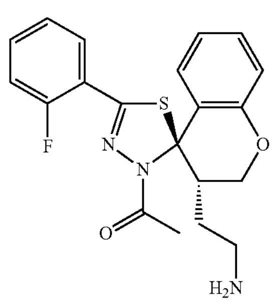 [SMILES: CC(=O)N1N=C(c2ccccc2F)S[C@]12c1ccccc1OC[C@@H]2CCN] | 385.1 | 386.2 | 3.91 | (CD₃OD) δ: 7.95 (t, J = 7.4 Hz, 1 H), 7.57-7.51 (m, 2 H), 7.34-7.16 (m, 3 H), 6.94 (t, J = 7.0 Hz, 1 H), 6.81 (d, J = 8.2, Hz, 1 H), 4.55 (t, J = 10.9 Hz, 1 H), 4.26 (dd, J = 10.9, 4.7 Hz, 1H), 3.18-3.02 (m, 2 H), 2.74-2.69 (m, 1 H), 2.38 (s, 3 H), 2.15-2.07 (m, 1 H), 1.77-1.67 (m, 1 H) | D |

TABLE 1201-continued
| Cpd ID | Structure | Exact mass | MS m/z (M⁺ + H) | tR (min) | 1H NMR | EC50 (nM) Range |
|---|---|---|---|---|---|---|
| 1805 | 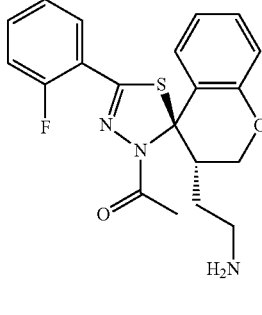 | 419.1 | 420.2 | 4.18 | (CD₃OD) δ: 7.94 (dd, J = 6.2, 2.7 Hz, 1 H), 7.59-7.53 (m, 2 H), 7.31 (dd, J = 10.5, 9.0 Hz, 1 H), 7.22-7.18 (m, 1 H), 6.97-6.93 (m, 1 H), 6.82 (dd, J = 8.2, 0.8 Hz, 1 H), 4.55 (t, J = 10.9 Hz, 1 H), 4.26 (dd, J = 10.9, 4.3 Hz, 1H), 3.18-3.02 (m, 2 H), 2.76-2.68 (m, 1 H), 2.38 (s, 3 H), 2.13-2.04 (m, 1 H), 1.73-1.64 (m, 1 H) | D |
| 1806 | 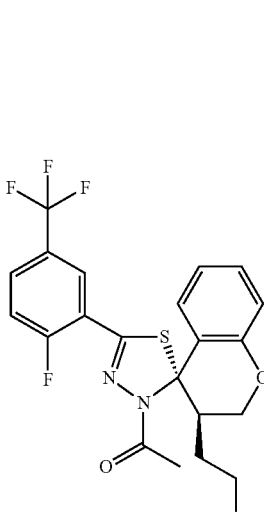 | 453.1 | 454.2 | 4.35 | (CD₃OD) δ: 8.22 (dd, J = 6.3, 2.0 Hz, 1 H), 7.93-7.89 (m, 1 H), 7.57 (dd, J = 7.8, 1.6 Hz, 1 H), 7.52 (dd, J = 10.5, 9.4 Hz, 1 H), 7.23-7.18 (m, 1 H), 6.98-6.94 (m, 1 H), 6.82 (dd, J = 8.6, 1.2 Hz, 1 H), 4.56 (t, J = 10.9 Hz, 1 H), 4.27 (dd, J = 10.9, 4.7 Hz, 1H), 3.18-3.02 (m, 2 H), 2.77-2.65 (m, 1 H), 2.39 (s, 3 H), 2.14-2.06 (m, 1 H), 1.75-1.65 (m, 1 H) | A |
| 1807 | 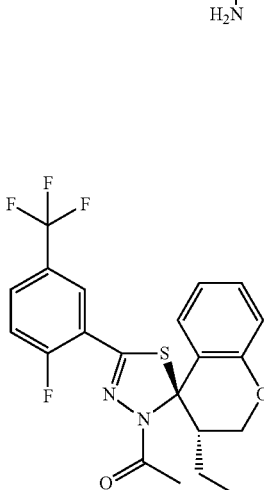 | 453.1 | 454.2 | 4.4 | (CD₃OD) δ: 8.22 (dd, J = 6.3, 2.0 Hz, 1 H), 7.93-7.89 (m, 1 H), 7.57 (dd, J = 7.8, 1.6 Hz, 1 H), 7.52 (dd, J = 10.5, 9.4 Hz, 1 H), 7.23-7.18 (m, 1 H), 6.98-6.94 (m, 1 H), 6.82 (dd, J = 8.6, 1.2 Hz, 1 H), 4.56 (t, J = 10.9 Hz, 1 H), 4.27 (dd, J = 10.9, 4.7 Hz, 1H), 3.18-3.02 (m, 2 H), 2.77-2.65 (m, 1 H), 2.39 (s, 3 H), 2.14-2.06 (m, 1 H), 1.75-1.65 (m, 1 H) | D |

TABLE 1201-continued

| Cpd ID | Structure | Exact mass | MS m/z (M+ + H) | tR (min) | 1H NMR | EC50 (nM) Range |
|---|---|---|---|---|---|---|
| 1808 | 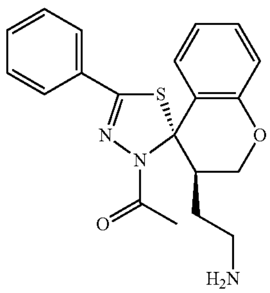 [SMILES: CC(=O)N1N=C(c2ccccc2)S[C@@]12c1ccccc1OC[C@H]2CCN] | 367.1 | 368.3 | 3.89 | (CD3OD) δ: 7.77-7.75 (m, 2 H), 7.54-7.48 (m, 4 H), 6.98-6.94 (m, 1 H), 7.21-7.17 (m, 1 H), 6.96-6.92 (m, 1 H), 6.82 (dd, J = 8.2, 1.2 Hz, 1 H), 4.57 (t, J = 11.3 Hz, 1 H), 4.26 (dd, J = 11.3, 4.7 Hz, 1H), 3.14-3.04 (m, 2 H), 2.77-2.74 (m, 1 H), 2.39 (s, 3 H), 2.14-2.06 (m, 1 H), 1.75-1.66 (m, 1 H) | A |
| 1809 | 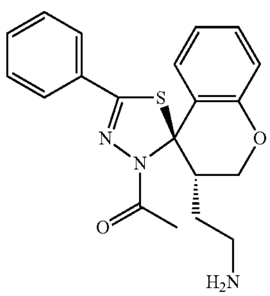 [SMILES: CC(=O)N1N=C(c2ccccc2)S[C@]12c1ccccc1OC[C@@H]2CCN] | 367.1 | 368.2 | 3.89 | (CD3OD) δ: 7.77-7.75 (m, 2 H), 7.54-7.48 (m, 4 H), 6.98-6.94 (m, 1 H), 7.21-7.17 (m, 1 H), 6.96-6.92 (m, 1 H), 6.82 (dd, J = 8.2, 1.2 Hz, 1 H), 4.57 (t, J = 11.3 Hz, 1 H), 4.26 (dd, J = 11.3, 4.7 Hz, 1H), 3.14-3.04 (m, 2 H), 2.77-2.74 (m, 1 H), 2.39 (s, 3 H), 2.14-2.06 (m, 1 H), 1.75-1.66 (m, 1 H) | D |
| 1810 | 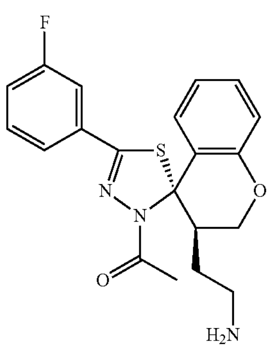 | 385.1 | 386.3 | 3.99 | (CD3OD) δ: 7.56-7.50 (m, 4 H), 7.32-7.27 (m, 1 H), 7.22-7.18 (m, 1 H), 6.96-6.92 (m, 1 H), 6.82 (dd, J = 8.2, 0.8 Hz, 1 H), 4.56 (t, J = 10.9 Hz, 1 H), 4.27 (dd, J = 10.9, 4.7 Hz, 1H), 3.17-3.01 (m, 2 H), 2.79-2.72 (m, 1 H), 2.39 (s, 3 H), 2.13-2.04 (m, 1 H), 1.75-1.66 (m, 1 H) | A |

TABLE 1201-continued

| Cpd ID | Structure | Exact mass | MS m/z (M⁺ + H) | tR (min) | 1H NMR | EC50 (nM) Range |
|---|---|---|---|---|---|---|
| 1811 | 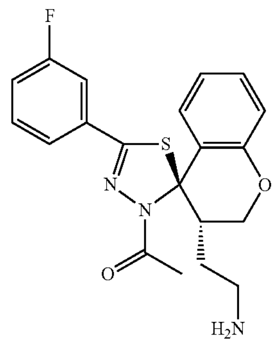 | 385.1 | 386.3 | 3.98 | (CD$_3$OD) δ: 7.56-7.50 (m, 4 H), 7.32-7.27 (m, 1 H), 7.22-7.18 (m, 1 H), 6.96-6.92 (m, 1 H), 6.82 (dd, J = 8.2, 0.8 Hz, 1 H), 4.56 (t, J = 10.9 Hz, 1 H), 4.27 (dd, J = 10.9, 4.7 Hz, 1H), 3.17-3.01 (m, 2 H), 2.79-2.72 (m, 1 H), 2.39 (s, 3 H), 2.13-2.04 (m, 1 H), 1.75-1.66 (m, 1 H) | D |
| 1812 | 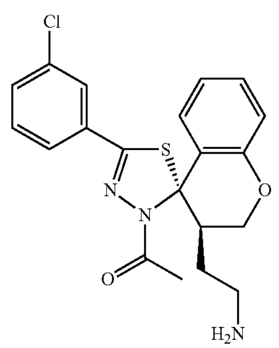 [SMILES: CC(=O)N1N=C(c2cccc(Cl)c2)S[C@@]12c1ccccc1OC[C@H]2CCN] | 401.1 | 402.2 | 4.26 | (CD$_3$OD) δ: 7.87 (t, J = 11.6 Hz, 1 H), 7.67-7.64 (m, 1 H), 7.57-7.48 (m, 3 H), 7.22-7.18 (m, 1 H), 6.97-6.93 (m, 1 H), 6.82 (dd, J = 8.2, 1.2 Hz, 1 H), 4.56 (t, J = 11.3 Hz, 1 H), 4.26 (dd, J = 10.9, 4.3 Hz, 1H), 3.17-3.01 (m, 2 H), 2.79-2.71 (m, 1 H), 2.39 (s, 3 H), 2.12-2.04 (m, 1 H), 1.74-1.64 (m, 1 H) | A |
| 1813 | 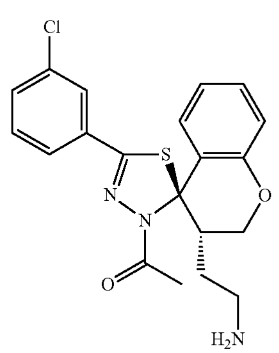 [SMILES: CC(=O)N1N=C(c2cccc(Cl)c2)S[C@]12c1ccccc1OC[C@@H]2CCN] | 401.1 | 402.3 | 4.25 | (CD$_3$OD) δ: 7.87 (t, J = 11.6 Hz, 1 H), 7.67-7.64 (m, 1 H), 7.57-7.48 (m, 3 H), 7.22-7.18 (m, 1 H), 6.97-6.93 (m, 1 H), 6.82 (dd, J = 8.2, 1.2 Hz, 1 H), 4.56 (t, J = 11.3 Hz, 1 H), 4.26 (dd, J = 10.9, 4.3 Hz, 1H), 3.17-3.01 (m, 2 H), 2.79-2.71 (m, 1 H), 2.39 (s, 3 H), 2.12-2.04 (m, 1 H), 1.74-1.64 (m, 1 H) | D |

TABLE 1201-continued

| Cpd ID | Structure | Exact mass | MS m/z (M+ + H) | tR (min) | 1H NMR | EC50 (nM) Range |
|---|---|---|---|---|---|---|
| 1814 | 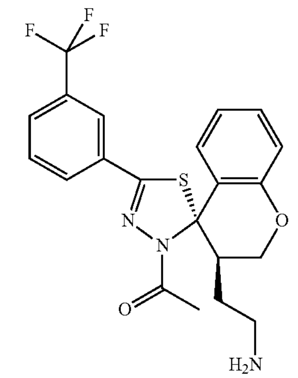 [SMILES: CC(=O)N1N=C(c2cccc(C(F)(F)F)c2)S[C@@]12c1ccccc1OC[C@H]2CCN] | 435.1 | 436.2 | 4.35 | (CD3OD) δ: 8.00 (d, J = 8.6 Hz, 2 H), 7.85 (d, J = 7.5 Hz, 1 H), 7.73 (t, J = 7.8 Hz, 1 H), 7.22-7.18 (m, 1 H), 6.95 (t, J = 7.8 Hz, 1 H), 6.83 (d, J = 8.6, 1.2 Hz, 1 H), 4.56 (t, J = 10.9 Hz, 1 H), 4.28 (dd, J = 10.9, 4.2 Hz, 1H), 3.18-3.02 (m, 2 H), 2.81-2.74 (m, 1 H), 2.41 (s, 3 H), 2.14-2.03 (m, 1 H), 1.76-1.66 (m, 1 H) | A |
| 1815 | 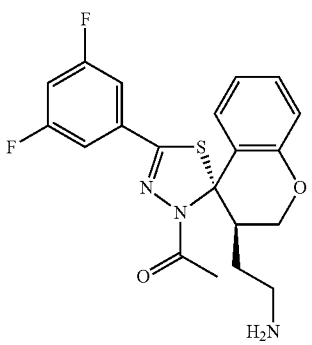 [SMILES: CC(=O)N1N=C(c2cc(F)cc(F)c2)S[C@@]12c1ccccc1OC[C@H]2CCN] | 403.1 | 404.2 | 4.06 | (CD3OD) δ: 7.53 (dd, J = 7.8, 1.2 Hz, 1 H), 7.41-7.36 (m, 2 H), 7.22-7.16 (m, 2 H), 6.97-6.93 (m, 1 H), 6.82 (dd, J = 8.2, 0.8 Hz, 1 H), 4.55 (t, J = 10.9 Hz, 1 H), 4,27 (dd, J = 10.9, 4.3 Hz, 1H), 3.18-3.01 (m, 2 H), 2.79-2.65 (m, 1 H), 2.39 (s, 3 H), 2.12-2.03 (m, 1 H), 1.74-1.64 (m, 1 H) | A |
| 1816 | 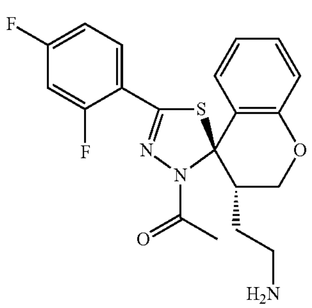 [SMILES: CC(=O)N1N=C(c2ccc(F)cc2F)S[C@]12c1ccccc1OC[C@@H]2CCN] | 403.1 | 404.2 | 3.99 | (CD3OD) δ: 8.03-7.97 (m, 1 H), 7.53 (dd, J = 7.8, 1.2 Hz, 1 H), 7.22-7.13 (m, 3 H), 6.97-6.93 (m, 1 H), 6.82 (dd, J = 8.2, 0.8 Hz, 1 H), 4.56 (t, J = 10.9 Hz, 1 H), 4.26 (dd, J = 10.9, 4.3 Hz, 1H), 3.18-3.02 (m, 2 H), 2.76-2.69 (m, 1 H), 2.37 (s, 3 H), 2.14-2.06 (m, 1 H), 1.74-1.64 (m, 1 H) | D |

TABLE 1201-continued

| Cpd ID | Structure | Exact mass | MS m/z (M⁺ + H) | tR (min) | 1H NMR | EC50 (nM) Range |
|---|---|---|---|---|---|---|
| 1817 | 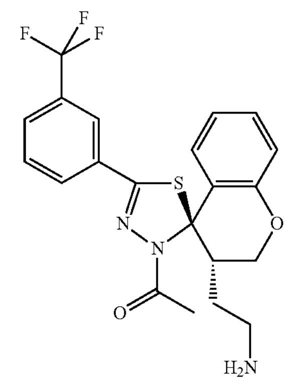 [SMILES: CC(=O)N1N=C(c2cccc(C(F)(F)F)c2)S[C@]12c1ccccc1OC[C@@H]2CCN] | 435.1 | 436.3 | 4.31 | (CD₃OD) δ: 8.00 (d, J = 8.6 Hz, 2 H), 7.85 (d, J = 7.5 Hz, 1 H), 7.73 (t, J = 7.8 Hz, 1 H), 7.22-7.18 (m, 1 H), 6.95 (t, J = 7.8 Hz, 1 H), 6.83 (d, J = 8.6, 1.2 Hz, 1 H), 4.56 (t, J = 10.9 Hz, 1 H), 4.28 (dd, J = 10.9, 4.2 Hz, 1H), 3.18-3.02 (m, 2 H), 2.81-2.74 (m, 1 H), 2.41 (s, 3 H), 2.14-2.03 (m, 1 H), 1.76-1.66 (m, 1 H) | D |
| 1818 | 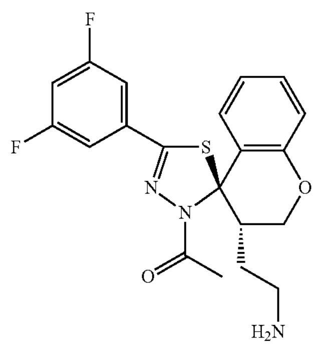 [SMILES: CC(=O)N1N=C(c2cc(F)cc(F)c2)S[C@]12c1ccccc1OC[C@@H]2CCN] | 403.1 | 404.2 | 4.03 | (CD₃OD) δ: 7.53 (dd, J = 7.8, 1.2 Hz, 1 H), 7.41-7.36 (m, 2 H), 7.22-7.16 (m, 2 H), 6.97-6.93 (m, 1 H), 6.82 (dd, J = 8.2, 0.8 Hz, 1 H), 4.55 (t, J = 10.9 Hz, 1 H), 4.27 (dd, J = 10.9, 4.3 Hz, 1H), 3.18-3.01 (m, 2 H), 2.79-2.65 (m, 1 H), 2.39 (s, 3 H), 2.12-2.03 (m, 1 H), 1.74-1.64 (m, 1 H) | D |
| 1819 | 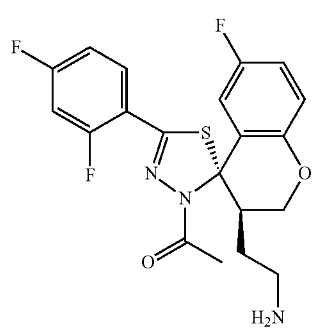 [SMILES: CC(=O)N1N=C(c2ccc(F)cc2F)S[C@@]12c1cc(F)ccc1OC[C@H]2CCN] | 421.1 | 422.3 | 3.93 | (CD₃OD) δ: 8.04-7.98 (m, 1 H), 7.25 (dd, J = 9.4, 3.1 Hz, 1 H), 7.21-7.13 (m, 2 H), 6.99-6.95 (m, 1 H), 6.83 (dd, J = 9.4, 4.7 Hz, 1 H), 4.52 (t, J = 10.9 Hz, 1 H), 4.25 (dd, J = 10.9, 4.3 Hz, 1H), 3.18-3.01 (m, 2 H), 2.75-2.65 (m, 1 H), 2.39 (s, 3 H), 2.12-2.03 (m, 1 H), 1.74-1.64 (m, 1 H) | A |

TABLE 1201-continued

| Cpd ID | Structure | Exact mass | MS m/z (M⁺ + H) | tR (min) | 1H NMR | EC50 (nM) Range |
|---|---|---|---|---|---|---|
| 1820 | 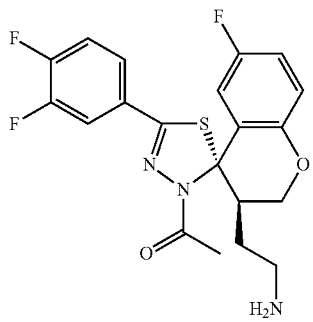 [SMILES: CC(=O)N1N=C(c2ccc(F)c(F)c2)S[C@@]12c1cc(F)ccc1OC[C@H]2CCN] | 421.1 | 422.3 | 3.98 | (CD₃OD) δ: 7.78-7.74 (m, 1 H), 7.57-7.53 (m, 1 H), 7.47-7.40 (m, 1 H), 7.26 (dd, J = 9.0, 2.7 Hz, 1 H), 7.00-6.95 (m, 1 H), 6.84 (dd, J = 9.0, 4.7 Hz, 1 H), 4.51 (t, J = 10.9 Hz, 1 H), 4.26 (dd, J = 10.9, 4.3 Hz, 1H), 3.17-3.01 (m, 2 H), 2.75-2.70 (m, 1 H), 2.40 (s, 3 H), 2.10-2.01 (m, 1 H), 1.74-1.64 (m, 1 H) | A |
| 1821 | 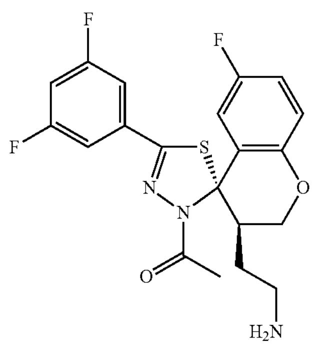 [SMILES: CC(=O)N1N=C(c2cc(F)cc(F)c2)S[C@@]12c1cc(F)ccc1OC[C@H]2CCN] | 421.1 | 422.2 | 4.09 | (CD₃OD) δ: 7.42-7.38 (m, 2 H), 7.28 (dd, J = 9.5, 3.1 Hz, 1 H), 7.23-7.17 (m, 1 H), 7.01-6.83 (m, 1 H), 6.84 (dd, J = 9.0, 4.7 Hz, 1 H), 4.51 (t, J = 11.3 Hz, 1 H), 4.26 (dd, J = 11.3, 4.7 Hz, 1H), 3.17-3.01 (m, 2 H), 2.75-2.70 (m, 1 H), 2.41 (s, 3 H), 2.09-2.01 (m, 1 H), 1.73-1.64 (m, 1 H) | A |
| 1822 | 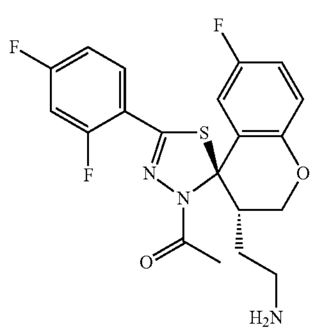 [SMILES: CC(=O)N1N=C(c2ccc(F)cc2F)S[C@]12c1cc(F)ccc1OC[C@@H]2CCN] | 421.1 | 422.2 | 4.04 | (CD₃OD) δ: 8.04-7.98 (m, 1 H), 7.25 (dd, J = 9.4, 3.1 Hz, 1 H), 7.21-7.13 (m, 2 H), 6.99-6.95 (m, 1 H), 6.83 (dd, J = 9.4, 4.7 Hz, 1 H), 4.52 (t, J = 10.9 Hz, 1 H), 4.25 (dd, J = 10.9, 4.3 Hz, 1H), 3.18-3.01 (m, 2 H), 2.75-2.65 (m, 1 H), 2.39 (s, 3 H), 2.12-2.03 (m, 1 H), 1.74-1.64 (m, 1 H) | D |

TABLE 1201-continued

| Cpd ID | Structure | Exact mass | MS m/z (M+ + H) | tR (min) | 1H NMR | EC50 (nM) Range |
|---|---|---|---|---|---|---|
| 1823 | 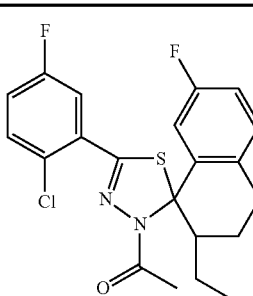 | 421.1 | 422.3 | 4.11 | (CD$_3$OD) δ: 7.78-7.74 (m, 1 H), 7.57-7.53 (m, 1 H), 7.47-7.40 (m, 1 H), 7.26 (dd, J = 9.0, 2.7 Hz, 1 H), 7.00-6.95 (m, 1 H), 6.84 (dd, J = 9.0, 4.7 Hz, 1 H), 4.51 (t, J = 10.9 Hz, 1 H), 4.26 (dd, J = 10.9, 4.3 Hz, 1H), 3.17-3.01 (m, 2 H), 2.75-2.70 (m, 1 H), 2.40 (s, 3 H), 2.10-2.01 (m, 1 H), 1.74-1.64 (m, 1 H) | D |
| 1824 | 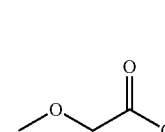 | 421.1 | 422.2 | 4.10 | (CD$_3$OD) δ: 7.42-7.38 (m, 2 H), 7.28 (dd, J = 9.5, 3.1 Hz, 1 H), 7.23-7.17 (m, 1 H), 7.01-6.83 (m, 1 H), 6.84 (dd, J = 9.0, 4.7 Hz, 1 H), 4.51 (t, J = 11.3 Hz, 1 H), 4.26 (dd, J = 11.3, 4.7 Hz, 1H), 3.17-3.01 (m, 2 H), 2.75-2.70 (m, 1 H), 2.41 (s, 3 H), 2.09-2.01 (m, 1 H), 1.73-1.64 (m, 1 H) | D |

It is contemplated that the following compound represents an additional non-limiting example of a compound of the invention which may be made, for example, according to the procedure described above:

| Cpd ID | Structure |
|---|---|
| 1825 | (structure shown: chlorofluorophenyl substituted thiadiazole spirochromane with acetyl and aminoethyl groups) |

Example 1901

(structure 1901A: methoxy lactic acid)

Part A →

(structure 1901B: methoxy propanoyl chloride)

Part B →

-continued

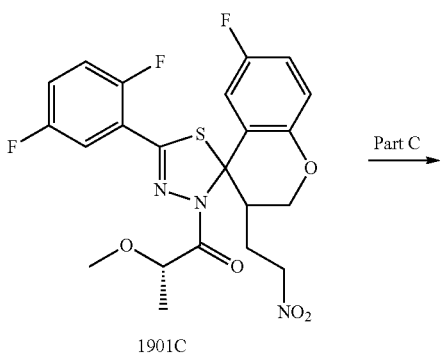

1901C

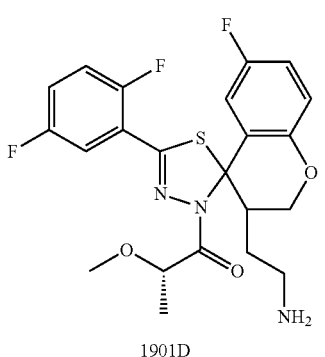

1901D

Part A:

Oxalyl chloride (560 μL, 6.4 mmol) was added to a stirring ice-cooled solution of (S)-(−)-2-methoxypropionic acid (1901A, 668 mg, 6.4 mmol) and DMF (2 drops) in DCM (10 mL). The reaction mixture was warmed to room temperature and sirred for 1 hour. The volatiles were removed in vacuo, and the resulting acid chloride used as crude 1901B in the next step.

Part B:

A solution of compound 1901B (6.4 mmol) in DCM (5 mL) was slowly added to an ice-cooled stirring mixture of compound 801C from example 801 (1.75 g, 4.28 mmol) and pyridine (1.04 mL, 12.83 mmol) in DCM (10 mL). The reaction mixture was warmed to room temperature and stirred for 16 hours. Product formation was confirmed by LC-MS. The reaction mixture was quenched by the addition of 1 N HCl, and extracted with DCM. Drying over magnesium sulfate and purification by flash silica chromatography, gradient elution (0 to 100%) petroleum ether/DCM/ethyl acetate afforded diastereomeric separation of compound 1901C (1.5 g, 71%). HPLC-MS $t_R$=2.07 min ($UV_{254\,nm}$); mass calculated for formula $C_{22}H_{20}F_3N_3O_5S$ 495.1, observed LCMS m/z 496.1 (M+H). Compound 1901C was subjected to chiral HPLC (ChiralPak AD 50×500 mm 20μ, 30:70 hexane/ethanol) to afford the trans isomers as white solids.

Part C:

A mixture containing compound 1901C (360 mg, 0.73 mmol) and zinc dust (720 mg) in ethanol (15 mL) and acetic acid (1.5 mL) was stirred for at room temperature for 16 hours. Product formation was confirmed by LC-MS. The reaction mixture was filtered by passing through celite, concentrated and purified by prep.HPLC to afford compound 1901 as a white solid (140.7 mg, 42%).

The following compounds were synthesized using this procedure:

| Cpd ID | Structure | Exact mass | MS m/z ($M^+$ + H) | tR (min) | 1H NMR | EC50 (nM) Range |
|---|---|---|---|---|---|---|
| 1901 | 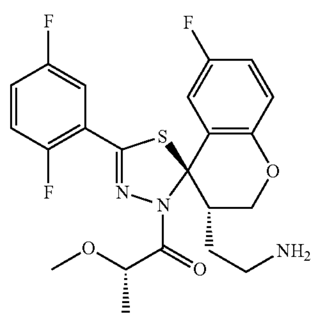 [SMILES: CO[C@@H](C)C(=O)N1N=C(c2cc(F)ccc2F)S[C@]12c1cc(F)ccc1OC[C@@H]2CCN] | 465.1 | 466.1 | 3.70 | ($CD_3OD$) 7.72-7.66 (m, 1H), 7.40-7.33 (m, 2H), 7.31 (dd, J = 9.4, 3.16 Hz, 1H), 7.03-6.97 (ddd, J = 16.4, 8.6, 3.1 Hz, 1H), 6.89-6.84 (dd, J = 8.6, 4.7 Hz, 1H), 4.73-4.67 (q, J = 6.2 Hz, 1H), 4.55 (t, J = 10.9 Hz, 1H), 4.32-4.26 (dd, J = 10.9, 4.7 Hz, 1H), 3.19 (s, 3H), 3.17-3.00 (m, 2H), 2.79-2.70 (m, 1H), 2.09-1.99 (m, 1H), 1.67-1.57 (m, 1H), 1.47 (d, J = 6.2 Hz, 3H). | D |

| Cpd ID | Structure | Exact mass | MS m/z (M+ + H) | tR (min) | 1H NMR | EC50 (nM) Range |
|---|---|---|---|---|---|---|
| 1902 | 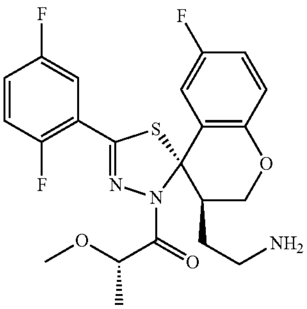 [SMILES: CO[C@@H](C)C(=O)N1N=C(c2cc(F)ccc2F)S[C@@]12c1cc(F)ccc1OC[C@H]2CCN] | 465.1 | 466.1 | 3.73 | (CD₃OD) δ: 7.72-7.66 (m, 1H), 7.40-7.33 (m, 2H), 7.21 (dd, J = 9.4, 3.16 Hz, 1H), 7.03-6.97 (ddd, J = 16.4, 7.8, 3.1 Hz, 1H), 6.88-6.84 (dd, J = 9.4, 4.7 Hz, 1H), 4.81-4.75 (q, J = 6.2 Hz, 1H), 4.61 (t, J = 10.9 Hz, 1H), 4.33-4.27 (dd, J = 10.9, 4.7 Hz, 1H), 3.36 (s, 3H), 3.20-3.03 (m, 2H), 2.80-2.71 (m, 1H), 2.15-2.05 (m, 1H), 1.73-1.62 (n, 1H), 1.33 (d, J = 7.0 Hz, 3H). | A |
| 1903 | 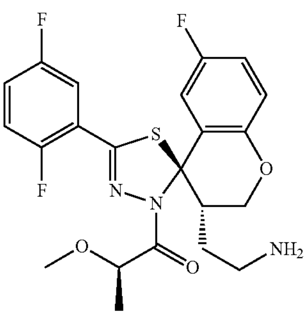 [SMILES: CO[C@H](C)C(=O)N1N=C(c2cc(F)ccc2F)S[C@]12c1cc(F)ccc1OC[C@@H]2CCN] | 465.1 | 466.1 | 4.04 | (CD₃OD) δ: 7.72-7.66 (m, 1H), 7.40-7.33 (m, 2H), 7.31 (dd, J = 9.4, 3.16 Hz, 1H), 7.03-6.97 (ddd, J = 16.4, 8.6, 3.1 Hz, 1H), 6.89-6.84 (dd, J = 8.6, 4.7 Hz, 1H), 4.73-4.67 (q, J = 6.2 Hz, 1H), 4.55 (t, J = 10.9 Hz 1H), 4.32-4.26 (dd, J = 10.9, 4.7 Hz, 1H), 3.19 (s, 3H), 3.17-3.00 (m, 2H), 2.79-2.70 (m, 1H), 2.09-1.99 (m, 1H), 1.67-1.57 (m, 1H), 1.47 (d, J = 6.2 Hz, 3H). | D |
| 1904 | 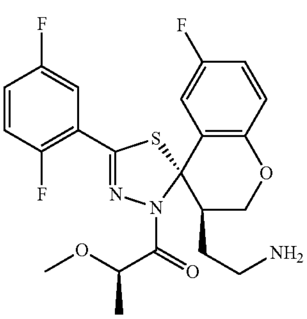 [SMILES: CO[C@H](C)C(=O)N1N=C(c2cc(F)ccc2F)S[C@@]12c1cc(F)ccc1OC[C@H]2CCN] | 465.1 | 466.1 | 4.07 | (CD₃OD) δ: 7.72-7.66 (m, 1H), 7.40-7.33 (m, 2H), 7.21 (dd, J = 9.4, 3.16 Hz, 1H), 7.03-6.97 (ddd, J = 16.4, 7.8, 3.1 Hz, 1H), 6.88-6.84 (dd, J = 9.4, 4.7 Hz, 1H), 4.81-4.75 (q, J = 6.2 Hz, 1H), 4.61 (t, J = 10.9 Hz, 1H), 4.33-4.27 (dd, J = 10.9, 4.7 Hz, 1H), 3.36 (s, 3H), 3.20-3.03 (m, 2H), 2.80-2.71 (m, 1H), 2.15-2.05 (m, 1H), 1.73-1.62 (m, 1H), 1.33 (d, J = 7.0 Hz, 3H). | A |

-continued

| Cpd ID | Structure | Exact mass | MS m/z (M+ + H) | tR (min) | 1H NMR | EC50 (nM) Range |
|---|---|---|---|---|---|---|
| 1905 | 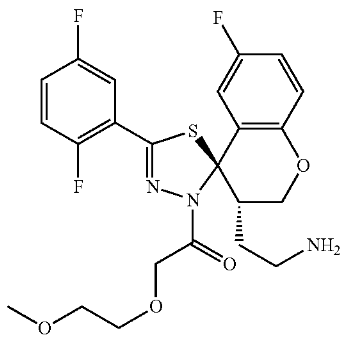 [SMILES: COCCOCC(=O)N1N=C(c2cc(F)ccc2F)S[C@]12c1cc(F)ccc1OC[C@@H]2CCN] | 495.1 | 496.1 | 4.03 | (CD$_3$OD) δ: 7.74-7.68 (m, 1H), 7.39-7.28 (m, 3H), 7.03-6.97 (ddd, J = 17.2, 7.8, 3.1 Hz, 1H), 6.88-6.83 (dd, J = 8.6, 4.7 Hz 1H), 4.71-4.51 (m, 3H), 4.32-4.26 (dd, J = 10.9, 3.9 Hz, 1H), 3.68-3.64 (m, 1H), 3.55-3.51 (m, 1H), 3.33 (s, 3H), 3.19-3.00 (m, 2H), 2.76-2.67 (m, 1H), 2.09-2.00 (m, 1H), 1.74-1.62 (m, 1H). | D |
| 1906 | 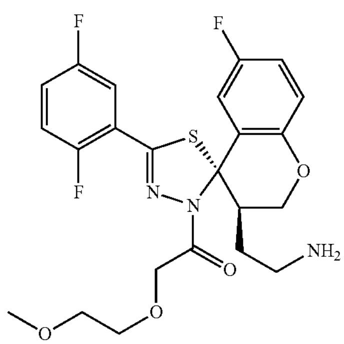 [SMILES: COCCOCC(=O)N1N=C(c2cc(F)ccc2F)S[C@@]12c1cc(F)ccc1OC[C@H]2CCN] | 495.1 | 496.1 | 4.03 | (CD$_3$OD) δ: 7.74-7.68 (m, 1H), 7.39-7.28 (m, 3H), 7.03-6.97 (ddd, J = 17.2, 7.8, 3.1 Hz, 1H), 6.88-6.83 (dd, J = 8.6, 4.7 Hz, 1H), 4.71-4.51 (m, 3H), 4.32-4.26 (dd, J = 10.9, 3.9 Hz, 1H), 3.68-3.64 (m, 1H), 3.55-3.51 (m, 1H), 3.33 (s, 3H), 3.19-3.00 (m, 2H), 2.76-2.67 (m, 1H), 2.09-2.00 (m, 1H), 1.74-1.62 (m, 1H). | A |
| 1907 | 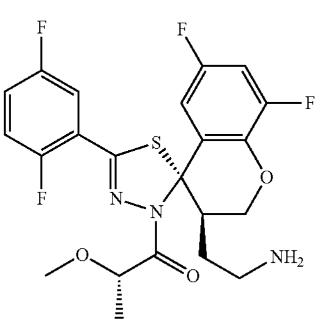 [SMILES: CO[C@@H](C)C(=O)N1N=C(c2cc(F)ccc2F)S[C@@]12c1cc(F)cc(F)c1OC[C@H]2CCN] | 483.12 | 483.13 | 3.99 | (CD3OD) δ: 7.72-7.68 (m, 1H), 7.39-7.34 (m, 2H), 7.13-7.10 (m, 1H), 7.03-7.0 (m, 1H) 4.80-4.75 (m, 1H) 4.64 (t, J = 10.9 Hz, 1H), 4.4 (dd, J = 11.7, 4.7 Hz, 1H), 3.36 (s, 3H), 3.19-3.04 (m, 2H), 2.84-2.77 (m, 1H), 2.15-2.06 (m, 1H), 2.15-2.06 (m, 1H), 1.72-1.62 (m, 1H), 1.32 (d, J = 6.3 Hz, 3H). | A |

-continued

| Cpd ID | Structure | Exact mass | MS m/z (M⁺ + H) | tR (min) | 1H NMR | EC50 (nM) Range |
|---|---|---|---|---|---|---|
| 1908 | 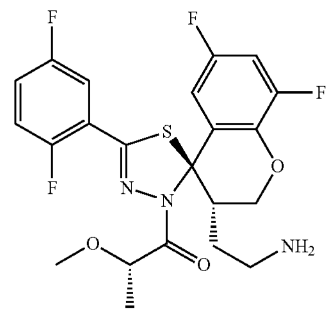 [SMILES: CO[C@@H](C)C(=O)N1N=C(c2cc(F)ccc2F)S[C@]12c1cc(F)cc(F)c1OC[C@@H]2CCN] | 483.12 | 484.12 | 4.11 | (CD3OD) δ: 7.72-7.68 (m, 1H), 7.39-7.34 (m, 2H), 7.13-7.10 (m, 1H), 7.03-7.0 (m, 1H) 4.80-4.75 (m, 1H) 4.64 (t, J = 10.9 Hz, 1H), 4.4 (dd, J = 11.7, 4.7 Hz, 1H), 3.36 (s, 3H), 3.19-3.04 (m; 2H), 2.84-2.77 (m, 1H), 2.15-2.06 (m, 1H), 2.15-2.06 (m, 1H), 1.72-1.62 (m, 1H), 1.32 (d, J = 6.3 Hz, 3H). | D |
| 1909 | 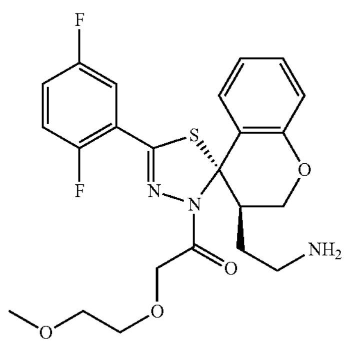 [SMILES: COCCOCC(=O)N1N=C(c2cc(F)ccc2F)S[C@@]12c1ccccc1OC[C@H]2CCN] | 477.15 | 478.15 | 3.85 | (CD3OD) δ: 7.72-7.68 (m, 1H), 7.54 (dd, J = 8.6, 1.6 Hz, 1H), 7.36-7.32 (m, 2H), 7.24-7.20 (m, 1H), 6.97 (t, J = 8.6, 1H), 6.84 (d, J = 7.8, 1H), 4.70-5.52 (m, 3H), 4.30 (dd, J = 10.9, 3.9 Hz, 1H), 3.65-3.62 (m, 2H), 3.53-3.51 (m, 2H), 3.32 (s, 3H), 3.18-3.02 (m, 2H), 2.77-2.70 (m, 1H), 2.11-2.03 (m, 1H), 1.73-1.63 (m, 1H). | A |
| 1910 | 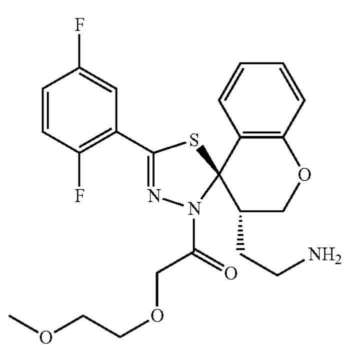 [SMILES: COCCOCC(=O)N1N=C(c2cc(F)ccc2F)S[C@]12c1ccccc1OC[C@@H]2CCN] | 477.15 | 478.15 | 3.81 | (CD3OD) δ: 7.72-7.68 (m, 1H), 7.54 (dd, J = 8.6, 1.6 Hz, 1H), 7.36-7.32 (m, 2H), 7.24-7.20 (m, 1H), 6.97 (t, J = 8.6, 1H), 6.84 (d, J = 7.8, 1H), 4.70-5.52 (m, 3H), 4.30 (dd, J = 10.9, 3.9 Hz, 1H), 3.65-3.62 (m, 2H), 3.53-3.51 (m, 2H), 3.32 (s, 3H), 3.18-3.02 (m, 2H), 2.77-2.70 (m, 1H), 2.11-2.03 (m, 1H), 1.73-1.63 (m, 1H). | D |

-continued
| Cpd ID | Structure | Exact mass | MS m/z (M+ + H) | tR (min) | 1H NMR | EC50 (nM) Range |
|---|---|---|---|---|---|---|
| 1911 | 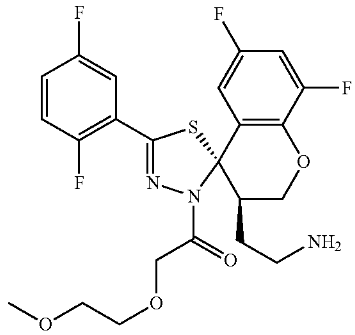 [SMILES: COCCOCC(=O)N1N=C(c2cc(F)ccc2F)S[C@@]12c1cc(F)cc(F)c1OC[C@H]2CCN] | 513.52 | 514.52 | 4.03 | (CD3OD) δ: 7.74-7.70 (m,, 1H), 7.38-7.34 (m, 2H), 7.21-7.19 (m, 1H), 7.03-7.00 (m, 1H) 4.71-4.57 (m, 3H), 4.40 (dd, J = 11.2, 4.4 Hz, 1H), 3.69-3.66 (m, 2H), 3.56-3.54 (m, 2H) 3.35 (s, 3H), 3.19 (m, 2H), 2.81-2.75 (m, 1H), 2.10-2.04 (m, 1H), 1.74-1.66 (m, 1H). | A |
| 1912 | 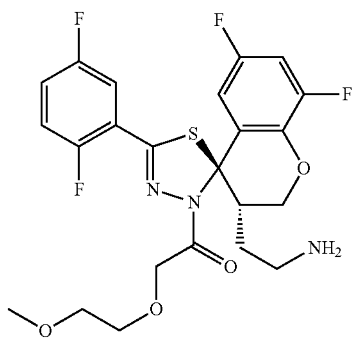 [SMILES: COCCOCC(=O)N1N=C(c2cc(F)ccc2F)S[C@]12c1cc(F)cc(F)c1OC[C@@H]2CCN] | 513.52 | 514.52 | 4.12 | (CD3OD) δ: 7.74-7.70 (m,, 1H), 7.38-7.34 (m, 2H), 7.21-7.19 (m, 1H), 7.03-7.00 (m, 1H) 4.71-4.57 (m, 3H), 4.40 (dd, J = 11.2, 4.4 Hz, 1H), 3.69-3.66 (m, 2H), 3.56-3.54 (m, 2H) 3.35 (s, 3H), 3.19 (m, 2H), 2.81-2.75 (m, 1H), 2.10-2.04 (m, 1H), 1.74-1.66 (m, 1H). | D |
Example 2001
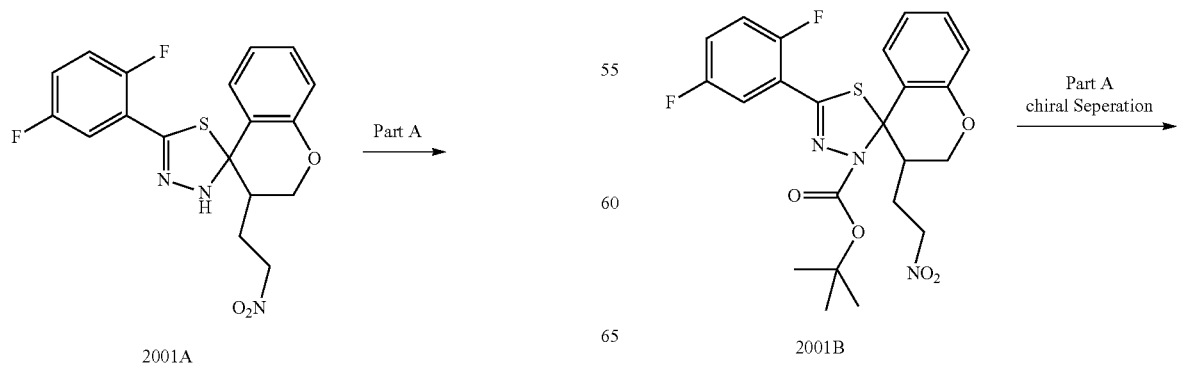

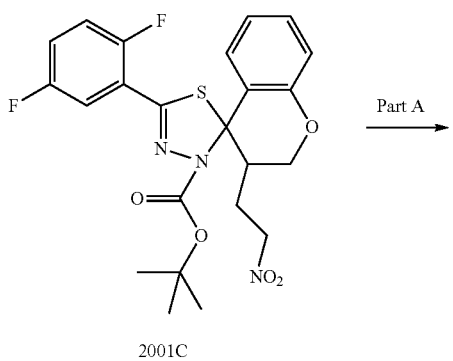

2001C

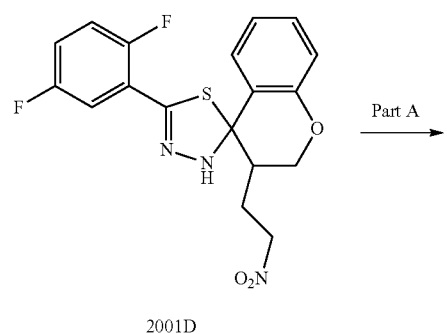

2001D

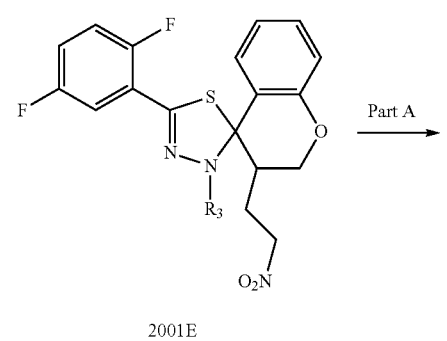

2001E

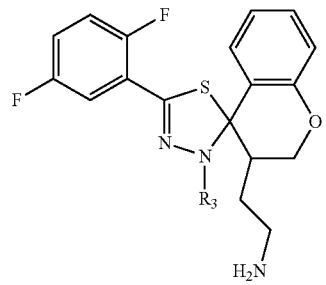

2001F

Part A

To a solution of 2001A (prepared in the same procedure as 801A of example 801) (1.51 g, 3.86 mmols) in DCM 20 mL at 0° C. was added DMAP (0.047 g, 0.384 mmol), DIEA (0.672 mL, 3.85 mmol) and (BOC)$_2$O (0.843 g, 3.86 mmol). The reaction was warm up to RT. After 18 h, the reaction was diluted with DCM and washed with 1N HCl, the organic layer dried with MgSO$_4$ and concentrated. Purification by flash column chromatography (SiO$_2$, 20% ethyl acetate in hexanes) to afford compound 2001B (1.10 g, 58% yield) as a yellow oil. HPLC-MS $t_R$=2.261 min (UV$_{254\,nm}$); mass calculated for formula C23H$_{23}$F$_2$N$_3$O$_5$S 491.13, observed LCMS m/z 436.12 (M+H-$^t$Butyl).

Part B:

Chiral Separation Chiralcel OD Column with HexaneIsopropanol/60:40 to afford isomer 2001C.

Part C:

In a vial, compound 2001C (0.10 g, 0.20 mmol) was dissolved in TFA (1 mL) and stirred for 5 min. The reaction was concentrated, diluted with DCM and washed with sat. NaHCO$_3$. The organic layer dried with MgSO$_4$ and concentrated to give compound 2001D (0.054 g, 68%) as a brownish oil.

Part D:

To a solution of compound 2001D (1 eq) in DCM was cool to 0° C. and was added DIEA (1 eq) and appropriate acid chloride (leg). After 1h, the reaction diluted with DCM and washed with sat. NaHCO$_3$. The organic layer dried with MgSO$_4$ and concentrated. Purification by flash column chromatography to give compound 2001E.

Part E:

To a solution of compound 2001E (0.052 g) in EtOH (2 mL) was added Zn dust (0.100g), and Acetic Acid (0.200 mL). The reaction was stirred at RT overnight, passed through celite, washed with EtOH and concentrated. Purified by HPLC to give compound 2001.

The following compounds were synthesized using this procedure:

| Cpd ID | Structure | Exact mass | MS m/z (M⁺ + H) | tR (min) | 1H NMR | EC50 (nM) Range |
|---|---|---|---|---|---|---|
| 2001 | 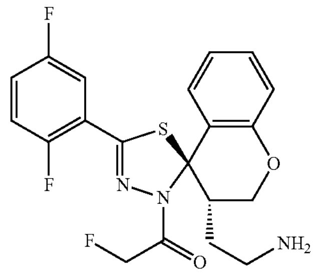 [SMILES: NCC[C@H]1COc2ccccc2[C@]12SC(c1cc(F)ccc1F)=NN2C(=O)CF] | 421.11 | 422.12 | 3.90 | (CD3OD) δ: 7.73-7.68 (m, 1H), 7.57 (dd, J = 7.8, 1.6 Hz, 1H), 7.38-7.31 (m, 2H), 7.26-7.21 (m, 1H), 6.99 (t, J = 7.8 Hz, 1H), 6.85 (d, J = 9.4 Hz, 1H), 5.52-5.23 (m, 1H), 4.57 (t, J = 10.9 Hz, 1H) 4.32 (dd, J = 10.9, 4.7 Hz, 1H) 3.18-3.30 (m, 2H), 2.78-2.71 (m, 1H), 2.11-2.03 (m, 1H), 1.75-1.65 (m, 1H), 1.15 (d,, J = 6.2 Hz, 1H). | A |
| 2002 | 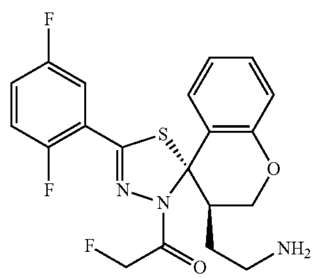 [SMILES: NCC[C@@H]1COc2ccccc2[C@@]12SC(c1cc(F)ccc1F)=NN2C(=O)CF] | 421.11 | 422.11 | 3.92 | (CD3OD) δ: 7.73-7.68 (m, 1H), 7.57 (dd, J = 7.8, 1.6 Hz, 1H), 7.38-7.31 (m, 2H), 7.26-7.21 (m, 1H), 6.99 (t, J = 7.8 Hz, 1H), 6.85 (d, J = 9.4 Hz, 1H), 5.52-5.23 (m, 1H), 4.57 (t, J = 10.9 Hz, 1H), 4.32 (dd, J = 10.9, 4.7 Hz, 1H) 3.18-3.30 (m, 2H), 2.78-2.71 (m, 1H), 2.11-2.03 (m, 1H), 1.75-1.65 (m, 1H), 1.15 (d,, J = 6.2 Hz, 1H). | A |
| 2003 | 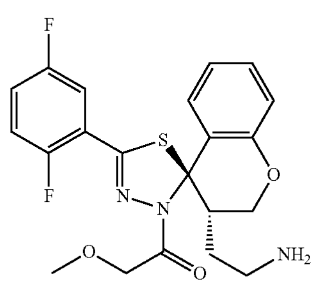 [SMILES: COCC(=O)N1N=C(c2cc(F)ccc2F)S[C@]12c1ccccc1OC[C@@H]2CCN] | 433.13 | 434.13 | 3.89 | (CD3OD) δ: 7.73-7.66 (m, 1H), 7.54 (d, J = 7.8 Hz, 1H), 7.37-7.30 (m, 1H), 7.22 (t, J = 8.6 Hz, 1H), 6.97 (t, J = 7.8 Hz, 1H), 6.84 (d, J = 7.8 Hz, 1H) 4.62-4.42 (m, 3H), 4.30 (dd, J = 10.9, 4.7 Hz, 1H), 3.37 (s, 3H), 3.18-3.01 (m, 2H), 2.78-2.70 (m, 1H,) 2.12-2.03 (m, 1H), 1.73-1.63 (m, 1H). | A |

| Cpd ID | Structure | Exact mass | MS m/z (M⁺ + H) | tR (min) | 1H NMR | EC50 (nM) Range |
|---|---|---|---|---|---|---|
| 2004 | 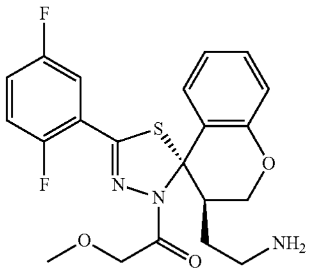 [SMILES: COCC(=O)N1N=C(c2cc(F)ccc2F)S[C@@]12c1ccccc1OC[C@H]2CCN] | 433.13 | 434.13 | 3.87 | (CD3OD) δ: 7.73-7.66 (m,1H), 7.54 (d, J = 7.8 Hz, 1H), 7.37-7.30 (m, 1H), 7.22 (t, J = 8.6 Hz, 1H), 6.97 (t, J = 7.8 Hz, 1H), 6.84 (d, J = 7.8 Hz, 1H) 4.62-4.42 (m, 3H), 4.30 (dd, J = 10.9, 4.7 Hz, 1H), 3.37 (s, 3H), 3.18-3.01 (m, 2H), 2.78-2.70 (m, 1H) 2.12-2.03 (m, 1H), 1.73-1.63 (m, 1H). | A |
| 2005 | 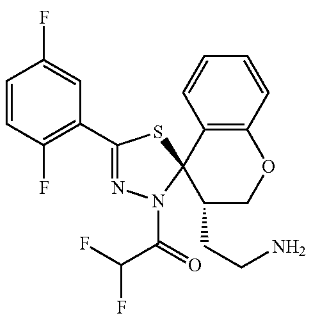 [SMILES: NCC[C@H]1COc2ccccc2[C@]12SC(c1cc(F)ccc1F)=NN2C(=O)C(F)F] | 439.10 | 440.10 | 4.14 | (CD3OD) δ: 7.77-7.72 (m, 1H), 7.57 (d, J = 7.8 Hz, 1H), 7.41-7.32 (m, 2H), 7.26 (t, J = 8.6 Hz, 1H), 7.0 (t, J = 7.8 Hz, 1H), 6.87 (d, J = 8.6 Hz, 1H), 6.82 (t, J = 53.1 Hz, 1H), 4.53 (t, J = 10.9 Hz, 1H), 4.33 (dd, J = 10.9, 3.9 Hz, 1H), 3.19-3.03 (m, 1H), 2.83-2.75 (m, 1H), 2.13-2.05 (m, 1H), 1.75-1.65 (m, 1H). | A |
| 2006 | 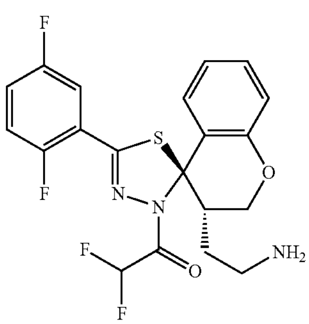 [SMILES: NCC[C@H]1COc2ccccc2[C@]12SC(c1cc(F)ccc1F)=NN2C(=O)C(F)F] | 439.10 | 440.10 | 4.15 | (CD3OD) δ: 7.77-7.72 (m, 1H), 7.57 (d, J = 7.8 Hz, 1H), 7.41-7.32 (m, 2H), 7.26 (t, J = 8.6 Hz, 1H), 7.0 (t, J = 7.8 Hz, 1H), 6.87 (d, J = 6.82 (t, J = 53.1 Hz, 1H), 4.53 (t, J = 10.9, 1H), 4.33 (dd, J = 10.9, 3.9 Hz, 1H), 3.19-3.03 (m, 1H), 2.83-2.75 (m, 1H), 2.13-2.05 (m, 1H), 1.75-1.65 (m, 1H). | A |

| Cpd ID | Structure | Exact mass | MS m/z (M+ + H) | tR (min) | 1H NMR | EC50 (nM) Range |
|---|---|---|---|---|---|---|
| 2007 | 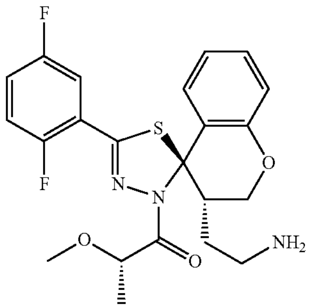 [SMILES: CO[C@@H](C)C(=O)N1N=C(c2cc(F)ccc2F)S[C@]12c1ccccc1OC[C@@H]2CCN] | 447.14 | 448.14 | 3.97 | (CD3OD) δ: 7.70-7.66 (m, 1H), 7.48 (dd, J = 7.8, 1.5 Hz, 1H), 7.38-7.34 (m, 2H), 7.22 (ddd, J = 15.6, 7.0, 1.6 Hz, 1H), 7.0 (t, J = 7.8 Hz, 1H), 6.84 (d, J = 8.6 Hz, 1H), 4.77 (q, J = 7.0, 6.2 Hz, 1H), 4.66 (t, J = 10.9 Hz, 1H), 4.30 (dd, J = 10.9, 4.7 Hz, 1H), 3.35 (s, 3H), 3.23-3.04 (m, 2H) 2.80-2.73 (m, 1H), 2.17-2.07 (m, 1H), 1.73-1.63 (m, 1H), 1.3 (d, J = 7.0 Hz, 3H). | A |
| 2008 | 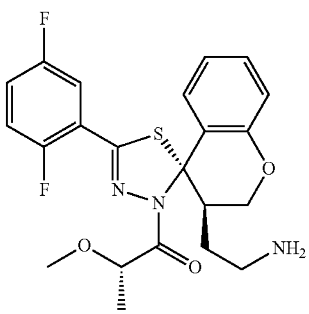 [SMILES: CO[C@@H](C)C(=O)N1N=C(c2cc(F)ccc2F)S[C@@]12c1ccccc1OC[C@H]2CCN] | 447.14 | 448.14 | 3.97 | (CD3OD) δ: 7.70-7.66 (m, 1H), 7.48 (dd, J = 7.8, 1.5 Hz, 1H), 7.38-7.34 (m, 2H), 7.22 (ddd, J = 15.6, 7.0, 1.6, 1H), 7.0 (t, J = 7.8 Hz, 1H), 6.84 (d, J = 8.6 Hz, 1H), 4.77 (q, J = 7.0, 6.2 Hz, 1H), 4.66 (t, J = 10.9 Hz, 1H), 4.30 (dd, J = 10.9, 4.7 Hz, 1H), 3.35 (s, 3H), 3.23-3.04 (m, 2H) 2.80-2.73 (m, 1H), 2.17-2.07 (m, 1H), 1.73-1.63 (m, 1H), 1.3 (d, J = 7.0 Hz, 3H). | A |
Example 2101
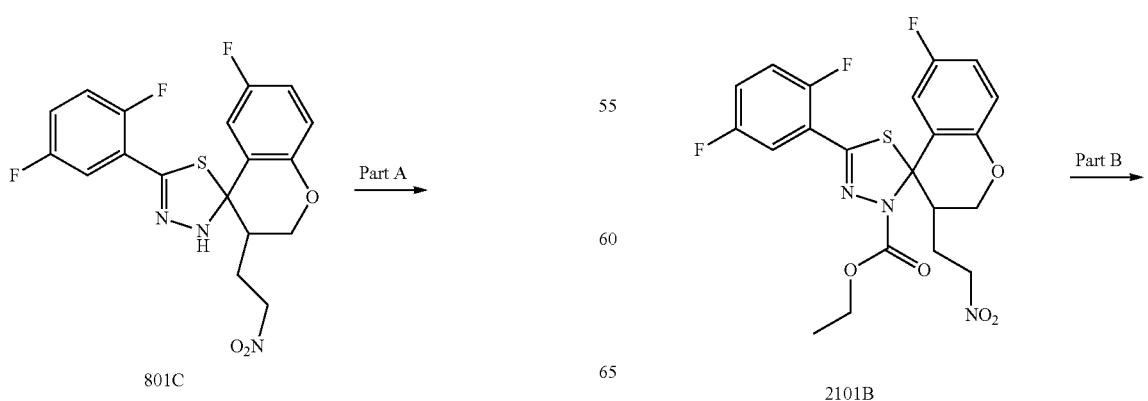

-continued

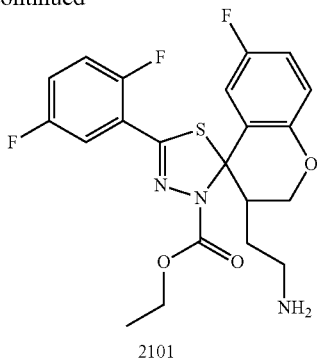

2101

Part A:

A solution of ethyl chloroformate (82 µL, 0.86 mmol) in THF (2 mL) was slowly added over 15 minutes to a salt-water ice cooled (−10° C.) stirring mixture of compound 801C (234 mg, 0.57 mmol) and N-methylmorpholine (94 µL, 0.86 mmol) in THF (20 mL). The reaction mixture was stirred for an additional 1 hour at −10° C., quenched by the addition of 1N HCl and extracted with ethyl acetate. Drying over magnesium sulfate, concentration and purification by flash silica chromatography, gradient elution (0 to 100%) hexane/ethyl acetate afforded diastereomeric separation of compound 2101B (178 mg, 65%). HPLC-MS $t_R$=2.20 min (UV$_{254\ nm}$); mass calculated for formula $C_{21}H_{18}F_3N_3O_5S$ 481.1, observed LCMS m/z 482.0 (M+H). Compound 2101B was subjected to chiral HPLC (ChiralPak AD 50×500 mm 20µ, 100% methanol) to afford the trans isomers as white solids.

Part B:

Compound 2101 was prepared from compound 2101B using the reducing method described in Example 1901, Part C.

The following compounds were synthesized using this procedure:

| Cpd ID | Structure | Exact mass | MS m/z (M⁺ + H) | tR (min) | 1H NMR | EC50 (nM) Range |
|---|---|---|---|---|---|---|
| 2101 | 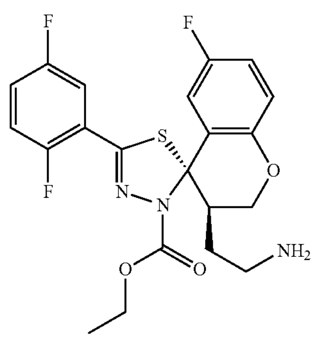 [SMILES: CCOC(=O)N1N=C(c2cc(F)ccc2F)S[C@@]12c1cc(F)ccc1OC[C@H]2CCN] | 451.1 | 452.1 | 3.79 | (CD₃OD) δ: 7.79-7.73 (m, 1H), 7.36-7.26 (m, 3H), 7.05-6.98 (ddd, J = 16.4, 7.8, 3.1 Hz, 1H), 6.89-6.84 (dd, J = 9.4, 4.7 Hz, 1H), 4.49 (t, J = 11.7 Hz 1H), 4.29-4.24 (dd, J = 11.7, 4.7 Hz, 1H), 4.19-4.09 (m, 2H), 3.20-3.11 (m, 1H), 3.10-3.01 (m, 1H), 2.74-2.65 (m, 1H), 2.16-2.06 (m, 1H), 1.80-1.68 (m, 1H), 1.21-1.11 (m, 3H). | A |
| 2102 | 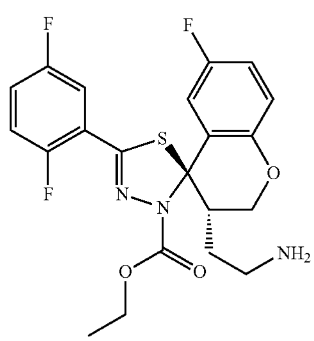 [SMILES: CCOC(=O)N1N=C(c2cc(F)ccc2F)S[C@]12c1cc(F)ccc1OC[C@@H]2CCN] | 451.1 | 452.1 | 3.87 | (CD₃OD) δ: 7.79-7.73 (m, 1H), 7.36-7.26 (m, 3H), 7.05-6.98 (ddd, J = 16.4, 7.8, 3.1 Hz, 1H), 6.89-6.84 (dd, J = 9.4, 4.7 Hz, 1H), 4.49 (t, J = 11.7 Hz 1H), 4.29-4.24 (dd, J = 11.7, 4.7 Hz, 1H), 4.19-4.09 (m, 2H), 3.20-3.11 (m, 1H), 3.10-3.01 (m, 1H), 2.74-2.65 (m, 1H), 2.16-2.06 (m, 1H), 1.80-1.68 (m, 1H), 1.21-1.11 (m, 3H). | D |

| Cpd ID | Structure | Exact mass | MS m/z (M+ + H) | tR (min) | 1H NMR | EC50 (nM) Range |
|---|---|---|---|---|---|---|
| 2103 | 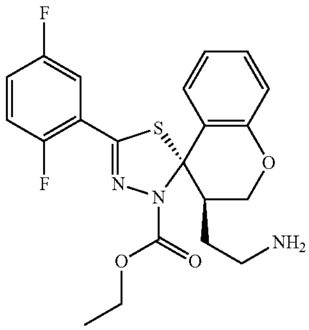 [SMILES: CCOC(=O)N1N=C(c2cc(F)ccc2F)S[C@@]12c1ccccc1OC[C@H]2CCN] | 433.13 | 434.13 | 3.74 | (CD3OD) δ: 7.81-7.73 (m, 1H), 7.58 (dd, J = 7.8, 1.6 Hz, 1H), 7.33-7.29 (m, 2H), 7.24 (ddd, J = 15.6, 7.0 Hz, 1.6, 1H), 6.99 (t, J = 7.0 Hz, 1H), 6.85 (d, J = 9.4, 1H), 4.51 (t, J = 10.9, Hz 1H), 4.26 (dd, J = 10.9, 4.7 Hz, 1H), 4.12-4.07 (m, 1H), 3.19-3.02 (m, 2H), 2.74-2.67 (m, 1H), 2.17-2.08 (m, 1H), 1.78-1.68 (m, 1H), 1.11 (s, 3H). | D |
| 2104 | 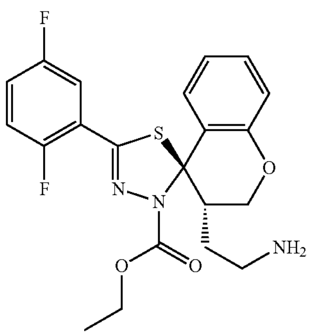 [SMILES: CCOC(=O)N1N=C(c2cc(F)ccc2F)S[C@]12c1ccccc1OC[C@@H]2CCN] | 433.13 | 434.13 | 3.80 | (CD3OD) δ: 7.81-7.73 (m, 1H), 7.58 (dd, J = 7.8, 1.6 Hz, 1H), 7.33-7.29 (m, 2H), 7.24 (ddd, J = 15.6, 7.0, 1.6 Hz, 1H), 6.99 (t, J = 7.0 Hz, 1H), 6.85 (d, J = 9.4 Hz, 1H), 4.51 (t, J = 10.9, Hz 1H), 4.26 (dd, J = 10.9, 4.7 Hz, 1H), 4.12-4.07 (m, 1H), 3.19-3.02 (m, 2H), 2.74-2.67 (m, 1H), 2.17-2.08 (m, 1H), 1.78-1.68 (m, 1H), 1.11 (s, 3H). | A |
Example 2201
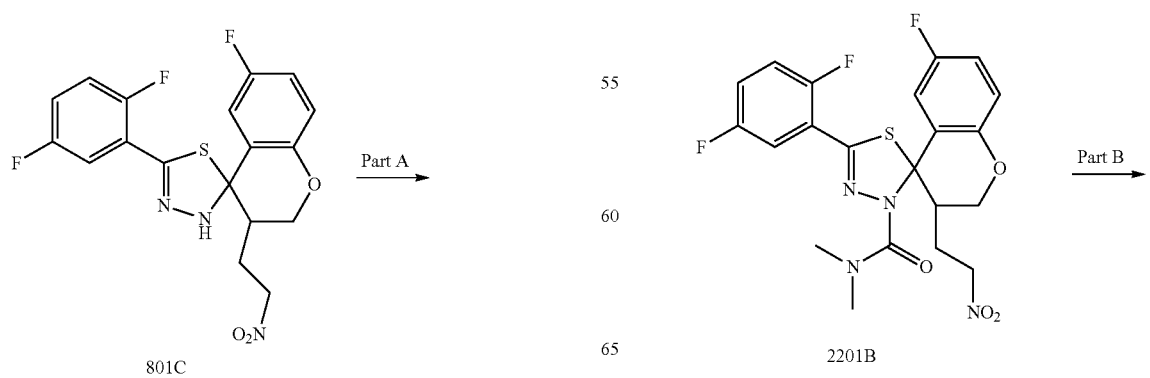

-continued

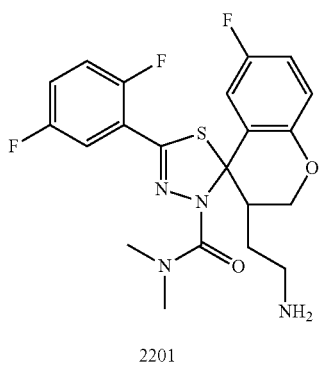

2201

Part A:

A mixture of compound 801C (115 mg, 0.28 mmol), dimethylcarbamoyl chloride (45 mg, 0.42 mmol), pyridine (500 uL) and. DMAP (3.4 mg, 0.028 mmol) in DCM (5 mL) was heated at 60° C. for 16 hours. Product formation was confirmed by LC-MS. The reaction mixture was quenched by the addition of 1N HCl, and extracted with DCM. Drying over magnesium sulfate and purification by flash silica chromatography, gradient elution (0 to 100%) hexane/ethyl acetate afforded compound 2201B (90 mg, 67%). HPLC-MS $t_R$=1.97 min (UV$_{254}$.); mass calculated for formula $C_{21}H_{19}F_3N_4O_4S$ 480.1, observed LCMS m/z 481.1 (M+H). Compound 2201B was subjected to chiral HPLC (ChiralCel OD 50×500 mm 20μ, 100% ethanol) to afford single isomers.

Part B:

Compound 2201 was prepared from compound 2201B using the reducing method described in Example 10, Part B.

The following compounds were synthesized using this procedure:

| Cpd ID | Structure | Exact mass | MS m/z (M⁺ + H) | tR (min) | 1H NMR | EC50 (nM) Range |
|---|---|---|---|---|---|---|
| 2201 | 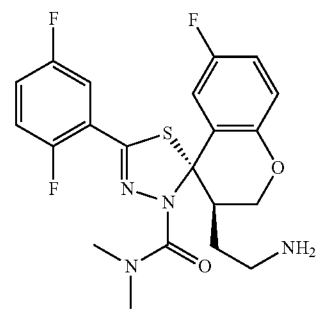 [SMILES: CN(C)C(=O)N1N=C(c2cc(F)ccc2F)S[C@@]12c1cc(F)ccc1OC[C@H]2CCN] | 450.1 | 451.1 | 3.94 | (CDCl₃) δ: 8.21-8.09 (s, 3H), 7.41-7.35 (m, 1H), 7.03 (t, J = 5.5 Hz, 2H), 6.92-6.85 (dd, J = 9.4, 3.1 Hz, 1H), 6.84-6.77 (m, 1H), 6.75-6.69 (dd, J = 8.6, 4.7, 1H), 4.27 (d, J = 10.1 Hz, 1H), 3.75-3.65 (m, 2H), 2.93 (s, 6H), 2.45-2.30 (m, 2H), 2.03-1.92 (m, 1H), 1.67-1.57 (m, 1H). | D |
| 2202 | 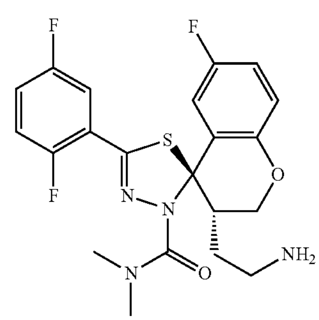 [SMILES: CN(C)C(=O)N1N=C(c2cc(F)ccc2F)S[C@]12c1cc(F)ccc1OC[C@@H]2CCN] | 450.1 | 451.1 | 4.07 | (CDCl₃) δ: 8.21-8.09 (s, 3H), 7.41-7.35 (m, 1H), 7.03 (t, J = 5.5 Hz, 2H), 6.92-6.85 (dd, J = 9.4, 3.1 Hz, 1H), 6.84-6.77 (m, 1H), 6.75-6.69 (dd, J = 8.6, 4.7, 1H), 4.27 (d, J = 10.1 Hz, 1H), 3.75-3.65 (m, 2H), 2.93 (s, 6H), 2.45-2.30 (m, 2H), 2.03-1.92 (m, 1H), 1.67-1.57 (m, 1H). | D |

-continued

| Cpd ID | Structure | Exact mass | MS m/z (M⁺ + H) | tR (min) | 1H NMR | EC50 (nM) Range |
|---|---|---|---|---|---|---|
| 2203 | 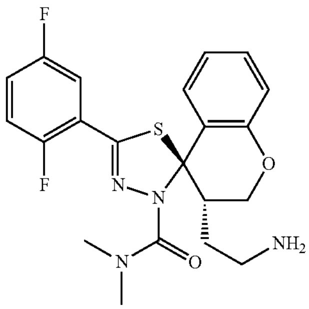 [SMILES: CN(C)C(=O)N1N=C(c2cc(F)ccc2F)S[C@]12c1ccccc1OC[C@@H]2CCN] | 432.14 | 433.14 | 5.42 | (CD3OD) δ: 7.58-7.54 (m, 1H), 7.47 (dd, J = 7.8, 1.5 Hz, 1H), 7.30-7.27 (m, 2H), 7.23-7.19 (m, 1H), 6.98 (ddd, J = 15.2, 8.3, 1.0 Hz, 1H), 6.82 (dd, J = 8.3, 1.0, 1H), 4.40 (dd, J = 11.7, 3.4 Hz, 1H), 4.02 (t, J = 11.7, 1H), 3.85-3.79 (m, 1H), 3.17-2.99 (m, 2H), 3.08 (s, 6H), 2.08-2.01 (m, 1H), 1.86-1.78 (m, 1H). | A |
| 2204 | 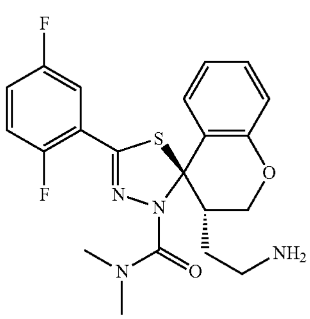 [SMILES: CN(C)C(=O)N1N=C(c2cc(F)ccc2F)S[C@]12c1ccccc1OC[C@@H]2CCN] | 432.14 | 433.14 | 4.03 | (CD3OD) δ: 7.58-7.54 (m, 1H), 7.47 (dd, J = 7.8, 1.5 Hz, 1H), 7.30-7.27 (m, 2H), 7.23-7.19 (m, 1H), 6.98 (ddd, J = 15.2, 8.3, 1.0 Hz, 1H), 6.82 (dd, J = 8.3, 1.0, 1H), 4.40 (dd, J = 11.7, 3.4 Hz, 1H), 4.02 (t, J = 11.7, 1H), 3.85-3.79 (m, 1H), 3.17-2.99 (m, 2H), 3.08 (s, 6H), 2.08-2.01 (m, 1H), 1.86-1.78 (m, 1H). | A |

-continued
| Cpd ID | Structure | Exact mass | MS m/z (M⁺ + H) | tR (min) | 1H NMR | EC50 (nM) Range |
|---|---|---|---|---|---|---|
| 2205 | 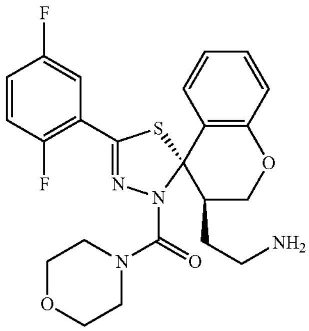 [SMILES: NCC[C@@H]1COc2ccccc2[C@@]12SC(c1cc(F)ccc1F)=NN2C(=O)N1CCOCC1] | 474.15 | 475.15 | 3.88 | (CD3OD) δ: 7.54-7.50 (m, 1H), 7.48 (dd, J = 8.3, 2.0 Hz, 1H), 7.32-7.29 (m, 2H), 7.25-7.21 (m, 1H), 7.0 (ddd, J = 15.2, 8.3, 1.0, Hz 1H), 6.83 (dd, J = 15.2, 8.3, 1.0 Hz, 1H), 4.41 (dd, J = 11.7, 3.4 Hz, 1H), 4.02 (t, J = 11.7, 1H), 3.86-3.76 (m, 1H) 3.76-3.66 (m, 6H), 3.57-3.53 (m, 2H), 3.17-3.01 (m, 2H), 2.08-2.01 (m, 1H), 1.87-1.79 (m, 1H). | D |
| 2206 | 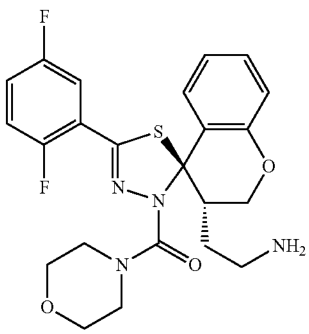 [SMILES: NCC[C@H]1COc2ccccc2[C@]12SC(c1cc(F)ccc1F)=NN2C(=O)N1CCOCC1] | 474.15 | 475.15 | 3.82 | (CD3OD) δ: 7.54-7.50 (m, 1H), 7.48 (dd, J = 8.3, 2.0 Hz, 1H), 7.32-7.29 (m, 2H), 7.25-7.21 (m, 1H), 7.0 (ddd, J = 15.2, 8.3, 1.0 Hz, 1H), 6.83 (dd, J = 15.2, 8.3, 1.0 Hz, 1H), 4.41 (dd, J = 11.7, 3.4 Hz, 1H), 4.02 (t, J = 11.7, Hz 1H), 3.86-3.76 (m, 1H) 3.76-3.66 (m, 6H), 3.57-3.53 (m, 2H), 3.17-3.01 (m, 2H), 2.08-2.01 (m, 1H), 1.87-1.79 (m, 1H). | D |
Example 2301
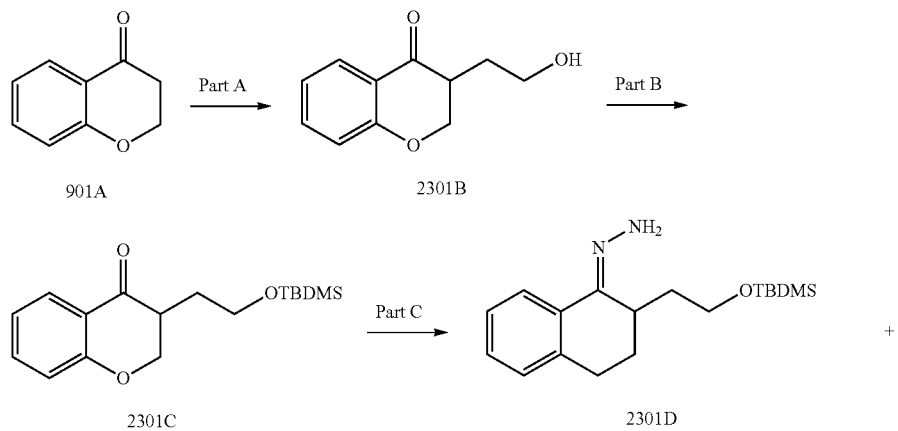

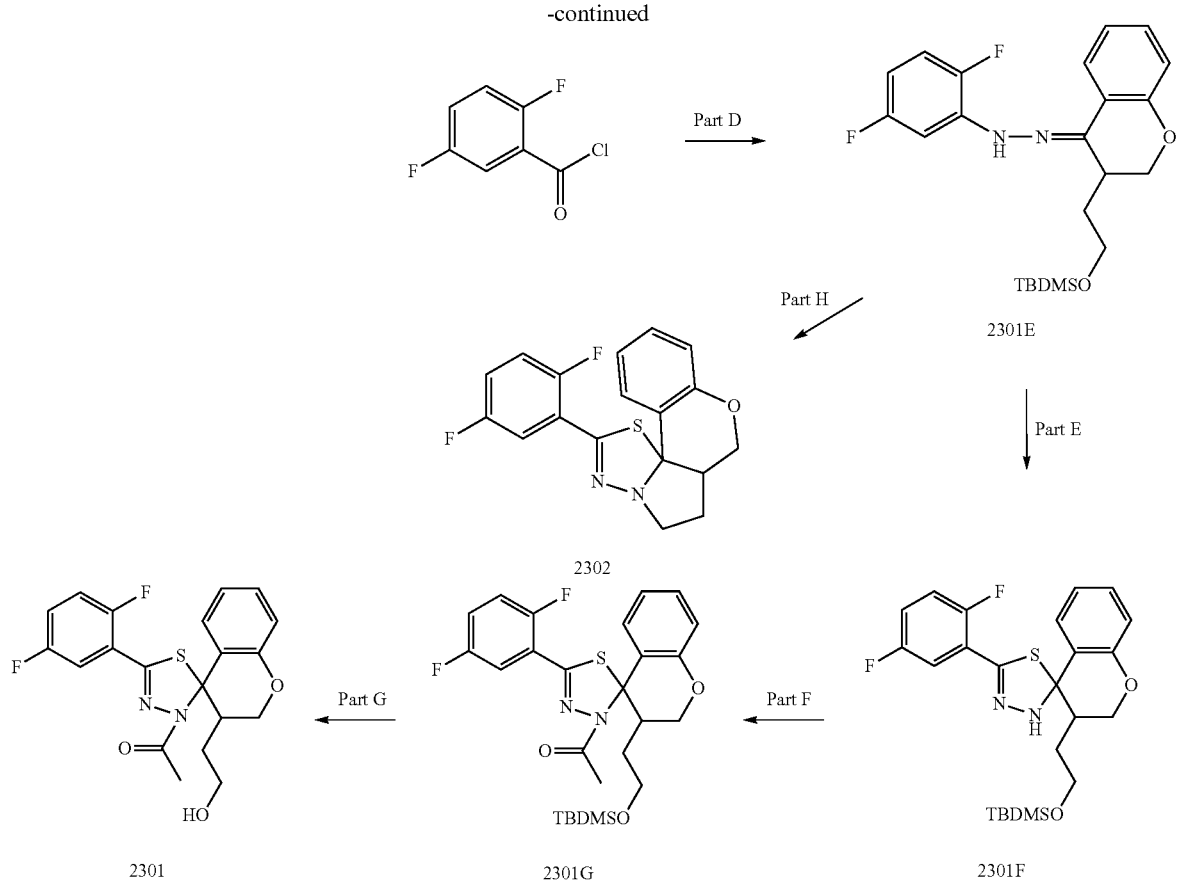

Part A:

A mixture of 4-Chromanone 901A (0.912 g, 6.16 mmol), Pd/C (0.106 g), Glycoaldehyde (0.740 g, 6.16 mmols) 0.5 M NaOMe (2.6 mL) in MeOH (20 mL) was hydrogenated at 1 atm over 4 days. The reaction was passed through celite, washed with MeOH and concentrated. Purification by flash column chromatography (SiO$_2$, 50% ethyl acetate in hexanes) to afford compound 1 (0.167 g, 15% yield) as a colorless oil.

Part B:

To a solution of compound 2301B (0.135 g, 0.703 mmol) in DMF 10 mL was added imidazole (0.072 g, 1.06 mmol) and TBDMSCl (0.159 g, 1.05 mmol). The reaction was heated to 70° C. overnight. Next day, the reaction was cool to RT, diluted with EtOAC and washed with water. The organic layer dried with MgSO$_4$ and concentrated to give compound 2301C (0.210g, 97%) as a colorless oil.

Part C:

To a solution of compound 2301C (0.132 g, 0.431 mmol) in EtOH (3 mL) was added Hydrazine hydrate (0.042 mL, 0.864 mmol) and Acetic acid (0.050 mL).

The reaction was stirred at RT overnight. The reaction was concentrated, diluted with EtOAc and washed with sat. NaHCO$_3$. The organic layer dried with MgSO$_4$ and concentrated to give compound 2301D (0.131 g, 95%) as a colorless oil.

Part D:

To a solution of compound 2301D (0.131 g, 0.409 mmol) in THF (10 mL) at 0° C. was added pyridine (0.050 mL). Difluorobenzoyl chloride (0.040 mL, 0.322 mmol) in THF 5 mL was added drop wise to the above mixture. After 10 min, the reaction was quenched with sat. NaHCO$_3$ and extracted with EtOAc. The organic layer dried with MgSO$_4$ and concentrated to give compound 2301E (0.180 g, 96%) as a white solid.

Part E:

A mixture of compound 2301E (0.063 g, 0.137 mmol) and P$_2$S$_5$ (0.061 g, 0.137 mmol) in THF (3 mL) was heated in microwave at 100° C. for 5 min. The reaction was diluted with DCM and washed with sat. NaHCO$_3$, the organic layer dried with MgSO$_4$ and concentrated to give compound 2301F (0.060g, 92%) as yellow oil. HPLC-MS $t_R$=2.939 min (UV$_{254\ nm}$); mass calculated for formula C$_{24}$H$_{30}$F$_2$N$_2$O$_2$SSi 476.18, observed LCMS m/z 477.18 (M+H).

Part F:

To a solution of compound 2301F (0.060 g, 0.126 mmol) in THF 3 mL was added DIEA (0.109 mL, 0.628 mmol) and AcCl (0.025 mL, 0.370 mmol). The reaction was stirred at RT overnight. The reaction was diluted with EtOAc and washed with sat. NaHCO$_3$. The organic layer dried with MgSO$_4$ and concentrated to give compound 2301G (0.064 g, 98%) as a brownish solid. HPLC-MS $t_R$=2.796 min (UV$_{254\ nm}$); mass calculated for formula C$_{26}$H$_{32}$F$_2$N$_2$O$_3$SSi 518.19, observed LCMS m/z 519.19 (M+H).

Part G:

In a flask, compound 2301G (0.064 g, 0.123 mmol) were stirred in with TFA (1 mL). After 5 min, rxn was concentrated. Purified by HPLC to provide compound 2301 (0.004 g, 8%) as a white powder. HPLC-MS $t_R$=5.42 min (UV$_{254\ nm}$); mass calculated for formula C$_{20}$H$_{18}$F$_2$N$_2$O$_3$S 404.10, observed LCMS m/z 405.10 (M+H).

Part H:

To a mixture of compound 2301E (0.063 g, 0.137 mmol) and P$_2$S$_5$ (0.122 g, 0.274 mmol) in THF 5 mL was heated in microwave at 100° C. for 20 min. The reaction was diluted with DCM and washed with sat. NaHCO$_3$, the organic layer dried with MgSO$_4$ and concentrated. HPLC purification gave compound 2302 (0.008 g, 17%) as a white solid. HPLC-MS t$_R$=6.77 min (UV$_{254\ nm}$); mass calculated for formula C$_{18}$H$_{14}$F$_2$N$_2$OS 344.08, observed LCMS m/z 345.08 (M+H).

The following compounds were synthesized using this procedure:

| Cpd ID | Structure | Exact mass | MS m/z (M$^+$ + H) | tR (min) | 1H NMR | EC50 (nM) Range |
|---|---|---|---|---|---|---|
| 2301 | 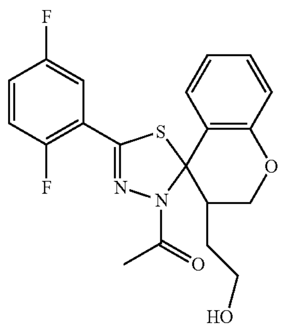 [SMILES: CC(=O)N1N=C(c2cc(F)ccc2F)SC12c1ccccc1OCC2CCO] | 404.10 | 405.10 | 5.42 | | A |
| 2302 | 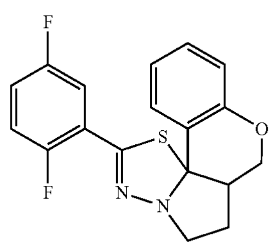 [SMILES: Fc1ccc(F)c(C2=NN3CCC4COc5ccccc5C43S2)c1] | 344.08 | 345.08 | 6.77 | | D |

Example 2401

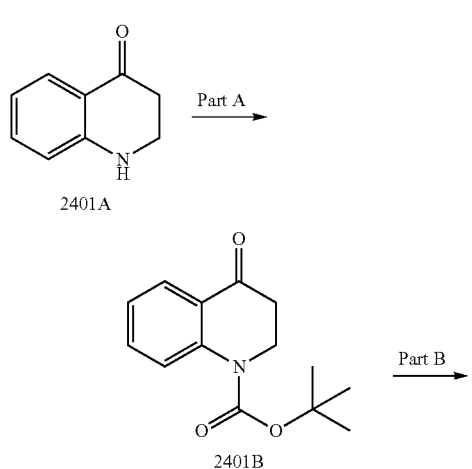

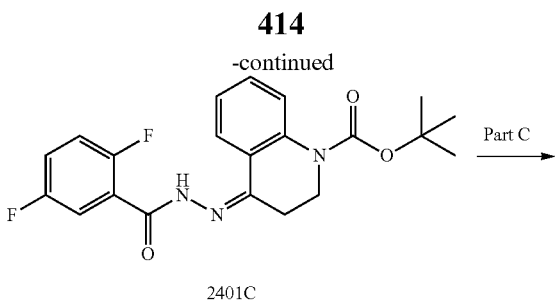

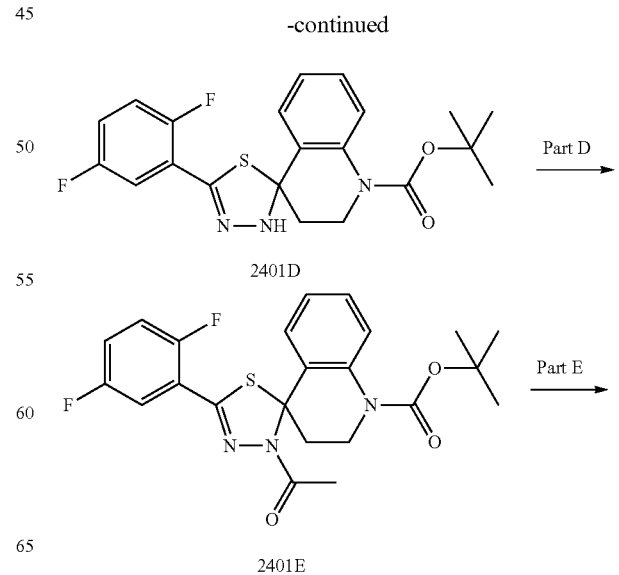

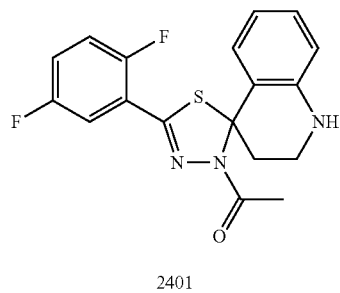

2401

Part A:

A solution containing 2,3-dihydroquinolin-4-one 2401A (294 mg, 2 mmol), di-tert-butyl dicarbonate (480 mg, 2.2 mmol), DIEA (383 2.2 mmol) and DMAP (24.4 mg, 0.2 mmol) in DCM (5 mL) was heated at 60° C. for 16 hours. The reaction mixture was cooled to room temperature, quenched with the addition of 1 N HCl (10 mL), extracted with DCM, dried over magnesium sulfate, concentrated and purified by flash silica chromatography, gradient elution (0 to 100%) hexane /ethyl acetate to afford compound 2401B as a yellow solid (494 mg, 2 mmol, 100%). HPLC-MS $t_R$=2.03 min (UV$_{254\ nm}$); mass calculated for formula $C_{14}H_{17}NO_3$ 247.1, observed LCMS m/z 248.3 (M+H).

Part B:

To a solution of 2,5-difluorobenzoyl hydrazide 101C from example 101 (177 mg, 1 mmol) in DCM (10 mL) was added compound 2401B (195 mg, 0.79 mmol) and acetic acid (100 μL). The reaction mixture was stirred at room temperature for 16 hours. Concentration and recrystallization from cold ethanol yielded compound 2401C as a white solid after filtration. HPLC-MS $t_R$=1.96 min (UV$_{254\ nm}$); mass calculated for formula $C_{21}H_{21}F_2N_3O_3$ 401.2, observed LCMS m/z 402.2 (M+H).

Part C:

To a solution of compound 2401C (150 mg, 0.37 mmol) in THF (10 mL) was added $P_2S_5$ (332 mg, 0.74 mmol) and the reaction mixture was heated in a microwave at 100° C. for 20 minutes. The reaction mixture was quenched with the addition of saturated NaHCO$_3$, and extracted with DCM. Drying over magnesium sulfate and concentration afforded crude compound 2401D as a yellow solid. HPLC-MS $t_R$=2.30 min (UV$_{254\ nm}$), mass calculated for formula $C_{21}H_{21}F_2N_3O_2S$ 417.1, observed LCMS m/z 418.1 (M+H).

Part E:

A mixture of compound 2401D (0.36 mmol), acetyl chloride (51 μL, 0.72 mmol) and DIEA (188 μL, 1.08 mmol) in DCM (5 mL) was stirred at room temperature for 16 hours. The reaction mixture was concentrated and purified by purified by flash silica chromatography., gradient elution (0 to 100%) hexane/ethyl acetate to afford compound 2404E as a white solid. HPLC-MS $t_R$=2.60 min (UV$_{254\ nm}$); mass calculated for formula $C_{23}H_{23}F_2N_3O_3S$ 459.1, observed LCMS m/z 404.1 (M+H-tBu). Compound 2401E was subjected to chiral HPLC (ChiralPak AD 50×500 mm 20μ, gradient 95:5 hexane/ethanol).

Part F:

A solution of compound 2401E (50 mg, 0.11 mmol) in trifluoroacetic acid (2 mL) was stirred at room temperature for 5 minutes. The reaction mixture was concentrated and purified by prep.HPLC to afford compound 2401 as a white solid.

The following compounds were synthesized using this procedure:

| Cpd ID | Structure | Exact mass | MS m/z (M$^+$ + H) | tR (min) | 1H NMR | EC50 (nM) Range |
|---|---|---|---|---|---|---|
| 2401 | 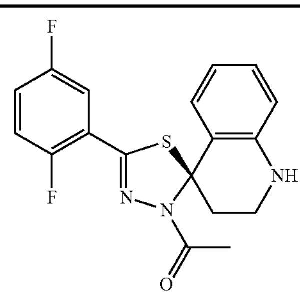 | 359.1 | 360.1 | 2.03 | | A |
| 2402 | 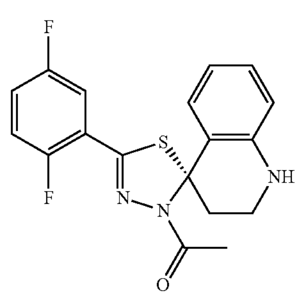 [SMILES: CC(=O)N1N=C(c2cc(F)ccc2F)S[C@]12CCNc1ccccc12] | 359.1 | 360.1 | 2.03 | | D |

Example 2501

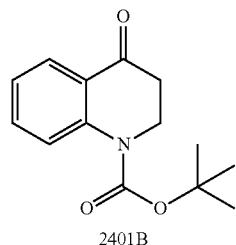
2401B

Part A →

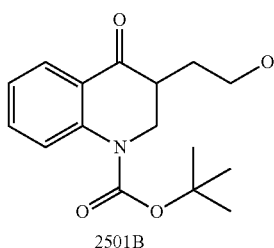
2501B

Part B →

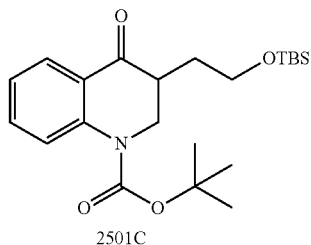
2501C

Part C →

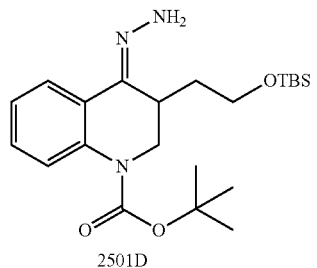
2501D

Part D →

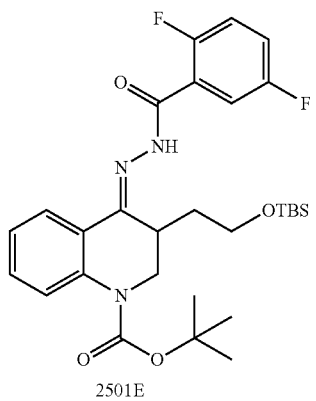
2501E

Part E →

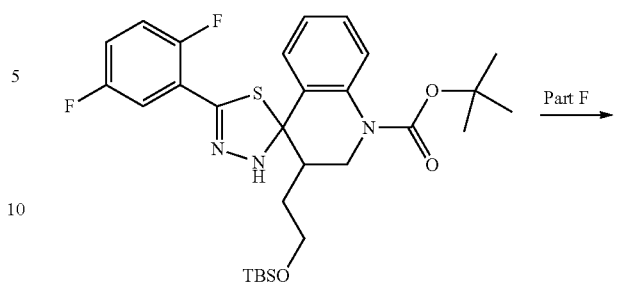
2501F

Part F →

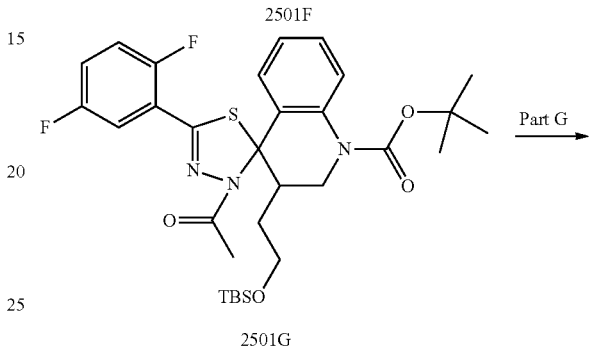
2501G

Part G →

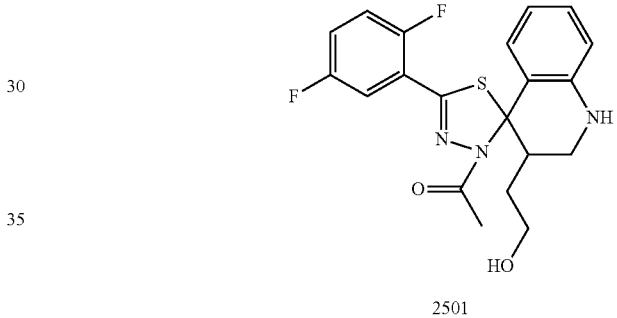
2501

Part A:

A mixture containing compound 2401B (761 mg, 3.08 mmol), glycoaldehyde dimer (370 mg, 3.08 mmol), 10% palladium on charcoal (53 mg) and sodium methoxide (0.5M solution, 1.3 mL, 0.65 mmol) in methanol (10 mL) was stirred under an hydrogen atmosphere for 72 hours at room temperature. Product formation was confirmed by LC-MS. The reaction mixture was filtered by passing through celite, concentrated, re-dissolved in DCM and washed with 1N HCl. Drying over magnesium sulfate, concentration and purification by flash silica chromatography, gradient elution (0 to 100%) hexane/ethyl acetate afforded compound 2501B as a colorless oil (330 mg, 50%). HPLC-MS $t_R$=1.65 min (UV$_{254\,nm}$); mass calculated for formula $C_{16}H_{21}NO_4$ 291.1, observed LCMS m/z 292.1 (M+H).

Part B:

A mixture containing compound 2501B (310 mg, 1.07 mmol), tert-butyldimethylsilyl chloride (241 mg, 1.6 mmol) and imidazole (109 mg, 1.6 mmol) in DMF (10 mL) was stirred at room temperature for 16 hours. Product formation was confirmed by LC-MS. The volatiles were removed in vacuo, and the resulting residue re-dissolved in ethyl acetate (20 mL) and washed with water (2×50 mL). Drying over magnesium sulfate and concentration afforded crude compound 2501C as a colorless oil (431 mg, 100%). HPLC-MS $t_R$=2.77 min (UV$_{254\,nm}$); mass calculated for formula $C_{22}H_{35}NO_4Si$ 405.2, observed LCMS m/z 406.3 (M+H).

Part C:

To a mixture of compound 2501C (1.18 g, 2.92 mmol) and hydrazine hydrate (272 µL, 8.74 mmol) in ethanol (20 mL) was added acetic acid (1 mL). The resulting reaction mixture was stirred at room temperature for 16 hours. The volatiles were removed in vacuo, and the resulting residue re-dissolved in ethyl acetate (20 mL) and washed with saturated $NaHCO_3$. Drying over magnesium sulfate, concentration and purification by flash silica chromatography, gradient elution (0 to 100%) hexane/ethyl acetate afforded compound 2501D as a white solid (916 mg, 75%). HPLC-MS $t_R$=2.56 min ($UV_{254\ nm}$); mass calculated for formula $C_{22}H_{37}N_3O_3Si$ 419.3, observed LCMS m/z 420.3 (M+H).

Part D:

A solution of 2,5-difluorobenzoyl chloride (42 mg, 0.24 mmol) in THF (5 mL) was slowly added over 15 minutes to a salt-water ice cooled (−10° C.) stirring mixture of compound 2501D (100 mg, 0.24 mmol) and N-ethylmorpholine (52 µL, 0.48 mmol) in THF (10 mL). The reaction mixture was stirred for an additional 30 minutes at −10° C., quenched by the addition of saturated $NaHCO_3$ and extracted with ethyl acetate. Drying over magnesium sulfate and concentration afforded crude compound 2501E as white solid (110 mg, 83%). HPLC-MS $t_R$=2.70 min ($UV_{254\ nm}$); mass calculated for formula $C_{29}H_{39}F_2N_3O_4Si$ 559.3, observed LCMS m/z 560.2 (M+H).

Part E:

Compound 2501F was prepared from compound 2501E using the conditions described in Example 2, Part D. HPLC-MS $t_R$=2.86 min ($UV_{254\ nm}$); mass calculated for formula $C29H_{39}F_2N_3O_3SSi$ 5752, observed LCMS m/z 576.2 (M+H).

Part F:

A mixture of compound 2501F (0.2 mmol), acetyl chloride (42 µL, 0.59 mmol) and DIEA (171 µL, 0.98 mmol) in DCM (5 mL) was stirred at room temperature for 16 hours. The reaction mixture was quenched by the addition of saturated $NaHCO_3$ and extracted with ethyl acetate. Drying over magnesium sulfate and purification by flash silica chromatography, gradient elution (0 to 100%) hexane/ethyl acetate afforded compound 2501G as a white solid (50 mg, 41%). HPLC-MS $t_R$=2.91 min ($UV_{254nm}$); mass calculated for formula $C31H_{41}F_2N_3O_4SSi$ 617.3, observed LCMS m/z 640.2 (M+Na).

Part G:

A solution of compound 2501G (50 mg, 0.08 mmol) in trifluoroacetic acid (3 mL) was stirred at room temperature for 10 minutes. The reaction mixture was concentrated and purified by prep.HPLC affording diastereomeric separation of compound 2501.

The following compounds were synthesized using this procedure:

| Cpd ID | Structure | Exact mass | MS m/z (M⁺+H) | tR (min) | 1H NMR | EC50 (nM) Range |
|---|---|---|---|---|---|---|
| 2501 | 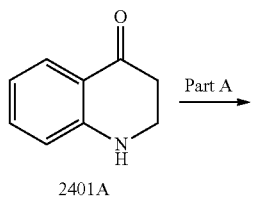 | 403.1 | 404.1 | 3.39 | | A |
| 2502 | 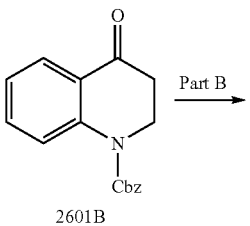 | 403.1 | 404.1 | 3.56 | | A |

Example 2601

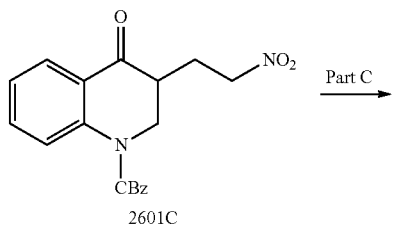

2601C

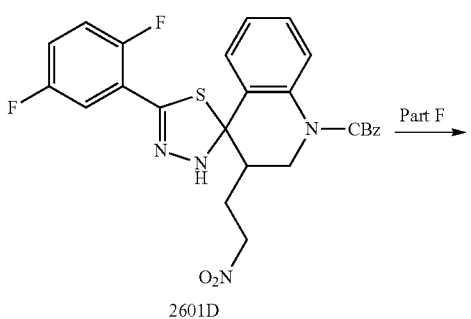

2601D

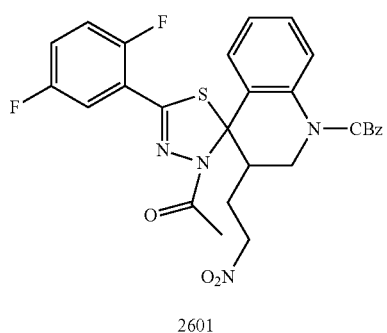

2601

Part A:

Compound 2601B (2.42 g, 63%) was prepared from the reaction of compound 2401A (2.0 g, 13.59 mmol) with benzyl chloroformate (2.3 mL, 16.3 mmol) using the conditions described in Example 1, Part A. HPLC-MS $t_R$=1.83 min ($UV_{254\ nm}$); mass calculated for formula $C_{17}H_{15}NO_3$ 281.1, observed LCMS m/z 282.1 (M+H).

Part B:

Compound 2601C (150 mg, 15%) was prepared from the Michael addition reaction of compound 2601B (790 mg, 2.81 mmol) with nitroethylene (308 mg, 4.22 mmol) using the conditions described in Example 801, Part D. HPLC-MS $t_R$=1.94 min ($UV_{254\ nm}$); mass calculated for formula $C_{19}H_{18}N_2O_5$ 354.1, observed LCMS m/z 355.1 (M+H).

Part C:

Compound 2601D (160 mg, 74%) was prepared from the condensation reaction of compound 2601C (150 mg, 0.42 mmol) with 2,5-difluorobenzoyl thiohydrazide hydrochloride (142 mg, 0.64 mmol) using the conditions described in Example 801, Part E. HPLC-MS $t_R$=2.27 min ($UV_{254\ nm}$); mass calculated for formula $C_{26}H_{22}F_2N_4O_4S$ 524.1, observed LCMS m/z 525.1 (M+H).

Part D:

Compound 2601D was prepared from the acetylation reaction of compound 2601C (160 mg, 0.31 mmol) with acetyl chloride (16 μL, 0.23 mmol) using the conditions described in Example 801, Part F. HPLC-MS $t_R$=2.24 min ($UV_{254\ nm}$); mass calculated for formula $C_{28}H_{24}F_2N_4O_5S$ 566.1, observed LCMS m/z 567.1 (M+H). Compound 2601 was subjected to chiral HPLC (ChiralPak AD 50×500 mm 20μ, gradient 30:70 hexane/ethanol) to afford compound 2601-1 (16 mg), compound 2601-2 (16 mg), compound 2601-3 (40 mg) and compound 2601-4 (40 mg).

Example 2701

2601-4

2701, 2702

R = H, Ac

Part A:

A mixture containing compound 2601-4 (40 mg, 0.071 mmol) and 20% palladium hydroxide on charcoal (10 mg) in methanol (20 mL) and acetic acid (500 μL) was stirred under an hydrogen atmosphere at 55 p.s.i. for 16 hours at room temperature. Product formation was confirmed by LC-MS. The reaction mixture was filtered by passing through celite, concentrated, re-dissolved in DCM and washed with 1 N HCl. Drying over magnesium sulfate, concentration and purification by prep.HPLC afforded compound 2701 as a white solid (6.6 mg). Compound 2702 (4.8 mg), a by-product of the reaction was also isolated during prep. HPLC purification.

The following compounds were synthesized using this procedure:

| Cpd ID | Structure | Exact mass | MS m/z (M+ + H) | tR (min) | 1H NMR | EC50 (nM) Range |
|---|---|---|---|---|---|---|
| 2701 | 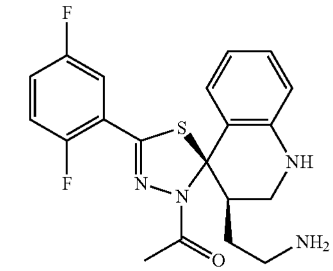 [SMILES: CC(=O)N1N=C(c2cc(F)ccc2F)S[C@]12c1ccccc1NC[C@H]2CCN] | 402.1 | 403.1 | 3.89 | (CD3OD) δ: 7.73-7.67 (m, 1H), 7.55 (dd, J = 7.8, 1.6 Hz, 1H), 7.36-7.29 (m, 2H), 7.18 (ddd, J = 15.6, 7.0, 1.6 Hz, 1H), 6.97-6.91 (ddd, J = 15.6, 7.0, 1.6 Hz, 1H), 6.84 (dd, J = 7.8, 1.6 Hz, 1H), 3.72 (t, J = 11.7 Hz, 1H), 3.45 (dd, J = 11.7, 4.7 Hz, 1H), 3.21-3.11 (m, 1H), 3.09-3.00 (m, 1H), 2.69-2.60 (m, 1H), 2.37 (s, 1H), 2.19-2.09 (m, 1H), 1.78-1.67 (m, 1H). | A |
| 2702 | 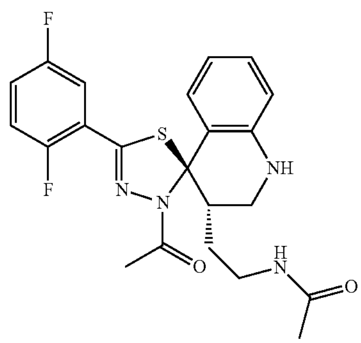 [SMILES: CC(=O)NCC[C@H]1CNc2ccccc2[C@]12SC(c1cc(F)ccc1F)=NN2C(C)=O] | 444.1 | 445.1 | 4.23 | | C |
Example 2801
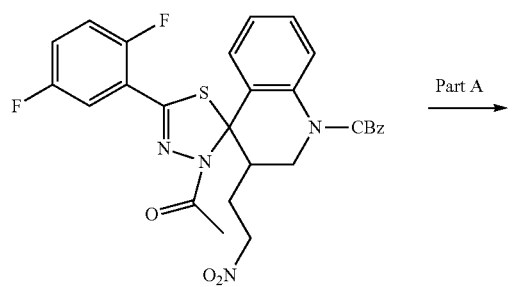
2601-1
2601-2
2601-3
Part A →
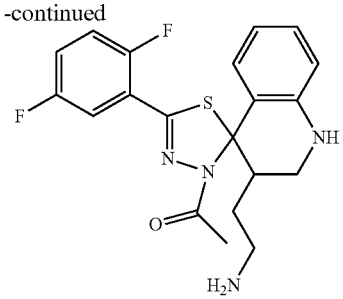
2801
2802
2803
Part A:
A mixture containing compound 2601-3 (40 mg, 0.071 mmol) and zinc dust (80 mg) in ethanol (1.6 mL) and acetic acid (160 μL) was stirred for 2 hours at room temperature. Reduction of the nitro group was confirmed by LC-MS. The reaction mixture was filtered by passing through celite, concentrated and re-dissolved in acetonitrile (2 mL). Iodotrimethylsilane (57 mg, 0.28 mmol) was added and the reaction mixture stirred at room temperature for 1 hour. The volatiles were removed in vacuo, the residue re-dissolved in ethyl acetate and washed with saturated sodium thiosulfate. Drying over magnesium sulfate, concentration and purification by prep.HPLC afforded compound 2803 as a white solid.

The following compounds were synthesized using this procedure:

| Cpd ID | Structure | Exact mass | MS m/z (M$^+$ + H) | tR (min) | 1H NMR | EC50 (nM) Range |
|---|---|---|---|---|---|---|
| 2801 | 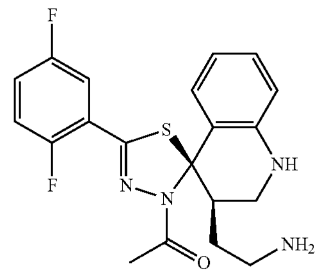 [SMILES: CC(=O)N1N=C(c2cc(F)ccc2F)S[C@]12c1ccccc1NC[C@H]2CCN] | 402.1 | 403.1 | 3.89 | (CD$_3$OD) δ: 7.69-7.63 (m, 1H), 7.34-7.24 (m, 1H), 7.11 (dd, J = 7.0, 1.6 Hz, 1H), 7.03 (ddd, J = 14.8, 7.0, 1.6 Hz, 1H), 6.68 (ddd, J = 14.8, 7.0, 1.6 Hz, 1H), 6.62 (d, J = 7.0 Hz, 1H), 3.60-3.50 (m, 2H), 3.16-3.06 (m, 1H), 3.02-2.92 (m, 1H), 2.49 (s, 1H), 2.01-1.91 (m, 1H), 1.89-1.78 (m, 1H). | A |
| 2802 | 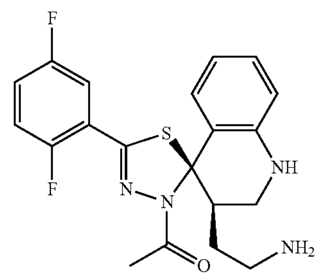 [SMILES: CC(=O)N1N=C(c2cc(F)ccc2F)S[C@]12c1ccccc1NC[C@H]2CCN] | 402.1 | 403.1 | 3.94 | (CD$_3$OD) δ: 7.69-7.63 (m, 1H), 7.34-7.24 (m, 1H), 7.11 (dd, J = 7.0, 1.6 Hz, 1H), 7.03 (ddd, J = 14.8, 7.0, 1.6 Hz, 1H), 6.68 (ddd, J = 14.8, 7.0, 1.6 Hz, 1H), 6.62 (d, J = 7.0 Hz, 1H), 3.60-3.50 (m, 2H), 3.16-3.06 (m, 1H), 3.02-2.92 (m, 1H), 2.49 (s, 1H), 2.01-1.91 (m, 1H), 1.89-1.78 (m, 1H). | A |
| 2803 | 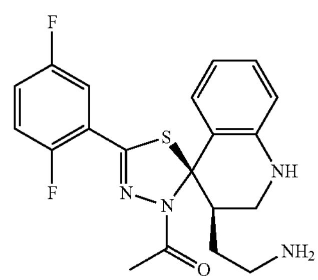 [SMILES: CC(=O)N1N=C(c2cc(F)ccc2F)S[C@]12c1ccccc1NC[C@H]2CCN] | 402.1 | 403.1 | 3.94 | (CD$_3$OD) δ: 7.71-7.66 (m, 1H), 7.42 (dd, J = 7.8, 1.6 Hz, 1H), 7.35-7.28 (m, 2H), 7.03 (ddd, J = 14.8, 7.0, 1.6 Hz, 1H), 6.69 (ddd, J = 14.8, 7.0, 1.6 Hz, 1H), 6.63 (dd, J = 7.8, 1.6 Hz, 1H), 3.59 (t, J = 10.9 Hz, 1H), 3.32 (dd, J = 9.4, 4.7 Hz, 1H), 3.17-3.08 (m, 1H), 3.07-2.97 (m, 1H), 2.58-2.48 (m, 1H), 2.36 (s, 1H), 2.16-2.06 (m, 1H), 1.76-1.65 (m, 1H). | |

Example 2901

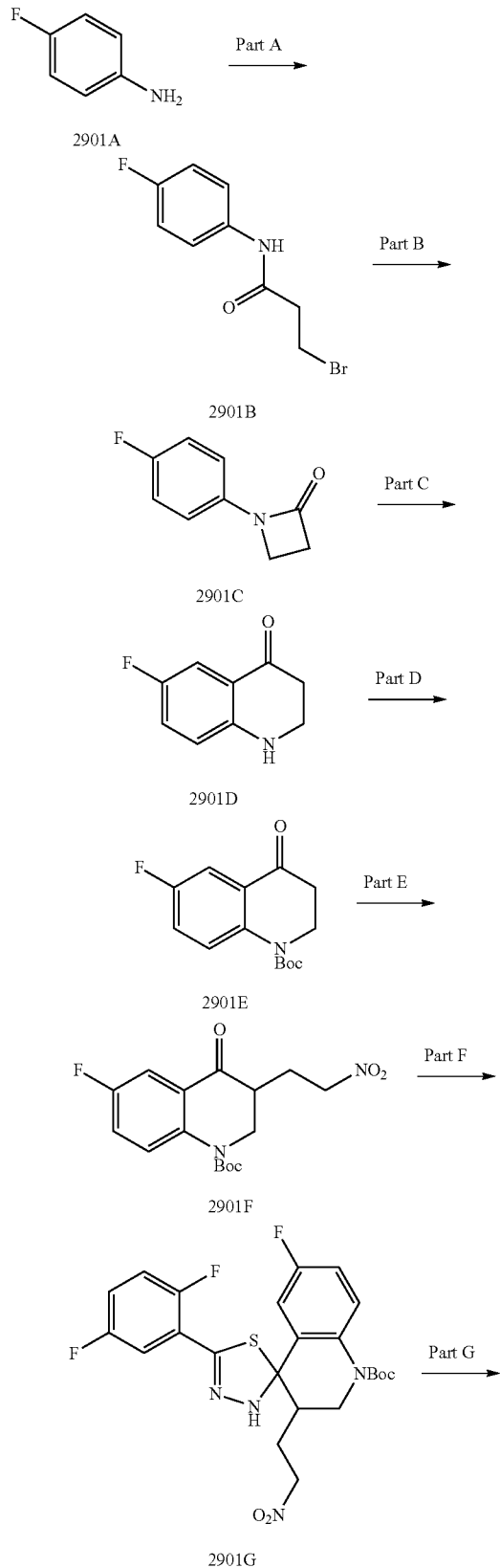

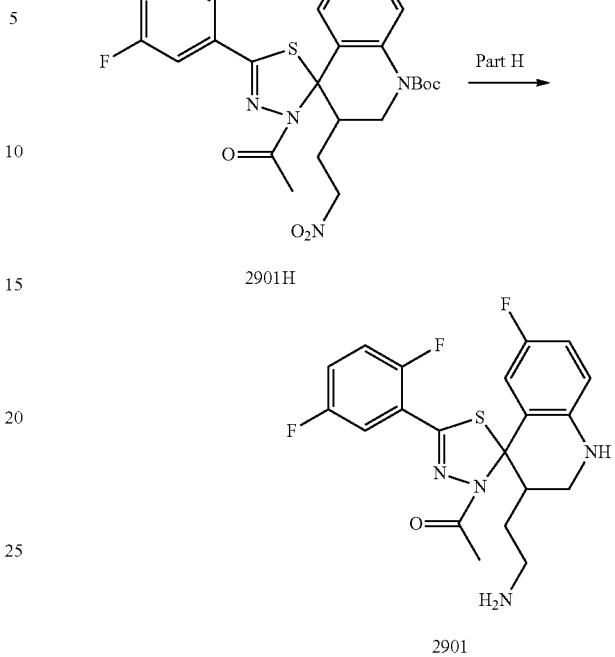

Part A:

To a solution of compound 2901A (8.8 mL, 91.6 mmols) in THF (50 mL) at −78° C. was added 2.0M Trimethylaluminum in Hexane (46 mL). The reaction was warmed up to RT and stirred for 20 min. Above solution was added to a flask containing methyl 3-bromopropionate (5 mL, 45.8 mmol) in THF (50 mL). After 2 h, reaction was cool to 0° C. and added 1N HCl, poured into a separatory funnel and extracted with EtOAc. The organic layer was dried with $MgSO_4$, concentrated to give compound 2901B as a light brown solid (10.2 g, 91%).

Part B:

To a solution of compound 2901B (10.12 g, 41.3 mmols) in DCM (100 mL) were added Potassium hydroxide (2.4 g, 42.77 mmols) and 18-crown-6 (11.5 g, 43.50 mmol). The reaction was stirred at RT overnight. The reaction was quenched with $NH_4Cl$ and extracted with EtOAc, the organic layer was dried with MgSO4 and concentrated. Purification by flash column chromatography ($SiO_2$, 25% ethyl acetate in hexanes) to afford compound 2901C (4.1 g, 60% yield) as a white solid.

Part C:

To a solution of compound 2901C (4.1 g, 24.8 mmol) in Dichloroethane (100 mL) at 0° C. was added Trifluoromethanesulfonic acid (4.4 mL). The reaction was stirred at RT for 5 h., quenched with sat. $NaHCO_3$ and extracted with DCM to give compound 2901D (3.3 g, 80%) as an off-white solid.

Part D:

To a solution of compound 2901D (3.27 g, 19.82 mmol) at 0° C. was added DMAP (0.242 g, 1.98 mmols), DIEA (3.8 mL, 21.8 mots) and $(BOC)_2O$ (5.2 g, 23.8 mmols). The reaction was heated to 50° C. overnight. The reaction was cool to RT and quenched with 1N HCl, extracted with DCM, the organic layer was dried with $MgSO_4$ and concentrated. Purification by flash column chromatography (SiO$_2$, 20% ethyl acetate in hexanes) afforded compound 2901E (2.4 g, 46% yield) as a white solid.

Part E:

To a solution of compound 2901E (2.5 g, 9.43 mmol) in THF (20 mL) at −78° C. was added 1.0M LHMDS (10.3 mL, 10.3 mols). The reaction was stirred at −78° C. for 30 min. and added slowly a solution of nitroethylene (1.1 g, 15.07 mmols) in THF (10 mL). After 5 min, reaction was quenched with NH$_4$Cl and extracted with EtOAc, the organic layer dried with MgSO$_4$ and concentrated. Purification by flash column chromatography (SiO$_2$, 20% ethyl acetate in hexanes) afforded compound 2901F (2.15 g, 68% yield) as a colorless oil.

Part F:

To a solution of compound 2901F (2.15 g, 6.36 mmol) in EtOH (25 mL) was added 2,5-difluorothiobenzoyl hydrazide hydrochloride salt (2.2 g, 9.82 mmol). The reaction was stirred at RT for 2 days. The solid material was filtered out and concentrated. The crude was diluted in EtOAc and washed with sat. NaHCO$_3$, the organic layer was dried with MgSO$_4$ and concentrated. Purification by flash column chromatography (SiO$_2$, 20% ethyl acetate in hexanes) afforded compound 2901G (2.65 g, 82% yield) as a yellow oil.

Part G:

To a solution of compound 2901G (1.3 g, 2.56 mmols) in DCM (10 mL) at 0° C. was added pyridine (0.621 mL, 7.67 mmols) and acetic anhydride (0.363 mL, 3.84 mmols). The reaction was warmed up to RT overnight. The reaction was quenched with NH$_4$Cl and extracted with DCM, the organic layer was dried with MgSO$_4$ and concentrated. Purification by flash column chromatography (SiO$_2$, 20% ethyl acetate in hexanes) afforded compound 2901H (0.950g, 68% yield) as a yellow oil. HPLC-MS $t_R$=2.586 min (UV$_{254\ nm}$); mass calculated for formula C$_{25}$H$_{25}$F$_3$N$_4$O$_5$S 550.15, observed LCMS m/z 495.15 (M+H-$^t$Butyl).

Chiral separation: Chiralcel OD column with 70:30/Hexane:EtOH.

Part H: To a solution of compound 2901H (0.337 g, 0.613 mmols) in EtOH (10 mL) was added Zn dust (0.650g) and AcOH (0.800 mL) and stirred at RT overnight. The reaction was passed through celite and concentrated. To the crude was added TFA (1 mL) and was stirred for about 30 min. The reaction was concentrated and purified by HPLC to obtain 2901 (0.062 g, 24%) as a white solid. HPLC-MS $t_R$=3.82 min (UV$_{254\ nm}$); mass calculated for formula C$_{20}$H$_{25}$F$_3$N$_4$OS 420.12, observed LCMS m/z 421.12 (M+H).

The following compounds were synthesized using this procedure:

| Cpd ID | Structure | Exact mass | MS m/z (M$^+$ + H) | tR (min) | 1H NMR | EC50 (nM) Range |
|---|---|---|---|---|---|---|
| 2901 | 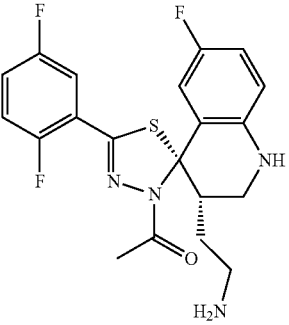 [SMILES: CC(=O)N1N=C(c2cc(F)ccc2F)S[C@@]12c1cc(F)ccc1NC[C@@H]2CCN] | 420.12 | 421.12 | 3.91 | (CD3OD) δ: 7.69-7.65 (m, 1H), 7.32-7.28 (m, 2H), 6.84-6.77 (m, 2H), 6.56 (dd, J = 8.6, 4.7 Hz, 1H), 3.53-3.43 (m, 2H), 3.15-2.92 (m, 4H), 2.50 (s, 3H), 1.97-1.77 (m, 2H). | A |
| 2902 | 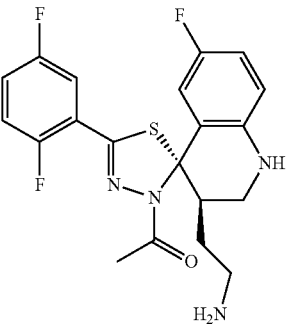 [SMILES: CC(=O)N1N=C(c2cc(F)ccc2F)S[C@@]12c1cc(F)ccc1NC[C@H]2CCN] | 420.12 | 421.12 | 3.98 | (CD3OD) δ: 7.72-7.68 (m, 1H), 7.34-7.31 (m, 2H), 7.21 (dd, J = 9.4, 2.3 Hz, 1H)), 6.90 (ddd, J = 16.4, 8.6, 2.3 Hz, 1H), 6.73 (dd, J = 9.4, 5.46 Hz, 1H), 3.60 (t, J = 11.7 Hz, 1H), 3.38-3.34 (m, 1H), 3.16-3.10 (m, 1H), 2.58-2.52 (m, 1H), 2.39 (s, 3H), 2.13-2.05 (m, 1H), 1.76-1.66 (m, 1H). | A |

-continued

| Cpd ID | Structure | Exact mass | MS m/z (M+ + H) | tR (min) | 1H NMR | EC50 (nM) Range |
|---|---|---|---|---|---|---|
| 2903 | 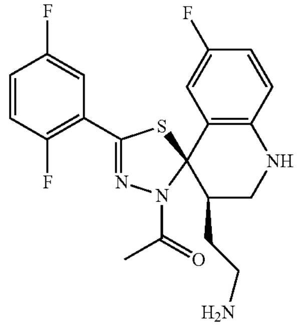 [SMILES: CC(=O)N1N=C(c2cc(F)ccc2F)S[C@]12c1cc(F)ccc1NC[C@H]2CCN] | 420.12 | 421.12 | 3.94 | (CD3OD) δ: 7.69-7.64 (m, 1H), 7.32-7.27 (m, 2H), 6.84-6.77 (m, 2H), 6.55 (dd, J = 8.6, 4.7 Hz, 1H), 3.51-3.45 (m, 2H), 3.15-2.93 (m, 3H), 2.50 (s, 3H), 1.96-1.77 (m, 2H). | A |
| 2904 | 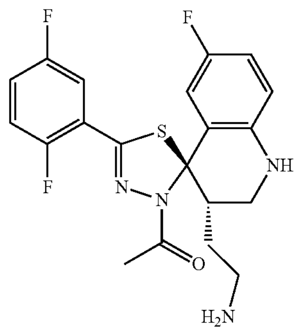 [SMILES: CC(=O)N1N=C(c2cc(F)ccc2F)S[C@]12c1cc(F)ccc1NC[C@@H]2CCN] | 420.12 | 421.12 | 3.90 | (CD3OD) δ: 7.71-7.67 (m, 1H), 7.33-7.30 (m, 2H), 7.12 (dd, J = 10.1, 3.1 Hz, 1H), 6.81 (ddd, J = 17.1, 9.4, 3.1 Hz, 1H), 6.58 (dd, J = 8.6, 4.7, 1H), 3.51 (t, J = 10.9 Hz, 1H), 3.15-2.70 (m, 2H), 2.54-2.45 (m, 1H), 2.38 (s, 3H) 2.11 (m, 1H), 1.75-1.66 (m, 1H). | D |

It is contemplated that the following compounds represent additional non-limiting examples of compounds of the invention which can be made, for example, according to the above procedure:

| Cpd. | Structure |
|---|---|
| 2905 | 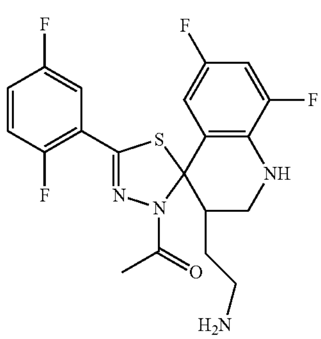 [SMILES: CC(=O)N1N=C(c2cc(F)ccc2F)SC12c1cc(F)cc(F)c1NCC2CCN] |
| 2906 | |

| Cpd. | Structure |
|---|---|
| 2907 | 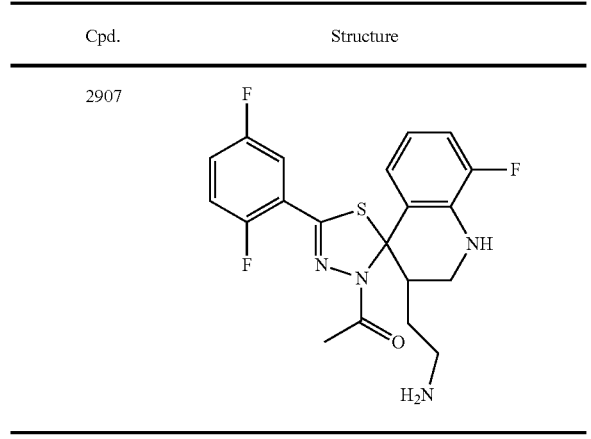 |

Example 3001

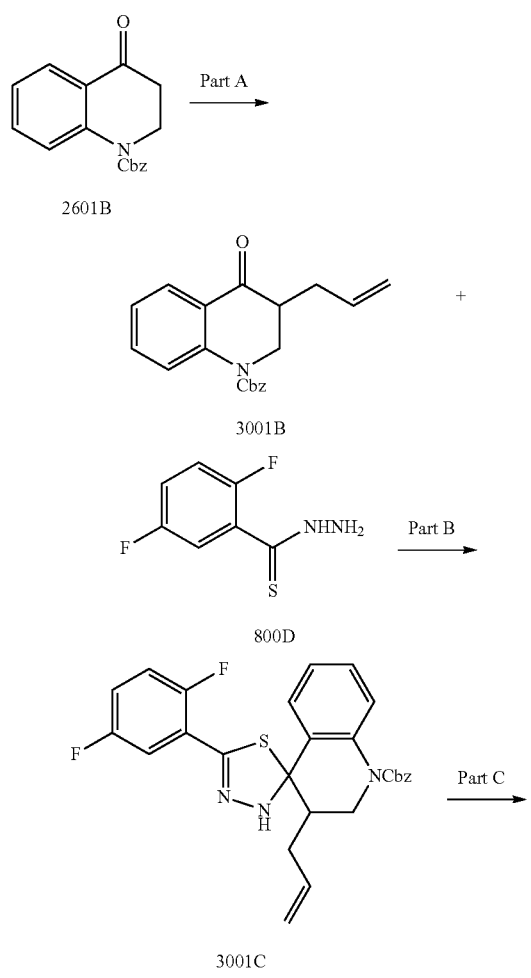

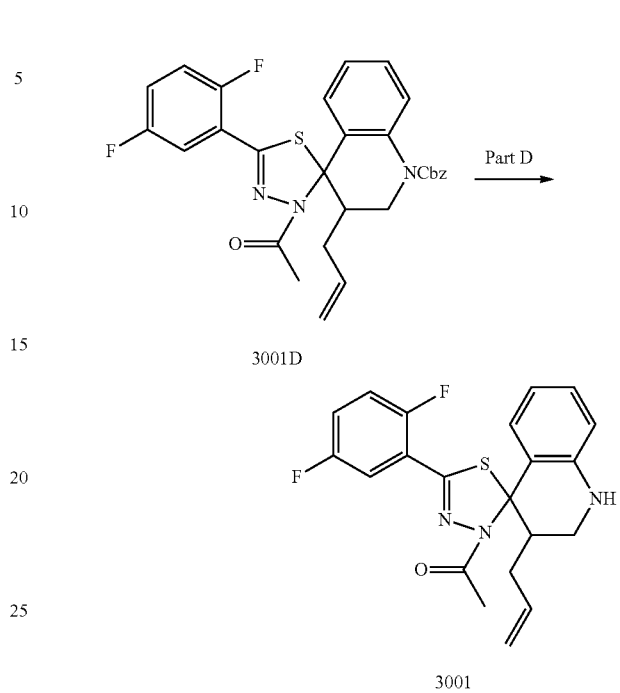

Part A:

To a solution of 2601B (from example 2601) (0.500 g, 1.78 mmols) in toluene (200 mL) was added Allyl alcohol (0.517 g, 8.9 mmols), 2,2-dimethoxy propane (0.328 mL, 2.67 mmol) and p-toluene sulfonic acid (0.068 g, 0.36 mmol). The reaction was refluxed using dean Stark apparatus for 18 h. Reaction was concentrated, diluted with EtOAc and washed with sat. $NaHCO_3$. The organic layer dried with $MgSO_4$ and concentrated. Biotage purification ($SiO_2$, 25% ethyl acetate in hexanes) to obtain compound 3001B (0.400g, 70%) as a colorless oil.

Part B:

In to a microwave vial was added compound 3001B (0.159 g, 0.495 mmols), 800D (0.332 g, 1.48 mmol) and THF (5 mL). The reaction was heated at 100° C. for 40 min and diluted with DCM, washed with sat. $NaHCO_3$. The organic layer dried with MgSO4 and concentrated to give compound 3001C (0.240g, 99%0 as yellow solid.

Part C:

Follow the same procedure as Part G of example 2501. Chiral separation using Chiralpak AD column with 50:50/hexane:EtOH afforded compound 3001D.

Part D:

To a solution of compound 3001D (0.002 g, 0.004 mmols) in MeOH (1 mL) was added sat. $H_2SO_4$ (0.200 mL) and the reaction was refluxed for 2 h. The Reaction was cool to RT, concentrated, diluted with EtOAc and washed with sat. $NaHCO_3$. Purified by HPLC to obtain compound 3001 (0.001 g, 69%) as a white solid:

| Cpd ID | Structure | Exact mass | MS m/z (M⁺ + H) | tR (min) | 1H NMR | EC50 (nM) Range |
|---|---|---|---|---|---|---|
| 3001 | 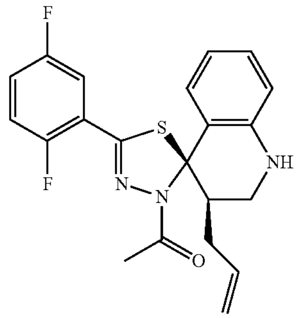 [SMILES: C=CC[C@@H]1CNc2ccccc2[C@]12SC(c1cc(F)ccc1F)=NN2C(C)=O] | 399.12 | 400.12 | 6.32 | (CD3OD) δ: 7.66-7.62 (m, 1H), 7.29-7.26 (m, 2H), 7.09 (d, J = 7.0 Hz, 1H), 6.98 (ddd, J = 7.0, 1.6 Hz, 1H), 6.60 (t, J = 7.0 Hz, 1H), 6.54 (d, J = 9.4 Hz, 1H), 5.88-5.78 (m, 1H), 5.06 (t, J = 14.8 Hz, 1H), 3.56-3.41 (m, 3H) 2.97 (t, J = 11.7 Hz, 1H), 2.44 (s, 3H), 2.41-2.33 (m, 1H), 2.22-2.15 (m, 1H). | A |
Example 3101
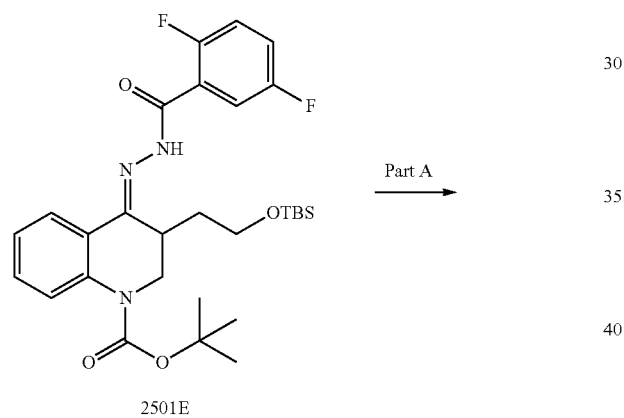
2501E
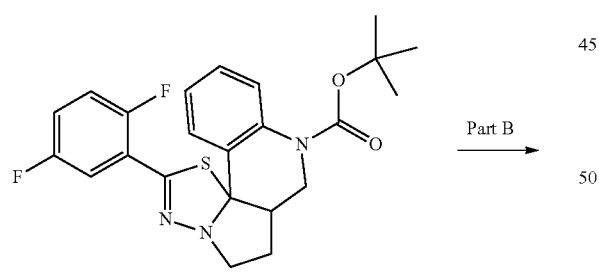
3101B
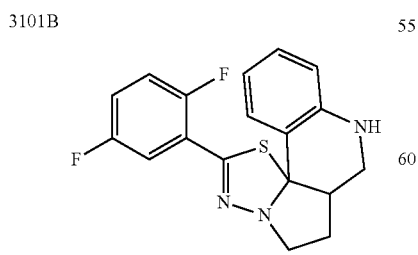
3101

Part A:

Compound 3101B was prepared from compound 2501E as a by-product using the conditions described in Example 2501, Part D. HPLC-MS $t_R$=2.62 min (UV$_{254\,nm}$); mass calculated for formula $C_{23}H_{23}F_2N_3O_2S$ 443.2, observed LCMS m/z 444.1 (M+H).

Part B:

A solution of compound 3101B (50 mg, 0.12 mmol) in trifluoroacetic acid (3 mL) was stirred at room temperature for 10 minutes. The reaction mixture was concentrated and purified by prep.HPLC affording compound 3101 as a white solid (12 mg, 29%).

KSP Cellular Assay:

HCT116 colon cancer cells were grown in DMEM:F12 media with 10% heat inactivated FBS at 37 degrees with 5% CO2. Cells were plated at 7,500 cells per well in PDL coated 384-well tissue culture plates. 6 hours later media was removed and new media containing drug was added. Cells were incubated with drug for 16 hours. All further steps were performed at room temperature in the dark. Cells were fixed with 25 ul/well Prefer fixation solution plus 250 nM Hoechst dye and incubated for 30 minutes. The fixation solution was removed and cells were washed with PBS. Cells were then permeabilized with 25 ul/well 0.2% Triton-X in PBS and

| Cpd ID | Structure | Exact mass | MS m/z (M$^+$ + H) | tR (min) | 1H NMR | EC50 (nM) Range |
|---|---|---|---|---|---|---|
| 3101 | 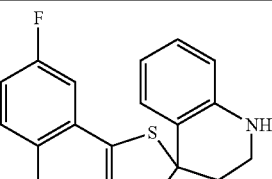 | 343.1 | 344.1 | 3.94 | (CDCl$_3$) δ: 7.85 (d, J = 7.0 Hz, 1H), 7.48-7.42 (m, 1H), 7.12 (t, J = 7.0 Hz, 1H), 7.03-6.90 (m, 5H), 6.76 (d, J =7.8 Hz, 1H), 3.80 (m, 1H), 3.60 (dd, J = 8.6, 3.9 Hz, 1H), 3.39-3.30 (m, 2H), 2.87 (m, 1H), 2.05-1.95 (m, 1H), 1.93-1.83 (m, 2H). | D |

The pharmacological properties of the compounds of this invention, including their efficacy as inhibitors of KSP activity, may be confirmed by a number of pharmacological assays. The inhibitory activity of the compounds of the invention towards KSP may be assayed by methods known in the art, for example, by using the methods as described below and in the examples above.

KSP Biochemical Assay

KSP biochemical enzyme assays were performed in 384-well plates. All reagents were thawed on ice. Compounds were diluted in 100% DMSO to desirable concentrations. 10 mg microtubules (Cytoskeleton) were reconstituted in 10 mL tubulin buffer (80 mM PIPES pH 6.8, 1 mM EGTA, 1 mM MgCl$_2$, 0.005% sodium azide) plus 100 ul 2 mM paclitaxel (Cytoskeleton).

Each reaction consisted of 10 nM KSP motor domain (amino acid 15-368), 20 uM paclitaxel (Cytoskeleton), 0.18 uM microtubules, 100 uM ATP (Roche) and kinesin buffer (20 mM ACES pH 7.0, 1 mM EGTA, 1 mM MgCl$_2$, 25 mM KCl, 1 mM DTT). For each reaction, 19 uL of mixture containing KSP motor domain, paclitaxel, microtubules and kinesin buffer were combined with 1 uL diluted compound. The reaction was started by the addition of 5 uL ATP. The reaction was allowed to run for 1 hour at room temperature. The reaction was stopped by adding 50 ul Biomol Green (Biomol International). After an additional 30 minutes, absorbance at OD620 nm was measured using an Envision.

IC50 Determinations: Dose-response curves were plotted from inhibition data generated each in duplicate, from 8 point serial dilutions of inhibitory compounds. Concentration of compound was plotted against enzyme activity (OD reading). To generate IC50 values, the dose-response curves were then fitted to a standard sigmoidal curve and IC50 values were derived by nonlinear regression analysis.

incubated for 10 minutes. Cells were washed with PBS and then incubated with 25 ul/well PBS containing 3% FBS for 30 minutes. Cells were then stained overnight at 4 degrees with 25 ul/well antibody solution in PBS plus 3% FBS. Antibodies used were Phos-Histone H3 (ser10)-Alexa Flur 488 Conjugate and Phos-MPM2 Texas Red Conjugate. Cells were washed with PBS and then immunofluorescence images captured with HT Pathway microscope. The percent of cells staining positive was calculated and EC$_{50}$ values for the compounds of the invention that were tested were determined using Excel XLfit.

EC50 Determinations: Dose-response curves were plotted from inhibition data generated each in duplicate, from 8 point serial dilutions of inhibitory compounds. Concentration of compound was plotted against enzyme activity (OD reading). To generate EC50 values, the dose-response curves were then fitted to a standard sigmoidal curve and EC50 values were derived by nonlinear regression analysis.

Exemplary compounds of the invention that were tested in the above cellular assays exhibited EC$_{50}$ values reported as ranges in the Tables above.

Methods of Use

As inhibitors of KSP activity, the compounds of the invention are contemplated as being useful in treating a wide variety of diseases, conditions, or disorders ("diseases").

In one embodiment, the present invention provides a method of inhibiting KSP kinesin activity in a subject (e.g., cells, animals, or humans) in need thereof, comprising administering to said subject at least one compound or composition of the invention or a pharmaceutically acceptable salt, ester, isomer, tautomer, or prodrug thereof.

In one embodiment, the present invention provides a method of selectively inhibiting KSP kinesin activity in a subject (e.g., cells, animals, or humans) in need thereof, comprising administering to said subject at least one compound or composition of the invention or a pharmaceutically acceptable salt, ester, isomer, tautomer, or prodrug thereof.

In some embodiments, diseases which are amenable to treatment include those susceptible to alteration of mitosis by KSP activity inhibition. As will be appreciated by those skilled in the art, mitosis may be altered in a variety of ways, such as by increasing or decreasing the activity of a component in the mitotic pathway or by disturbing equilibrium (e.g., by inhibiting or activating certain components).

In one embodiment, the invention provides a method of treating or preventing a disease associated with KSP activity in a subject in need thereof comprising administering a therapeutically effective amount of at least one compound of the invention or a pharmaceutically acceptable salt or ester thereof to said subject.

In one embodiment, the compounds of the invention can be used to inhibit mitotic spindle formation, thus causing prolonged cell cycle arrest in mitosis. "Inhibit" in this context means decreasing or interfering with mitotic spindle formation or causing mitotic spindle dysfunction. "Mitotic spindle formation" means the organization of microtubules into bipolar structures by mitotic kinesins. "Mitotic spindle dysfunction" means mitotic arrest and monopolar spindle formation.

In one embodiment, the compounds of the invention can be useful for binding to, and/or inhibiting the activity of, KSP. In one embodiment, the KSP is human KSP. In one embodiment, such KSP activity is inhibited in vitro, in vivo (e.g., in a patient in need thereof), or ex vivo.

In other embodiments, the compounds of the invention may be used to bind to or inhibit the activity of KSP kinesins from non-human organisms. In this context, "inhibit" means increasing or decreasing spindle pole separation, causing malformation, i.e., splaying, of mitotic spindle poles, or otherwise causing morphological perturbation of the mitotic spindle.

Also included within the definition of KSP for purposes of the present invention are variants and/or fragments of KSP (see, e.g., U.S. Pat. No. 6,437,115).

The compounds of the invention can be used to treat diseases associated with or caused by aberrant cellular proliferation. Such disease states include, but are not limited to, cancer (further discussed below), hyperplasia, cardiac hypertrophy, autoimmune diseases, fungal disorders, arthritis, graft rejection, inflammatory bowel disease, immune disorders, inflammation, cellular proliferation induced after medical procedures, including, but not limited to, surgery, angioplasty, and the like. Treatment includes inhibiting cellular proliferation. It is appreciated that in some cases the cells may not be in an abnormally proliferative state and yet require treatment. For example, during wound healing, the cells may be proliferating "normally", but inhibition of cellular proliferation may be desired. Thus, in one embodiment, the invention herein includes application to cells or subjects afflicted with or subject to impending affliction with any one of these conditions, disorders or states.

The terms "treating cancer" and "treatment of cancer" refer to administration to a mammal afflicted with a cancerous condition and to an effect that alleviates the cancerous condition by killing at least some of the cancerous cells, and also to an effect that results in the inhibition of growth and/or metastasis of the cancer.

Due to their KSP inhibitory action, the compounds, compositions and methods provided herein are useful for the treatment of a wide variety of cancers. Non-limiting examples of such cancers include solid tumors and hematological cancers, such as those of the skin, breast, brain, colon, gall bladder, thyroid, cervical carcinomas, testicles, and blood. Additional non-limiting examples of cancers suitable for treatment include:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic: blood (myeloid leukemia (acute and chronic), acute lymphoblastic leukemia, acute and chronic lymphocytic leukemia, myeloproliferative diseases, multiple myeloma, myelodysplastic syndrome), Hodgkin's disease, non-Hodgkin's lymphoma (malignant lymphoma), B-cell lymphoma, T-cell lymphoma, hairy cell lymphoma, Burkett's lymphoma, promyelocytic leukemia;

Skin: malignant melanoma, basal cell carcinoma, squamous cell carcinoma, Karposi's sarcoma, moles dysplastic nevi, lipoma, angioma, dermatofibroma, keloids, psoriasis;

Adrenal glands: neuroblastoma; and

Other tumors: including xenoderoma pigmentosum, keratoctanthoma and thyroid follicular cancer.

As used herein, treatment of cancer includes treatment of cancerous cells, including cells afflicted by any one of the conditions, states, or disorders described above.

The compounds of the present invention may also be useful in the chemoprevention of cancer. Chemoprevention is defined as inhibiting the development of invasive cancer by either blocking the initiating mutagenic event or by blocking the progression of pre-malignant cells that have already suffered an insult. The compounds of the present invention may also be useful in inhibiting cancer relapse.

The compounds of the present invention may also be useful in inhibiting tumor angiogenesis and metastasis.

The compounds of the present invention may also be useful as antifungal agents, by modulating the activity of the fungal members of the bimC kinesin subgroup, as is described in U.S. Pat. No. 6,284,480.

For each of the foregoing embodiments, the amount of the at least one compound of the invention administered is preferably an effective amount for the intended purpose. The phrase "effective amount" means that amount of a compound of the invention, and other pharmacological or therapeutic agents described herein, that will elicit a biological or medical response of a tissue, a cell, a population of cells (e.g., a population of aberrantly proliferating cells such as cancer cells or psioratic cells), a system, or a subject (e.g., animal or human) that is being sought by the administrator (such as a researcher, doctor or veterinarian) which includes alleviation of the symptoms of the condition or disease being treated and the prevention, slowing or halting of progression of one or more cellular proliferation diseases. "Therapeutically effective amount" means effective amount where the purpose includes a therapeutic purpose, such as in a human or non-human patient in need of treatment. The formulations or compositions, combinations and treatments of the present invention can be administered by any suitable means which produce contact of these compounds with the site of action in the targeted population of aberrantly proliferating cells or the body of the subject being treated.

Suitable dosage ranges for the various embodiments of the invention are readily determined by those skilled in the art and depend upon intended use. Suitable dose ranges include from about 0.001 to about 500 mg/kg of body weight/day of a compound of the invention or a pharmaceutically acceptable salt, ester, or prodrug (etc.) thereof. Another suitable dosage ranges from about 0.01 to about 25 mg/kg of body weight/day. For administration of pharmaceutically acceptable salts of the above compounds, the weights indicated above refer to the weight of the acid equivalent or the base equivalent of the therapeutic compound derived from the salt.

It may be preferable to administer KSP kinesin inhibitors which can specifically inhibit KSP kinesin activity at low concentrations, for example, those that cause a level of inhibition of 50% or greater at a concentration of 50 µM or less, 100 nM or less, or 50 nM or less. The administration of such compounds of the invention represents various embodiments of the present invention.

Compositions

In some embodiments, the at least one compound of the invention is administered as the neat chemical. In other embodiments, the compounds of the invention are administered as a pharmaceutical composition. Thus, pharmaceutical compositions comprising at least one compound of the invention are within the scope of the present invention. Such pharmaceutical compositions of the present invention comprise at least one compound of the invention (e.g., doses of one, two, three, or more different compounds of the invention), together with one or more acceptable carriers, and optionally other therapeutic agents. Each carrier (including, e.g., adjuvants or vehicles) must be acceptable in the sense of being compatible with the other ingredients of the composition and not injurious to the intended purpose or, in the case of therapy, the subject being treated. Accordingly, in another embodiment, this invention also provides pharmaceutical compositions comprising at least one compound of the invention, or a pharmaceutically acceptable salt, solvate, ester, prodrug, or isomer thereof and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a subject by administering a pharmaceutical composition of the present invention is also intended to encompass the administration of the afore-said bulk composition and individual dosage units.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use; to liquid form preparations for either oral or parenteral (e.g., subcutaneous, intramuscular, introrbital, intracapsular, intraspinal, intrasternal, intravenous, etc.) administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the at least one compound or composition of the invention is formulated for subcutaneous administration.

In one embodiment, the at least one compound or composition of the invention is formulated for oral administration.

In one embodiment, the at least one compound or composition of the invention is formulated for parenteral administration.

In one embodiment, the at least one compound or composition of the invention is formulated for intravenous administration.

In one embodiment, the pharmaceutical preparation is provided in a unit dosage form. In such form, the preparation is subdivided into suitably sized unit doses containing appropriate quantities of the active component, e.g., an effective amount to achieve the desired purpose.

As stated elsewhere herein, the quantity of active compound in a unit dose of preparation may be varied or adjusted to suit intended purpose. Additional non-limiting examples of such doses range from about 1 mg to about 100 mg, alternatively from about 1 mg to about 50 mg, or alternatively from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts or esters thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

In another embodiment, the present invention provides a kit comprising a therapeutically effective amount of at least one compound of the invention or a pharmaceutically acceptable salt or ester thereof and at least one pharmaceutically acceptable carrier, adjuvant or vehicle, and, optionally, inserts and/or labels which include instructions for use.

In another embodiment, the present invention provides a kit comprising an amount of at least one compound of the invention or a pharmaceutically acceptable salt or ester thereof and an amount of at least one additional therapeutic agent listed above, wherein the amounts of the two or more ingredients result in desired therapeutic effect.

In another embodiment, the present invention provides for: the use of at least one compound of the invention, or a pharmaceutically acceptable salt, solvate, ester or prodrug thereof, to manufacture a medicament for inhibiting KSP kinesin activity in a subject in need thereof.

In another embodiment, the present invention provides for: the use of at least one compound of the invention, or a pharmaceutically acceptable salt, solvate, ester or prodrug thereof, to manufacture a medicament for treating one or more diseases by inhibiting KSP kinesin activity in a patient in need thereof.

In another embodiment, the present invention provides for: the use of at least one compound of the invention, or a pharmaceutically acceptable salt, solvate, ester or prodrug thereof, to manufacture a medicament for treating any one of the conditions, disease, or disorders described herein.

In another embodiment, the present invention provides for: the use of a combination comprising (i) at least one compound of the invention, or a pharmaceutically acceptable salt, solvate, ester or prodrug thereof; and (ii) at least one second active ingredient described herein.

Combination Therapies

The compounds of the invention (and the compositions comprising at least one compound of the invention) are also useful in combination with one or more therapeutic agents other than a compound of the invention. Such therapeutic agents are selected according to intended purpose. Non-limiting examples of such agents include those which are effective for treating the underlying disease or condition, and/or for minimizing one or more side effects of a therapeutic agent, and/or for enhancing or altering the bioavailability of an administered therapeutic agent, etc.

Combinations of the compounds of the invention with other anti-cancer or chemotherapeutic agents are within the scope of the invention. Non-limiting examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer (or other indication) involved. The following description provides additional non-limiting examples of such combination agents. Those of ordinary skill in the art will readily be able to determine additional suitable agents.

Thus, anti-cancer agents suitable for use in combination with at least one compound of the invention (or composition comprising at least one compound of the invention) include, but are not limited to the following: estrogen receptor modulators, androgen receptor modulators, retinoid receptor modulators, cytotoxic agents, microtubule inhibitors/stabilizing agents, topoisomerase inhibitors, antisense RNA and DNA oligonucleotides, antimetabolites, antibodies coupled to cyclotoxic agents or radioisotypes, HMG-CoA reductase inhibitors, prenyltransferase inhibitors, farnesyl protein transferase inhibitors, angiogenesis inhibitors, kinase inhibitors, COX2 inhibitors, integrin blockers, PPAR agonists, and MDR inhibitors. Additional anticancer agents also include hypoxia activatable agents, proteasome inhibitors, ubiquitin inhibitors, HDM2 inhibitors, TNF activators, BUB-R inhibitors, CENP-E inhibitors, and interferons (e.g., alpha interferon). Such anti-cancer agents can be small molecules or biologics (e.g., RNA antisense and antibodies). The compounds of the invention are also useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-ydrazone, aid SH646. Additional examples include anastrozole and letrazole.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, a difluoromethylornithine, ILX23-7553, trans-N-(4'-hydroxyphenyl)retinamide, and N-4-carboxyphenyl retinamide.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide (TEMODAR™ from Schering-Plough Corporation, Kenilworth, N.J.), cyclophosphamide, heptaplatin, estramustine, improsulfan tosilate, trofosfamide, nimustine, dibrospidium chloride, pumitepa, lobaplatin, satraplatin, profiromycin, cisplatin, doxorubicin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(11)]bis[diamine(chloro)platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deansino-3'-morpholino-13-deoxo-10-hydroxycaminomycin, annamycin, galarubicin, elinafide, MEN10755, 4-demethoxy-3-deamino-3-aziridinyl-4-methylsulphonyl-daunombicin (see WO 00/50032), methoxtrexate, gemcitabine, and mixture thereof.

Examples of microtubule inhibitors/microtubule-stabilising agents include paclitaxel, vindesine sulfate, 3',4'-didehydro-4'-deoxy-8'-norvincaleukoblastine, docetaxel, vincristine, vinblastin, vinorelobine, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino) ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylannino)ethyl]-N-methylamino]ethyl]-5-[4-hydroxy-3,5-climethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-nnethoxybenzo[c]-pherisnthridinium, 6,9-bis[(2-aminoethyl)amino] benzo[g]isoquinoline-5,10-dione, 5-(3-: aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, dimesna, and camptostar.

Examples of Antisense RNA and DNA oligonucleotides include: G3139, ODN698, RVASKRAS, GEM231, and INX3001.

Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and gene therapy to interferon gamma (*J Immunol* 2000; 164:217-222). For an overview of genetic strategies to treating cancer, see Hall et al (*Am J Hum Genet.* 61:785-789, 1997) and Kufe et al (*Cancer Medicine*, 5th Ed, pp 876-889, BC Decker, Hamilton 2000).

Examples of antimetabolites include: 5-fluorouracil, enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin(ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open acid and lactone forms is included in the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, 5,602,098, European Patent Publ. 0 618 221, European Patent Publ. 0 675 112, European Patent Publ. 0 604181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO, 97/30053, WO 97/44350, WO 98/02436, and U.S. Pat. No. 5,532,359. For an example of the role of a prenyl-protein transferase inhibitor on angiogenesis see *European of Cancer, Vol.* 35, No. 9, pp. 1394-1401 (1999).

Examples of farnesyl protein transferase inhibitors include SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, VoL 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chforoacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrol]-carbonylimino]-bis-(1,3-naphthalene disulfonate), and 3-[(2,4-dimethylpyrrol-5-yl)methylene]-2-indolinone (SU5416).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). Examples of TAFIa inhibitors have been described in PCT Publication WO 03/013,526.

Examples of kinase inhibitors include: agents that inhibit cell surface receptors and signal transduction cascades downstream of those surface receptors. Such agents inhibit cell proliferation and survival. These include inhibitors of EGFR (for example gefitinib and erlotinib), antibodies to EGFR (for example C225), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059), inhibitors of mTOR (for example Wyeth CCI-779), and inhibitors of C-abl kinase (for example GLEEVEC™, Novartis Pharmaceuticals). Additional kinase inhibitors include those that inhibit proteins involved in the cell cycle. These include Aurora kinase inhibitors, CDK inhibitors (e.g., flavopiridol, CYC202, BMS387032 and polo-like kinase inhibitors.) These also include agents that interfere with cell cycle checkpoints and thereby sensitize cancer cells to DNA damaging agents. Such agents include, e.g., inhibitors of ART, ATM, Chk1 and Chk2.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5 pyridinyl)pyridine; or a pharmaceutically acceptable salt thereof.

Compounds that have been described as specific inhibitors of COX-2 and are therefore useful in the present invention include, but are not limited to, parecoxib, CELIEBREX® and BEXTRA® or a pharmaceutically acceptable salt thereof.

"Integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Combinations with compounds other than anti-cancer compounds are also encompassed in the instant methods. For example, combinations of the compounds of the invention with PPAR-γ (i.e., PPAR-gamma) agonists and PPAR-δ (i.e., PPAR-delta) agonists (collectively "PPAR agonists") are useful in the treatment of certain malingnancies. PPAR-γ and PPAR-δ are the nuclear peroxisome proliferator-activated receptors γ and δ, respectively. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice (*Arch. Ophthamol.* 2001; 119: 709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy)phenoxy)propoxy)-2-ethylchromane-2-carboxylic acid.

The compounds of the invention can also be administered in combination with one or more inhibitor of inherent multidrug resistance (MDR), in particular MDR associated with high levels of expression of transporter proteins. Such MDR inhibitors include inhibitors of p-glycoprotein (P-gp), such as LY335979, XR9576; OC144-093, R101922, VX853 and PSC833 (valspodar).

Additional anticancer agents also include hypoxia activatable agents (e.g., tirapazamine), proteasome inhibitors (e.g., lactacystin and bortezomib), ubiquitin inhibitors, HDM2 inhibitors, TNF activators, BUB-R inhibitors, CENP-E inhibitors, and interferon alpha.

The compounds of the invention can also be employed in conjunction with one or more anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with one or more other anti-emetic agents, especially neurokinin-1 receptor antagonists, 5HT3 receptor, antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or those as described in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In one embodiment, an anti-emesis agent selected from a neurokinin-1 receptor antagonist, a 5HT3 receptor antagonist and a corticosteroid is administered as an adjuvant for the treatment or prevention of emesis that may result upon administration of the compounds of the invention.

Examples of neurokinin-1 receptor antagonists that can be used in conjunction with the compounds of the invention are described in U.S. Pat. Nos. 5,162,339, 5,232,929, 5,242,930, 5,373,003, 5,387,595, 5,459,270, 5,494,926, 5,496,833, 5,637,699, and 5,719,147, content of which are incorporated herein by reference. In an embodiment, the neurokinin-1 receptor antagonist for use in conjunction with the compounds of the present invention is selected from: 2-(R)-(1-(R)-(3,5-bis(trifluoronnethyl)phenyl)ethoxy)-3-(S)-(4-fluorophenyl)-4-(3-(5-oxo-1H,4H-1,2,4-triazolo)methyl) morpholine, or a pharmaceutically acceptable salt thereof, which is described in U.S. Pat. No. 5,719,147.

A compound of the present invention may also be administered with one or more immunologic-enhancing drug, such as for example, levamisole, isoprinosine and Zadaxin.

As described above, the present invention includes combinations comprising an amount of at least one compound (or a composition comprising a compound) of the invention or a pharmaceutically acceptable salt or ester thereof, and an amount of one or more additional therapeutic agents listed above (administered together or sequentially) wherein the amounts of the compounds/treatments result in desired therapeutic effect.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for illustration purposes, a compound of the invention and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

If formulated as a fixed dose, such combination products employ the compounds of this invention within the dosage range described herein and the other pharmaceutically active agent or treatment within its dosage range. Compounds of the invention may also be administered sequentially with known therapeutic agents when a combination formulation is inappropriate. The invention is not limited in the sequence of administration; compounds of the invention may be administered either prior to or after administration of the known therapeutic agent. Such techniques are within the skills of persons skilled in the art as well as attending physicians.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

We claim:

1. A compound having the general structure shown in Formula (I), or a pharmaceutically acceptable salt, or an ester thereof:

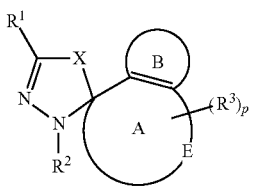

(I)

wherein X, R¹, R², R³, p, E, ring A, and ring B are selected independently of each other and wherein:

p is 0, 1, 2, 3, or 4;

X is S;

ring A (including E and the unsaturation shown) is a 4-7 membered cycloalkenyl ring and E is —C(R⁴)(R⁵)—; or ring A (including E and the unsaturation shown) is a 5-6 membered heterocycloalkylenyl ring and E is selected from the group consisting of —O—, —S—, —S(O)—, —S(O)₂—, and —N(R⁶)—;

ring B is a 5-6 membered aromatic ring optionally substituted with halogen;

R¹ is phenyl optionally substituted with one or more substituents, which can be the same or different, each substituent being independently selected from the group consisting of halogen, —OH, —CN, —NO₂, haloalkyl, and —NR²¹R²²;

R² is selected from the group consisting of —C(Z)R⁷, —C(Z)NR⁹R¹⁰, and —C(Z)OR⁸, wherein each Z is independently selected from the group consisting of (=O), (=S), (=N(R¹³)), (=N(CN)), (=N(OR¹⁴)), (=N(R¹⁵)(R¹⁶)), and (=C(R¹⁷)(R¹⁸));

each R³ (when present) is independently selected from the group consisting of alkyl, alkenyl, —CN, —NO₂, —C(O)R²⁴, —C(S)R²⁴, and —C(O)OR²⁰, wherein each is optionally independently substituted with one or more substituents, which can be the same or different, each substituent being independently selected from the group of oxo, halogen, —CN, —NO₂, alkyl, cycloalkyl, heterocycloalkyl, —OR¹⁹, —NR²¹R²², —C(O)R²⁴, or, alternatively, when p is 2, 3, or 4, any two R³ groups bound to the same ring carbon atom are taken together with the carbon atom to which they are attached to form a spirocycloalkyl, a spirocycloalkenyl, or a spiroheterocycloalkyl ring containing from one to three ring heteroatoms independently selected from the group consisting of —NH—, —NR⁶—, —S—, —S(O)—, —S(O)₂—, and —O—, or a spiroheterocycloalkenyl ring containing from one to three ring heteroatoms independently selected from the group consisting of —NH—, —NR⁶—, —S—, —S(O)—, —S(O)₂—, and —O—, or, alternatively, R² and R³, together with the atom to which they are attached, are taken together with the carbon atom to which they are attached to form a cycloalkyl, a cycloalkenyl, a heterocycloalkyl ring containing from one to three ring heteroatoms independently selected from the group consisting of —NH—, —NR⁶—, —S—, —S(O)—, —S(O)₂—, and —O—, or a heterocycloalkenyl ring containing from one to three ring heteroatoms independently selected from the group consisting of —NH—, —NR⁶—, —S—, —S(O)—, —S(O)₂—, and —O—;

each R⁴ (when not joined with R⁵) is independently selected from the group consisting of H and alkyl;

each R⁵ (when not joined with R⁴) is independently selected from the group consisting of H and alkyl;

or, alternatively, R⁴ and R⁵, together with the carbon atom to which they are attached, form a cycloalkyl, a cycloalkenyl, a heterocycloalkyl ring containing from one to three heteroatoms selected from the group consisting of N, O, and S, or a heterocycloalkenyl ring containing from one to three heteroatoms selected from the group consisting of N, O, and S, wherein each is optionally independently substituted with one or more substituents, which can be the same or different, each substituent being independently selected from the group consisting of oxo, halogen, alkyl, heteroalkyl, haloalkyl, cycloalkyl, —OR¹⁹, —NR²¹R²², and —C(O)R²⁴;

each R⁶ is independently selected from the group consisting of H, alkyl, and —C(O)R²⁴ wherein each is optionally independently substituted with one or more substituents, which can be the same or different, each substituent being independently selected from the group of oxo, halogen, alkyl, heteroalkyl, haloalkyl, cycloalkyl, heterocycloalkyl, —OR¹⁹, —NR²¹R²², and —C(O)R²⁴;

each R⁷ is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —OR¹⁹, —NR²¹R²², and —C(O)R²⁴;

each R⁸ is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —OR¹⁹, —NR²¹R²², and —C(O)R²⁴;

each R⁹ (when not joined with R¹⁰) is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —OR¹⁹, —NR²¹R²², and —C(O)R²⁴;

each R¹⁰ (when not joined with R⁹) is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —OR¹⁹, —NR²¹R²², and —C(O)R²⁴;

or, alternatively, R⁹ and R¹⁰, together with the N atom to which they are attached, form a heterocycloalkyl or a heterocycloalkenyl ring containing from one to three heteroatoms selected from the group consisting of N, O, and S, wherein each is optionally independently substituted with one or more substituents, which can be the same or different, each substituent being independently selected from the group consisting of oxo, halogen, alkyl, heteroalkyl, haloalkyl, cycloalkyl, heterocycloalkyl, —$OR^{19}$, —$NR^{21}R^{22}$, and —$C(O)R^{24}$;

each $R^{13}$ is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —$OR^{19}$, —$NR^{21}R^{22}$, and —$C(O)R^{24}$;

each $R^{14}$ is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —$OR^{19}$, and —$C(O)R^{24}$;

each $R^{15}$ (when not joined with $R^{16}$) is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —$OR^{19}$, —$NR^{21}R^{22}$, and —$C(O)R^{24}$;

each $R^{16}$ (when not joined with $R^{15}$) is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —$OR^{19}$, —$NR^{21}R^{22}$, and —$C(O)R^{24}$;

or, alternatively, $R^{15}$ and $R^{16}$, together with the N atom to which they are attached, form a heterocycloalkyl or a heterocycloalkenyl ring containing from one to three heteroatoms selected from the group consisting of N, O, and S, wherein each is optionally independently substituted with one or more substituents, which can be the same or different, each substituent being independently selected from the group consisting of oxo, halogen, alkyl, heteroalkyl, haloalkyl, cycloalkyl, heterocycloalkyl, —$OR^{19}$, —$NR^{21}R^{22}$, and —$C(O)R^{24}$;

each $R^{17}$ (when not joined with $R^{18}$) is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —$OR^{19}$, —$NR^{21}R^{22}$, and —$C(O)R^{24}$;

each $R^{18}$ (when not joined with $R^{17}$) is independently selected from the group consisting of H, alkyl, heteroalkyl, cycloalkyl, and heterocycloalkyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —$OR^{19}$, —$NR^{21}R^{22}$, and —$C(O)R^{24}$;

or, alternatively, $R^{17}$ and $R^{18}$, together with the N atom to which they are attached, form a heterocycloalkyl or a heterocycloalkenyl ring containing from one to three heteroatoms selected from the group consisting of N, O, and S, wherein each is optionally independently substituted with one or more substituents, which can be the same or different, each substituent being independently selected from the group consisting of oxo, halogen, alkyl, heteroalkyl, haloalkyl, cycloalkyl, heterocycloalkyl, —$OR^{19}$, —$NR^{21}R^{22}$, and —$C(O)R^{24}$;

each $R^{19}$ is independently selected from the group consisting of H and alkyl;

each $R^{20}$ is independently selected from the group consisting of H and alkyl;

each $R^{21}$ (when not joined with $R^{22}$) is independently selected from the group consisting of H and alkyl;

each $R^{22}$ (when not joined with $R^{21}$) is independently selected from the group consisting of H and alkyl; and each $R^{24}$ is independently selected from the group consisting of H, alkyl, haloalkyl, heteroalkyl, haloheteroalkyl, aryl, heteroaryl, cycloalkyl, halocycloalkyl.

2. A compound of claim 1, wherein ring A is a 5-6-membered heterocycloalkylenyl ring and E is selected from the group consisting of —O— and —$N(R^6)$—.

3. A compound of claim 1, wherein ring A is a 5-membered heterocycloalkylenyl ring.

4. A compound of claim 1, wherein ring A is a 6-membered heterocycloalkylenyl ring.

5. A compound of claim 1, wherein ring B is a benzo ring optionally substituted with one or more substituents, which can be the same or different, each substituent being independently selected from the group consisting of halogen, alkyl, heteroalkyl, haloalkyl, cycloalkyl, heterocycloalkyl, —$OR^{19}$, —$NR^{21}R^{22}$, and —$C(O)R^{24}$.

6. A compound of claim 1, wherein ring B is an optionally substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl.

7. A compound of claim 1, wherein $R^1$ is selected from the group consisting of:

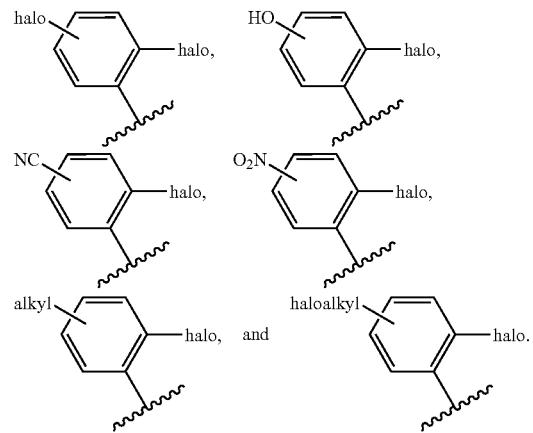

8. A compound of claim 1, wherein $R^1$ is a moiety selected from the group consisting of:

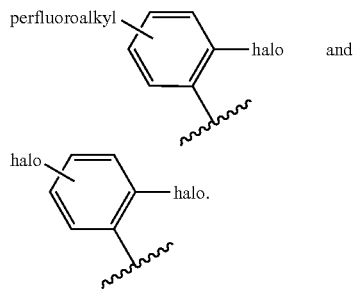

9. A compound of claim 1, wherein $R^1$ is:

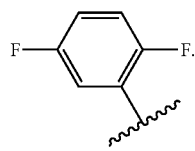

10. A compound of claim 1, wherein $R^2$ is selected from the group consisting of —C(O)$R^7$, —C(O)N$R^9R^{10}$, and —C(O)O$R^8$.

11. A compound of claim 1, wherein p is 0 and $R^3$ is not present.

12. A compound of claim 1, wherein p is 1, 2, 3, or 4.

13. A compound of claim 1, wherein p is 2, 3, or 4, and any two $R^3$ groups bound to the same ring A atom are taken together with the carbon atom to which they are attached to form a spirocycloalkyl, a spirocycloalkenyl, a spiroheterocycloalkyl ring containing from one to three ring heteroatoms independently selected from the group consisting of —NH—, —N$R^6$—, —S—, —S(O)—, —S(O)$_2$—, and —O—, or a spiroheterocycloalkenyl ring containing from one to three ring heteroatoms independently selected from the group consisting of —NH—, —N$R^6$—, —S—, —S(O)—, —S(O)$_2$—, and —O—.

14. A compound of claim 1, wherein $R^2$ and $R^3$ are taken together with the carbon atom to which they are attached to form a cycloalkyl, a cycloalkenyl, a heterocycloalkyl ring containing from one to three ring heteroatoms independently selected from the group consisting of —NH—, —N$R^6$—, —S—, —S(O)13 , —S(O)$_2$—, and —O—, or a heterocycloalkenyl ring containing from one to three ring heteroatoms independently selected from the group consisting of —NH—, —N$R^6$—, —S—, —S(O)—, —S(O)$_2$—, and —O—.

15. A compound of claim 1, or a pharmaceutically acceptable salt, or an ester thereof, having the general structure shown in Formula (II):

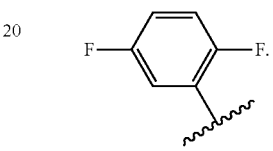

(II)

wherein $R^1$, $R^2$, E, and ring B are selected independently of each other.

16. A compound of claim 15, wherein ring B is an optionally substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl;

$R^1$ is phenyl substituted with one to four substituents, which can be the same or different, each substituent being independently selected from the group consisting of halo, —OH, —CN, —NO$_2$, —N$R^{21}R^{22}$, and haloalkyl; and $R^2$ is selected from the group consisting of —C(O)$R^7$, —C(O)N$R^9R^{10}$, and —C(O)O$R^8$.

17. A compound of claim 16, wherein $R^1$ is:

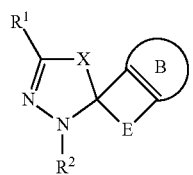

18. A compound of claim 1, or a pharmaceutically acceptable salt, or an ester thereof, having the general structure shown in Formula (III.1):

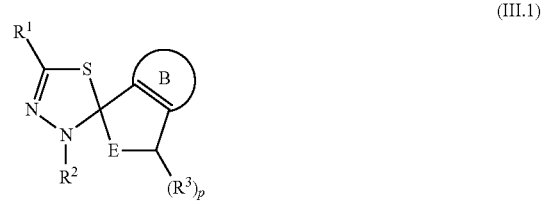

(III.1)

wherein $R^1$, $R^2$, $R^3$, p, E, and ring B are selected independently of each other and p is 0, 1, or 2.

19. A compound of claim 18, wherein $R^2$ is selected from the group consisting of —C(O)$R^7$, —C(O)N$R^9R^{10}$, and —C(O)O$R^8$ and p is 0 or 1.

20. A compound of claim 19, wherein ring B is an optionally substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl;

$R^1$ is phenyl substituted with one to four substituents, which can be the same or different, each substituent being independently selected from the group consisting of halo, —OH, —CN, —NO$_2$, —N$R^{21}R^{22}$, and haloalkyl;

$R^2$ is selected from the group consisting of —C(O)$R^7$, —C(O)N$R^9R^{10}$, and —C(O)O$R^8$;

p is 0 or 1; and each $R^3$ (when present) is independently selected from the group consisting of alkyl and alkenyl, wherein each is optionally independently substituted with one or more substituents, which can be the same or different, each substituent being independently selected from the group of oxo, halogen, alkyl, heteroalkyl, haloalkyl, cycloalkyl, heterocycloalkyl, —O$R^{19}$, —N$R^{21}R^{22}$, and —C(O)$R^{24}$.

21. A compound of claim 20, wherein $R^1$ is:

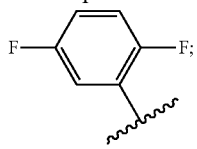

and $R^6$ is selected from the group consisting of H, alkyl, and —C(O)$R^{24}$.

22. A compound of claim 1, or a pharmaceutically acceptable salt, or an ester thereof, having the general structure shown in Formula (III.2):

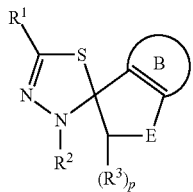

(III.2)

wherein $R^1$, $R^2$, $R^3$, p, E, and ring B are selected independently of each other and wherein p is 0, 1, or 2.

23. A compound of claim 22, wherein $R^2$ is selected from the group consisting of —C(O)$R^7$, —C(O)N$R^9R^{10}$, and —C(O)O$R^8$ and p is 0 or 1.

24. A compound of claim 23, wherein ring B is an optionally substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl;

$R^1$ is phenyl substituted with one to four substituents, which can be the same or different, each substituent being independently selected from the group consisting of halo, —OH, —CN, —NO$_2$, —N$R^{21}R^{22}$, and haloalkyl;

$R^2$ is selected from the group consisting of —C(O)$R^7$, —C(O)N$R^9R^{10}$, and —C(O)O$R^8$;

p is 0 or 1; and each $R^3$ (when present) is independently selected from the group consisting of alkyl and alkenyl,
    wherein each is optionally independently substituted with one or more substituents, which can be the same or different, each substituent being independently selected from the group of oxo, halogen, alkyl, heteroalkyl, haloalkyl, cycloalkyl, heterocycloalkyl, —O$R^{19}$, —N$R^{21}R^{22}$, and —C(O)$R^{24}$—.

25. A compound of claim 24, wherein $R^1$ is:

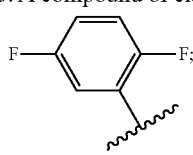

and $R^6$ is selected from the group consisting of H, alkyl, and —C(O)$R^{24}$.

26. A compound of claim 1, or a pharmaceutically acceptable salt, or an ester thereof, having the general structure shown in Formula (IV):

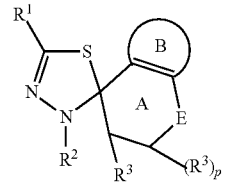

(IV)

wherein $R^1$, $R^3$, E, and ring B are selected independently of each other and wherein $R^2$ is selected from the group consisting of —C(O)$R^7$, —C(O)N$R^9R^{10}$, and —C(O)O$R^8$ and p is 0, 1, or 2.

27. A compound of claim 26, wherein:

E is selected from the group consisting of —O— and —N($R^6$)—;

ring B is an optionally substituted moiety selected from the group consisting of benzo, furanyl, thiophenyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, and triazinyl;

$R^1$ is phenyl substituted with one to four substituents, which can be the same or different, each substituent being independently selected from the group consisting of halo, —OH, —CN, —NO$_2$, N$R^{21}R^{22}$, and haloalkyl;

$R^2$ is selected from the group consisting of —C(O)$R^7$, 13 C(O)N$R^9R^{10}$, and —C(O)O$R^8$;

p is 0 or 1; and each $R^3$ (when present) is independently selected from the group consisting of alkyl and alkenyl,
    wherein each is optionally independently substituted with one or more substituents, which can be the same or different, each substituent being independently selected from the group of oxo, halogen, alkyl, heteroalkyl, haloalkyl, cycloalkyl, heterocycloalkyl, —O$R^{19}$, —N$R^{21}R^{22}$, and —C(O)$R^{24}$.

28. A compound of claim 27, wherein $R^1$ is:

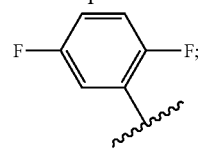

and $R^6$ is selected from the group consisting of H, alkyl, and —C(O)$R^{24}$.

29. A compound, or a pharmaceutically acceptable salt, or an ester thereof, selected from the group consisting of:

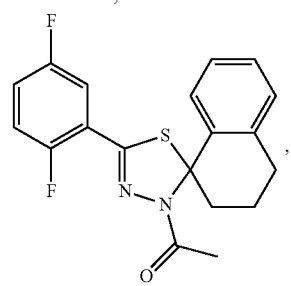

459
-continued
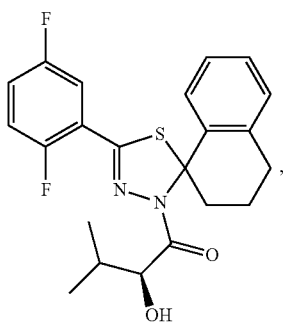
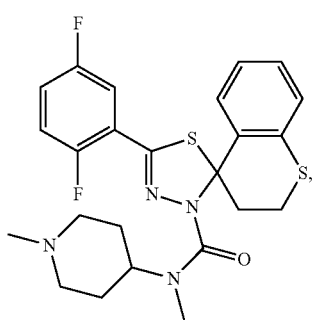
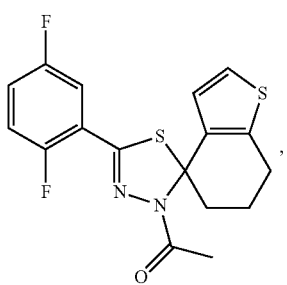
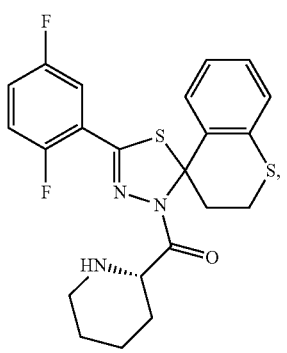
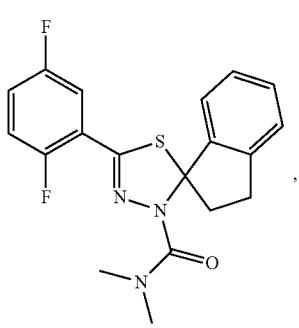
460
-continued
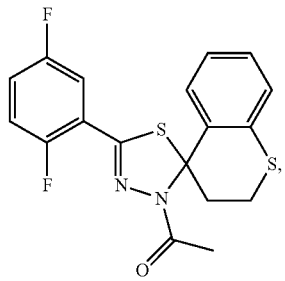
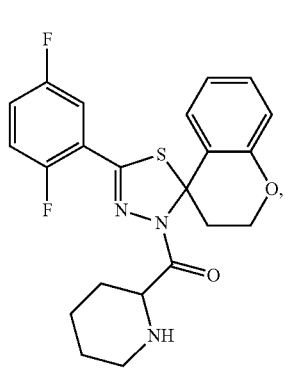
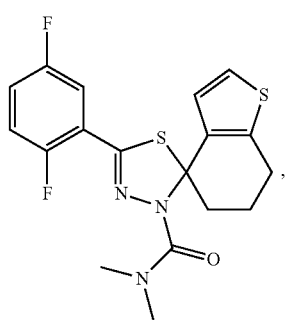
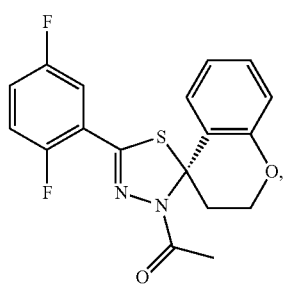
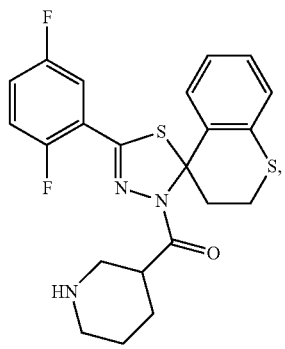

461
-continued
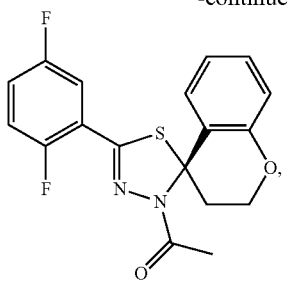
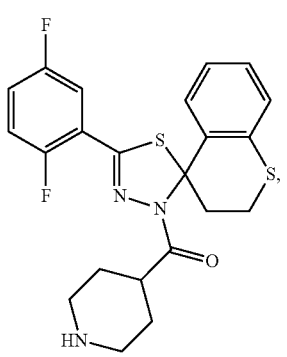
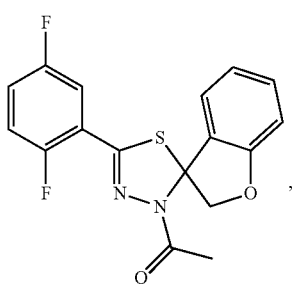
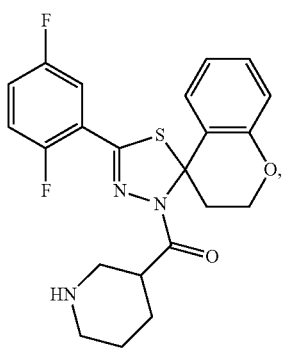
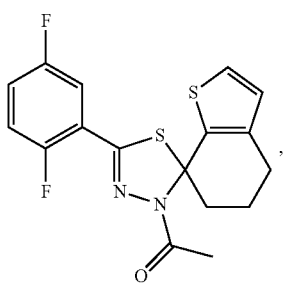
462
-continued
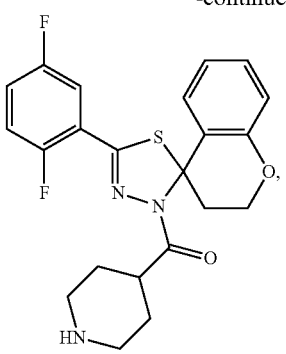
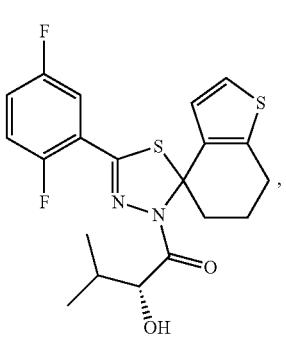
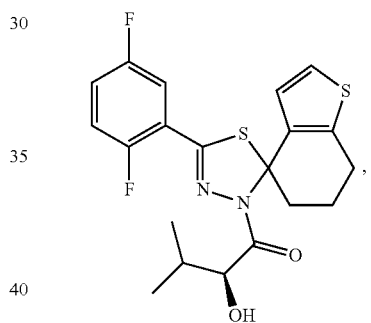
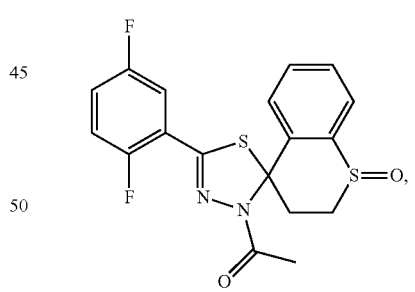
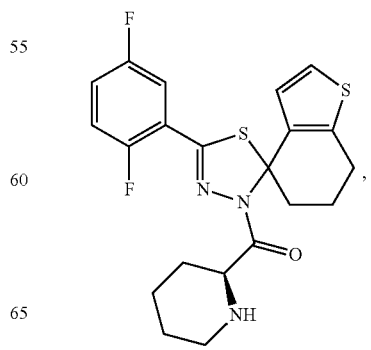

463
-continued
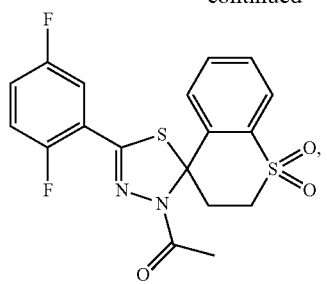
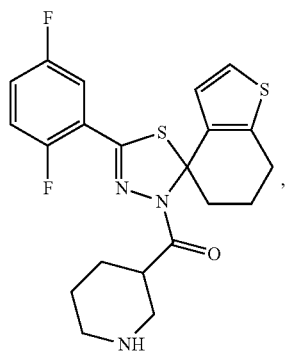
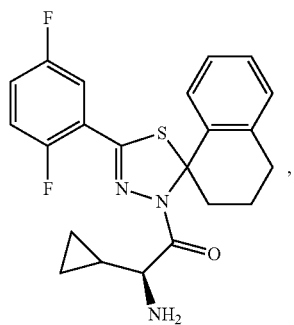
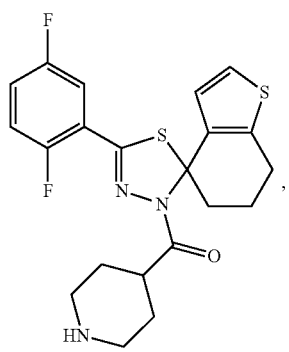
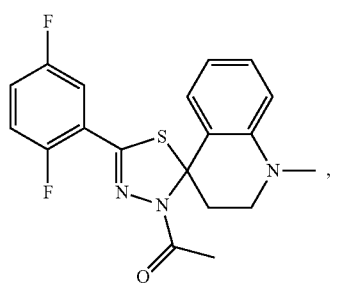
464
-continued
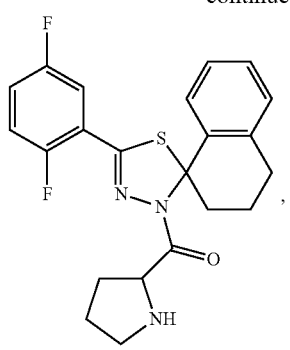
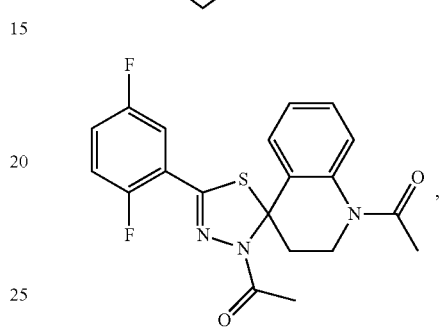
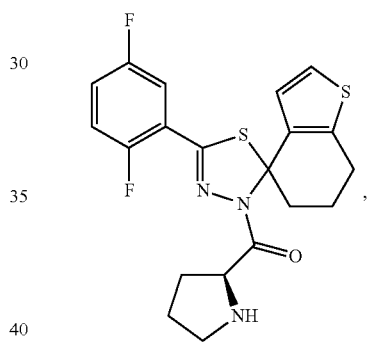
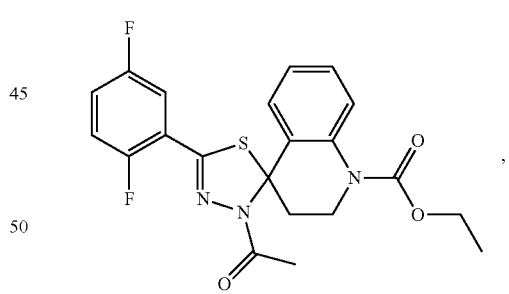
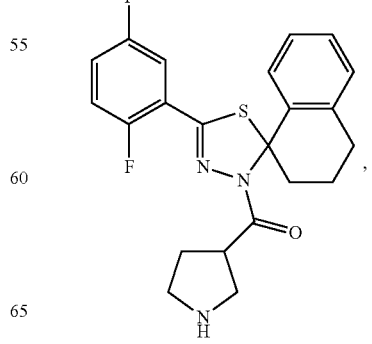

465
-continued
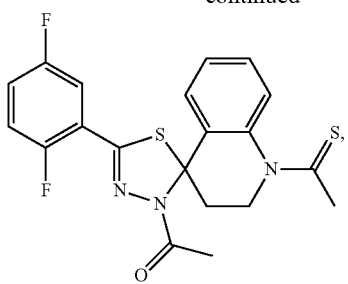
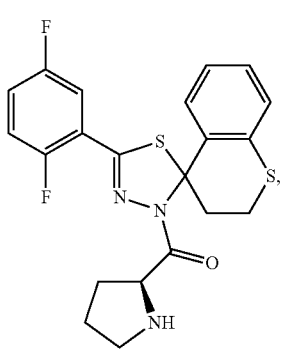
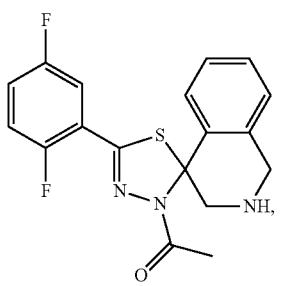
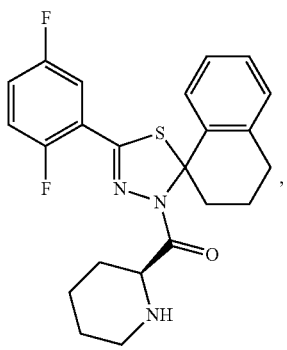
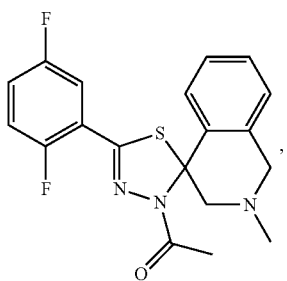
466
-continued
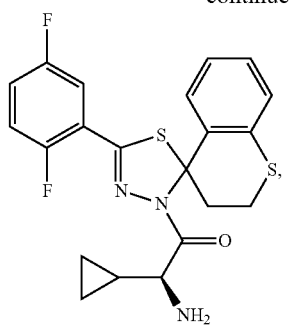
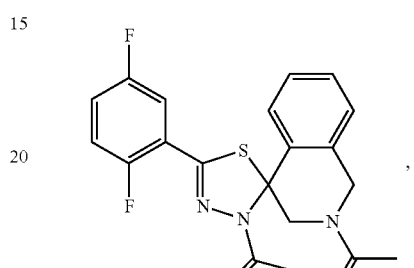
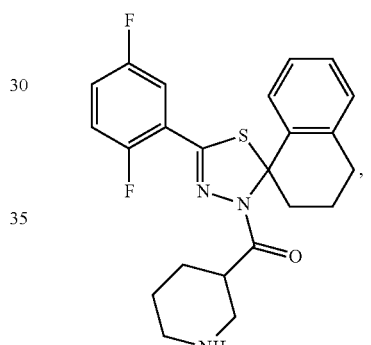
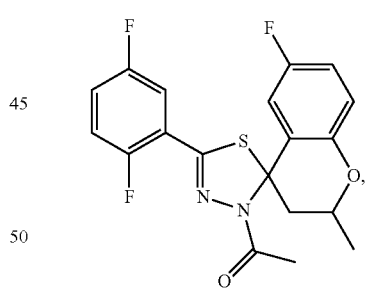
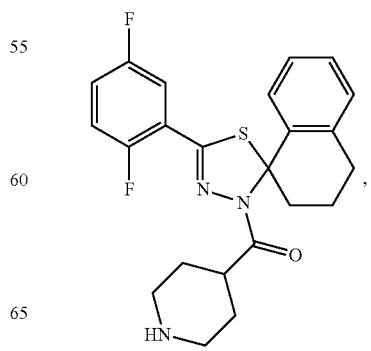

467
-continued
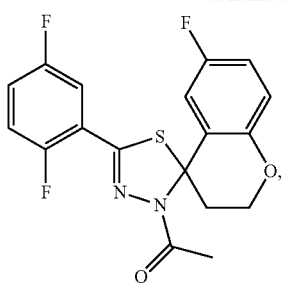
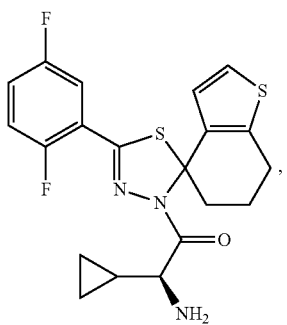
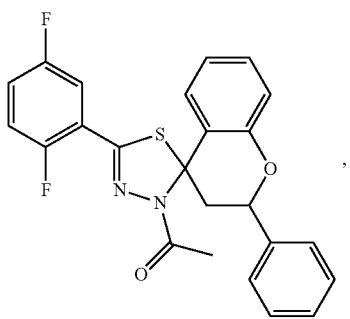
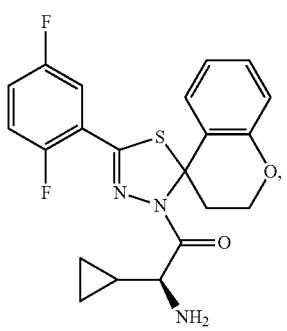
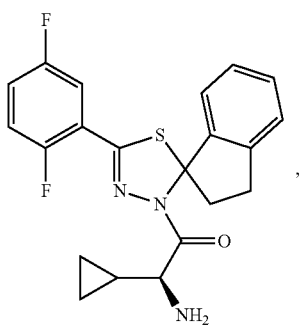
468
-continued
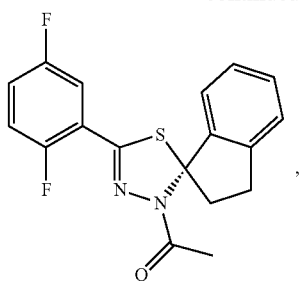
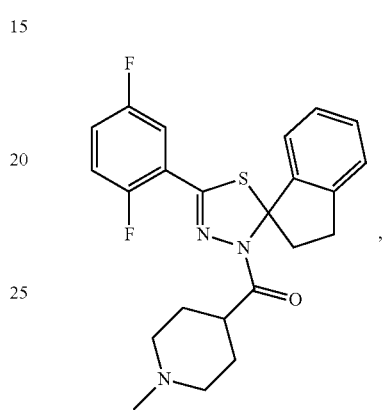
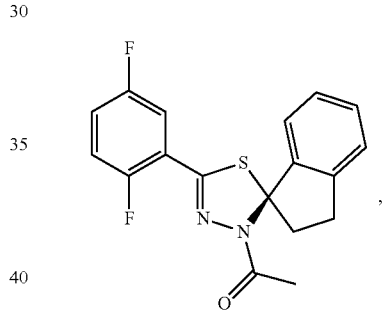
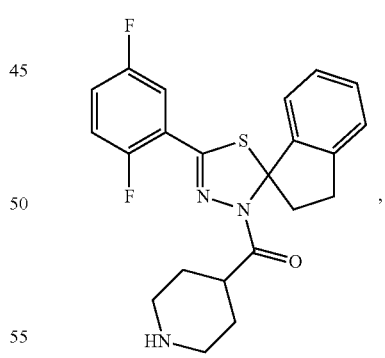
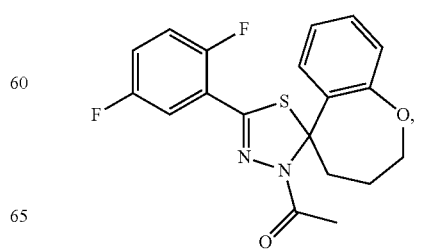

469
-continued
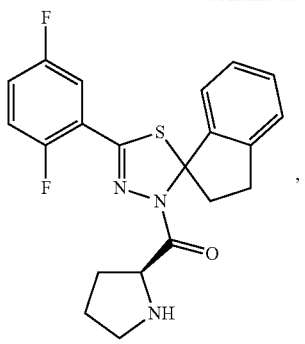
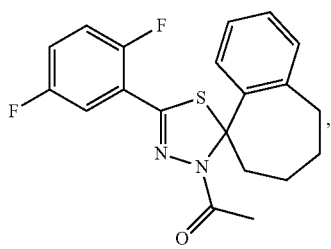
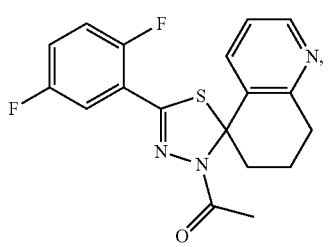
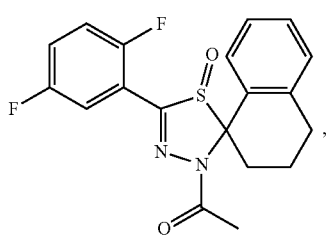
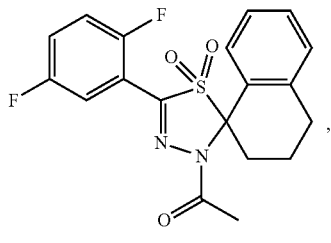
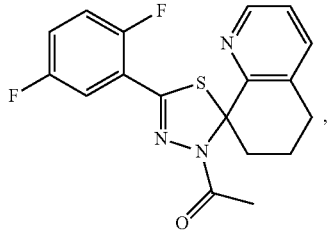
470
-continued
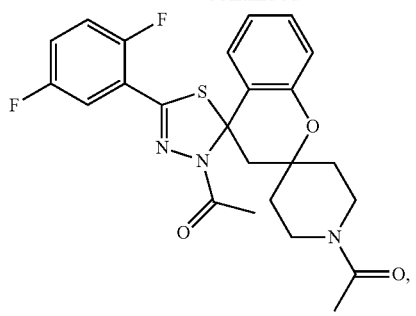
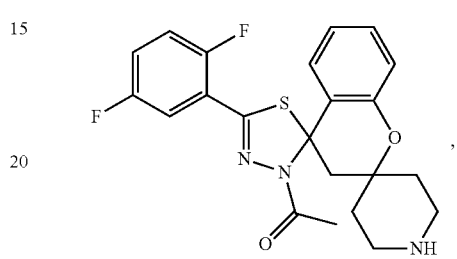
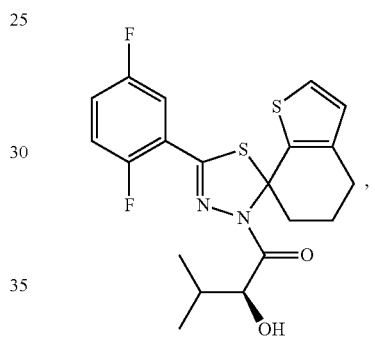
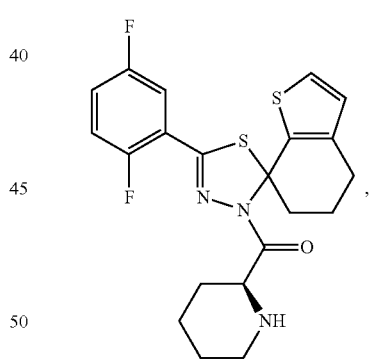
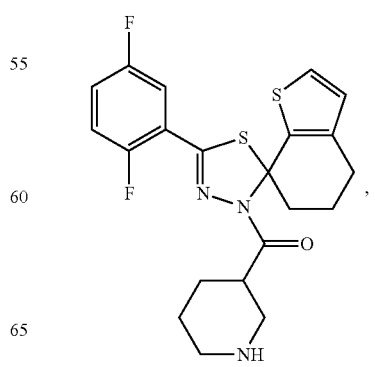

471
-continued
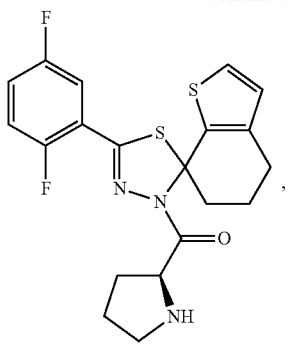
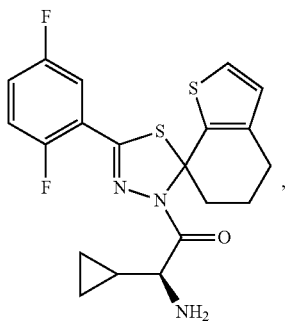
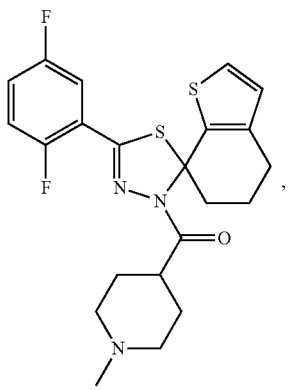
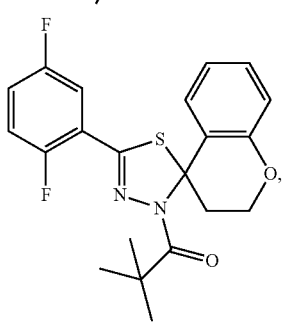
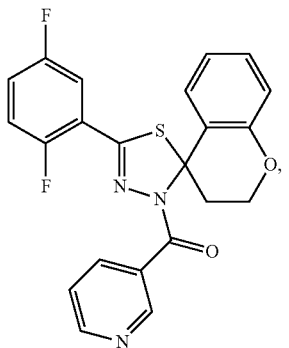
472
-continued
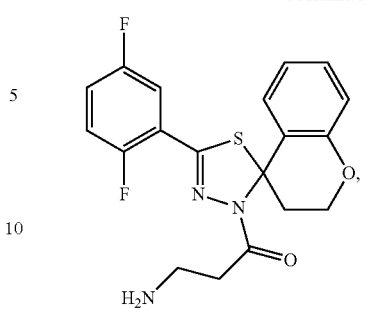
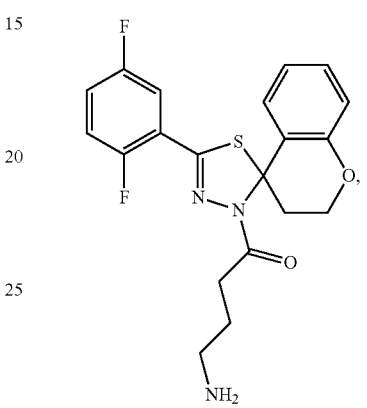
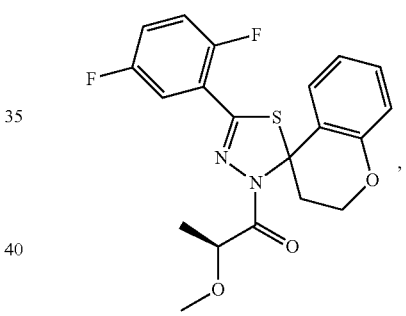
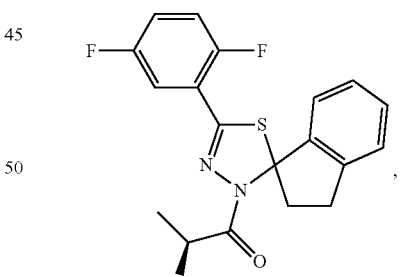
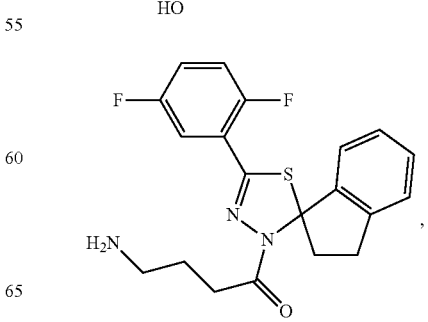

473
-continued
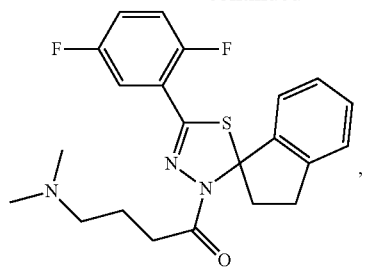
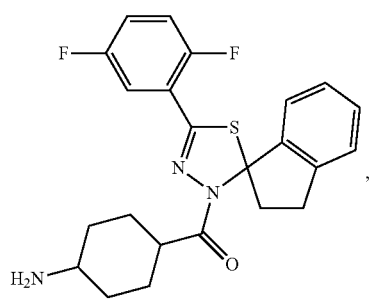
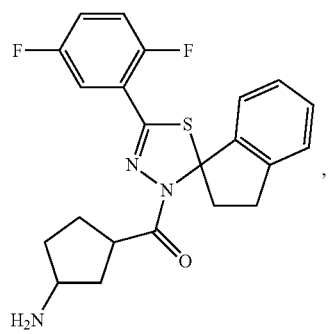
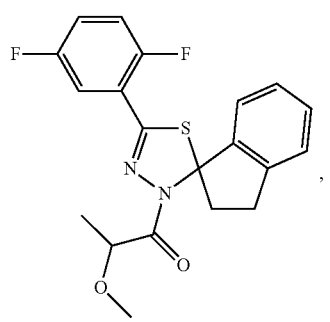
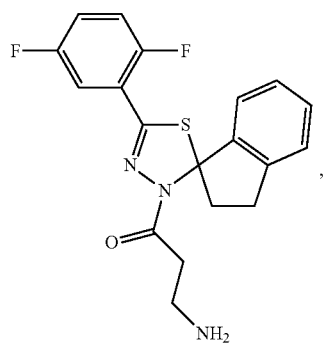
474
-continued
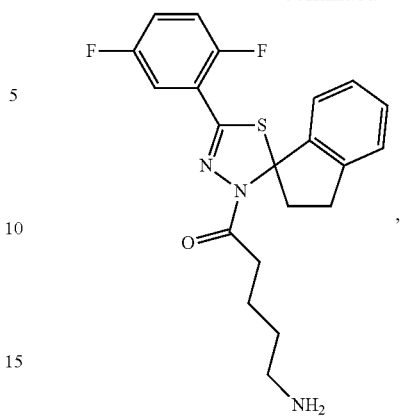
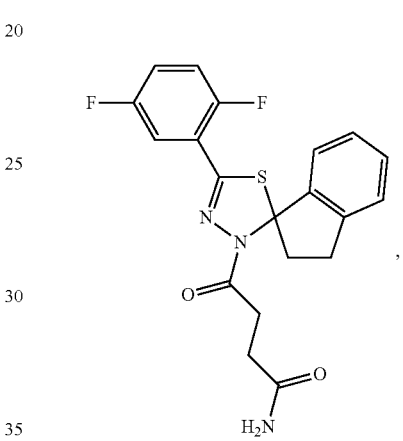
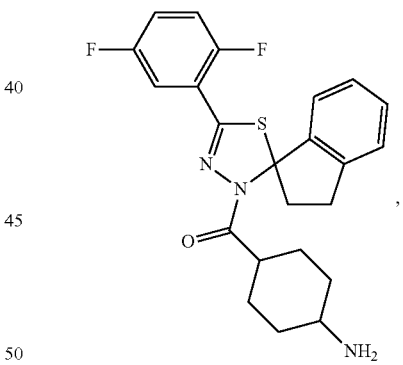
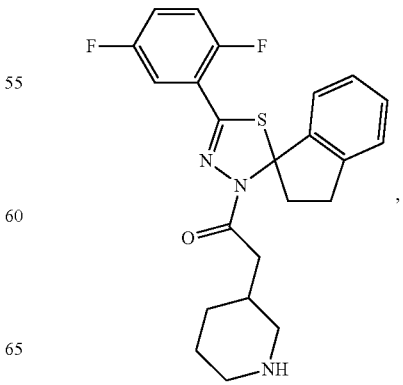

475
-continued
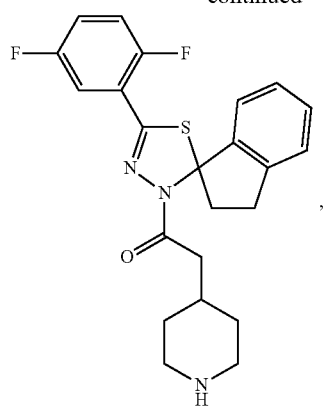
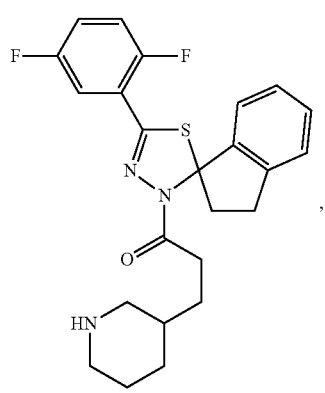
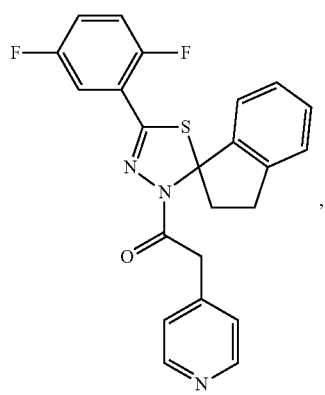
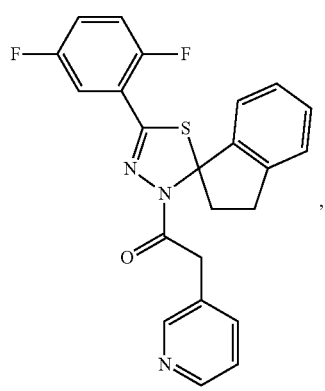
476
-continued
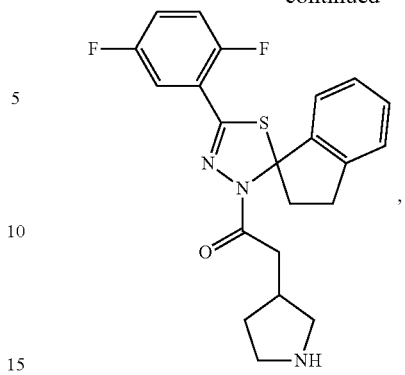
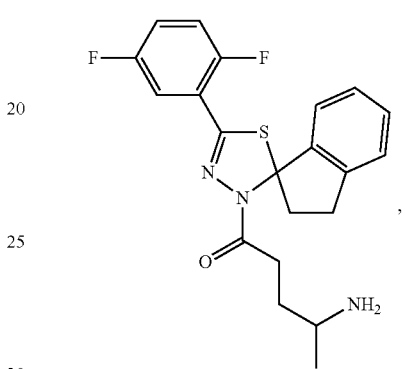
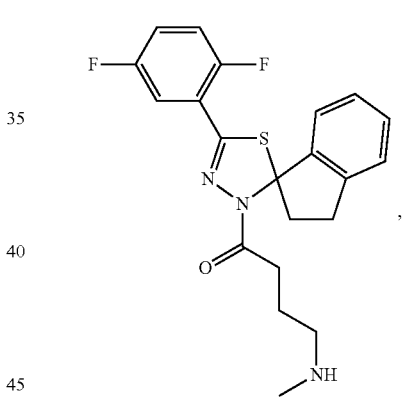
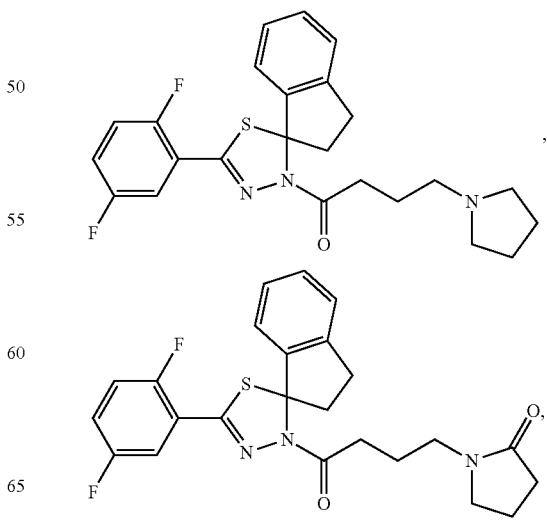

477
-continued
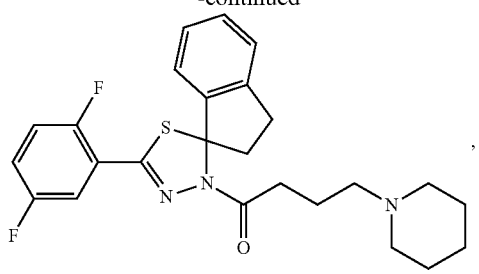
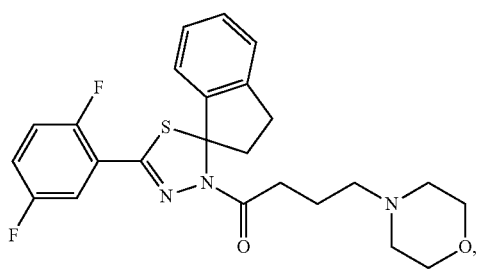
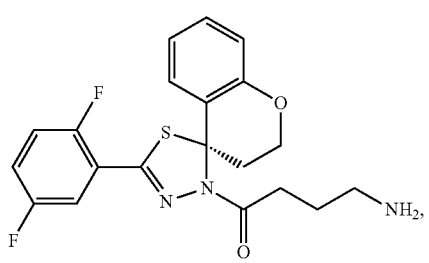
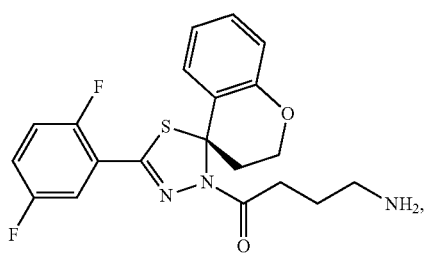
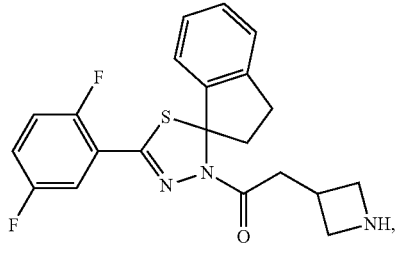
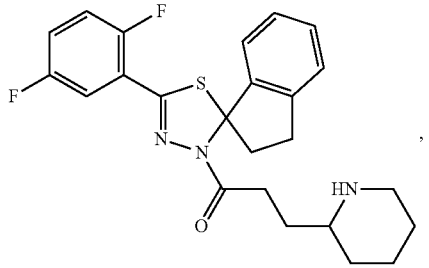
478
-continued
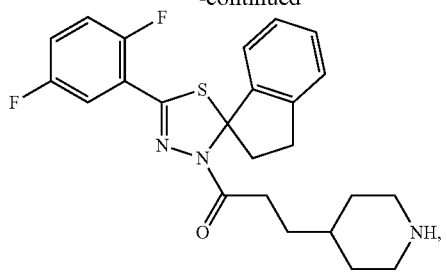
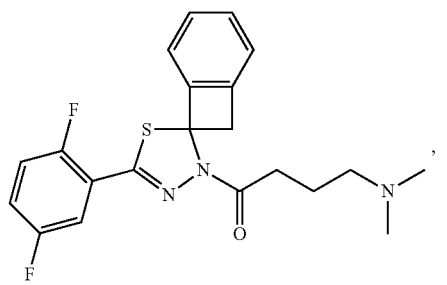
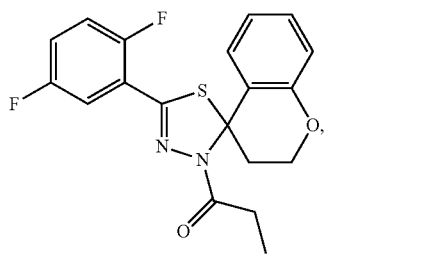
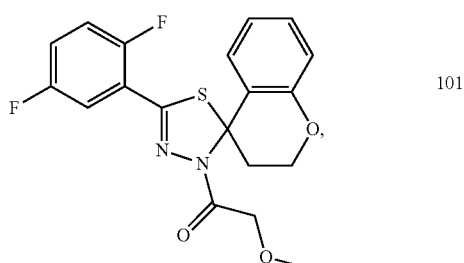
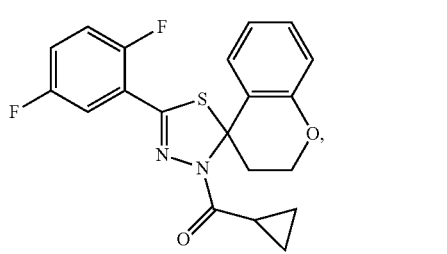
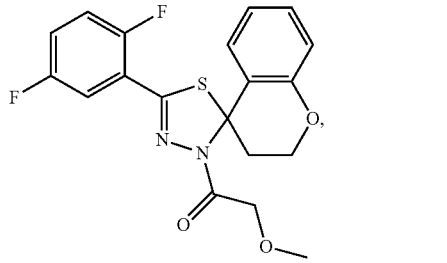

479
-continued
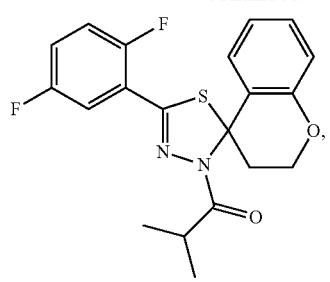
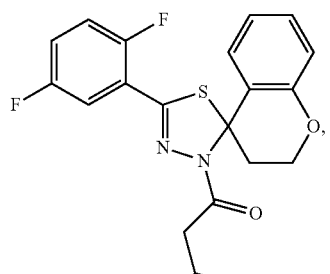
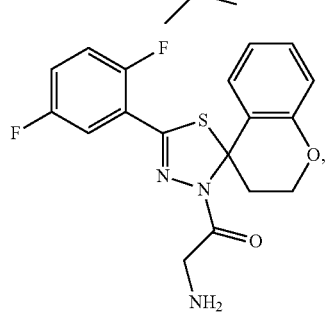
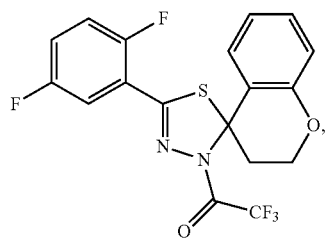
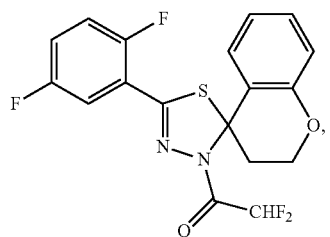
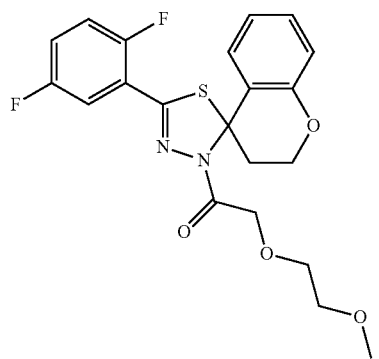
480
-continued
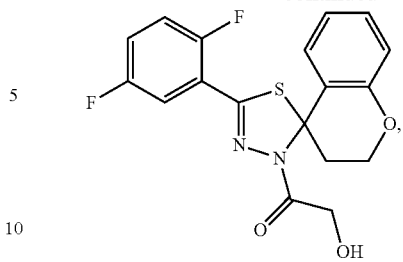
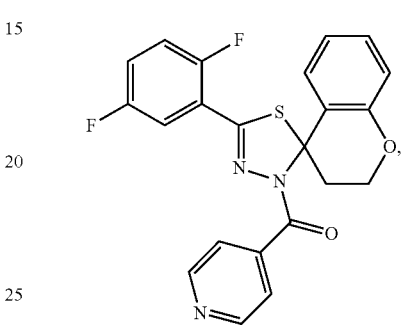
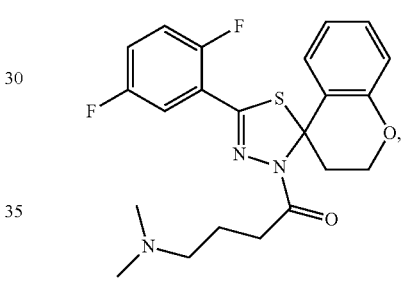
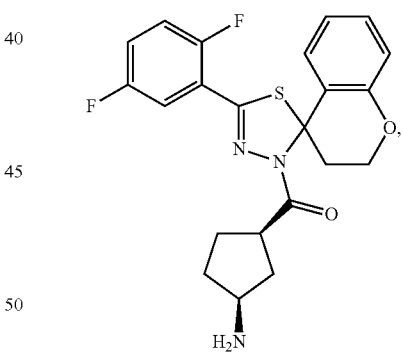
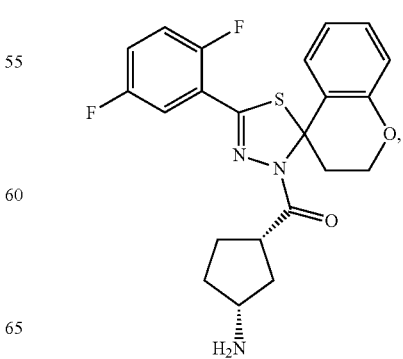

481
-continued
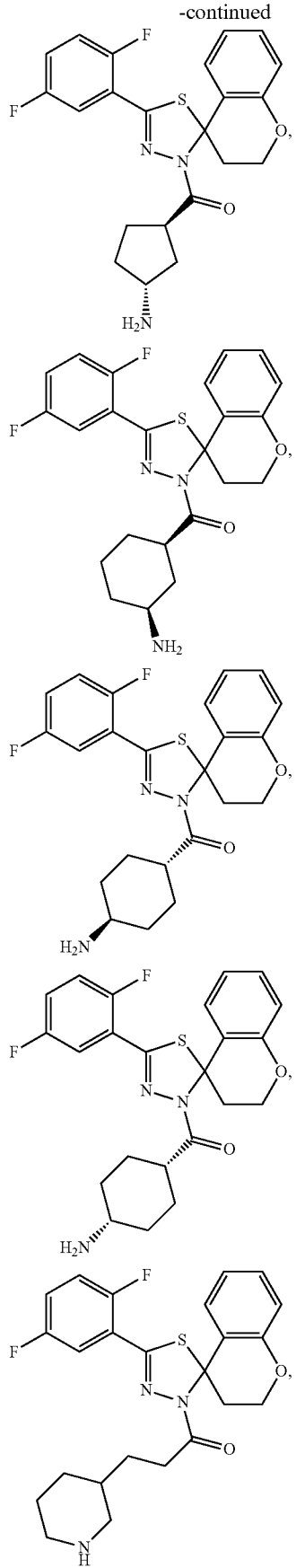
482
-continued
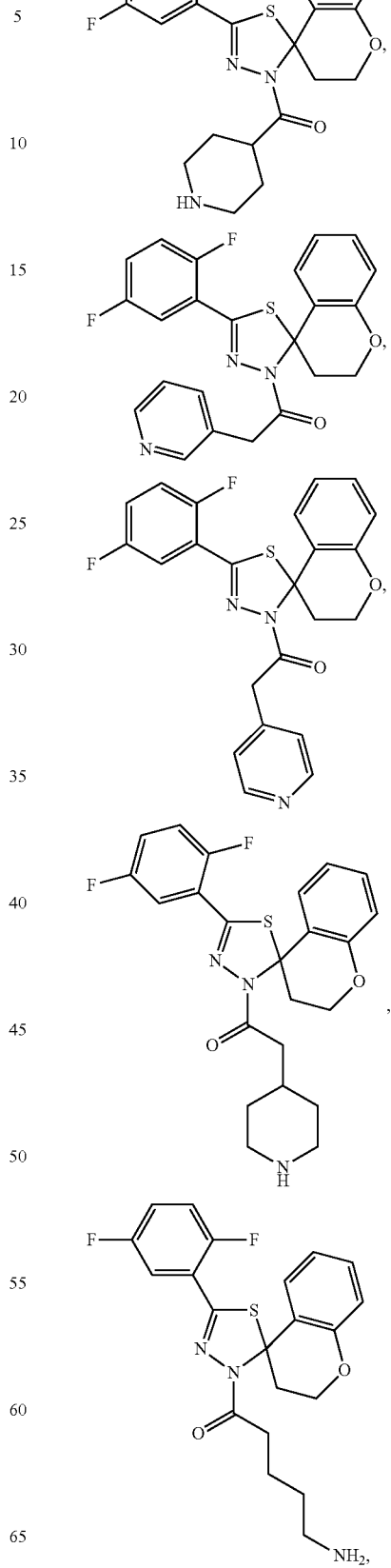

483
-continued
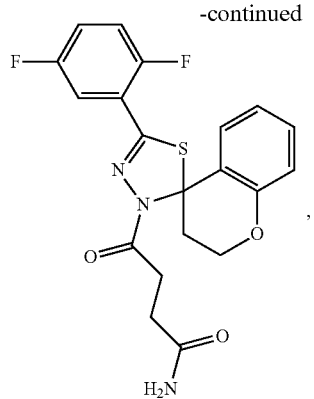
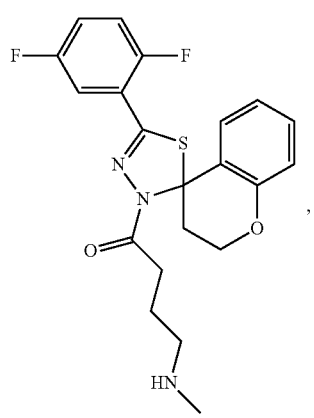
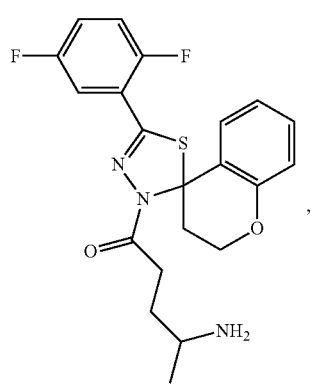
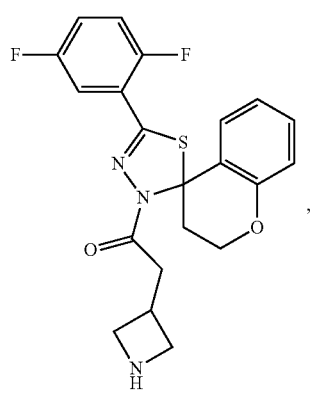
484
-continued
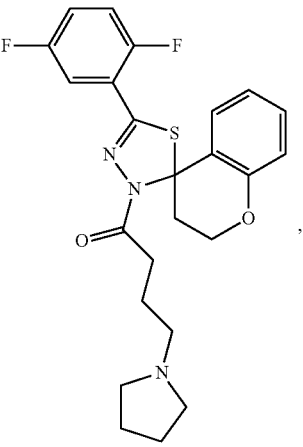
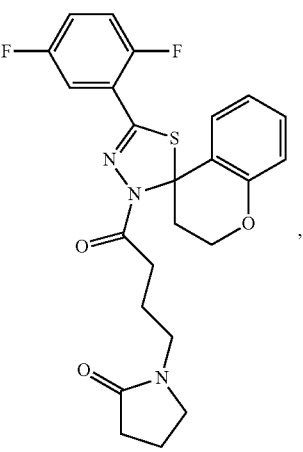
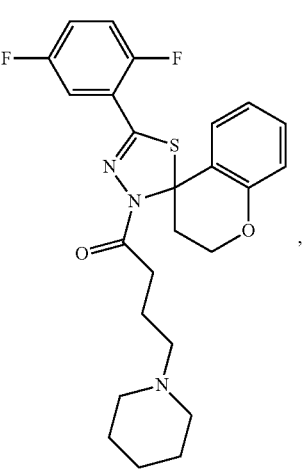

485
-continued
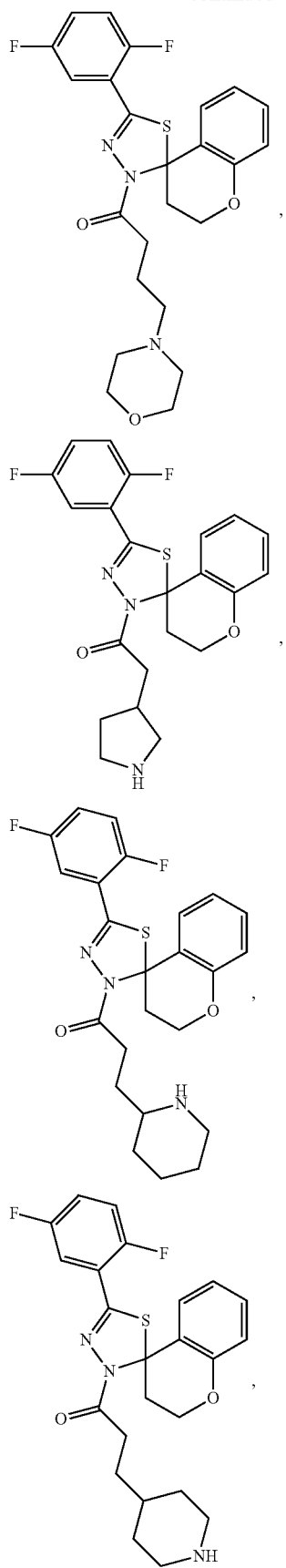
486
-continued
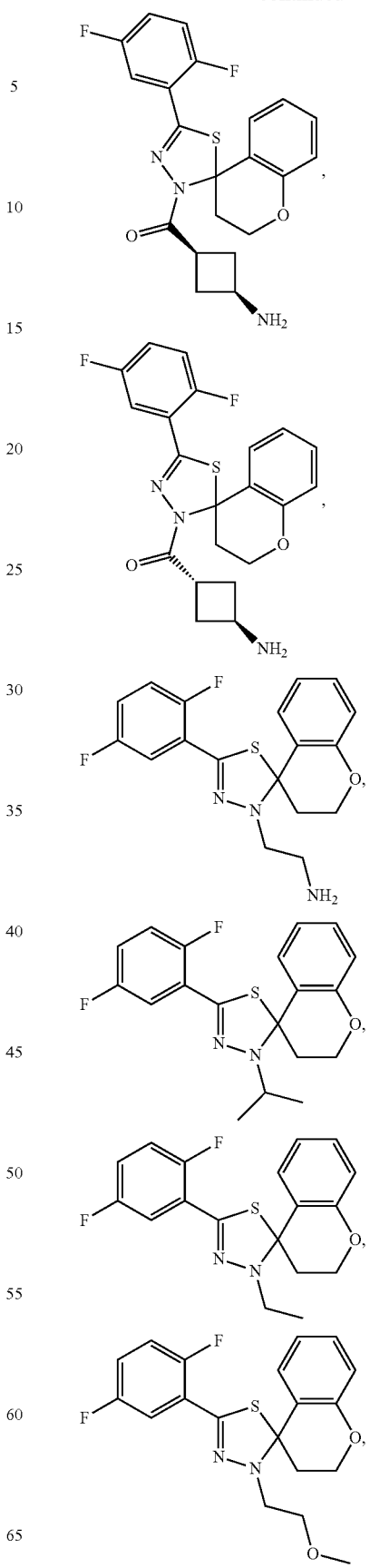

487
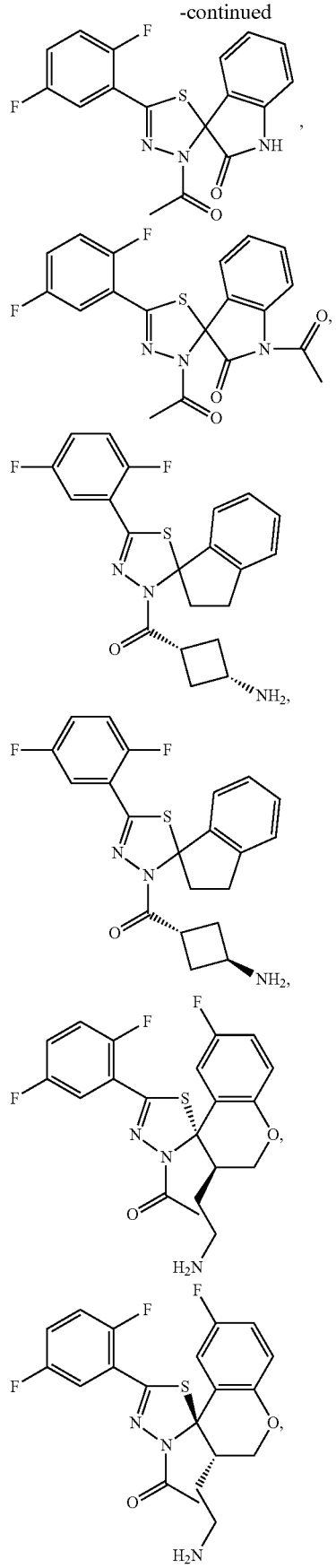
488
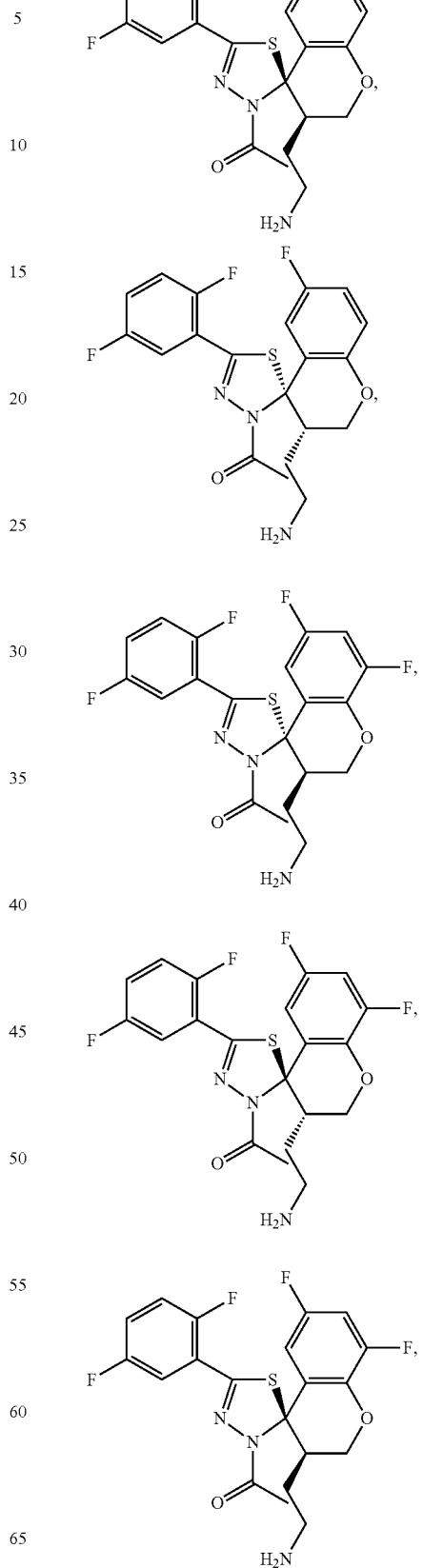

489
-continued
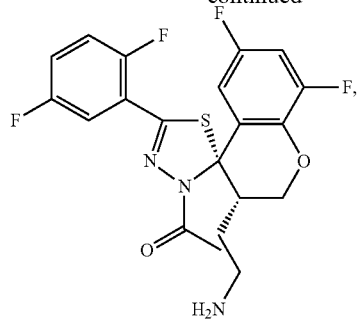
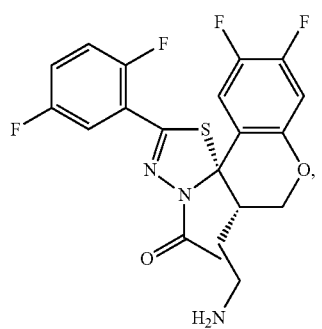
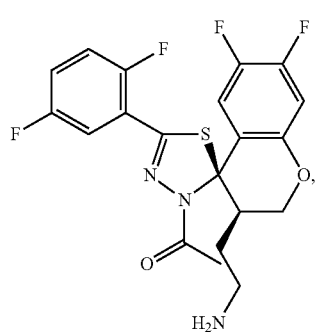
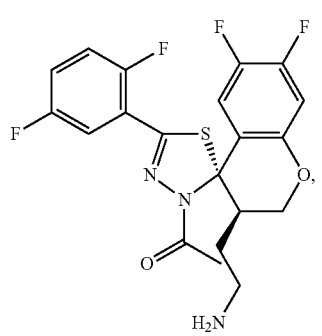
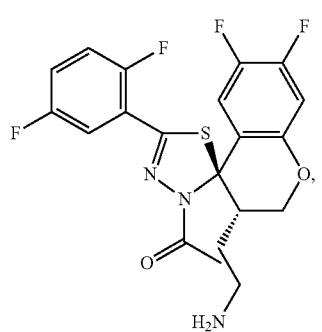
490
-continued
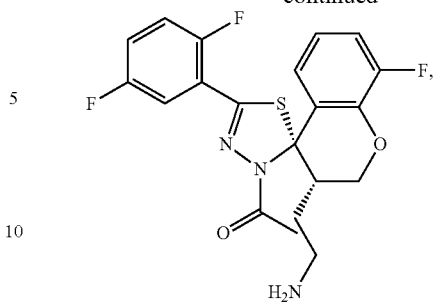
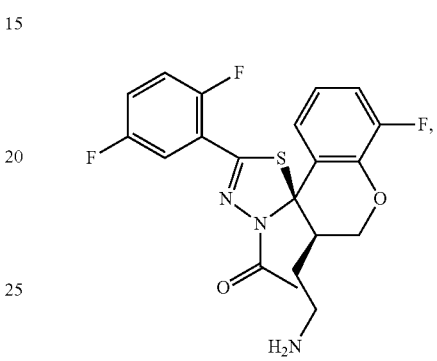
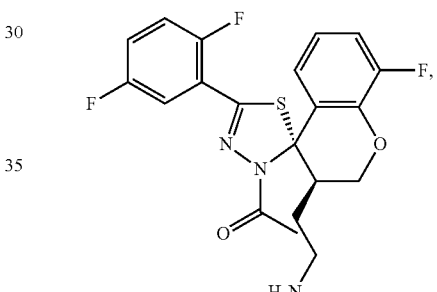
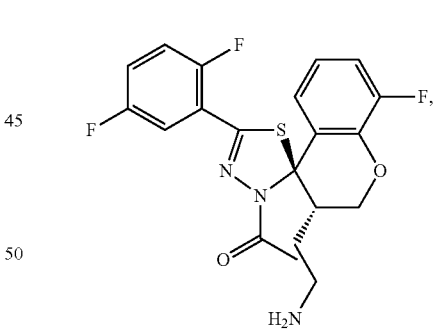
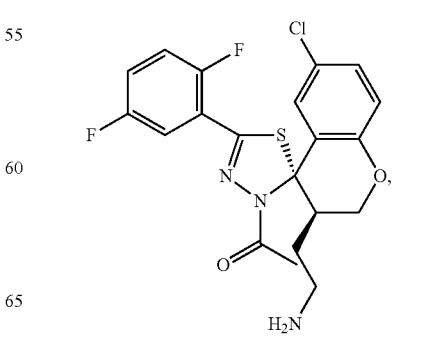

491
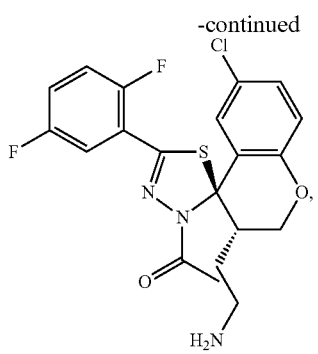
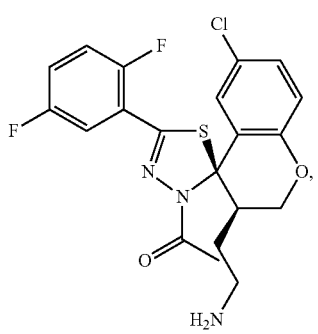
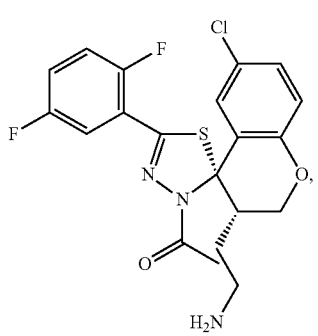
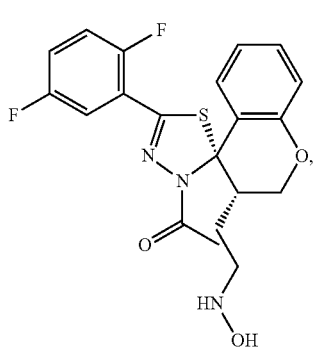
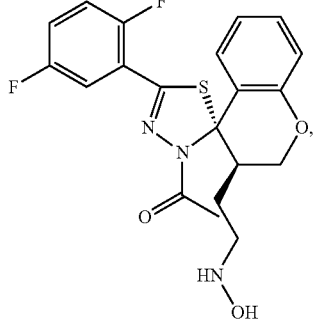
492
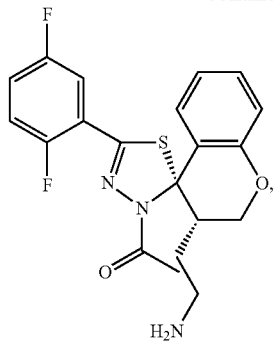
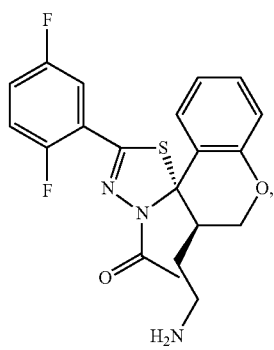
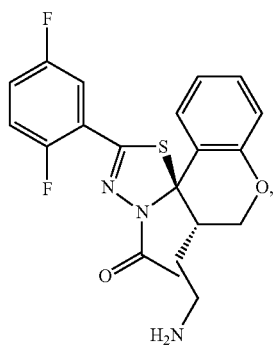
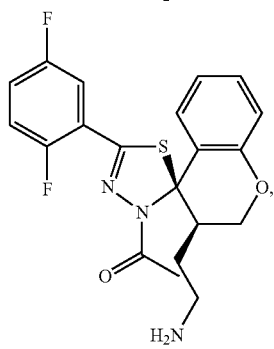
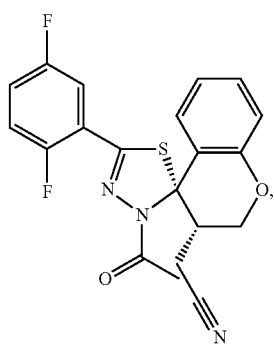

-continued
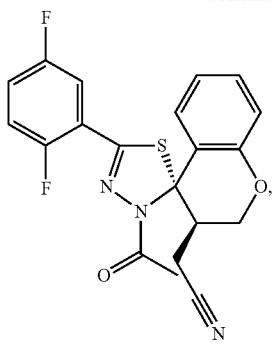
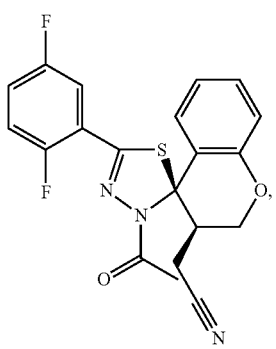
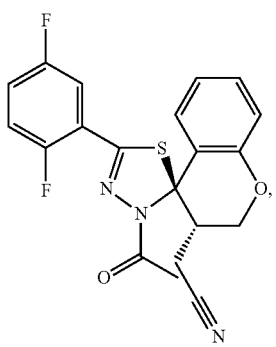
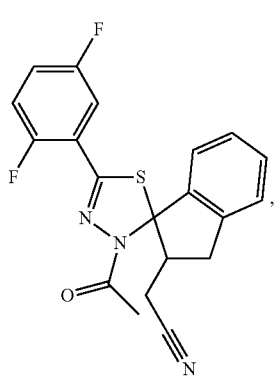
-continued
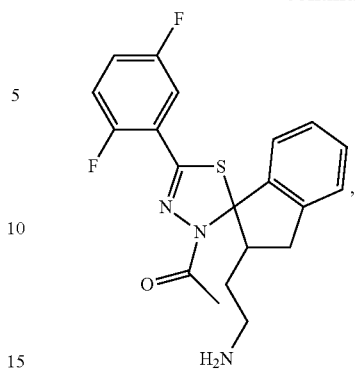
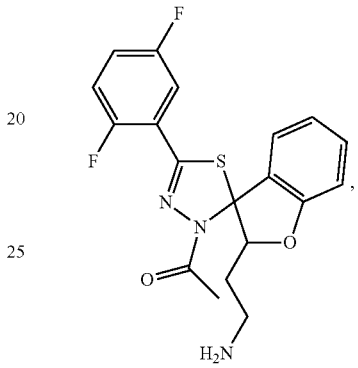
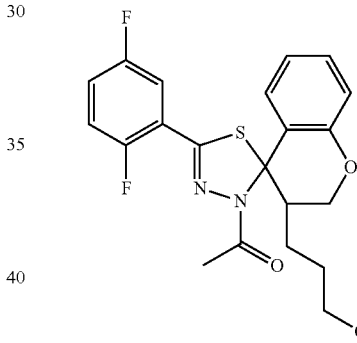
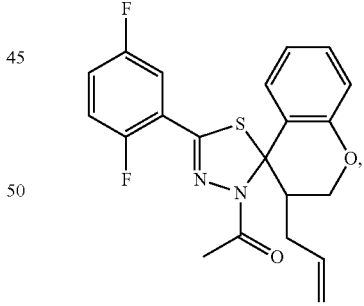
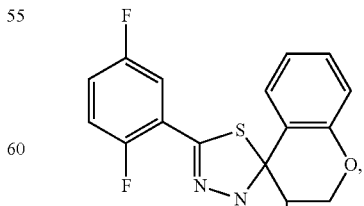

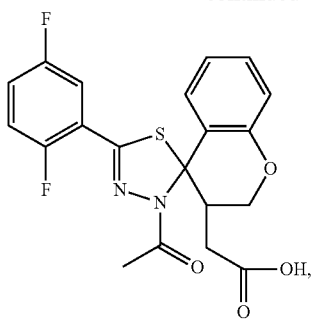
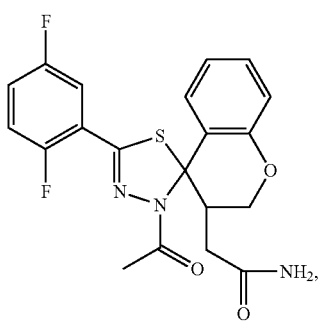
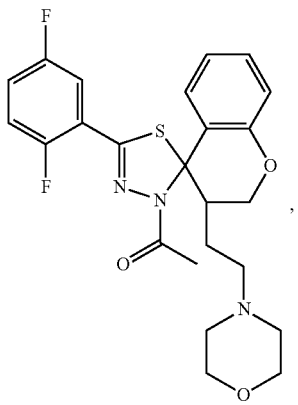
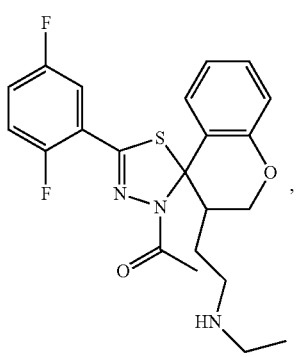
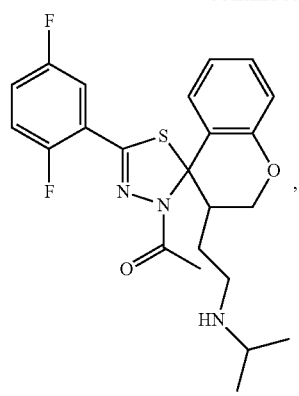
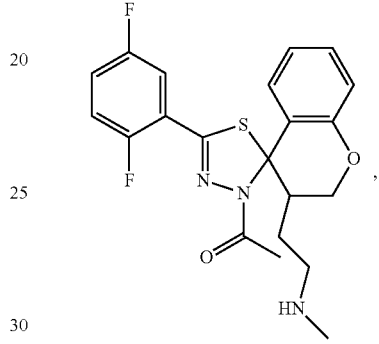
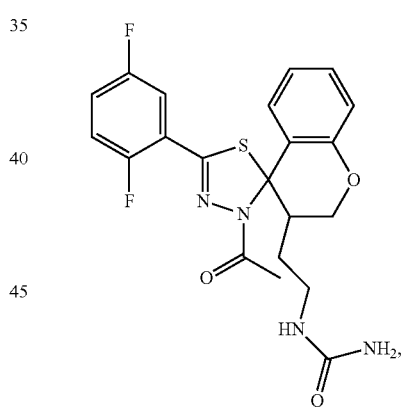
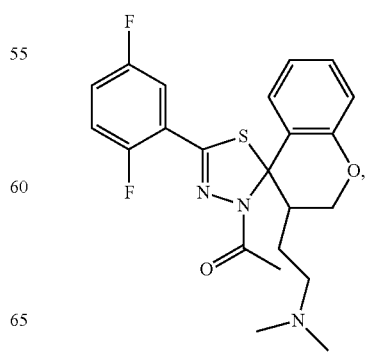

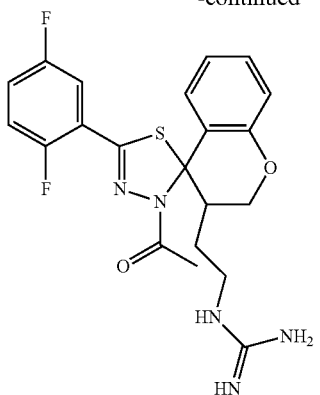
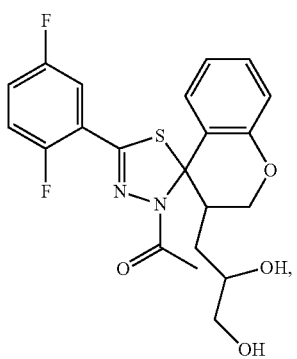
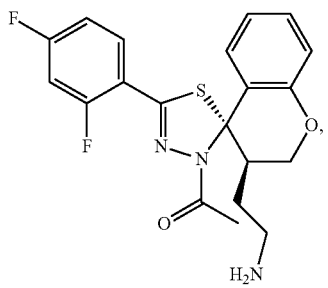
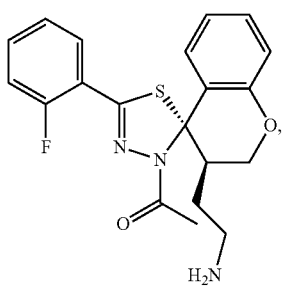
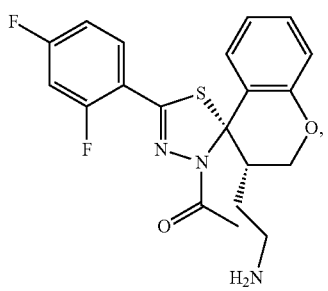
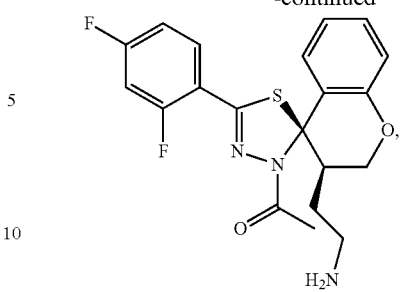
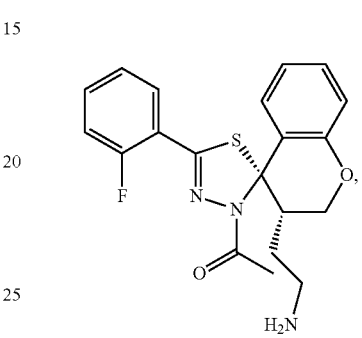
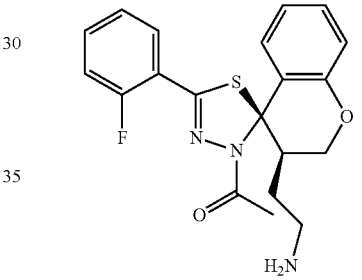
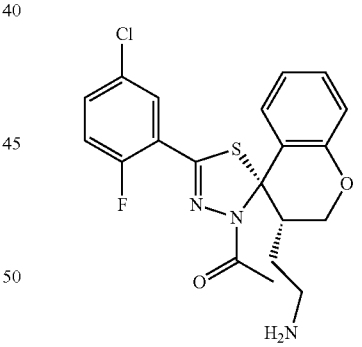
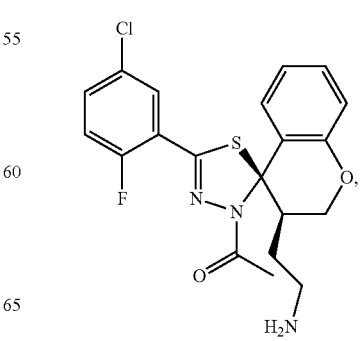

499
-continued
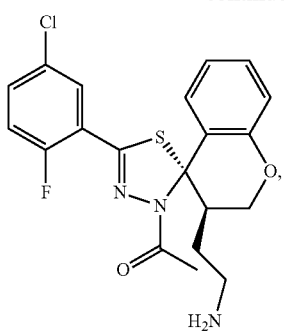
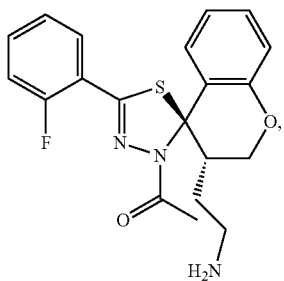
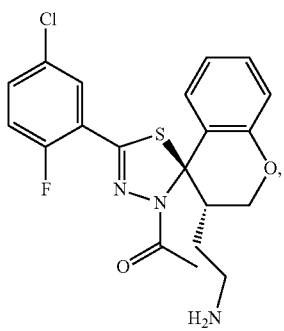
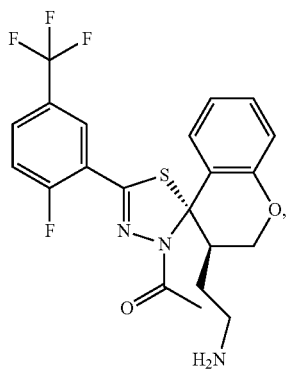
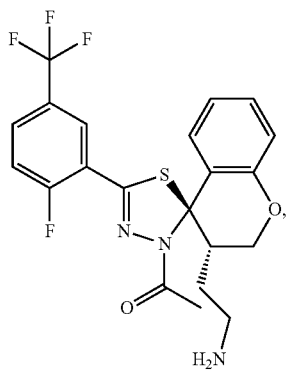
500
-continued
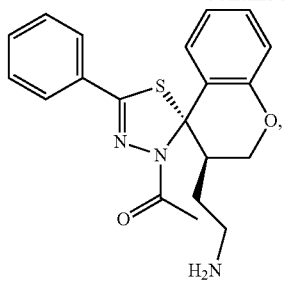
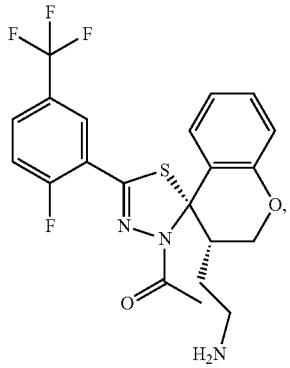
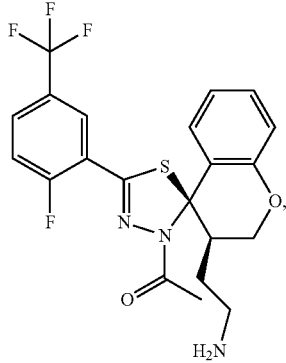
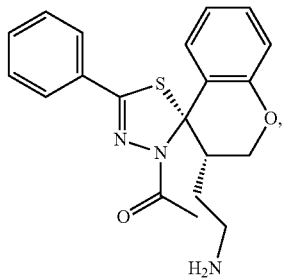
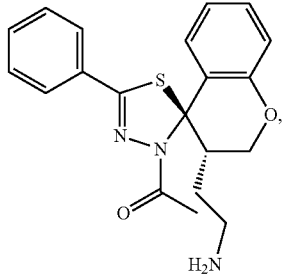

501
-continued
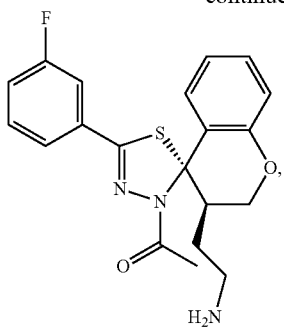
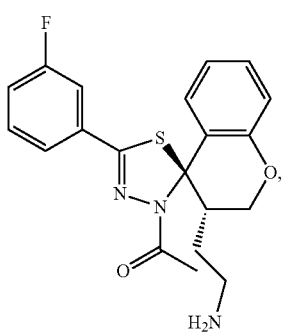
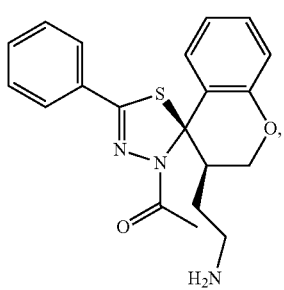
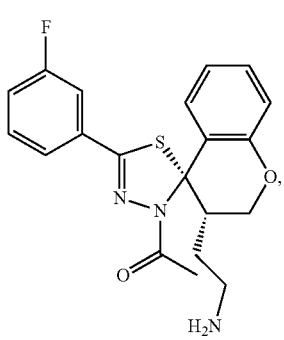
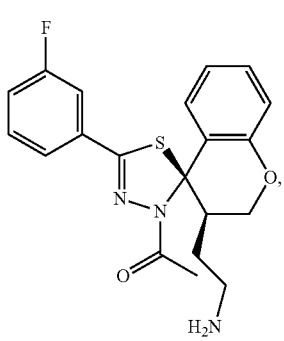
502
-continued
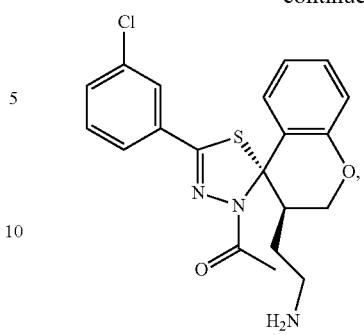
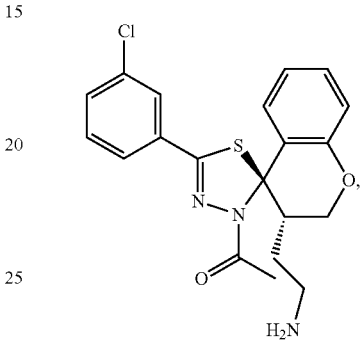
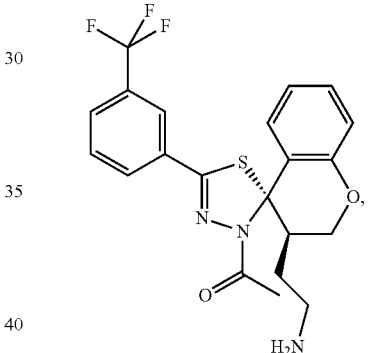
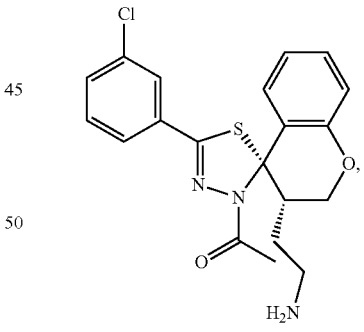
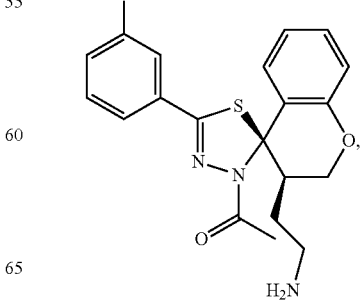

503
-continued
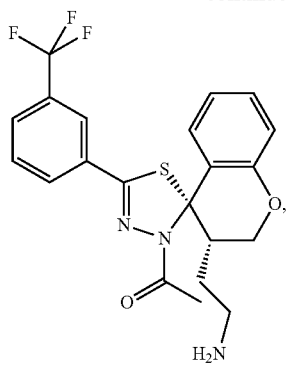
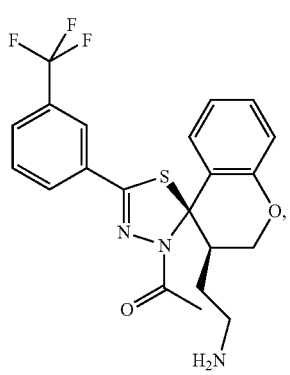
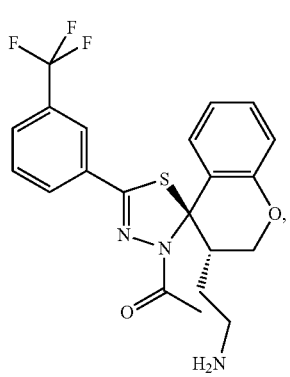
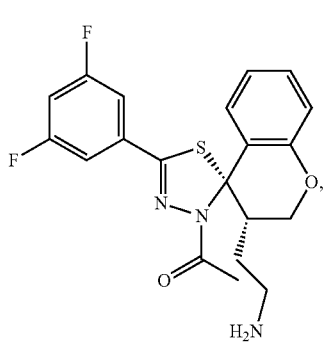
504
-continued
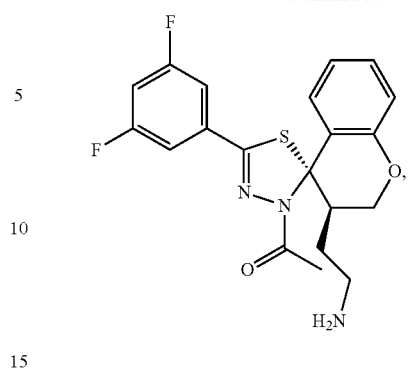
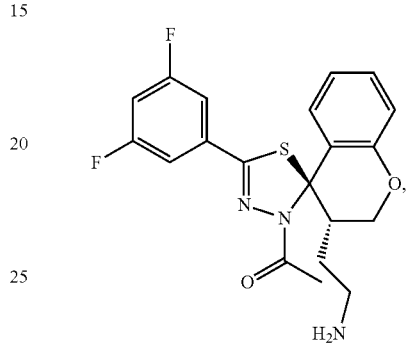
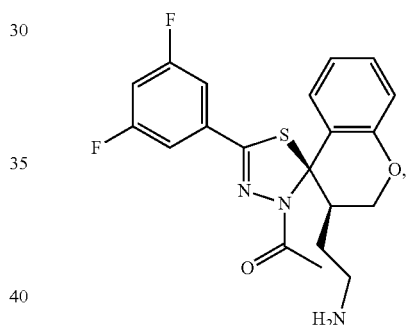
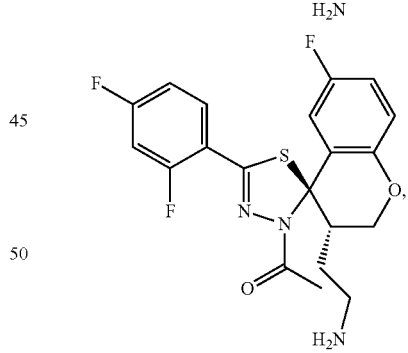
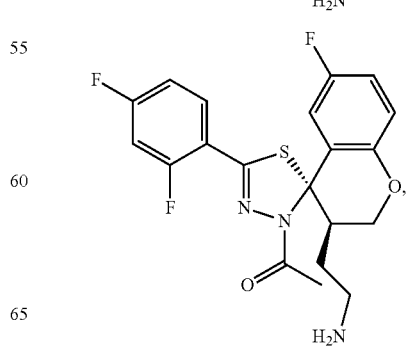

505
-continued
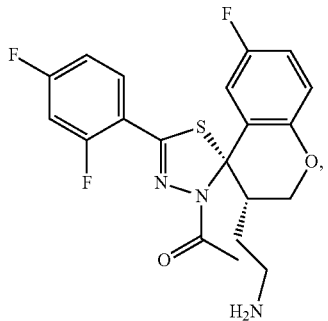
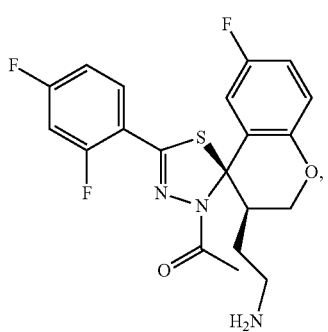
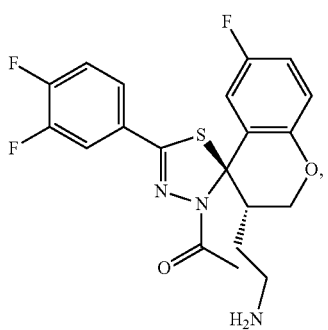
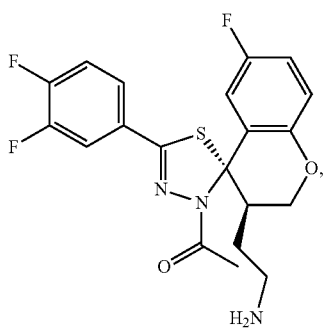
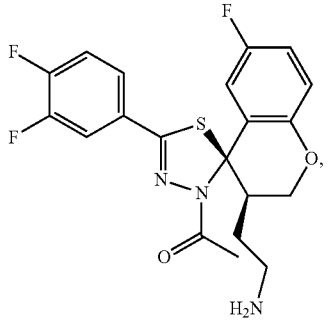
506
-continued
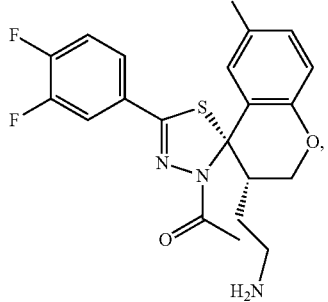
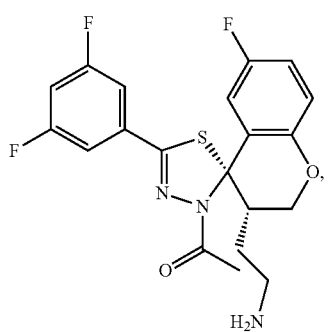
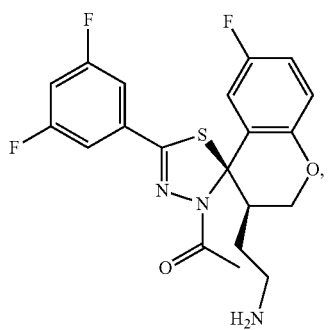
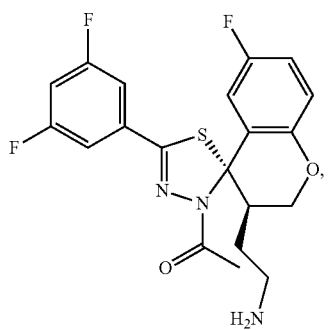
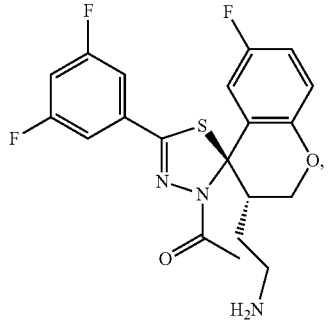

507
-continued
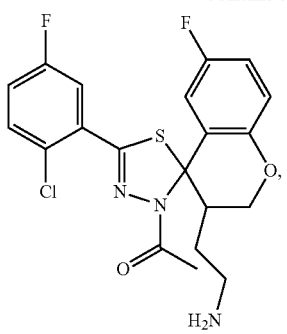
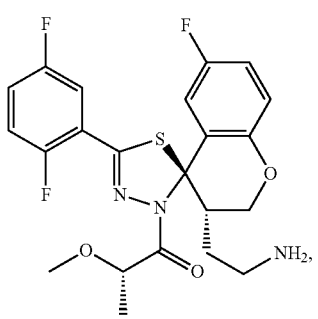
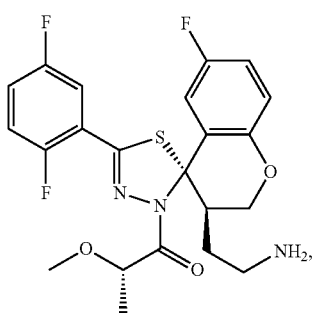
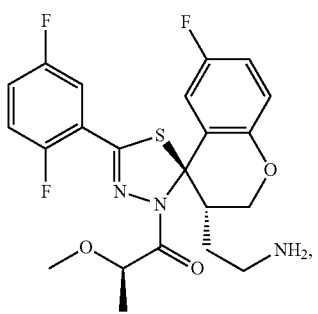
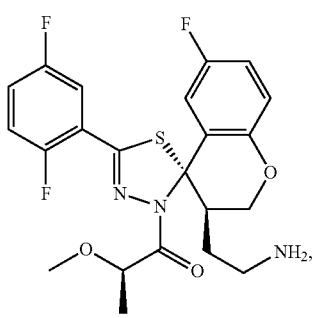
508
-continued
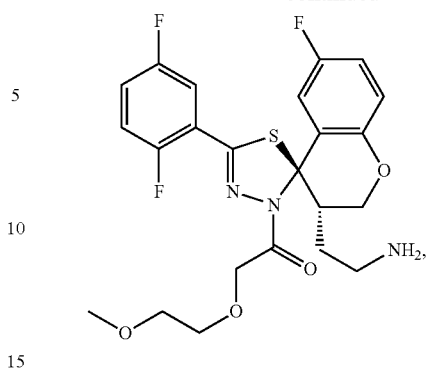
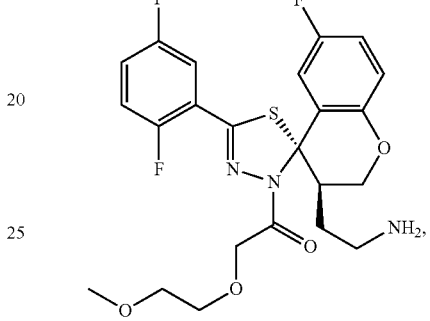
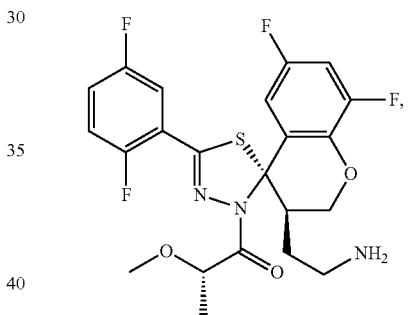
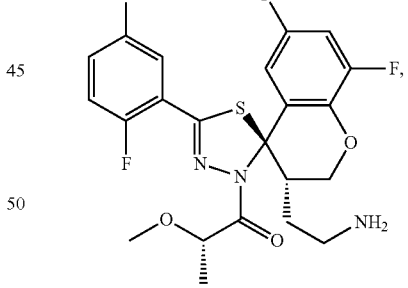
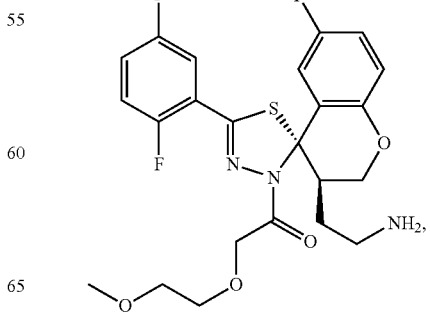

509
-continued
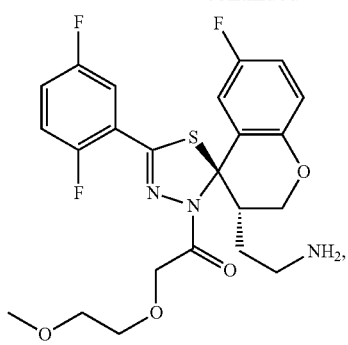
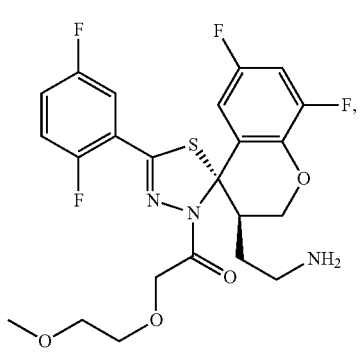
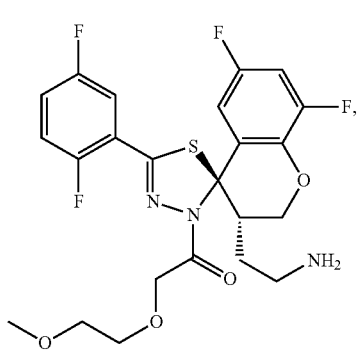
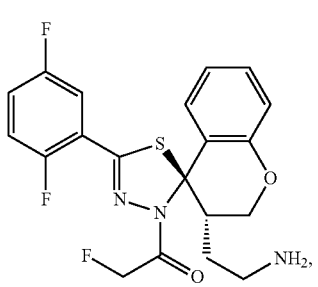
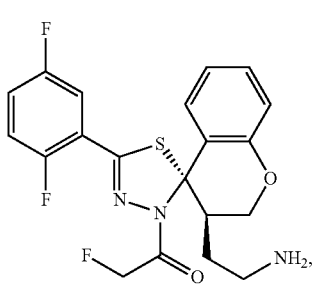
510
-continued
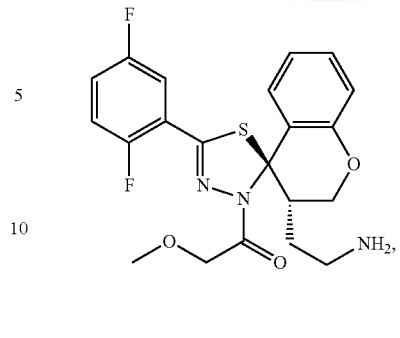
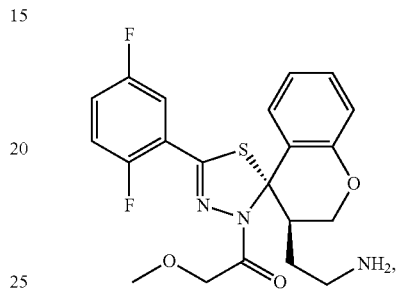
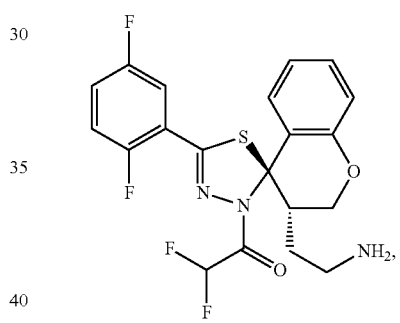
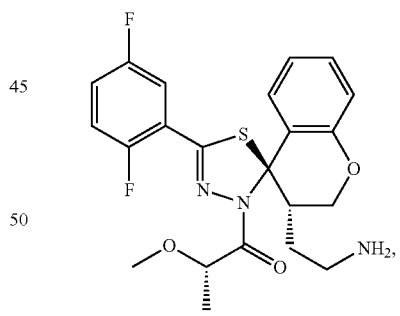
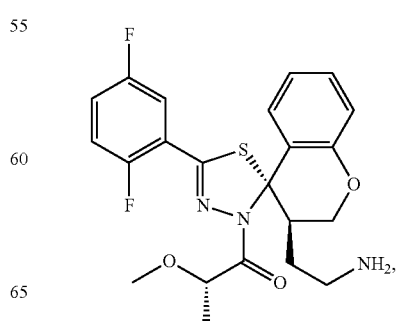

511
-continued
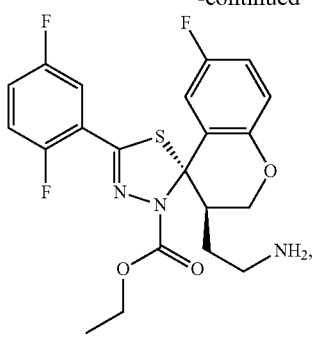
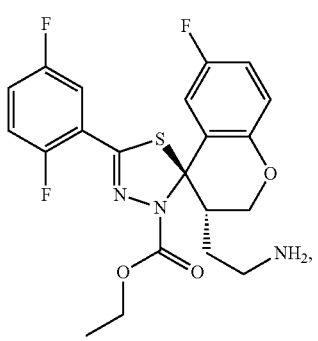
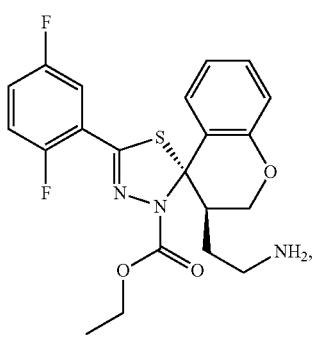
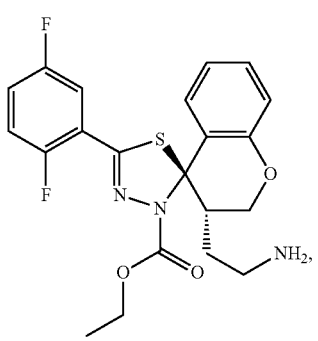
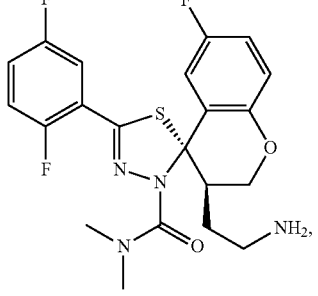
512
-continued
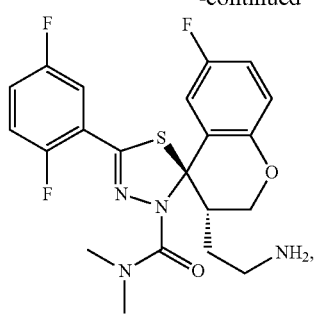
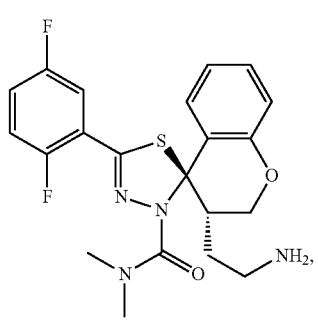
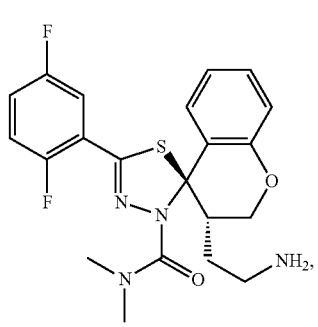
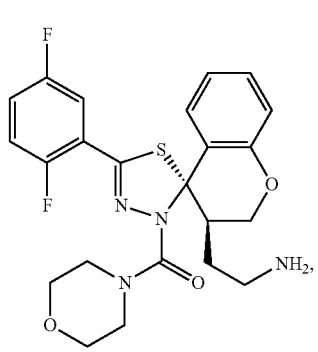
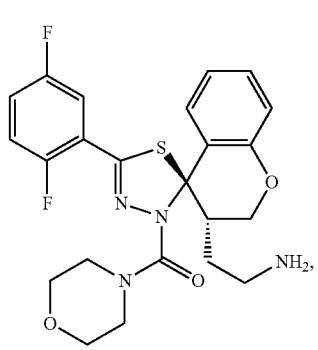

513
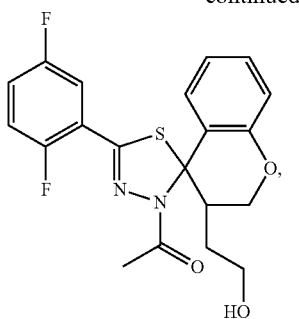
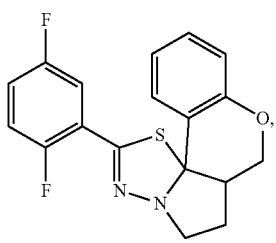
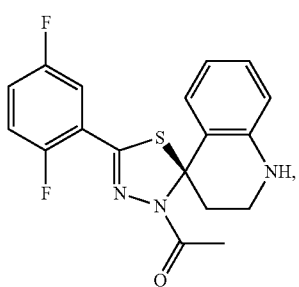
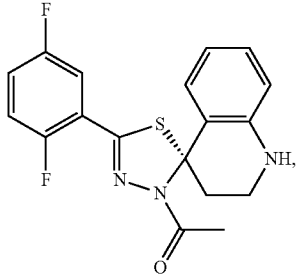
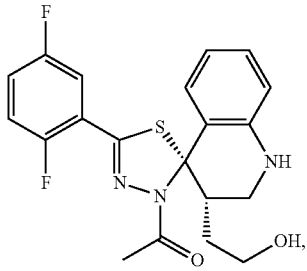
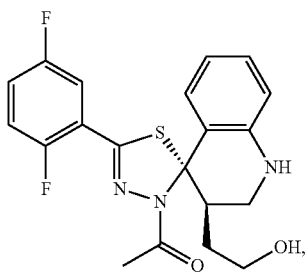
514
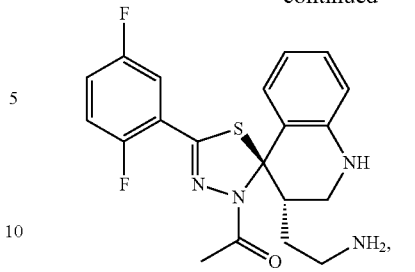
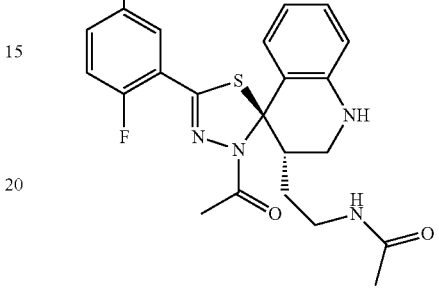
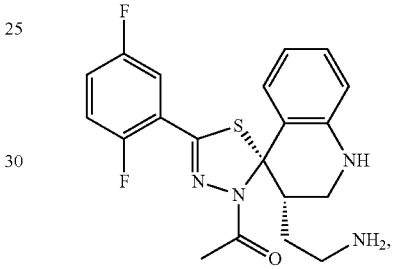
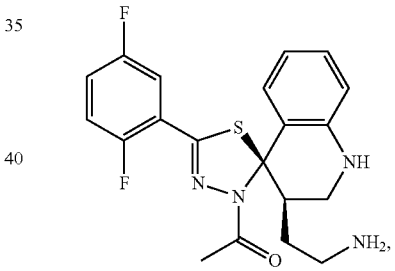
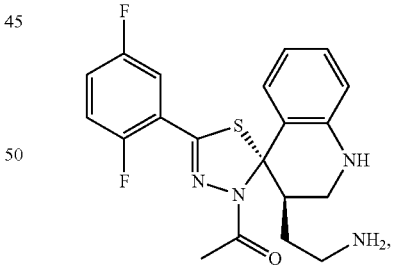
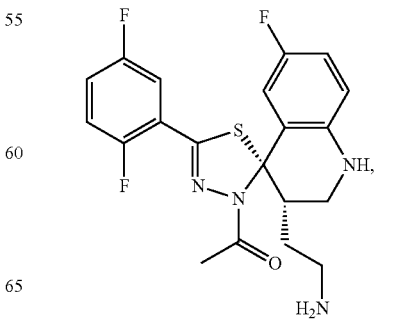

515
-continued
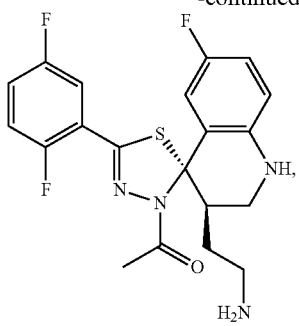
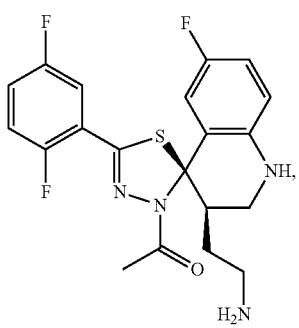
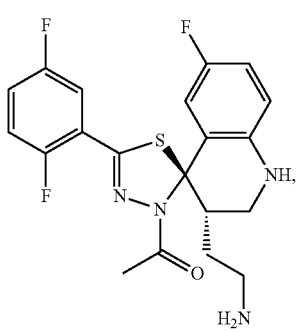
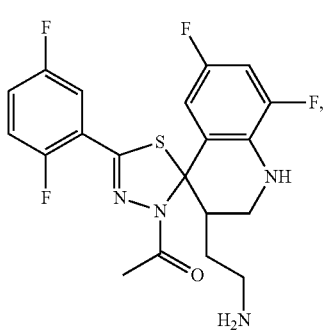
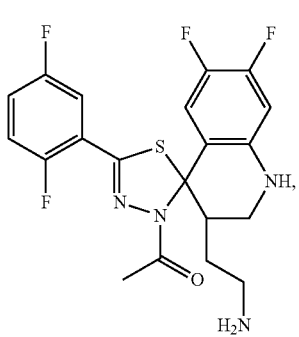
516
-continued
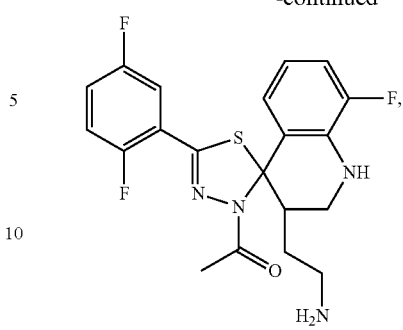
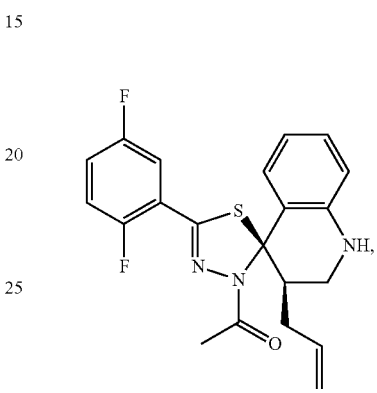
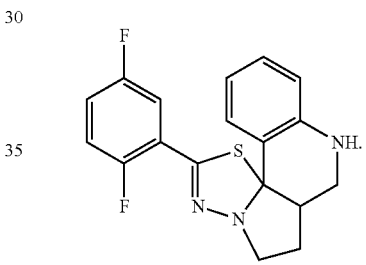
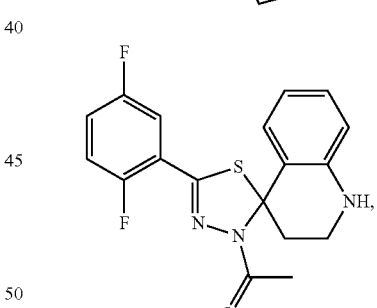
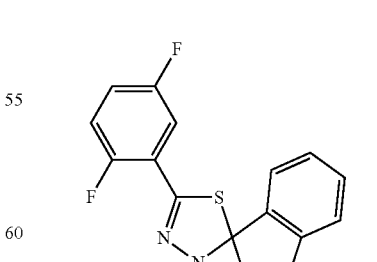
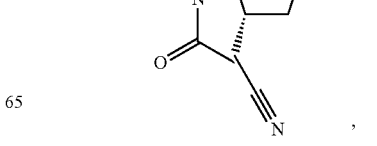

517
-continued
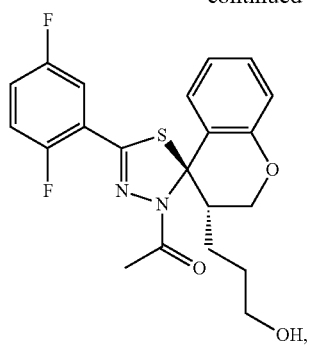
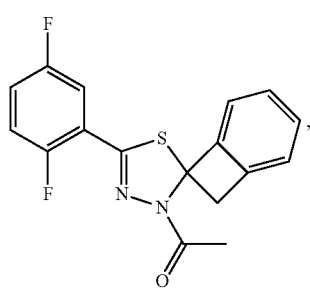
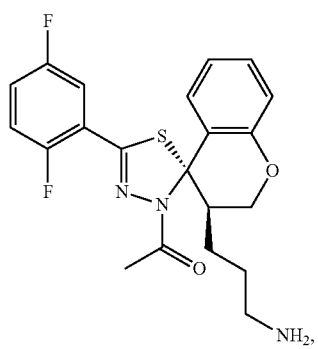
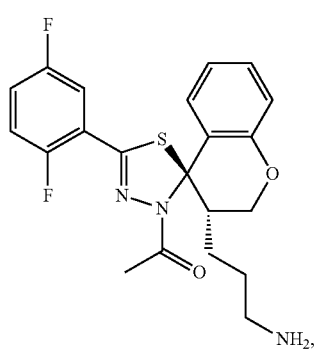
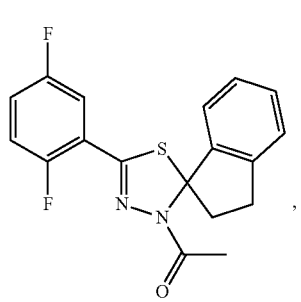
518
-continued
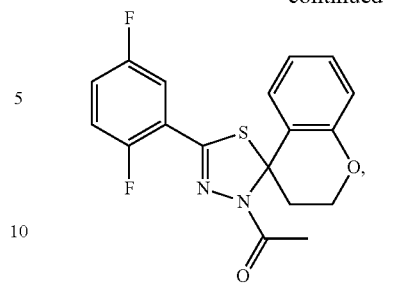
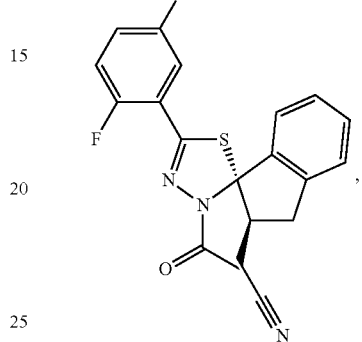
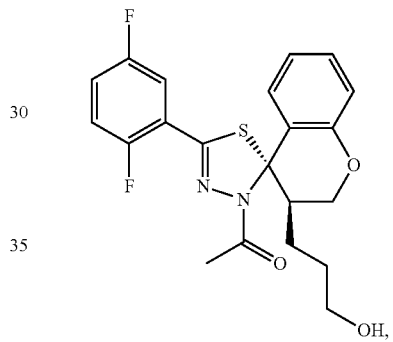
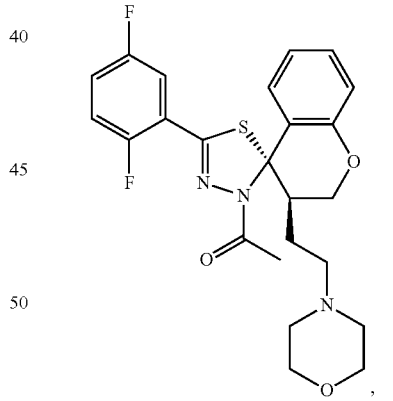
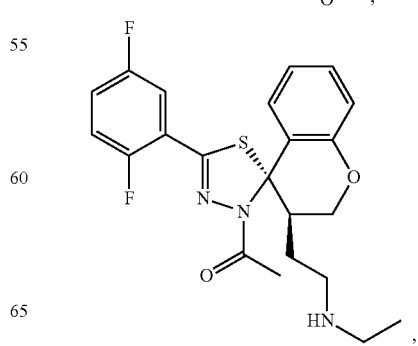

-continued

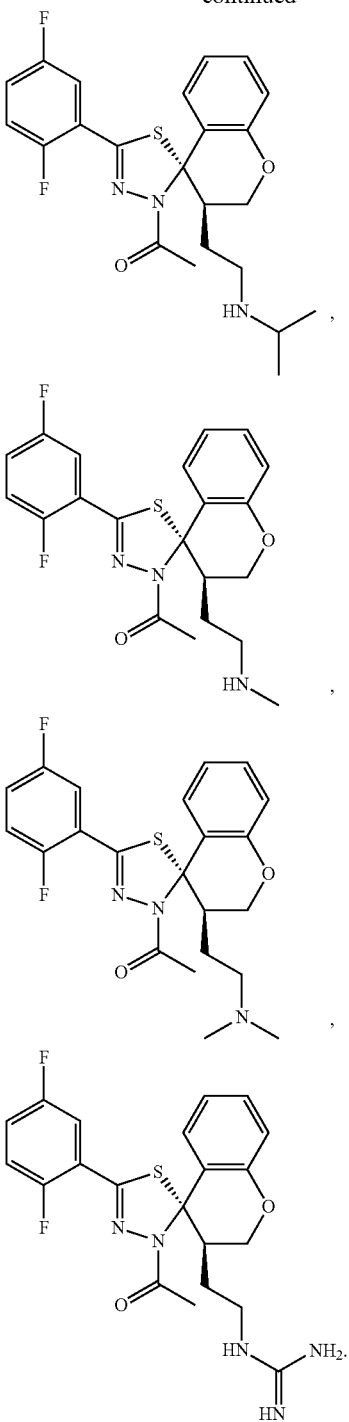

30. A pharmaceutical composition comprising a therapeutically effective amount of at least one compound of claim 1, or a pharmaceutically acceptable salt, or an ester thereof, and at least one pharmaceutically acceptable carrier.

31. A pharmaceutical composition of claim 30, further comprising at least one additional therapeutically active agent.

32. A pharmaceutical composition of claim 31, wherein said at least one additional therapeutically active agent is selected from:
estrogen receptor modulators, androgen receptor modulators, retinoid receptor modulators, cytotoxic agents, microtubule inhibitors/stabilizing agents, topoisomerase inhibitors, antisense RNA and DNA oligonucleotides, antimetabolites, antibodies coupled to cyctotoxic agents, radioisotypes, HMG-CoA reductase inhibitors, prenyltransferase inhibitors, farnesyl protein transferase inhibitors, angiogenesis inhibitors, kinase inhibitors, COX2 inhibitors, integrin blockers, PPAR agonists, MDR inhibitors, hypoxia activatable agents, proteasome inhibitors, ubiquitin inhibitors, HDM2 inhibitors, TNF activators, BUB-R inhibitors, CENP-E inhibitors, interferon, and radiation.

33. The compound of claim 29 that has the structure:

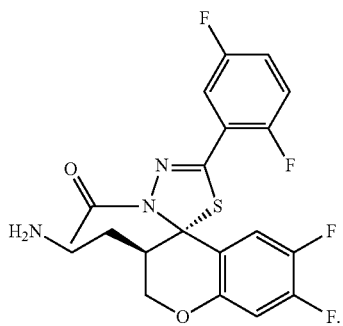 [SMILES: CC(=O)N1N=C(c2cc(F)ccc2F)S[C@@]12c1cc(F)c(F)cc1OC[C@H]2CCN]

34. A pharmaceutically acceptable salt of the compound of claim 33.

35. A pharmaceutical composition comprising a therapeutically effective amount of the compound of claim 33, or a pharmaceutically acceptable salt thereof and at least one pharmaceutically acceptable carrier.

36. The pharmaceutical composition of claim 35, further comprising at least one additional therapeutically active agent.

37. The pharmaceutical composition of claim 36, wherein said at least one additional therapeutically active agent is selected from:
estrogen receptor modulators, androgen receptor modulators, retinoid receptor modulators, cytotoxic agents, microtubule inhibitors/stabilizing agents, topoisomerase inhibitors, antisense RNA and DNA oligonucleotides, antimetabolites, antibodies coupled to cyctotoxic agents, radipisptypes, HMG-CoA reductase inhibitors, prenyltransferase inhibitors, farnesyl protein transferase inhibitors, angiogenesis inhibitors, kinase inhibitors, COX2 inhibitors, integrin blockers, PPAR agonists, MDR inhibitors, hypoxia activatable agents, proteasome inhibitors, ubiquitin inhibitors, HDM2 inhibitors, TNF activators, BUB-R inhibitors, CENP-E inhibitors, interferon, and radiation.

\* \* \* \* \*